US012741960B2

(12) United States Patent
Smrcina et al.

(10) Patent No.: US 12,741,960 B2
(45) Date of Patent: Sep. 22, 2026

(54) PIKfyve KINASE INHIBITORS

(71) Applicant: ACURASTEM INCORPORATED, Pasadena, CA (US)

(72) Inventors: Martin Smrcina, Pasadena, CA (US); Ronghua Li, Pasadena, CA (US); Anil Nair, Pasadena, CA (US); Paul August, Pasadena, CA (US); Kirsten Bjergarde, Pasadena, CA (US); Jennifer Ludington, Buffalo, NY (US)

(73) Assignee: ACURASTEM INCORPORATED, Monrovia, CA (US)

( * ) Notice: Subject to any disclaimer, the term of this patent is extended or adjusted under 35 U.S.C. 154(b) by 839 days.

(21) Appl. No.: 17/760,384

(22) PCT Filed: Feb. 11, 2021

(86) PCT No.: PCT/US2021/070144

§ 371 (c)(1),
(2) Date: Aug. 9, 2022

(87) PCT Pub. No.: WO2021/163727

PCT Pub. Date: Aug. 19, 2021

(65) Prior Publication Data

US 2023/0135152 A1 May 4, 2023

Related U.S. Application Data

(60) Provisional application No. 62/975,092, filed on Feb. 11, 2020.

(51) Int. Cl.

| | |
|---|---|
| *C07D 403/14* | (2006.01) |
| *C07D 239/48* | (2006.01) |
| *C07D 401/14* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 473/18* | (2006.01) |
| *C07D 473/34* | (2006.01) |
| *C07D 475/06* | (2006.01) |
| *C07D 487/04* | (2006.01) |
| *C07D 491/048* | (2006.01) |
| *C07D 498/08* | (2006.01) |

(52) U.S. Cl.

CPC ......... *C07D 403/14* (2013.01); *C07D 239/48* (2013.01); *C07D 401/14* (2013.01); *C07D 405/14* (2013.01); *C07D 413/14* (2013.01); *C07D 417/14* (2013.01); *C07D 471/04* (2013.01); *C07D 473/18* (2013.01); *C07D 473/34* (2013.01); *C07D 475/06* (2013.01); *C07D 487/04* (2013.01); *C07D 491/048* (2013.01); *C07D 498/08* (2013.01)

(58) Field of Classification Search

CPC .. C07D 403/14; C07D 239/48; C07D 401/14; C07D 405/14; C07D 413/14; C07D 417/14; C07D 471/04; C07D 473/18; C07D 473/34; C07D 475/06; C07D 487/04; C07D 491/048; C07D 498/08

See application file for complete search history.

(56) References Cited

U.S. PATENT DOCUMENTS

| | | | |
|---|---|---|---|
| 2,309,663 | A | 2/1943 | Oldham et al. |
| 3,687,808 | A | 8/1972 | Thomas, Jr. et al. |
| 6,268,490 | B1 | 7/2001 | Imanishi et al. |
| 6,525,191 | B1 | 2/2003 | Ramasamy |
| 6,660,733 | B2 | 12/2003 | Sun et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,858,606 | B2 | 2/2005 | Sun et al. |
| 7,034,133 | B2 | 4/2006 | Wengel et al. |
| 7,053,207 | B2 | 5/2006 | Wengel |
| 7,547,684 | B2 | 6/2009 | Seth et al. |
| 7,572,582 | B2 | 8/2009 | Wengel et al. |
| 7,666,854 | B2 | 2/2010 | Seth et al. |
| 7,750,131 | B2 | 7/2010 | Seth et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,153,365 | B2 | 4/2012 | Wengel et al. |

(Continued)

FOREIGN PATENT DOCUMENTS

| | | | |
|---|---|---|---|
| DE | 4031798 | A1 | 4/1992 |
| EP | 3676264 | A1 | 7/2020 |

(Continued)

OTHER PUBLICATIONS

PubChem CID 22349769, National Center for Biotechnology Information. PubChem Compound Summary for CID 22349769, N-(6-amino-2-propan-2-ylsulfanylpyrimidin-4-yl)-4-tert-butylbenzamide. https://pubchem.ncbi.nlm.nih.gov/compound/22349769. Accessed Apr. 9, 2025, create date Dec. 5, 2007. (Year: 2007).*

Chemical Abstracts Registry No. 1479135-91-5, indexed in the Registry file on STN CAS Online Nov. 22, 2013. (Year: 2013).*

Chemical Abstracts Registry No. 1496907-98-2, indexed in the Registry file on STN CAS Online Dec. 17, 2013. (Year: 2013).*

Chemical Abstracts Registry No. 1491869-49-8, indexed in the Registry file on STN CAS Online Dec. 10, 2013. (Year: 2013).*

(Continued)

*Primary Examiner* — Laura L Stockton

(74) *Attorney, Agent, or Firm* — Sterne, Kessler, Goldstein & Fox P.L.L.C.

(57) ABSTRACT

The present invention relates to compounds useful as inhibitors of phosphatidylinositol-3-phosphate 5-kinase (PIKfyve) as well as their use for treating diseases and disorders associated with PIKfyve.

15 Claims, No Drawings

(56) References Cited

U.S. PATENT DOCUMENTS

| | | | |
|---|---|---|---|
| 8,236,795 | B2 | 8/2012 | Sun et al. |
| 8,268,980 | B2 | 9/2012 | Seth et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 9,012,421 | B2 | 4/2015 | Migawa et al. |
| 9,234,885 | B2 | 1/2016 | Chandran et al. |
| 10,729,694 | B2 | 8/2020 | Lichenstein et al. |
| 12,104,159 | B2 | 10/2024 | Chang et al. |
| 2003/0104410 | A1 | 6/2003 | Mittmann |
| 2005/0026164 | A1 | 2/2005 | Zhou |
| 2005/0038023 | A1 | 2/2005 | Bebbington et al. |
| 2006/0024715 | A1 | 2/2006 | Liu et al. |
| 2006/0199804 | A1 | 9/2006 | Hummersone et al. |
| 2008/0039618 | A1 | 2/2008 | Allerson et al. |
| 2012/0009151 | A1 | 1/2012 | Han et al. |
| 2013/0273070 | A1 | 10/2013 | Purcell Ngambo |
| 2015/0065519 | A1 | 3/2015 | Chakravarty et al. |
| 2015/0191727 | A1 | 7/2015 | Migawa et al. |
| 2018/0161335 | A1 | 6/2018 | Ichida et al. |
| 2020/0199136 | A1 | 6/2020 | Smrcina et al. |
| 2021/0009718 | A1 | 1/2021 | Ambrogelly et al. |
| 2021/0338683 | A1 | 11/2021 | Ichida et al. |
| 2022/0193204 | A1 | 6/2022 | Cruz et al. |
| 2024/0197747 | A1 | 6/2024 | Ichida et al. |
| 2024/0352026 | A1 | 10/2024 | Smrcina et al. |

FOREIGN PATENT DOCUMENTS

| | | | |
|---|---|---|---|
| EP | 3753937 | A1 | 12/2020 |
| EP | 3960875 | A1 | 3/2022 |
| EP | 3967694 | A1 | 3/2022 |
| EP | 4103281 | A1 | 12/2022 |
| WO | WO-9914226 | A2 | 3/1999 |
| WO | WO-0250065 | A2 | 6/2002 |
| WO | WO-03101989 | A1 | 12/2003 |
| WO | WO-2004106356 | A1 | 12/2004 |
| WO | 2005007648 | A2 | 1/2005 |
| WO | 2006128129 | A2 | 11/2006 |
| WO | WO-2007134181 | A2 | 11/2007 |
| WO | 2008067871 | A1 | 6/2008 |
| WO | WO-2008125839 | A2 | 10/2008 |
| WO | WO-2009016410 | A2 | 2/2009 |
| WO | WO-2009083553 | A1 | 7/2009 |
| WO | WO-2009150462 | A1 | 12/2009 |
| WO | WO-2010149459 | A1 | 12/2010 |
| WO | WO-2012101654 | A2 | 8/2012 |
| WO | WO-2013014074 | A1 | 1/2013 |
| WO | 2013052395 | A1 | 4/2013 |
| WO | WO-2014016849 | A2 | 1/2014 |
| WO | 2016210372 | A2 | 12/2016 |
| WO | 2017012576 | A1 | 1/2017 |
| WO | WO-2017015555 | A1 | 1/2017 |
| WO | WO-2017070189 | A1 | 4/2017 |
| WO | WO-2018137573 | A1 | 8/2018 |
| WO | WO-2018137607 | A1 | 8/2018 |
| WO | 2019046316 | A1 | 3/2019 |
| WO | 2019222173 | A1 | 11/2019 |
| WO | WO-2021154687 | A1 | 8/2021 |
| WO | WO-2021155067 | A1 | 8/2021 |
| WO | WO-2021163727 | A1 | 8/2021 |
| WO | WO-2022271836 | A2 | 12/2022 |
| WO | WO-2023215133 | A1 | 11/2023 |
| WO | WO-2024167945 | A1 | 8/2024 |

OTHER PUBLICATIONS

Baird, A.M., et al., "IL-23R is Epigenetically Regulated and Modulated by Chemotherapy in Non-small Cell Lung Cancer," Frontiers in Oncology 3:162, pp. 1-9, Lausanne : Frontiers Research Foundation, Switzerland (Jun. 2013).

Shetty, R., et al., "Therapeutic opportunities to manage COVID-19/SARS-CoV-2 infection: Present and future," Indian Journal of Ophthalmology 68(5):693-702, Medknow Publications, India (Mar. 2020).

Cai, X., et al., "PIKfyve, a Class III PI Kinase, is the Target of the Small Molecular IL-12/IL-23 Inhibitor Apilimod and a Player in Toll-like Receptor Signaling," Chemistry & Biology 20(7):912-921, Elsevier, United States (Jul. 2013).

Higuchi, T., and Stella, V., *Pro-drugs as Novel Delivery Systems*, vol. 14 of the A.C.S. Symposium Series, American Chemical Society, Washington, D.C., United States (1987).

Wada, Y., et al., "Selective Abrogation of Thl Response by STA-5326, a Potent IL-12/IL-23 Inhibitor," Blood 109(3):1156-1164, Elsevier, United States (Feb. 2007).

Adamson, C.S., et al., "Antiviral Drug Discovery: Preparing for the Next Pandemic," Chemical Society Reviews 50(6):3647-3655, Chemical Society, United Kingdom (Mar. 2021).

Albaek, N., et al., "Analogues of a Locked Nucleic Acid with Three-Carbon 2,4-Linkages: Synthesis by Ring-Closing Metathesis and Influence on Nucleic Acid Duplex Stability and Structure," The Journal of Organic Chemistry 71(20):7731-7740, American Chemical Society, United States (Sep. 2006).

Yamaya, M., et al., "Protease Inhibitors: Candidate Drugs to Inhibit Severe Acute Respiratory Syndrome Coronavirus 2 Replication," The Tohoku Journal of Experimental Medicine 251(1):27-30, Tohoku University Medical Library, Japan (May 2020).

Balfour, H., "Nafamostat Inhibits SARS-CoV-2 Infection, Preventing COVID-19 Transmission," Drug Target Review, Mar. 2020, accessed at https://www.drugtargetreview.com/news/58915/nafamostat-inhibits-sars-cov-2-infection-preventing-covid-19-transmission/, 4 pages.

Yamamoto, M., et al., "The Anticoagulant Nafamostat Potently Inhibits SARS-CoV-2 Infection in Vitro: an Existing Drug With Multiple Possible Therapeutic Effects," BioRxiv 2020.04.22. 054981, pp. 1-19, Cold Spring Laboratory Press, United Kingdom (Apr. 2020).

Barciszewski, J., et al., "Chapter 10: Locked Nucleic Acid Aptamers," Methods in Molecular Biology 535:165-186, Humana Press, United States (2009).

CAS Registry No. 1501782-42-8, which entered STN on Dec. 23, 2013 (Year: 2013).

CAS Registry No. 696636-91-6, which entered STN on Jun. 21, 2004 (Year: 2004).

Co-pending U.S. Appl. No. 18/818,329, inventors Chang, W-H., et al., filed Aug. 28, 2024, 68 pages (Not yet Published).

Co-pending U.S. Appl. No. 18/862,354, inventor Bjergarde, K., filed Nov. 1, 2024, 53 pages (Not yet Published).

Wils, H., et al., "TDP-43 Transgenic Mice Develop Spastic Paralysis and Neuronal Inclusions Characteristic of Als and Frontotemporal Lobar Degeneration," Proceedings of the National Academy of Sciences of the United States of America 107(8):3858-3863, National Academy of Sciences, United States (Feb. 2010).

Cuesta-Geijo, M.A., et al., "Endosomal Maturation, Rab7 GTPase and Phosphoinositides in African Swine Fever Virus Entry," PLoS One 7(11):e48853, Public Library of Science, United States (Nov. 2012).

Cuesta-Geijo, M.A., et al., "Redistribution of Endosomal Membranes to the African Swine Fever Virus Replication Site," Viruses 9(6):133, MDPI, Switzerland (Jun. 2017).

Englisch, U., and Gauss, D.H., "Chemically Modified Oligonucleotides as Probes and Inhibitors," Angewandte Chemie International Edition in English 30(6):613-629, Wiley-VCH, Germany (Jun. 1991).

EurekAlert, "Nafamostat is Expected to Prevent the Transmission of New Coronavirus Infection (COVI D-1 9)," The Institute of Medical Science, The University of Tokyo, News Release, Mar. 2020, accessed at https://www.eurekalert.org/news-releases/838150, 4 Pages.

Freier, S.M., and Altmann, K.H., "The Ups and Downs of Nucleic Acid Duplex Stability: Structure-stability Studies on Chemically-modified DNA: RNA Duplexes," Nucleic Acids Research 25(22):4429-4443, Oxford University Press, United Kingdom (Nov. 1997).

Godwin, P., et al., "Targeting Nuclear Factor-kappa B to Overcome Resistance to Chemotherapy," Frontiers in Oncology 3:120, Frontiers Media S.A., Switzerland (May 2013).

(56) References Cited

OTHER PUBLICATIONS

Hagedorn, P.H., et al., "Acute Neurotoxicity of Antisense Oligonucleotides After Intracerebroventricular Injection Into Mouse Brain Can Be Predicted from Sequence Features," Nucleic Acid Therapeutics 32(3):151-162, Mary Ann Liebert, Inc., United States (Jun. 2022).
Hoffmann, M., et al., "SARS-CoV-2 Cell Entry Depends on ACE2 and TMPRSS2 and Is Blocked by a Clinically Proven Protease Inhibitor," Cell 181(2):271-280, Cell Press, United States (Apr. 2020).
Wikipedia, "Coronavirus," Wikipedia.org, 2023, accessed at https://en.wikipedia.org/wiki/Coronavirus, 33 Pages.
Weir, M., et al., "Canine Coronavirus Disease," Coronavirus Disease in Dogs, 2021, accessed at https://vcahospitals.com/know-your-pet/coronavirus-disease-in-dogs, 2 Pages.
International Search Report and Written Opinion for Application No. PCT/US2018/048369, European Patent Office, Netherlands, mailed on Feb. 11, 2019, 23 pages.
International Search Report and Written Opinion for Application No. PCT/US2021/070144, European Patent Office, Netherlands, mailed on May 10, 2021, 18 pages.
International Search Report and Written Opinion for Application No. PCT/US2022/034539, European Patent Office, Netherlands, mailed on Dec. 21, 2022, 20 pages.
International Search Report and Written Opinion for Application No. PCT/US2023/019770, European Patent Office, Netherlands, mailed on Jul. 20, 2023, 13 pages.
International Search Report and Written Opinion for Application No. PCT/US2024/014647, European Patent Office, Netherlands, mailed on Jul. 19, 2024, 16 pages.
Kang, Y-L., et al., "Inhibition of PIKfyve kinase prevents infection by Zaire ebolavirus and SARS-CoV-2," PNAS 117(34):20803-20813, National Academy of Sciences (Aug. 2020).
Kausar, S., et al., "A Review: Mechanism of Action of Antiviral Drugs," International Journal of Immunopathology and Pharmacology 35:1-12, SAGE Publishing, United States (Mar. 2021).
Wan, W.B., et al., "Synthesis, Biophysical Properties and Biological Activity of Second Generation Antisense Oligonucleotides Containing Chiral Phosphorothioate Linkages," Nucleic Acids Research 42(22):13456-13468, Oxford University Press, United Kingdom (Dec. 2014).
Koshkin, A.A., et al., "LNA (Locked Nucleic Acids): Synthesis of the Adenine, Cytosine, Guanine, 5-methylcytosine, Thymine and Uracil Bicyclonucleoside Monomers, Oligomerisation and Unprecedented Nucleic Acid Recognition," Tetrahedron 54:3607-3630, Pergamon Press, United Kingdom (Apr. 1998).
Kroschwitz, J.I., ed., "Polynucleotides," in *Concise Encyclopedia of Polymer Science and Engineering*, pp. 858-859, John Wiley & Sons, Hoboken, United States (1990).
Kumar, R., et al., "The First Analogues of LNA (Locked Nucleic Acids): Phosphorothioate-LNA and 2'-thio-LNA," Bioorganic & Medicinal Chemistry Letters 8(16):2219-2222, Elsevier Science Limited, United Kingdom (Aug. 1998).
Tompa, D.R., et al., "Trends and Strategies to Combat Viral Infections: A Review on FDA Approved Antiviral Drugs," International Journal of Biological Macromolecules 172:524-541, Elsevier, Netherlands (Mar. 2021).
Meyer, D., et al., "Identification of the First Synthetic Inhibitors of the Type II Transmembrane Serine Protease TMPRSS2 Suitable for Inhibition of Influenza Virus Activation," The Biochemical Journal 452(2):331-343, Published by Portland Press on behalf of the Biochemical Society, United Kingdom (Jun. 2013).
National Institutes of Allergy and Infectious Diseases, "Coronaviruses," niaid.nih.gov, 2022, accessed at https://www.niaid.nih.gov/diseases-conditions/coronaviruses, 4 Pages.
Oka, N., et al., "An Oxazaphospholidine Approach for the Stereocontrolled Synthesis of Oligonucleoside Phosphorothioates," Journal of the American Chemical Society 125(27):8307-8317, American Chemical Society, United States (Jul. 2003).
Ou, X., et al., "Characterization of Spike Glycoprotein of SARS-CoV-2 on Virus Entry and Its Immune Cross-reactivity With SARS-CoV," Nature Communications 11:1620, Springer Nature, Germany (Apr. 2021).
Paszti-Gere, E., et al., "In Vitro Characterization of TMPRSS2 Inhibition in IPEC-J2 Cells," Journal of Enzyme Inhibition and Medicinal Chemistry 31(Suppl 2):123-129, Taylor & Francis, United Kingdom (Nov. 2016).
Rensi, S., et al., "Homology Modeling of TMPRSS2 Yields Candidate Drugs That May Inhibit Entry of SARS-CoV-2 Into Human Cells," ChemRxiv 12009582, pp. 1-22, Cambridge University Press, United Kingdom (Mar. 2020).
Riva, L., et al., "A Large-scale Drug Repositioning Survey for SARS-CoV-2 Antivirals," BioRxiv 2020.04.16.044016, pp. 1-43, Cold Spring Harbor Laboratory Press, United States (Apr. 2020).
Rizopoulos, Z., et al., "Vaccinia Virus Infection Requires Maturation of Macropinosomes," Traffic 16(8):814-831, Wiley, United Kingdom (Aug. 2015).
Sanghvi, Y.S., "Chapter 15: Heterocycle Base Modifications in Nucleic Acids and their Applications in Antisense Oligonucleotides," Antisense Research and Applications, Crooke, S.T. and Lebien, B., eds., pp. 273-288, CRC Press, United States (1993).
Shi, Y., et al., "Haploinsufficiency Leads to Neurodegeneration in C9ORF72 ALS/FTD Human Induced Motor Neurons," Nature Medicine 24(3):313-325, Springer, Germany (Mar. 2018).
Singh, S.K., et al., "LNA (locked nucleic acids): Synthesis and High-affinity Nucleic acid Recognition," Chemical Communication 4:455-456, Royal Society of Chemistry, United States (1998).
Singh, S.K., et al., "Synthesis of 2'-Amino-LNA: A Novel Conformationally Restricted High-Affinity Oligonucleotide Analogue with a Handle," Journal of Organic Chemistry 63(26):10035-10039, American Chemical Society, United States (Dec. 1998).
Srivastava, P., et al., "Five- and Six-membered Conformationally Locked 2',4'-carbocyclic Ribo-thymidines: Synthesis, Structure, and Biochemical Studies," Journal of the American Chemical Society 129(26):8362-8379, American Chemical Society, United States (Jul. 2007).
Tang, T., et al., "Coronavirus Membrane Fusion Mechanism Offers a Potential Target for Antiviral Development," Antiviral Research 178:104792, Elsevier, Netherlands (Jun. 2020).
Taylor, M., and Gerriets, V., "Acyclovir," NCBI Bookshelf, StatPearls Publishing, United States (May 2023), accessed at https://www.ncbi.nlm.nih.gov/books/NBK542180/, 8 Pages.
International Search Report issued in PCT/US21/70144 on May 10, 2021.
Park, Byung Sun, et al., "Structure-based Optimization and Biological Evaluation of Trisubstituted Pyrazole as a Core Structure of Potent ROS1 Kinase Inhibitors", Bioorganic & Medicinal Chemistry, 2014, 22:3871-3878.
Aleem, A., et al., "Emerging Variants of SARS-CoV-2 and Novel Therapeutics Against Coronavirus (COVID-19)," StatPearls, NCBI Bookshelf, last updated on May 8, 2023, accessed at https://www.ncbi.nlm.nih.gov/books/NBK570580/, accessed on Apr. 11, 2025, 23 pages.
Morgan, K.K., and Seed, S., "COVID Variants," WebMD, last updated on Nov. 15, 2023, accessed at https://www.webmd.com/covid/coronavirus-strains#1, accessed on Apr. 11, 2025, 4 pages.
CAS Registry No. 1467559-07-4, which entered STN on Nov. 1, 2013 (Year: 2013).
CAS Registry No. 1500340-86-2, which entered STN on Dec. 22, 2013 (Year: 2013).
American Veterinary Medical Association, "African swine fever," AVMA, accessed at https://www.avma.org/resources-tools/animal-health-and-welfare/animal-health/african-swine-fever, accessed on Jun. 30, 2025, 3 pages.
Boehringer Ingelheim Animal Health USA, "African swine fever: 5 questions and answers," Boehringer Ingelheim, accessed at https://www.boehringer-ingelheim.com/us/animal-health/trends-insights/african-swine-fever-important-facts-boehringer-ingelheim-us, accessed on Jun. 30, 2025, 4 pages.
Department of Homeland Security, "African Swine Fever Virus: An Emerging Transboundary Threat," DHS.gov, accessed at https://

(56) References Cited

OTHER PUBLICATIONS www.dbs.gov/sites/default/files/2024-01/23_1116_st_african_swine_fever_virus_factsheet.pdf, accessed on Jun. 30, 2025, 1 page.
World Organisation for Animal Health, "African Swine Fever," WOAH Technical Disease Card: African swine fever, accessed at https://www.woah.org/app/uploads/2021/03/a-african-swine-fever-v2-0.pdf, accessed on Jun. 30, 2025, 6 pages.
CAS Registry No. 1499689-68-7, indexed in the Registry file on STN CAS Online Dec. 20, 2013, 1 page.
CAS Registry No. 1978735-76-0, indexed in the Registry file on STN CAS Online Aug. 24, 2016, 1 page.

* cited by examiner

PIKfyve KINASE INHIBITORS

This application is a U.S. national phase of International Application No. PCT/US21/70144, filed Feb. 11, 2021, which claims the benefit of U.S. Patent Application No. 62/975,092, filed Feb. 11, 2020, which is hereby incorporated by reference.

STATEMENT OF GOVERNMENT SUPPORT

This invention was made with government support under NS105156 awarded by the National Institutes of Health. The government has certain rights in the invention.

FIELD OF THE INVENTION

The present invention relates to compounds useful as inhibitors of phosphatidylinositol-3-phosphate 5-kinase (PIKfyve).

BACKGROUND OF THE INVENTION

Apilimod is recognized as a potent transcriptional inhibitor of IL-12 and IL-23. See Wada et al., Blood 109 (2007): 1156-1164. IL-12 and IL-23 are inflammatory cytokines normally produced by immune cells, such as B-cells and macrophages, in response to antigenic stimulation.

Autoimmune disorders and other disorders characterized by chronic inflammation are characterized in part by inappropriate production of these cytokines. In immune cells, the selective inhibition of IL-12/IL-23 transcription by apilimod was recently shown to be mediated by apilimod's direct binding to phosphatidylinositol-3-phosphate 5-kinase (PIKfyve). See Cai et al., *Chemistry and Biol.* 20 (2013): 912-921. PIKfyve plays a role in Toll-like receptor signaling, which is important in innate immunity.

Based upon its activity as an immunomodulatory agent and a specific inhibitor of IL-12/IL-23, apilimod has been proposed as useful in treating autoimmune and inflammatory diseases and disorders. See U.S. Pat. Nos. 6,858,606 and 6,660,733 (describing a family of pyrimidine compounds, including apilimod, purportedly useful for treating diseases and disorders characterized by IL-12 or IL-23 overproduction, such as rheumatoid arthritis, sepsis, Crohn's disease, multiple sclerosis, psoriasis, or insulin dependent diabetes mellitus). Similarly, apilimod was suggested to be useful for treating certain cancers based upon its activity to inhibit c-Rel or IL-12/23, particularly in cancers where these cytokines were believed to play a role in promoting aberrant cell proliferation. See WO 2006/128129 and Baird et al., Frontiers in Oncology 3:1 (2013, respectively). International Publication Nos. WO 2016/210372 and WO 2019/046316 and U.S. Patent Publication No. 2018/0161335, which are hereby incorporated by reference, disclose methods of treating a neurological disease such as amyotrophic lateral sclerosis with a PIKfyve kinase inhibitor.

SUMMARY OF THE INVENTION

In one aspect, the present invention is directed to a compound of the formula (I):

(I)

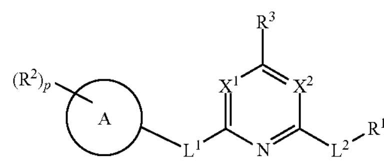

or a pharmaceutically acceptable salt thereof, wherein $R^1$ is hydroxy, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

each occurrence of $R^2$ is independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a nitrogen- or oxygen-containing moiety;

Ring A is (i) a 5 or 6-membered heteroaryl, a 5-6, 6-5 or 6-6 membered bicyclic heteroaryl, or a heterocyclyl, each having at least one nitrogen or oxygen ring atom, or (ii) phenyl;

$L^1$ is absent, $C_1$-$C_2$ alkylene, —$NR^c$—, —O—, —S—, —C(O)—, —NHC(O)—, —C(O)NH—, —$NR^cC(O)$—, or —$NR^cC(O)(CR^aR^b)_m$—;

$L^2$ is —O—, —O—$(CR^aR^b)_m$—, —$(CR^aR^b)_m$—, —$NR^c$—$(CR^aR^b)_m$—, or —S—$(CR^aR^b)_m$—;

(i) $X^1$ is CH or $CR^c$ and $X^2$ is N, or (ii) $X^1$ is N and $X^2$ is N, CH, or $CR^c$;

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

each occurrence of $R^c$ is independently a hydrogen or $C_{1-6}$ alkyl (e.g., $C_1$-$C_4$ alkyl);

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

each occurrence of m is independently 1-4; and p is 1 or 2, with the proviso that the compound of formula (I) possesses at least one of:

(i) Ring A is a 5-6, 6-5 or 6-6 membered bicyclic heteroaryl, or a heterocyclyl (such as a lactone or lactam), (ii) $L^1$ is —$NR^cC(O)$— or —$NR^cC(O)(CR^aR^b)_m$—, (iii) $L^2$ is —O—, or (iv) $X^2$ is CH or $CR^c$.

These compounds are useful as PIKfyve kinase inhibitors.

In one embodiment, $R^1$ is heterocyclyl or heteroaryl. For example, $R^1$ may be selected from (the squiggly lines indicate the point of attached to the rest of the molecule)

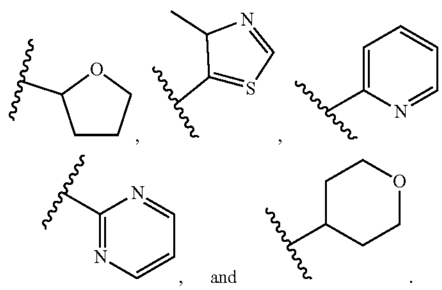

In another embodiment, $R^1$ is hydroxy.

In one embodiment, each occurrence of $R^2$ is independently substituted or unsubstituted aryl, such as a substituted or unsubstituted phenyl. For instance, $R^2$ may be phenyl, a halogen-substituted phenyl, an alkyl-substituted phenyl (e.g., a $C_{1-4}$ alkyl-substituted phenyl), a halogenated alkyl-substituted phenyl, or an alkoxy-substituted phenyl. In one embodiment, $R^2$ is selected from phenyl, 3-methoxyphenyl, 3-methylphenyl, 3-trifluoromethylphenyl, and 3-chlorophenyl. In a preferred embodiment, $R^2$ is selected from phenyl, 3-methoxyphenyl, and 3-methylphenyl.

In another embodiment, each occurrence of $R^2$ is independently substituted or unsubstituted alkyl (such as a $C_{1-4}$ alkyl). For instance, $R^2$ can be unsubstituted isopropyl.

In one embodiment, $R^3$ is a substituted or unsubstituted, saturated or unsaturated nitrogen- or oxygen-containing heterocyclyl. For instance, $R^3$ can be a substituted or unsubstituted, saturated or unsaturated 5-10 membered (such as a 5-8 membered) mono- or bi-cyclic heterocyclyl having at least one nitrogen or oxygen ring atom. In one embodiment, $R^3$ is a substituted or unsubstituted 5-10 membered (such as a 5-8 membered) mono- or bi-cyclic heterocyclyl having at least one nitrogen atom and optionally an oxygen ring atom, where the nitrogen ring atom is directly attached to the rest of the molecule. In one preferred embodiment, $R^3$ is a substituted or unsubstituted (unsaturated) 5-membered monocyclic heterocyclyl having an oxygen ring atom or a nitrogen ring atom.

In another embodiment, $R^3$ is a substituted or unsubstituted, saturated or unsaturated 6-membered monocyclic heterocyclyl having an oxygen ring atom and optionally a nitrogen ring atom. In yet another embodiment, $R^3$ is a saturated 8-membered bicyclic heterocyclyl having a nitrogen ring atom and an oxygen ring atom. In one embodiment, $R^3$ is selected from

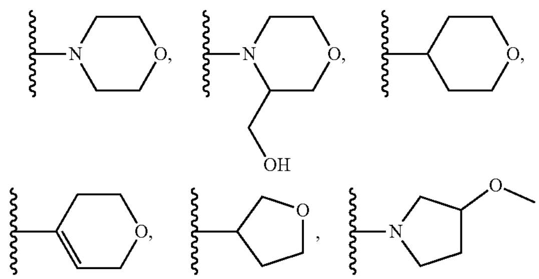

-continued

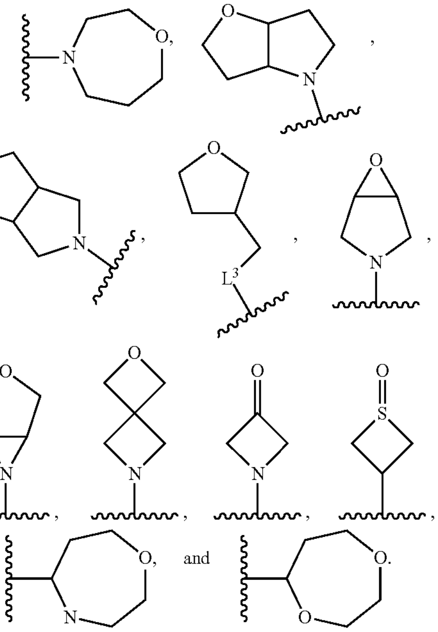

and

In one preferred embodiment, $R^3$ is selected from

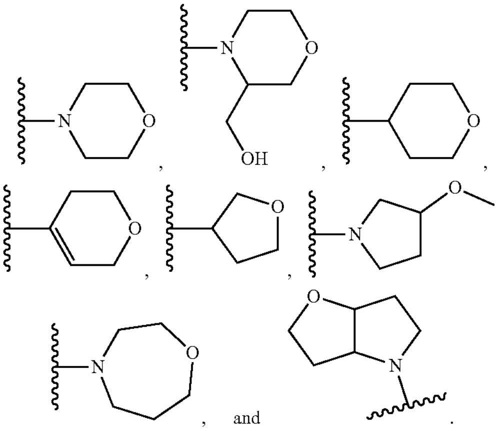

and

In another preferred embodiment, $R^3$ is

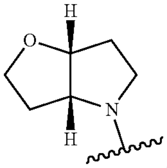

In yet another embodiment, $R^3$ is a sulfonyl group of the formula —$S(O)(CH_2)_qOR^4$, where $R^4$ is hydrogen or $C_1$-$C_4$ alkyl and q is 1-4.

In one embodiment, ring A is a 5-membered heteroaryl having at least one nitrogen ring atom. In one preferred embodiment, ring A includes two heteroatoms as ring atoms (such as two nitrogen ring atoms, or one nitrogen ring atom with one sulfur ring atom). In another preferred embodiment, ring A is selected from

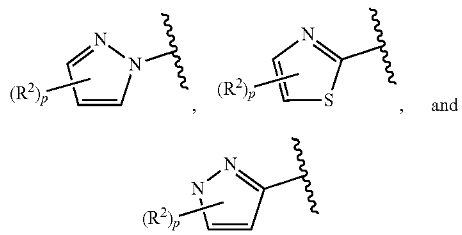

, , and .

For instance, ring A can be selected from

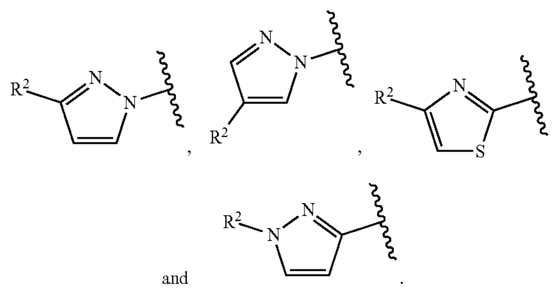

, , , and .

In one preferred embodiment, the $R^2$ group in ring A above is selected from substituted or unsubstituted aryl, such as a substituted or unsubstituted phenyl. For instance, $R^2$ may be phenyl, an alkyl-substituted, or an alkoxy-substituted phenyl. In a preferred embodiment, $R^2$ is selected from phenyl, 3-methoxyphenyl, and 3-methylphenyl.

In one embodiment, ring A is a heterocyclyl having at least one oxygen ring atom. In one preferred embodiment, the heterocyclyl is a lactone.

In one embodiment, ring A is a heterocyclyl having at least one nitrogen ring atom. In one preferred embodiment, the heterocyclyl is a lactam. In preferred embodiments, the lactam is a 5-membered lactam. In preferred embodiments, the 5-membered lactam is selected from

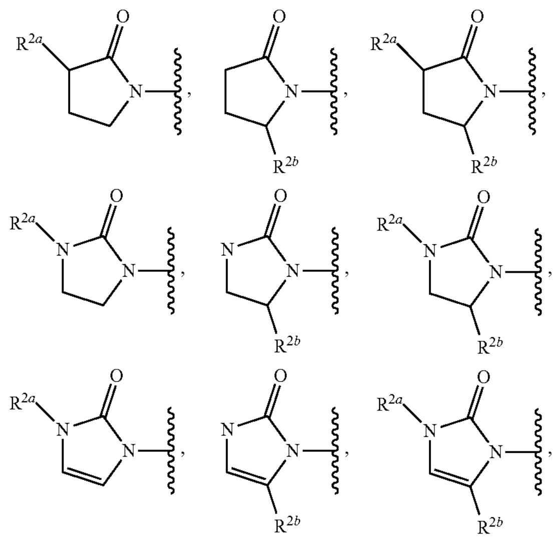

-continued

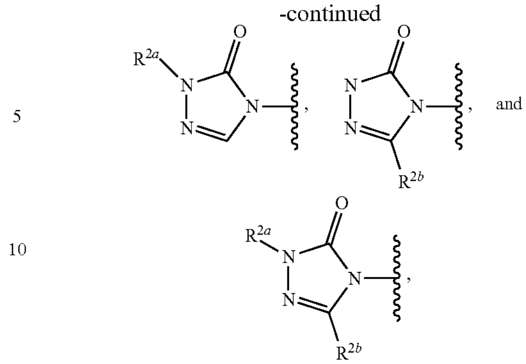

, , and , wherein each of $R^{2a}$ and $R^{2b}$ are independently selected from the $R^2$ groups listed above. In some instances, each of $R^{2a}$ and $R^{2b}$ are the same functional group. In some instances, $R^{2a}$ and $R^{2b}$ are different functional groups.

In one embodiment, $L^1$ is absent.

In another embodiment, $L^1$ is —NH—, —N($CH_3$)—, —O—, or —$CH_2$—. In one embodiment, $L^1$ is —NH—. In another embodiment, $L^1$ is —C(O)NH— (where the carbonyl is attached to the rest of the molecule and the nitrogen is attached to ring A). In yet another embodiment, $L^1$ is —NHC(O)— (where the nitrogen atom is attached to the rest of the molecule and the carbonyl is attached to ring A).

In one embodiment, $L^2$ is —O—$(CR^aR^b)_m$—. In one preferred embodiment, $L^2$ is —$OCH_2CH_2$— or —$OCH_2$—. In another embodiment, $L^2$ is —$OCH_2CH_2CH(OH)CH_2$—.

In another embodiment, $L^2$ is —$(CR^aR^b)_m$—. In one preferred embodiment, $L^2$ is —$CH_2CH_2$—.

In yet another embodiment, $L^2$ is —$NR^c$—$(CR^aR^b)_m$—, such as —NH—$(CR^aR^b)_m$— (e.g., —NH—, —$NHCH_2$—, and —$NHCH_2CH_2$—).

In one embodiment, -$L^2$-$R^1$ is —$OCH_2CH_2CH(OH)CH_2OH$.

In one preferred embodiment, $X^1$ is CH. In another embodiment, $X^1$ is N.

In one embodiment, each occurrence of $R^a$ and $R^b$ are independently hydrogen, hydroxy, or hydroxy($C_{1-4}$)alkyl. In another embodiment, each occurrence of $R^a$ and $R^b$ are independently hydrogen or hydroxy.

In one embodiment, m is 1. In another embodiment, m is 2. In a preferred embodiment, m is 1 or 2 when $R^1$ is cyclic. In another preferred embodiment, m is 3 or 4 when $R^1$ is acyclic.

In a preferred embodiment, p is 1.

In another embodiment, p is 2.

In one preferred embodiment, the moiety

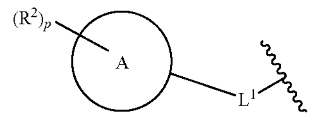

is selected from

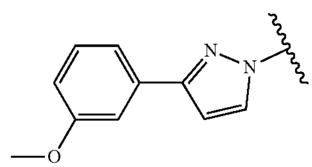

-continued

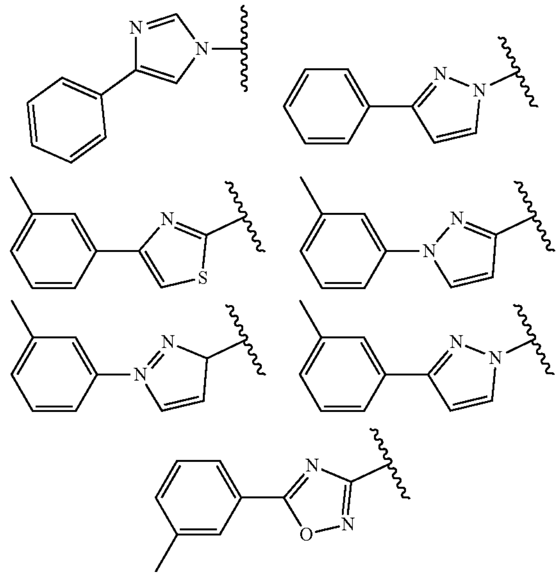

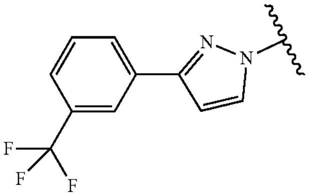

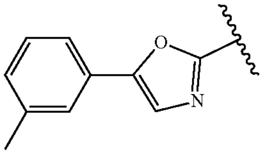

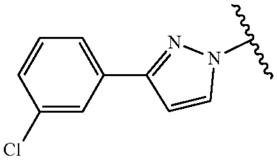

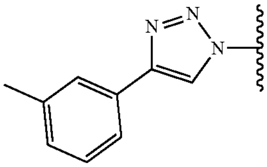

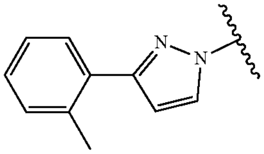

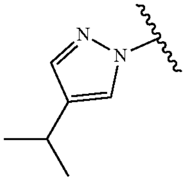

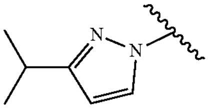

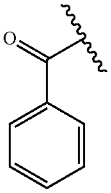

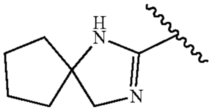

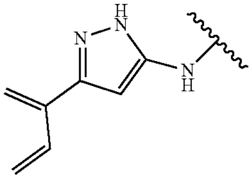

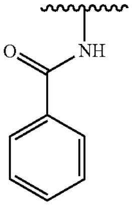

-continued

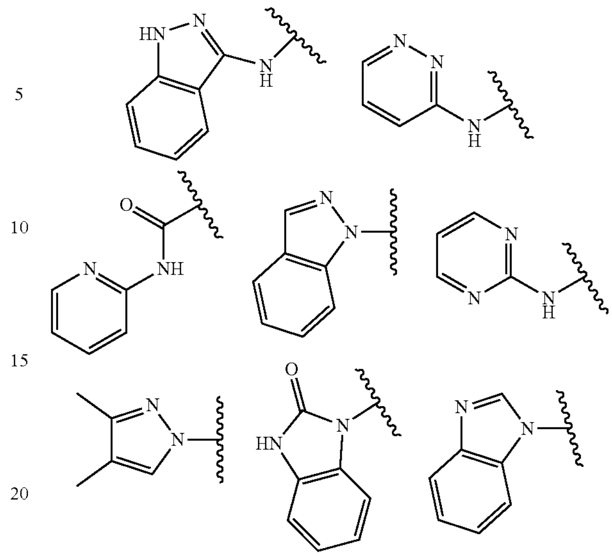

Another embodiment is a compound of the formula (II):

(II)

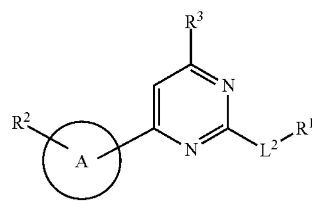

or a pharmaceutically acceptable salt thereof, wherein $R^1$ is hydrogen, hydroxy, substituted or unsubstituted heteroaryl, or substituted or unsubstituted heterocyclyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a substituted or unsubstituted oxygen-containing heterocyclyl;

Ring A is a 5-membered heteroaryl having at least one nitrogen ring atom, or a 5-membered heterocyclyl having at least one nitrogen ring atom or one oxygen ring atom (e.g., a lactam or lactone);

$L^2$ is absent, —O—$(CR^aR^b)_m$—, —O—, —$CH_2$—, —$CHR^a$—, —NH—, —$NR^a$—, —C(O)—, —NHC(O)—, —C(O)NH—, or a 5-membered heterocyclyl having at least one nitrogen ring atom or one oxygen ring atom (e.g., a lactam or lactone);

each occurrence of $R^a$ and $R^b$ are independently hydrogen, hydroxy, or hydroxy$(C_{1-4})$alkyl; and m is 1-4, with the proviso that the compound of the formula (II) possesses at least one of:

(i) Ring A is a 5-membered heterocyclyl having at least one nitrogen ring atom or one oxygen ring atom; and (ii) $L^2$ is —$CH_2$—, —$CHR^a$—, —NH—, —$NR^a$—, —C(O)—, —NHC(O)—, C(O)NH—, or a 5-membered heterocyclyl having at least one nitrogen ring atom or one oxygen ring atom.

In one embodiment of the compound of formula (II), $R^1$ is heterocyclyl or heteroaryl. For example, $R^1$ may be selected from

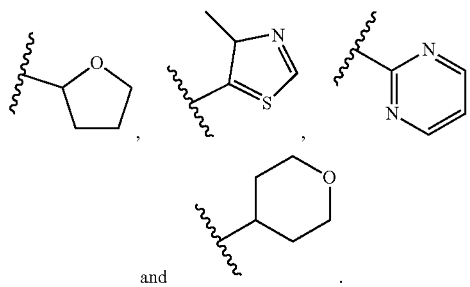

and

In one embodiment of the compound of formula (II), $R^2$ is substituted phenyl, such as an alkoxy-substituted phenyl, halogen-substituted phenyl, or alkyl-substituted phenyl. For example, $R^2$ can be methoxyphenyl (e.g., 3-methoxyphenyl) or methylphenyl (e.g., 3-methylphenyl).

In another embodiment of the compound of formula (II), $R^2$ is hydroxy.

In one preferred embodiment of the compound of formula (II), $R^3$ is selected from

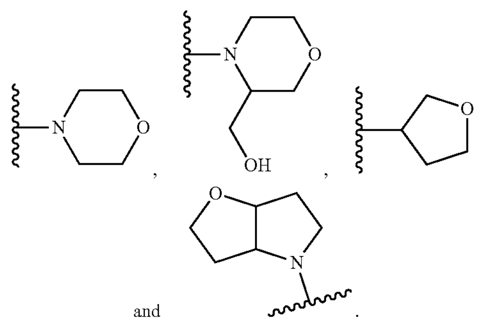

and

In another preferred embodiment, $R^3$ is

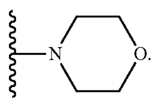

In another preferred embodiment, $R^3$ is

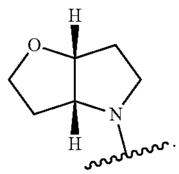 [SMILES: *N1CC[C@H]2OCC[C@H]21]

In one embodiment of the compound of formula (II), ring A is a 5-membered heteroaryl having (i) two nitrogen ring atoms or (ii) one nitrogen ring atom and one sulfur ring atom. In another embodiment, ring A is selected from

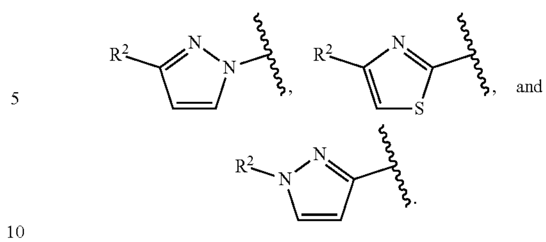

and

In another embodiment of the compound of formula (II), ring A is a 5-membered lactone.

In another embodiment of the compound of formula (II), ring A is a 5-membered lactam. In preferred embodiments, the 5-membered lactam is selected from

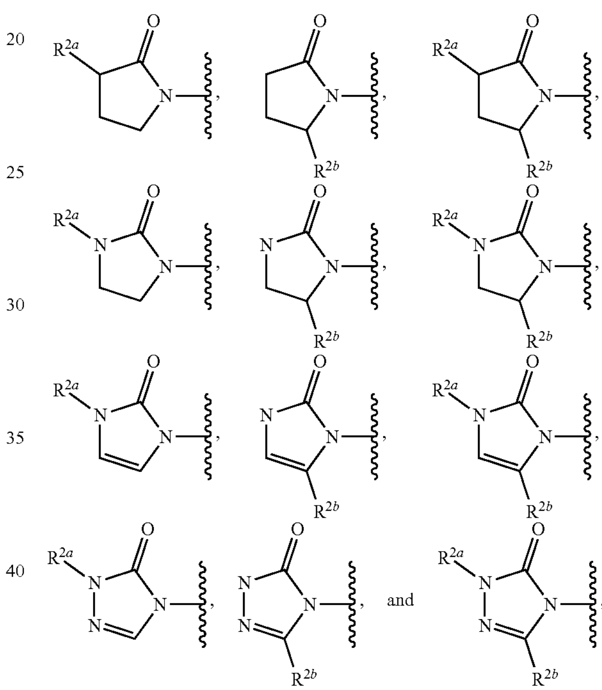

and wherein each of $R^{2a}$ and $R^{2b}$ are independently selected from the $R^2$ groups listed above. In some instances, each of $R^{2a}$ and $R^{2b}$ are the same functional group. In some instances, $R^{2a}$ and $R^{2b}$ are different functional groups.

In one embodiment of the compound of formula (II), $L^1$ is $—OCH_2—$, $—OCH_2CH_2—$, $—OCH_2CH_2CH(OH)CH_2—$, or $—CH_2CH_2—$. In one preferred embodiment, $L^2$ is $—OCH_2—$, $—OCH_2CH_2—$ or $—OCH_2CH_2CH(OH)CH_2—$.

In another embodiment of the compound of formula (II), $L^2$ is a 5-membered lactone. In another embodiment of the compound of formula (II), $L^2$ is a 5-membered lactam.

In yet another embodiment of the compound of formula (II), $L^2$ is $—CH_2—$, $—CHR^a—$, $—NH—$, $—NR^a—$, $—C(O)—$, $—NHC(O)—$, $—C(O)NH—$, or a 5-membered heterocyclyl having at least one nitrogen ring atom or one oxygen ring atom (e.g., a lactam or lactone).

Yet another embodiment is a compound of the formula (III):

(III)

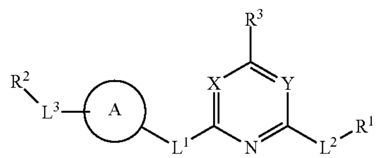

or a pharmaceutically acceptable salt thereof, wherein $R^1$ is hydroxy, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

$R^2$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a nitrogen- or oxygen-containing moiety;

$L^1$ is —$CH(CH_3)$—, —$CH_2CH(CH_3)$—, —$CH(CH_3)CH_2$—, —$N(CH_3)$—, —$N(CH_3)C(O)$—, $C(O)N(CH_3)$—, or —$N(CH_3)C(O)(CR^aR^b)_m$—;

$L^2$ is —O—$(CR^aR^b)_m$—, —$(CR^aR^b)_m$—, —$NR^c$—$(CR^aR^b)_m$—, or —S—$(CR^aR^b)_m$—, —$CH_2$—, —$CHR^a$—, —NH— —$NR^a$—, —C(O)—, —NHC(O)—, C(O)NH—, or a 5-membered heterocyclyl having at least one nitrogen ring atom or one oxygen ring atom;

$L^3$ is —O—$(CR^aR^b)_m$—, —$(CR^aR^b)_m$—, —$NR^c$—$(CR^aR^b)_m$—, or —S—$(CR^aR^b)_m$—, —$CH_2$—, —$CHR^a$—, —NH—, —$NR^a$—, —C(O)—, —NHC(O)—, C(O)NH—, or a 5-membered heterocyclyl having at least one nitrogen ring atom or one oxygen ring atom;

(i) X is CH or $CR^c$ and Y is N, or (ii) X is N and Y is N, CH, or $CR^c$;

Ring A is (i) a 5 or 6-membered heteroaryl, a 5-6, 6-5 or 6-6 membered bicyclic heteroaryl, or a heterocyclyl, each having at least one nitrogen or oxygen ring atom, or (ii) phenyl;

each occurrence of $R^a$ and $R^b$ are independently hydrogen, hydroxy, hydroxy$(C_{1-4})$alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

$R^c$ is a hydrogen or $C_{1-6}$ alkyl (e.g., $C_1$-$C_4$ alkyl);

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl; and each occurrence of m is independently 1-4.

In one preferred embodiment of the compound of formula (III), $R^3$ is selected from

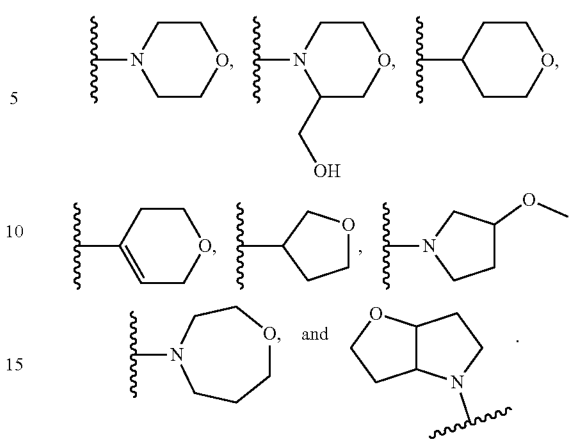

In another preferred embodiment, $R^3$ is

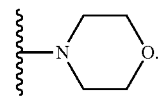

In another preferred embodiment, $R^3$ is

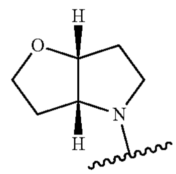

In yet another embodiment, $R^3$ is a sulfonyl group of the formula —$S(O)(CH_2)_qOR^4$, where $R^4$ is hydrogen or $C_1$-$C_4$ alkyl and q is 1-4.

In another embodiment of the compound of formula (III), $L^2$ is a 5-membered lactone.

In another embodiment of the compound of formula (III), $L^2$ is a 5-membered lactam.

In another embodiment of the compound of formula (III), $L^3$ is a 5-membered lactone.

In another embodiment of the compound of formula (III), $L^3$ is a 5-membered lactam.

In yet another embodiment, preferred $R^1$-$R^3$ $L^2$, and ring A groups are those presented above for formulae (I) and (II).

Yet another embodiment is a compound of one of formulae (IV)-(XII):

(IV)

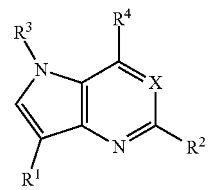

-continued (V)

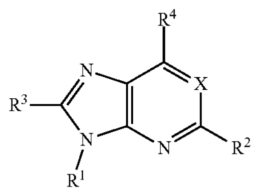

(VI)

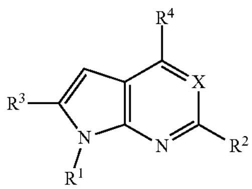

(VII)

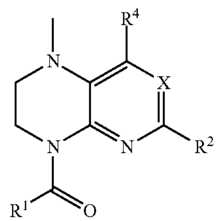

(VIII)

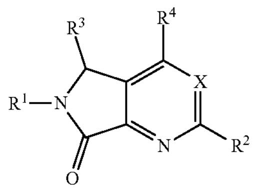

(IX)

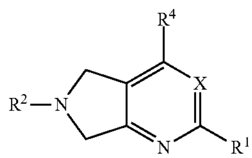

(X)

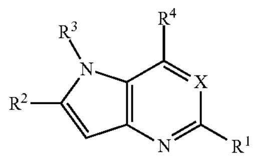

(XI)

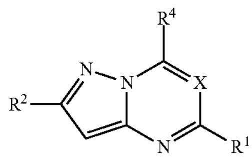

(XII)

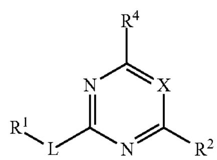

or a pharmaceutically acceptable salt thereof, wherein $R^1$, $R^2$, and $R^3$ are each independently hydrogen, hydroxy, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

$R^4$ is a substituted or unsubstituted nitrogen- and/or oxygen-containing heterocyclyl;

X is N, CH, or $CR^a$;

L is —$CH(CH_3)$—, —$CH_2CH(CH_3)$—, —$CH(CH_3)CH_2$—, —$N(CH_3)$—, —$N(R^c$—$N(R^c)_2)$—, —$N(CH_3)C(O)$—, $C(O)N(CH_3)$—, —$N(CH_3)C(O)(CR^aR^b)_m$—, $C_1$-$C_2$ alkylene, —$NR^c$—, —O—, —S—, —C(O)—, —NHC(O)—, —C(O)NH—, —$NR^cC(O)$—, —$NR^cC(O)(CR^aR^b)_m$—, —O—$(CR^aR^b)_m$—, —$(CR^aR^b)_m$—, —$NR^c$— $(CR^aR^b)_m$—, or —S—$(CR^aR^b)_m$—;

m is 1-4;

$R^a$ is hydrogen, hydroxy, hydroxy$(C_{1-4})$alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$, where $R^c$ is a hydrogen or $C_{1-6}$ alkyl (e.g., $C_1$-$C_4$ alkyl), and each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl.

In preferred embodiments of the compounds of formulae (IV)-(XII), $R^1$ is selected from

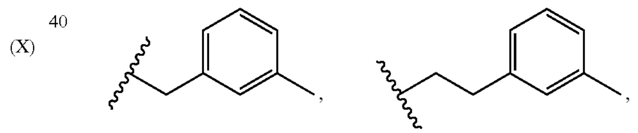

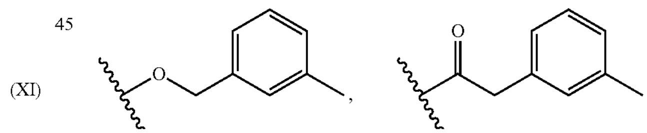

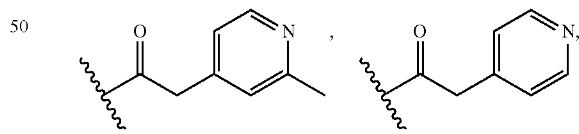

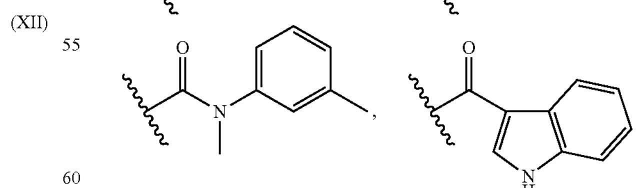

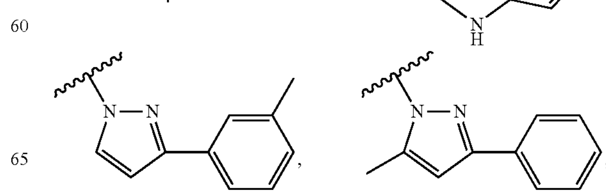

-continued

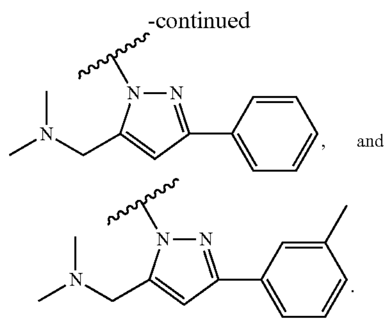

In preferred embodiments of the compounds of formulae (IV)-(XII), $R^2$ is selected from

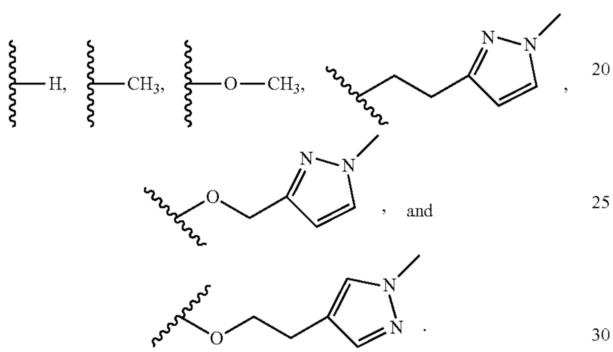

In preferred embodiments of the compounds of formulae (IV)-(XI), $R^3$ is selected from

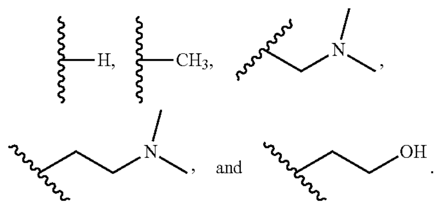

In some embodiments, $R^4$ is a substituted or unsubstituted, saturated or unsaturated nitrogen- or oxygen-containing heterocyclyl. For instance, $R^4$ can be a substituted or unsubstituted, saturated or unsaturated 5-10 membered (such as a 5-8 membered) mono- or bi-cyclic heterocyclyl having at least one nitrogen or oxygen ring atom. In some embodiments, $R^4$ is a substituted or unsubstituted 5-10 membered (such as a 5-8 membered) mono- or bi-cyclic heterocyclyl having at least one nitrogen atom and optionally an oxygen ring atom, where the nitrogen ring atom is directly attached to the rest of the molecule (the bicyclic core shown in one of formulae (IV)-(XI)). In some instances, $R^4$ is a substituted or unsubstituted (unsaturated) 5-membered monocyclic heterocyclyl having an oxygen ring atom or a nitrogen ring atom.

In some embodiments, $R^4$ is a substituted or unsubstituted, saturated or unsaturated 6-membered monocyclic heterocyclyl having an oxygen ring atom and optionally a nitrogen ring atom. In yet another embodiment, $R^4$ is a saturated 8-membered bicyclic heterocyclyl having a nitrogen ring atom and an oxygen ring atom. In some embodiments of the compounds of formulae (IV)-(XII), $R^4$ is selected from

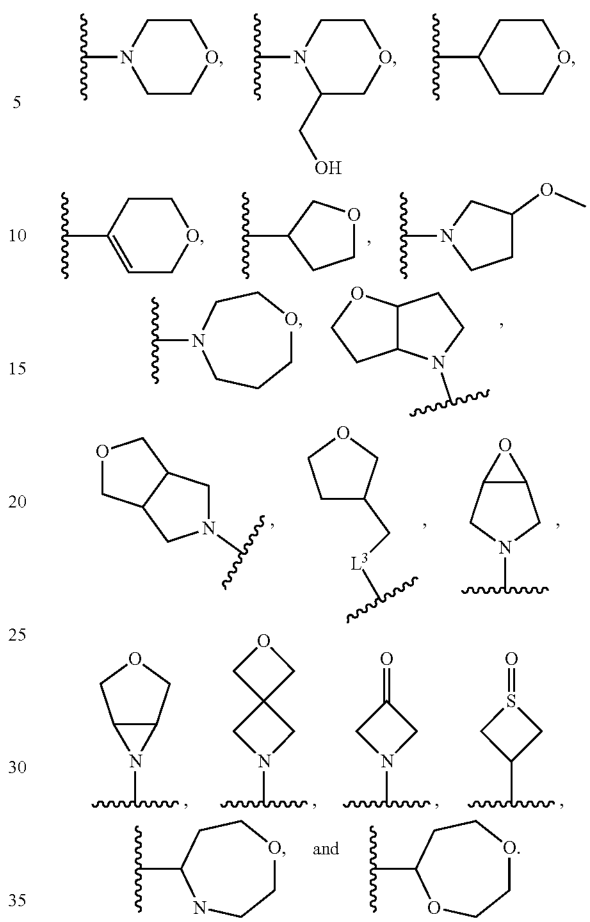

In preferred embodiments of the compounds of formulae (IV)-(XI), $R^4$ is selected from

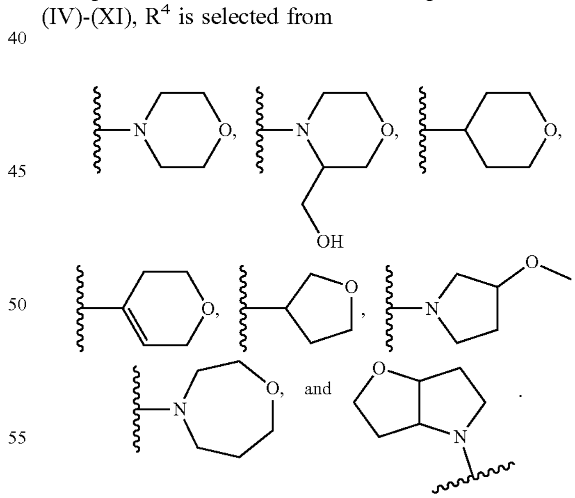

In another preferred embodiment, $R^4$ is

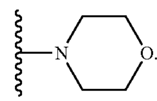 [SMILES: *N1CCOCC1]

In another preferred embodiment, $R^4$ is

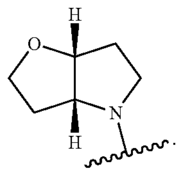 [SMILES: *N1CC[C@H]2OCC[C@H]21].

The variable $L^2$ in formulae II and III and ring A and $L^3$ in formula III can be a 5-membered lactam. The 5-membered lactam in each of these positions can be selected from:

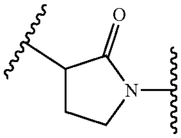, 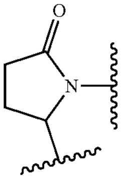, 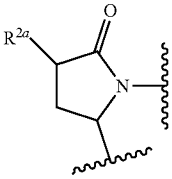, 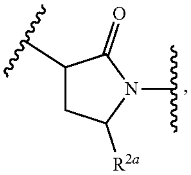, 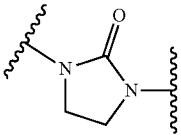, 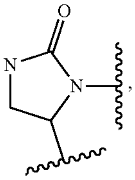, 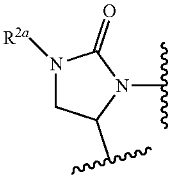, 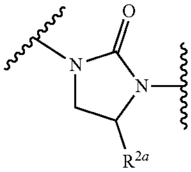, 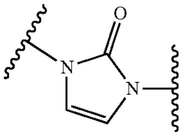, 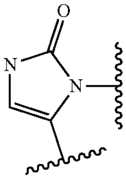, 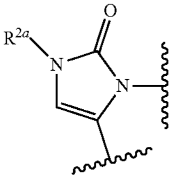, 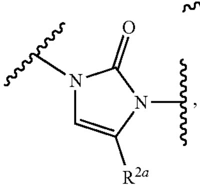, 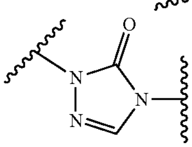, 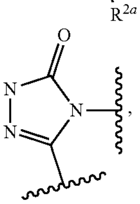, 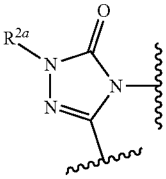, and 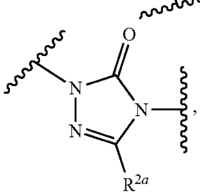, wherein each squiggly line represents a point of attachment to adjacent groups (e.g., when the lactam is at position $L^2$ in formula II, one squiggly line represents a point of attachment to the $R^1$ group and the other squiggly line represents a point of attachment to the central pyrimidine ring), and $R^{2a}$ is selected from the $R^2$ groups listed above.

Yet another embodiment is a compound of the formula (XIII):

(XIII)

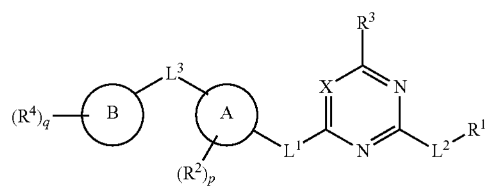

or a tautomer or pharmaceutically acceptable salt thereof, wherein $R^1$ is hydrogen, hydroxy, substituted or unsubstituted alkyl, substituted or unsubstituted alkenyl, substituted or unsubstituted alkynyl, substituted or unsubstituted alkoxy, substituted or unsubstituted amino, substituted or unsubstituted aryl, substituted or unsubstituted arylalkyl, substituted or unsubstituted heteroaryl, substituted or unsubstituted heteroarylalkyl, substituted or unsubstituted cycloalkyl, or substituted or unsubstituted heterocyclyl;

each occurrence of $R^2$ is, independently, hydrogen, nitro, cyano, hydroxyl, halogen, substituted or unsubstituted amino (e.g., —$NH_2$, —NHMe, —$NHMe_2$), substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy (e.g., —COOH, —COO($C_{1-6}$)alkyl), substituted or unsubstituted mercaptane, or substituted or unsubstituted heterocyclyl;

$R^3$ is a nitrogen- and/or oxygen-containing moiety (e.g., morpholine);

each occurrence of $R^4$ is, independently, hydrogen, nitro, hydroxyl, halogen, cyano, substituted or unsubstituted amino (e.g., —$NH_2$, —NHMe, —$NHMe_2$), substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy (e.g., —COOH, — COO($C_{1-6}$)alkyl), substituted or unsubstituted mercaptane, or substituted or unsubstituted heterocyclyl;

$L^1$ is absent, $C_1$-$C_4$ alkylene (e.g., $C_1$-$C_2$ alkylene), —$NR^c$—, —O—, —S—, —C(O)—, —$NR^c$C(O)—, —C(O)$NR^c$—, or —$NR^c$C(O)($CR^aR^b$)$_m$—;

$L^2$ is absent, —O—($CR^aR^b$)$_m$—, —O—($CR^aR^b$)$_m$—O—, —O—($CR^aR^b$)$_m$—ONR—, —O—($CR^aR^b$)$_m$—S—, —($CR^aR^b$)$_m$—, —$NR^c$—($CR^aR^b$)$_m$—, —S—($CR^aR^b$)$_m$—, —$CHR^a$—, —NH—, —$NR^a$—, —C(O)—, —$NR^c$C(O)—, $NR^c$C(O)— —($CR^aR^b$)$_m$—, C(O)$NR^c$—, —$NR^c$C(O)—($CR^aR^b$)$_m$—, or a 5-membered heterocyclyl having at least one nitrogen ring atom and/or one oxygen ring atom;

$L^3$ is absent, optionally substituted $C_1$-$C_7$ alkylene (e.g., optionally substituted $C_1$-$C_4$ or optionally substituted $C_1$-$C_4$ alkylene), —$NR^c$—, —O—, —S—, —C(O)—, —$NR^cC(O)$—, —$C(O)NR^c$—, —$NR^cC(O)$— or —$NR^cC(O)(CR^aR^b)_m$—;

X is N or $CR^c$ (e.g., CH);

Ring A is (i) a 5 or 6-membered heteroaryl (e.g., pyrazolyl, thiazolyl), a 5-6, 6-5 or 6-6 membered bicyclic heteroaryl (e.g., indazolyl), or a heterocyclyl, each having at least one nitrogen or oxygen ring atom, or (ii) aryl (e.g., phenyl);

Ring B is absent or (i) a 5 or 6-membered heteroaryl (e.g., pyridyl), a 5-6, 6-5 or 6-6 membered bicyclic heteroaryl (e.g., indole, azaindole, benzothiophene) or a heterocyclyl, each having at least one nitrogen, oxygen or sulfur ring atom, or (ii) aryl (e.g., phenyl);

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

$R^c$ is hydrogen or $C_{1-6}$ alkyl (e.g., $C_1$-$C_4$ alkyl, such as methyl);

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl; and each occurrence of m is independently 0, 1, 2, 3, 4, 5, 6 or 7 (such as 1, 2, 3, 4, 5, 6 or 7, such as 1, 2, 3 or 4, such as 1 or 2);

each occurrence of p is independently 0, 1, 2, 3 or 4, such as 0, 1 or 2; and q is 0, 1, or 2, such as 0 or 1.

In one embodiment of the compounds of formula (XIII), $R^1$ is hydroxy.

In one embodiment of the compounds of formula (XIII), $R^1$ is substituted or unsubstituted aryl, for example, substituted or unsubstituted phenyl.

In one embodiment of the compounds of formula (XIII), $R^1$ is substituted or unsubstituted heterocyclyl or heteroaryl.

For further example, $R^1$ may be selected from (the squiggly lines indicate the point of attached to the rest of the molecule)

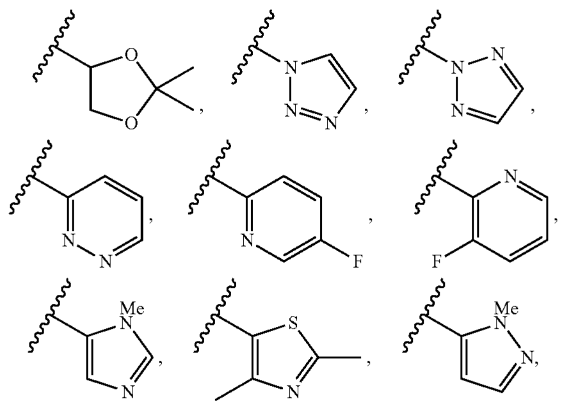

-continued

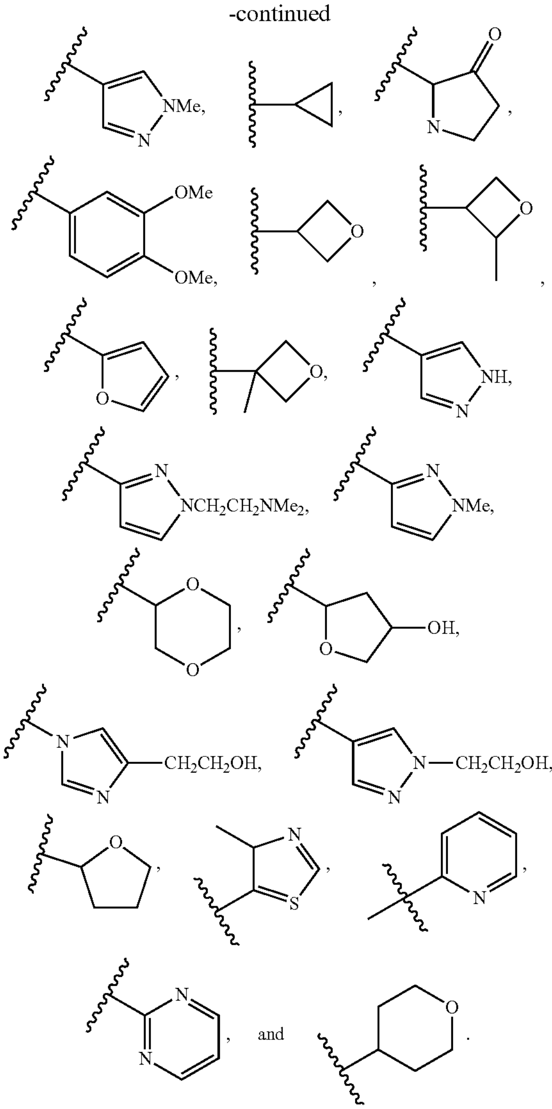

In another embodiment, $R^1$ is hydroxy. In another embodiment, $R^1$ is methoxy.

In another embodiment, $R^1$ is hydroxy or

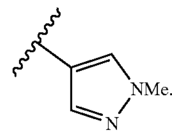 [SMILES: *c1cnn(C)c1]

In another embodiment, $L^1$ is absent. In another embodiment, $L^1$ is —$CH_2$— —NH—, —NMe-, —O—, or —S—. In another embodiment, $L^1$ is —O—. In another embodiment, $L^1$ is absent or —O—.

In another embodiment, $L^2$ is absent or —O—$(CR^aR^b)_m$—. In one embodiment, $L^2$ is —$OCH_2CH_2$— or —$OCH_2$—. In another embodiment, $L^2$ is —$OCH_2CH_2CH(OH)CH_2$—.

In another embodiment, $L^2$ is —$(CR^aR^b)_m$—. In one embodiment, $L^2$ is —$CH_2CH_2$—. In another embodiment, $L^2$ is —CH(OH)—$CH_2$—. In another embodiment, $L^2$ is —CH(OMe)-$CH_2$—.

In yet another embodiment, $L^2$ is $-NR^c-(CR^aR^b)_m-$, such as $-NH-(CR^aR^b)_m-$ (e.g., $-NH-$, $-NHCH_2-$, and $-NHCH_2CH_2-$).

In one embodiment, $-L^2-R^1$ is $-OCH_2CH_2CH(OH)CH_2OH$.

In another embodiment, $-L^2-R^1$ is $-OCH(CH_2OH)(OCH_3)$.

In one preferred embodiment, X is CH. In another embodiment, X is N.

In one embodiment, Ring A is a 5-membered heteroaryl (e.g., pyrazolyl, thiazolyl).

In one embodiment, Ring A is a 5-6, 6-5 or 6-6 membered bicyclic heteroaryl (e.g., indazolyl).

In one embodiment, Ring A is unsubstituted. In another embodiment, Ring A is substituted at the ortho-position. For example, in one embodiment, p is 1 and substituent $R^2$ attached to Ring A is selected from hydroxyl, substituted or unsubstituted alkyl (e.g., methyl, ethyl, propyl, $-CH(Me)(OH)$, $-CH_2$(morpholine), $-CH_2OH$, $-CH_2NMe_2$), substituted or unsubstituted alkoxy (e.g., methoxy), substituted or unsubstituted aryl (e.g., phenyl), substituted or unsubstituted heterocyclyl (e.g., morpholine), substituted or unsubstituted cycloalkyl (e.g., cyclopropyl).

In one embodiment, Ring A is unsubstituted pyrazole.

In one embodiment, Ring B is a 5 or 6-membered heteroaryl (e.g., pyridinyl).

In another embodiment, Ring B is a 5-6, 6-5 or 6-6 membered bicyclic heteroaryl (e.g., indole, azaindole, or benzothiophene).

In another embodiment, Ring B is aryl (e.g., phenyl or (3-methyl)phenyl).

In another embodiment, Ring B is heterocyclyl (e.g., 3,4-dihydro-2H-benzo[b][1,4]oxazine).

In one embodiment, Ring B is unsubstituted. In one embodiment, Ring B is mono-substituted (q=1). In one embodiment, Ring B is di-substituted (q=2).

In another embodiment, Ring B is substituted at the meta-position.

For example, in one embodiment, substituent $R^4$ attached to Ring B is selected from one or more of hydroxy, cyano, halogen (e.g., F, Cl), substituted or unsubstituted alkyl (e.g., methyl, isobutyl, trifluromethyl, $-CH_2OH-CH_2OMe$, $-CH(Me)OCH_3$), substituted or unsubstituted alkoxy (e.g., methoxy).

In one embodiment of the compounds of formula (XIII), $R^3$ is a substituted or unsubstituted, saturated or unsaturated nitrogen- and/or oxygen-containing heterocyclyl. For instance, $R^3$ can be a substituted or unsubstituted, saturated or unsaturated 5-10 membered (such as a 5-8 membered, such as 6-membered) mono- or bi-cyclic heterocyclyl having at least one nitrogen or oxygen ring atom. In one embodiment, $R^3$ is a substituted or unsubstituted 5-10 membered (such as a 5-8 membered, such as 6-membered) mono- or bi-cyclic heterocyclyl having at least one nitrogen atom and optionally an oxygen ring atom, where the nitrogen ring atom is directly attached to the rest of the molecule. In one preferred embodiment, $R^3$ is a substituted or unsubstituted (unsaturated) 5 or 6-membered monocyclic heterocyclyl having an oxygen ring atom and/or a nitrogen ring atom.

In another embodiment, $R^3$ is a substituted or unsubstituted, saturated or unsaturated 6-membered monocyclic heterocyclyl having an oxygen ring atom and optionally a nitrogen ring atom. In yet another embodiment, $R^3$ is a saturated 8-membered bicyclic heterocyclyl having a nitrogen ring atom and an oxygen ring atom.

In one embodiment, $R^3$ is selected from

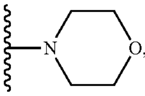, 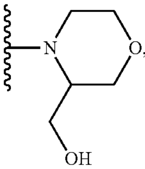, 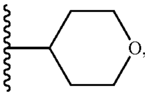, 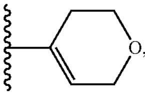, 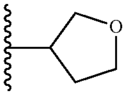, 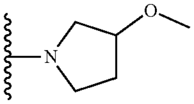, 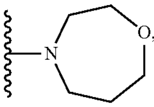, 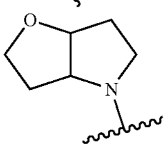, 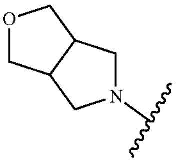, 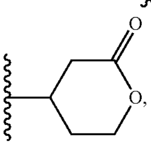, 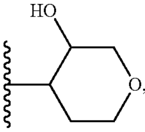, 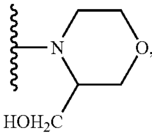, 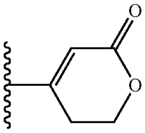, 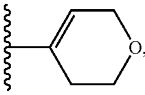, 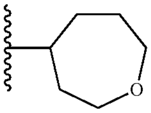, 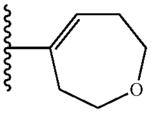, 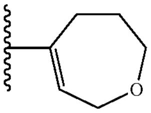, 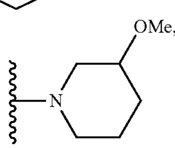, 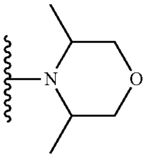, 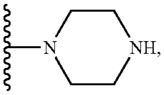, 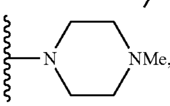, 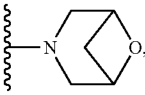, 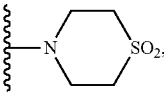, 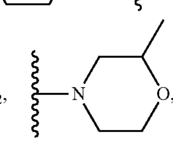, 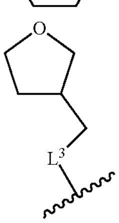, 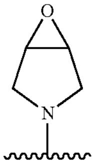, 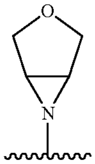, 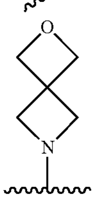, 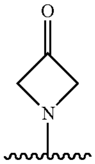, 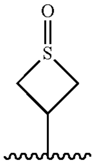, 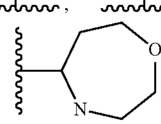 and 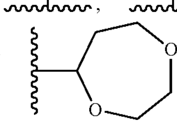.

In one preferred embodiment, $R^3$ is selected from

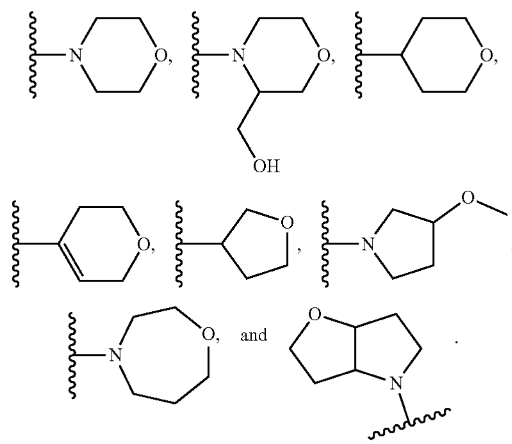

In yet another embodiment, $R^3$ is a sulfonyl group of the formula $—S(O)_2(CH_2)_qOR^4$, where $R^4$ is hydrogen or $C_1$-$C_4$ alkyl and q is 1-4.

In one preferred embodiment of the compound of formula (XIII), $R^3$ is selected from

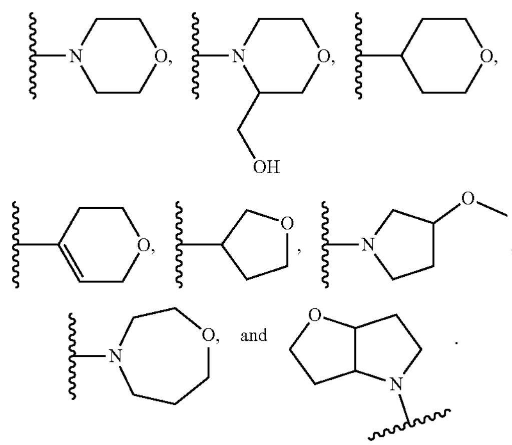

In another preferred embodiment, $R^3$ is

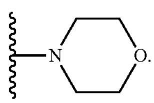 [SMILES: *N1CCOCC1]

In another preferred embodiment, $R^3$ is

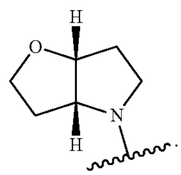 [SMILES: *N1CC[C@H]2OCC[C@H]21]

In a preferred embodiment, the moiety

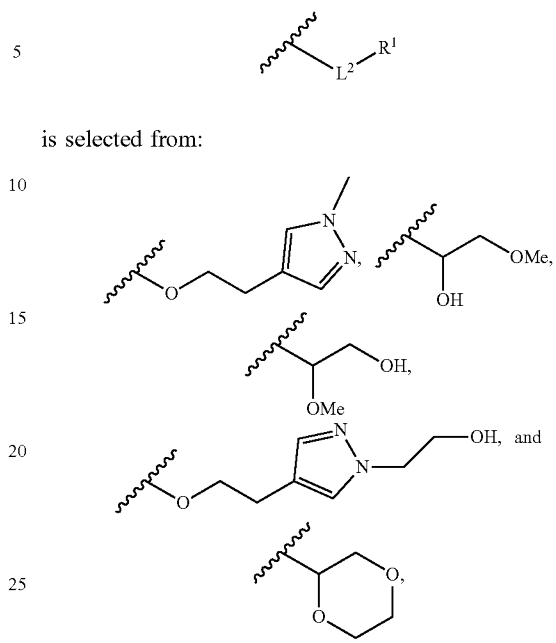

is selected from:

wherein each squiggly line represents the point of attachment to the adjacent group.

In a preferred embodiment, the moiety

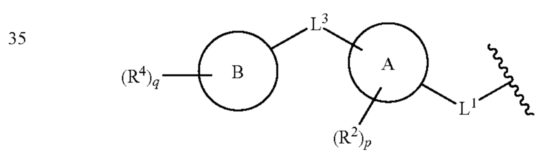

is selected from:

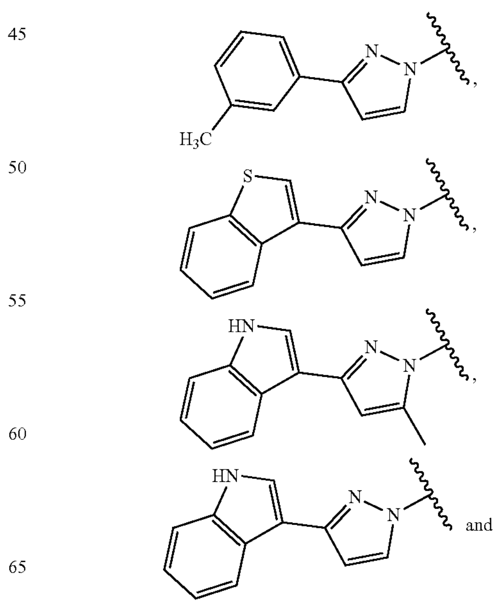

-continued

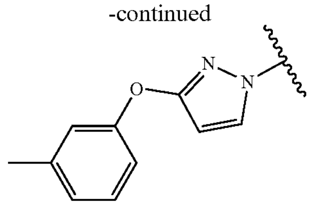

wherein each squiggly line represents the point of attachment to the adjacent group.

In yet another embodiment of the compounds of formula (XIII), one or more of criteria (i), (ii), (iii) and/or (iv) apply:

(i) A is selected from

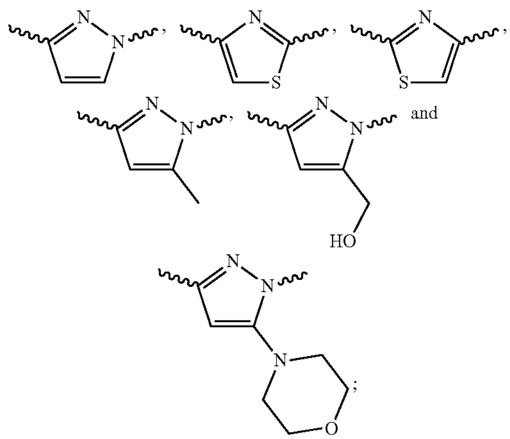

(ii) B is selected from

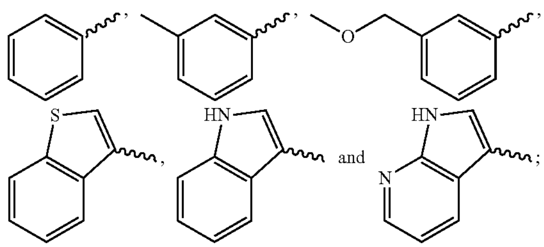

(iii) $R^3$ is

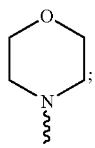

iv) $R^1$ is selected from

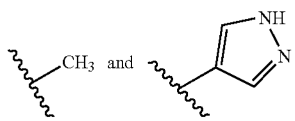

wherein each squiggly line represents the point of attachment to the adjacent group(s).

Yet another embodiment is a compound of the formula (XIII-A):

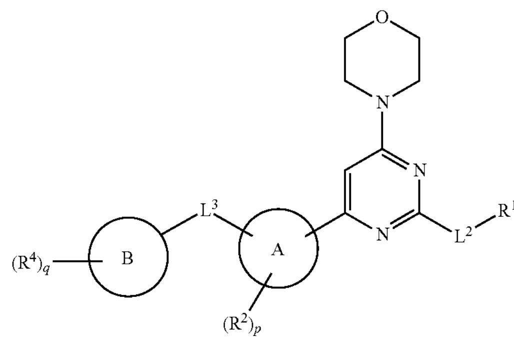

or a tautomer or pharmaceutically acceptable salt thereof, wherein

Ring A is a 5 or 6-membered heteroaryl (e.g., pyrazolyl or thiazolyl), a 5-6, 6-5 or 6-6 membered bicyclic heteroaryl (e.g., indazolyl), or a heterocyclyl, each having at least one nitrogen or oxygen ring atom;

Ring B is (i) a 5 or 6-membered heteroaryl (e.g., pyridyl), a 5-6, 6-5 or 6-6 membered bicyclic heteroaryl (e.g., indole, azaindole, benzothiophene) or a heterocyclyl, each having at least one nitrogen, oxygen or sulfur ring atom, or (ii) aryl (e.g., phenyl);

$R^1$ is hydrogen, hydroxy, nitro, cyano, substituted or unsubstituted alkyl, substituted or unsubstituted alkenyl, substituted or unsubstituted alkynyl, substituted or unsubstituted alkoxy, substituted or unsubstituted amino, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted carboxy (e.g., —COOH, —COO($C_{1-6}$) alkyl, substituted or unsubstituted mercaptane, or substituted or unsubstituted heterocyclyl;

each occurrence of $R^2$ is, independently, hydrogen, nitro, cyano, hydroxyl, halogen, substituted or unsubstituted amino (e.g., —$NH_2$, —NHMe, —$NHMe_2$), substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy (e.g., —COOH, —COO($C_{1-6}$)alkyl, substituted or unsubstituted mercaptane, or substituted or unsubstituted heterocyclyl;

each occurrence of $R^4$ is, independently, hydroxyl, halogen, cyano, substituted or unsubstituted amino (e.g., —$NH_2$, —NHMe, —$NHMe_2$), substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

$L^2$ is absent, —O—$(CR^aR^b)_m$—, —O—$(CR^aR^b)_m$—O—, —O—$(CR^aR^b)_m$—ONR—, —O—$(CR^aR^b)_m$—S—, —$(CR^aR^b)_m$—, —$NR^c$—$(CR^aR^b)_m$—, —S—$(CR^aR^b)_m$—, —$CHR^a$—, —NH—, —$NR^a$—, —C(O)—, —$NR^c$C(O)—, $NR^c$C(O)— —$(CR^aR^b)_m$—, C(O)

$NR^c$—, —$NR^cC(O)$—$(CR^aR^b)_m$—, or a 5-membered heterocyclyl having at least one nitrogen ring atom and/or one oxygen ring atom;

$L^3$ is absent, optionally substituted $C_1$-$C_7$ alkylene (e.g., optionally substituted $C_1$-$C_4$ or optionally substituted $C_1$-$C_4$ alkylene), —$NR^c$—, —O—, —S—, —C(O)—, —$NR^cC(O)$—, —$C(O)NR^c$—, —$NR^cC(O)$— or —$NR^cC(O)(CR^aR^b)_m$—;

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —SC(O)$R^d$, OC(S)$R^d$, SC(S)$R^d$, —$NR^cC(O)R^d$, —$NR^cC(S)R^d$, —$SO_2R^c$, —$S(O)R^c$, —$NR^cSO_2R^d$, —$OS(O)_2R^d$, —$OP(O)R^dR^e$, or —$P(O)R^dR^e$;

$R^c$ is hydrogen or $C_{1-6}$ alkyl (e.g., $C_1$-$C_4$ alkyl, such as methyl);

each occurrence of $R^d$ and $R^e$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl; and each occurrence of m is independently 0, 1, 2, 3, 4, 5, 6 or 7 (such as 1, 2, 3, 4, 5, 6 or 7, such as 1, 2, 3 or 4, such as 1 or 2); and each occurrence of p is independently 0, 1, 2, 3 or 4, such as 0 or 1.

q is 0, 1, or 2, such as 0 or 1.

Yet another embodiment is a compound of the formula (XIV):

(XIV)

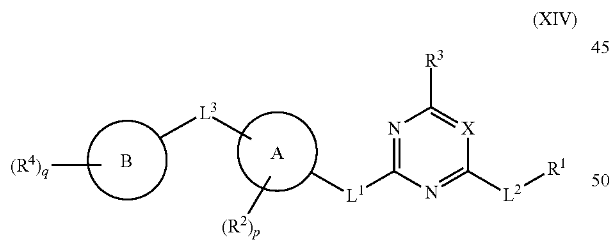

or a tautomer or pharmaceutically acceptable salt thereof, wherein the variables (including X, $R^1$, $R^2$, $R^3$, $R^4$, $L^1$, $L^2$, $L^3$, p, q, Ring A and Ring B) are the same as any of the embodiments described above for compounds of formula (XIII).

In a preferred embodiment, the moiety

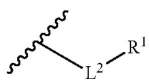

is selected from:

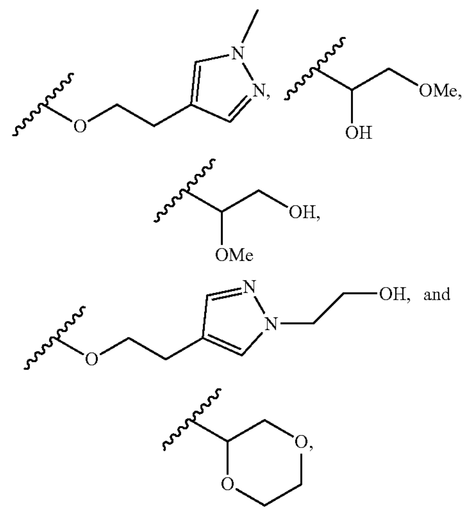

wherein each squiggly line represents the point of attachment to the adjacent group.

In a preferred embodiment, the moiety

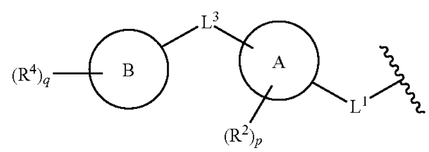

is selected from:

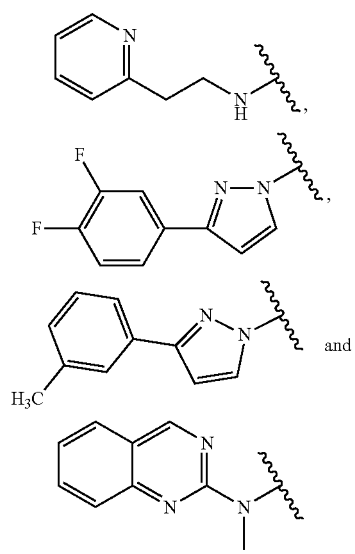

wherein each squiggly line represents the point of attachment to the adjacent group.

Yet another embodiment is a compound of the formula (XV):

(XV)

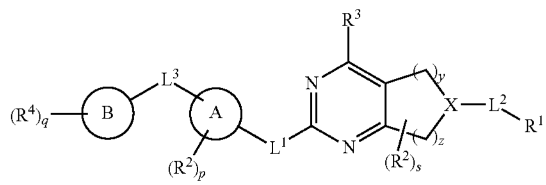

or a tautomer or pharmaceutically acceptable salt thereof, wherein wherein variables X, $R^1$, $R^2$, $R^3$, $R^4$, $L^1$, $L^2$, $L^3$, p, q, Ring A and Ring B are the same as any of the embodiments described above for compounds of formula (XIII);

y is 1 or 2 (e.g., 1);

z is 1 or 2 (e.g., 1); and s is 0, 1, 2, 3 or 4 (e.g., 0, 1 or 2).

In a preferred embodiment, the moiety

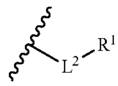

is selected from:

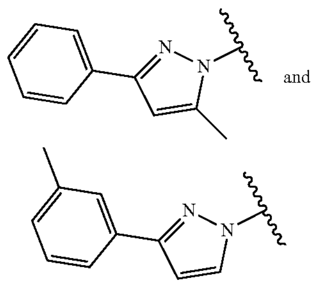

and wherein each squiggly line represents the point of attachment to the adjacent group.

In a preferred embodiment, the moiety

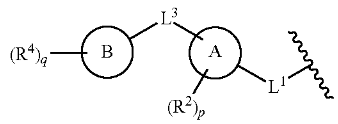

is selected from:

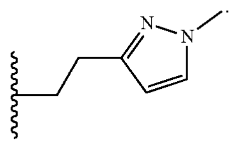 [SMILES: *CCc1ccn(C)n1]

wherein each squiggly line represents the point of attachment to the adjacent group.

In another preferred embodiment, the moiety

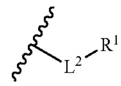

is selected from:

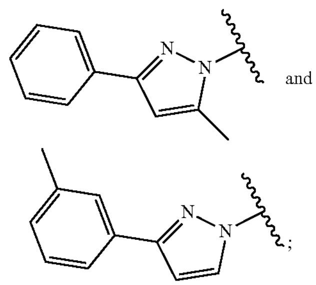

and

;

and the moiety

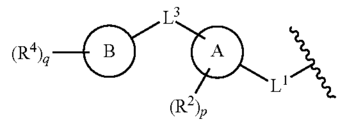

is selected from:

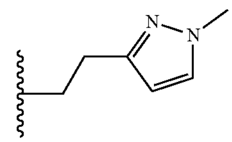

wherein each squiggly line represents the point of attachment to the adjacent group.

Yet another embodiment is a compound of the formula (XVI):

(XVI)

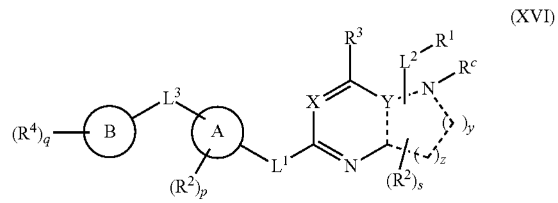

or a tautomer or pharmaceutically acceptable salt thereof, wherein wherein variables X, $R^1$, $R^2$, $R^3$, $R^4$, $L^1$, $L^2$, $L^3$, p, q, Ring A and Ring B are the same as any of the embodiments described above for compounds of formula (XIII);

Y is C or N;

$R^c$ is absent, hydrogen or $C_{1-6}$ alkyl (e.g., $C_1$-$C_4$ alkyl, such as methyl);

each ----- is, independently, a single or double bond, with the proviso that a maximum of two ---- are double bonds;

y is 1, 2 or 3 (e.g., 1 or 2, such as 1);

z is 1, 2 or 3 (e.g., 1 or 2, such as 1); and s is 0, 1, 2, 3 or 4 (e.g., 0, 1 or 2).

In one embodiment, the compound of formula (XVI) is of formula (XVI-A), (XVI-B) or (XVI-C):

(XVI-A)

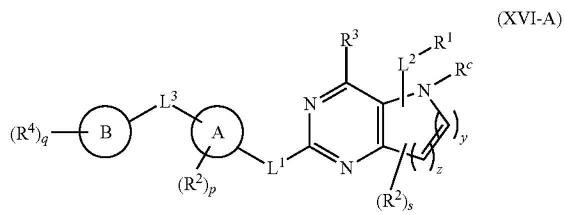

(XVI-B)

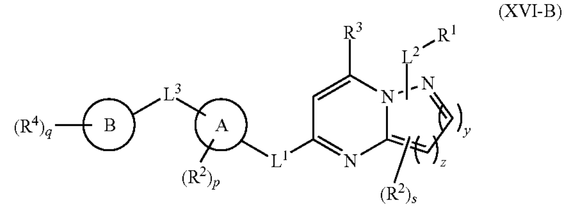

(XVI-C)

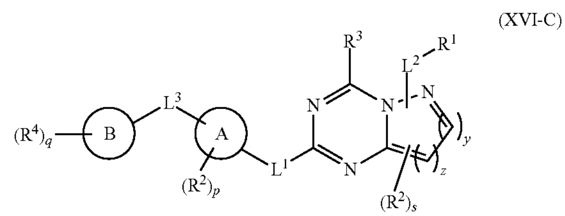

or a tautomer or pharmaceutically acceptable salt thereof, wherein the variables (including X, $R^1$, $R^2$, $R^3$, $R^4$, $R^c$, $L^1$, $L^2$, p, q, s, y, z, Ring A and Ring B) are the same as any of the embodiments described above for compounds of formula (XVI).

In a preferred embodiment, the moiety

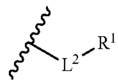

is hydrogen (i.e., $L^2$ is absent and $R^1$ is hydrogen)

In a preferred embodiment, the moiety

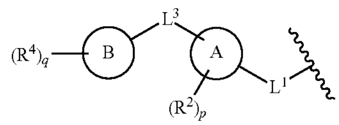

is selected from:

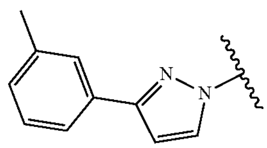

-continued

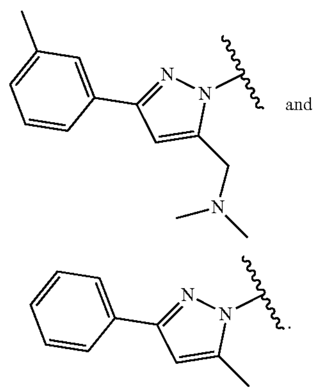

wherein each squiggly line represents the point of attachment to the adjacent group.

In another preferred embodiment, s is 1 and $R^2$ is methyl.

Yet another embodiment is a compound of the formula (XVIII):

(XVII)

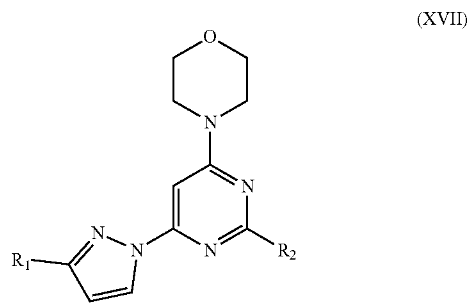

or a tautomer or pharmaceutically acceptable salt thereof, wherein $R^1$ is selected from

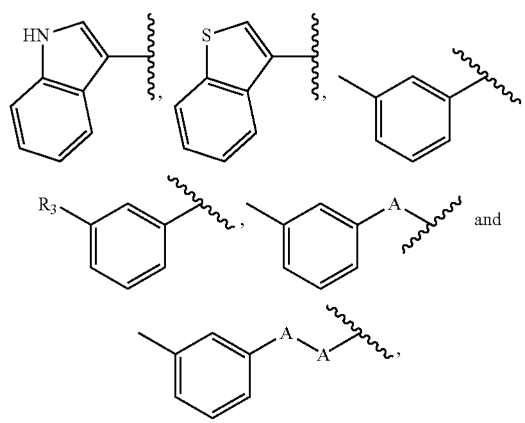

wherein $R^3$ is $C_{1-6}$ alkyl (e.g., $C_{1-4}$ alkyl), optionally containing one or more heteroatoms (e.g., 0, S, NH, or N($C_{1-4}$ alkyl)), and A is selected from —$CH_2$—, —CHMe-, —C($Me_2$)-, —O—, —S—, —NH—, and —N($C_{1-4}$ alkyl)-; and $R^2$ is selected from
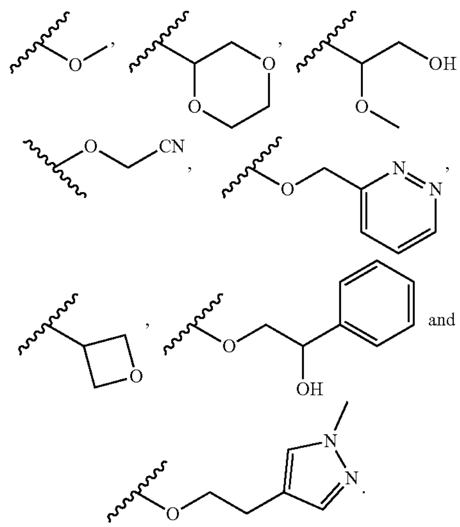
wherein each squiggly line represents the point of attachment to the adjacent group.
Exemplary compounds of the present include those listed below, and tautomers and pharmaceutically salts thereof.
1
2
3
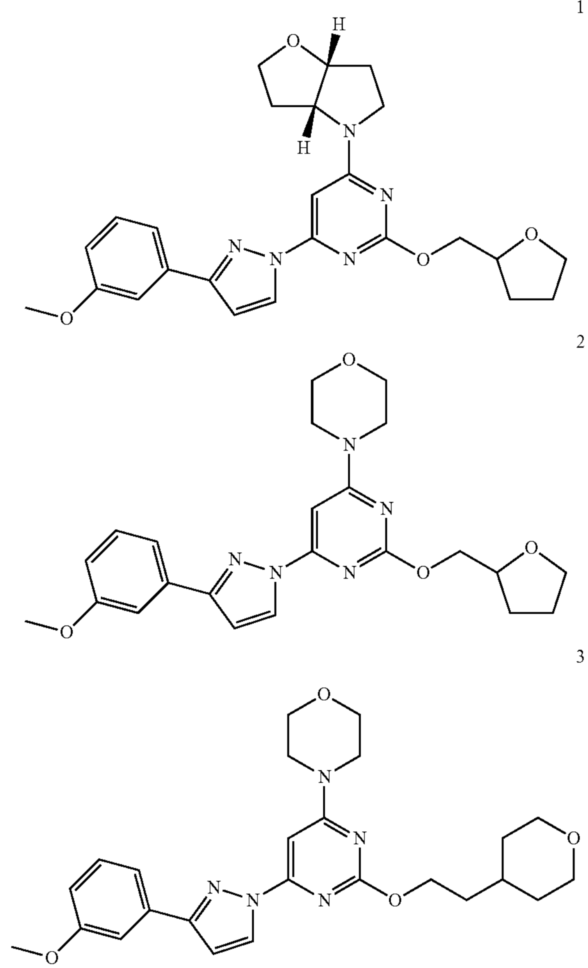
-continued
4
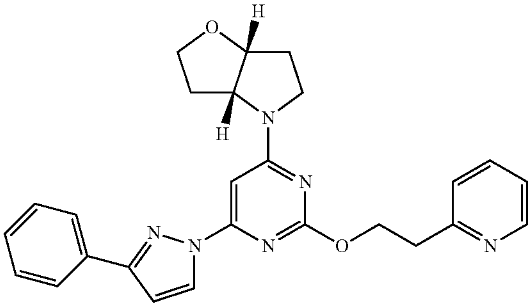
5
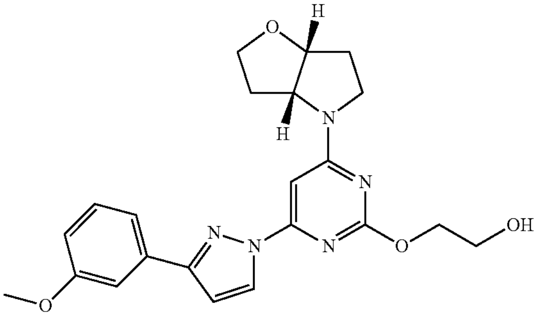
6
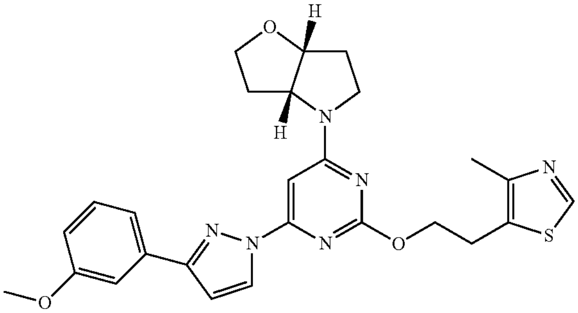
7
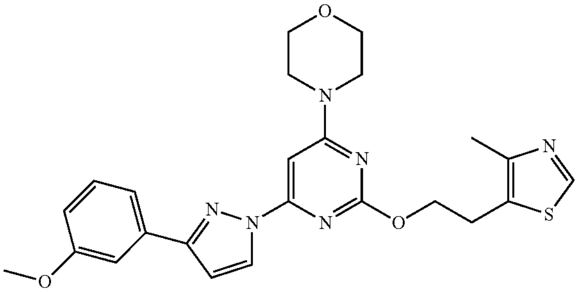

-continued
8
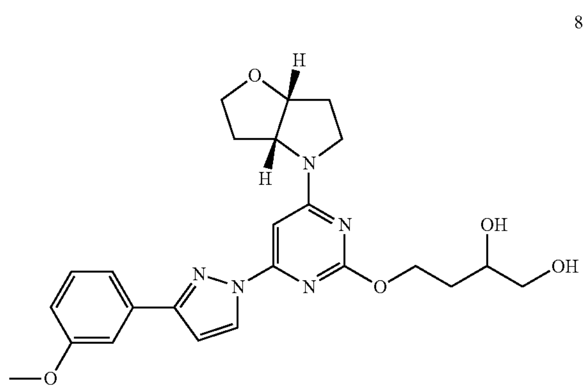
9
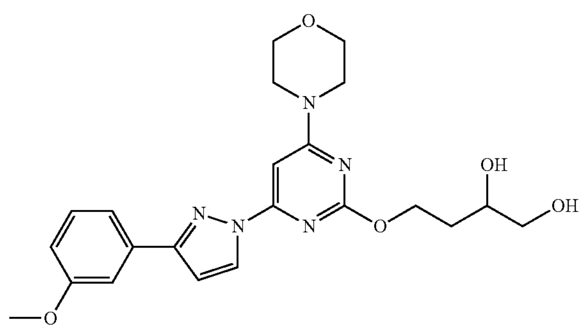
10
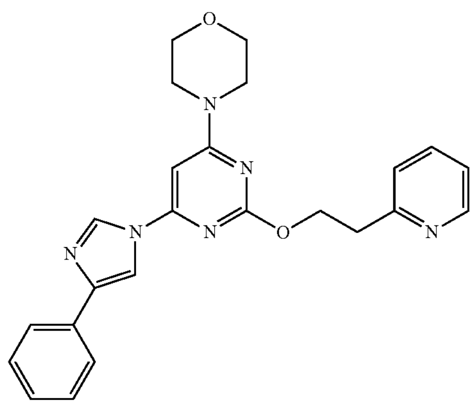
11
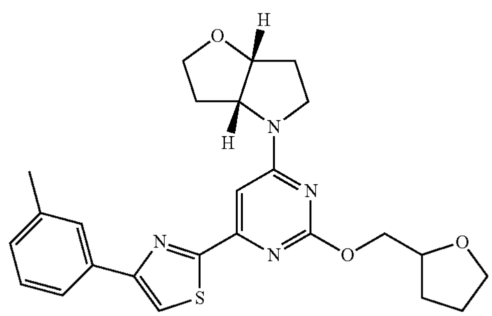
-continued
12
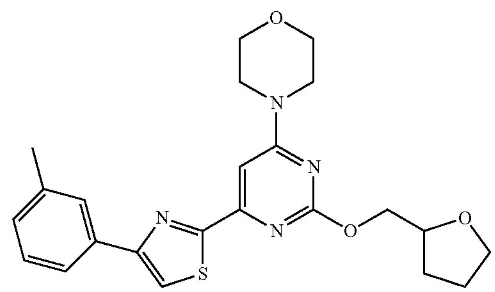
13
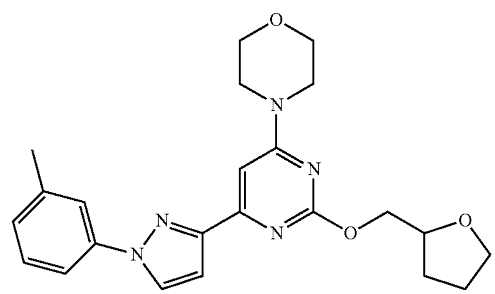
14
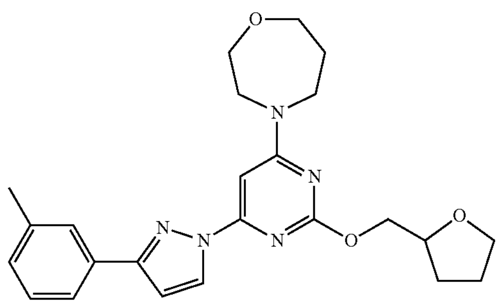
15
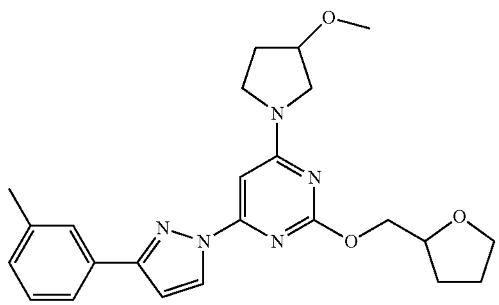
16
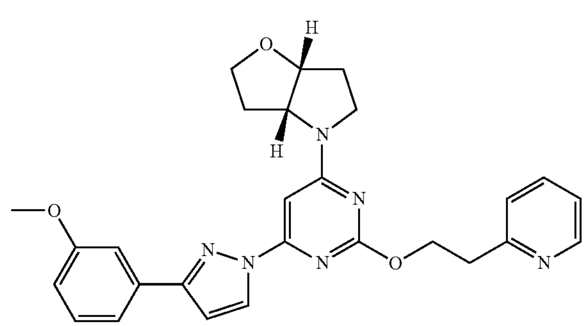

17
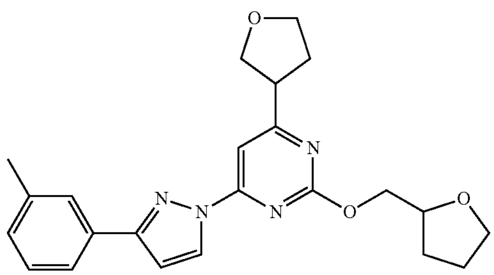
18
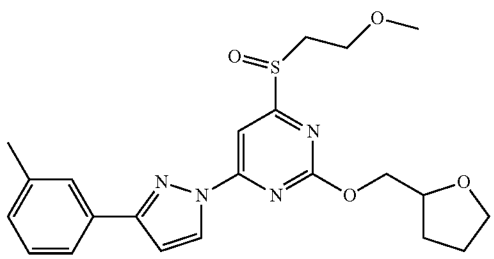
19
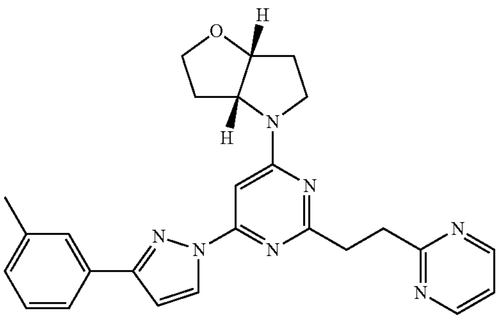
20
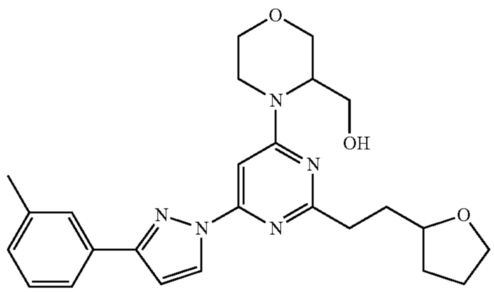
21
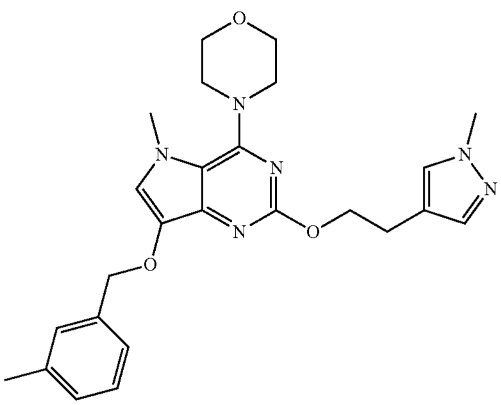
22
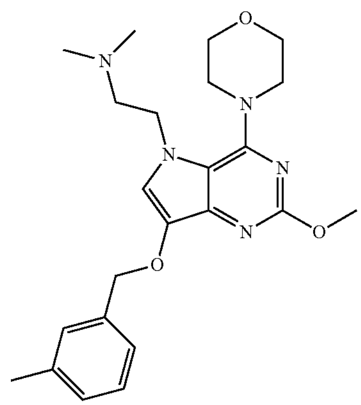
23
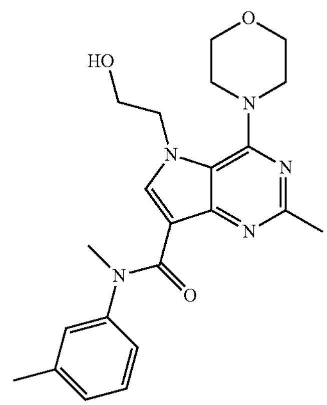
24
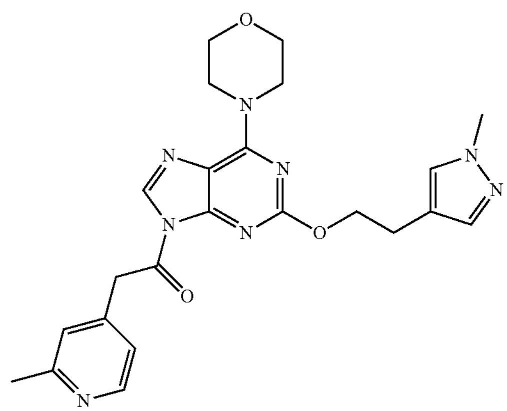
25
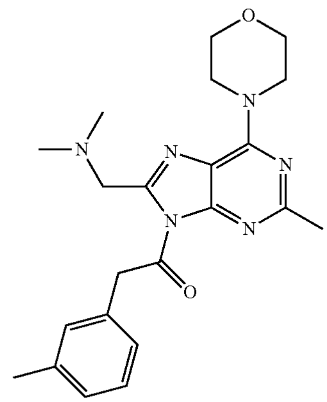

-continued
26
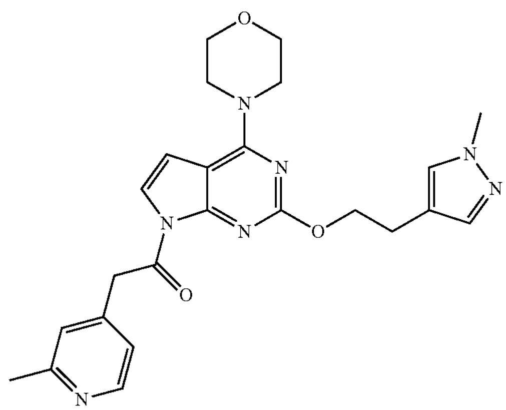
27
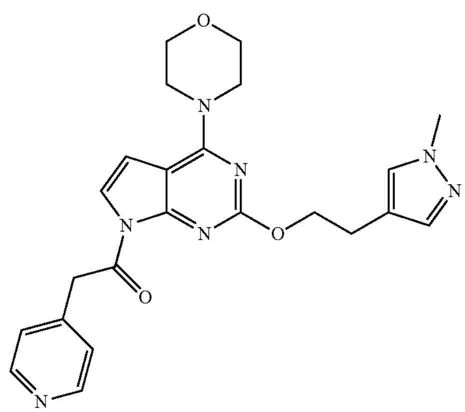
28
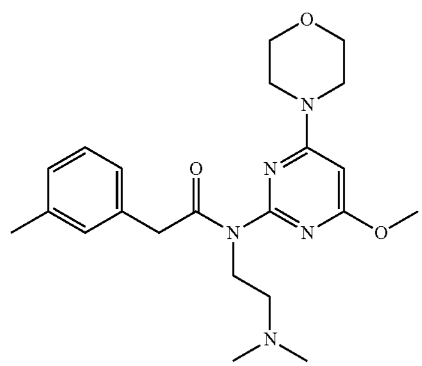
29
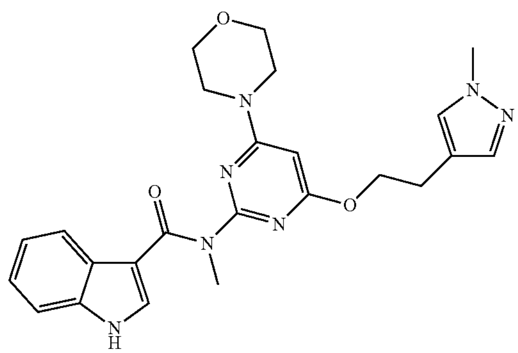
-continued
30
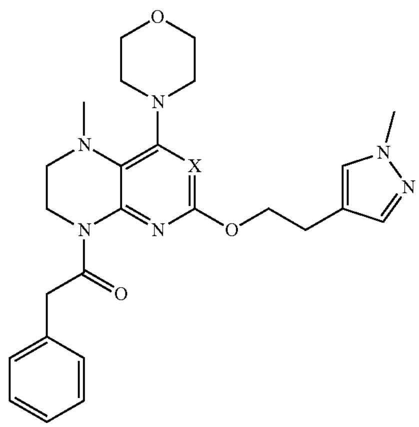
31
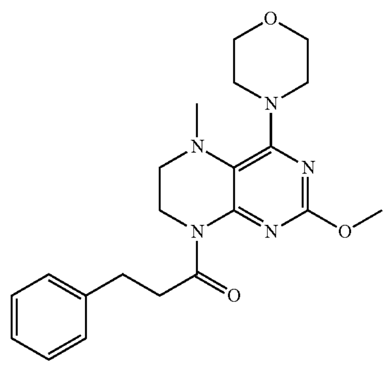
32
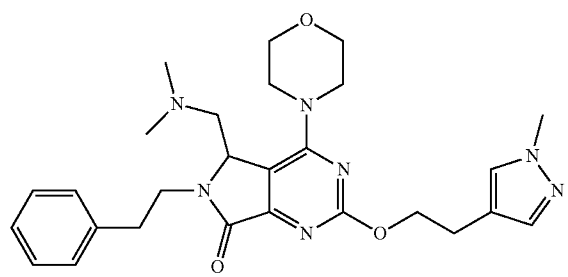
33
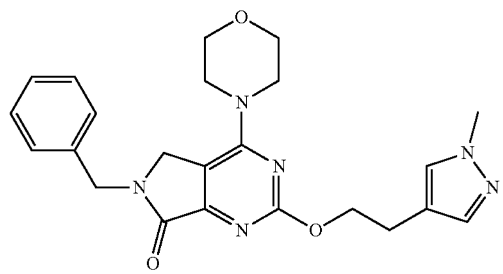

-continued
34
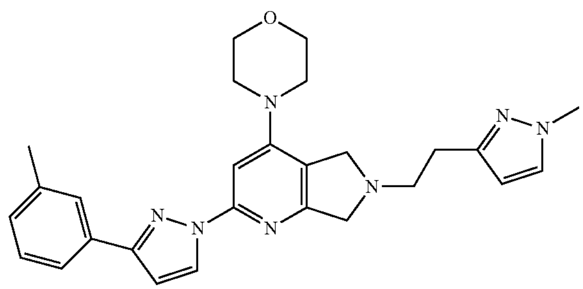
35
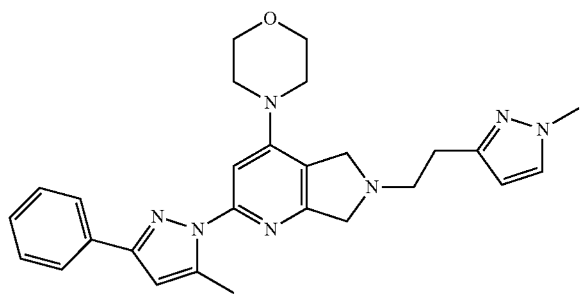
36
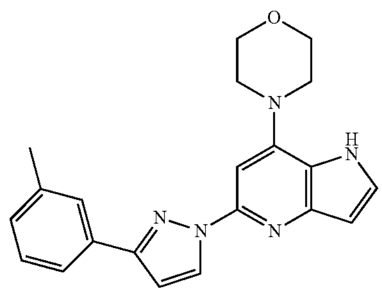
37
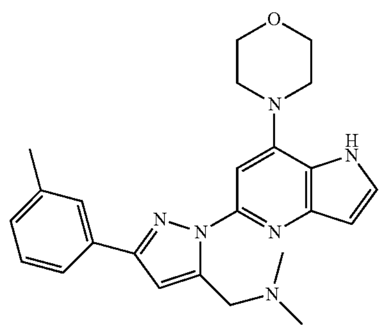
38
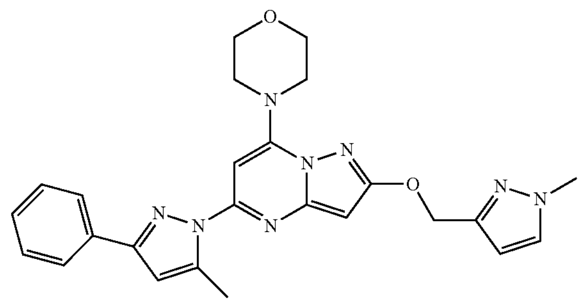
-continued
39
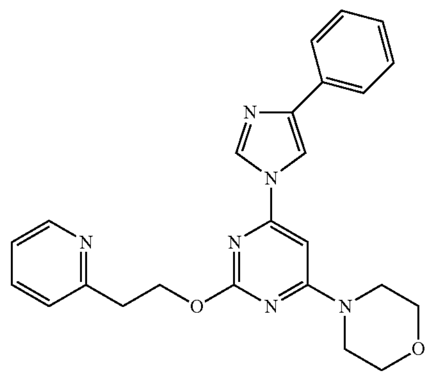
40
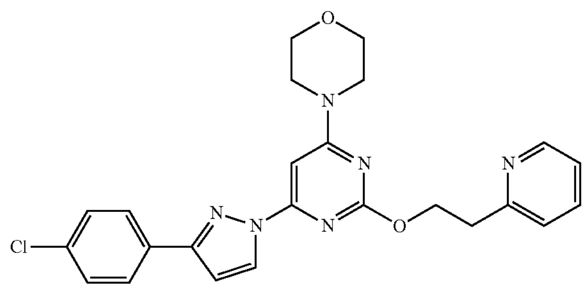
41
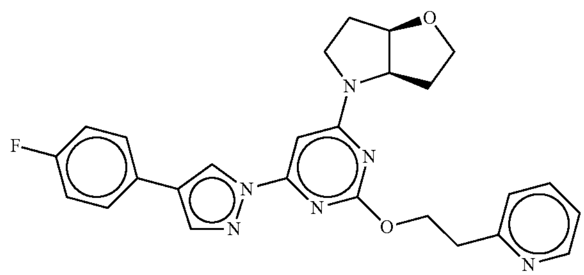
42
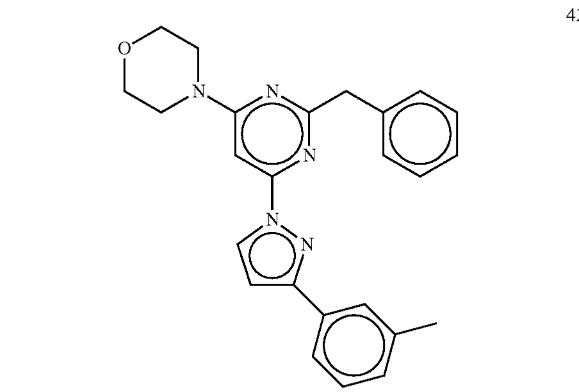

-continued
43
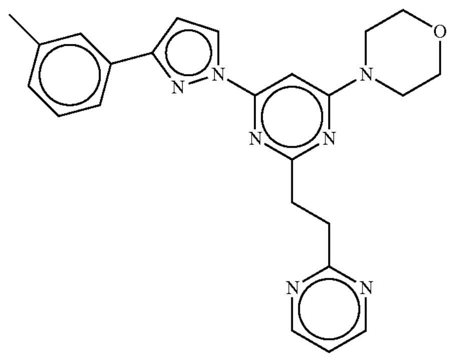
44
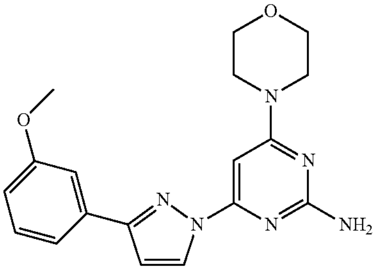
45
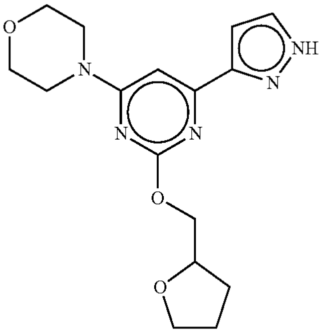
46
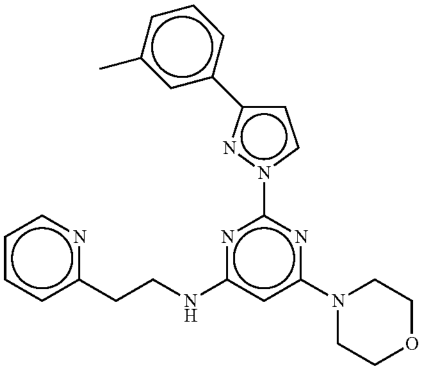
-continued
47
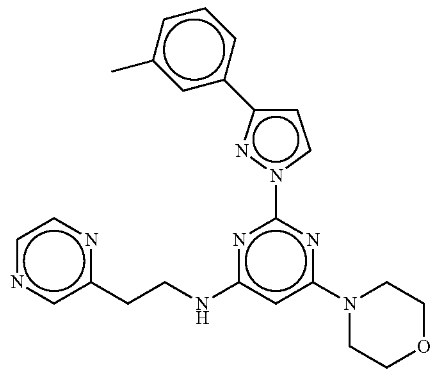
48
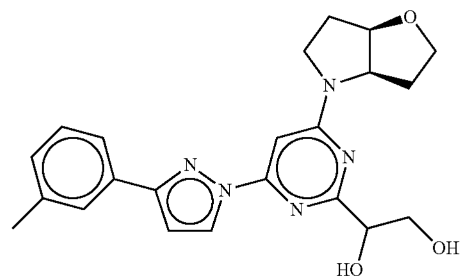
49
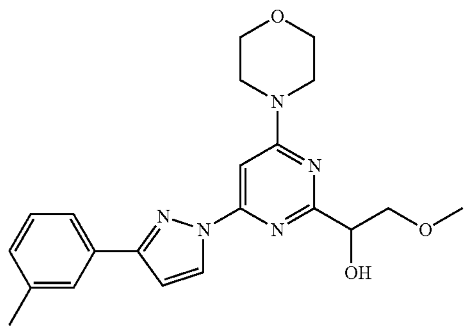
50
51
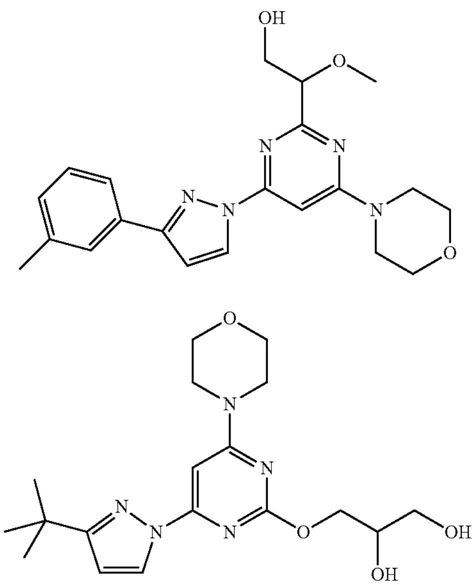

-continued
52
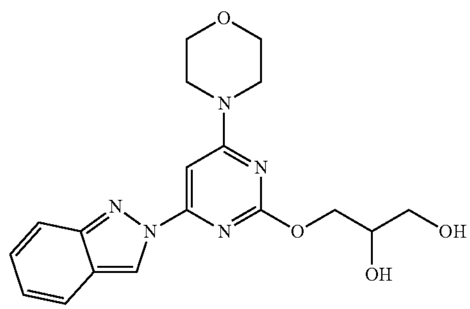
53
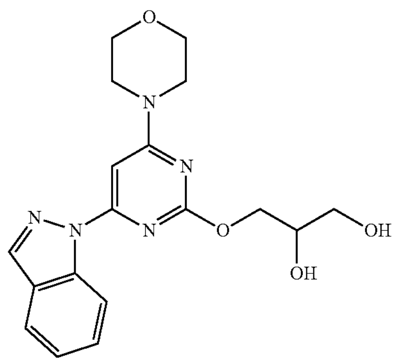
54
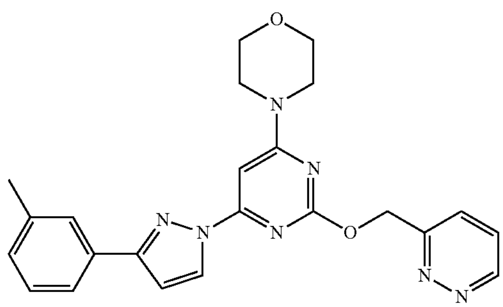
55
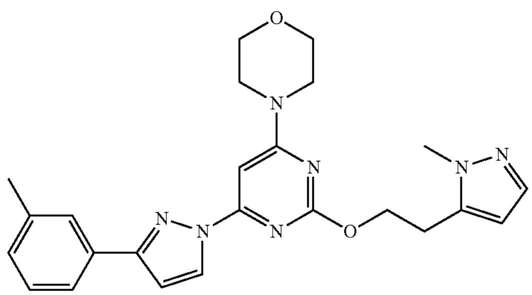
56
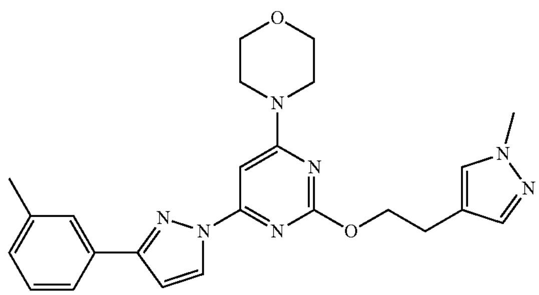
-continued
57
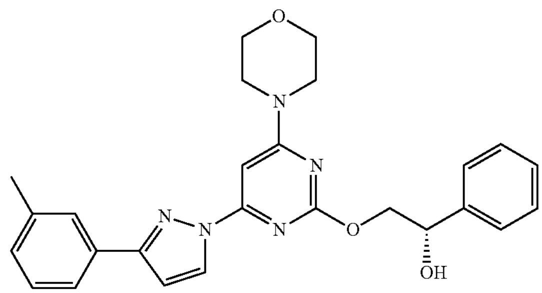
58
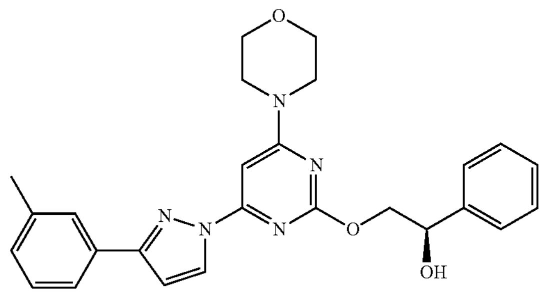
59
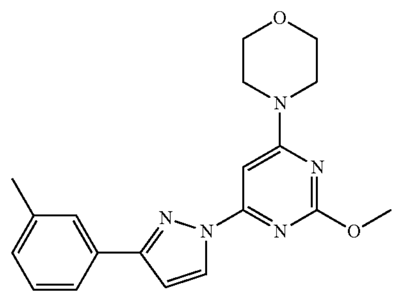
60
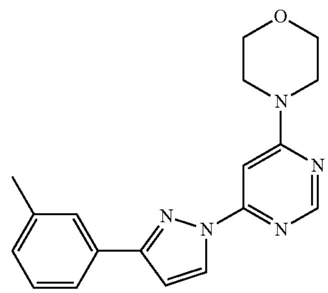
61
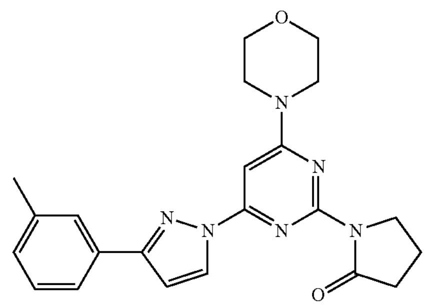

-continued
62
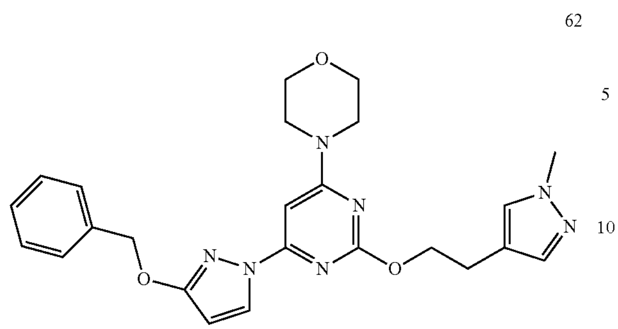
63
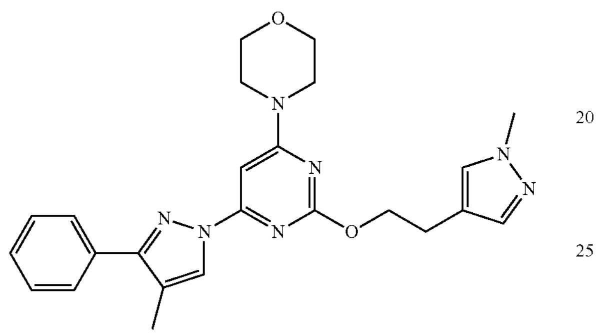
64
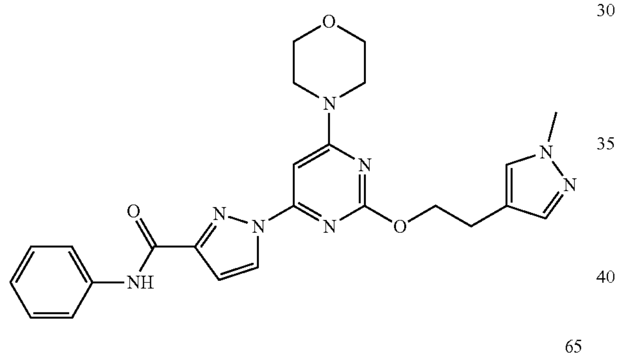
65
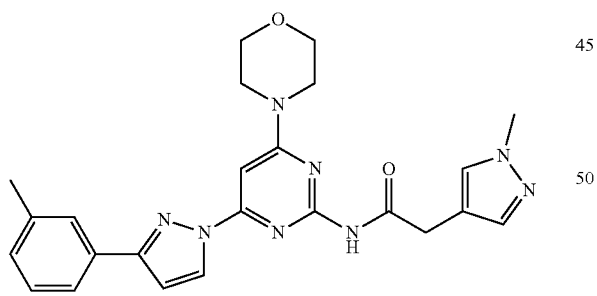
66
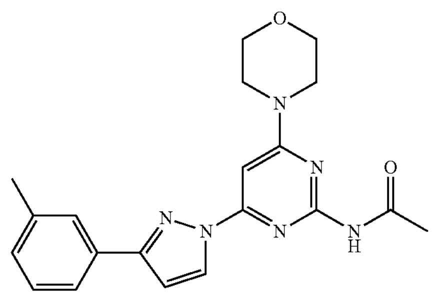
-continued
67
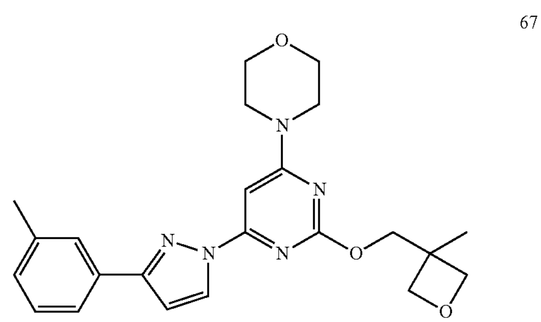
68
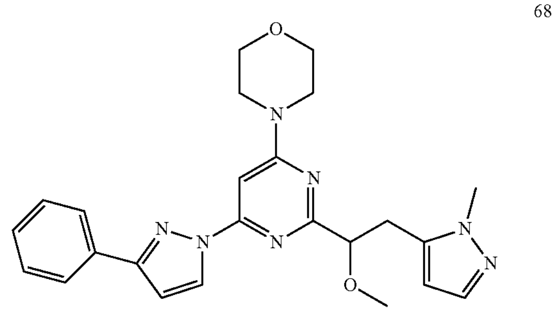
69
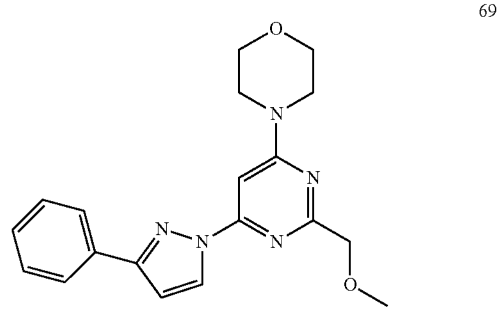
70
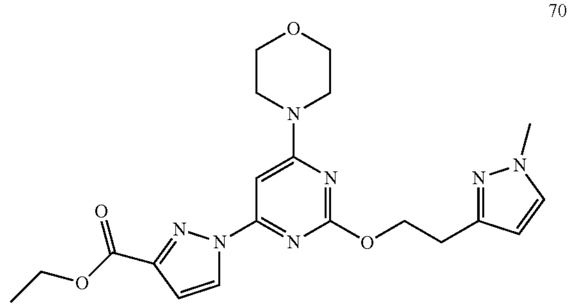
71
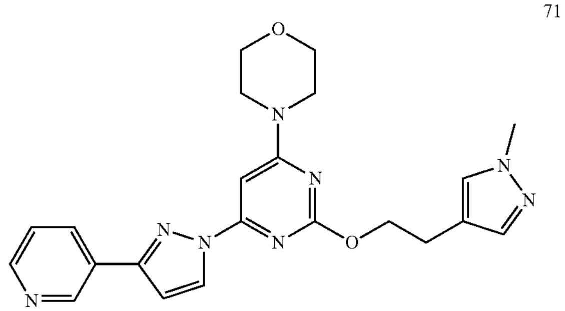

-continued
72
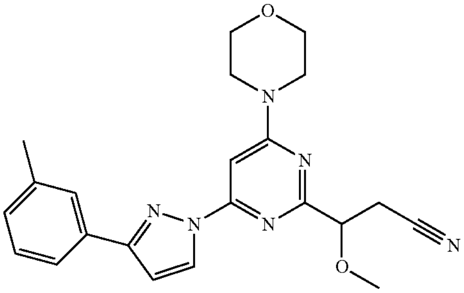
73
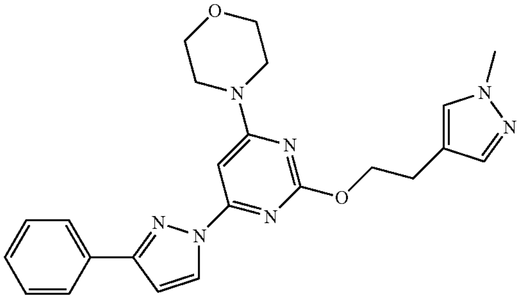
74
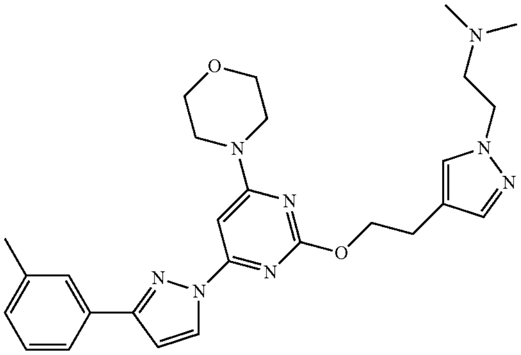
75
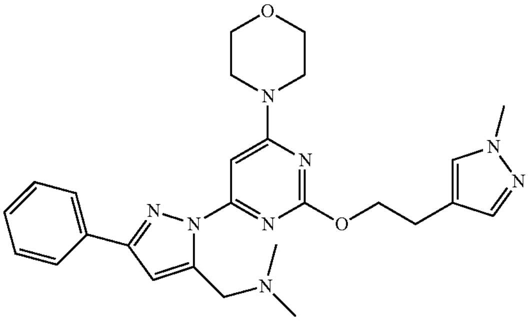
76
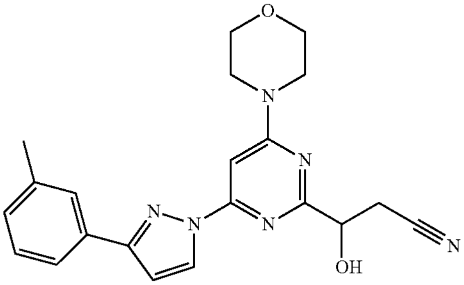
-continued
77
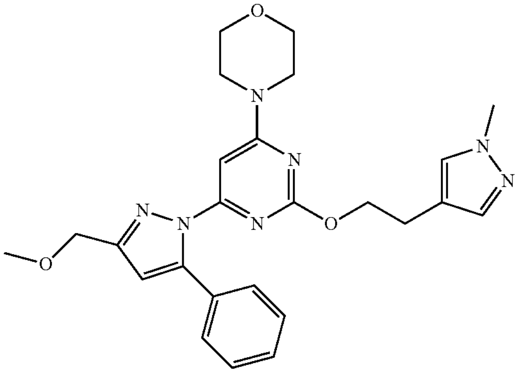
78
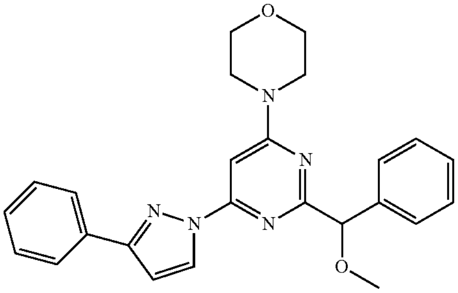
79
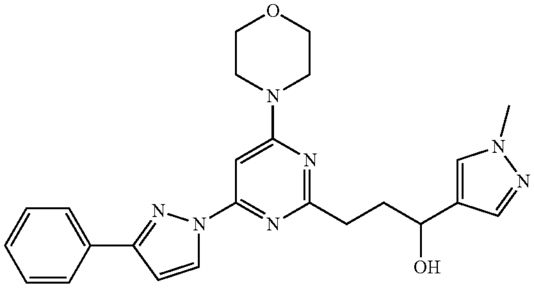
80
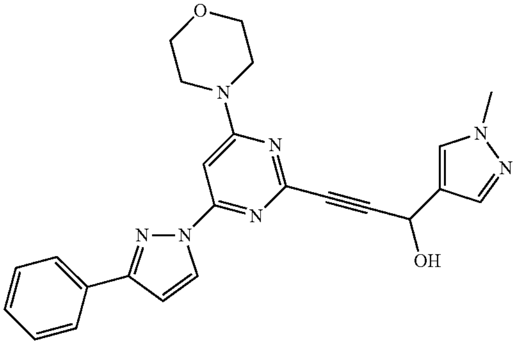
81
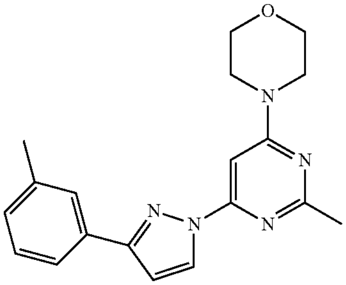

-continued
82
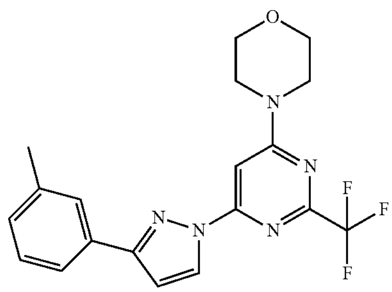
83
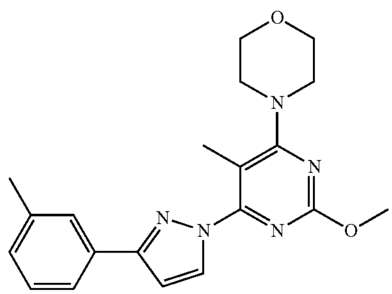
84
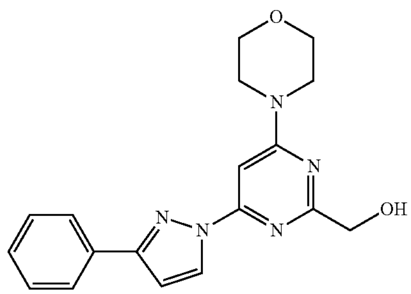
85
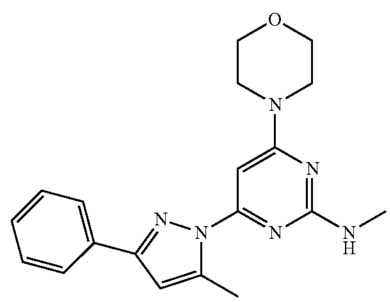
86
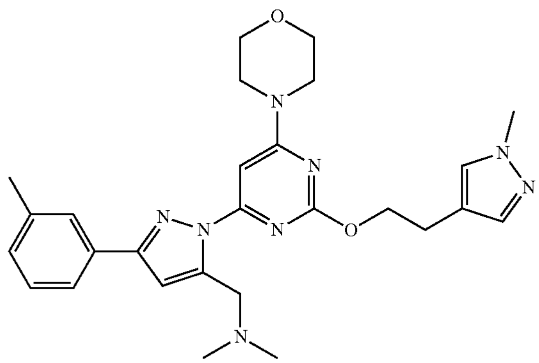
-continued
87
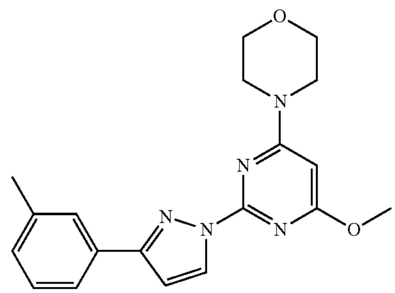
88
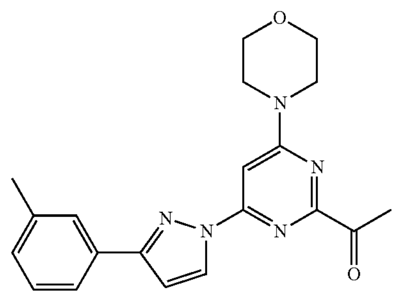
89
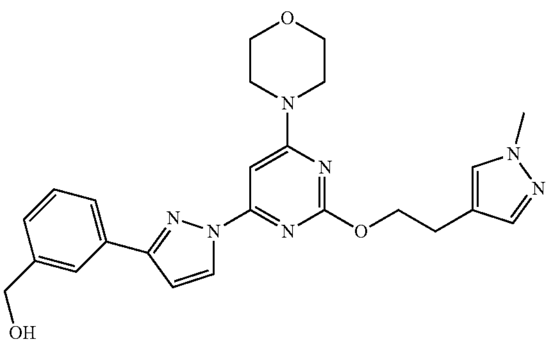
90
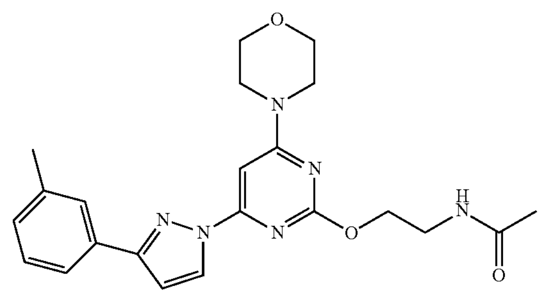

-continued
91
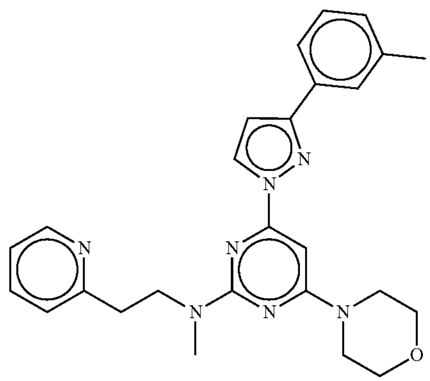
220
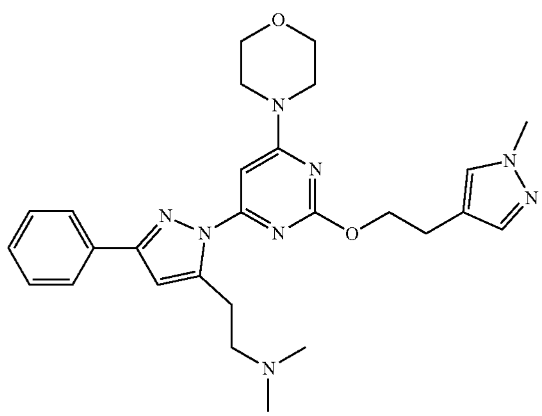
92
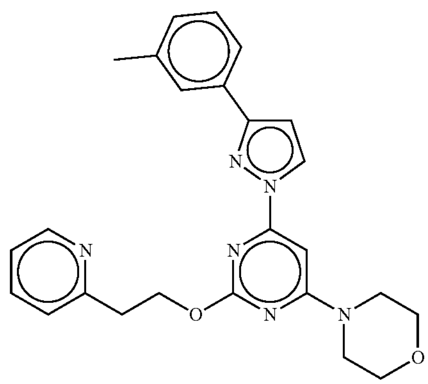
221
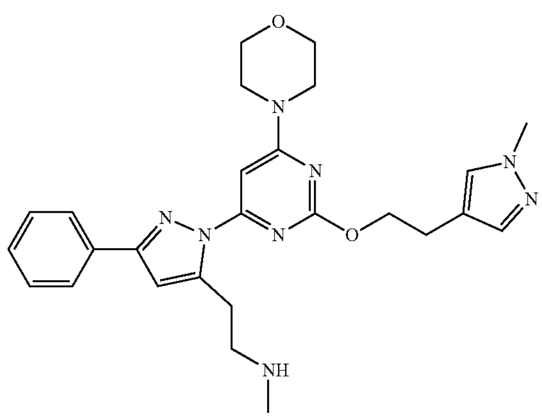
93
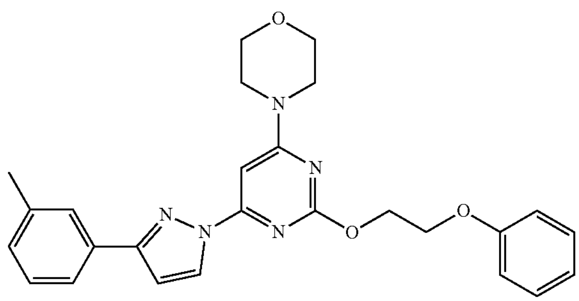
222
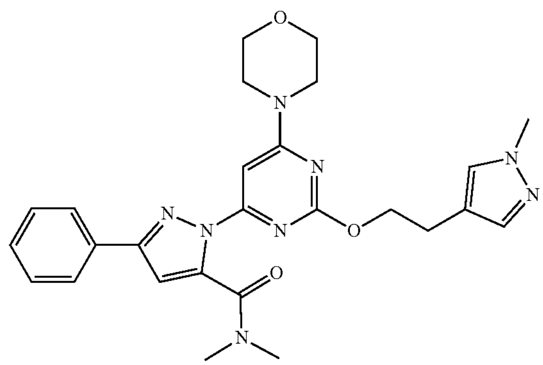
94
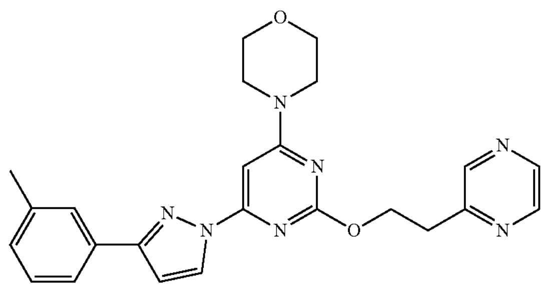
223
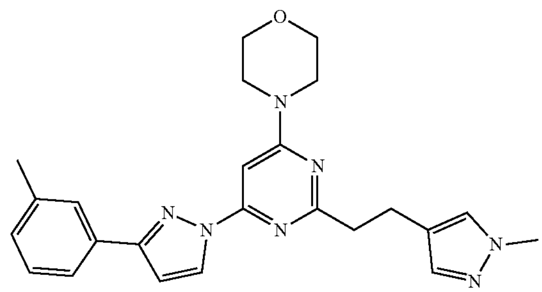
95
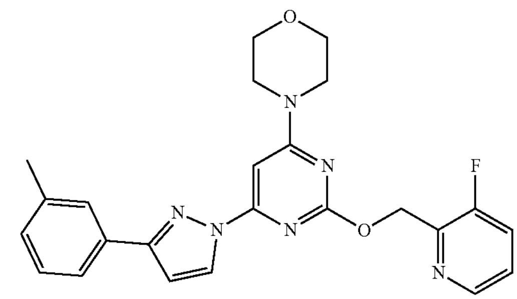

-continued
224
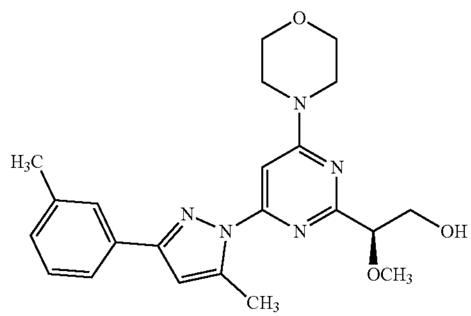
96
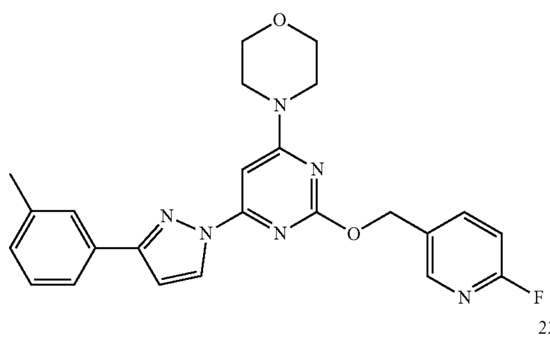
225
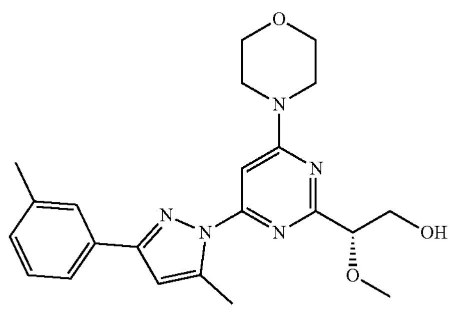
97
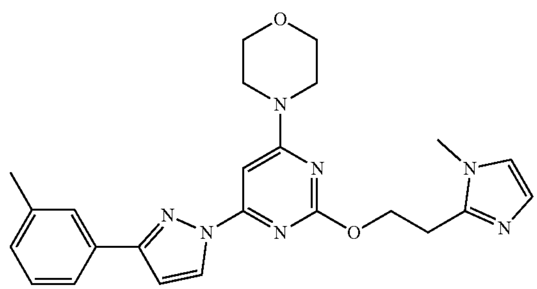
226
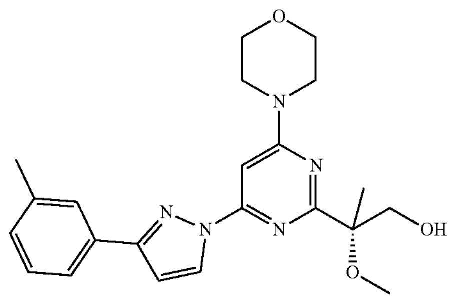
-continued
98
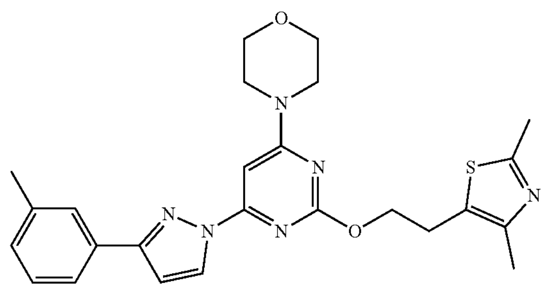
227
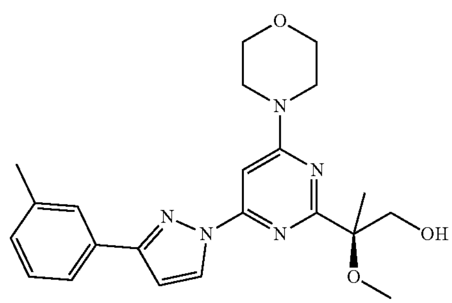
99
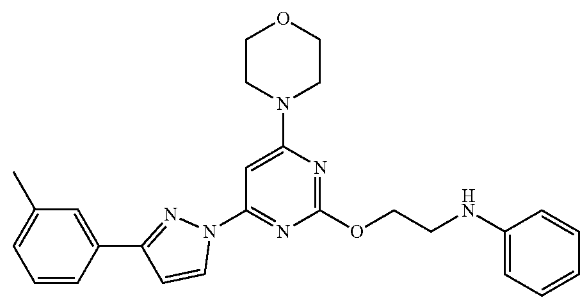
228
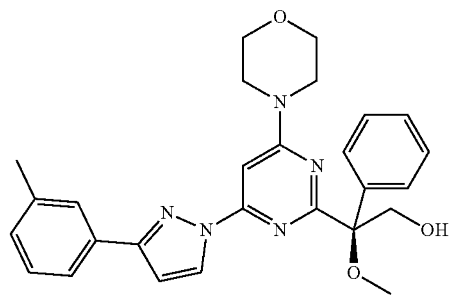
100
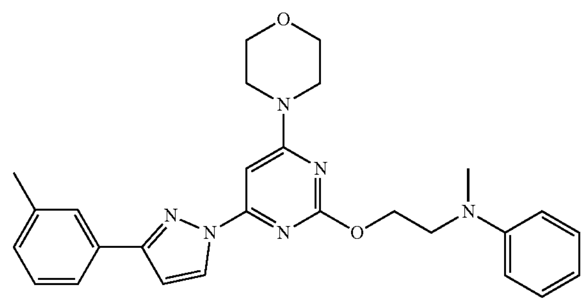

-continued
229
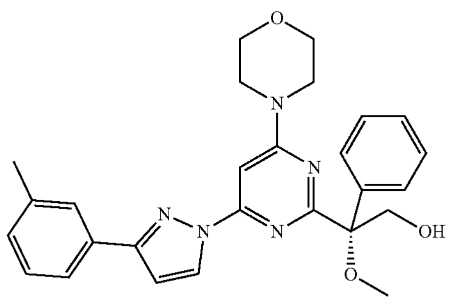
101
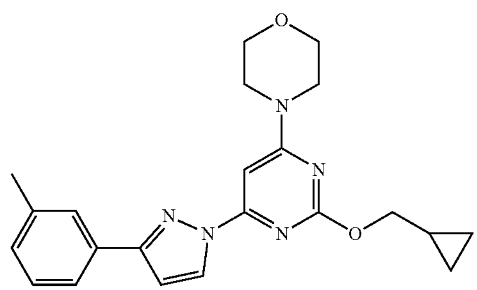
230
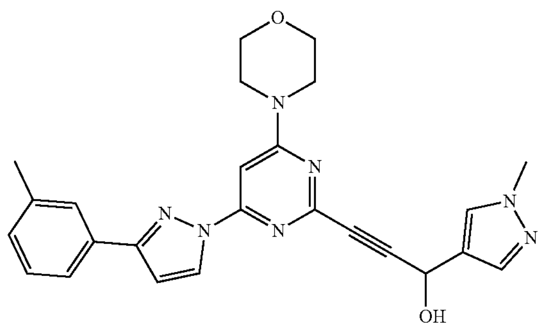
102
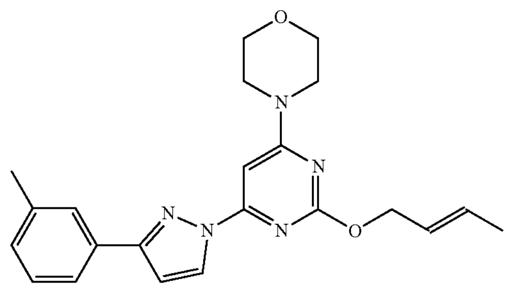
231
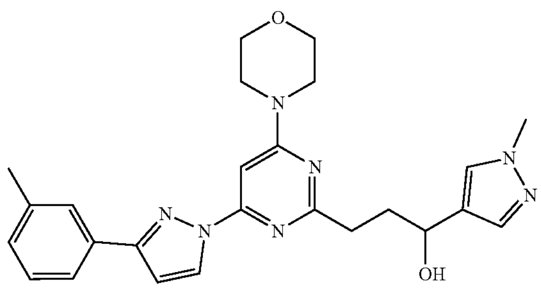
-continued
103
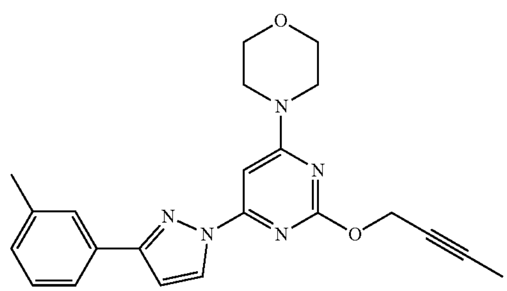
232
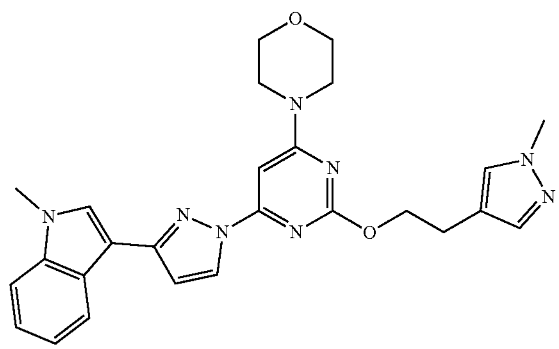
104
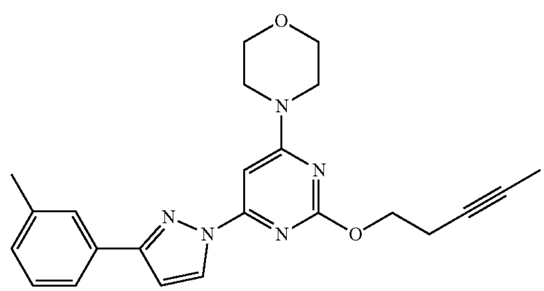
233
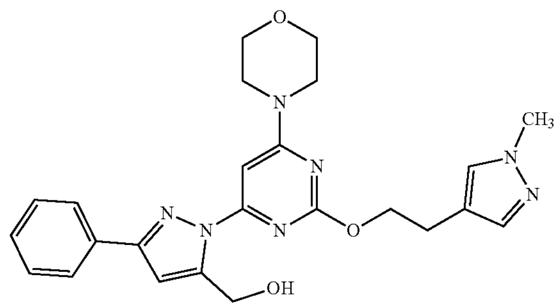
105
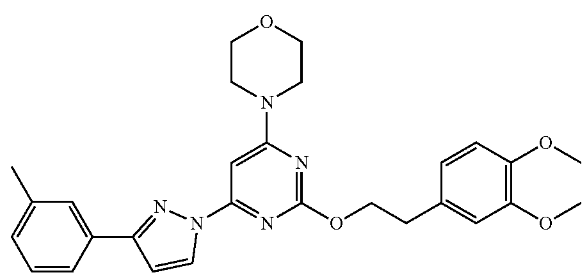

-continued
234
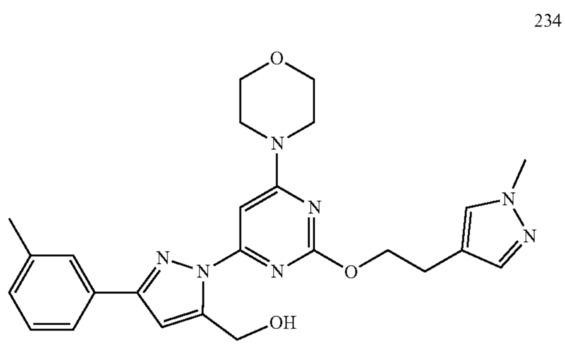
106
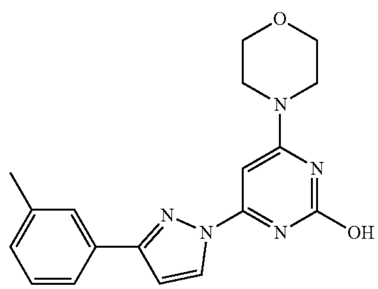
235
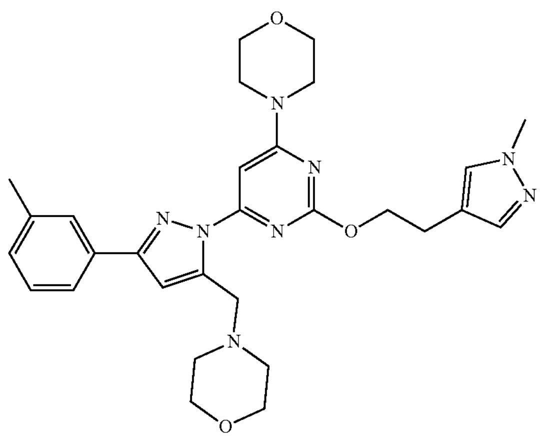
107
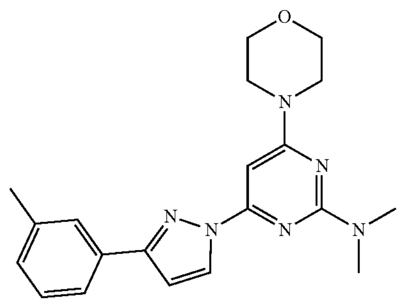
-continued
236
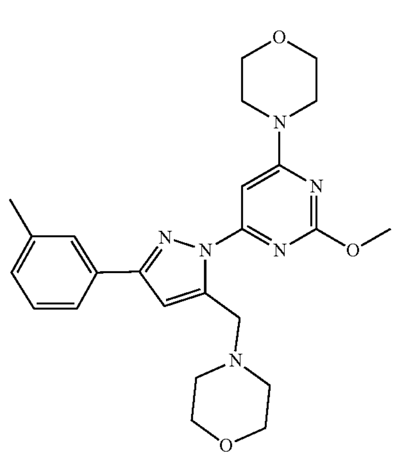
108
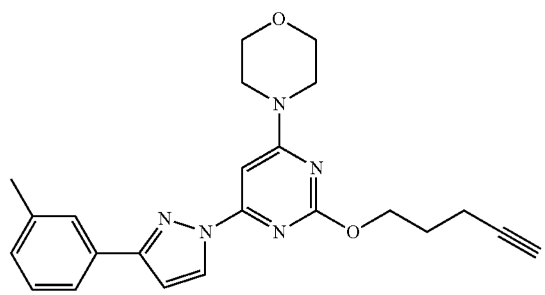
237
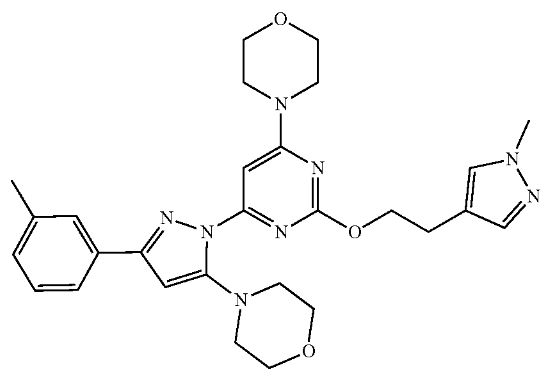
109
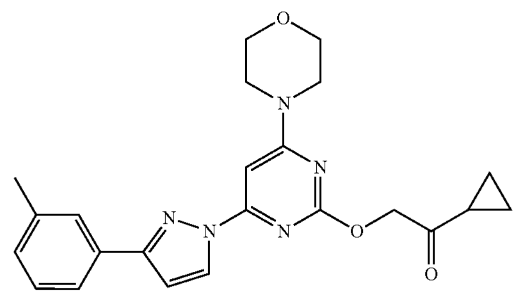

238
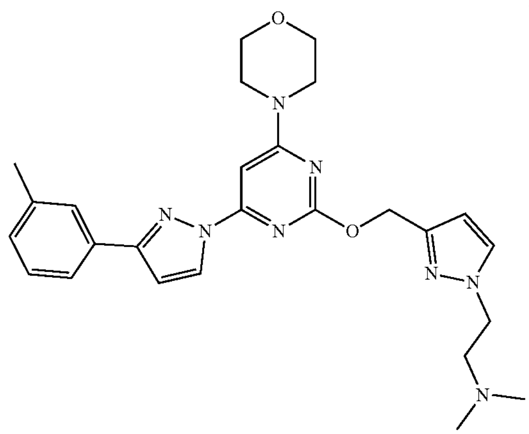
110
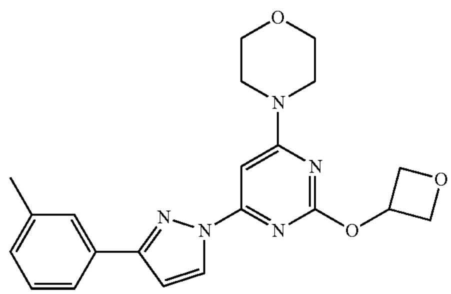
239
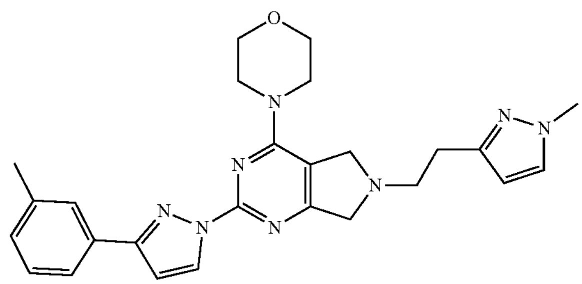
111
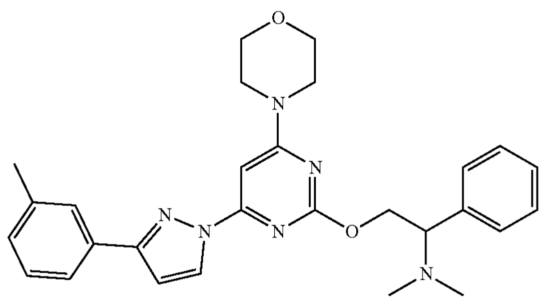
240
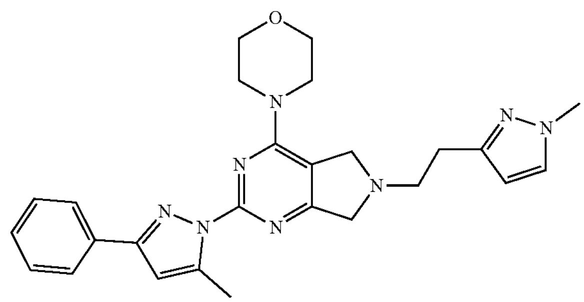
112
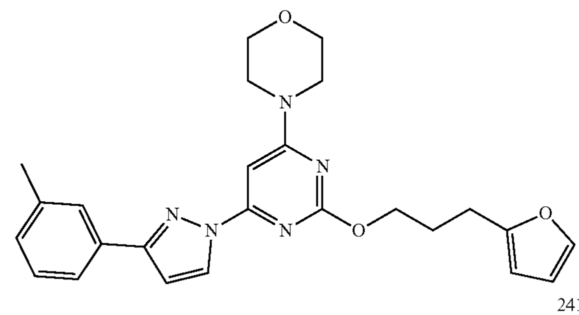
241
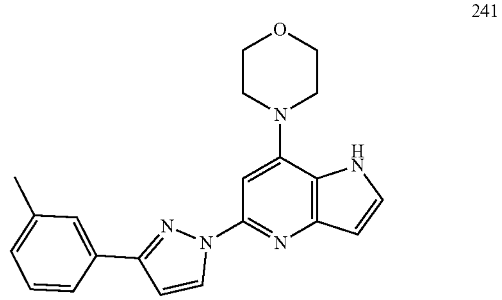
113
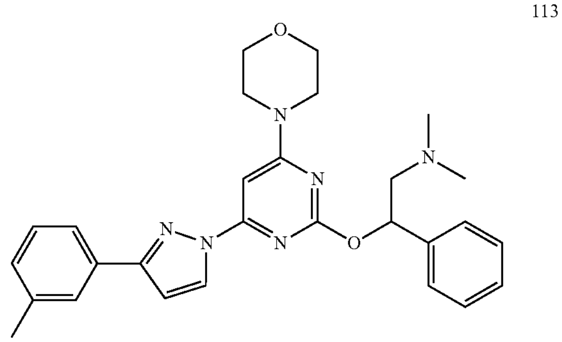
242
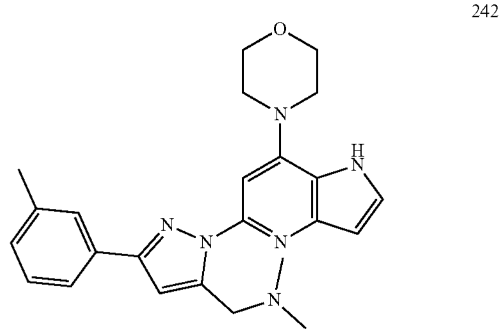

-continued
114
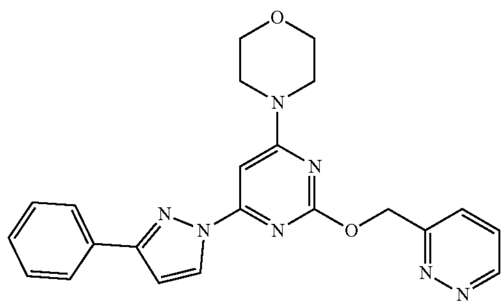
243
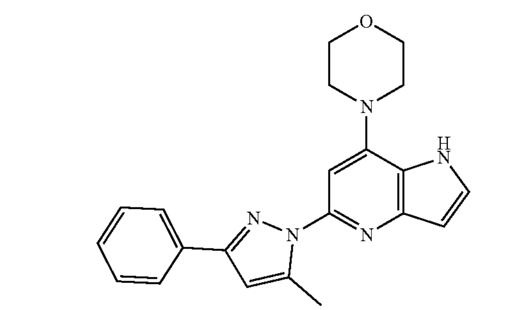
115
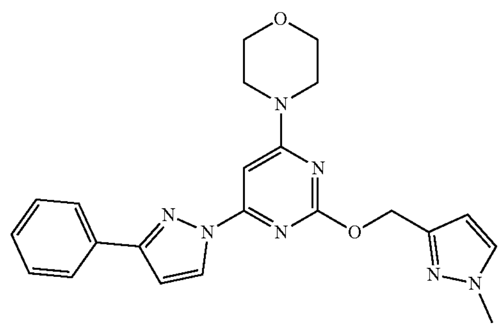
244
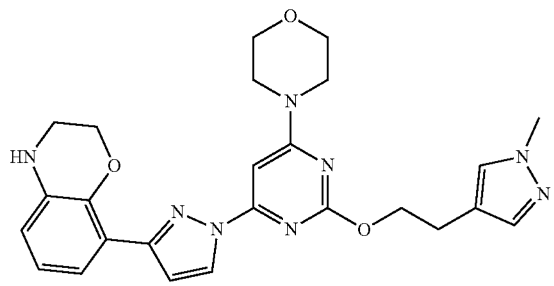
116
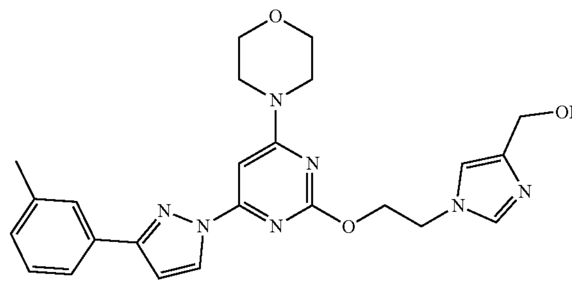
-continued
245
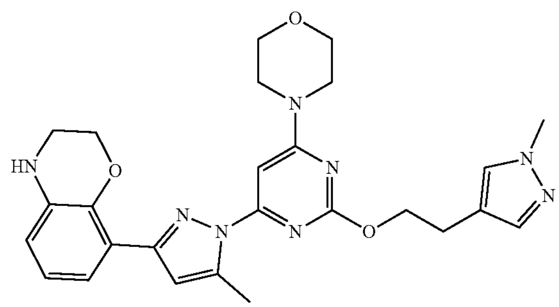
117
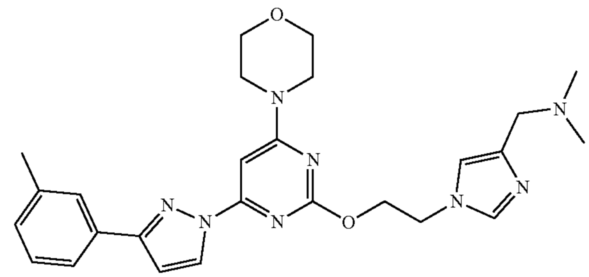
246
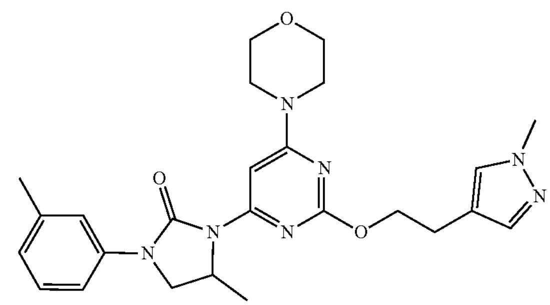
118
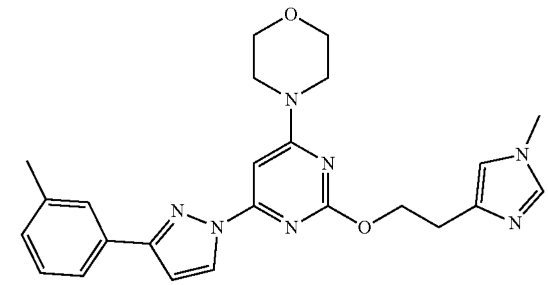
247
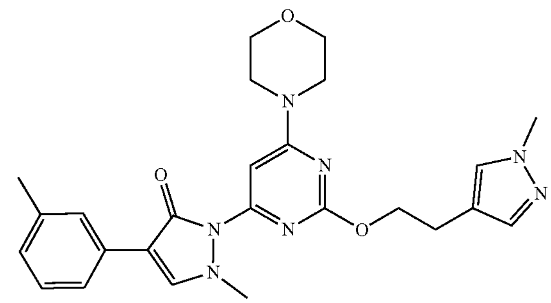

-continued
119
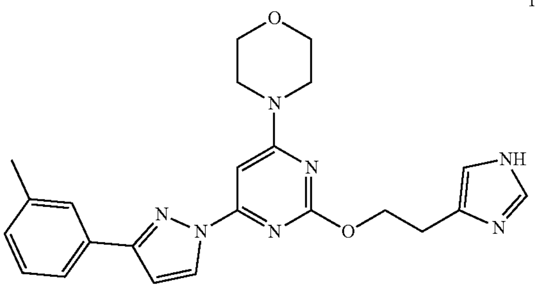
248
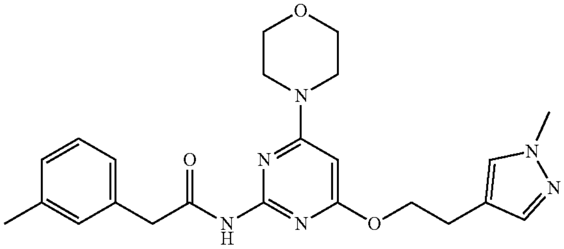
120
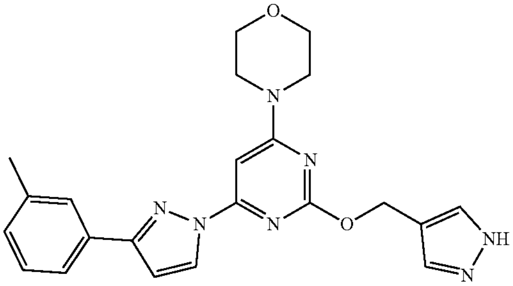
249
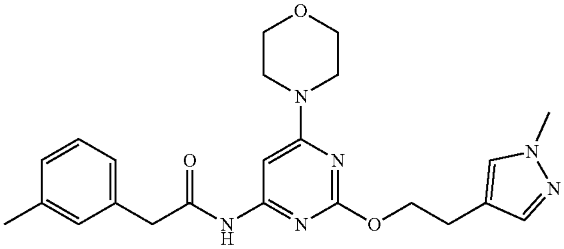
121
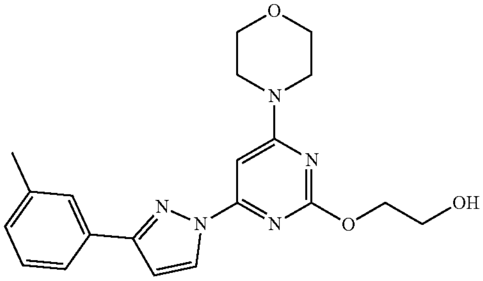
-continued
250
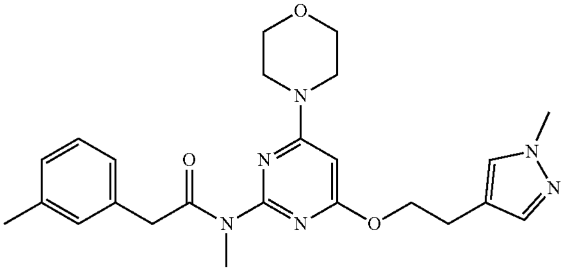
122
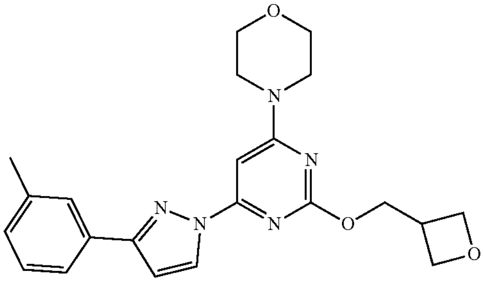
251
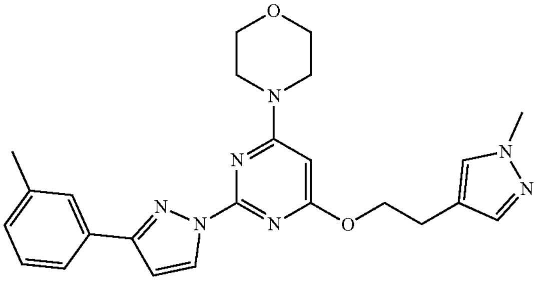
123
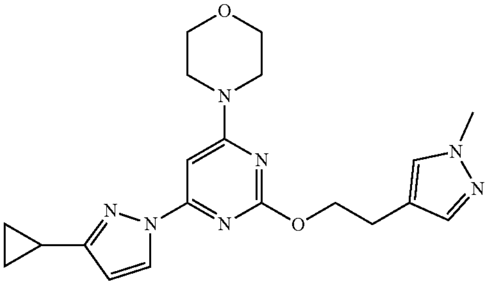
252
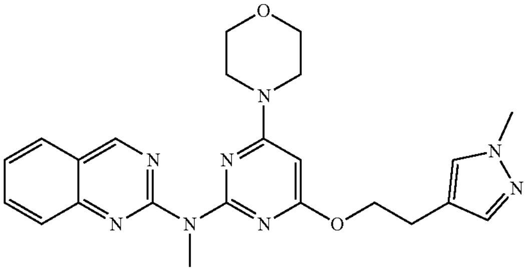

-continued
124
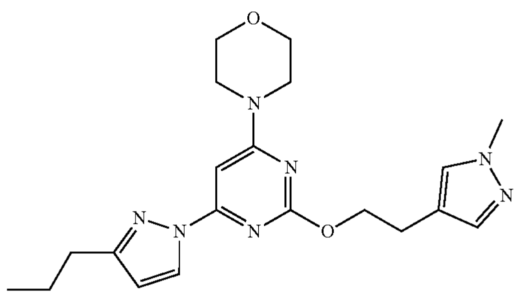
253
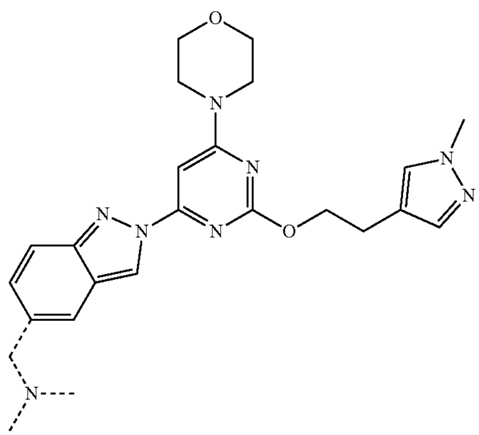
125
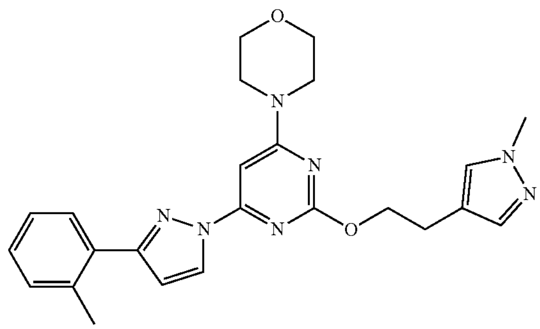
254
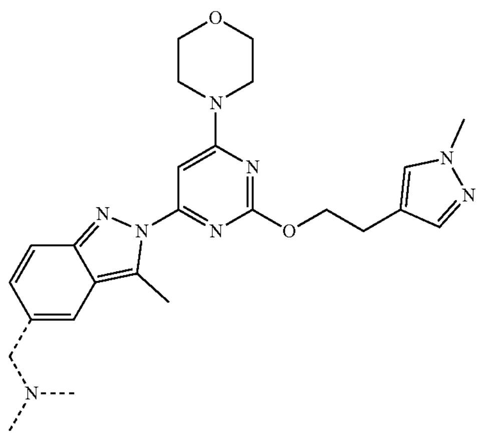
-continued
126
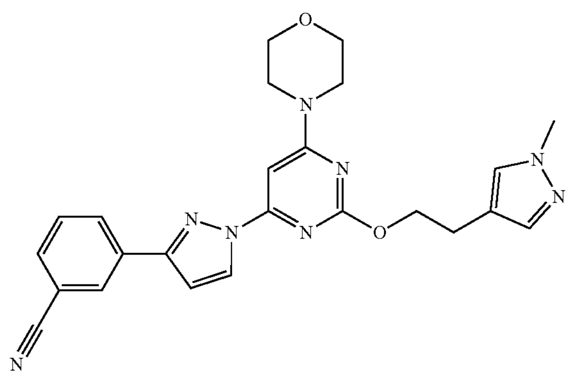
255
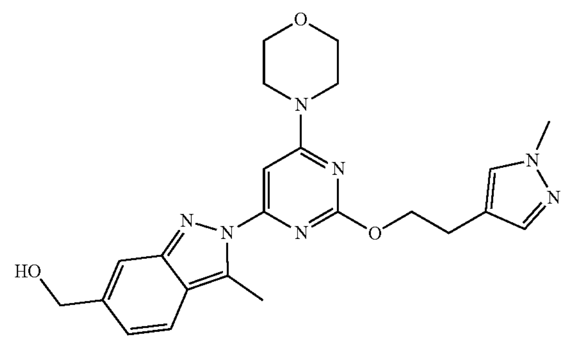
127
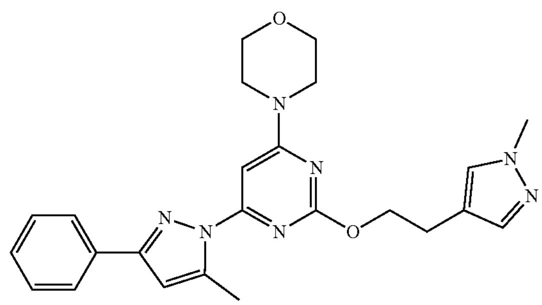
256
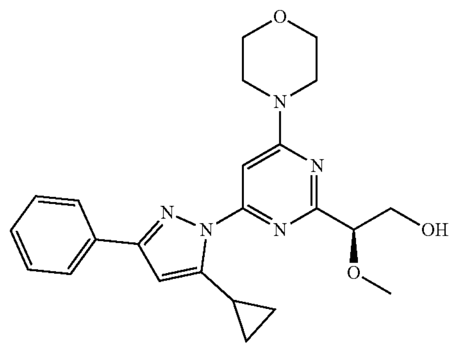

-continued
128
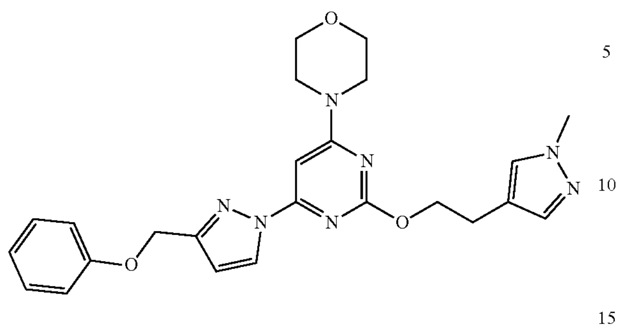
257
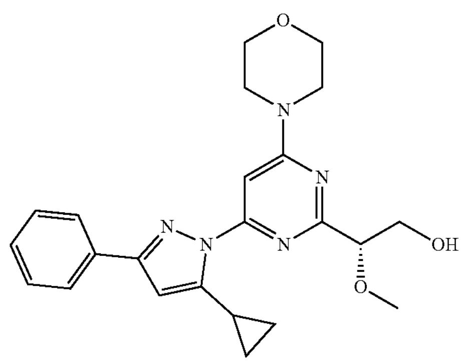
129
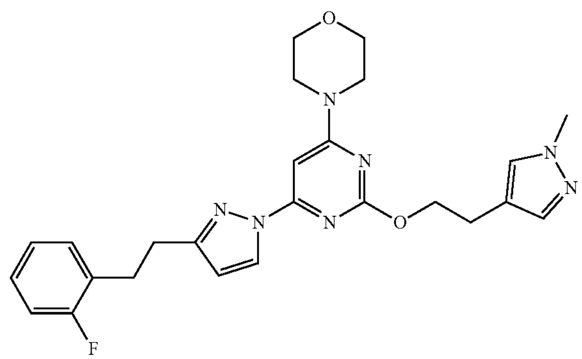
258
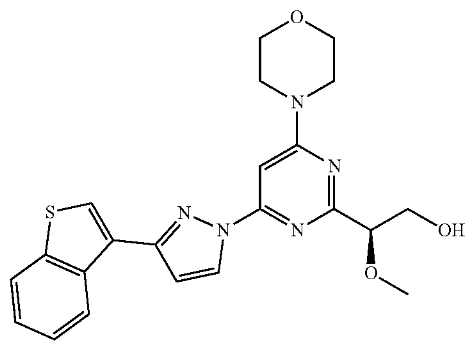
-continued
130
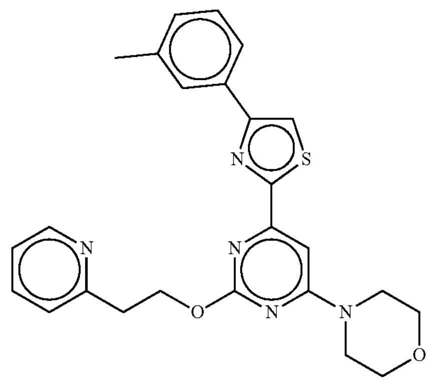
259
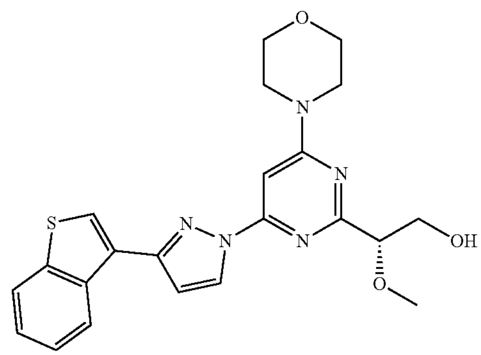
131
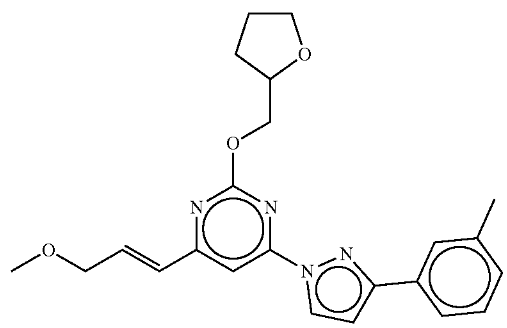
260
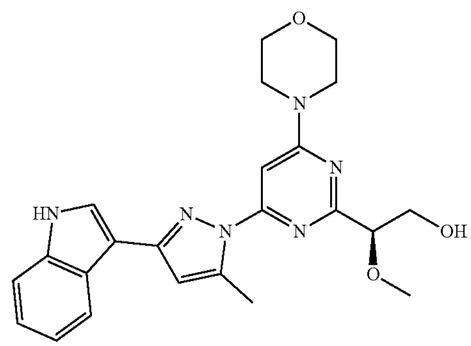

-continued
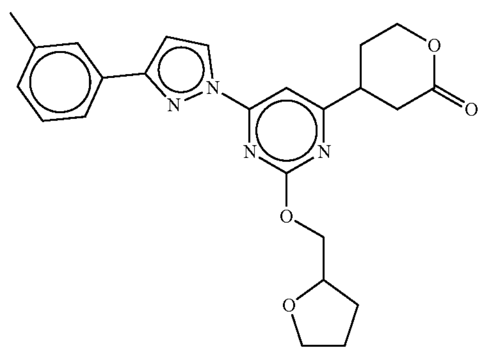
132
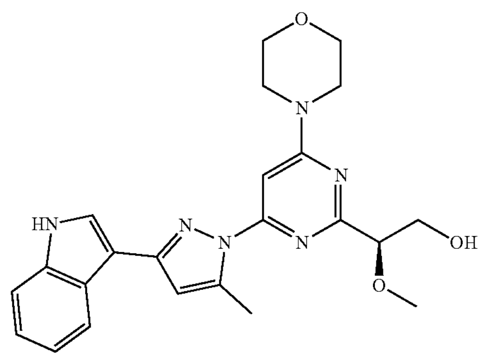
261
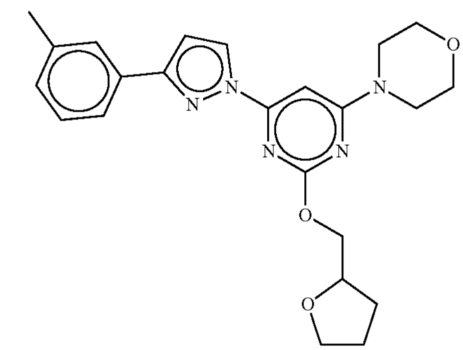
133
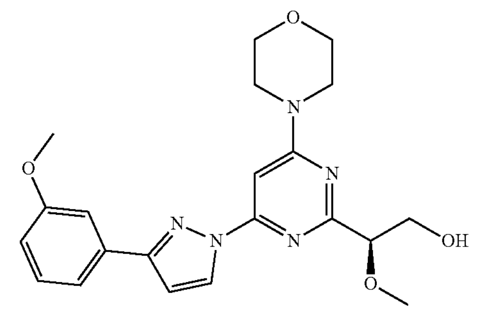
262
-continued
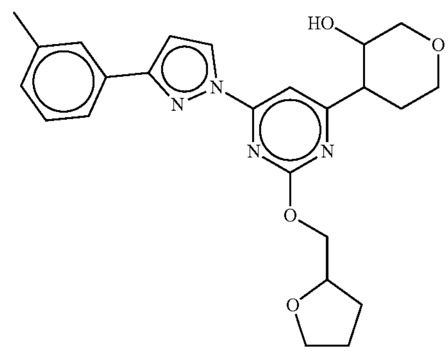
134
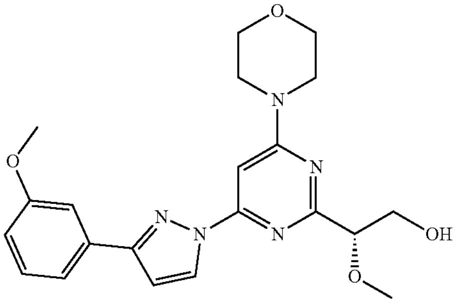
263
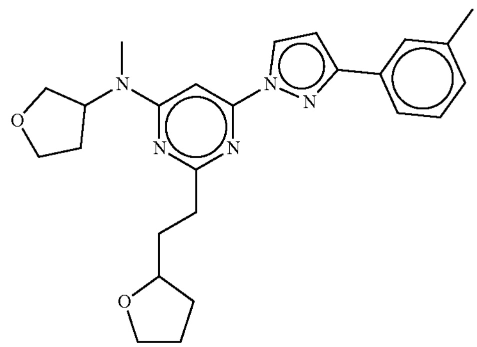
135
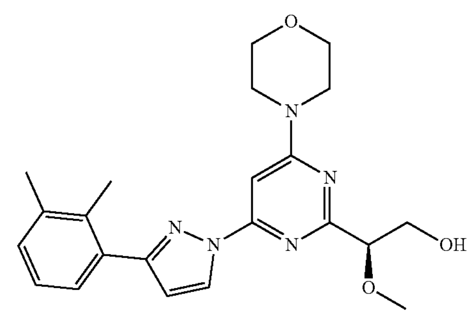
264

-continued
136
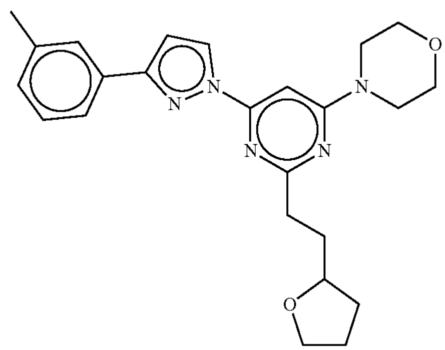
265
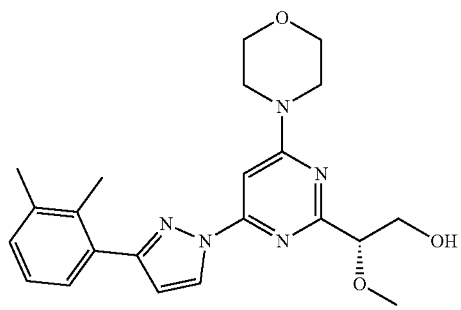
137
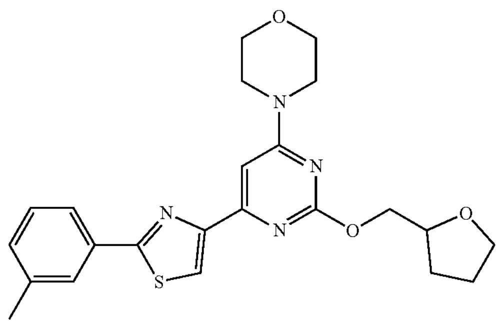
266
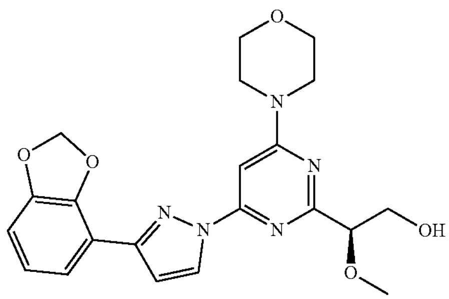
138
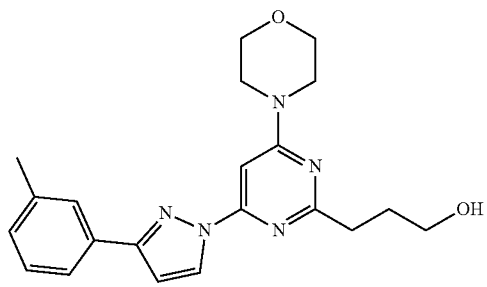
-continued
267
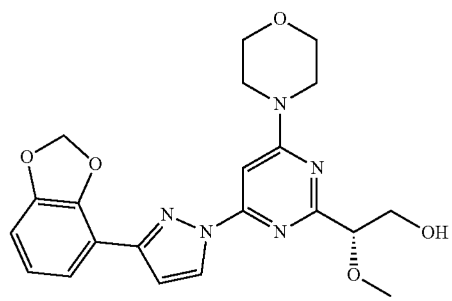
139
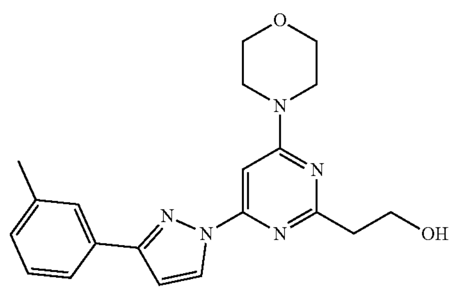
268
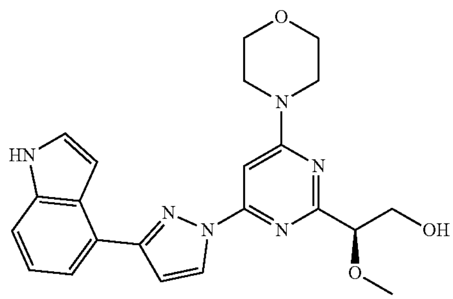
140
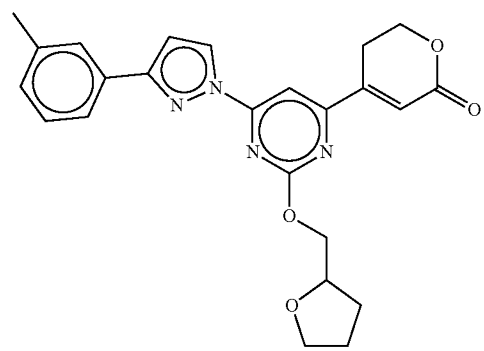
269
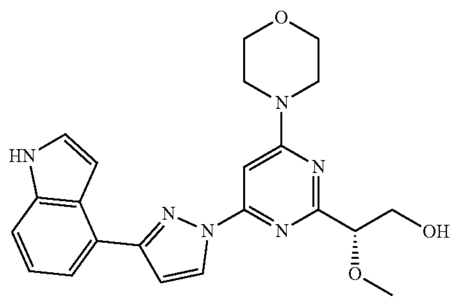

-continued
141
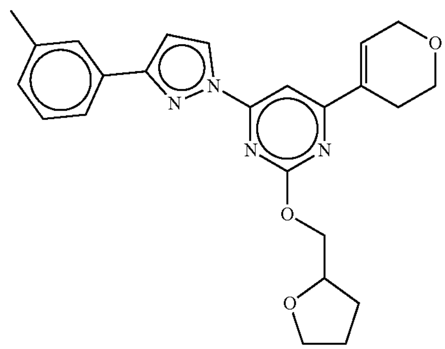
270
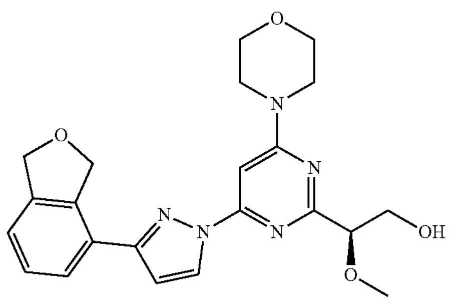
142
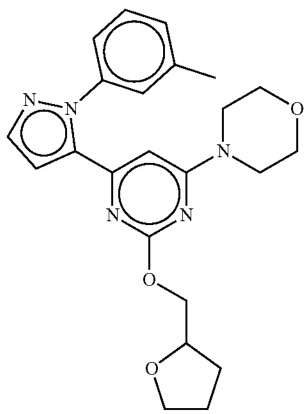
271
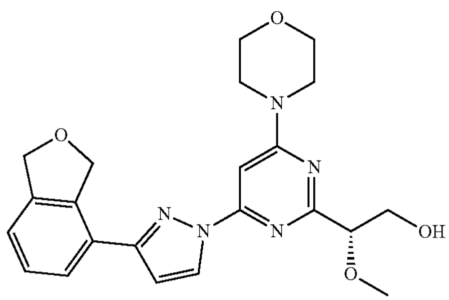
-continued
143
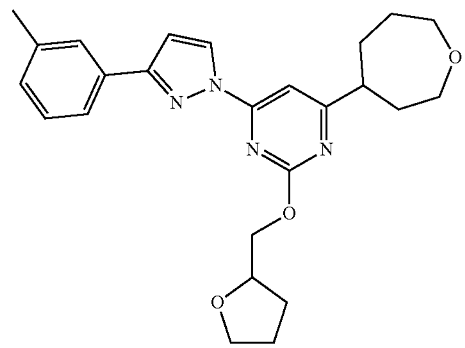
272
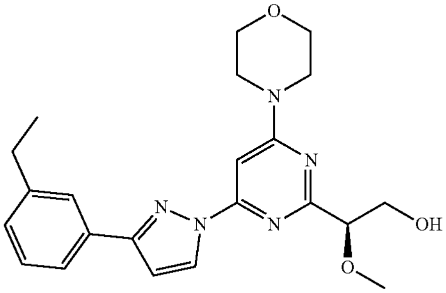
144
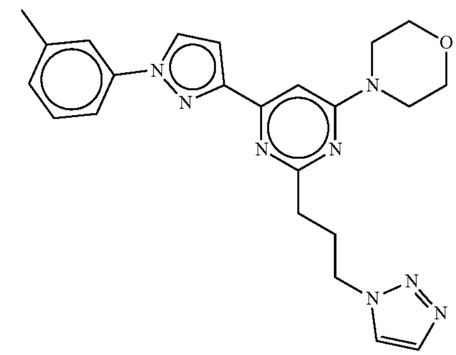
273
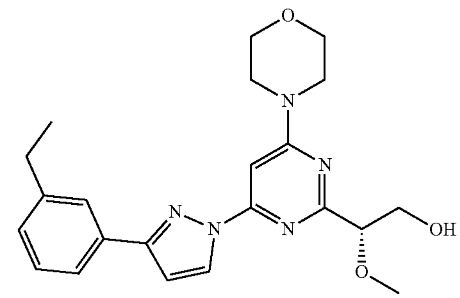

-continued
145
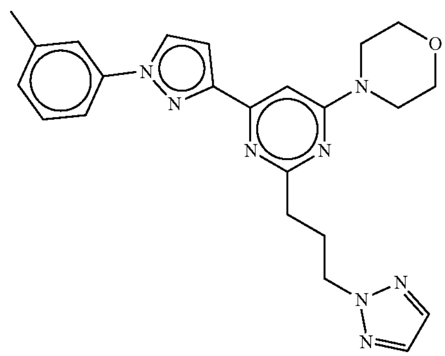
274
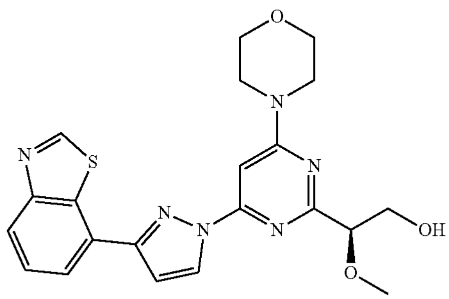
146
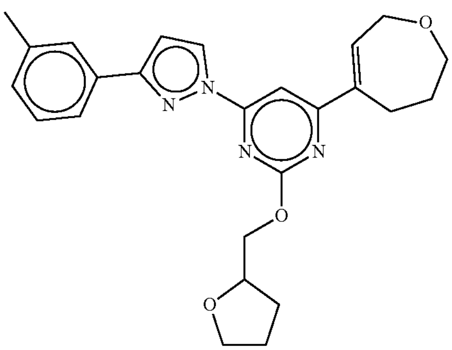
275
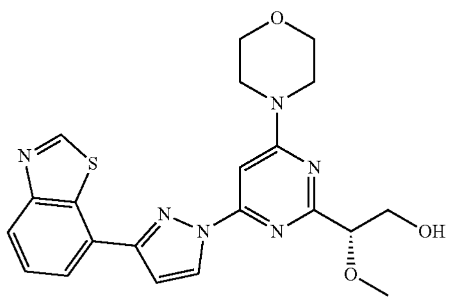
147
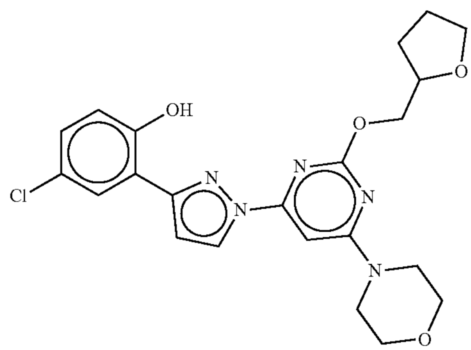
-continued
276
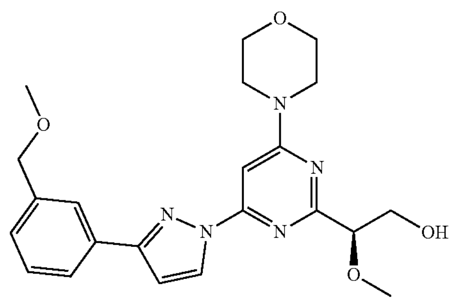
148
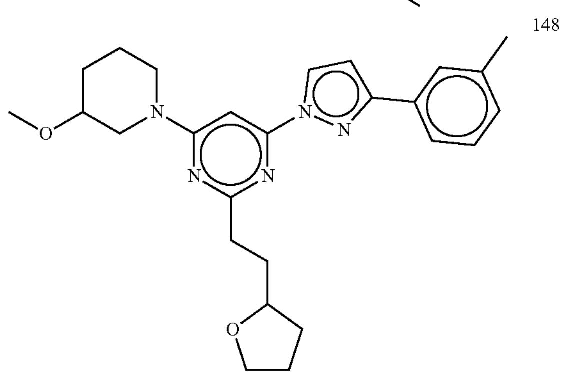
277
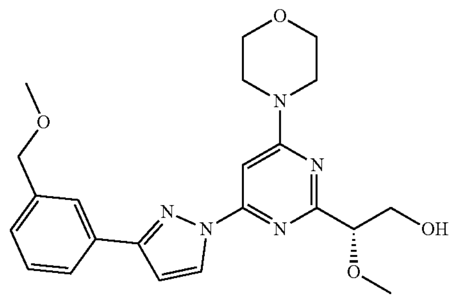
149
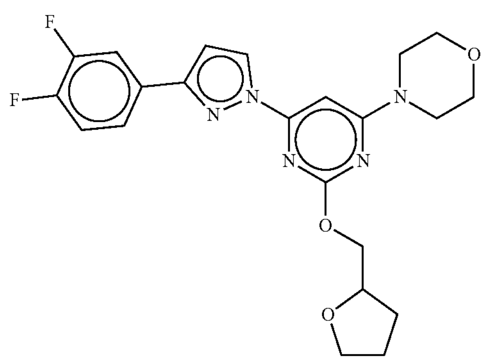
278
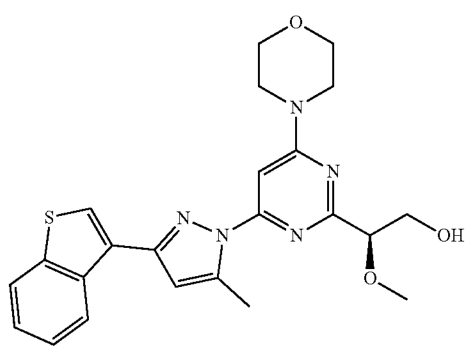

-continued
150
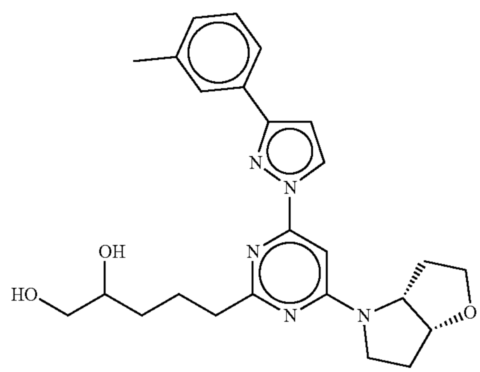
279
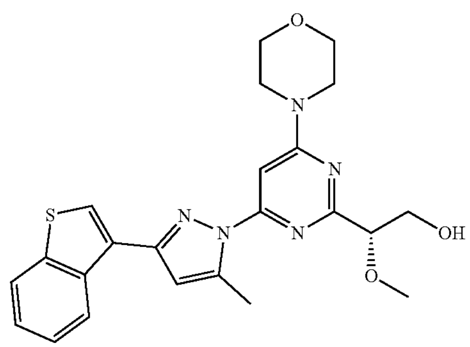
151
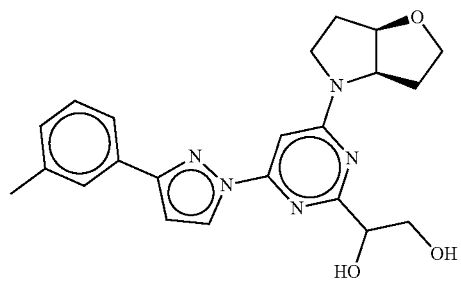
280
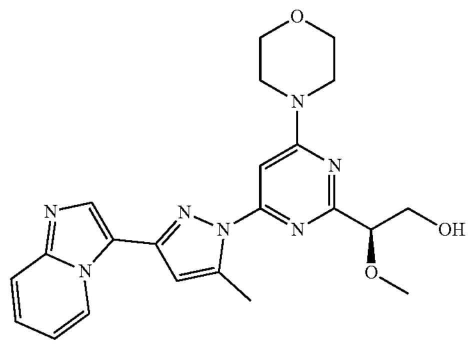
152
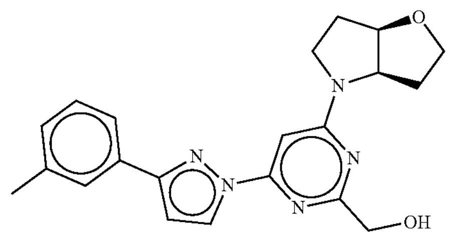
-continued
281
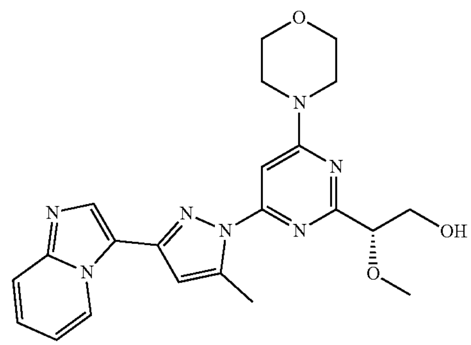
153
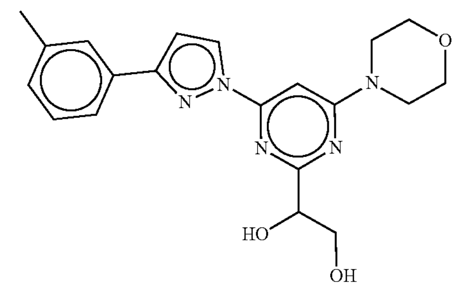
282
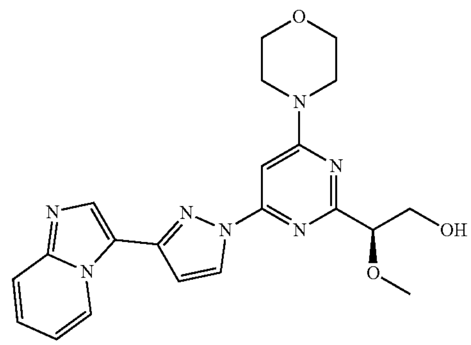
154
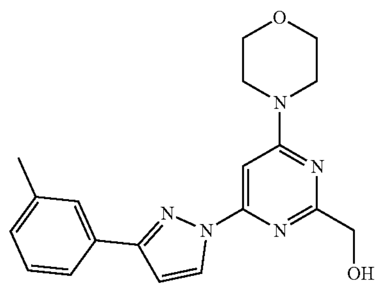
283
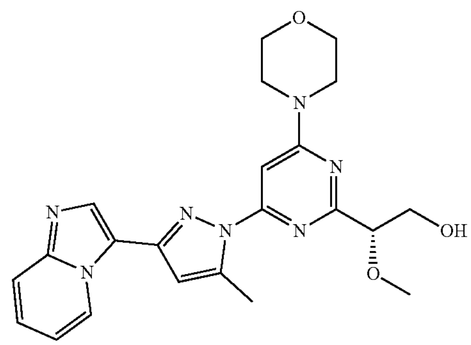

-continued
155
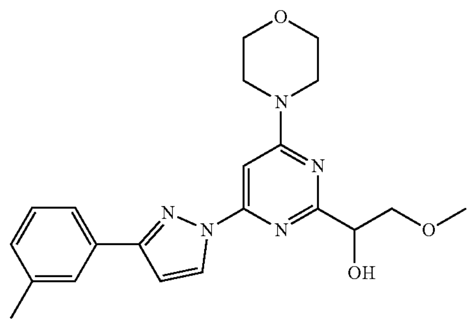
284
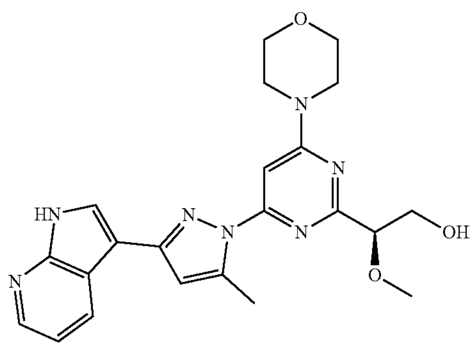
156
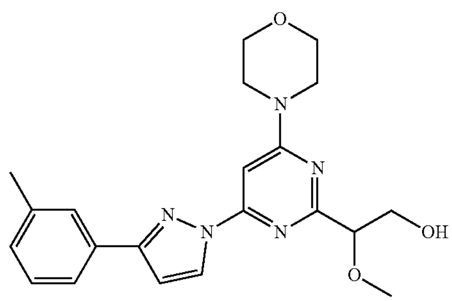
285
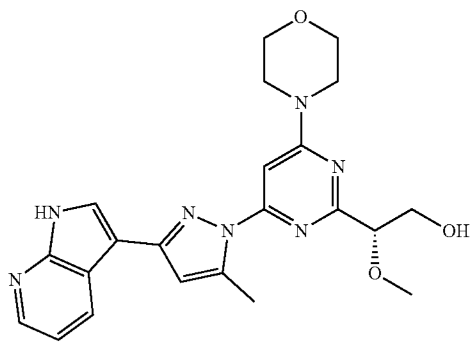
-continued
157
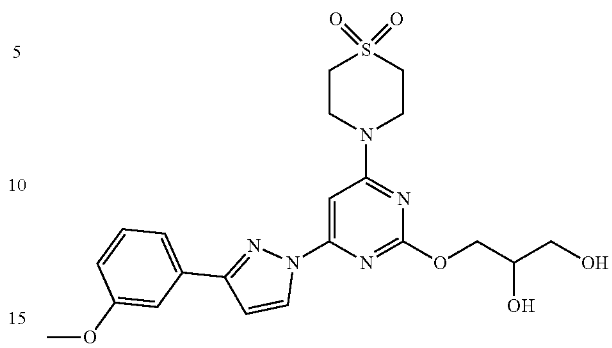
286
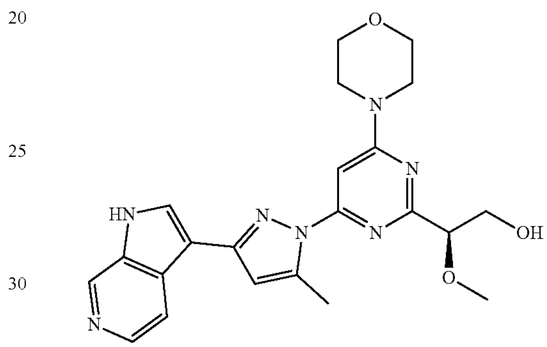
158
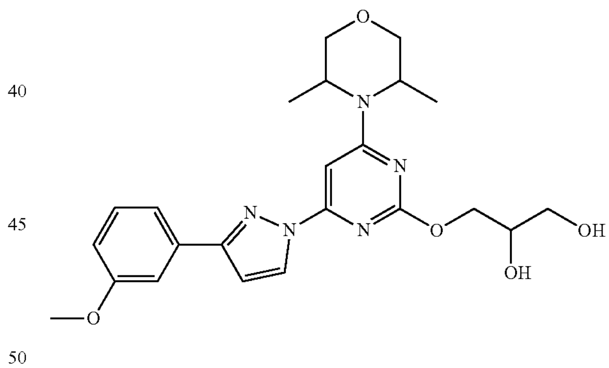
287
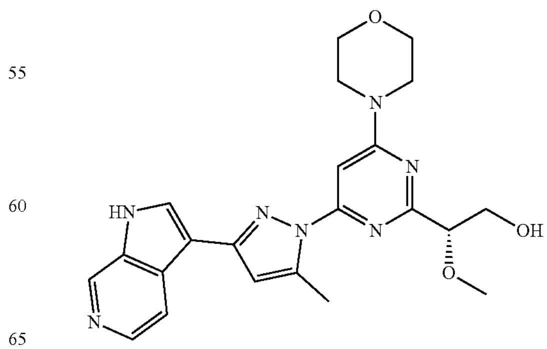

-continued
159
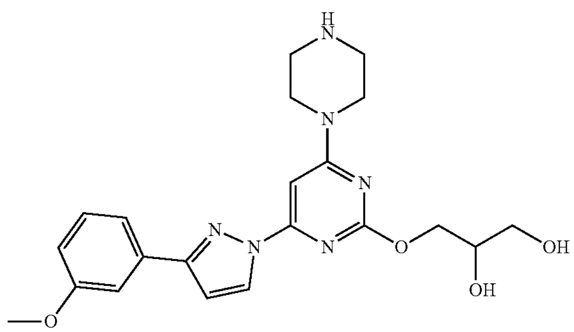
288
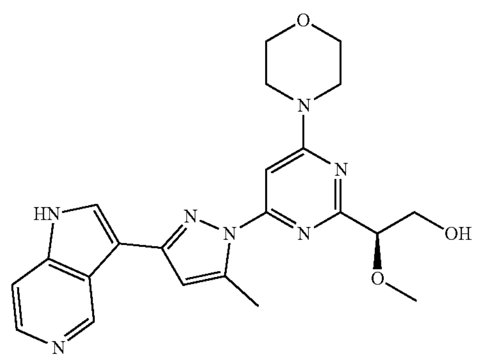
160
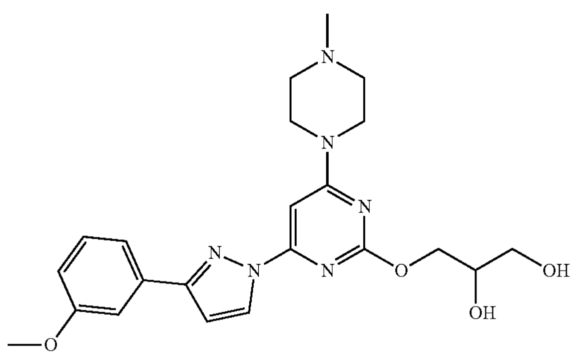
289
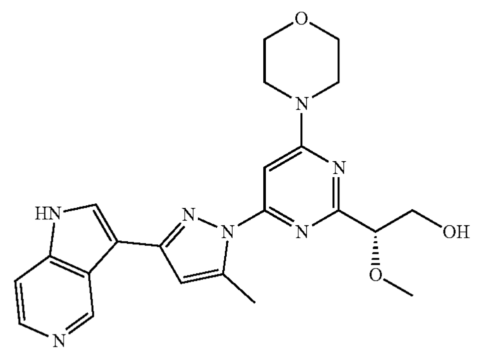
-continued
161
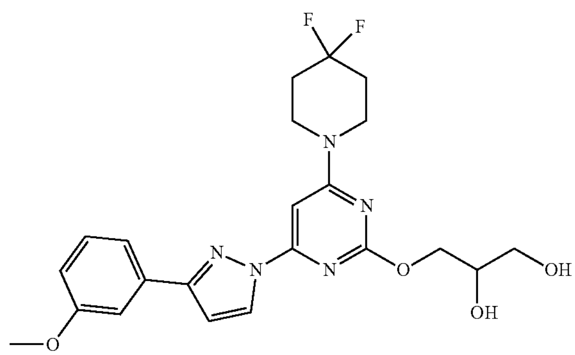
290
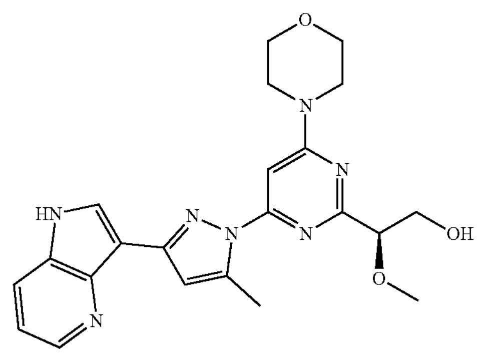
162
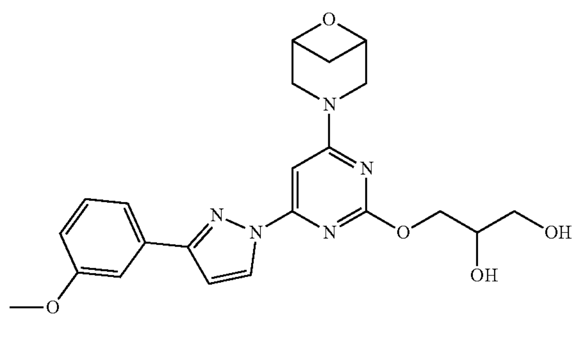
291
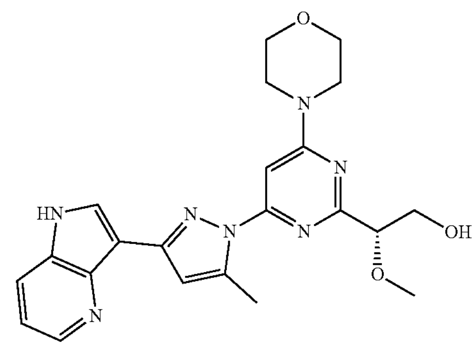

163
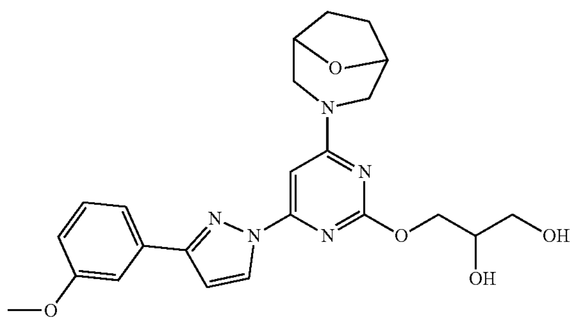
292
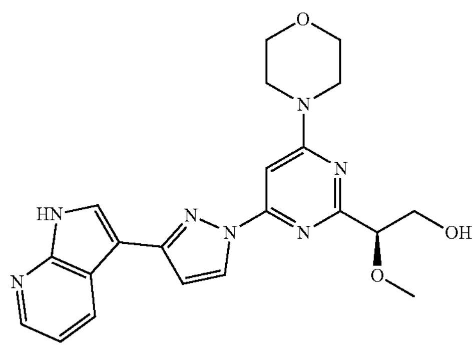
164
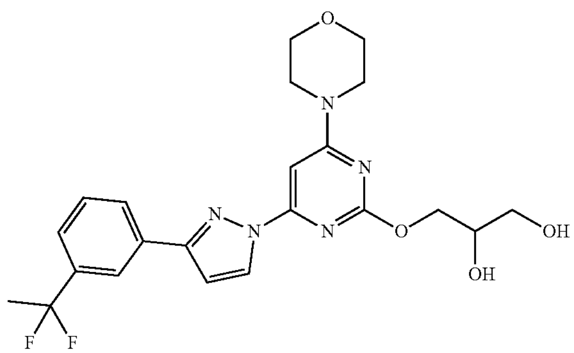
293
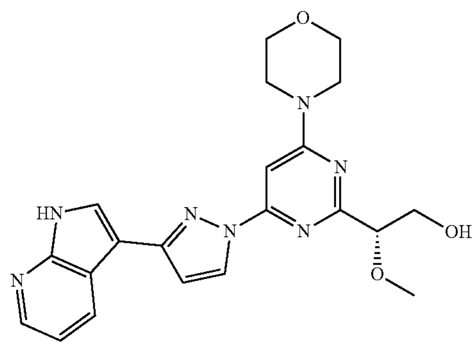
165
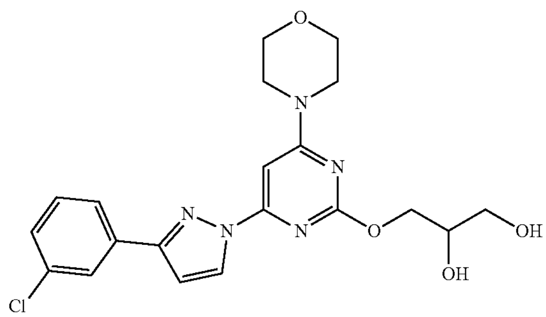
294
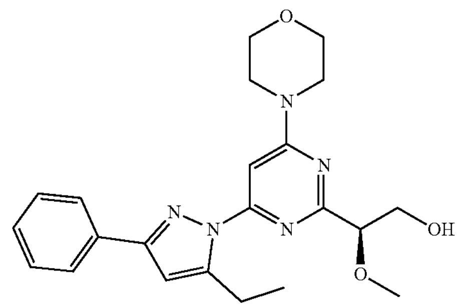
166
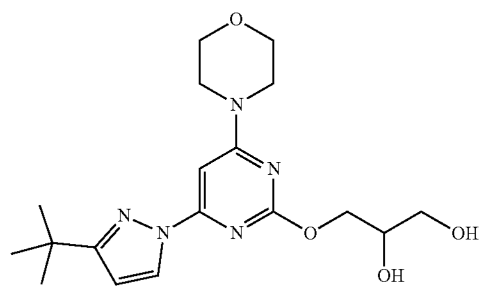
295
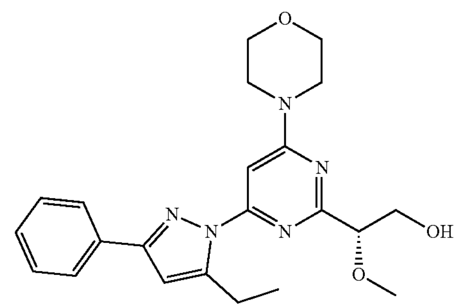
167
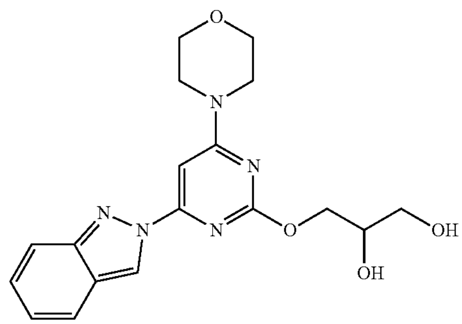

-continued
296
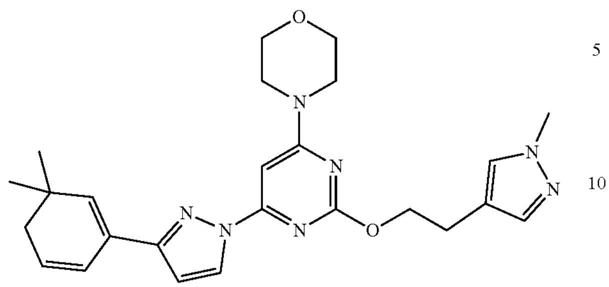
168
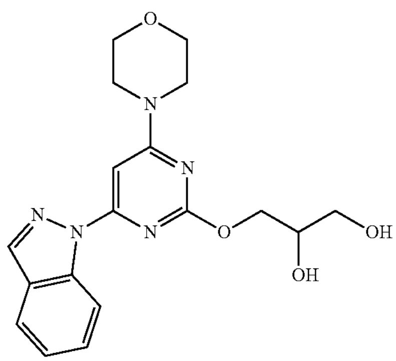
297
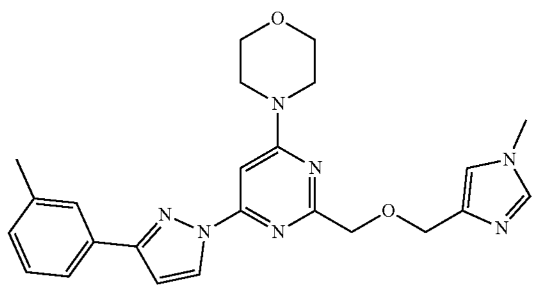
169
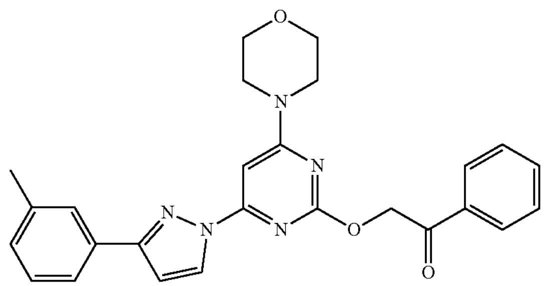
298
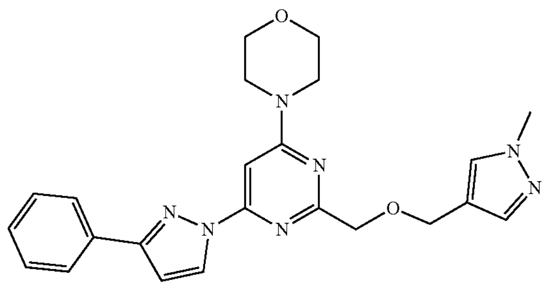
-continued
170
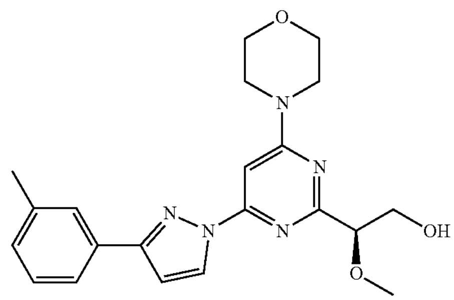
299
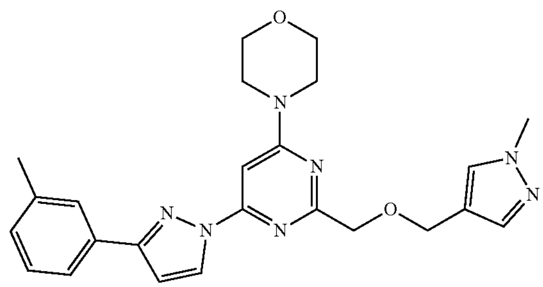
171
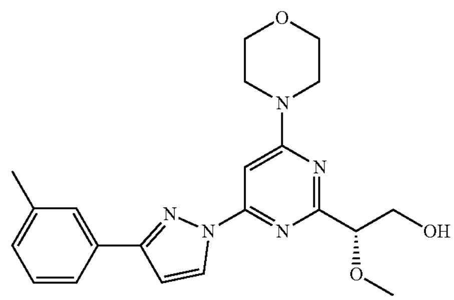
300
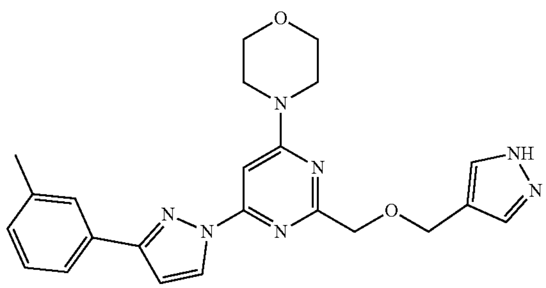
172
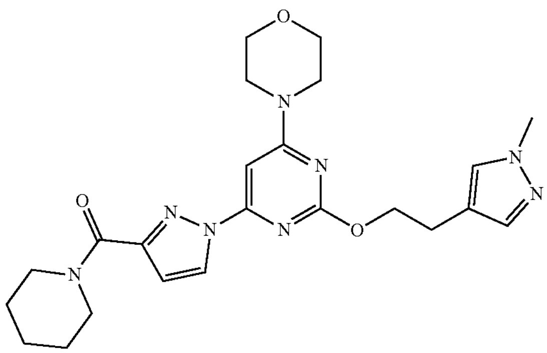

-continued
301
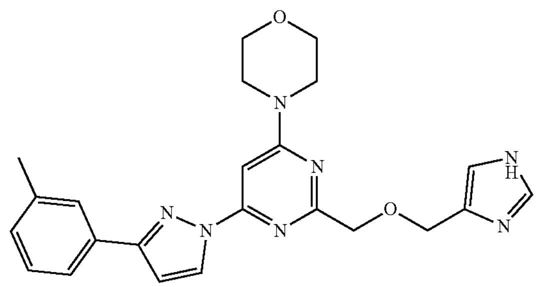
173
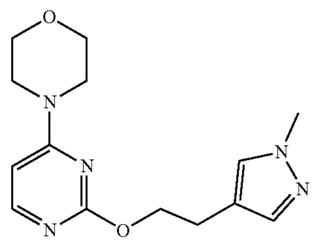
302
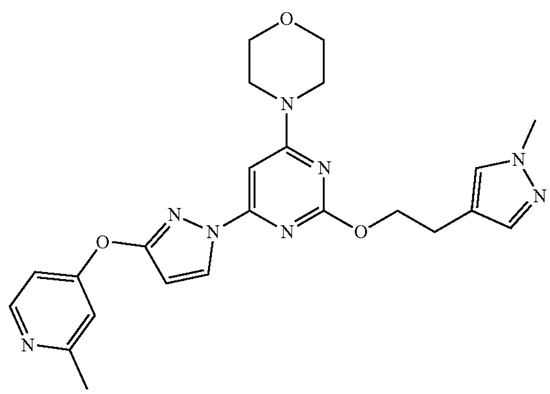
174
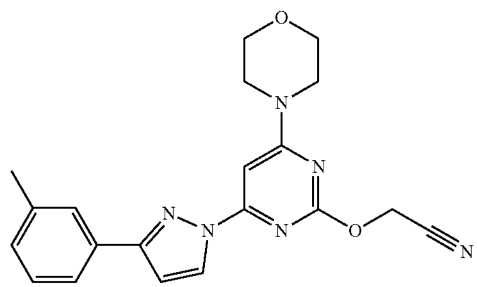
303
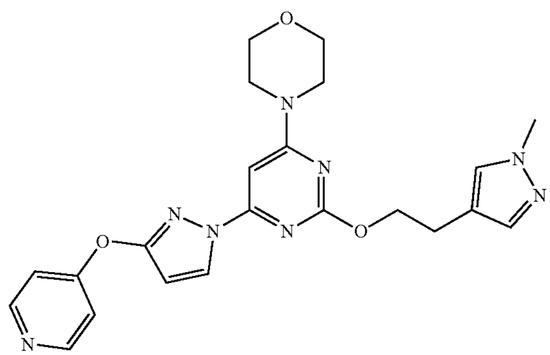
-continued
175
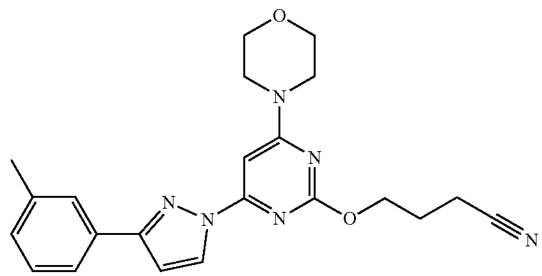
304
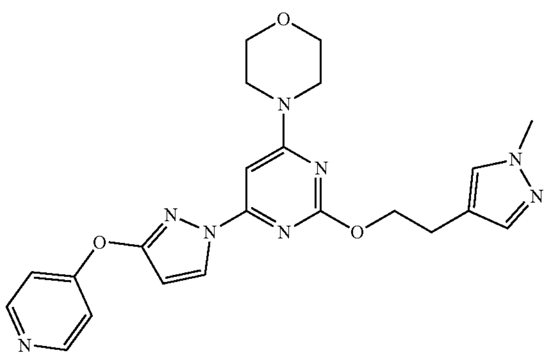
176
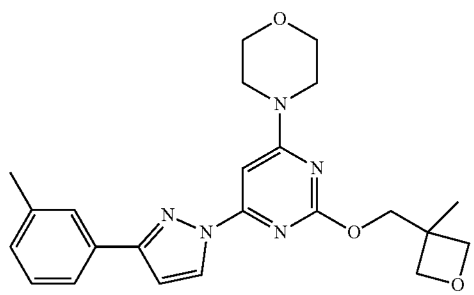
305
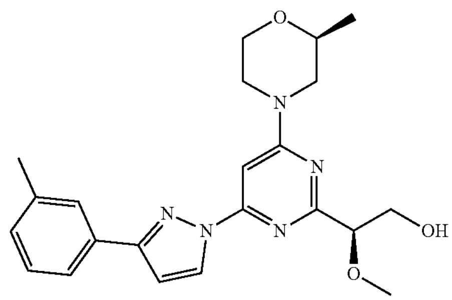
177
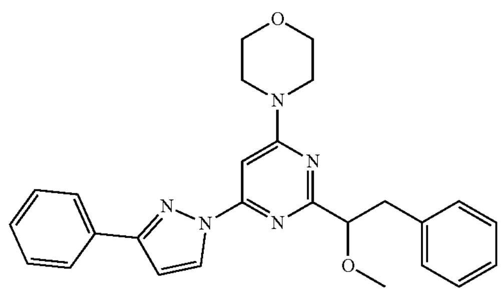

-continued
306
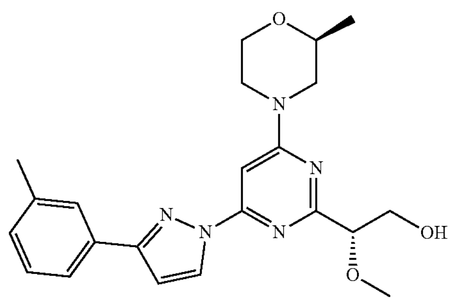
178
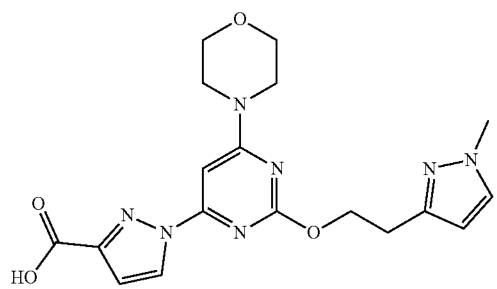
307
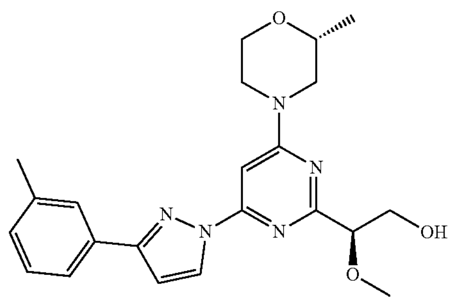
179
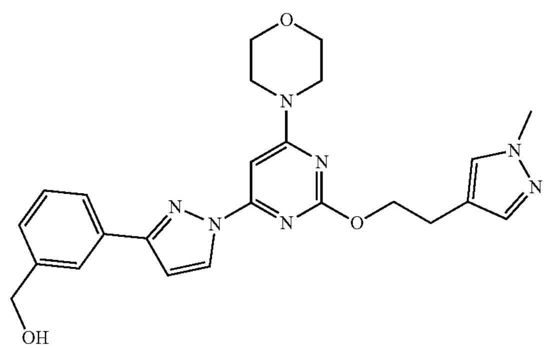
308
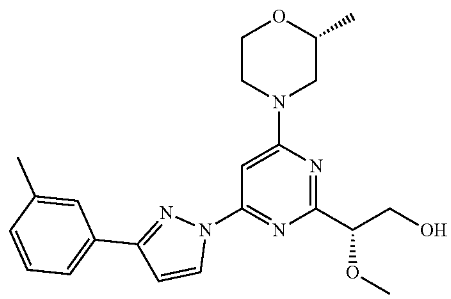
-continued
180
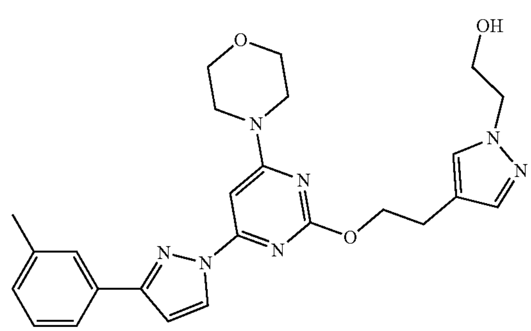
309
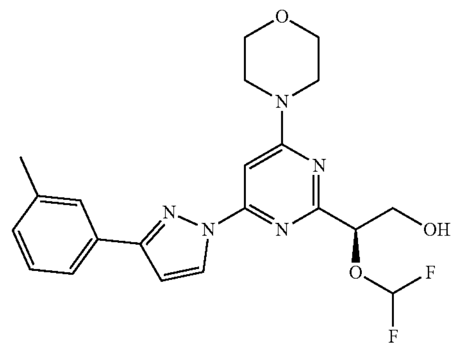
181
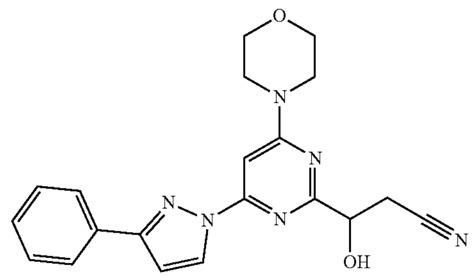
310
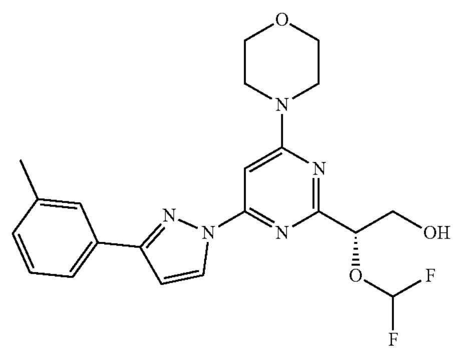
182
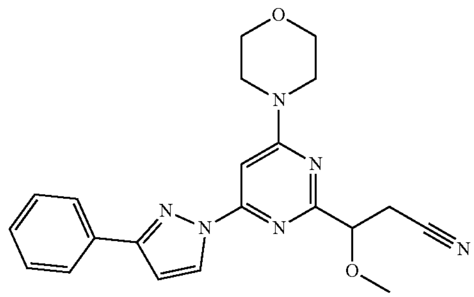

-continued
311
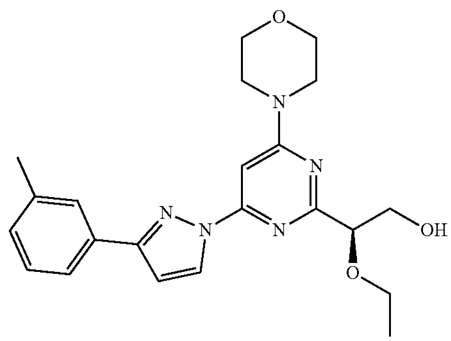
183
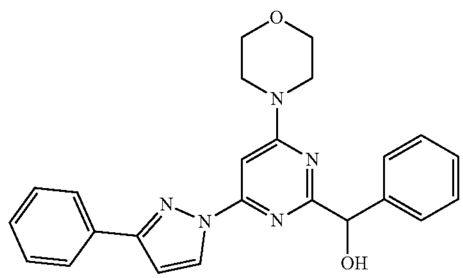
312
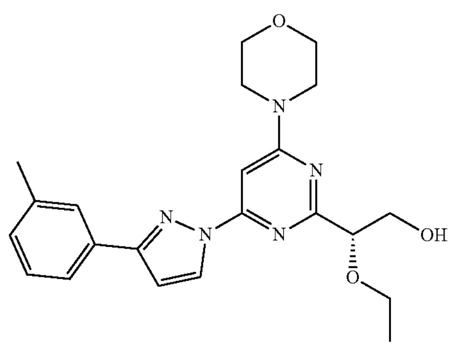
184
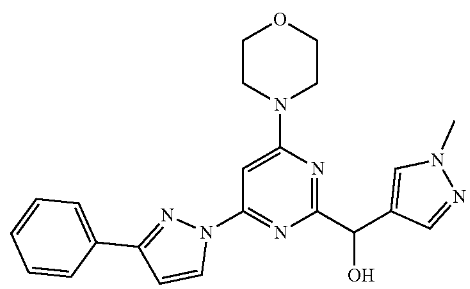
313
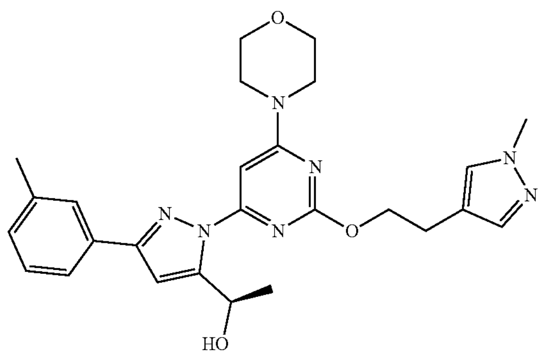
-continued
185
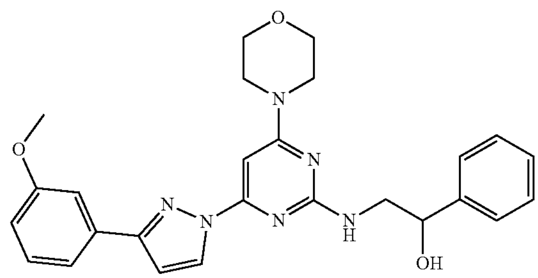
314
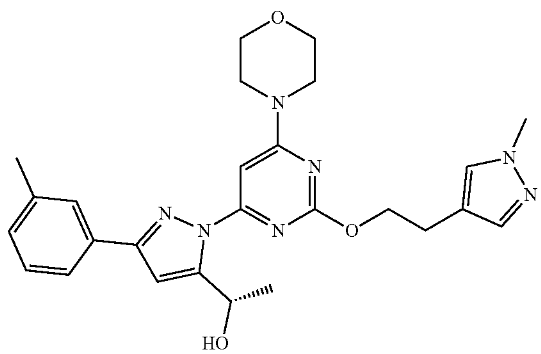
186
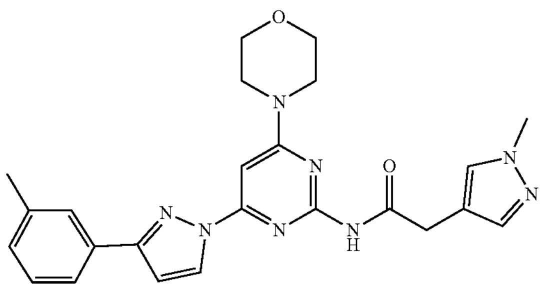
315
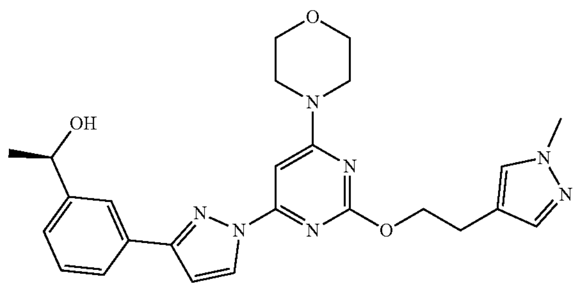
187
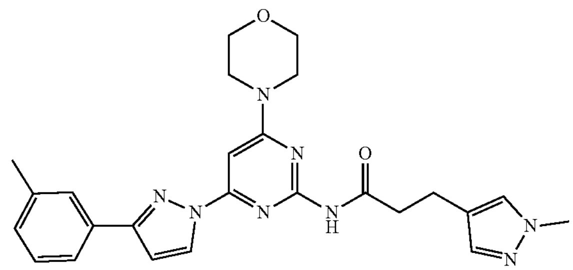

-continued
316
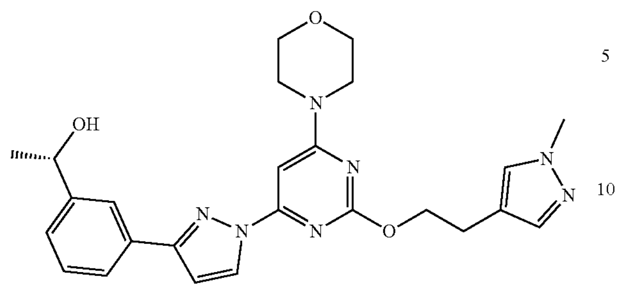
188
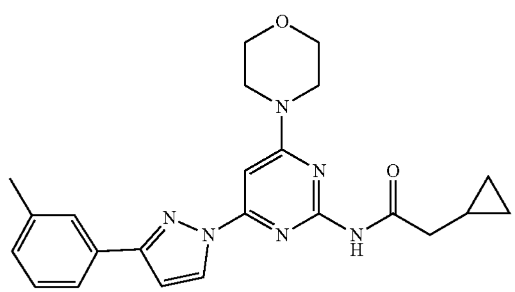
317
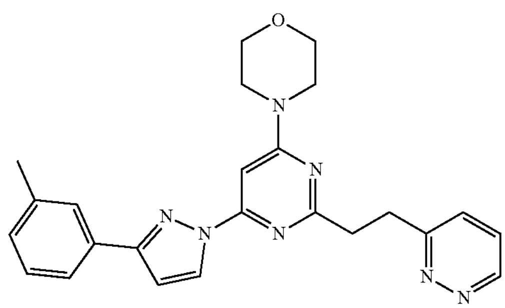
189
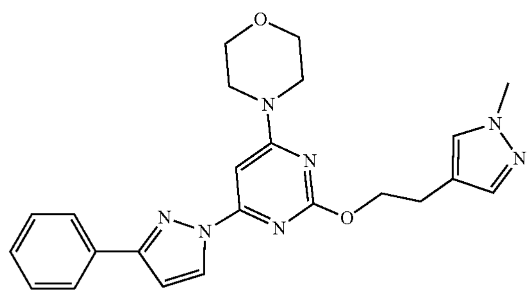
318
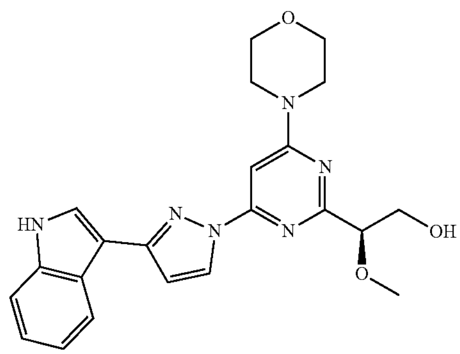
-continued
190
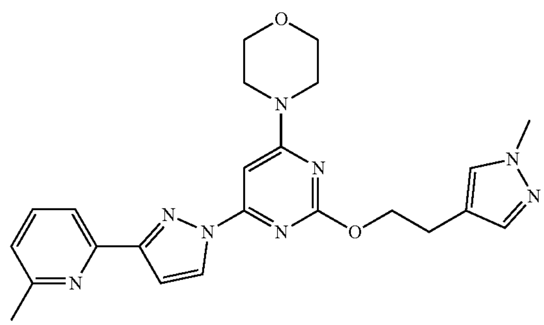
319
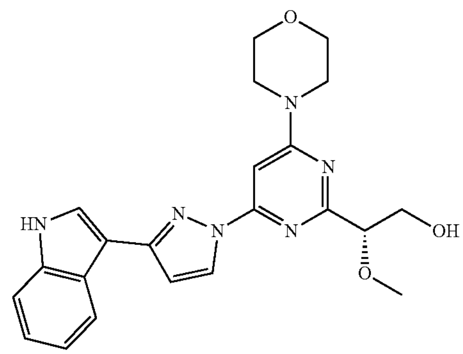
191
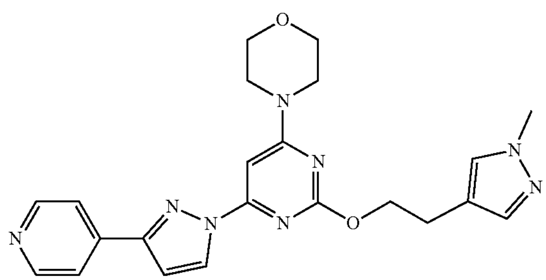
320
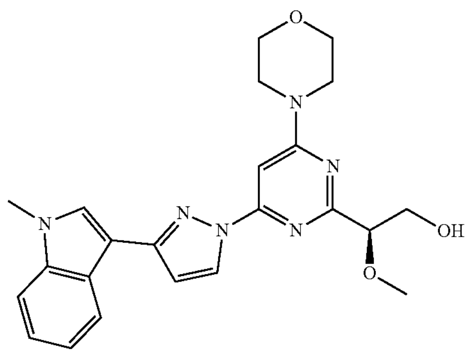
192
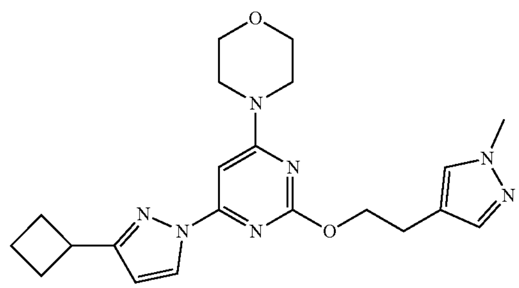

-continued
321
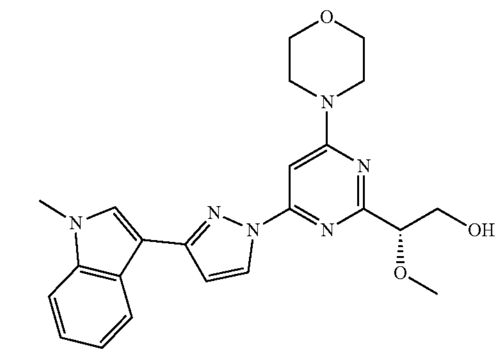
193
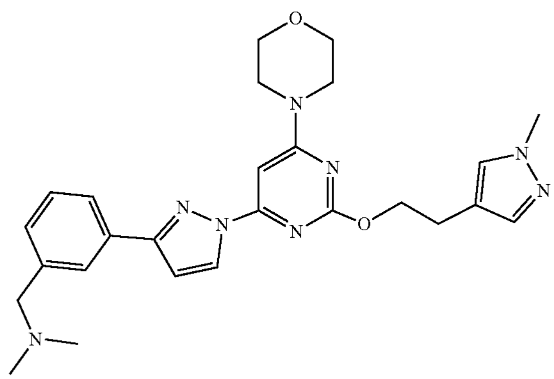
322
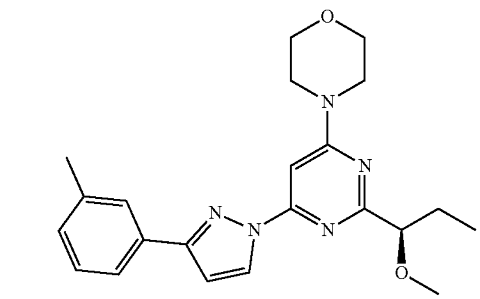
194
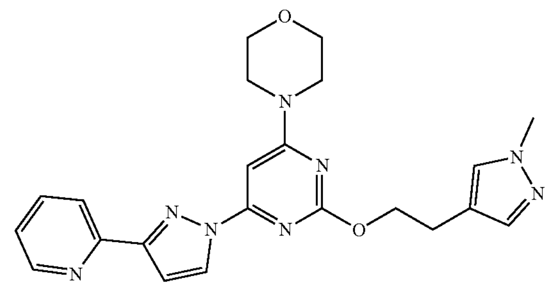
323
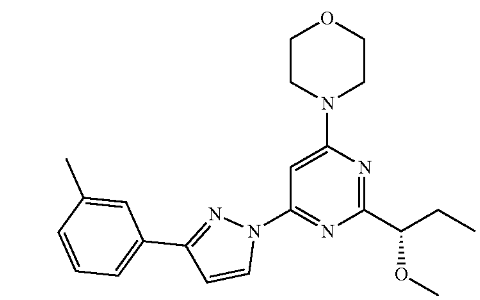
-continued
195
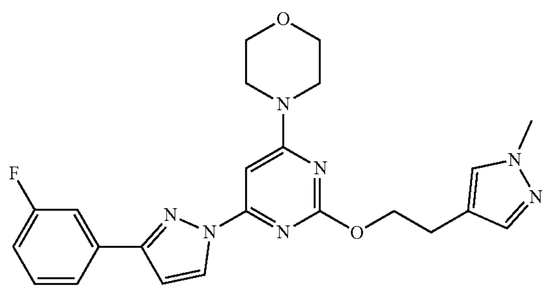
324
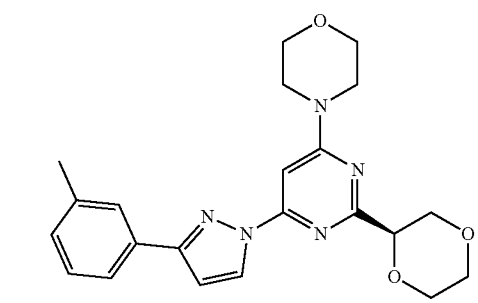
196
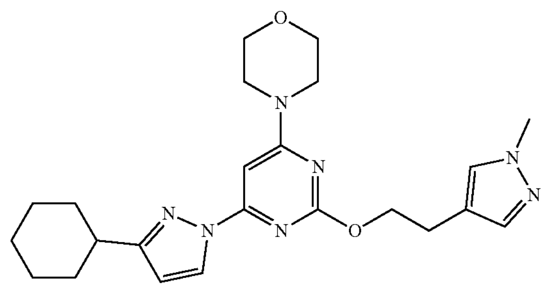
325
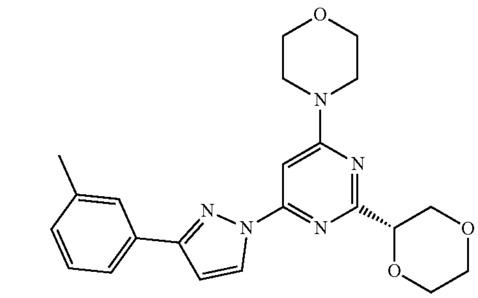
197
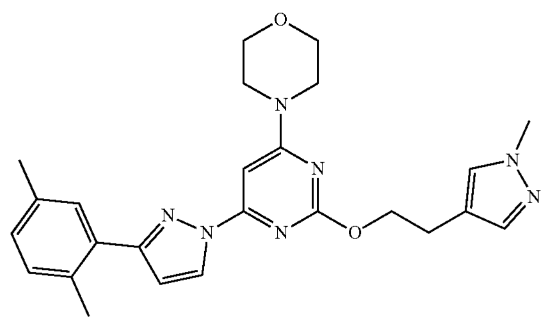

326
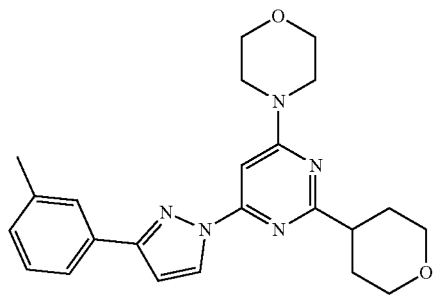
198
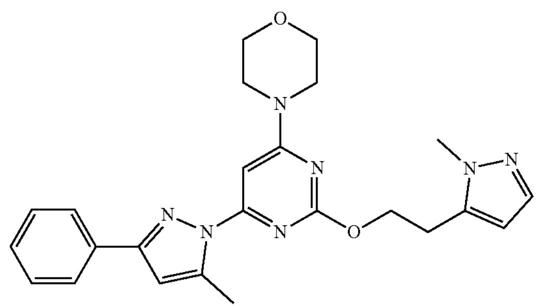
327
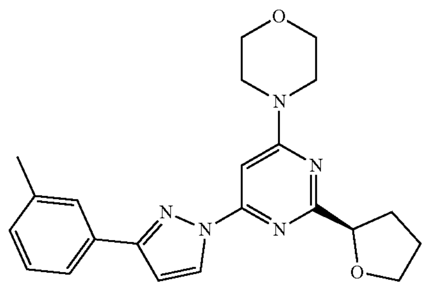
199
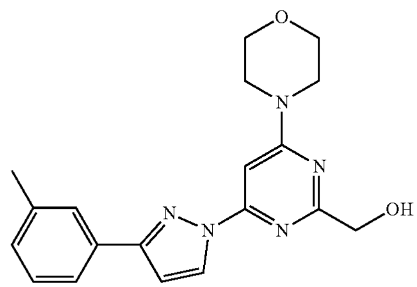
328
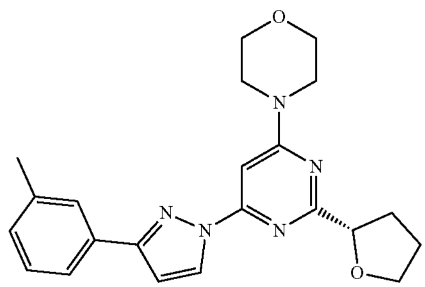
200
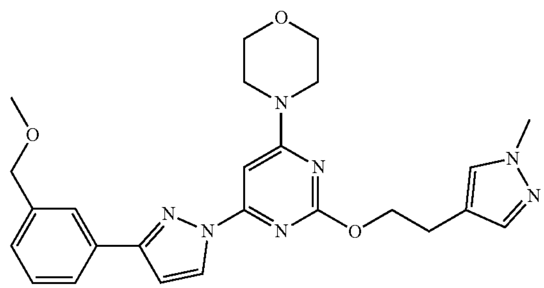
329
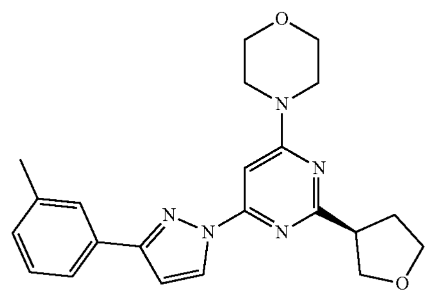
201
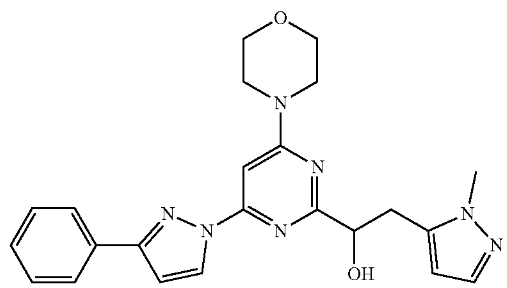
330
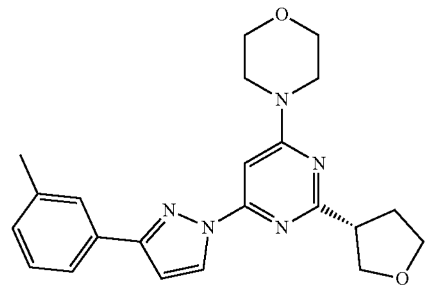
202
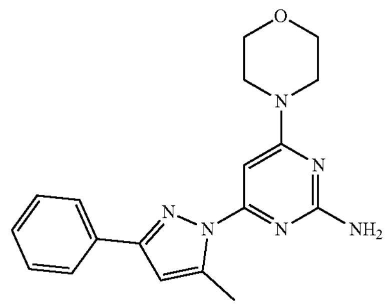

-continued
331
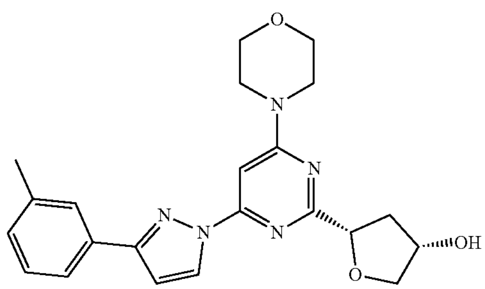
203
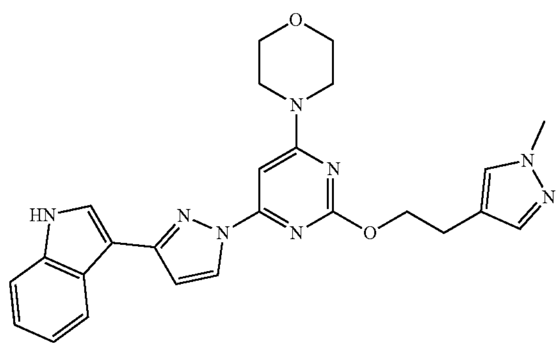
332
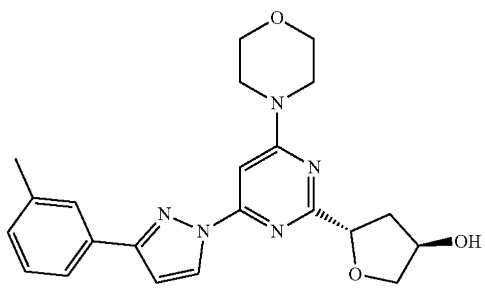
204
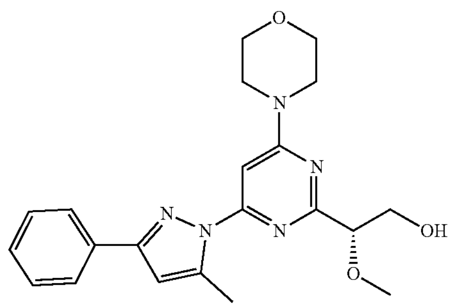
333
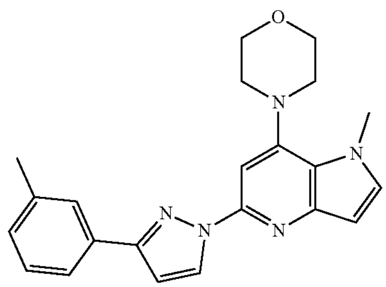
-continued
205
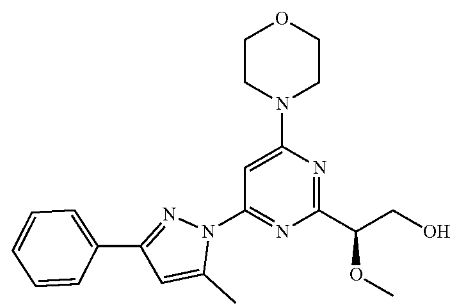
334
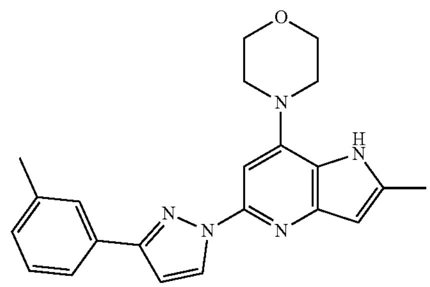
206
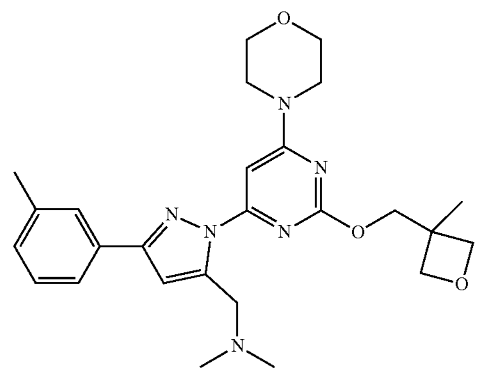
335
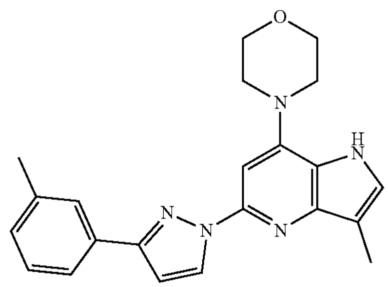
207
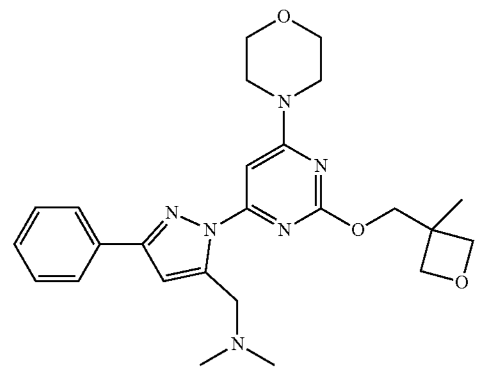

336
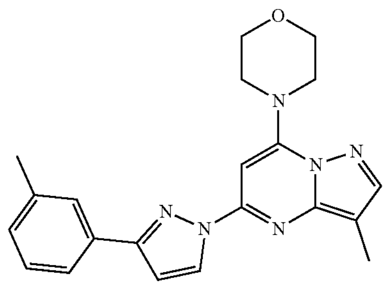
208
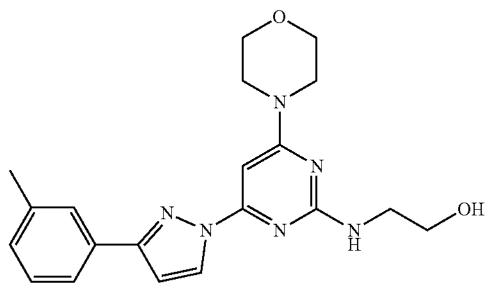
337
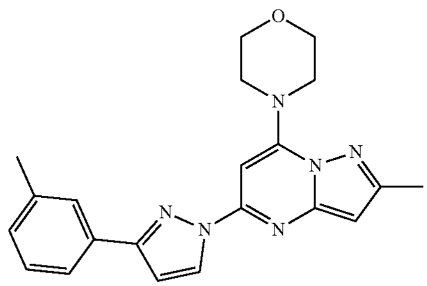
209
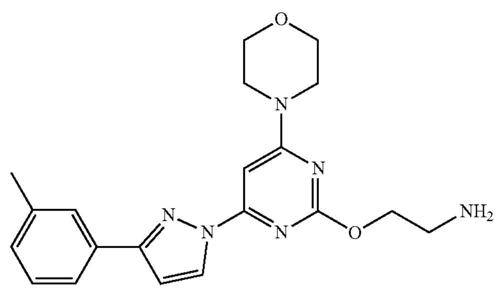
338
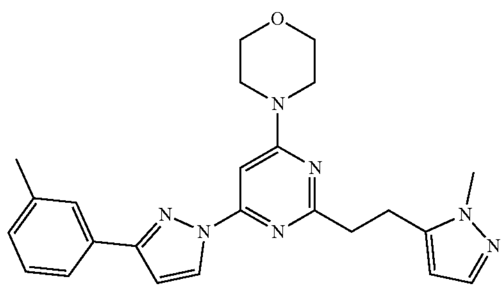
210
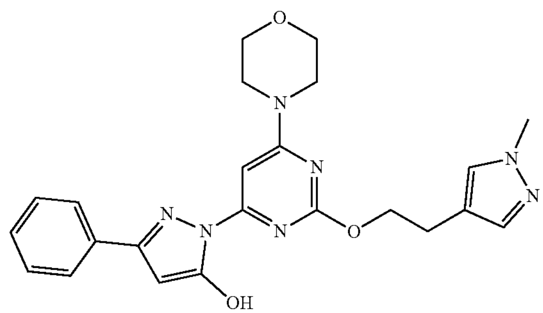
339
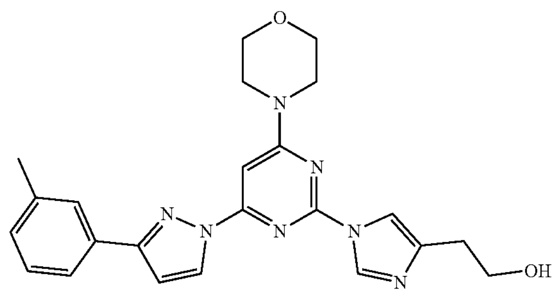
211
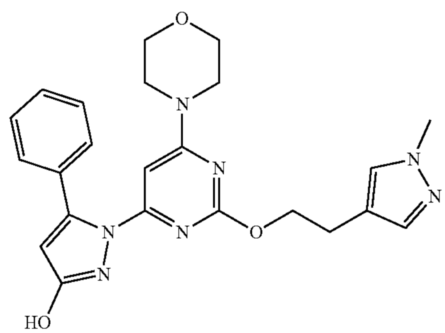
340
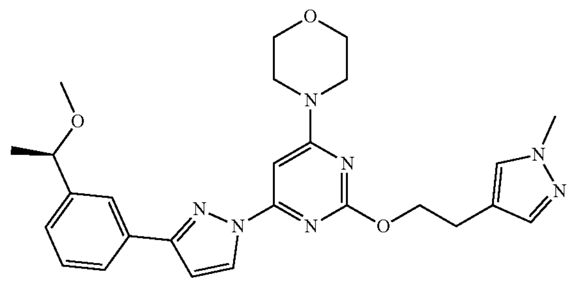
212
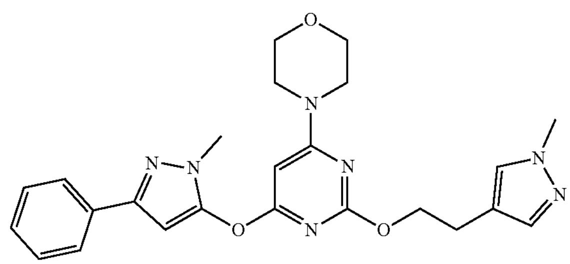

-continued
341
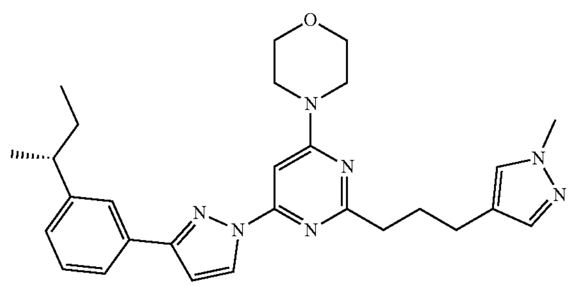
213
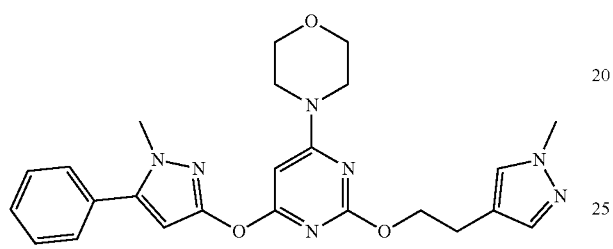
342
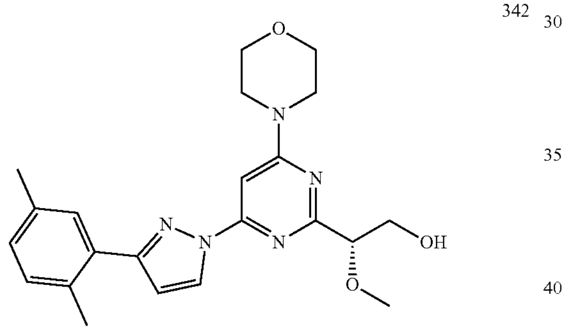
214
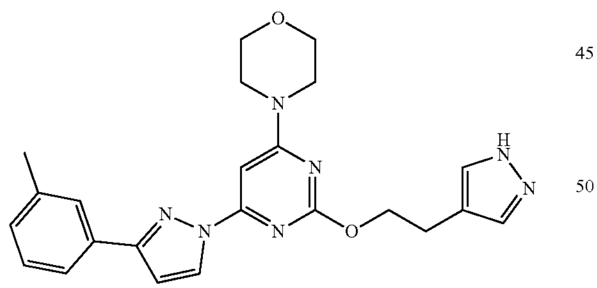
343
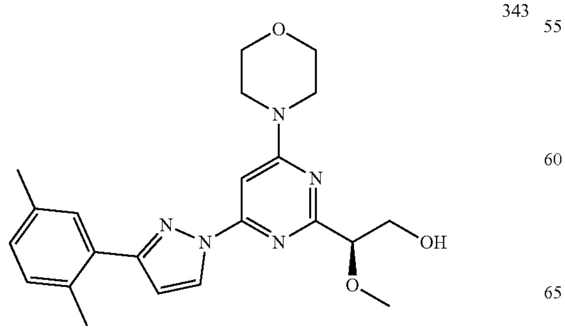
-continued
215
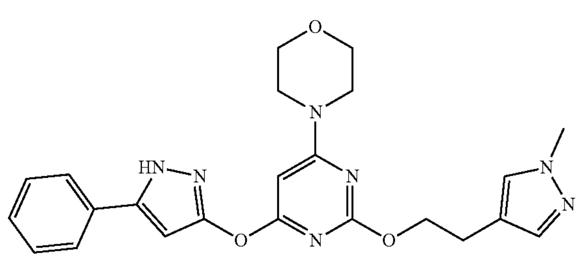
344
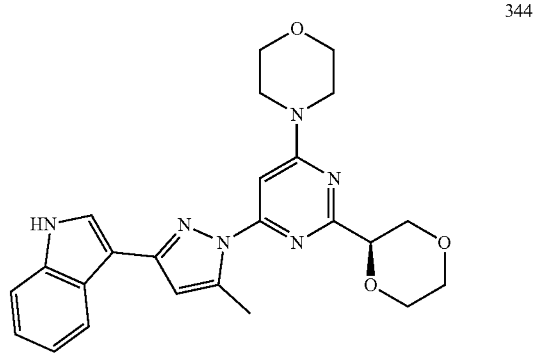
216
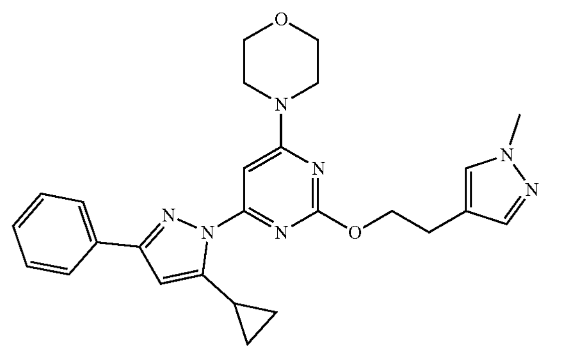
345
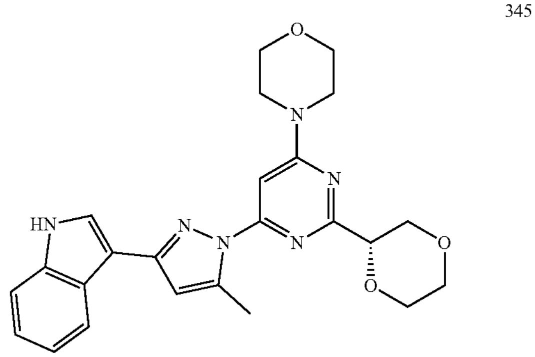

-continued
217
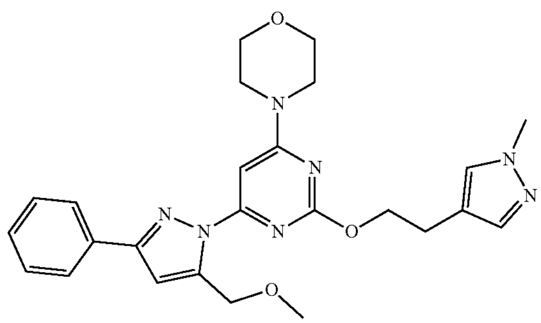
346
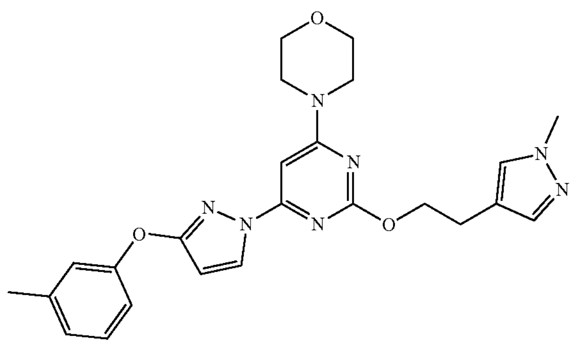
218
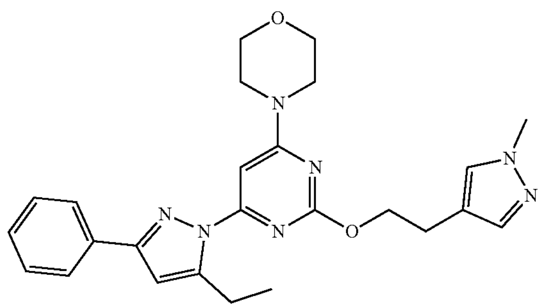
347
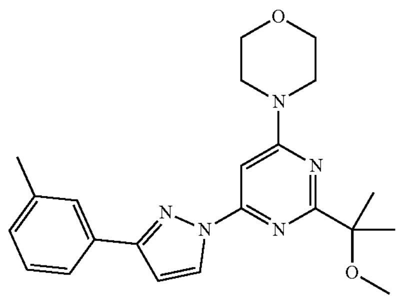
-continued
219
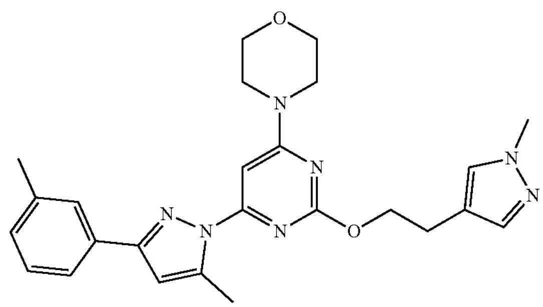
One embodiment is a compound selected from
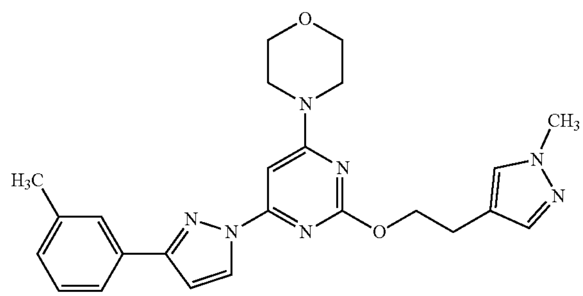
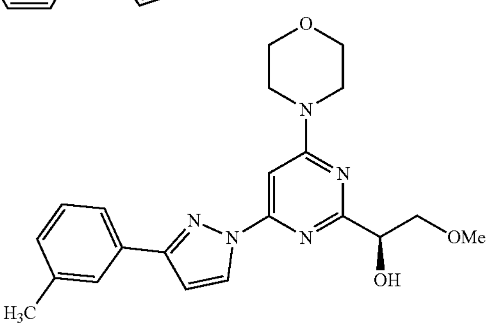
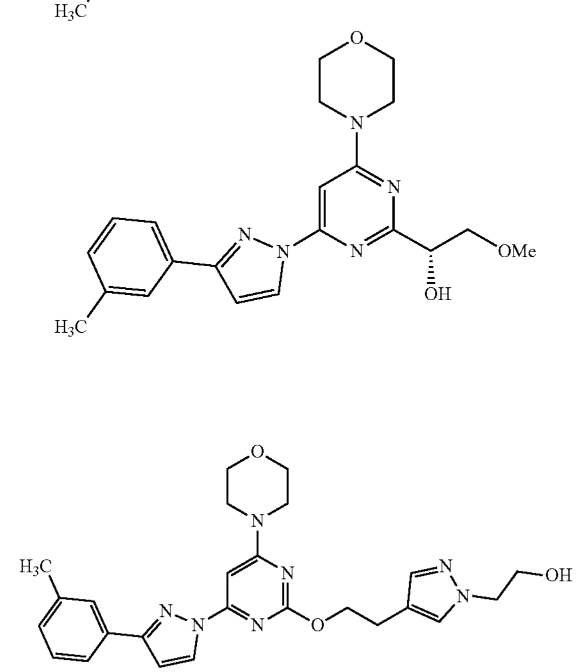

-continued
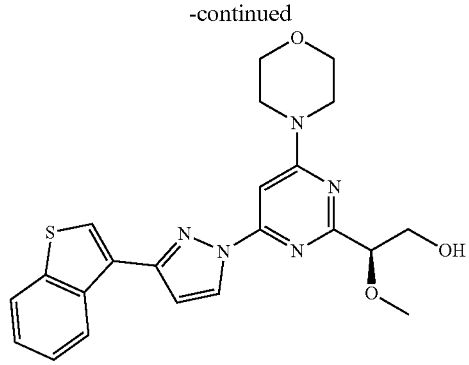
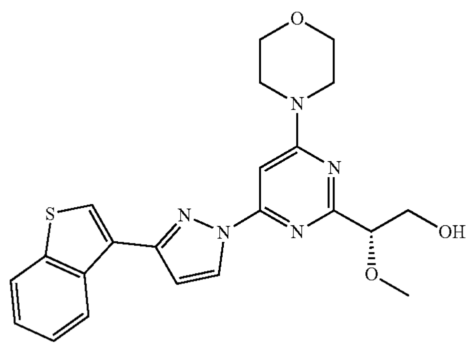
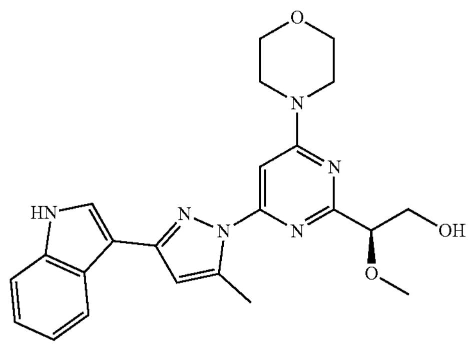
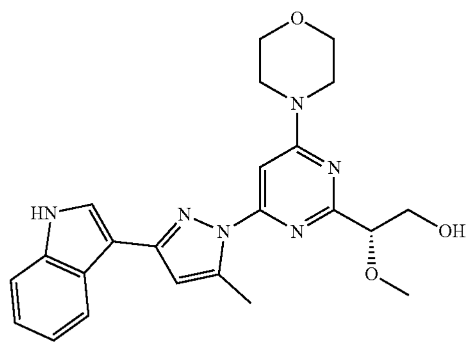
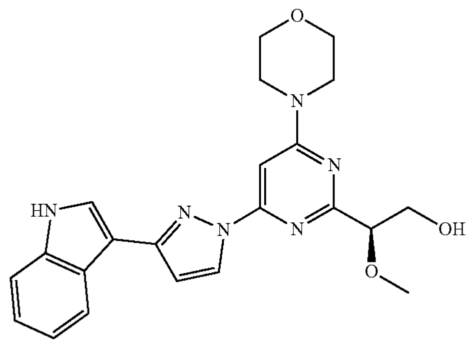
-continued
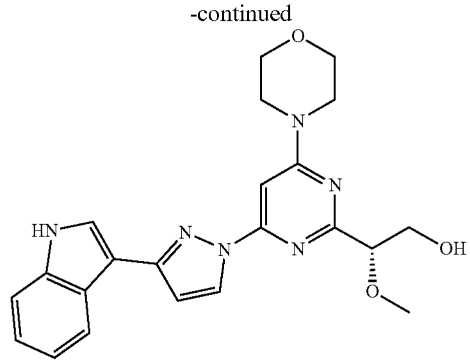
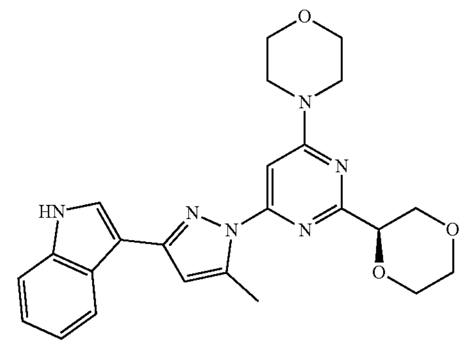
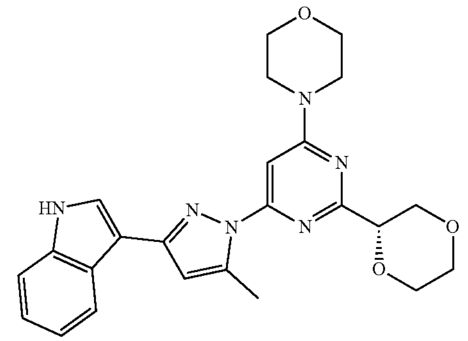
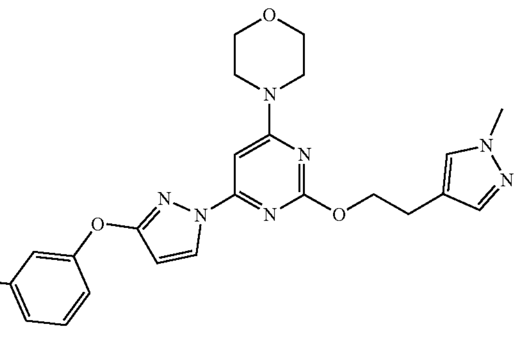
or a tautomer or pharmaceutically acceptable salt thereof.

Another embodiment is a compound selected from
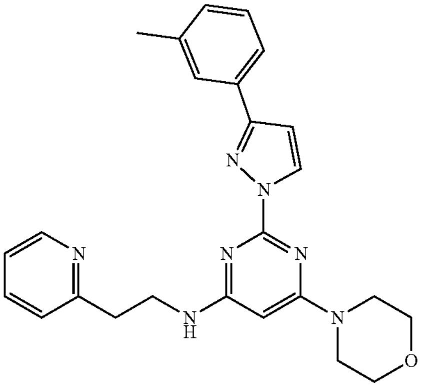
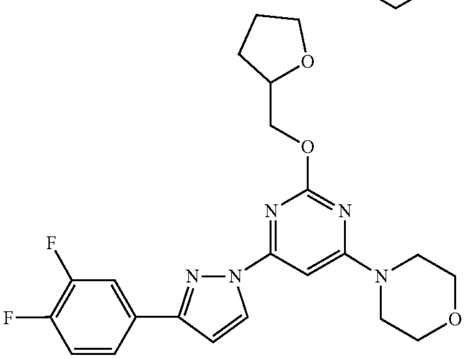
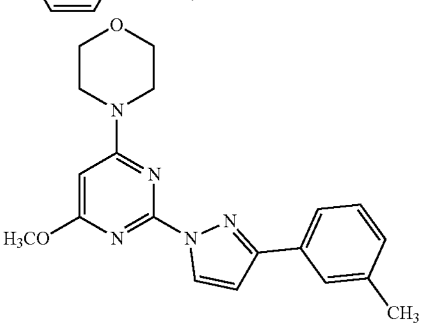
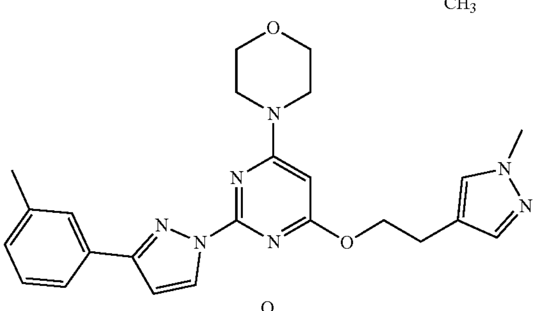
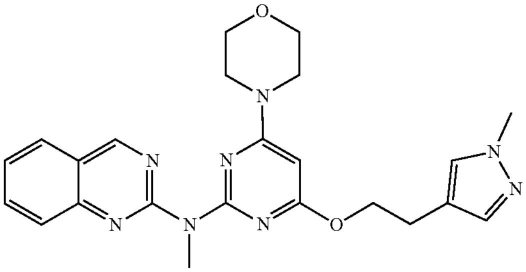
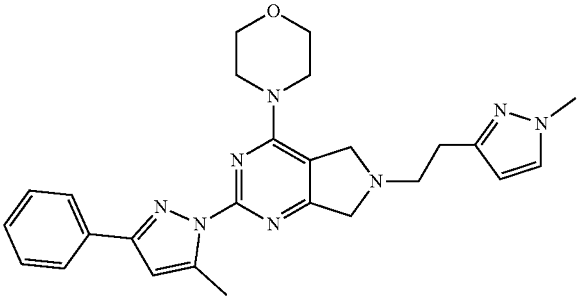
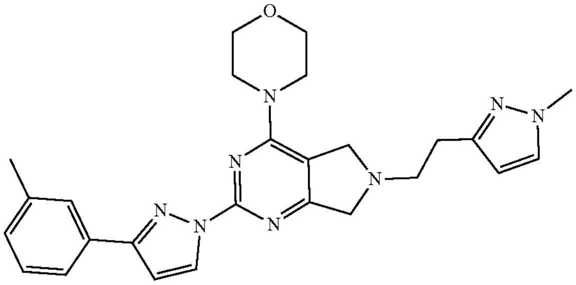
or a tautomer or pharmaceutically acceptable salt thereof.
Another embodiment is a compound selected from
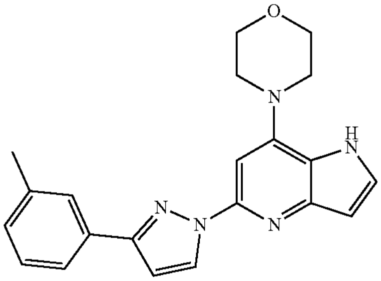
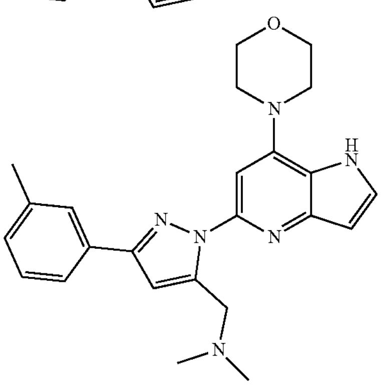
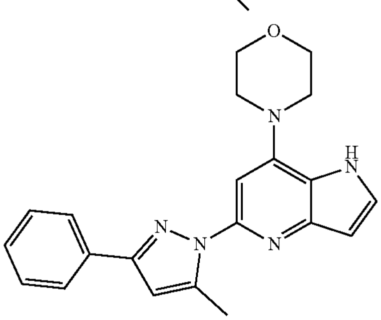
or a tautomer or pharmaceutically acceptable salt thereof.
Yet another embodiment is a compound selected from -continued

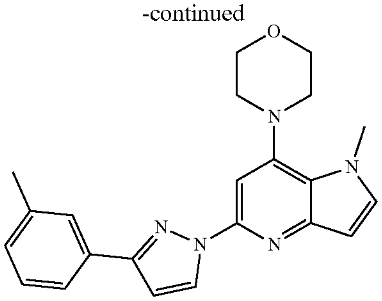

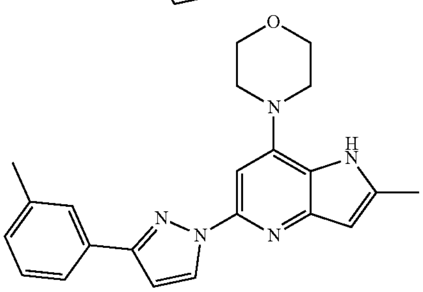

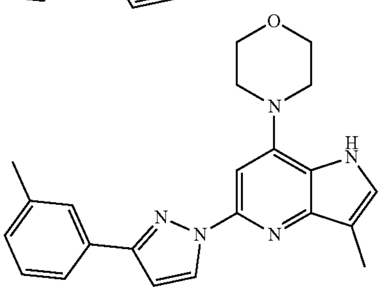

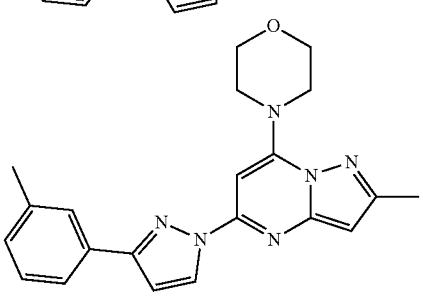

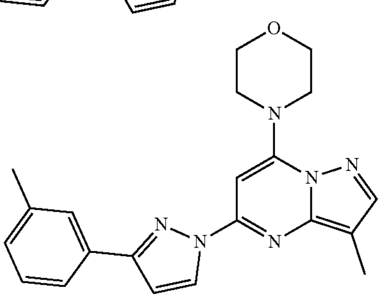

or a tautomer or pharmaceutically acceptable salt thereof.

Another embodiment is a method of inhibiting PIKfyve in a subject (such as a human subject) in need thereof comprising administering an effective amount of a compound of the present invention to the subject.

Yet another embodiment is a method for treating a disease or disorder associated with PIKfyve in a human subject in need thereof comprising administering an effective amount of a compound of the present invention to the subject.

Yet another embodiment is a method of treating a subject (preferably a human subject) having a neurological disease comprising administering an effective amount of a compound of the present invention to the subject. In one embodiment, the neurological disease is amyotrophic lateral sclerosis (ALS). In another embodiment, the neurological disease is frontotemporal dementia (FTD). In yet another embodiment, the neurological disease is Alzheimer's disease. In yet another embodiment, the neurological disease is Parkinson's disease. In yet another embodiment, the neurological disease is Huntington's disease. In yet another embodiment, the neurological disease is Charcot-Marie-Tooth disease (CMT).

In one embodiment, the effective amount of the compound is the amount effective to inhibit cellular PIKfyve activity in target cells in the subject. In another embodiment, the effective amount is the amount effective to induce vacuolization and disrupts intracellular trafficking in target cells.

In one embodiment, the target cell is a cancer cell. In one embodiment, the cancer cell is a lymphoma cell. In one embodiment, the lymphoma cell is a non-Hodgkin's lymphoma cell.

In one embodiment, the disease or disorder is selected from a cancer, a viral infection, or a cell proliferative disorder. For example, the cancer can be a lymphoma or melanoma. In one embodiment, the cancer is refractory or resistant to standard therapy. In one embodiment, the cancer is a non-Hodgkin's lymphoma.

One embodiment is a method of treating a viral infection in a subject in need thereof comprising administering an effective amount of a compound of the present invention to the subject. The viral infection can be caused by any type of virus such as RNA and DNA viruses. In one embodiment, the virus is Ebola virus. In another embodiment, the virus is middle east respiratory syndrome virus (MERS). In yet another embodiment, the virus is JC polyomavirus (JC). In yet another embodiment, the virus is BK polyomavirus (BK). In yet another embodiment, the virus is Herpes Simplex Virus (HSV). In yet another embodiment, the virus is Marburg virus (MarV). In yet another embodiment, the virus is Venezuelan equine encephalitis virus (VEEV). In yet another embodiment, the virus is Lymphocytic choriomeningitis virus (LCMV).

Another embodiment is method of treating Charcot-Marie-Tooth disease (CMT) in a subject, preferably a human subject, in need of such treatment, by administering an effective amount of a compound of the present invention to the subject.

One embodiment is a method for treating a lymphoma comprising administering (e.g., an effective amount of) a compound of the present invention and at least one additional active agent. In one embodiment, the at least one additional active agent is selected from ibrutinib, rituximab, doxorubicin, prednisolone, vincristine, velcade, and everolimus, and combinations thereof. In one embodiment, the method includes a therapeutic regimen comprising administering a compound of the present invention and a CHOP regimen.

In one embodiment, the method is a method for treating melanoma and the method further comprises administering at least one additional active agent to the subject in a therapeutic regimen comprising a compound of the present invention and the at least one additional active agent. In one embodiment, the at least one additional active agent is selected from dacarbazine, temozolomide, Nab-paclitaxel, carmustine, cisplatin, carboplatin, or vinblastine.

In one embodiment, the method is a method for treating a viral infection and the method further comprises administering at least one additional active agent to the subject in a therapeutic regimen comprising a compound of the present invention and the at least one additional active agent. In one embodiment, the at least one additional active agent is selected from selected from the group consisting of apilimod, APY0201, and YM-201636.

In accordance with any of the methods described herein, a compound of the present invention may also be administered in combination with a non-therapeutic agent which mitigates one or more side effects associated with the compound or increases the bioavailability of the compound. In one embodiment, the non-therapeutic agent is selected from the group consisting of ondansetron, granisetron, dolasetron and palonosetron. In another aspect, the non-therapeutic agent is selected from the group consisting of pindolol and risperidone. In another aspect, the non-therapeutic agent is selected from a cytochrome P450 3A (CYP3A) inhibitor. In one embodiment, the CYP3A inhibitor is selected from ritonavir and cobicistat.

In one embodiment, the viral infection is caused by a virus selected from the group consisting of measles, Ebola (EboV), Marburg (MarV), borna disease, and human immunodeficiency virus (HIV), severe acute respiratory system virus (SARS), and middle east respiratory syndrome virus (MERS). In one embodiment, the viral infection is caused by an EboV virus.

In one embodiment, the compound is in the form a pharmaceutical composition comprising the compound and at least one pharmaceutically acceptable carrier.

In one embodiment, the compound comprises at least 95% or at least 99% enantiomeric excess of the (R)-enantiomer. In one embodiment, the compound comprises at least 95% or at least 99% enantiomeric excess of the (S)-enantiomer.

Another embodiment is pharmaceutical composition comprising a compound of the present invention wherein the compound comprises at least 95% or at least 99% enantiomeric excess of the (R)-enantiomer or the (S)-enantiomer.

DETAILED DESCRIPTION OF THE INVENTION

Definitions

As used herein the following definitions shall apply unless otherwise indicated. Further, many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl group as defined above having up to 6 carbon atoms. The term "$C_{1-3}$ alkyl" refers to an alkyl group as defined above having up to 3 carbon atoms. In appropriate circumstances, the term "alkyl" refers to a hydrocarbon chain radical as mentioned above which is bivalent.

The term "alkenyl", unless otherwise specified, refers to an aliphatic hydrocarbon group containing one or more carbon-carbon double bonds and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl. The term "$C_{2-6}$ alkenyl" refers to an alkenyl group as defined above having up to 6 carbon atoms. In appropriate circumstances, the term "alkenyl" refers to a hydrocarbon group as mentioned above which is bivalent.

The term "alkynyl", unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butnyl. The term "$C_{2-6}$ alkynyl" refers to an alkynyl group as defined above having up to 6 carbon atoms. In appropriate circumstances, the term "alkynyl" refers to a hydrocarbyl radical as mentioned above which is bivalent.

The term "alkoxy" unless otherwise specified, denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O-(substituted alkyl). For example "alkoxy" refers to the group —O-alkyl, including from 1 to 8 carbon atoms of a straight, branched, cyclic configuration and combinations thereof attached to the parent structure through an oxygen atom. Examples include methoxy, ethoxy, propoxy, isopropoxy, cyclopropyloxy, and cyclohexyloxy. In appropriate circumstances, the term "alkoxy" refers to a group as mentioned above which is bivalent.

The term "cycloalkyl", unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., spiro[4.4]non-2-yl. The term "$C_{3-6}$ cycloalkyl" refers to a cycloalkyl group as defined above having up to 6 carbon atoms.

The term "cycloalkylalkyl", unless otherwise specified, refers to a cyclic ring-containing radical containing in the range of about 3 up to 8 carbon atoms directly attached to an alkyl group which is then attached to the main structure at any carbon from the alkyl group, such as cyclopropylmethyl, cyclobutylethyl, and cyclopentylethyl.

The term "cycloalkenyl", unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which is then attached to the main structure at any carbon from the alkyl group.

The term "aryl", unless otherwise specified, refers to aromatic radicals having in the range of 6 up to 20 carbon atoms such as phenyl, naphthyl, tetrahydronaphthyl, indanyl, and biphenyl.

The term "arylalkyl", unless otherwise specified, refers to an aryl group as defined above directly bonded to an alkyl group as defined above, e.g., $—CH_2C_6H_5$ and $—C_2H_5C_6H_5$.

The term "heterocyclic ring", unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom.

The term "heterocyclyl", unless otherwise specified, refers to a heterocylic ring radical as defined above. The heterocylcyl ring radical may be attached to the main structure at any heteroatom or carbon ring atom. In appropriate circumstances, the term "heterocyclyl" refers to a hydrocarbon chain radical as mentioned above which is bivalent.

The term "heterocyclylalkyl", unless otherwise specified, refers to a heterocylic ring radical as defined above directly bonded to an alkyl group. The heterocyclylalkyl radical may be attached to the main structure at any carbon atom in the alkyl group. Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl", unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamo holinyl, thiamorpholinyl sulfoxide, thiamo holinyl sulfone, dioxaphospholanyl, oxadiazolyl, chromanyl, and isochromanyl.

The term "5 or 6-membered heteroaryl" refers to a heteroaryl having 5- or 6-ring atoms. The term "5-6 or 6-5 membered bicyclic heteroaryl" refers to a bicyclic heteroaryl with a five-membered ring fused to a six-membered ring, where the 5-membered ring is bound to the rest of the molecule (referred as a "5-6 membered bicyclic heteroaryl") or the 6-membered ring is bound to the rest of the molecule (referred as a "6-5 membered bicyclic heteroaryl"). The term "6-6 membered bicyclic heteroaryl" refers to a bicyclic heteroaryl with a six-membered ring fused to a another six-membered ring, where one of the 6-membered rings is bound to the rest of the molecule.

The heteroaryl ring radical may be attached to the main structure at any heteroatom or carbon atom. The term "substituted heteroaryl" also includes ring systems substituted with one or more oxide (—O—) substituents, such as pyridinyl N-oxides.

The term "heteroarylalkyl", unless otherwise specified, refers to a heteroaryl ring radical as defined above directly bonded to an alkyl group. The heteroarylalkyl radical may be attached to the main structure at any carbon atom from alkyl group.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)RX, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, =N—NR$^x$R$^y$, —NR$^x$C(O)OR$^y$, —NR$^x$R$^y$, —NR$^x$C(O)R$^y$, —NR$^x$C(S)R$^y$—NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^x$ (e.g., R$^x$ can be hydrogen or C$_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Non-limiting examples of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound.

Additionally, the instant invention also includes the compounds which differ only in the presence of one or more isotopically enriched atoms for example replacement of hydrogen with deuterium or tritium, the replacement of a carbon by $^{13}C$- or $^{14}C$-enriched carbon, or the replacement of a nitrogen by $^{15}N$.

The compounds of the present invention may also contain unnatural proportions of atomic isotopes at one or more of atoms that constitute such compounds. For example, the compounds may be radiolabeled with radioactive isotopes, such as for example tritium, iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, and alkyl sulphates. Salts may include acid addition salts where appropriate which are sulphates, nitrates, phosphates, perchlorates, borates, hydrohalides (e.g., hydrochlorides), acetates, tartrates, maleates, citrates, fumarates, succinates, palmoates, methanesulphonates, benzoates, salicylates, benzenesulfonates, ascorbates, glycerophosphates, and ketoglutarates. Salts can be formed by methods known in the art.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried. In one embodiment, the amount of compound administered ranges from about 0.1 mg to 5 g, from about 1 mg to 2.0 g, from about 100 mg to 1.5 g, from about 200 mg to 1.5 g, from about 400 mg to 1.5 g, and from about 400 mg to 1.0 g.

As used herein, the term "treating" refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

A "neurological disease" is any disease that causes electrical, biochemical, or structural abnormalities in the brain, spine, or neurons. For example, a neurological disease may be a neurodegenerative disease. The neurodegenerative disease may result in motor neuron degeneration, for example. The neurological disease may be amyloid lateral sclerosis, Huntington's disease, Alzheimer's disease, or frontotemporal dementia, for example. Further examples of neurological diseases include, but are not limited to, Parkinson's disease, multiple sclerosis, peripheral myopathy, Rasmussen's encephalitis, attention deficit hyperactivity disorder, autism, central pain syndromes, anxiety, and/or depression, for example.

Neurodegenerative diseases result in the progressive destruction of neurons that affects neuronal signaling. For example, a neurodegeneration may be amyotrophic lateral sclerosis, Alzheimer's disease, Huntington's disease, Friedreich's ataxia, Lewy body disease, Parkinson's disease, spinal muscle atrophy, primary lateral sclerosis, progressive muscle atrophy, progressive bulbar palsy, and pseudobulbar palsy.

The term "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The term "patient" refers to a human subject.

In accordance with the methods described herein, a "subject in need of" is a subject having a disease, disorder or condition, or a subject having an increased risk of developing a disease, disorder or condition relative to the population at large. The subject in need thereof can be one that is "non-responsive" or "refractory" to a currently available therapy for the disease or disorder, for example cancer. In this context, the terms "non-responsive" and "refractory" refer to the subject's response to therapy as not clinically adequate to relieve one or more symptoms associated with the disease or disorder. In one aspect of the methods described here, the subject in need thereof is a subject having cancer whose cancer is refractory to standard therapy or whose cancer has recurred following standard treatment.

Pharmaceutical Compositions

One embodiment is a pharmaceutical composition suitable for use in a subject, such as a human. The pharmaceutical composition may comprise at least one pharmaceutically acceptable excipient or carrier.

The pharmaceutical composition may also include at least one additional active agent, such as an alkylating agent, an intercalating agent, a tubulin binding agent, a corticosteroid, or any combination of any of the foregoing. Examples of additional active agents include, but are not limited to, ibrutinib, rituximab, doxorubicin, prednisolone, vincristine, velcade, and everolimus. In one embodiment, the at least one additional active agent is a therapeutic agent selected from cyclophosphamide, hydroxydaunorubicin (also referred to as doxorubicin) vincristine, prednisone, prednisolone, and any combination of any of the foregoing.

The pharmaceutical composition may include one or more non-therapeutic agents, such as ondansetron, granisetron, dolasetron, palonosetron, pindolol, risperidone, or any combination of any of the foregoing.

A pharmaceutical composition can be provided as a dosage unit form, such as an ampoule, a vial, a suppository, a dragee, a tablet, or a capsule.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration, in the form of a sterile aqueous solution or dispersion suitable for administration by either direct injection or by addition to sterile infusion fluids for intravenous infusion, or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Preparation of the Compounds

As an example, some of the compounds of the present invention may be prepared as follows.

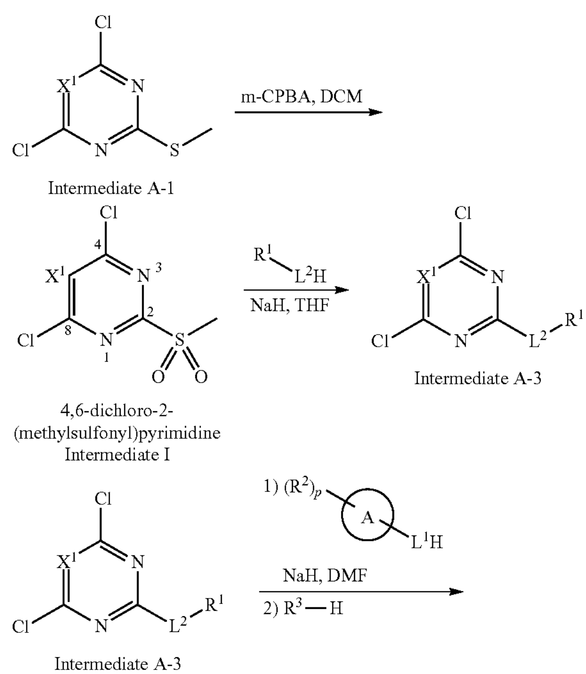

Intermediate A-1

4,6-dichloro-2-(methylsulfonyl)pyrimidine
Intermediate I

Intermediate A-3

Intermediate A-3

-continued

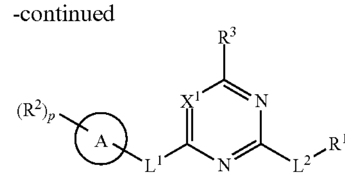

Starting intermediate A-1 is oxidized, for example by reaction with m-CPBA (meta-chloroperoxybenzoic acid) in a solvent, such as dichloromethane, to produce intermediate I. Intermediate I is then reacted with $R^1$-$L^2$H, for example, in the presence of a base (such as NaH) and in a solvent, such as THF, to form Intermediate A-3. Intermediate A-3 is first reacted with

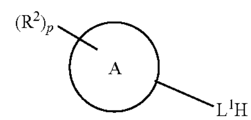

and then with $R^3$—H to form the final compound. The other compounds of the present invention can be prepared in an analogous manner.

Methods of Treatment

The compounds of the present invention are useful as PIKfyve kinase inhibitors.

One embodiment a method of treating a subject having a neurological disease comprising administering to the subject an effective amount of a compound of the present invention (or a pharmaceutical composition of the present invention) to the subject. In a preferred embodiment, the subject is a human subject. The PIKfyve kinase inhibitors described herein may be used in the methods for treating a neurological disease described in U.S. Patent Publication No. 2018/0161335, which is hereby incorporated by reference in its entirety. For example, the neurological disease may be one that has neuronal death generated by intracellular aggregates.

In certain embodiments, the method includes treating amyotrophic lateral sclerosis (ALS). In certain embodiments, the method includes treating frontotemporal dementia (FTD). In certain embodiments, the method includes treating a neurological disease that is associated with aberrant endosomal trafficking. In certain embodiments, the method includes treating a neurological disease that is associated with aberrant lysosomal trafficking. In further embodiments, the method includes treating a subject who has a $(GGGGCC)_n$ repeat expansion in the C9ORF72 gene. In further embodiments, the subject is haploinsufficient for C9ORF72. In further embodiments, the method includes treating patients who have a 50% or greater reduction in C9ORF72 protein activity. In further embodiments, the method includes a C9ORF72 gene product that comprises a dipeptide repeat resulting from the $(GGGGCC)_n$ expansion. In further embodiments, the method includes a gain-of-function or loss of function mutation resulting from the $(GGGGCC)_n$ expansion. In further embodiments, the neurological disease is associated with neuronal hyperexcitability.

One embodiment is a method of treating a subject having amyotrophic lateral sclerosis (ALS) comprising administering to the subject (preferably a human subject) an effective amount of a compound of the present invention. Another embodiment is a method of treating a subject having frontotemporal dementia (FTD) comprising administering to the subject (preferably a human subject) an effective amount of a compound of the present invention. Yet another embodiment is a method of treating a subject having Alzheimer's disease comprising administering to the subject (preferably a human subject) an effective amount of a compound of the present invention. Yet another embodiment is a method of treating a subject having Parkinson's disease comprising administering to the subject (preferably a human subject) an effective amount of a compound of the present invention. Yet another embodiment is a method of treating a subject having Huntington's disease comprising administering to the subject (preferably a human subject) an effective amount of a compound of the present invention. Yet another embodiment is a method of treating a subject having Charcot-Marie-Tooth disease (CMT) comprising administering to the subject (preferably a human subject) an effective amount of a compound of the present invention.

The method may further comprise also administering an effective amount of a potassium channel activator, an inhibitor of a glutamate receptor (such as the receptor NMDA, AMPA, or kainite) (e.g., AP5, CNQX, and NBQX), or any combination of any of the foregoing.

PIKfyve is a phosphoinositide kinase (PIK) that contains a FYVE-type zinc finger domain, which binds phosphatidylinositol 3-phosphate (PI3P). PIKfyve phosphorylates PUP to produce $PI(3,5)P_2$, which is involved in cellular processes including membrane trafficking and cytoskeletal reorganization. The inhibition of PIKfyve by a compound described herein is useful in treating not only cancer, but also Charcot-Marie-Tooth disease and certain viral infections, such as those caused by a virus selected from measles, Ebola virus (EboV), Marburg virus (MarV), borna disease, and human immunodeficiency virus (HIV), severe acute respiratory system virus (SARS), middle east respiratory syndrome virus (MERS), JC polyomavirus (JC), BK polyomavirus (BK), Herpes Simplex Virus (HSV), Venezuelan equine encephalitis virus (VEEV) and Lymphocytic choriomeningitis virus (LCMV). The viral infection can be caused by any type of virus such as RNA and DNA viruses.

One embodiment is a method of treating a viral infection in a subject in need thereof comprising administering an effective amount of a compound of the present invention to the subject. In one embodiment, the virus is Ebola virus. In another embodiment, the virus is middle east respiratory syndrome virus (MERS). In yet another embodiment, the virus is JC polyomavirus (JC). In yet another embodiment, the virus is BK polyomavirus (BK). In yet another embodiment, the virus is Herpes Simplex Virus (HSV). In yet another embodiment, the virus is Marburg virus (MarV). In yet another embodiment, the virus is Venezuelan equine encephalitis virus (VEEV). In yet another embodiment, the virus is Lymphocytic choriomeningitis virus (LCMV).

One embodiment is a method for treating a cell proliferative disease, a cancer, or a viral infection in a subject, preferably a human subject, in need of such treatment, by administering an effective amount of a compound of the present invention or a pharmaceutical composition comprising the same, to the subject.

The compounds described herein are useful for treating cancer. In one embodiment, the cancer is brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, von Hippel Lindau disease, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, hematological malignancy, or leukemia. In another embodiment, the cancer is B cell lymphoma. In another embodiment, the cancer is a melanoma.

In one embodiment the cancer is a lymphoma. In one embodiment, the lymphoma is a B cell lymphoma. In one embodiment, the B cell lymphoma is selected from the group consisting of a Hodgkin's B cell lymphoma and a non-Hodgkin's B cell lymphoma. In one embodiment, the B cell lymphoma is a non-Hodgkin's B cell lymphoma selected from the group consisting of DLBCL, follicular lymphoma, marginal zone lymphoma (MZL) or mucosa associated lymphatic tissue lymphoma (MALT), small cell lymphocytic lymphoma (overlaps with chronic lymphocytic leukemia) and mantle cell lymphoma. In one embodiment, the B cell lymphoma is a non-Hodgkin's B cell lymphoma selected from the group consisting of Burkitt's lymphoma, Primary mediastinal (thymic) large B-cell lymphoma, Lymphoplasmacytic lymphoma, which may manifest as Waldenstrom macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma, leg type (Primary cutaneous DLBCL, leg type), EBV positive diffuse large B-cell lymphoma of the elderly, Diffuse large B-cell lymphoma associated with inflammation, Intravascular large B-cell lymphoma, ALK-positive large B-cell lymphoma, and Plasmablastic lymphoma.

In one embodiment, the method is a method of treating a lymphoma using a combination therapy comprising a compound of the present invention and a chemotherapy regimen for the treatment of the lymphoma. In one embodiment, the chemotherapy regimen is the CHOP regimen. In another embodiment, the chemotherapy regimen is selected from COOP, CVP, EPOCH, Hyper-CVAD, ICE, R-CHOP, and R-CVP.

In the methods described here, the compounds can be administered by any suitable route, such as an oral, intravenous, or subcutaneous route.

EXAMPLES

The examples are illustrative only and do not limit the claimed invention.

Synthesis of 4,6-dichloro-2-(methylsulfonyl)pyrimidine (Intermediate I)

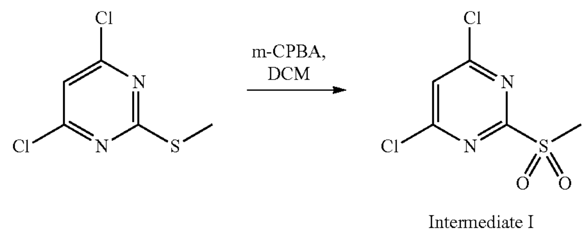

Intermediate I

To a solution of 4,6-dichloro-2-(methylthio)pyrimidine (9.75 g, 50 mmol) in dichloromethane (DCM) was slowly added meta-chloroperoxybenzoic acid (mCPBA) 22.4 g, 130 mmol) at 0° C. The reaction was allowed to warm to room temperature (RT) and stirred overnight. The mixture was quenched with an aqueous solution of 1M NaOH, extracted with DCM, washed with sat. aq. (saturated aqueous) $NaHCO_3$ as well as brine, and the organic phase dried ($MgSO_4$), filtered and evaporated to give Intermediate I, 4,6-dichloro-2-(methylsulfonyl)pyrimidine, as a white solid (11.39 g). The product was used crude.

LC/MS (mobile phase 5-100% ACN in 3 min), Rt=0.94 min, $(M+H)^+$ 227

$^1H$ NMR (300 MHz DMSO-d6): δ 8.30 (1H, s), 3.32 (3H, s)

Synthesis of 4,6-dichloro-2-(2-pyridin-2-yl)ethoxy) pyrimidine (Intermediate II)

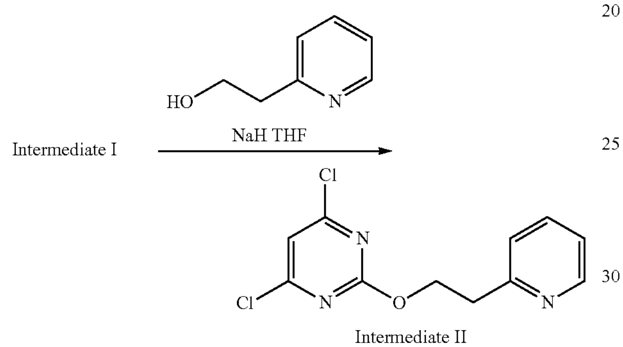

To a solution of Intermediate I (11.3 g, 50 mmol) in tetrahydrofuran (THF) (60 ml) was added NaH (2.9 g, 72.5 mmol). The temperature was lowered to −78° C. and 2-(pyridin-2-yl)ethan-1-ol (6.5 g, 52.5 mmol) in THF (60 ml) was added dropwise. The reaction was stirred for 1 h at −78° C., and worked up by addition of water, followed by extraction with ethyl acetate (EtOAc), dried ($MgSO_4$), filtered and evaporated. The crude product was purified by silica gel chromatography using a gradient of hexane:EtOAc 9:1 to hexane:EtOAc 7:3. After evaporation of the correct fractions, 6.7 g of Intermediate II, 4,6-dichloro-2-(2-pyridin-2-yl)ethoxy)pyrimidine was obtained as a white solid.

LC/MS (mobile phase 5-100% ACN in 3 min), Rt=1.68 min, $(M+H)^+$ 270

$^1H$ NMR (300 MHz DMSO-d6): δ 8.43 (1H, d), 7.66 (2H, m), 7.22 (1H, d), 7.15 (1H, m), 4.21 (2H, m), 3.29 (2H, m)

Synthesis of (3aR,6aR)-hexahydro-2H-furo[3,2-b] pyrrole (Intermediate III)

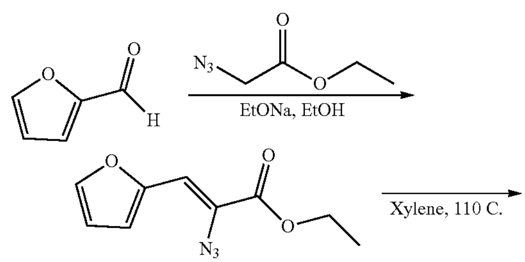

-continued

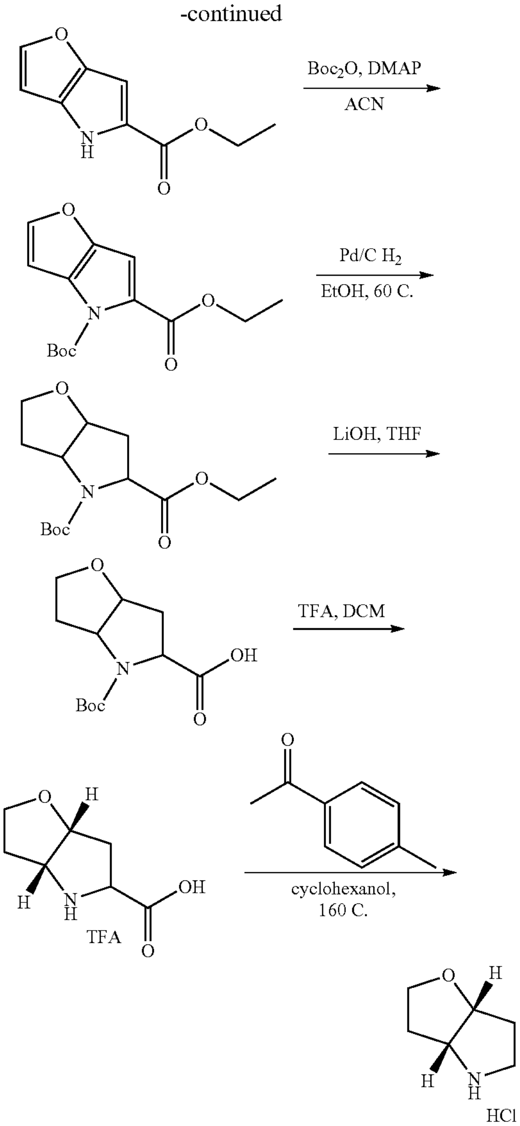

Intermediate III

To a solution of furan-2-carbaldehyde and ethyl 2-azidopropanoate in ethanol (EtOH) was added sodium ethoxide (1.1 eq) and the reaction heated at reflux overnight. Evaporated, redissolved in ethyl acetate, and washed with sat. aq. sodium bicarbonate, the organic phase dried ($MgSO_4$), filtered and evaporated. The crude product was redissolved in xylene and heated at 160° C. for 4 hours, then evaporated and purified by silica gel chromatography (EtOAc/hexane). Re-dissolved in ACN, 4-Dimethylaminopyridine (DMAP) added (0.1 eq) and $Boc_2O$ and stirred at rt (room temperature) for 5 h, worked up (as before), redissolved in EtOH and hydrogenated at 40 psi with Pd/C 105 for 2 h. Evaporated and treated with sat. aq. LiOH in THF at RT for 2 h. Evaporated and purified by LC/MS. The solid was redissolved in TFA/DCM 1:2 and stirred and rt for 2 h, evaporated, decarboxylated by heating, purified by LC/MS and covered to the HCl salt.

$^1H$ NMR (300 MHz DMSO-d6): δ 83.68 (3H, m), 2.79 (3H, m), 2.01 (3H, m), 1.76 (2H, m)

Synthesis of 4-chloro-6-(3-(3-methoxyphenyl)-1H-pyrazol-1-yl)-2-(2-(pyridin-2-yl)ethoxy)pyrimidine (Intermediate IV)

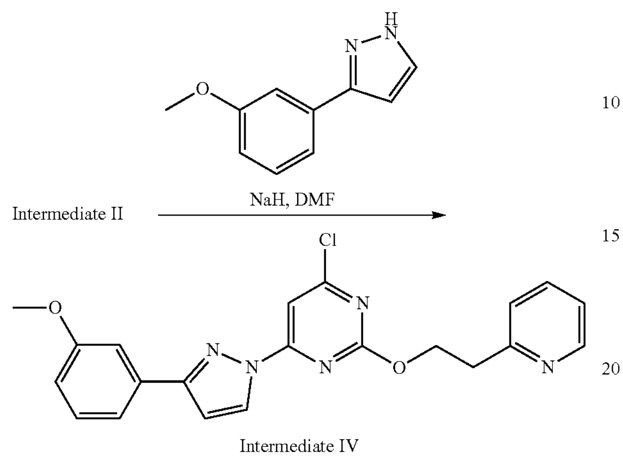

Intermediate IV

To a solution of Intermediate II, 4,6-dichloro-2-(2-(pyridin-2-yl)ethoxy)pyrimidine (269 mg, 1 mmol) in DMF (10 ml) was added 3-(3-methoxyphenyl)-1H-pyrazole (191 mg, 1.1 mmol) and NaH (19 mg, 1.2 mmol). The reaction was stirred at RT overnight, quenched with water, extracted with EtOAc, dried ($MgSO_4$), filtered, evaporated and purified by LCMS to give 4-chloro-6-(3-phenyl-1H-pyrazol-1-yl)-2-(2-(pyridin-2-yl)ethoxy)pyrimidine (Intermediate IV) (188 mg).

LC/MS $(M+H)^{+x}$408

$^1$H NMR (300 MHz DMSO-d6): δ 8.43 (1H, m), 8.09 (1H, m), 7.76 (1H, s), 7.72 (2H, m), 7.47 (1H, m), 7.39 (1H, s), 7.18 (3H, m), 6.95 (1H, m), 4.25 (2H, m), 3.81 (3H, S), 3.30 (2H, m),

Synthesis of (3aR,6aR)-4-(6-chloro-2-((tetrahydrofuran-2-yl)methoxy)pyrimidin-4-yl)hexahydro-2H-furo[3,2-b]pyrrole (Intermediate V)

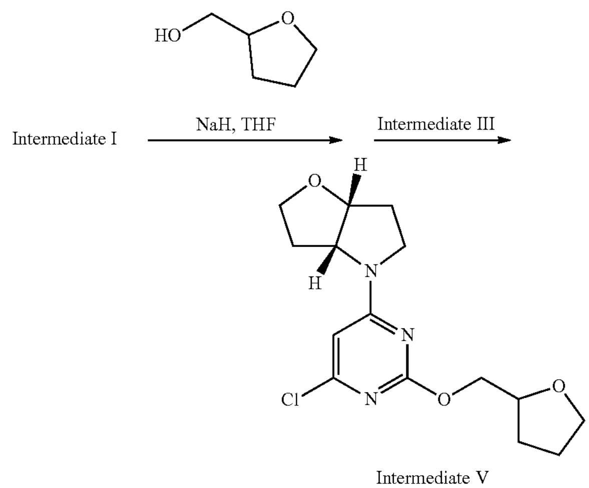

Intermediate V

To 2.8 g of Intermediate I (12.3 mml) was added NaH (770 mg, 32 mmol) and tetrahydrofuran-2-yl)methanol (1.81 g, 16 mmol) at 0° C. in THF (200 ml). The reaction was stirred at 2 h at RT, and Intermediate III (1.81 g, 16 mmol) added, and the reaction stirred overnight at RT. The reaction was worked up by quenching with water, evaporation, re-dissolved in ethyl acetate, washed (saturated aq. sodium bicarbonate), dried ($MgSO_4$), filtered and evaporated. The crude mixture was purified by silica gel chromatography (hexane/ethyl acetate) to give 2.2 g of Intermediate V.

LC/MS (mobile phase 5-100% ACN in 5 min), Rt=3.36 min, $(M+H)^+$326

$^1$H NMR (300 MHz $CDCl_3$): δ 7.29 (s, 1H), 4.49 (m, 5H), 3.37 (m, 6H), 2.24 (m, 2H), 2.13 (m, 1H), 1.90 (m, 5H)

Synthesis of 4-(6-chloro-2-((tetrahydrofuran-2-yl)methoxy)pyrimidin-4-yl)morpholine (Intermediate VI)

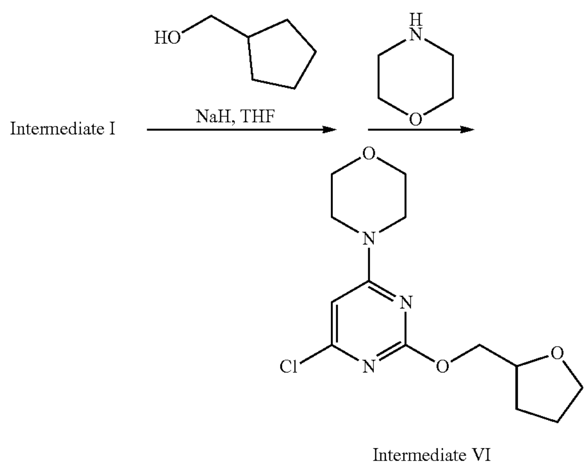

Intermediate VI

Intermediate VI was prepared by a method analogous to Intermediate V, except morpholine was added instead of Intermediate III.

LC/MS (mobile phase 5-100% ACN in 4 min), Rt=2.22 min, $(M+H)^+$300

$^1$H NMR (300 MHz DMSO-d6): δ 6.62 (s, 1H), 4.19 (m, 1H), 4.14 (m, 1H), 3.77 (m, 1H), 3.62 (m, 9H), 1.97 (m, 1H), 1.85 (m, 2H), 1.62 (m, 1H)

Synthesis of 4-chloro-2-((tetrahydrofuran-2-yl)methoxy)-6-(3-(m-tolyl)-1H-pyrazol-1-yl)pyrimidine (Intermediate VII)

Intermediate VII

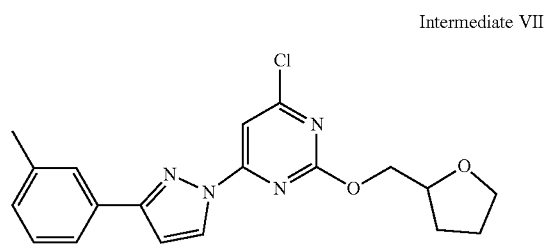 [SMILES: Cc1cccc(-c2ccn(-c3cc(Cl)nc(OCC4CCCO4)n3)n2)c1]

Intermediate VII was prepared by a method analogous to Intermediate IV, except tetrahydrofuran-2-yl)methanol was added in place of 2-(pyridin-2-yl)ethan-1-ol to generate the equivalent of Intermediate II and 5-(m-tolyl)-1H-pyrazole was added in place of 3-(3-methoxyphenyl)-1H-pyrazole to generate Intermediate VII.

LC/MS (mobile phase 5-100% ACN in 4 min), Rt=3.52 min, $(M+H)^+$ 371

$^1$H NMR (300 MHz DMSO-d6): δ 8.75 (s, 1H), 7.77 (s, 1H), 7.81 (d, 1H), 7.68 (s, 1H), 7.39 (m, 1H), 7.27 (m, 1H), 7.21 (s, 1H), 4.40 (m, 2H), 2.16 (m, 1H), 3.83 (m, 1H), 3.72 (m, 1H), 2.40 (s, 3H), 2.06 (m, 1H), 1.88 (m, 2H), 1.72 (m, 1H)

Synthesis of 4-chloro-2-(2-(tetrahydrofuran-2-yl) ethyl)-6-(3-(m-tolyl)-1H-pyrazol-1-yl)pyrimidine (Intermediate VIII)

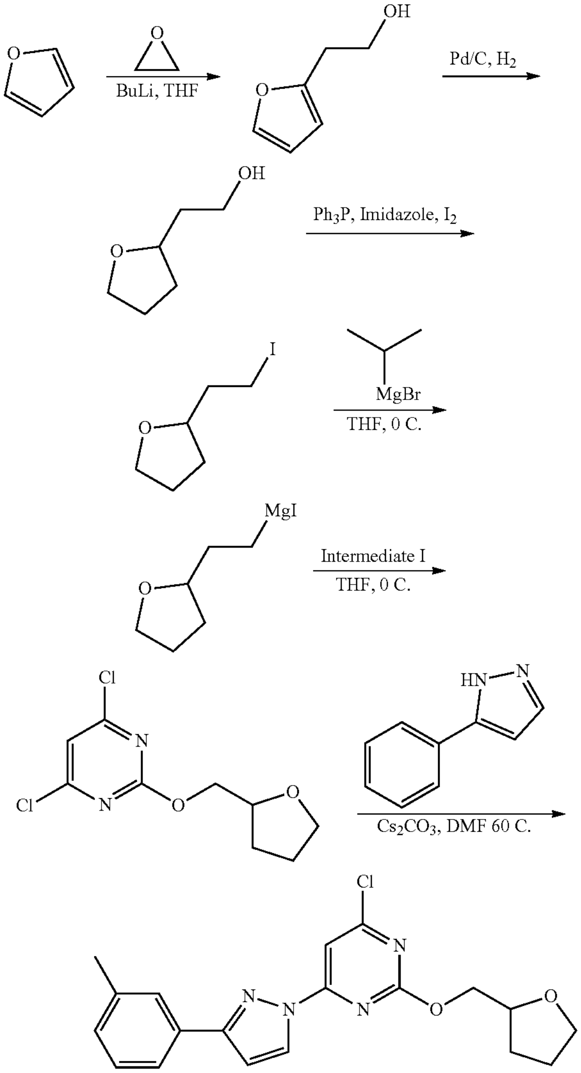

Intermediate VIII

Intermediate VIII was prepared by the scheme shown above.

LC/MS (mobile phase 5-100% ACN in 5 min), Rt=4.32 min, $(M+H)^+$ 369

$^1$H NMR (300 MHz DMSO-d6): δ 8.72 (s, 1H), 7.89 (m, 2H), 7.81 (m, 1H), 7.39 (m, 1H), 7.26 (m, 1H), 7.20 (s, 1H), 3.82 (m, 1H), 3.75 (m, 1H), 3.60 (m, 1H), 2.90 (m, 2H), 2.40 (s, 3H), 2.00 (m, 3H), 1.82 (m, 2H), 1.49 (m, 1H)

Example 1: Synthesis of 3aR,6aR)-4-(6-(3-(3-methoxyphenyl)-1H-pyrazol-1-yl)-2-((tetrahydrofuran-2-yl)methoxy)pyrimidin-4-yl)hexahydro-2H-furo[3,2-b]pyrrole (Compound 1)

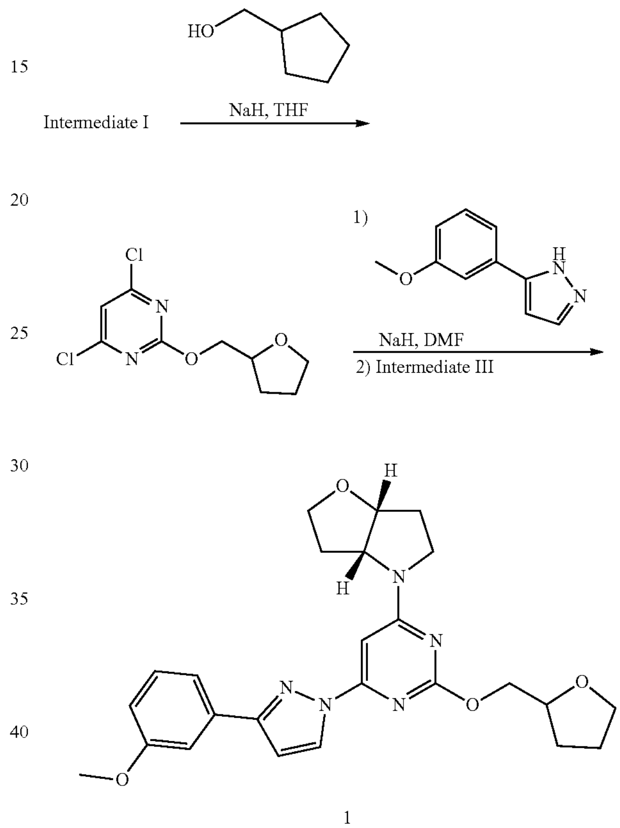

1

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. Tetrahydrofuran-2-yl)methanol (51 mg, 0.48 mmol) was added dropwise as a solution in THF (1 ml), and the solution stirred for 1 h at −78° C., then quenched with water, extracted with EtOAc, dried ($MgSO_4$), filtered, evaporated and purified by silica gel chromatography (hexane/EtOAc) to give 16 mg of 4,6-dichloro-2-((tetrahydrofuran-2-yl) methoxy)pyrimidine. This was dissolved in dimethylformamide (DMF) (1 ml), NaH (4 mg, 0.18 mmol) was added, followed by 5-(3-methoxyphenyl)-1H-pyrazole (16 mg, 0.09 mmol), and the reaction mixture stirred for 1 h at RT. Intermediate III (44 mg) was added, and the reaction stirred overnight at RT, then quenched with water, extracted with EtOAc, dried ($MgSO_4$), filtered, evaporated and purified by LC/MS to give 8 mg of (3aR,6aR)-4-(6-(3-(3-methoxyphenyl)-1H-pyrazol-1-yl)-2-((tetrahydrofuran-2-yl)methoxy) pyrimidin-4-yl)hexahydro-2H-furo[3,2-b]pyrrole Compound 1.

LC/MS (mobile phase 5-100% ACN in 5 min), Rt=3.91 min, $(M+H)^+$ 464

Example 2: Synthesis of 4-(6-(3-(3-methoxyphenyl)-1H-pyrazol-1-yl)-2-((tetrahydrofuran-2-yl)methoxy)pyrimidin-4-yl)morpholine (Compound 2)

2

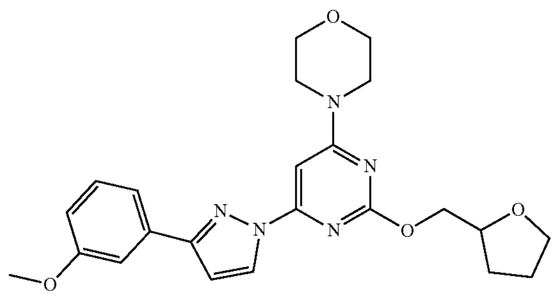

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. Tetrahydrofuran-2-yl)methanol (51 mg, 0.48 mmol) was added dropwise as a solution in THF (1 ml), and the solution stirred for 1 h at −78° C., then quenched with water, extracted with EtOAc, dried ($MgSO_4$), filtered, evaporated and purified by silica gel chromatography (hexane/EtOAc) to give 23 mg of 4,6-dichloro-2-((tetrahydrofuran-2-yl)methoxy)pyrimidine. This was dissolved in DMF (3 ml), NaH (6 mg) was added, followed by 5-(3-methoxyphenyl)-1H-pyrazole (16 mg) and the reaction mixture stirred for 1 h at RT. Morpholine (9 ul) was added, and the reaction stirred overnight at rt, then quenched with water, extracted with EtOAc, dried ($MgSO_4$), filtered, evaporated and purified by LC/MS to give 6 mg of 4-(6-(3-(3-methoxyphenyl)-1H-pyrazol-1-yl)-2-((tetrahydrofuran-2-yl)methoxy)pyrimidin-4-yl)morpholine, Compound 2.

LC/MS (mobile phase 5-100% ACN in 5 min), Rt=3.90 min, $(M+H)^+$ 438

Example 3: Synthesis of 4-(6-(3-phenyl-1H-pyrazol-1-yl)-2-(2-(tetrahydro-2H-pyran-4-yl)ethoxy)pyrimidin-4-yl)morpholine (Compound 3)

3

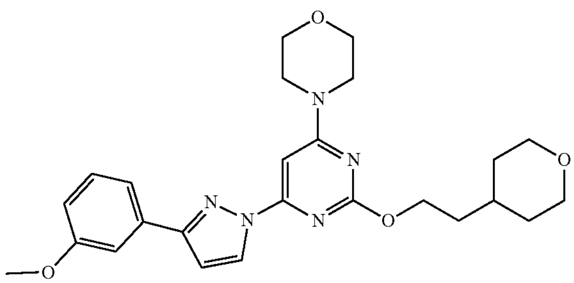

To a solution of Intermediate I, 4,6-dichloro-2-(methylsulfonyl)pyrimidine (113 mg, 0.5 mmol) in THF (5 ml), was added NaH (14 mg, 0.64 mmol) and the solution cooled to −78° C. 2-(tetrahydro-2H-pyran-4-yl)ethan-1-ol (65 mg) was added dropwise as a solution in THF (1 ml), and the solution stirred for 1 h at −78° C., then quenched with water, extracted with EtOAc, dried ($MgSO_4$), filtered, evaporated and purified by silica gel chromatography (hexane/EtOAc) to give 65 mg of 4-(2-(3,5-dichlorophenoxy)ethyl)tetrahydro-2H-pyran. This was dissolved in DMF (3 ml), NaH (9 mg) was added, followed by 5-(3-methoxyphenyl)-1H-pyrazole (41 mg) and the reaction mixture stirred for 1 h at RT. Morpholine (21 ul) was added, and the reaction stirred overnight at rt, then quenched with water, extracted with EtOAc, dried ($MgSO_4$), filtered, evaporated and purified by LC/MS to give 9 mg of 4-(6-(3-(3-methoxyphenyl)-1H-pyrazol-1-yl)-2-(2-(tetrahydro-2H-pyran-4-yl)ethoxy)pyrimidin-4-yl)morpholine, Compound 3.

LC/MS (mobile phase 5-100% ACN in 5 min), Rt=4.14 min, $(M+H)^+$ 466

Example 4: Synthesis of (3aR,6aR)-4-(6-(3-phenyl-1H-pyrazol-1-yl)-2-(2-(pyridin-2-yl)ethoxy)pyrimidin-4-yl)hexahydro-2H-furo[3,2-b]pyrrole (Compound 4)

4

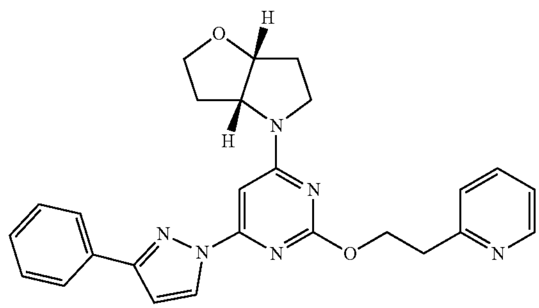

Compound 4 was prepared by a method analogous to that for Compound 1, except Intermediate III was used in place of morpholine and 5-phenyl-1H-pyrazole was used in place of 5-(3-methoxyphenyl)-1H-pyrazole.

LC/MS (mobile phase 5-100% ACN in 5 min), Rt=3.16 min, $(M+H)^+$ 455

Example 5: Synthesis of 2-((4-((3aR,6aR)-hexahydro-4H-furo[3,2-b]pyrrol-4-yl)-6-(3-(3-methoxyphenyl)-1H-pyrazol-1-yl)pyrimidin-2-yl)oxy)ethan-1-ol (Compound 5)

5

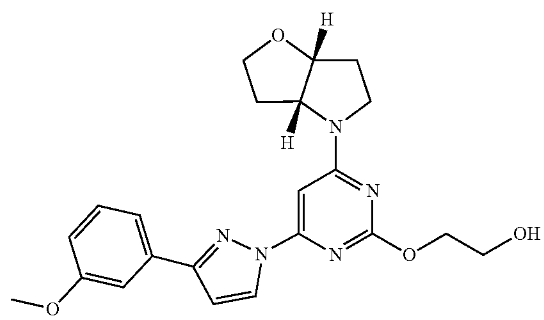

Compound 5 was prepared by a method analogous to that for Compound 1, except 2-(tert-butoxy)ethan-1-ol was added instead of tetrahydrofuran-2-yl)methanol, and the end product was treated with trifluoroacetic acid (TFA)/DCM 1:2 for 1 h at RT and evaporated prior to purification by LC/MS.

LC/MS (mobile phase 5-100% ACN in 5 min), Rt=3.16 min, $(M+H)^+$ 424

Example 6: Synthesis of (3aR,6aR)-4-(6-(3-(3-methoxyphenyl)-1H-pyrazol-1-yl)-2-(2-(4-methylthiazol-5-yl)ethoxy)pyrimidin-4-yl)hexahydro-2H-furo[3,2-b]pyrrole (Compound 6)

6

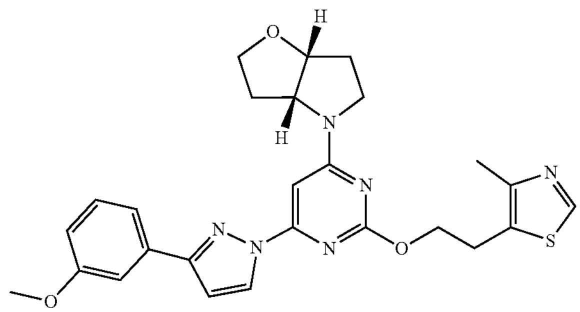

Compound 6 was prepared by a method analogous to that for Compound 1, except 2-(4-methylthiazol-5-yl)ethan-1-ol was added instead of tetrahydrofuran-2-yl)methanol.

LC/MS (mobile phase 5-100% ACN in 5 min), Rt=3.60 min, $(M+H)^+$ 505

Example 7: Synthesis of 4-(6-(3-(3-methoxyphenyl)-1H-pyrazol-1-yl)-2-(2-(4-methylthiazol-5-yl)ethoxy)pyrimidin-4-yl)morpholine (Compound 7)

7

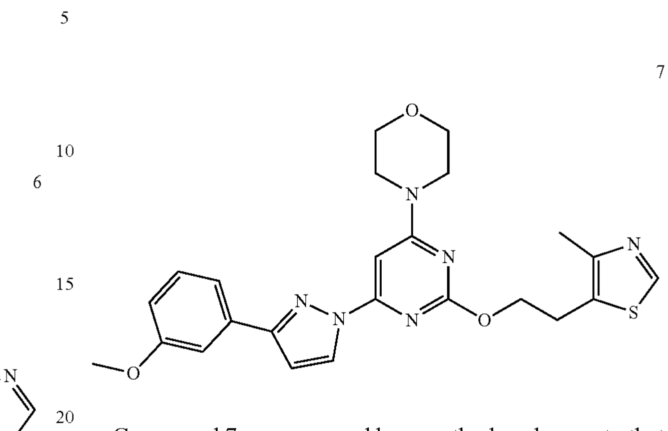

Compound 7 was prepared by a method analogous to that for Compound 6, except morpholine was used in place of Intermediate III.

LC/MS (mobile phase 5-100% ACN in 5 min), Rt=3.56 min, $(M+H)^+$ 479

Example 8: Synthesis of 4-((4-((3aR,6aR)-hexahydro-4H-furo[3,2-b]pyrrol-4-yl)-6-(3-(3-methoxyphenyl)-1H-pyrazol-1-yl)pyrimidin-2-yl)oxy)butane-1,2-diol (Compound 8)

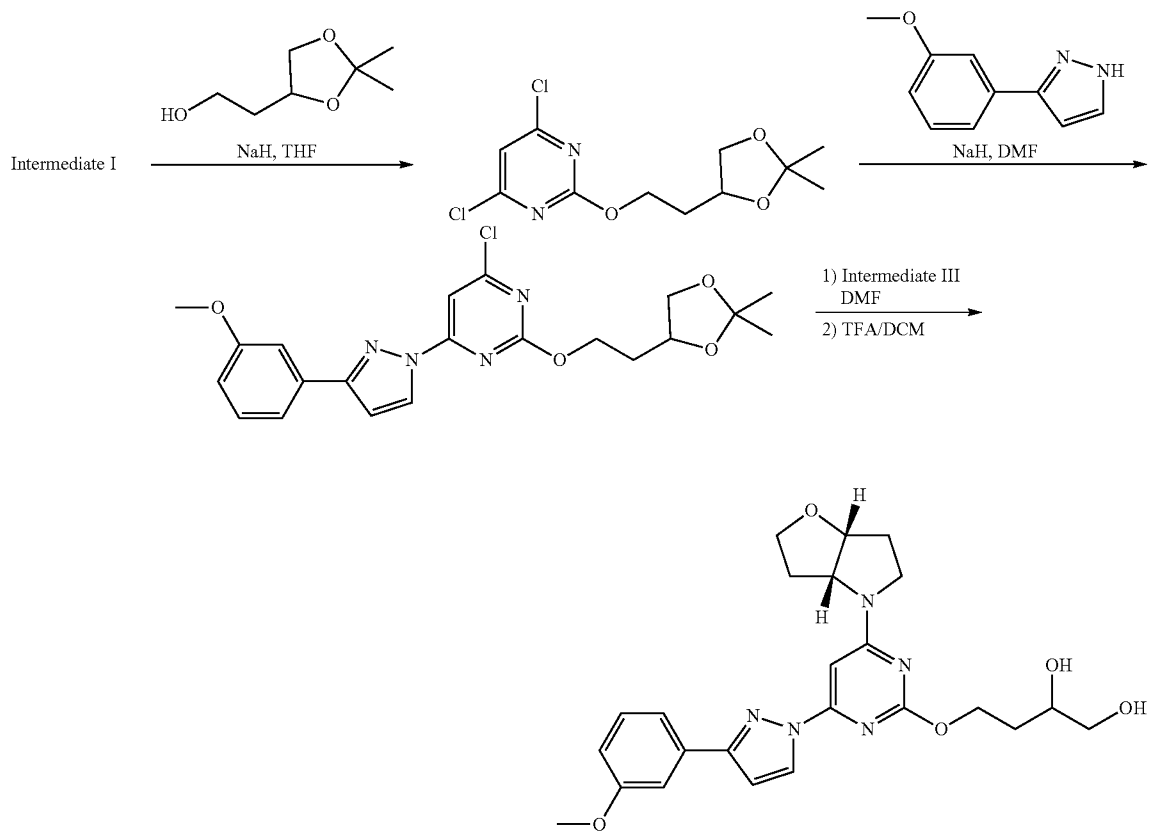

8

To a solution of Intermediate I, (113 mg, 0.5 mmol) in THF (5 ml) was added NaH (18.4 mg, 0.8 mmol) and the temperature lowered to −78° C. 2-(2,2-dimethyl-1,3-dioxolan-4-yl)ethan-1-ol 71 ul, 0.5 mmol) in THF (1 ml) was added dropwise and the reaction stirred at 1 h at −78° C., worked up by quenching with water, extraction with EtOAc, dried ($MgSO_4$), filtered and evaporated. Dissolved in THF (3 ml), 3-(3-methoxyphenyl)-1H-pyrazole (18 mg) and NaH (7.5 mg) were added, and the reaction was stirred for 1 h at rt. Intermediate III (35 mg) was added, and the reaction stirred overnight at rt. Quenched with water, evaporated and purified on HPLC, then treated with TFA/DCM 1:2 (0.5 ml), evaporated and purified by LC/MS to give 6 mg of 4-(3-((3aR,6aR)-hexahydro-4H-furo[3,2-b]pyrrol-4-yl)-5-(3-(3-methoxyphenyl)-1H-pyrazol-1-yl)phenoxy)butane-1,2-diol (Compound 8).

LC/MS (mobile phase 5-100% ACN in 5 min), Rt=3.20 min, $(M+H)^+$ 468

Example 9: Synthesis of 4-((4-(3-(3-methoxyphenyl)-1H-pyrazol-1-yl)-6-morpholinopyrimidin-2-yl)oxy)butane-1,2-diol (Compound 9)

9

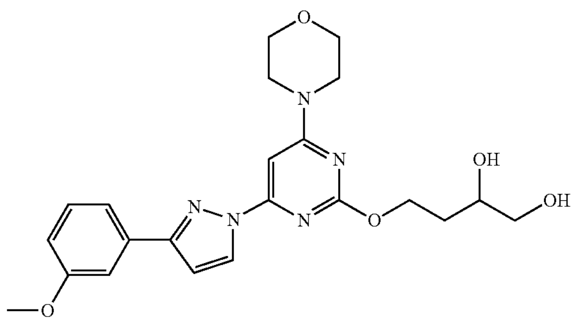

Compound 9 was prepared by a method analogous to that for Compound 8, except morpholine was used in place of Intermediate III.

LC/MS (mobile phase 5-100% ACN in 5 min), Rt=3.18 min, $(M+H)^+$ 442

Example 10: Synthesis 4-(6-(4-phenyl-1H-imidazol-1-yl)-2-(2-(pyridin-2-yl)ethoxy)pyrimidin-4-yl)morpholine (Compound 10)

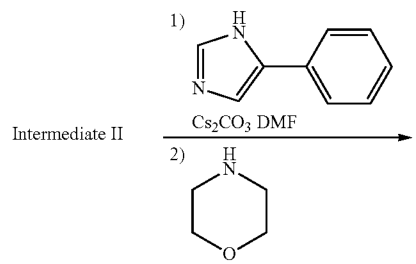

-continued

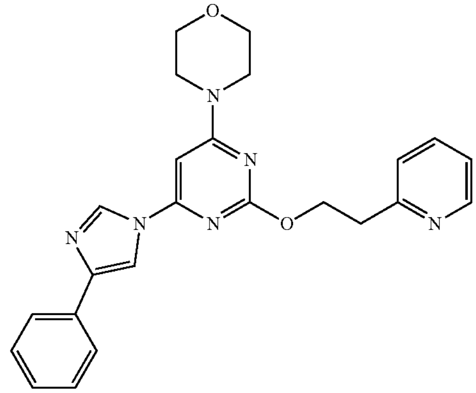

10

To a solution of Intermediate 11 (27 mg, 0.1 mmol) in DMF (1 ml) was added $Cs_2CO_3$ (65 mg, 0.2 mmol), followed by 5-phenyl-1H-imidazole (5 mg, 0.1 mmol). The reaction was stirred for 70 min at RT, and morpholine (30 ul) was added and the reaction stirred for 60 min. The mixture was evaporated and purified by LC/MS to give 18 mg of 4-(6-(4-phenyl-1H-imidazol-1-yl)-2-(2-(pyridin-2-yl)ethoxy)pyrimidin-4-yl)morpholine (Compound 10).

LC/MS (mobile phase 5-100% ACN in 5 min), Rt=3.18 min, $(M+H)^+$ 429

Example 11: Synthesis of (3aR,6aR)-4-(2-((tetrahydrofuran-2-yl)methoxy)-6-(4-(m-tolyl)thiazol-2-yl)pyrimidin-4-yl)hexahydro-2H-furo[3,2-b]pyrrole (Compound 11)

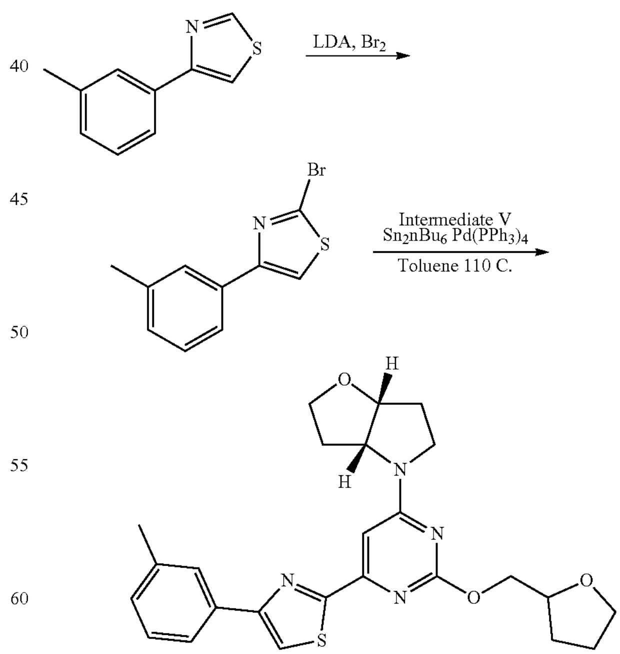

11

400 mg of 4-(m-tolyl)thiazole was treated with LDA (1.1 eq) and bromine (1.5 eq) to give 2-bromo-4-(m-tolyl)thiazole. 2-bromo-4-(m-tolyl)thiazole was further converted to (3aR,6aR)-4-(2-((tetrahydrofuran-2-yl)methoxy)-6-(4-(m-tolyl)thiazol-2-yl)pyrimidin-4-yl)hexahydro-2H-furo[3,2-b] pyrrole (Compound 11) as illustrated in the scheme above. 4 mg of product was obtained.

LC/MS (mobile phase 5-100% ACN in 5 min), Rt=3.78 min, $(M+H)^+$ 465

Example 12: Synthesis of 4-(2-((tetrahydrofuran-2-yl)methoxy)-6-(4-(m-tolyl)thiazol-2-yl)pyrimidin-4-yl)morpholine (Compound 12)

12

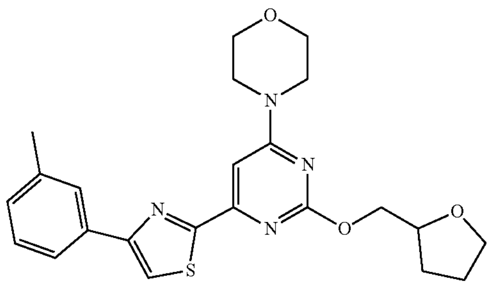

Compound 12 was prepared by a method analogous to that for Compound 11, except Intermediate VI was added instead of Intermediate V.

LC/MS (mobile phase 5-100% ACN in 3 min), Rt=2.18 min, $(M+H)^+$ 439

$^1$H NMR (300 MHz MeOD): δ 8.26 (s, 1H), 7.86 (m, 2H), 7.38 (m, 2H), 7.24 (s, 1H), 3.35 (m, 3H), 3.94 (m, 1H), 3.80 (m, 9H), 2.47 (s, 3H), 2.01 (m, 4H)

Example 13: Synthesis of 4-(2-((tetrahydrofuran-2-yl)methoxy)-6-(1-(m-tolyl)-1H-pyrazol-3-yl)pyrimidin-4-yl)morpholine (Compound 13)

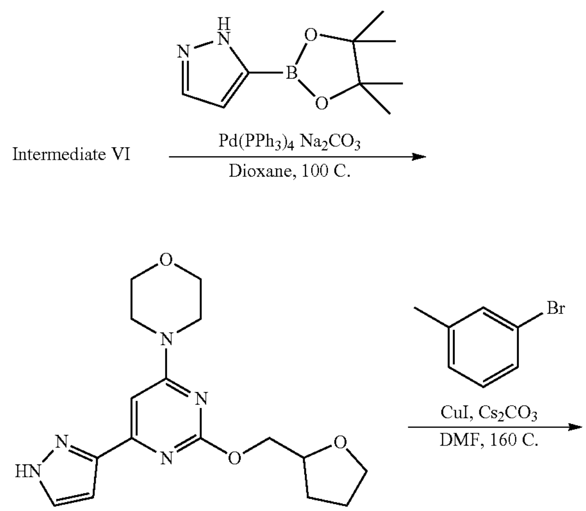

-continued

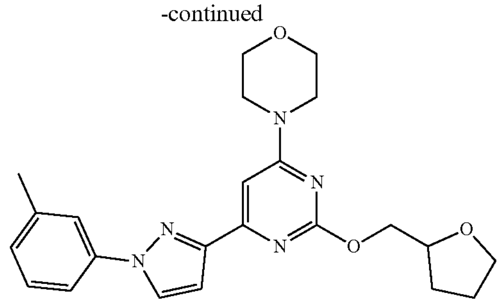

13

To 200 mg of Intermediate VI in degassed dioxane (10 ml) was added $Na_2CO_3$ (1.5 eq), $Pd(PPh_3)_4$ (0.1 eq) and 5-(4,4,5,5-tetramethyl-1,3,2-dioxaborolan-2-yl)-1H-pyrazole (1.3 eq). The reaction was stirred at 100° C. for 2 h under argon. The mixture was evaporated, re-dissolved in EtOAc, washed (saturated aq. sodium bicarbonate), dried ($MgSO_4$), filtered and evaporated. Re-dissolved in DMF (10 ml), 3-bromotoluene (30 eq), CuI (1 eq) and $Cs_2CO_3$ (1.1 eq) were added, and the mixture heated at 160° C. for 4 h. The mixture was evaporated, re-dissolved in EtOAc, washed (saturated aq. bicarbonate), dried ($MgSO_4$), filtered, evaporated, and purified by LC/MS to give 147 mg of Compound 13.

LC/MS (mobile phase 5-100% ACN in 3 min), Rt=1.52 min, $(M+H)^+$ 422

$^1$H NMR (300 MHz MeOD): δ 8.28 (s, 1H), 7.71 (s, 1H), 7.65 (m, 1H), 7.39 (m, 1H), 7.21 (d, 1H), 7.11 (m, 2H), 4.39 (m, 3H), 3.93 (m, 1H), 3.78 (m, 9H), 2.49 (s, 3H), 2.00 (m, 4H)

Example 14: Synthesis of 4-(2-((tetrahydrofuran-2-yl)methoxy)-6-(3-(m-tolyl)-1H-pyrazol-1-yl)pyrimidin-4-yl)-1,4-oxazepane (Compound 14)

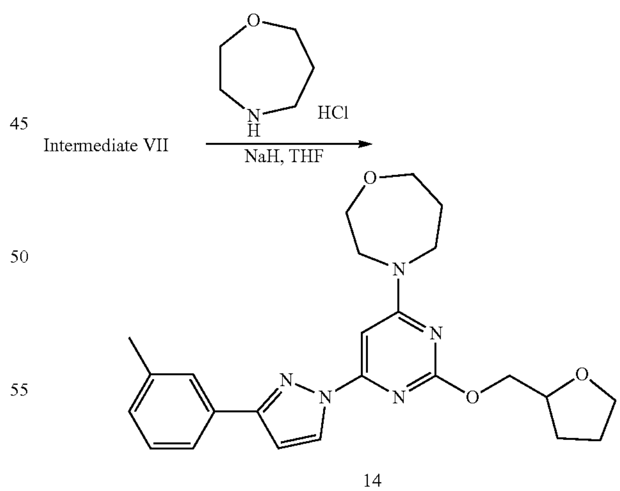

14

To Intermediate VII in THF was added NaH (3.1 eq.) and 1,4-oxepane (3 eq). The mixture was stirred at RT for 2 h. Purified by LC/MS to give Compound 14.

LC/MS (mobile phase 5-100% ACN in 5 min), Rt=3.19 min, $(M+H)^+$ 436

$^1$H NMR (300 MHz $CDCl_3$): δ 8.60 (s, 1H), 7.79 (s, 1H), 7.73 (m, 1H), 7.35 (m, 1H), 7.20 (m, 1H) 6.88 (s, 1H), 6.76

(s, 1H), 4.43 (m, 1H), 4.34 (m, 2H), 3.90 (m, 7H), 3.77 (m, 3H), 2.46 (s, 3H), 2.12 (m, 3H), 1.99 (m, 2H), 1.83 (m, 1H)

Example 15: Synthesis of 4-(3-methoxypyrrolidin-1-yl)-2-((tetrahydrofuran-2-yl)methoxy)-6-(3-(m-tolyl)-1H-pyrazol-1-yl)pyrimidine (Compound 15)

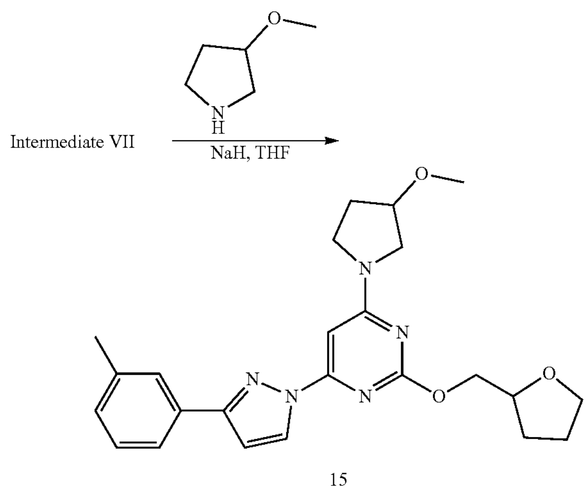

15

Compound 15 was prepared by a method analogous to that for Compound 14.

LC/MS (mobile phase 5-100% ACN in 5 min), Rt=3.71 min, $(M+H)^+$ 436

$^1$H NMR (300 MHz $CDCl_3$): δ 8.58 (s, 1H), 7.78 (s, 1H), 7.72 (m, 1H), 7.34 (m, 1H), 7.20 (m, 1H), 6.71 (d, 2H), 4.48 (m, 1H), 4.35 (m, 2H), 4.11 (m, 1H), 3.97 (m, 3H), 3.69 (m, 3H), 3.41 (s, 3H), 2.43 (s, 3H), 2.26 (m, 3H), 2.00 (m, 2H), 1.83 (m, 1H)

Example 16: Synthesis of (3aR,6aR)-4-(6-(3-(3-methoxyphenyl)-1H-pyrazol-1-yl)-2-(2-(pyridin-2-yl)ethoxy)pyrimidin-4-yl)hexahydro-2H-furo[3,2-b] pyrrole (Compound 16)

16

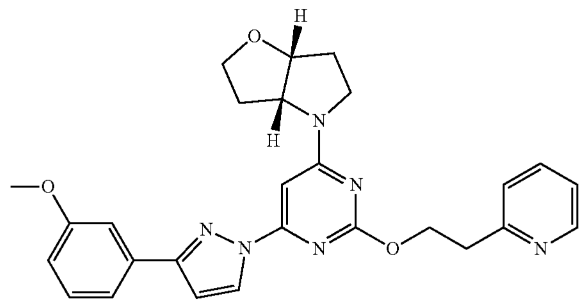

Compound 16 was prepared by a method analogous to that for Compound 4, except 5-(3-methoxyphenyl)-1H-pyrazole was added instead of 5-phenyl-1H-pyrazole.

LC/MS (mobile phase 5-100% ACN in 5 min), Rt=3.89 min, $(M+H)^+$ 485

Example 17: Synthesis of 2-((tetrahydrofuran-2-yl) methoxy)-4-(tetrahydrofuran-3-yl)-6-(3-(m-tolyl)-1H-pyrazol-1-yl)pyrimidine (Compound 17)

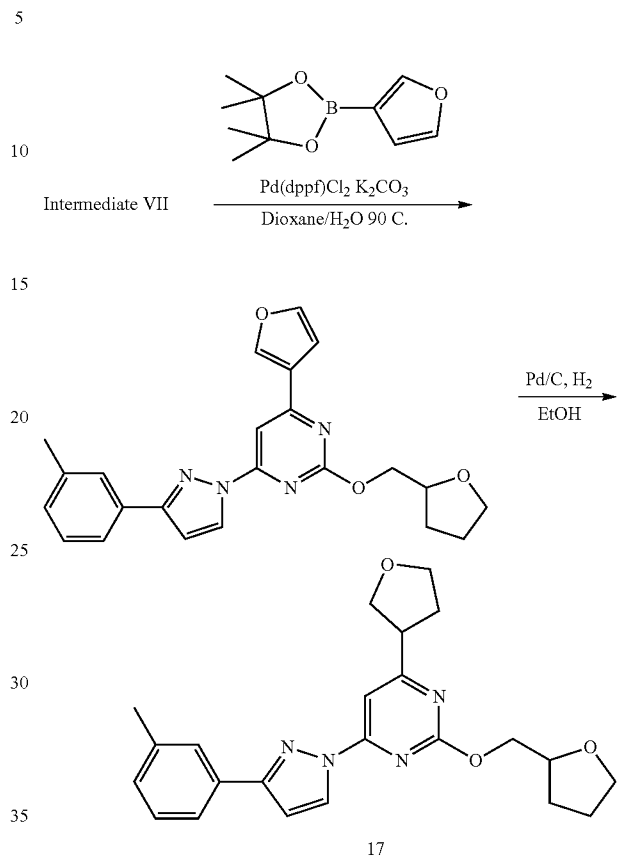

17

To 100 mg of Intermediate VII in degassed dioxane/water 9:1 was added 2-(furan-3-yl)-4,4,5,5-tetramethyl-1,3,2-dioxaborolane (1.2 eq), $K_2CO_3$ (1.1 eq) and $Pd(dppf)Cl_2$ (0.3 eq) and the mixture was heated under argon at 90° C. overnight. The mixture was evaporated, re-dissolved in EtOAc and saturated aq. bicarbonate, the layers separated, washed with bicarbonate, dried ($MgSO_4$), filtered, and evaporated. Re-dissolved in EtOH, Pd/C added and hydrogenated for 4 h at RT. Purified by LC/MS.

LC/MS (mobile phase 5-100% ACN in 3 min), Rt=2.34 min, $(M+H)^+$ 407

$^1$H NMR (300 MHz $CDCl_3$): δ 8.62 (s, 1H), 7.79 (s, 1H), 7.73 (d, 1H), 7.61 (s, 1H), 7.35 (m, 1H), 7.24 (m, 1H), 6.81 (s, 1H), 4.45 (m, 3H), 4.22 (m, 1H), 4.12 (m, 1H), 3.85 (m, 1H), 3.61 (m, 1H), 3.39 (m, 2H), 2.49 (s, 3H), 2.11 (m, 3H), 1.83 (m, 1H)

Example 18: Synthesis of 4-((2-methoxyethyl)thio)-2-((tetrahydrofuran-2-yl)methoxy)-6-(3-(m-tolyl)-1H-pyrazol-1-yl)pyrimidine (Compound 18)

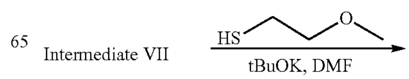

-continued

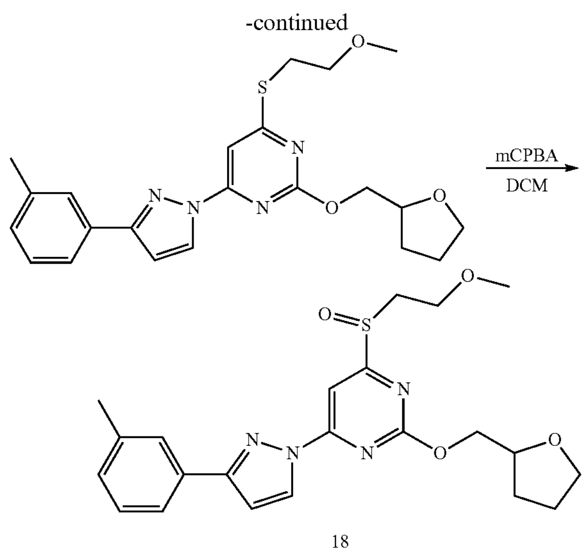

18

To 60 mg of Intermediate VII in DMF (4 ml) was added tBuOK (1.1 eq) and 2-methoxyethane-1-thiol (1.2 eq) and the reaction stirred at RT overnight. The mixture was evaporated, re-dissolved in EtOAc, washed with sat aq. $NaHCO_3$, dried ($MgSO_4$), filtered and evaporated. Re-dissolved in DCM (4 ml) and 1.5 eq of mCPBA added, stirred at RT for 4 h, worked up as described for the last step and purified by LC/MS to give Compound 18.

LC/MS (mobile phase 5-100% ACN in 3 min), Rt=1.92 min, $(M+H)^+$ 443

$^1$H NMR (300 MHz $CDCl_3$): δ 8.61 (1H, s), 8.33 (1H, s), 7.82 (1H, s), 7.71 (1H, m), 7.35 (1H, m), 7.24 (1H, m), 6.86 (1H, s), 4.42 (3H, m), 3.90 (4H, m), 3.47 (4H, m), 3.19 (1H, m), 2.48 (3H, s), 2.08 (3H, m), 1.82 (1H, m)

Example 19: Synthesis of (3aR,6aR)-4-(6-(3-phenyl-1H-pyrazol-1-yl)-2-(2-(pyrimidin-2-yl)ethyl)pyrimidin-4-yl)hexahydro-2H-furo[3,2-b]pyrrole (Compound 19)

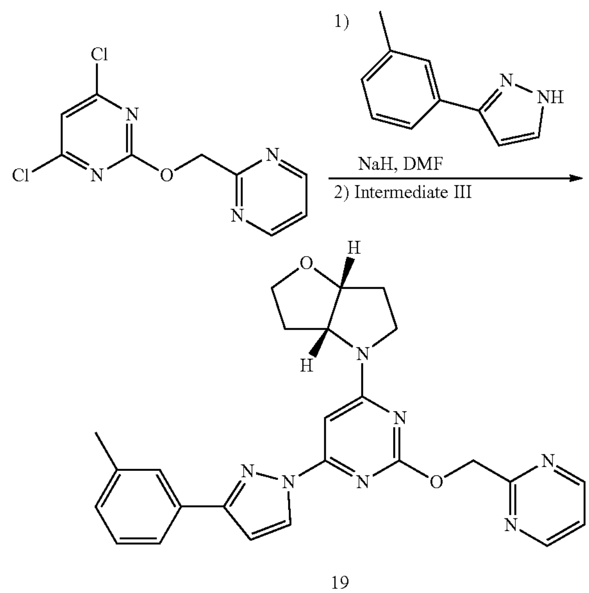

19

To 4,6-dichloro-2-(2-(pyrimidin-2-yl)ethyl)pyrimidine (22 mg, 0.09 mmol) in DMF (4 ml) was added 3-(m-tolyl)-1H-pyrazole (47 mg, 0.3 mmol) and NaH (50 mg). The mixture was shaken for 2 h at RT and (3aR,6aR)-hexahydro-412-furo[3,2-b]pyrrole (27 mg, 0.09 mmol) added. The reaction was heated to 80° C. for 4 h and purified by LC/MS to give 7 mg of (3aR,6aR)-4-(6-(3-phenyl-1H-pyrazol-1-yl)-2-(2-(pyrimidin-2-yl)ethyl)pyrimidin-4-yl)hexahydro-2H-furo[3,2-b]pyrrole (Compound 19).

LC/MS (mobile phase 5-100% ACN in 5 min), Rt=4.02 min, $(M+H)^+$ 454

Example 20: Synthesis of (4-(2-(2-(tetrahydrofuran-2-yl)ethyl)-6-(3-(m-tolyl)-1H-pyrazol-1-yl)pyrimidin-4-yl)morpholin-3-yl)methanol (Compound 20)

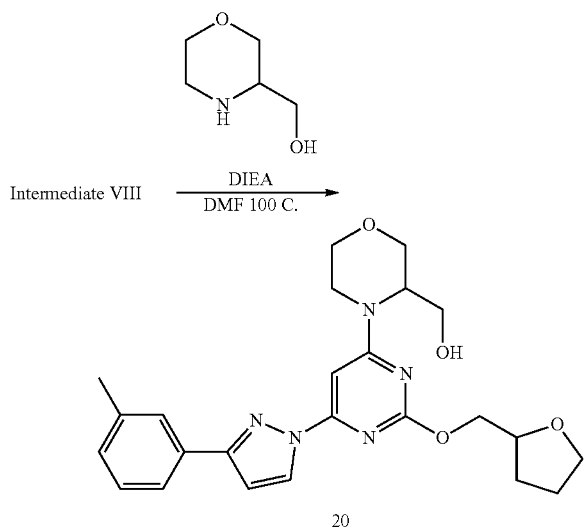

20

To 60 mg of Intermediate VIII in DMF (3 ml) was added $Cs_2CO_3$ (3 eq) and morpholin-3-ylmethanol (3 eq). The reaction was heated at 100° C. for 6 h, evaporated and purified by LC/MS to give 22 mg of Compound 20.

LC/MS (mobile phase 5-100% ACN in 3 min), Rt=2.03 min, $(M+H)^+$ 450

$^1$H NMR (300 MHz DMSO-d6): δ 8.62 (1H, s), 7.80 (2H, m), 7.36 (1H, m), 7.22 (1H, m), 7.03 (2H, m), 4.99 (1H, m), 4.29 (1H, b), 4.08 (1H, d), 3.95 (1H, m), 3.79 (3H, m), 3.55 (4H, m), 3.76 (2H, m), 2.40 (3H, s), 1.98 (3H, m), 1.82 (2H, m), 1.46 (1H, m)

Compounds 21-90 can be produced using synthetic protocols similar to those described above.

Synthesis of 4,6-dichloro-2-(2-pyridin-2-yl) ethoxy) pyrimidine (Intermediate 1)

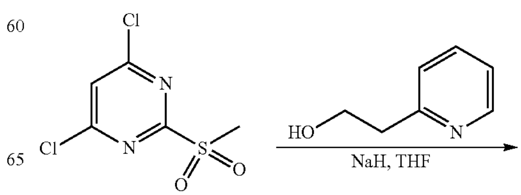

-continued

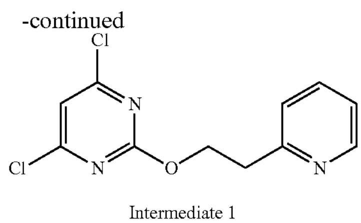

Intermediate 1

To a solution of 4,6-dichloro-2-(methylsulfonyl) pyrimidine (11.3 g, 50 mmol) in tetrahydrofuran (THF) (60 ml) was added NaH (2.9 g, 72.5 mmol). The temperature was lowered to −78° C. and 2-(pyridin-2-yl)ethan-1-ol (6.5 g, 52.5 mmol) in THF (60 ml) was added dropwise. The reaction was stirred for 1 h at −78° C., and worked up by addition of water, followed by extraction with ethyl acetate (EtOAc), dried ($MgSO_4$), filtered and evaporated. The crude product was purified by silica gel chromatography using a gradient of hexane:EtOAc 9:1 to hexane:EtOAc 7:3. After evaporation of the correct fractions, 6.7 g of Intermediate 1, 4,6-dichloro-2-(2-pyridin-2-yl)ethoxy)pyrimidine, was obtained as a white solid.

LC/MS (mobile phase 5-100% ACN in 3 min), Rt=1.68 min, $(M+H)^+$ 270

$^1$H NMR (300 MHz DMSO-d6): δ 8.43 (1H, d), 7.66 (2H, m), 7.22 (1H, d), 7.15 (1H, m), 4.21 (2H, m), 3.29 (2H, m)

Synthesis of 3-(m-tolyl)-1H-pyrazole (Intermediate 2)

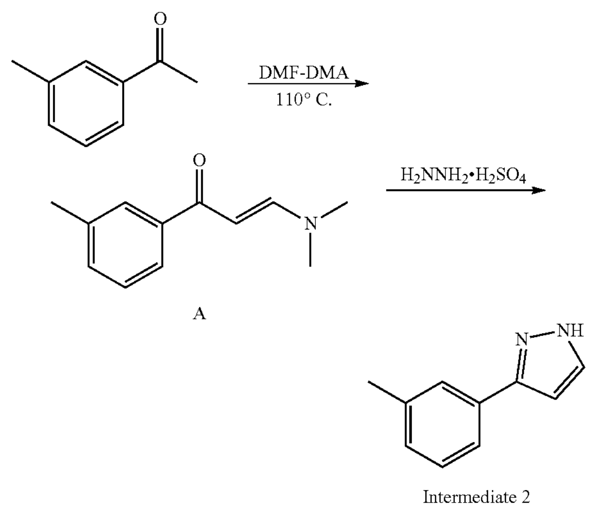

A

Intermediate 2

Preparation of A

To a stirred solution of 1-(m-tolyl)ethan-1-one (50 mL, 370 mmol) in toluene (250 mL), placed in a 3 neck round bottom flask, under $N_2$ atmosphere at rt, was added N,N-dimethylformamide dimethyl acetal (148 mL, 1110 mmol). The reaction mixture was gradually heated to 110° C. and stirred for 12 h. The reaction mixture was cooled to room temperature, excess toluene was removed under reduced pressure, diluted with water (250 mL) and extracted with EtOAc (3×250 mL), washed with brine (500 mL). The organic layer was dried over anhydrous $Na_2SO_4$, filtered and concentrated under reduced pressure to afford the crude product. The crude product was purified by silica-gel chromatography using (50-55% EtOAc:Hexanes). The fractions containing the product were combined and concentrated under vacuum to obtain A (24.0 g, 34% yield)) as a brown liquid.

MS (ESI+APCI; multimode): 190 $[M+H]^+$.

$^1$H NMR (400 MHz, $CDCl_3$): δ: 7.72 (d, J=12.4 Hz, 1H), 7.63 (s, 1H), 7.60 (d, J=7.2, Hz, 1H), 7.27-7.18 (m, 2H), 5.63 (d, J=12.4 Hz, 1H), 3.21-2.81 (m, 6H), 2.32 (s, 3H).

Preparation of Intermediate 2

To a stirred solution of A (24.0 g, 126 mmol) in $CH_3COOH$ (120 mL), under $N_2$ atmosphere at 0° C., Hydrazine hydrate (18.9 ml, 378 mmol) was added dropwise over a period of 10 mins. After complete addition, and the reaction mixture was gradually heated to 100° C. and stirred for 12 h. After completion of reaction, the reaction mixture was cooled to room temperature, quenched with sat. $NaHCO_3$ and extracted with EtOAc (3×200 mL). The combined organic extracts were washed with brine (200 mL), dried over anhydrous $Na_2SO_4$, filtered and concentrated under vacuum to obtain the crude product. The product was purified by silica-gel chromatography using (25-30% EtOAc:Hexane). The fractions containing the product were combined and concentrated under vacuum to obtain Intermediate 2 (5.00 g, 25% yield) as brown liquid.

MS (ESI+APCI; multimode): 159 $[M+H]^+$.

$^1$H NMR (400 MHz, $CDCl_3$): δ: 7.62 (d, J=2.4 Hz, 1H), 7.57 (brs, 1H), 7.53 (d, J=7.6, Hz, 1H), 7.31 (t, J=7.6, Hz, 1H), 7.15 (d, J=7.2 Hz, 1H), 6.61 (d, J=2.4 Hz, 1H), 2.40 (s, 3H).

Synthesis of 4-chloro-6-[3-(3-methylphenyl)-1H-pyrazol-1-yl]-2-[(oxolan-2-yl)methoxy]pyrimidine (Intermediate 3)

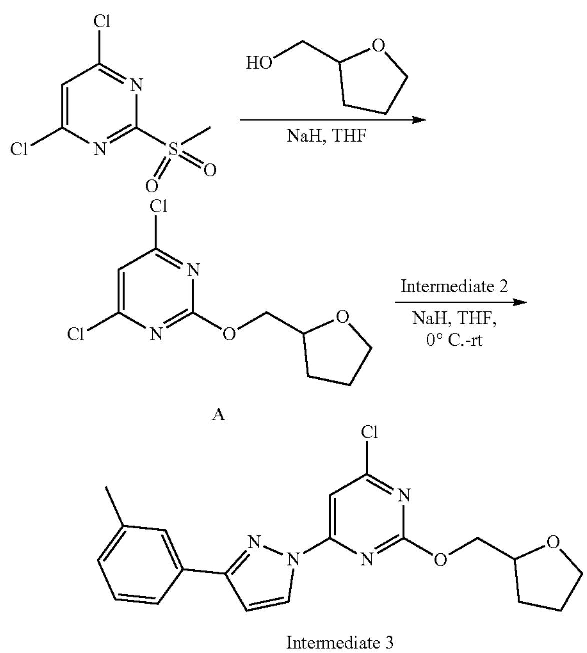

A

Intermediate 3

Preparation of A

To a mixture of 4,6-dichloro-2-methanesulfonylpyrimidine) and (oxolan-2-yl) methanol (4.50 g, 44.060 mmol, 1.00 equiv) in THF (120 mL) was added NaH (2.11 g, 52.849 mmol, 1.2 equiv, 60%) in portions at 0° C. and the mixture was stirred for 3 h at 0° C. Desired product could be detected by LCMS. The mixture was quenched with water (100 mL). The aqueous layer was extracted with EA (3×200 mL). The combine organic layers was washed with brine (200 mL), dried over $Na_2SO_4$, concentrated and purified by column chromatography on silica gel eluting with EA/PE (0-20%) to afford 4,6-dichloro-2-[(oxolan-2-yl)methoxy]pyrimidine (A) (5.5 g, 50.14%) as a light yellow oil.

Preparation of Intermediate 3

To a solution of (A) (50 mg, 0.201 mmol, 1 equiv), and Intermediate 2 (31.76 mg, 0.201 mmol, 1.00 equiv) in THF (50 mL) was added NaH (0.40 g, 1.00 equiv, 60%) and the mixture was stirred for 2 h at 0° C. The desired product could be detected by LCMS. The reaction was quenched with water (50 mL) and extracted with ethyl acetate (3×100 mL). The combined organic layers were washed with brine (50 mL), dried over anhydrous $Na_2SO_4$, concentrated and purified by reverse flash chromatography to afford 4-chloro-6-[3-(3-methylphenyl)-1H-pyrazol-1-yl]-2-[(oxolan-2-yl) methoxy]pyrimidine (Intermediate 3) (2.1 g, 53.60%) as a white solid.

LC-MS: RT=3.521 min, m/z=371.10 $[M+H]^+$ $^1$H NMR (400 MHz, DMSO-$d_6$) δ 8.75 (d, J=2.8 Hz, 1H), 7.86 (s, 1H), 7.80 (d, J=7.7 Hz, 1H), 7.68 (s, 1H), 7.38 (t, J=7.6 Hz, 1H), 7.26 (d, J=7.6 Hz, 1H), 7.21 (d, J=2.8 Hz, 1H), 4.44-4.35 (m, 2H), 4.29-4.13 (m, 1H), 3.92-3.76 (m, 1H), 3.76-3.62 (m, 1H), 2.40 (s, 3H), 2.08-1.97 (m, 1H), 1.96-1.82 (m, 2H), 1.78-1.62 (m, 1H).

Synthesis of 4-[6-chloro-2-[(oxolan-2-yl)methoxy] pyrimidin-4-yl]morpholine (Intermediate 4)

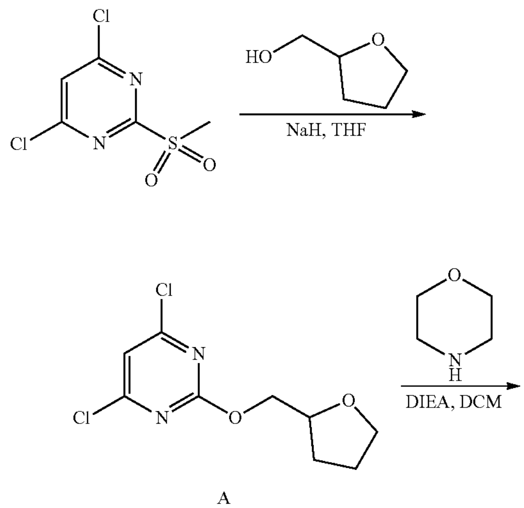

A

-continued

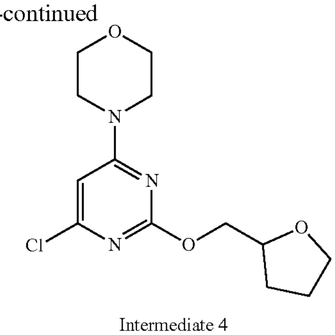

Intermediate 4

Preparation of A

To a mixture of 4,6-dichloro-2-methanesulfonylpyrimidine) and (oxolan-2-yl) methanol (4.50 g, 44.060 mmol, 1.00 equiv) in THF (120 mL) was added NaH (2.11 g, 52.849 mmol, 1.2 equiv, 60%) in portions at 0° C. and the mixture was stirred for 3 h at 0° C. Desired product could be detected by LCMS. The mixture was quenched with water (100 mL). The aqueous layer was extracted with EA (3×200 mL). The combine organic layers was washed with brine (200 mL), dried over $Na_2SO_4$, concentrated and purified by column chromatography on silica gel eluting with EA/PE (0-20%) to afford 4,6-dichloro-2-[(oxolan-2-yl)methoxy]pyrimidine (A) (5.5 g, 50.14%) as a light yellow oil.

Preparation of Intermediate 4

To a solution of A 2.3 g, 9.234 mmol, 1 equiv in DCM (25 mL) was successively added DIEA (1.43 g, 11.080 mmol, 1.20 equiv) and morpholine (0.80 g, 9.234 mmol, 1 equiv), and the solution was stirred for 2 h at room temperature. The desired product could be detected by LCMS. Then the mixture was concentrated and purified by column chromatography on silica gel eluting with EA/PE (0-100%) to afford 4-[6-chloro-2-[(oxolan-2-yl)methoxy]pyrimidin-4-yl]morpholine (Intermediate 4) (2.6 g, 91.12%) as a white solid.

LC-MS: RT=2.219 min, m/z=300.05$[M+H]^+$ $^1$H NMR (400 MHz, DMSO-$d_6$) δ 6.62 (s, 1H), 4.31-4.01 (m, 3H), 3.81-3.71 (m, 1H), 3.71-3.43 (m, 9H), 2.04-1.74 (m, 3H), 1.72-1.47 (m, 1H).

Synthesis of 4-chloro-6-[3-(3-methylphenyl)-1H-pyrazol-1-yl]-2-[2-(oxolan-2-yl)ethyl-pyrimidine (Intermediate 5)

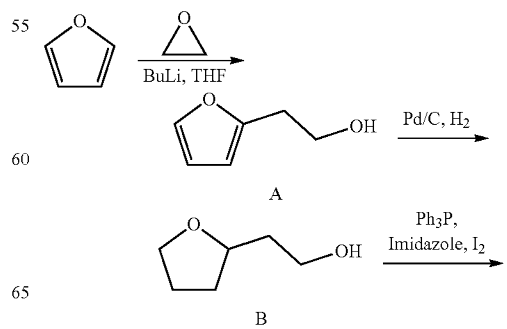

A

B

-continued

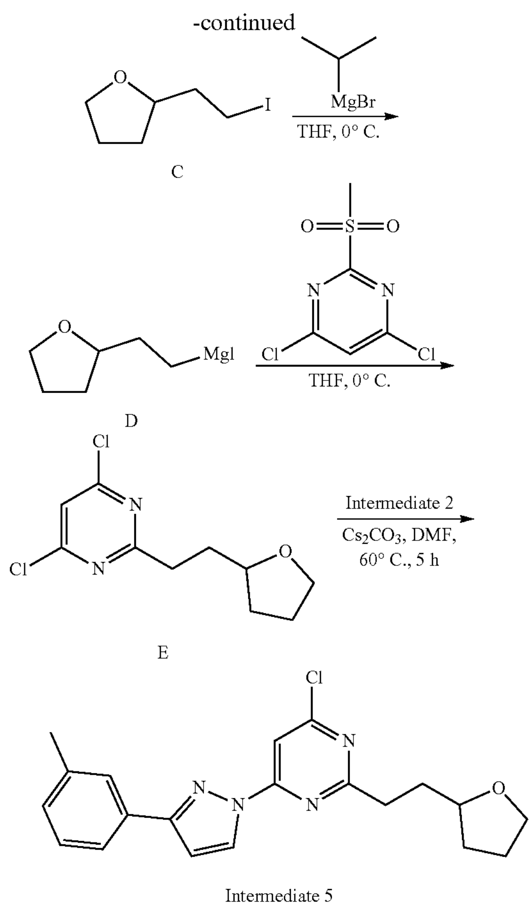

C

D

E

Intermediate 5

Preparation of A

To a solution of furan (13.6 g, 199.780 mmol, 1 eq.) in THF (95 mL) cooled to −80° C. was added n-BuLi in hexane (83.9 mL, 209.750 mmol, 1.05 eq.). The reaction mixture was slowly warmed to r.t. and stirred overnight. The reaction mixture was again cooled to −80° C. and a cooled THF (15 mL) solution of oxirane (17.60 g, 399.559 mmol, 2.00 eq.) was added slowly. The reaction mixture was allowed to reach r.t. and stirred 14 h. The reaction mixture was cooled to 0° C. and saturated ammonium chloride (50 mL) was added slowly. The product was extracted with ethyl acetate (2×100 mL) and the organic layer was washed with water, brine solution, dried over sodium sulfate and concentrated under reduced pressure. The residue was purified by silica gel column chromatography to afford 2-(furan-2-yl)ethan-1-ol (A) (12.2 g, 54.46%) as light yellow oil.

Preparation of B

To a solution A (9.2 g, 82.049 mmol, 1 eq.) in MeOH (60 mL) was added Pd/C (0.87 g, 8.205 mmol, 0.10 eq.) under $N_2$ atmosphere. Then the $N_2$ atmosphere was replaced by $H_2$ atmosphere. The mixture was stirred at room temperature overnight. The resulting mixture was filtered, the filtrate was concentrated under reduced pressure. The residue 2-(oxolan-2-yl)ethan-1-ol (B) (4.6 g, 48.26%) can be used for the next step without further purification.

Preparation of C

To a stirring solution of B (4.6 g, 39.601 mmol, 1 eq.) in THF (225 mL) and ACN (90 mL) were added $Ph_3P$ (15.58 g, 59.401 mmol, 1.5 eq.), Imidazole (4.04 g, 59.401 mmol, 1.5 eq. and $I_2$ (15.08 g, 59.401 mmol, 1.5 eq.) at 25° C. The mixture is stirred at 25° C. for 2 h, and then the solvent is evaporated in vacuo. The residue is purified on silica gel (1-2.5% EtOAc in petroleum ether) to afford 2-(2-iodoethyl) oxolane (C) (5.8 g, 64.79%) as light yellow oil.

Preparation of D

To a stirred solution of 2-(2-iodoethyl)oxolane C (4 g, 17.695 mmol, 1 eq.) was added bromo(propan-2-yl)magnesium (26.54 mL, 0.000 mmol, 1.50 eq.) in THF dropwise at 0° C. under $N_2$ atmosphere. After the addition, the mixture was stirred for 2 h at room temperature. The resulting solution of 2-[2-(iodomagnesio)ethyl]oxolane (D) can be used for the next step directly.

Preparation of E

To a stirred solution of 4,6-dichloro-2-methanesulfonylpyrimidine (6.027 g, 26.543 mmol, 1.50 equiv) in THF (18 mL) was added 2-[2-(iodomagnesio)ethyl]oxolane (D) (17.695 mL, 17.695 mmol, 1 equiv) in THF dropwise at 0° C. under $N_2$ atmosphere. After the addition, the mixture was stirred at room temperature for half an hour. The reaction was quenched by the addition of sat. $NH_4Cl$ aqueous solution. The resulting mixture was extracted with EtOAc/$H_2O$. The combined organic layers were dried over anhydrous $MgSO_4$. After filtration, the filtrate was concentrated under reduced pressure. The residue was purified by silica gel column chromatography, eluted with Petroleum ether/EtOAc (10:1) to afford 4,6-dichloro-2-[2-(oxolan-2-yl)ethyl]pyrimidine (E) (2.7 g, 15.46%) as a light yellow oil.

Preparation of Intermediate 5

To a stirred solution Intermediate 2 (1.64 g, 10.380 mmol, 0.95 equiv) and 4,6-dichloro-2-[2-(oxolan-2-yl)ethyl]pyrimidine (E) (2.7 g, 10.926 mmol, 1 equiv) in DMF (20 mL) was added $Cs_2CO_3$ (3.56 g, 10.926 mmol, 1 equiv). The resulting solution was stirred at 60° C. for 5 h. The reaction was quenched by the addition of $H_2O$. The resulting mixture was extracted with EtOAc. The combined organic layers were dried over anhydrous $MgSO_4$. After filtration, the filtrate was concentrated under reduced pressure. The residue was purified by silica gel column chromatography to afford 4-chloro-6-[3-(3-methylphenyl)-1H-pyrazol-1-yl]-2-[2-(oxolan-2-yl)ethyl]pyrimidine Intermediate 5 (2.5 g, 62.03%) as a yellow solid.

$^1$H NMR (400 MHz, DMSO-d6) δ 8.74 (d, J=2.8 Hz, 1H), 7.88 (s, 1H), 7.86 (s, 1H), 7.80 (d, J=7.8 Hz, 1H), 7.37 (t, J=7.6 Hz, 1H), 7.25 (d, J=7.6 Hz, 1H), 7.19 (d, J=2.8 Hz, 1H), 3.83 (p, J=6.7 Hz, 1H), 3.75 (td, J=7.7, 6.2 Hz, 1H), 3.60 (td, J=7.9, 6.3 Hz, 1H), 3.06-2.86 (m, 2H), 2.39 (s, 3H), 2.04-1.92 (m, 3H), 1.90-1.75 (m, 2H), 1.48 (ddt, J=11.8, 8.7, 7.3 Hz, 1H).

Synthesis of (3aR,6aR)-hexahydro-2H-furo[3,2-b] pyrrole hydrochloride (Intermediate 6)

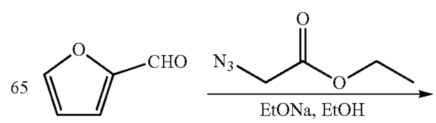

-continued

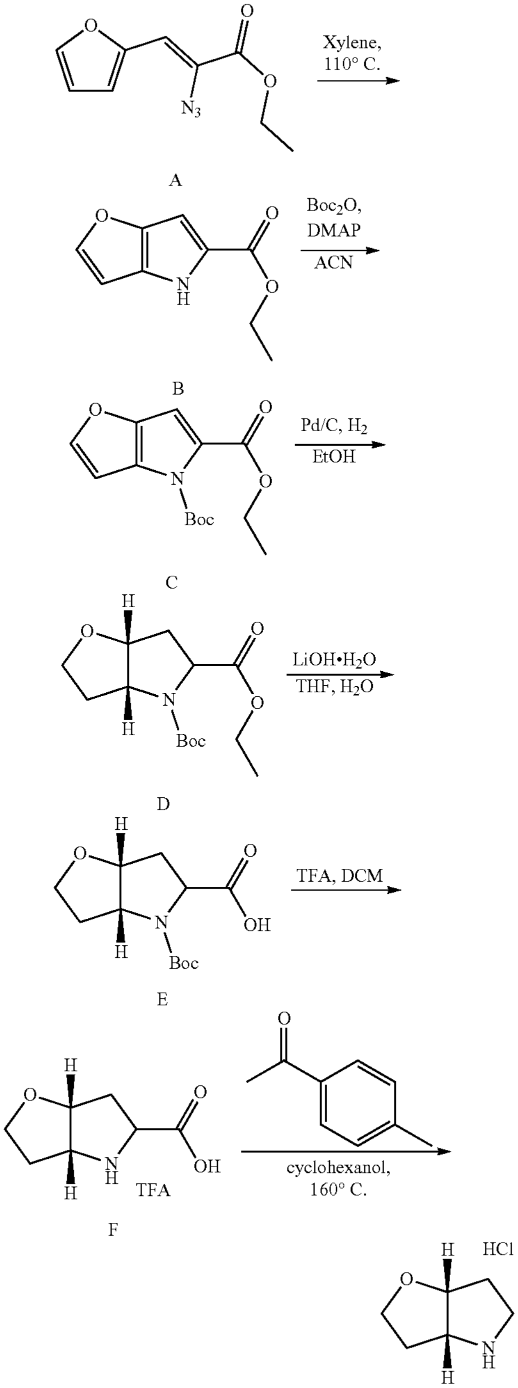

A

B

C

D

E

F

Intermediate 6

Preparation of A

To a stirred solution of EtONa (21.25 g, 312.224 mmol, 1.5 equiv) in EtOH (320.00 mL) was added furan-2-carbaldehyde (20.00 g, 208.149 mmol, 1.00 equiv) at 0° C. under $N_2$ atmosphere. This was followed by the addition of ethyl 2-azidoacetate (80.63 g, 624.447 mmol, 3.00 equiv) dropwise at 0° C. during a period of 45 minutes. The resulting solution was stirred for another 90 minutes at 0° C. Then the reaction was quenched by the addition of 70 mL of sat. $NH_4Cl$ aqueous solution. The mixture was extracted with EtOAc (300 mL). The organic layers were dried over anhydrous $Na_2SO_4$. After filtration, the filtrate was concentrated under reduced pressure. The residue was purified by silica gel chromatography to afford ethyl (2Z)-2-azido-3-(furan-2-yl)prop-2-enoate (A) (19 g, 44.06%) as light yellow oil.

Preparation of B

Into a 1000 mL round bottom flask was placed xylene (280 mL). This was followed by the addition of a solution of ethyl (2Z)-2-azido-3-(furan-2-yl)prop-2-enoate (A) (19.00 g, 91.704 mmol, 1.00 equiv) in xylene (70 mL), which was added dropwise with stirring over a period of 2 hours at 110° C. 1 h later, the mixture was concentrated by evaporation under vacuum. The residue was purified by eluting through a column with a 20:1 PE/EtOAc solvent system. This resulted in ethyl 4H-furo[3,2-b]pyrrole-5-carboxylate (B) (15 g, 91.29%) as a brown solid.

Preparation of C

To a stirred solution of ethyl 4H-furo[3,2-b]pyrrole-5-carboxylate (B) (15.00 g, 83.717 mmol, 1.00 equiv) and DMAP (511.38 mg, 4.186 mmol, 0.05 equiv) in ACN (38.00 mL) was added di-tert-butyl dicarbonate (21.93 g, 100.460 mmol, 1.20 equiv) dropwise over a period of 0.5 h at 0° C. under $N_2$ atmosphere. Then the solution was stirred at room temperature for 3 h. The resulting mixture was diluted with EtOAc (300 mL) and washed with water (300 mL). The organic phase was separated and dried over anhydrous $MgSO_4$. After filtration, the filtrate was evaporated under reduced pressure. The residue 4-tert-butyl 5-ethyl 4H-furo[3,2-b]pyrrole-4,5-dicarboxylate (C) (15 g, 64.15%) can be used for the next step without further purification.

Preparation of D

To a solution of 4-tert-butyl 5-ethyl 4H-furo[3,2-b]pyrrole-4,5-dicarboxylate (C) (15.00 g, 53.707 mmol, 1.00 equiv.) in EtOH (150.00 mL) was added Pd/C (5.72 g, 5.371 mmol, 0.10 equiv, 10%) under $N_2$ atmosphere. Then the $N_2$ atmosphere was replaced by $H_2$ atmosphere. The mixture was stirred at 60° C. overnight. The resulting mixture was filtered and the filtrate was concentrated under reduced pressure. The residue 4-tert-butyl 5-ethyl (3aR,6aR)-hexahydro-2H-furo[3,2-b]pyrrole-4,5-dicarboxylate (D) (11 g, 71.78%) can be used for the next step without further purification.

Preparation of E

To a stirred solution of 4-tert-butyl 5-ethyl (3aR,6aR)-hexahydro-2H-furo[3,2-b]pyrrole-4,5-dicarboxylate (D) (11.00 g, 38.551 mmol, 1.00 equiv) in THF (120.00 mL) was added a solution of $LiOH{\cdot}H_2O$ (8.09 g, 192.753 mmol, 5.00 equiv) in $H_2O$ (120.00 mL) at room temperature. The mixture was stirred at 50° C. overnight. The reaction was quenched by the addition of a solution of AcOH (11 mL) in water (200 mL). Then the mixture was extracted with EtOAc (5×300 mL). The combined organic layers were dried over anhydrous $MgSO_4$. After filtration, the filtrate was concentrated under reduced pressure. This resulted in the crude product (3aR,6aR)-4-[(tert-butoxy)carbonyl]-hexahydro- 2H-furo[3,2-b]pyrrole-5-carboxylic acid (E) (6 g, 60.49%) which can be used for the next step without further purification.

Preparation of F

To a stirred solution of (3aR,6aR)-4-[(tert-butoxy)carbonyl]-hexahydro-2H-furo[3,2-b]pyrrole-5-carboxylic acid (E) (6.00 g, 23.320 mmol, 1.00 equiv) in DCM (10.00 mL) was added TFA (80 mL) dropwise at room temperature. The resulting solution was stirred at room temperature overnight. Then the solvent was evaporated under reduced pressure. The residue (3aR,6aR)-hexahydro-2H-furo[3,2-b] pyrrole-5-carboxylic acid; trifluoroacetic acid (F) (4.8 g, 75.90%) can be used for the next step without further purification.

Preparation of Intermediate 6

Into a 100 ml round bottom flask, was placed a solution of (3aR,6aR)-hexahydro-2H-furo[3,2-b]pyrrole-5-carboxylic acid; trifluoroacetic acid (F) (4.80 g, 17.700 mmol, 1.00 equiv) in cyclohexanol (35.00 mL). To the mixture was added 1-(4-methylphenyl)ethan-1-one (0.24 g, 1.770 mmol, 0.10 equiv) (a catalytic amount). The resulting solution was allowed to react, with stirring, for 3 hours while the temperature was maintained at 160° C. in a bath of oil. The resulting solution was extracted three times with 60 ml of HCl (10%) and the aqueous layers combined. The resulting mixture was washed 3 times with 60 ml of toluene. The mixture was concentrated by evaporation under vacuum using a rotary evaporator. This resulted in (3aR,6aR)-hexahydro-2H-furo[3,2-b]pyrrole hydrochloride (Intermediate 6) (2.3 g, 86.85%) as a brown solid. Used crude.

Synthesis of 4-[(3aR,6aR)-hexahydro-2H-furo[3,2-b]pyrrol-4-yl]-2-chloro-6-[3-(3-methylphenyl)-1H-pyrazol-1-yl]pyrimidine (Intermediate 7)

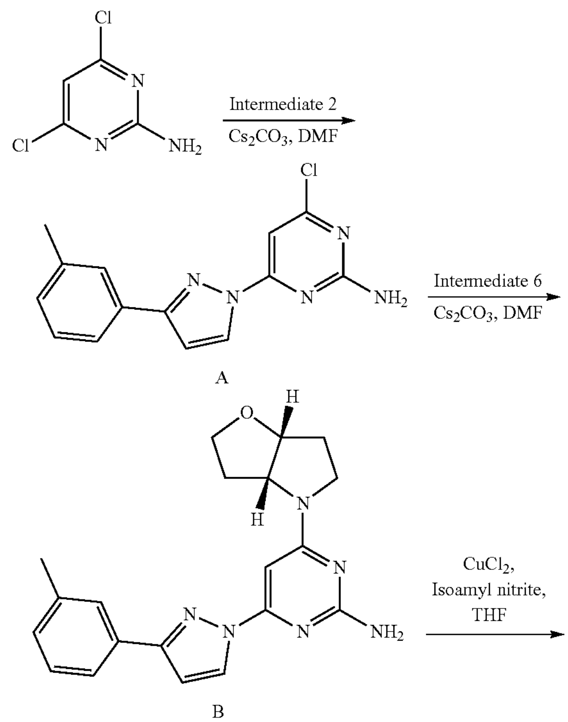

A

B

-continued

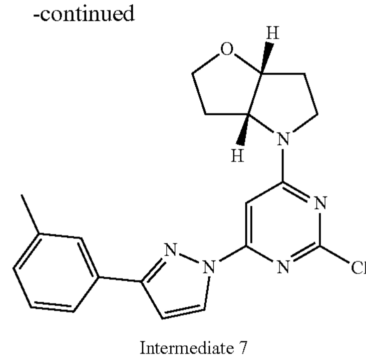

Intermediate 7

Preparation of A

A mixture of 4,6-dichloropyrimidin-2-amine (4.00 g, 25.284 mmol, 1.00 equiv) and Intermediate 2, (3 equiv) in DMF (50.00 mL) was stirred for 5 h at 100° C. under $N_2$ atmosphere. The resulting mixture was diluted with EtOAc (500 mL) and washed with water (300 mL) for 3 times. The organic phase was concentrated under reduced pressure. The residue was purified by silica gel column chromatography to afford 4-chloro-6-[3-(3-methylphenyl)-1H-pyrazol-1-yl]pyrimidin-2-amine (A) (5.2 g, 71.98%) as white solid.

Preparation of B

A mixture of 4-chloro-6-[3-(3-methylphenyl)-1H-pyrazol-1-yl]pyrimidin-2-amine (A) (5.10 g, 17.832 mmol, 1.16 equiv, Intermediate 6 (2.30 g, 15.372 mmol, 1.00 equiv) and $Cs_2CO_3$ (25.04 g, 76.861 mmol, 5.00 equiv) in DMF (40.00 mL) was stirred for 2 h at 130° C. under $N_2$ atmosphere. The resulting mixture was diluted with EtOAc (300 mL) and washed with water (100 mL) for 3 times. The organic phase was concentrated under reduced pressure. The residue was purified by silica gel column chromatography to afford 4-[(3aR,6aR)-hexahydro-2H-furo[3,2-b]pyrrol-4-yl]-6-[3-(3-methylphenyl)-1H-pyrazol-1-yl]pyrimidin-2-amine (B) (2.5 g, 44.9%) as white solid.

Preparation of Intermediate 7

A mixture of 4-[(3aR,6aR)-hexahydro-2H-furo[3,2-b]pyrrol-4-yl]-6-[3-(3-methylphenyl)-1H-pyrazol-1-yl]pyrimidin-2-amine (B) (2.30 g, 6.346 mmol, 1.00 equiv), 3-methylbutyl nitrite (3.72 g, 31.730 mmol, 5.00 equiv) and $CuCl_2$ (4.27 g, 31.759 mmol, 5.00 equiv) in THF (90.00 mL) was stirred for 2 h at 60° C. under $N_2$ atmosphere. The resulting mixture was diluted with EtOAc (500 mL). Then phen (11.446 g, 63.518 mmol, 10.00 equiv) was added into the mixture under vigorous stirring. The resulting mixture was stirred for 1 h. Then deposit was filtered off, the filtrate was concentrated under reduced pressure. The residue was purified by silica gel column chromatography to afford 4-[(3aR,6aR)-hexahydro-2H-furo[3,2-b]pyrrol-4-yl]-2-chloro-6-[3-(3-methylphenyl)-1H-pyrazol-1-yl]pyrimidine (Intermediate 7) (1 g, 41.3%) as white solid.

LC-MS: RT=2.776 min, m/z=382.1 $[M+H]^+$ $^1H$ NMR (400 MHz, DMSO-$d_6$) δ 8.54 (d, J=2.7 Hz, 1H), 7.90-7.69 (m, 2H), 7.37 (t, J=7.6 Hz, 1H), 7.23 (d, J=7.6 Hz, 1H), 7.10 (d, J=2.8 Hz, 1H), 6.97-6.83 (m, 1H), 4.58 (d, J=27.1 Hz, 2H), 4.06-3.70 (m, 3H), 3.57-3.36 (m, 1H), 2.39 (s, 3H), 2.32-1.86 (m, 4H).

Synthesis of (3aR,6aR)-4-(2-chloro-6-(3-(3-methoxyphenyl)-1H-pyrazol-1-yl)pyrimidin-4-yl) hexahydro-2H-furo[3,2-b]pyrrole (Intermediate 8)

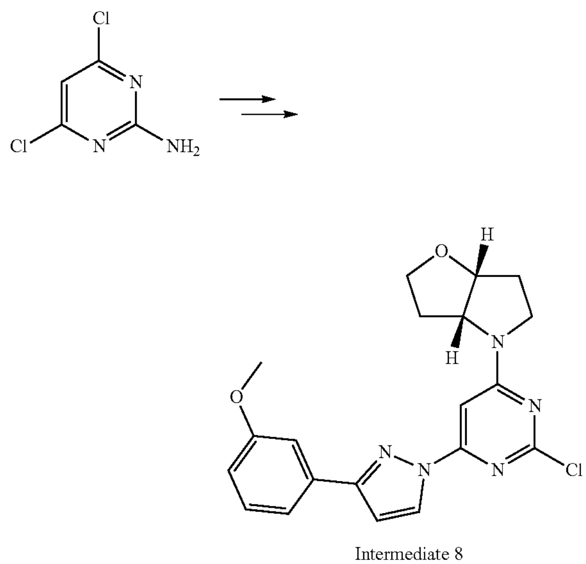

Intermediate 8

Intermediate 8 was prepared using a procedure similar to the procedure for Intermediate 7 using 3-methoxyphenyl-1H-pyrazole instead of Intermediate 2.

LC-MS: RT=2.776 min, m/z=398 $[M+H]^+$

Synthesis of 4-(2-chloro-6-(3-(3-methoxyphenyl)-1H-pyrazol-1-yl)pyrimidin-4-yl)morpholine (Intermediate 9)

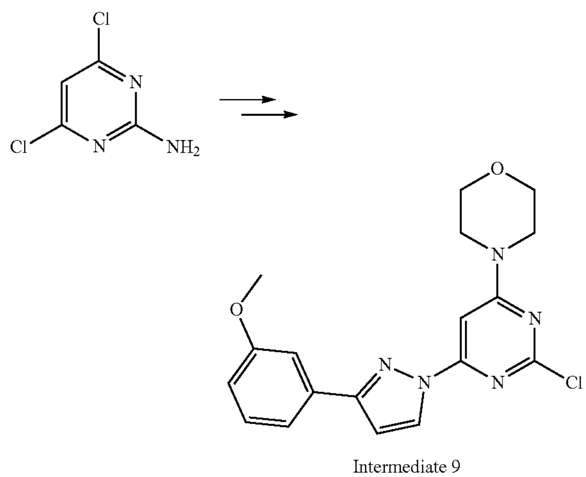

Intermediate 9

Intermediate 9 was prepared using a procedure similar to the procedure for Intermediate 8, except morpholine was used instead of Intermediate 6.

LC-MS: RT=2.776 min, m/z=371 $[M+H]^+$

Synthesis of 4-(2-chloro-6-(3-(m-tolyl)-1H-pyrazol-1-yl)pyrimidin-4-yl) morpholine (Intermediate 10) and 4-(6-chloro-2-(3-(m-tolyl)-1H-pyrazol-1-yl) pyrimidin-4-yl)-morpholine (Intermediate 11)

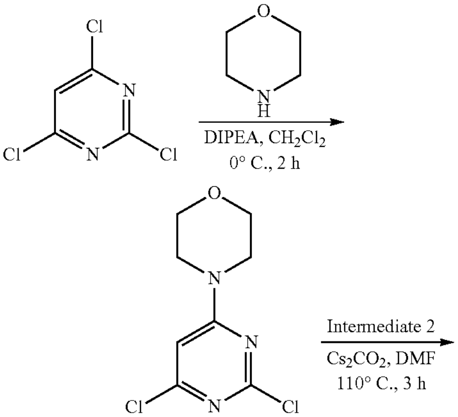

A

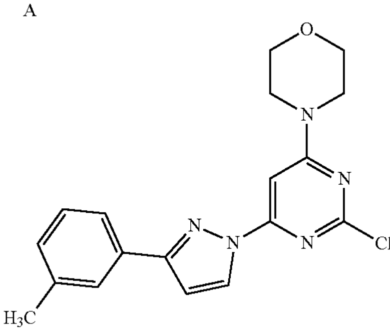

Intermediate 10

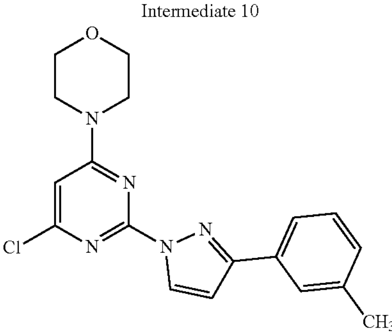

Intermediate 11

Preparation of A

To a stirred solution of 2,4,6-trichloropyrimidine (10.0 g, 54.5 mmol) in anhydrous $CH_2Cl_2$ (250 ml) at 0° C. under $N_2$ atmosphere was added morpholine (4.75 g, 54.5 mmol) followed with DIPEA (19.0 mL, 109 mmol). The reaction mixture was stirred at 0° C. for 2 h. The reaction mixture was diluted with water (300 mL) and extracted with EtOAc (2×300 mL). The combined organic extracts were washed with brine (300 mL), dried over anhydrous $Na_2SO_4$, filtered and concentrated under vacuum to obtain the crude product. The crude product was purified by silica-gel column chromatography using 20% EtOAc:Hexanes. Fractions containing the product were combined and concentrated under vacuum to obtain A (8.50 g, 36.3 mmol, 66% yield) as an off-white solid.

LCMS (ESI): m/z=235 $[M+H]^+$.

$^1$H NMR (400 MHz, $CDCl_3$) δ: 6.40 (s, 1H), 3.78-3.76 (m, 4H), 3.65 (brs, 4H).

Preparation of Intermediates 10 and 11

To a stirred solution of A (5.00 g, 21.3 mmol) in anhydrous DMF (50 mL) at room temperature under $N_2$ atmosphere was added Intermediate 2 (3.38 g, 21.3 mmol) followed with $Cs_2CO_3$ (13.9 g, 42.7 mmol). The reaction mixture was gradually heated to 110° C. and stirred for 3 h. The reaction mixture was cooled to room temperature, diluted with water (150 mL), and extracted with EtOAc (2×100 mL). The combined organic extracts were washed with brine (150 mL), dried over anhydrous $Na_2SO_4$, filtered and concentrated under vacuum to obtain the crude product. The crude product was purified by silica-gel column chromatography using 12-35% EtOAc:Hexanes. Fractions containing the product were combined and concentrated under vacuum to obtain 4-(2-chloro-6-(3-(m-tolyl)-1H-pyrazol-1-yl)pyrimidin-4-yl)morpholine (Intermediate 10) (836 mg, 2.35 mmol, 11% yield, as an off-white solid, and 4-(6-chloro-2-(3-(m-tolyl)-1H-pyrazol-1-yl)pyrimidin-4-yl)morpholine (Intermediate 11) (1.90 g, 5.34 mmol, 25% yield) as an off-white solid.

Intermediate 10

LCMS (ESI): m/z=356 $[M+H]^+$; HPLC: 98.6 (% of AUC).

$^1$H NMR (400 MHz, $CDCl_3$) δ: 8.51 (d, J=2.8 Hz, 1H), 7.73 (s, 1H), 7.68 (d, J=7.6 Hz, 1H), 7.33 (t, J=7.6 Hz, 1H), 7.19 (d, J=7.6 Hz, 1H), 7.08 (s, 1H), 6.76 (d, J=2.8 Hz, 1H), 3.81-3.80 (m, 4H), 3.76 (brs, 4H), 2.42 (s, 3H).

Intermediate 11

LCMS (ESI): m/z=356 $[M+H]^+$.

$^1$H NMR (400 MHz, $CDCl_3$) δ: 8.52 (d, J=2.8 Hz, 1H), 7.83 (s, 1H), 7.72 (d, J=7.6 Hz, 1H), 7.31 (t, J=7.6 Hz, 1H), 7.17 (d, J=7.6 Hz, 1H), 6.77 (d, J=2.8 Hz, 1H), 6.38 (s, 1H), 3.83-3.81 (m, 4H), 3.74 (brs, 4H), 2.41 (s, 3H).

Synthesis of 4-[2-ethenyl-6-[3-(3-methylphenyl)-1H-pyrazol-1-yl]pyrimidin-4-yl]-morpholine (Intermediate 12)

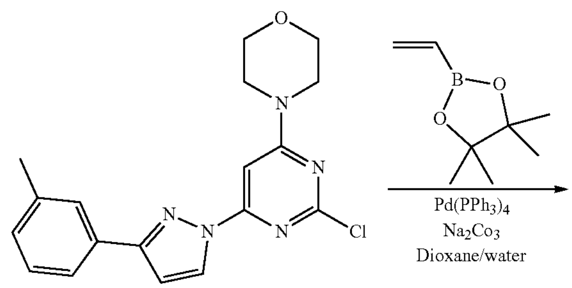

Intermediate 10

-continued

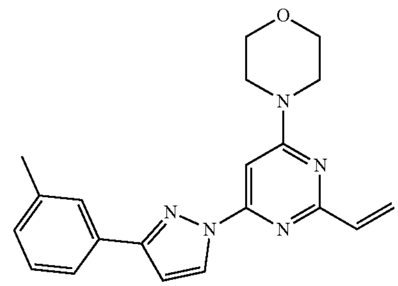

Intermediate 12

To a stirred solution of Intermediate 10 (1.00 g, 2.81 mmol) in 1,4-dioxane (10 ml) at room temperature under $N_2$ atmosphere was added 4,4,5,5-tetramethyl-2-vinyl-1,3,2-dioxaborolane (519 mg, 3.37 mmol) followed with $Na_2CO_3$ (0.745 g, 7.03 mmol), $Pd(PPh_3)_4$ (325 mg, 0.28 mmol) and water (2 mL). The reaction mixture was degassed for 5 min, gradually heated to 80° C. and stirred for 8 h. The reaction mixture is cooled to room temperature, filtered through celite and washed with EtOAc (50 mL). Filtrate was concentrated, diluted with water (50 mL) and extracted with EtOAc (2×70 mL). The combined organic extracts were washed with brine solution (50 mL), dried over anhydrous $Na_2SO_4$ and concentrated under reduced pressure to obtain the crude product. The crude compound was purified by silica-gel column chromatography using 5-6% EtOAc: Hexanes. Fractions containing the product were combined and concentrated under vacuum to obtain Intermediate 12 (650 mg, 1.87 mmol, 66% yield) as an off-white solid.

LCMS (ESI): m/z=348 $[M+H]^+$.

$^1$H NMR (400 MHz, $CDCl_3$) δ: 8.63 (d, J=2.8 Hz, 1H), 7.75 (s, 1H), 7.70 (d, J=7.6 Hz, 1H), 7.32 (t, J=7.6 Hz, 1H), 7.18 (d, J=7.2 Hz, 1H), 7.08 (s, 1H), 6.76-6.74 (m, 1H), 6.72-6.67 (m, 1H), 6.60-6.55 (m, 1H), 5.67 (dd, J=2.0 Hz, 10.0 Hz, 1H), 3.83-3.77 (m, 8H), 2.43 (s, 3H).

Synthesis of 4-chloro-2-((2,2-dimethyl-1,3-dioxolan-4-yl)methoxy)-6-(3-(3-methoxyphenyl)-1H-pyrazol-1-yl)pyrimidine (Intermediate 13)

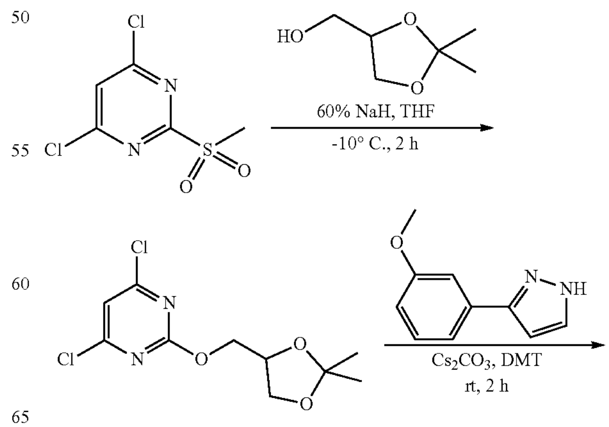

A

-continued

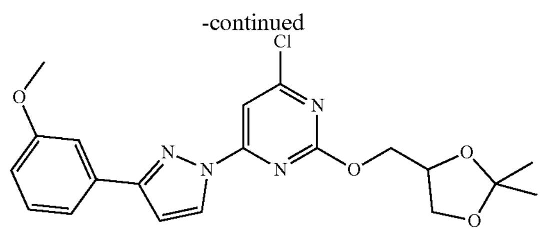

Intermediate 13

Intermediate 13 was synthesized as shown above, similar to the procedure for Intermediate 3, and purified by silica gel chromatography.

LCMS (ESI): m/z=417 $[M+H]^+$.

Synthesis of 4-(6-chloro-2-((2,2-dimethyl-1,3-dioxolan-4-yl)methoxy)pyrimidin-4-yl)morpholine (Intermediate 14)

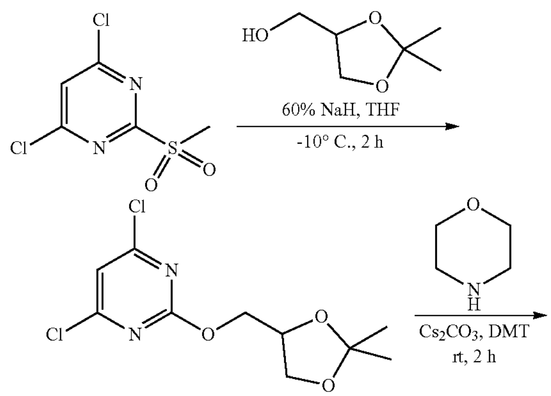

A

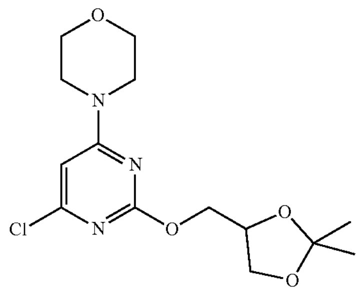

Intermediate 14

Preparation of A

A was synthesized as shown above, using 4,6-dichloro-2-(methylsulfonyl pyrimidine (18 g, 1 eq.) with 60% NaH in mineral oil (1.2 eq.) in 200 ml THF at −10° C. Stirred for 2 h at −10 C, purified by silica get. $^1$H NMR and MS consistent with A (17 g, 77%).

Preparation of Intermediate 14

Intermediate 14 was synthesized as shown above stirring A (3.0 g, 1 eq.), morpholine (1 eq.) and $Cs_2CO_3$ (1 eq.) in DMF (30 ml) for 2 h at rt. Purified by silica gel chromatography. $^1$H NMR and MS consistent with Intermediate 14 (3.02 g, 85%).

Synthesis of 4-(6-chloro-2-methoxypyrimidin-4-yl)morpholine (Intermediate 15)

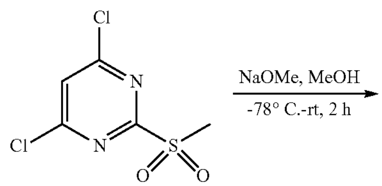

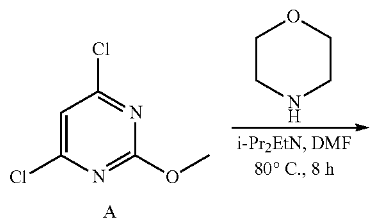

A

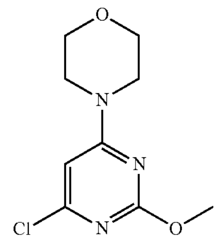

Intermediate 15

Preparation of A

A was synthesized as illustrated above using 4,6-dichloro-2-(methylsulfonyl pyrimidine (10 g, 1 eq.), NaOMe (1.1 eq.) in 100 mL MeOH. Yield: 4.2 g (52%).

Preparation of Intermediate 15

Intermediate 15 was synthesized using A (4 g, 1 eq), morpholine (1 eq) and $i\text{-}Pr_2EtN$ (2 eq) in DMF (50 ml) as illustrated above. Yield: 3.8 g (74%).

LCMS (ESI): m/z=230 $[M+H]^+$.

Synthesis of 4-morpholino-6-(3-(m-tolyl)-1H-pyrazol-1-yl) pyrimidin-2-amine (Intermediate 16)

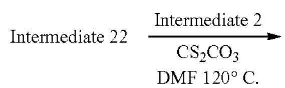

-continued

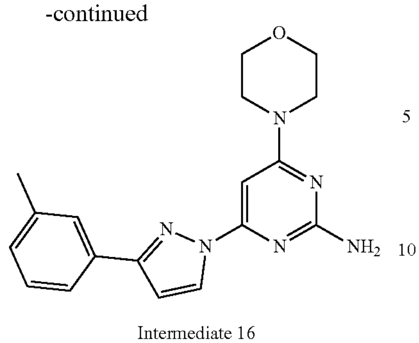

Intermediate 16

To a stirred solution of Intermediate 22 (10.4 g, 48.0 mmol) in DMF (100 mL), placed in a 3 neck round bottom flask, under $N_2$ atmosphere at rt, was added Intermediate 2 (7.00 g, 44.0 mmol) followed with $Cs_2CO_3$ (28.6 g, 88.0 mmol). The reaction mixture was refluxed at 120° C. for 5 h. After completion of reaction, the reaction mixture cooled to rt, and diluted with ice cold water (500 mL), whereupon the product precipitated. The precipitated product was collected by filtration under vacuum, washed with MTBE (50.0 mL) and dried under vacuum to obtain Intermediate 16 (11.0 g, 78% yield).

MS (ESI+APCI; multimode): 337 $[M+H]^+$.

$^1H$ NMR (400 MHz, DMSO-$d_6$): δ: 8.46 (d, J=2.4 Hz, 1H), 7.79 (s, 1H), 7.74 (d, J=8.0 Hz, 1H), 7.34 (t, J=7.6 Hz, 1H), 7.19 (d, J=7.2 Hz, 1H), 7.00 (d, J=2.4 Hz, 1H), 6.56 (s, 1H), 6.41 (brs, 2H), 3.71-3.56 (m, 8H), 2.37 (s, 3H).

Synthesis of 4-(2-iodo-6-(3-(m-tolyl)-1H-pyrazol-1-yl)pyrimidin-4-yl)morpholine (Intermediate 17)

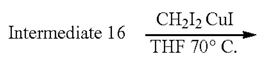

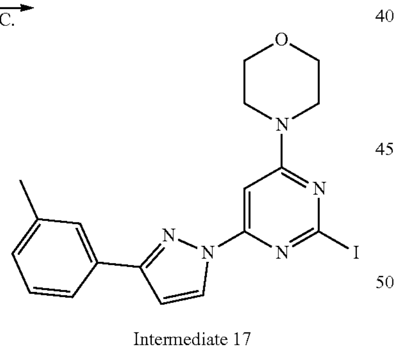

Intermediate 17

To a solution of Intermediate 16 (1.6 g, 4.7 mmol) in THF (20 mL) was added isoamyl nitrite (978 mg, 9.5 mmol), CuI (992 mg, 5.2 mmol) and $CH_2I_2$ (6.4 g, 23.3 mmol) under an atmosphere of nitrogen. The reaction mixture was stirred at 100° C. for 12 hrs. The mixture was then poured into water (30 mL) and stirred overnight before extraction with EtOAc (30 mL×2). The combined organic layers were washed with brine (20 mL×2), dried over $Na_2SO_4$, filtered and concentrated to dryness. The crude product was purified by chromatography on silica gel eluting with petroleum ether: EtOAc=3:1 to get the desired product 4-(2-iodo-6-(3-(m-tolyl)-1H-pyrazol-1-yl)pyrimidin-4-yl)morpholine (Intermediate 17) (288 mg, 12%) as a yellow solid.

Synthesis of 4-morpholino-6-(3-(m-tolyl)-1H-pyrazol-1-yl)pyrimidin-2-ol (Intermediate 18)

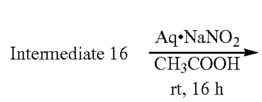

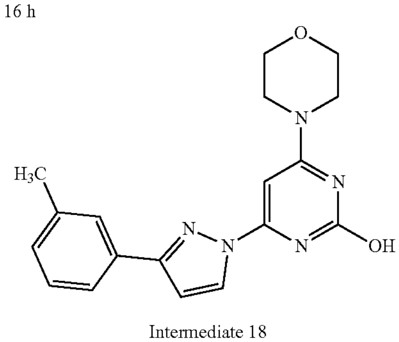

Intermediate 18

To a stirred solution of Intermediate 16 (150 g, 446 mmol) in $CH_3COOH$ (1000 mL) placed in a 3 neck round bottom flask, was added $NaNO_2$ (154 g, 2229 mmol) in $H_2O$ (1000 mL) slowly by dropping funnel at 0° C. under $N_2$ atmosphere. The reaction mixture was stirred at room temperature for 16 h. After completion of reaction, the reaction mixture was diluted with ice cold water (2.0 L), whereupon the product precipitated. The precipitated product was collected by filtration under vacuum, washed with MTBE (200 mL) and hexane (200 mL) and dried under vacuum to obtain crude compound. The obtained crude compound dissolved in THF:$H_2O$ (2.0 L, 1:1) at room temperature was added 6 N NaOH (450 mL). The reaction mixture was acidified 2M HCl (500 mL), whereupon the product precipitated. The precipitated product was collected by filtration under vacuum, washed with MTBE (200 mL) and hexane (200 mL) and dried under vacuum to obtain Intermediate 18 (127 g, 95% yield) as an off-white solid.

MS (ESI+APCI; multimode): 338 $[M+H]^+$.

$^1H$ NMR (400 MHz, DMSO-$d_6$): δ: 8.59 (d, J=2.4 Hz, 1H), 7.83 (s, 1H), 7.78 (d, J=8.0 Hz, 1H), 7.35 (t, J=7.6 Hz, 1H), 7.22 (d, J=7.6 Hz, 1H), 7.10 (d, J=2.8 Hz, 1H), 6.73 (s, 1H), 3.70-3.69 (m, 8H), 2.38 (s, 3H).

Synthesis of 4-morpholino-6-(3-(m-tolyl)-1H-pyrazol-1-yl)pyrimidin-2-yl trifluoromethanesulfonate (Intermediate 19)

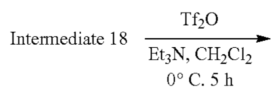

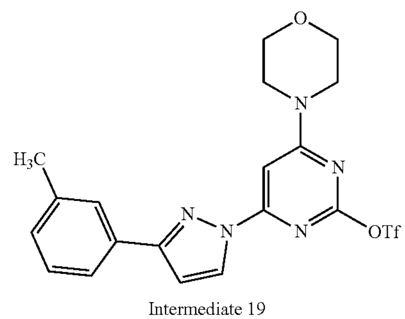

Intermediate 19

To a stirred solution of Intermediate 18 (60.0 g, 124 mmol) in $CH_2Cl_2$ (1200 mL), placed in a 3 neck round bottom flask, were added $Et_3N$ (180 g, 1778 mmol) and $Tf_2O$ (251 g, 889 mmol) by dropping funnel at 0° C. The reaction mixture was stirred at 0° C. for 5 h. After completion of reaction, the reaction mixture was quenched with saturated $NaHCO_3$ at 0° C., and extracted with $CH_2Cl_2$ (3×300 mL). The combined organic extract was washed with brine (500 mL), dried over anhydrous $Na_2SO_4$, filtered and concentrated under vacuum to obtain the crude product. The crude product was triturated with MTBE (250 mL), whereupon the product precipitated. The precipitated product was collected by filtration under vacuum, washed with MTBE (200 mL) and hexane (200 mL) and dried under vacuum to obtain Intermediate 19 (60.1 g, 72% yield) as a brown solid.

MS (ESI+APCI; multimode): 470 $[M+H]^+$.

$^1$H NMR (400 MHz, DMSO-$d_6$): δ: 8.47 (d, J=2.4 Hz, 1H), 7.85 (s, 1H), 7.81 (d, J=7.6 Hz, 1H), 7.36 (t, J=7.6 Hz, 1H), 7.22 (d, J=7.6 Hz, 2H), 7.14 (d, J=2.8 Hz, 71H), 3.73 (s, 8H), 2.39 (s, 3H).

Synthesis of 4-(2-(oxiran-2-yl)-6-(3-(m-tolyl)-1H-pyrazol-1-yl)pyrimidin-4-yl)morpholine (Intermediate 20)

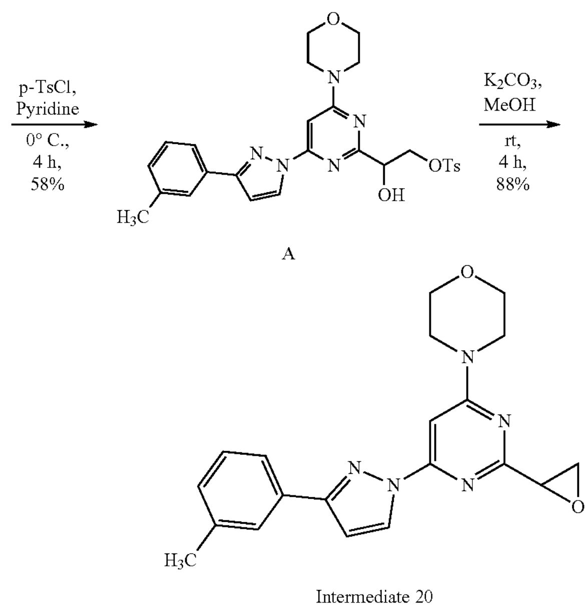

A

Intermediate 20

Preparation of A

To a stirred solution of Intermediate 13 (280 mg, 0.73 mmol) in pyridine (3 mL) at 0° C. under $N_2$ atmosphere was added p-toluenesulfonyl chloride (182 mg, 0.95 mmol). The reaction mixture was stirred at 0° C. for 4 h. The reaction mixture was diluted with water (20 mL), and extracted with EtOAc (2×30 mL). The combined organic extracts were washed with 1N HCl (30 mL), sat $NaHCO_3$ (30 mL) and brine (30 mL), dried over anhydrous $Na_2SO_4$, filtered and concentrated under vacuum to obtain the crude product. The crude product was purified by silica-gel column chromatography using 20% EtOAc:Hexanes. Fractions containing the product were combined and concentrated under vacuum to obtain A (230 mg, 0.42 mmol, 58% yield) as an off-white solid.

LCMS (ESI): m/z=536 $[M+H]^+$.

$^1$H NMR (400 MHz, $CDCl_3$) δ: 8.36 (d, J=2.8 Hz, 1H), 7.75 (s, 1H), 7.68 (d, J=8.0 Hz, 2H), 7.34 (t, J=8.0 Hz, 1H), 7.21 (d, J=8.4 Hz, 4H), 7.05 (s, 1H), 6.76 (d, J=2.8 Hz, 1H), 4.76 (d, J=2.8 Hz, 1H), 4.57-4.53 (m, 1H), 4.47-4.44 (m, 1H), 4.25 (d, J=5.2 Hz, 1H), 3.84-3.82 (m, 4H), 3.78-3.74 (m, 4H), 2.44 (s, 3H), 2.35 (s, 3H).

Preparation of Intermediate 20

To a stirred solution of A (500 mg, 0.93 mmol) in $CH_3OH$ (5 mL) at room temperature under $N_2$ atmosphere was added $K_2CO_3$ (258 mg, 1.86 mmol). The reaction mixture was stirred at room temperature for 4 h. The reaction mixture was diluted with water (30 mL), and extracted with EtOAc (2×30 mL). The combined organic extracts were washed with brine (30 mL), dried over anhydrous $Na_2SO_4$, filtered and concentrated under vacuum to obtain the crude product. The crude product was purified by silica-gel column chromatography using 10% EtOAc:Hexane. Fractions containing the product were combined and concentrated under vacuum to obtain Intermediate 20 (300 mg, 0.82 mmol, 88% yield) as an off-white solid.

LCMS (ESI): m/z=364 $[M+H]^+$.

$^1$H NMR (400 MHz, $CDCl_3$) δ: 8.59 (d, J=2.8 Hz, 1H), 7.74 (s, 1H), 7.69 (d, J=7.6 Hz, 1H), 7.32 (t, J=7.6 Hz, 1H), 7.18 (d, J=7.6 Hz, 1H), 7.11 (s, 1H), 6.75 (d, J=2.8 Hz, 1H), 3.91-3.89 (m, 1H), 3.82-3.80 (m, 4H), 3.77-3.75 (m, 4H), 3.28 (dd, J=2.8 Hz, 6.8 Hz, 1H), 3.10 (dd, J=4.0 Hz, 6.4 Hz, 1H), 2.42 (s, 3H)

Synthesis of 4-(2-(methylsulfonyl)-6-(3-(m-tolyl)-1H-pyrazol-1-yl)pyrimidin-4-yl)morpholine (Intermediate 21)

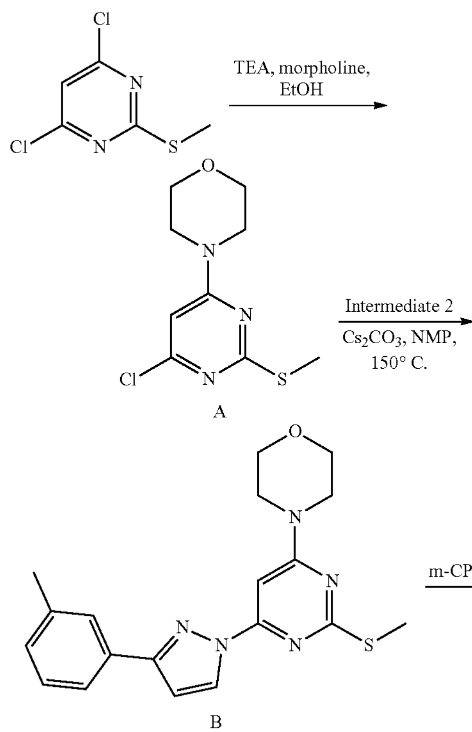

A

B

-continued

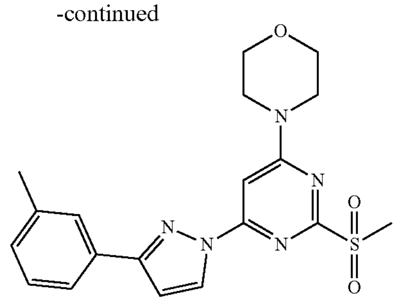

Intermediate 21

Preparation of A

To a solution of 4,6-dichloro-2-(methylthio)pyrimidine (10.0 g, 51.3 mmol) and $NEt_3$ (5.7 mL, 40.7 mmol) in EtOH (125 mL) was added morpholine (4.6 mL, 52.8 mmol). The resulting mixture was stirred at rt for 6 h. The precipitate was filtered and washed with EtOH to give the desired product A (11.5 g, 91%) as yellow oil.

Preparation of B

A mixture of A (2.50 g, 10.2 mmol), 3-methylphenylpyrazole (1.40 g, 8.85 mmol) and $Cs_2CO_3$ (4.33 g, 13.3 mmol) in NMP (5 mL) was stirred at 150° C. for 20 hours. After which period, the mixture was cooled down to room temperature and diluted with ethyl acetate. The system was washed with water and brine, dried over $Na_2SO_4$, filtered and concentrated to dryness under reduced pressure. The residue was purified by chromatography on silica gel eluting with petroleum ether:ethyl acetate=10:1 to get the desired product B (2.10 g, 65%) as a white solid.

Preparation of Intermediate 21

To a solution of B (2.04 g, 5.56 mmol) in DCM (30 mL) was added m-CPBA (2.10 g, 12.22 mmol) was portion wise. The mixture was stirred at rt for 4 h. and then quenched by addition of $Na_2SO_3$ (aq). The organic layer was separated and washed with brine, dried over $Na_2SO_4$, filtered and concentrated to dryness. The residue was purification by chromatography on silica gel eluting with petroleum ether: ethyl acetate=1:1 to give Intermediate 21 (950 mg, 41%) as a white solid.

LCMS (ESI): m/z=400 $[M+H]^+$.

Synthesis of 4-chloro-6-morpholinopyrimidin-2-amine (Intermediate 22)

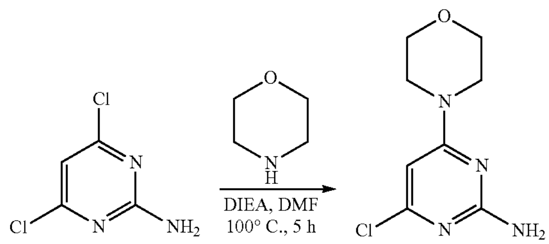

Intermediate 22

To a stirred solution of 4,6-dichloropyrimidin-2-amine (90.0 g, 540 mmol) in DMF (300 mL), placed in a 3 neck round bottom flask, under $N_2$ atmosphere at rt, was added morpholine (48.0 mL, 548 mmol) and DIPEA (147 mL, 820 mmol). The reaction mixture was refluxed at 100° C. for 5 h. The reaction mixture was cooled to room temperature, diluted with ice cold water (1.0 L), whereupon the product precipitated. The precipitated product was collected by filtration under vacuum, washed with MTBE (200 mL) and dried under vacuum to obtain Intermediate 22 (113 g, 96% yield) as a brown solid.

MS (ESI+APCI; multimode): 215 $[M+H]^+$.

$^1H$ NMR (400 MHz, DMSO-$d_6$): δ: 6.53 (brs, 2H), 6.09 (s, 1H), 3.65-3.44 (m, 8H).

Synthesis of 4-(2-iodo-6-(3-phenyl-1H-pyrazol-1-yl) pyrimidin-4-yl)morpholine (Intermediate 23)

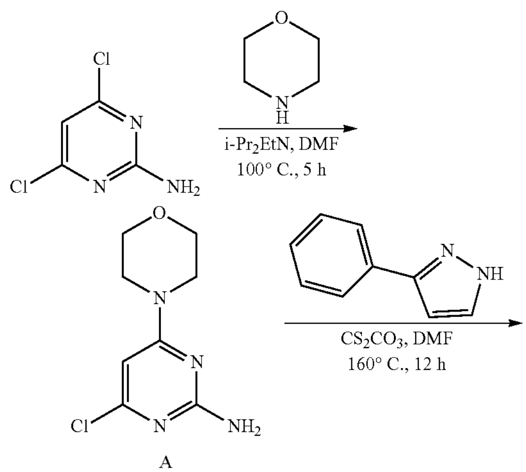

A

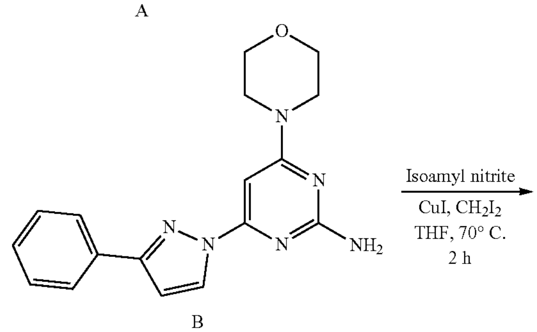

B

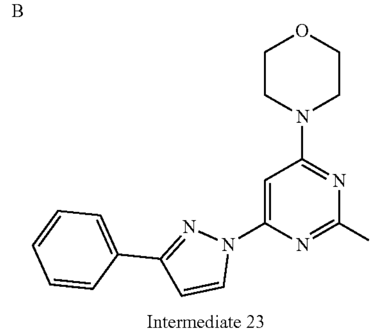

Intermediate 23

Preparation of A

To a stirred solution of 4,6-dichloropyrimidin-2-amine (90.0 g, 540 mmol) in DMF (300 mL), placed in a 3 neck round bottom flask, under $N_2$ atmosphere at rt, was added 2 (48.0 mL, 548 mmol) and DIPEA (147 mL, 820 mmol). The reaction mixture was refluxed at 100° C. for 5 h. The reaction mixture was cooled to room temperature, diluted with ice cold water (1.0 L), whereupon the product precipitated. The precipitated product was collected by filtration under vacuum, washed with MTBE (200 mL) and dried under vacuum to obtain A (113 g, 96% yield) as a brown solid.

MS (ESI+APCI; multimode): 215 $[M+H]^+$.

$^1H$ NMR (400 MHz, DMSO-$d_6$): δ: 6.53 (brs, 2H), 6.09 (s, 1H), 3.65-3.44 (m, 8H).

Preparation of B

To a stirred solution of A (52.0 g, 240 mmol) in DMF (520 mL), placed in a 3 neck round bottom flask, under $N_2$ atmosphere at rt, were added 4 (31.3 g, 220 mmol) and $Cs_2CO_3$ (141 g, 430 mmol). The reaction mixture was refluxed at 160° C. for 12 h. After completion of reaction, the reaction mixture was cooled to room temperature, and diluted with ice cold water (1.5 L), whereupon the product precipitated. The precipitated product was collected by filtration under vacuum, washed with MTBE (150 mL) and dried under vacuum to obtain B (38.0 g, 81% yield) as an off-white solid.

MS (ESI+APCI; multimode): 323 $[M+H]^+$.

$^1H$ NMR (400 MHz, DMSO-$d_6$): δ: 8.71 (d, J=2.8 Hz, 1H), 8.02 (d, J=8.4 Hz, 2H), 7.50-7.40 (m, 3H), 7.13-7.09 (m, 2H), 6.64-6.58 (m, 1H), 5.77-5.69 (m, 1H), 3.72 (brs, 8H).

Preparation of Intermediate 23

To a stirred solution of B (8.50 g, 25.0 mmol) in THF (80 mL), placed in a 3 neck round bottom flask, under $N_2$ atmosphere at rt, was added isoamyl nitrite (6.80 mL, 50.0 mmol) followed with CuI (5.2 g, 27.0 mmol) and $CH_2I_2$ (10.0 mL, 125 mmol). The reaction mixture was gradually heated to 70° C. and stirred for 2 h. The reaction was quenched by addition of sat. sodium thiosulfate (50 mL) and extracted with EtOAc (3×100 mL), washed with brine (150 mL). The organic layer was dried over anhydrous $Na_2SO_4$, filtered and concentrated under reduced pressure to afford the crude product. The crude product was purified by silica-gel chromatography using (15-20% EtOAc:Hexanes). The fractions containing the product were combined and concentrated under vacuum to obtain Intermediate 23 (2.40 g, 22% yield) as an off-white solid.

MS (ESI+APCI; multimode): 434 $[M+H]^+$.

Synthesis of 4-(2-(oxiran-2-yl)-6-(3-phenyl-1H-pyrazol-1-yl)pyrimidin-4-yl)morpholine (Intermediate 24)

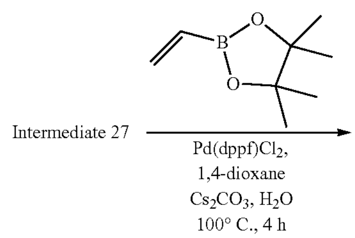

-continued

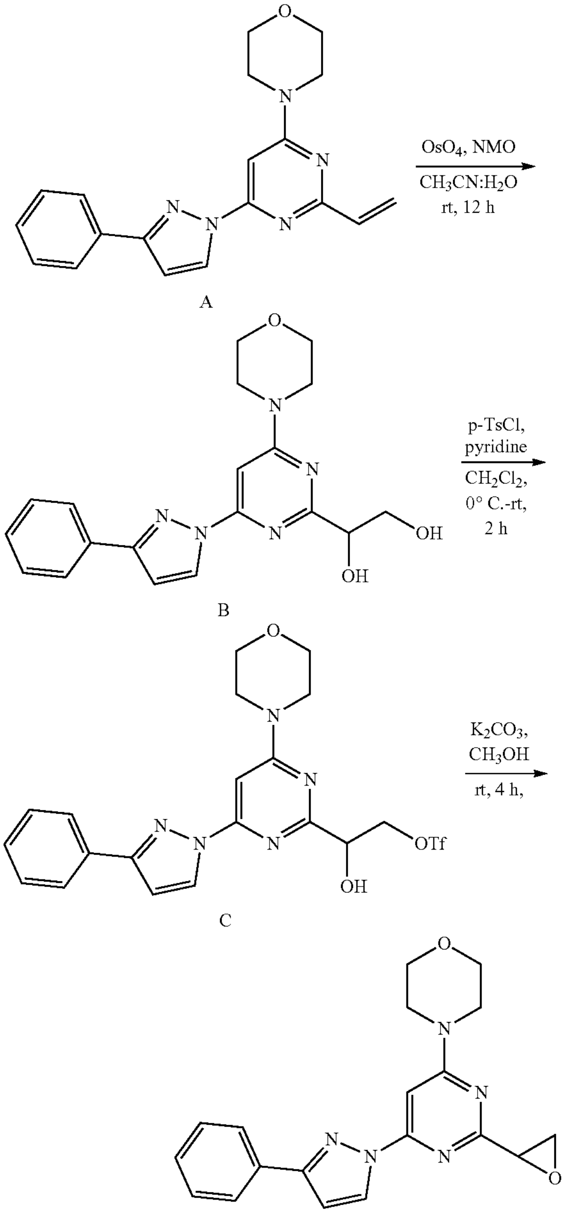

A

B

C

Intermediate 24

Preparation A

To a stirred solution of Intermediate 27 (13.0 g, 28.0 mmol) in 1,4 dioxane (100 mL), in a 3 neck round bottom flask, under $N_2$ atmosphere at rt, was added 4 (5.30 g, 34.0 mmol) followed with $Cs_2CO_3$ (18.3 g, 56.0 mmol) in $H_2O$ (20.0 mL). The mixture was de-gassed with Argon for 10 min, $Pd(dppf)Cl_2$ (2.0 g, 0.002 mmol) was added, and the reaction mixture was gradually heated to 100° C. for 4 h. The reaction mixture was cooled to room temperature, concentrated under vacuum to obtain the crude product. The crude product was purified by silica gel chromatography using (15-20% EtOAc:Hexanes) Fractions containing the product were combined and concentrated under vacuum to obtain A (4.80 g, 50% yield) as a white solid.

MS (ESI+APCI; multimode): 334 $[M+H]^+$.

$^1H$ NMR (400 MHz, DMSO-$d_6$): δ: 8.71 (d, J=2.8 Hz, 1H), 8.01 (d, J=1.2 Hz, 2H), 7.48 (t, J=7.2 Hz, 2H), 7.40 (t, J=7.2 Hz, 1H), 7.13-7.07 (m, 2H), 6.66-6.59 (m, 2H), 5.76-5.68 (m, 1H), 3.72 (brs, 8H).

Preparation of B

To a stirred solution of A (5.00 g, 14.9 mmol) in $CH_3CN$:$H_2O$ (1:1, 100 mL), placed in 2 neck round bottom flask at rt, were added NMO (5.00 mL, 22.4 mmol) followed with $OsO_4$ (50% in toluene, 2.60 mL, 22.4 mmol), and the mixture was stirred at rt for 12 h. After completion of reaction, the reaction mixture was quenched with sodium thiosulfate solution (50 mL) and then diluted with water (250 mL), whereupon the product precipitated. The precipitated product was collected by filtration under vacuum, washed with MTBE (100 mL) and dried under vacuum to obtain B (4.50 g, 81% yield) as an off-white solid.

MS (ESI+APCI; multimode): 368 $[M+H]^+$.

$^1H$ NMR (400 MHz, DMSO-$d_6$): δ: 8.80 (s, 1H), 8.01 (d, J=7.6 Hz, 2H), 7.46 (t, J=7.2 Hz, 2H), 7.41 (t, J=7.2 Hz, 1H), 7.10 (s, 2H), 5.04 (d, J=6.4 Hz, 1H), 4.63 (t, J=6.0 Hz, 1H), 4.46 (q, J=5.6 Hz, 1H), 3.85-3.77 (m, 1H), 3.75-3.64 (m, 9H).

Preparation of C

To a stirred solution of B (1.50 g, 4.08 mmol) in $CH_2Cl_2$ (30 mL), placed in a 3 neck round bottom flask, under $N_2$ atmosphere at 0° C., was added pyridine (3.20 mL, 40.8 mmol), followed with p-toluenesulfonyl chloride (900 mg, 4.89 mmol). The reaction mixture was stirred at 0° C. to room temperature for 2 h. After completion of reaction, the reaction mixture was quenched with sat. $NaHCO_3$ at 0° C., nd extracted with $CH_2Cl_2$ (3×150 mL). The combined organic extracts were washed with brine (200 mL), dried over anhydrous $Na_2SO_4$, filtered and concentrated under vacuum to obtain C (1.50 g, crude) as a brown liquid. The crude product C was unstable, and directly used for compound synthesis.

Preparation of Intermediate 24

To a stirred solution of C (350 mg, 0.67 mmol) in $CH_3OH$ (10.0 mL), placed in a 2 neck round bottom flask, under $N_2$ atmosphere at rt, was added $K_2CO_3$ (185 mg, 1.34 mmol). The reaction mixture was stirred at rt for 4 h. After completion of reaction, $CH_3OH$ was removed under reduced pressure, the reaction mixture was diluted with water (50 mL) and extracted with EtOAc (3×50 mL), washed with brine (50 mL). The organic layer was dried over anhydrous $Na_2SO_4$, filtered and concentrated under reduced pressure to afford the crude product. The crude product was purified by silica gel chromatography (15-20% EtOAc:Hexanes). Fractions containing the product were combined and concentrated under vacuum to obtain Intermediate 24 (160 mg, 68% yield) as an off-white solid.

MS (ESI+APCI; multimode): 350 $[M+H]^+$.

$^1H$ NMR (400 MHz, DMSO-$d_6$): δ: 8.63 (d, J=2.0 Hz, 1H), 8.00 (d, J=7.6 Hz, 2H), 7.47 (t, J=7.6 Hz, 2H), 7.42 (t, J=6.4 Hz, 1H), 7.15 (s, 1H), 7.10 (s, 1H), 3.86-3.80 (m, 1H), 3.71 (brs, 8H), 3.25-3.19 (m, 1H), 3.10-3.03 (m, 1H).

Synthesis of 4-morpholino-6-(3-phenyl-1H-pyrazol-1-yl)pyrimidine-2-carbaldehyde (Intermediate 25)

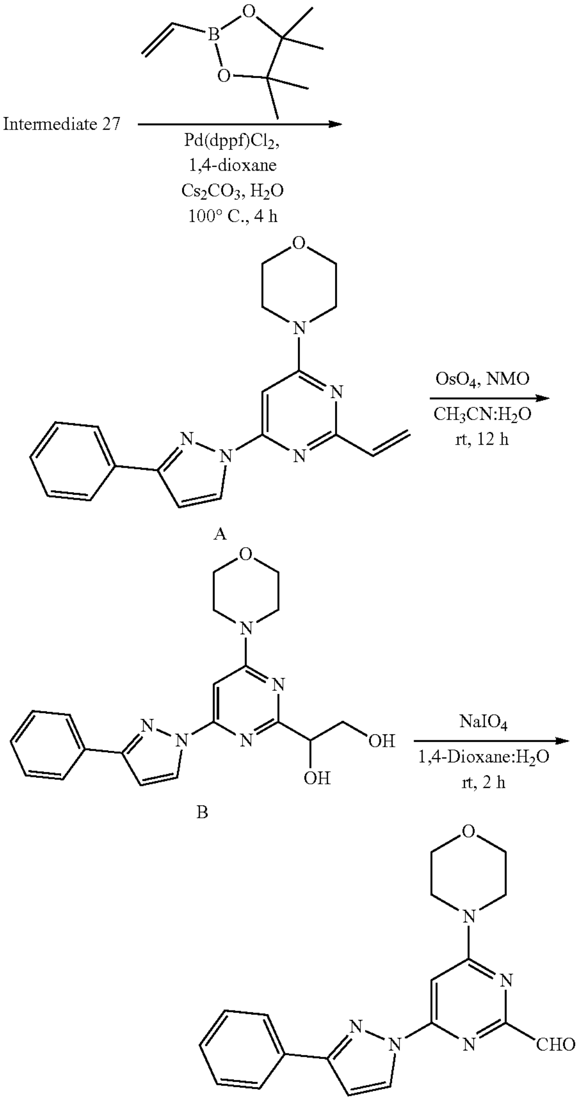

Intermediate 25

Preparation of A

To a stirred solution of 4,4,5,5-tetramethyl-2-vinyl-1,3,2-dioxaborolane (13.0 g, 28.0 mmol) in 1,4 dioxane (100 mL), in a 3 neck round bottom flask, under $N_2$ atmosphere at rt, was added 4 (5.30 g, 34.0 mmol) followed with $Cs_2CO_3$ (18.3 g, 56.0 mmol) in $H_2O$ (20.0 mL). The mixture was de-gassed with Argon for 10 min, Pd(dppf)$Cl_2$ (2.0 g, 0.002 mmol) was added, and the reaction mixture was gradually heated to 100° C. for 4 h. The reaction mixture was cooled to room temperature, concentrated under vacuum to obtain the crude product. The crude product was purified by silica gel chromatography using (15-20% EtOAc:Hexanes) Fractions containing the product were combined and concentrated under vacuum to obtain A (4.80 g, 50% yield) as a white solid.

MS (ESI+APCI; multimode): 334 $[M+H]^+$.

$^1$H NMR (400 MHz, DMSO-$d_6$): δ: 8.71 (d, J=2.8 Hz, 1H), 8.01 (d, J=1.2 Hz, 2H), 7.48 (t, J=7.2 Hz, 2H), 7.40 (t, J=7.2 Hz, 1H), 7.13-7.07 (m, 2H), 6.66-6.59 (m, 2H), 5.76-5.68 (m, 1H), 3.72 (brs, 8H).

Preparation of B

To a stirred solution of A (5.00 g, 14.9 mmol) in $CH_3CN$:$H_2O$ (1:1, 100 mL), placed in 2 neck round bottom flask at rt, were added NMO (5.00 mL, 22.4 mmol) followed with $OsO_4$ (50% in toluene, 2.60 mL, 22.4 mmol), and the mixture was stirred at rt for 12 h. After completion of reaction, the reaction mixture was quenched with sodium thiosulfate solution (50 mL) and then diluted with water (250 mL), whereupon the product precipitated. The precipitated product was collected by filtration under vacuum, washed with MTBE (100 mL) and dried under vacuum to obtain B (4.50 g, 81% yield) as an off-white solid.

MS (ESI+APCI; multimode): 368 $[M+H]^+$.

$^1$H NMR (400 MHz, DMSO-$d_6$): δ: 8.80 (s, 1H), 8.01 (d, J=7.6 Hz, 2H), 7.46 (t, J=7.2 Hz, 2H), 7.41 (t, J=7.2 Hz, 1H), 7.10 (s, 2H), 5.04 (d, J=6.4 Hz, 1H), 4.63 (t, J=6.0 Hz, 1H), 4.46 (q, J=5.6 Hz, 1H), 3.85-3.77 (m, 1H), 3.75-3.64 (m, 9H).

Preparation of Intermediate 25

To a stirred solution of B (2.00 g, 5.99 mmol) in $CH_3CN$:$H_2O$ (1:1, 30 mL), placed in 2 neck round bottom flask at rt, were added $NaIO_4$ (1.90 g, 8.99 mmol) followed with $OsO_4$ (50% in toluene, 4.50 mL, 17.9 mmol), and the mixture was stirred at rt for 12 h. The reaction mixture was quenched with sodium thiosulfate solution (20 mL), diluted with water (100 mL), and extracted with EtOAc (3×100 mL). The combined organic extracts were washed with brine (200 mL), dried over anhydrous $Na_2SO_4$, filtered and concentrated under vacuum to obtain the crude product. The crude product was triturated with MTBE (100 mL) to obtain 4-morpholino-6-(3-phenyl-1H-pyrazol-1-yl)pyrimidine-2-carbaldehyde (Intermediate 25) (1.70 g, 85% yield) as an off-white solid.

MS (ESI+APCI; multimode): 336 $[M+H]^+$.

$^1$H NMR (400 MHz, DMSO-$d_6$): δ: 9.78 (s, 1H), 8.68 (d, J=2.4 Hz, 1H), 8.03 (d, J=7.2 Hz, 2H), 7.49 (t, J=7.6 Hz, 2H), 7.42 (t, J=7.2 Hz, 1H), 7.35 (s, 1H), 7.16 (d, J=2.8 Hz, 1H), 3.84-3.67 (m, 8H).

Synthesis of 4-morpholino-6-(3-phenyl-1H-pyrazol-1-yl)pyrimidin-2-ol (Intermediate 26)

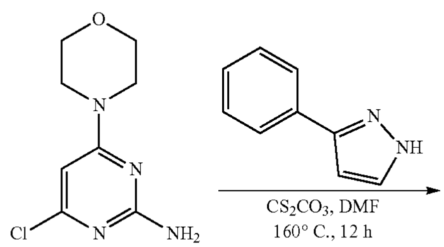

-continued

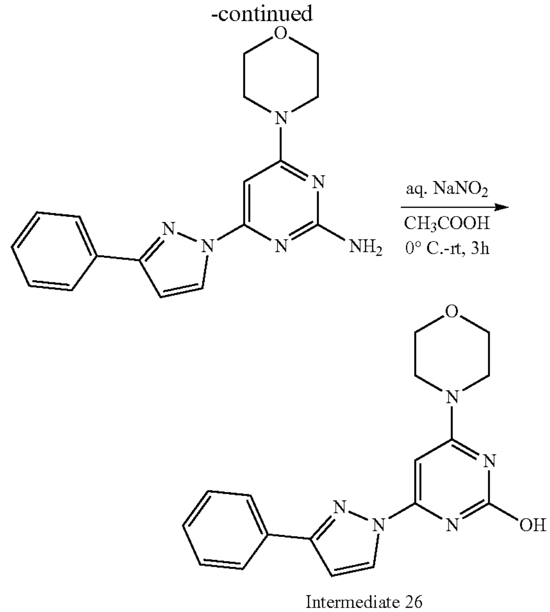

Intermediate 26

Preparation of 5

To a stirred solution of 4-chloro-6-morpholinopyrimidin-2-amine (52.0 g, 240 mmol) in DMF (520 mL), placed in a 3 neck round bottom flask, under $N_2$ atmosphere at rt, were added 3-phenyl-1H-pyrazole (31.3 g, 220 mmol) and $Cs_2CO_3$ (141 g, 430 mmol). The reaction mixture was refluxed at 160° C. for 12 h. After completion of reaction, the reaction mixture was cooled to room temperature, and diluted with ice cold water (1.5 L), whereupon the product precipitated. The precipitated product was collected by filtration under vacuum, washed with MTBE (150 mL) and dried under vacuum to obtain A (38.0 g, 81% yield) as an off-white solid.

MS (ESI+APCI; multimode): 323 $[M+H]^+$.

$^1$H NMR (400 MHz, DMSO-$d_6$): δ: 8.71 (d, J=2.8 Hz, 1H), 8.02 (d, J=8.4 Hz, 2H), 7.50-7.40 (m, 3H), 7.13-7.09 (m, 2H), 6.64-6.58 (m, 1H), 5.77-5.69 (m, 1H), 3.72 (brs, 8H).

Preparation of Intermediate 26

To a stirred solution of A (38.0 g, 110 mmol) in $CH_3COOH$ (760 mL) placed in a 3 neck round bottom flask, at 0° C. under $N_2$ atmosphere, was added $NaNO_2$ (38.2 g, 550 mol) in $H_2O$ (760 mL) dropwise over a period of 30 mins. After complete addition, the reaction mixture was stirred at room temperature for 3 h. After completion of reaction, the reaction mixture was diluted with ice cold water (2.0 L), whereupon the product precipitated. The precipitated product was collected by filtration under vacuum, washed with MTBE (200 mL), hexane (200 mL) and dried under vacuum to obtain Intermediate 26 (35.0 g, 92% yield) as an off-white solid.

MS (ESI+APCI; multimode): 324 $[M+H]^+$.

$^1$H NMR (400 MHz, DMSO-$d_6$): δ: 8.66 (s, 1H), 8.03 (d, J=6.8 Hz, 2H), 7.55-7.38 (m, 3H), 7.19 (s, 1H), 6.75 (s, 1H), 3.72 (brs, 8H).

Synthesis of 4-morpholino-6-(3-phenyl-1H-pyrazol-1-yl)pyrimidin-2-yl trifluoromethanesulfonate (Intermediate 27)

Intermediate 26

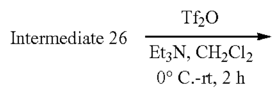

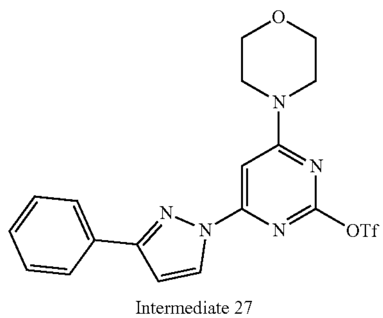

Intermediate 27

To a stirred solution of Intermediate 26 (38.0 g, 110 mmol) in $CH_2Cl_2$ (380 mL), placed in a 3 neck round bottom flask, under $N_2$ atmosphere at rt, was added $Et_3N$ (163 mL, 1170 mmol) followed with $Tf_2O$ (98.0 mL, 590 mmol) in a dropwise manner over a period of 15 mins. After complete addition, the reaction mixture was stirred at rt for 2 h. The reaction mixture was quenched with sat. $NaHCO_3$ at 0° C., and extracted with $CH_2Cl_2$ (3×200 mL). The combined organic extracts were washed with brine (200 mL), dried over anhydrous $Na_2SO_4$, filtered and concentrated under vacuum to obtain the crude product. The crude product was triturated with hexanes (200 mL), filtered under vacuum, washed with hexanes (50 mL) and dried to obtain Intermediate 27 (26.5 g, 50% yield) as a dark-brown solid.

MS (ESI+APCI; multimode): 456 $[M+H]^+$.

$^1H$ NMR (400 MHz, DMSO-$d_6$): δ: 8.48 (d, J=2.8 Hz, 1H), 8.02 (d, J=7.2 Hz, 2H), 7.53-7.39 (m, 3H), 7.24 (s, 1H), 7.16 (d, J=2.8 Hz, 1H), 3.73 (brs, 8H).

Synthesis of 1-(1-methyl-1H-pyrazol-4-yl)prop-2-yn-1-ol (Intermediate 28)

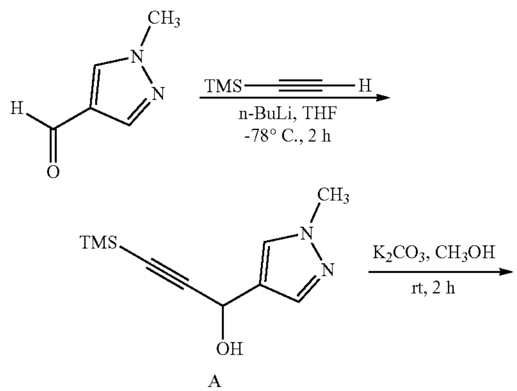

A

-continued

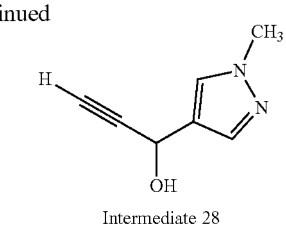

Intermediate 28

Synthesis of A

To a stirred solution of ethynyltrimethylsilane (1.00 g, 10.1 mmol) in anhydrous THF (10 ml), at −78° C., under $N_2$ atmosphere, was added n-BuLi (2.5 M in hexanes, 0.38 mL, 15.2 mmol) over a period of 5 min, and the reaction mixture was stirred at −78° C. for 15 min. 1-methyl-1H-pyrazole-4-carbaldehyde (1.12 g, 10.1 mmol) in THF (2 mL) was added at −78° C. over a period of 5 min. The reaction mixture was stirred at −78° C. for 2 h. The reaction mixture was quenched at 0° C. with sat. $NH_4Cl$ (5 ml), diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 20% EtOAc:Hexanes. Fractions containing the product were combined and concentrated under vacuum to obtain A (1.10 g, 5.28 mmol, 51% yield) as a brown liquid.

MS (ESI+APCI; multimode): 209 $[M+H]^+$.

$^1H$ NMR (400 MHz, DMSO-$d_6$): δ: 7.59 (s, 1H), 7.34 (s, 1H), 5.76 (d, J=6.4 Hz, 1H), 5.28 (d, J=6.0 Hz, 1H), 3.79 (s, 3H), 0.15 (s, 9H).

Synthesis of Intermediate 28

To a stirred solution of A in anhydrous $CH_3OH$ (10 mL), at room temperature, under $N_2$ atmosphere, was added $K_2CO_3$ (1.45 g, 10.5 mmol). The reaction mixture was stirred at room temperature for 2 h. The reaction mixture was filtered, washed with EtOAc (100 mL), and concentrated under vacuum to obtain the crude product. The crude product was purified by silica-gel column chromatography using 30% EtOAc:Hexanes. Fractions containing the product were combined and concentrated under vacuum to obtain Intermediate 28 (600 mg, 4.41 mmol, 83% yield) as a yellow gummy liquid.

MS (ESI+APCI; multimode): 137 $[M+H]^+$.

$^1H$ NMR (400 MHz, DMSO-$d_6$): δ: 7.62 (s, 1H), 7.36 (s, 1H), 5.75 (d, J=6.0 Hz, 1H), 5.27 (dd, J=2.4 Hz, 6.0 Hz, 1H), 3.79 (s, 3H), 3.40 (d, J=2.4 Hz, 1H).

Synthesis of 2-(1-methyl-1H-pyrazol-4-yl) ethan-1-ol (Intermediate 29)

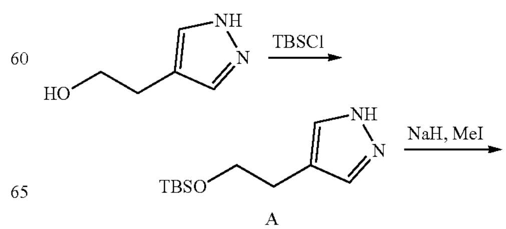

A

-continued

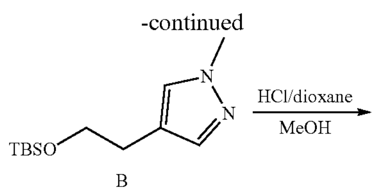

B

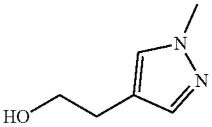

Intermediate 29

Preparation of A

To a solution of 2-(1H-pyrazol-4-yl)ethan-1-ol (10 g, 89 mmol) and imidazole (9.0 g, 133 mmol) in DMF (100 mL) was added TBSCl (14.8 g, 98 mmol) at room temperature. The mixture was stirred at room temperature overnight, then poured into water (300 mL) and extracted with EtOAc (100 mL×2). The combined organic layers were washed with brine (100 mL×2), dried over $Na_2SO_4$, filtered and concentrated to dryness. The resulting crude product was purified by chromatography on silica gel eluting with petroleum ether:EtOAc=5:1 to get the desired product A (19.9 g, 99%) as colorless oil.

Preparation of B

To a solution of A (19.9 g, 88 mmol) in THF (200 mL) was added NaH (5.3 g, 132 mmol) at 0° C. The resulting system was stirred for 30 min before the addition of MeI (13.7 g, 96.8 mmol). The mixture was stirred at room temperature overnight and then poured into water (600 mL), which was extracted with EtOAc (200 mL×2). The combined organic layers were washed with brine (200 mL), dried over $Na_2SO_4$, filtered, concentrated to dryness. The resulting crude product was purified by chromatography on silica gel eluting with petroleum ether:EtOAc=8:1-5:1 to give B.

Preparation of Intermediate 29

To a solution of compound B (18.2 g, 75.8 mmol) in MeOH (50 mL) was added HCl/MeOH (15 mL, 4M) at room temperature. The mixture was stirred overnight and concentrated under reduced pressure. The residue was basified with sat. $NaHCO_3$ to pH>7, and then extracted with DCM (200 mL×5). The combined organic layers were washed with brine (200 mL), dried over $Na_2SO_4$, filtered, concentrated to dryness. The resulting crude product was purified by chromatography on silica gel eluting with EtOAc to EtOAc:MeOH=20:1 to get the desired product Intermediate 29 (8 g, 84%) as a colorless oil.

MS (ESI+APCI; multimode): 127 $[M+H]^+$.

Synthesis of 4-(6-chloro-2-(2-(1-methyl-1H-pyrazol-4-yl)ethoxy)pyrimidin-4-yl)morpholine (Intermediate 30)

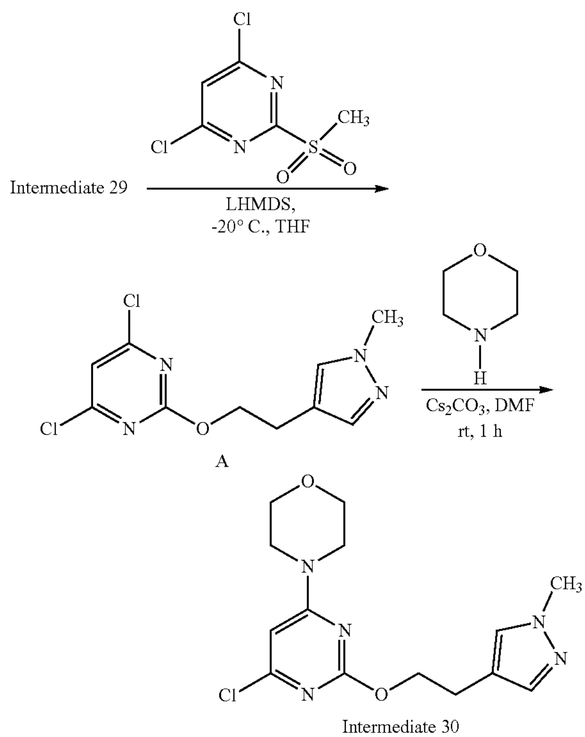

Intermediate 30

Preparation of A

To a solution of compound Intermediate 29 (6.4 g, 51 mmol) and 4,6-Dichloro-2-(methylsulfonyl)pyrimidine (11.5 g, 51 mmol) in THF (100 mL) was added LHMDS (60 mL, 1M, 60 mmol) dropwise below −20° C. After addition, the mixture was stirred for another 30 min, followed by the addition of HCl (1N) to adjust pH<6 to quench the reaction. The resulting mixture was extracted with EtOAc (100 mL×2). The combined organic layers were washed with brine (200 mL), dried over $Na_2SO_4$, filtered and concentrated to dryness. The crude product was purified by chromatography on silica gel eluting with petroleum ether: EtOAc, 1:1:1 to get the desired product A (11.5 g, 83%) as a light-yellow solid.

Preparation of Intermediate 30

The mixture of compound A (11.5 g, 42.1 mmol), morpholine (3.7 g, 42.1 mmol) and $Cs_2CO_3$ (13.7 g, 42.1 mmol) in DMF (100 mL) was stirred at room temperature for 2 hrs. Water (300 mL) was added and the resulting mixture was extracted with EtOAc (200 mL×2). The combined organic layers were washed with brine (100 mL×3), dried over $Na_2SO_4$, filtered, concentrated to dryness. The crude product was purified by chromatography on silica gel eluting with petroleum ether:EtOAc, 1:1 to EtOAc to get the desired compound Intermediate 30 (12 g, 88%) as a white solid.

$^1H$ NMR (400 MHz, $CDCl_3$) δ 7.41 (s, 1H), 7.32 (s, 1H), 6.17 (s, 1H), 4.40 (t, J=6.8 Hz, 2H), 3.89 (s, 3H), 3.77-3.74 (m, 4H), 3.62-3.60 (m, 4H), 2.93 (t, J=6.8 Hz, 2H).

Synthesis of 4-(2-(1-methyl-1H-pyrazol-4-yl)ethoxy)-6-morpholinopyrimidin-2-amine (Intermediate 31)

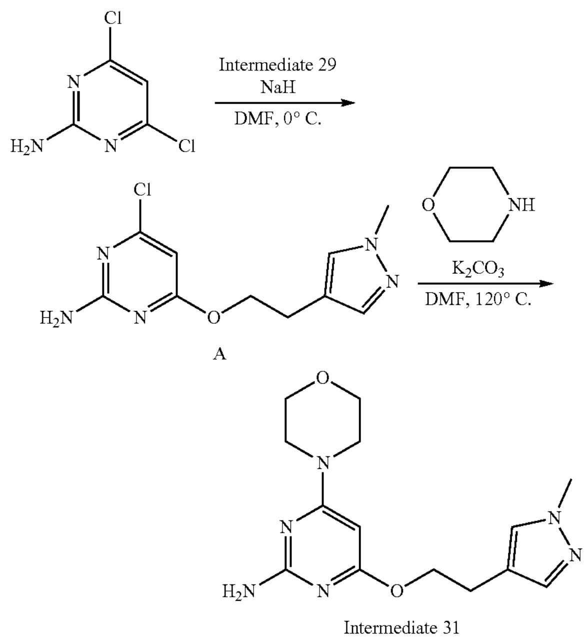

A

Intermediate 31

Preparation of A

To the solution of Intermediate 29 (3.8 g, 30.5 mmol) in N,N-dimethylformamide (6.0 mL) was added sodium hydride (60% in mineral oil, 1.46 g, 36.6 mmol) at 0° C., and the mixture was stirred for another 30 min. After which period, the solution of 4,6-dichloropyrimidin-2-amine (5.0 g, 30.5 mmol) in N,N-dimethylformamide (60 mL) was added to above system dropwise. After stirring at room temperature at room temperature overnight, the resulting mixture was poured into water and extracted with ethyl acetate (80 mL×3). The combined organic layers were dried over $Na_2SO_4$, filtered and concentrated to dryness. The resulting crude product was purified by chromatography on silica gel eluting with petroleum ether:EtOAc=10:1-1:1 to give the desired product A (5.4 g, 69.3%) as a white solid.

Preparation of Intermediate 31

To the solution of compound A (5.4 g, 21.2 mmol) in N,N-dimethylformamide (120 mL) was added morpholine (5.54 g, 63.70 mmol) and potassium carbonate (8.8 g, 63.7 mmol). And the resulting mixture was stirred at 120° C. overnight. After which period, the mixture was cooled to room temperature and poured into water, extracted with ethyl acetate (50 mL×2). The combined organic layers were dried over $Na_2SO_4$, filtered and concentrated to dryness. The resulting crude product was purified by chromatography on silica gel eluting with petroleum ether:EtOAc=1:1 to EtOAc to give Intermediate 31 (6.0 g, 92.9%) as a white solid.

MS (ESI+APCI; multimode): 305 $[M+H]^+$.

Synthesis of 4-(6-hydrazineyl-2-(2-(1-methyl-1H-pyrazol-4-yl)ethoxy)pyrimidin-4-yl)morpholine (Intermediate 32)

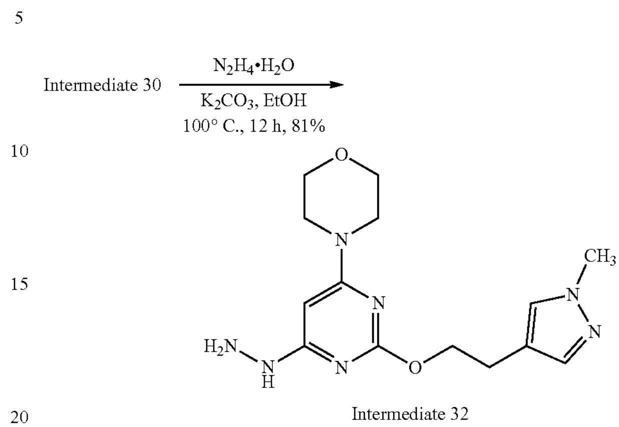

Intermediate 32

To a stirred solution of Intermediate 30 (500 mg, 1.54 mmol) in EtOH (15 mL), at room temperature, under $N_2$ atmosphere, was added $N_2H_4{\cdot}H_2O$ (0.05 mL, 1.85 mmol) followed with $K_2CO_3$ (341 mg, 2.47 mmol). The reaction mixture was gradually heated to 100° C. and stirred for 12 h. The reaction mixture was cooled to room temperature, diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc:Hexanes. Fractions containing the product were combined and concentrated under vacuum to obtain Intermediate 32 (400 mg, 1.25 mmol, 81% yield) as an off-white solid.

MS (ESI+APCI; multimode): 320.1 $[M+H]^+$.

$^1H$ NMR (400 MHz, DMSO-$d_6$): δ: 7.63 (s, 1H), 7.50 (s, 1H), 7.28 (s, 1H), 5.60 (s, 1H), 4.20 (t, J=6.8 Hz, 2H), 4.15 (brs, 2H), 3.76 (s, 3H), 3.64-3.62 (m, 4H), 3.41-3.39 (m, 4H), 2.75 (t, J= 6.8 Hz, 2H).

Synthesis of 1-(4-chloro-6-morpholinopyrimidin-2-yl)ethane-1,2-diol (Intermediate 33)

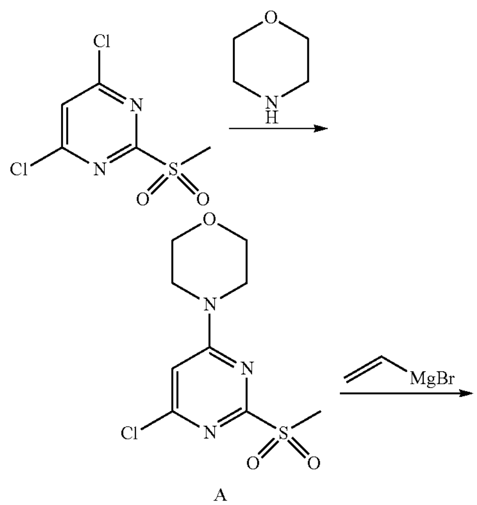

A

-continued

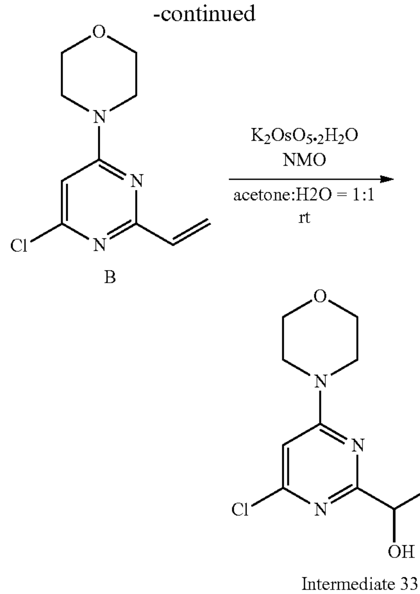

B

Intermediate 33

Preparation of A

To a solution of 4,6-dichloro-2-(methylsulfonyl)pyrimidine (50 g, 0.22 mol) in THF (300 mL) was added morpholine (19 g, 0.22 mol) and DIPEA (60 mL, 0.33 mmol) at 0° C. The mixture was stirred at room temperature for 4 hrs, then poured into water (300 mL) and extracted with EtOAc (200 mL×2). The combined organic layers were washed with brine (200 mL), dried over $Na_2SO_4$, filtered, concentrated to dryness. The resulting crude product was purified by chromatography on silica gel eluting with petroleum ether:EtOAc=1:1 to 0:1 to get the desired product A (53.4 g, 87%) as a yellow solid.

Preparation of B

To a solution of compound A (53.4 g, 0.19 mmol) in THF (1.0 L) was added vinylmagnesium bromide (483 mL, 0.48 mol, 1M in THF) slowly at −10° C. The resulting system was stirred for 1 h at 0° C., then quenched with sat. $NH_4Cl$ solution (500 mL). The mixture was extracted with EtOAc (500 mL×2). The combined organic layers were washed with brine (500 mL), dried over $Na_2SO_4$, filtered, concentrated to dryness. The resulting crude product was purified by chromatography on silica gel eluting with petroleum ether:EtOAc=5:1-3:1 to get the desired product B (20 g, 46%) as a white solid.

Preparation of Intermediate 33

To a solution of compound B (6.6 g, 29.3 mmol) and NMO (5.15 g, 44.0 mmol) in acetone:$H_2O$=1:1 (150 mL) was added $K_2OsO_5 \cdot 2H_2O$ (107 mg, 0.29 mmol, 0.01 eq)) at room temperature. The mixture was stirred for 4 hrs, and then quenched with sat. $Na_2SO_3$ solution (100 mL). The mixture was extracted with EtOAc (100 mL×5). The combined organic layers were washed with brine (100 mL), dried over $Na_2SO_4$, filtered, concentrated to get the desired product Intermediate 33 (7.5 g, 99%) as a white solid, which was directly.

Synthesis of 2-(4-chloro-6-morpholinopyrimidin-2-yl)-2-methoxyethan-1-ol (Intermediate 34)

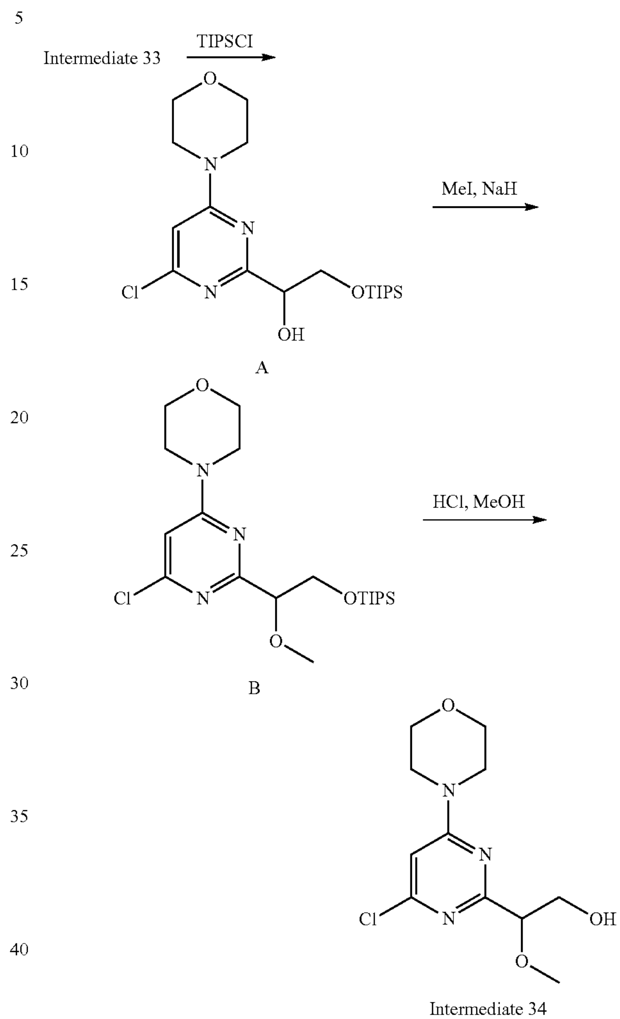

A

B

Intermediate 34

Preparation of A

To a solution of compound Intermediate 33 (2.0 g, 7.7 mmol) in DMF (20 mL) was added imidazole (0.8 g, 11.5 mmol) and TIPSCl (1.5 g, 7.7 mmol). The mixture was stirred at rt overnight, then poured into water (60 mL) and extracted with EtOAc (50 mL×2). The combined organic layers were washed with brine (50 mL×3), dried over $Na_2SO_4$, filtered, concentrated to dryness. The resulting crude product was purified by chromatography on silica gel eluting with petroleum ether:EtOAc=10:1 to 5:1 to get the desired product A (2.8 g, 87%) as colorless oil.

Preparation of B

To a solution of compound A (2.8 g, 6.7 mmol) in DMF (20 mL) was added NaH (540 mg, 13.4 mmol) at −10° C. and stirred for 10 min, Then MeI (1.9 g, 13.4 mmol) was added and the mixture was stirred at −10° C. for another 30 min. Water (60 mL) was added to quench the reaction, and the resulting mixture was extracted with EtOAc (100 mL×2). The combined organic layers were washed with brine (100 mL×3), dried over $Na_2SO_4$, filtered, concentrated to dryness. The crude product was purified by chromatography on silica gel eluting with petroleum ether:EtOAc=3:1 to get the desired product B (2.0 g, 69%) as light-yellow oil.

Preparation of Intermediate 34

To a solution of compound B (3.0 g, 7.0 mmol) in MeOH (30 mL) was added HCl/dioxane (5 mL, 4 M). The mixture was stirred at rt for 3 hours and then concentrated to dryness. The crude product was redissolved in MeOH (30 mL) and basified to pH=9-10 using basic resin and then filtered. The filtrate was concentrated to get Intermediate 34 (2.2 g, >100%) as light-yellow oil, which was used for next step directly.

$^1$H NMR (400 MHz, DMSO-$d_6$) δ 6.86 (s, 1H), 4.77 (t, J=6.0 Hz, 1H), 4.09-4.06 (m, 1H), 3.65-3.60 (m, 9H), 3.24 (s, 3H).

Synthesis of ethyl 3-phenyl-1H-pyrazole-5-carboxylate (Intermediate 35)

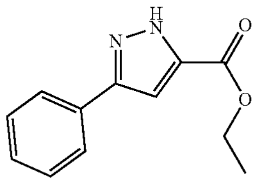 [SMILES: CCOC(=O)c1cc(-c2ccccc2)n[nH]1]

MS (ESI+APCI; multimode): 217 [M+H]$^+$.

Intermediate 35 can be synthesized using a similar procedure as described below for Intermediate 36.

Synthesis of Ethyl 3-(m-tolyl)-1H-pyrazole-5-carboxylate (Intermediate 36)

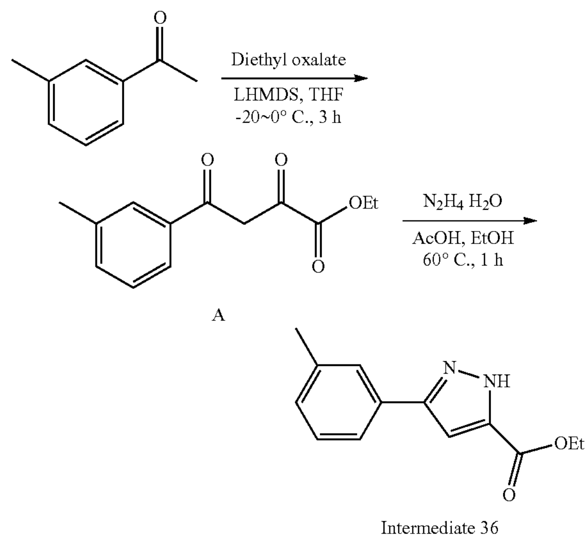

A

Intermediate 36

Preparation of A

To a solution of 1-(m-tolyl)ethan-1-one (5.0 g, 37.3 mmol) in THF (80 mL) was cooled to −20° C. under $N_2$ atmosphere. Then, LHMDS (1M, 56 mL, 56.0 mmol) was added slowly to maintain the internal temperature at −20° C. Afterward, the reaction was warmed to 0° C. and stirred for 1 hour. The reaction was cooled down to −20° C. again, and into which diethyl oxalate (6.0 g, 41.1 mmol) was added slowly. The resulting mixture was allowed to warm to room temperature and stirred for another 2 hours and then diluted with ethyl acetate (20 mL), followed by addition of HCl (1 M) solution to adjust pH=5-6. The mixture was washed by water (30 mL×3) and brine (30 mL×3), dried over $Na_2SO_4$, filtered and concentrated under reduced pressure. The residue was purified by chromatography on silica gel eluting with petroleum ether:ethyl acetate=5:1-3:1 to get the desired product (6.1 g, 70.0%) as a slight yellow solid.

Preparation of Intermediate 36

A mixture of compound A (6.74 g, 28.8 mmol), hydrazine monohydrate (1.45 g, 29.1 mmol) and AcOH (1.73 g, 28.8 mmol) in EtOH (40 mL) was stirred at room temperature for 16 hours and then concentrated under reduced pressure. The residue was purified by chromatography on silica gel eluting with petroleum ether:ethyl acetate=3:1-1:1 to get Intermediate 36 (6.3 g, 95.1%) as colorless oil.

MS (ESI+APCI; multimode): 231 [M+H]$^+$.

Synthesis of 4-methoxy-1-phenylbutane-1,3-dione (Intermediate 37)

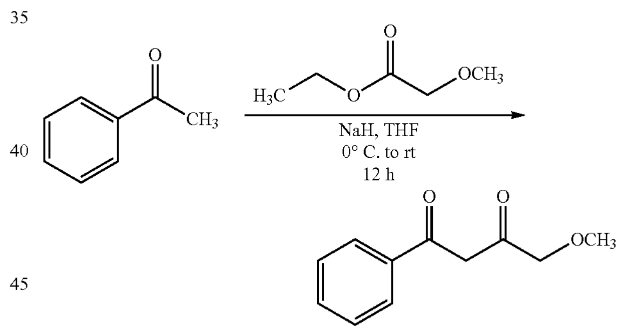

Intermediate 37

To a suspension of 50% NaH (200 mg, 8.32 mmol) in anhydrous THF (5 mL), at 0° C., under $N_2$ atmosphere was added acetophenone (250 mg, 2.08 mmol). The reaction mixture was stirred at 0° C. for 15 min. ethyl 2-methoxyacetate (433 mg, 4.16 mmol) in THF (2 mL) was added at 0° C. over a period of 2 min. The reaction mixture was stirred at 0° C. to room temperature for 12 h. The reaction mixture was quenched at 0° C. with ice cold water (5 mL), diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 20% EtOAc:Hexanes. Fractions containing the product were combined and concentrated under vacuum to obtain Intermediate 37 (250 mg, 1.30 mmol, 62% yield) as a light yellow gummy liquid.

MS (ESI+APCI; multimode): 193 [M+H]$^+$.

Synthesis of N,N-dimethyl-1-(3-(m-tolyl)-1H-pyrazol-5-yl)methanamine (Intermediate 38)

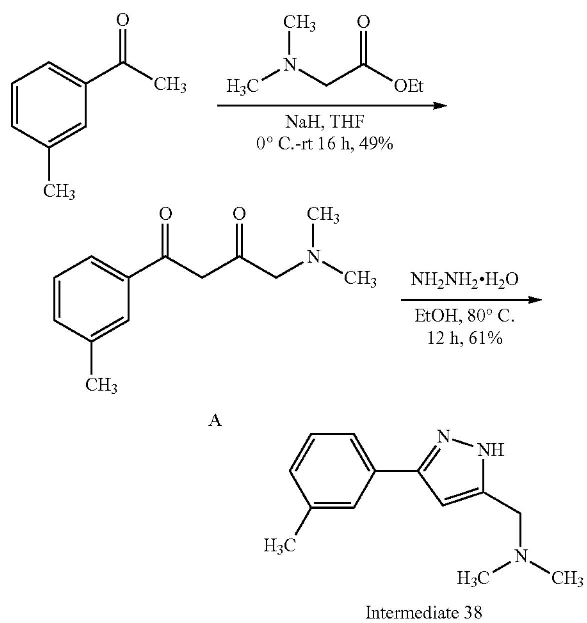

A

Intermediate 38

Preparation of A

To a suspension of 50% NaH (894 mg, 37.3 mmol) in anhydrous THF (10 mL) was added 1-(m-tolyl)ethan-1-one (2.50 g, 18.6 mmol) at 0° C., under $N_2$ atmosphere, and the reaction mixture was stirred at 0° C. for 15 min. A solution of ethyl dimethylglycinate (2.44 g, 18.6 mmol) in THF (2 mL) was slowly added to the reaction mixture at 0° C. over a period of 3 min. The reaction mixture was stirred at 0° C. room temperature for 16 h. The reaction mixture was quenched at 0° C. with water (30 mL), and extracted with EtOAc (2×100 mL). The combined organic extracts were washed with brine (50 mL), dried over anhydrous $Na_2SO_4$, filtered and concentrated under vacuum to obtain the crude product. The crude product was purified by silica-gel column chromatography using 3% $CH_3OH$:$CH_2Cl_2$. Fractions containing the product were combined and concentrated under vacuum to obtain A (2.00 g, 9.12 mmol, 49% yield) as a brown gummy solid.

MS (ESI+APCI; multimode): 220 $[M+H]^+$.

Preparation of Intermediate 38

To a suspension of A (2.00 g, 9.12 mmol) in EtOH (20 mL) was added $NH_2NH_2 \cdot H_2O$ (0.28 mL, 9.12 mmol) at room temperature, under $N_2$ atmosphere. The reaction mixture was gradually heated to 80° C. and stirred for 12 h. The reaction mixture was cooled to room temperature, EtOH evaporated, diluted with water (50 mL), and extracted with EtOAc (2×50 mL). The combined organic extracts were washed with brine (50 mL), dried over anhydrous $Na_2SO_4$, filtered and concentrated under vacuum to obtain the crude product. The crude product was purified by silica-gel column chromatography using 5-8% $CH_3OH$:$CH_2Cl_2$. Fractions containing the product were combined and concentrated under vacuum to obtain Intermediate 38 (1.20 g, 5.57 mmol, 61% yield) as a brown gummy solid.

MS (ESI+APCI; multimode): 216 $[M+H]^+$.

$^1H$ NMR (400 MHz, DMSO-$d_6$): δ: 7.57 (s, 1H), 7.52 (d, J=7.6 Hz, 1H), 7.29 (t, J=7.6 Hz, 1H), 7.13 (d, J=7.6 Hz, 1H), 6.49 (s, 1H), 3.59 (s, 2H), 2.39 (s, 3H), 2.32 (s, 6H).

Synthesis of 5-methyl-3-(m-tolyl)-1H-pyrazole (Intermediate 39)

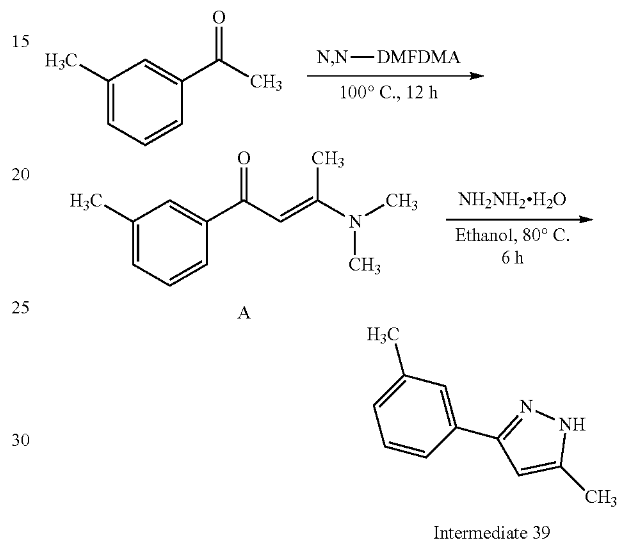

A

Intermediate 39

Preparation of A 1-(m-tolyl)ethan-1-one (6.40 g, 49.6 mmol) was dissolved in N,N-Dimethylformamide dimethyl acetal (6.00 mL, 45.1 mmol) at room temperature, and the reaction mixture gradually heated to 100° C. and stirred for 12 h. The reaction mixture was cooled to room temperature, diluted with water (100 mL) and extracted with methylene chloride (2×100 mL). The combined organic extracts were washed with brine (50 mL), dried over anhydrous Na2SO4, filtered and concentrated under vacuum to obtain the crude product. The product was triturated with MTBE (100 mL) to obtain A (4.40 g, 48% yield) as a brown solid.

$^1H$ NMR (400 MHz, DMSO-d6): δ 7.63-7.55 (m, 2H), 7.31-7.21 (m, 2H), 5.63 (s, 1H), 3.04 (brs, 6H), 2.57 (s, 3H), 2.34 (s, 3H); MS (ESI+APCI; multimode): 204 $[M+H]^+$.

Preparation of Intermediate 39

To a stirred solution of A (4.40 g, 21.60 mmol) in ethanol (15.0 mL), under $N_2$ atmosphere at r.t, Hydrazine hydrate (3.2 ml, 64.93 mmol) was added at 0° C., and the reaction mixture was refluxed at 80° C. for 6 h. The reaction mixture was cooled to room temperature, diluted with water (100 mL) and extracted with methylene chloride (2×100 mL). The combined organic extracts were washed with brine (50 mL), dried over anhydrous $Na_2SO_4$, filtered and concentrated under vacuum to obtain the crude product. The product was purified by silica-gel chromatography (40-45% EtOAc:Hexane). The fractions containing the product were combined and concentrated under vacuum to obtain Intermediate 39 (3.50 g, 94% yield) as a brown solid.

MS (ESI+APCI; multimode): 173 $[M+H]^+$.

$^1$H NMR (400 MHz, DMSO-d6): δ 12.51 (brs, 1H), 7.56 (s, 1H), 7.52 (d, J=8.7 Hz, 1H), 7.26 (t, J=7.8 Hz, 1H), 7.06 (d J=7.2 Hz, 1H), 6.41 (s, 1H), 2.30 (s, 3H), 2.24 (s, 3H);

Synthesis of 4-(2-(2-(1-methyl-1H-pyrazol-4-yl) ethoxy)-6-(methylsulfonyl)pyrimidin-4-yl)morpholine (Intermediate 40)

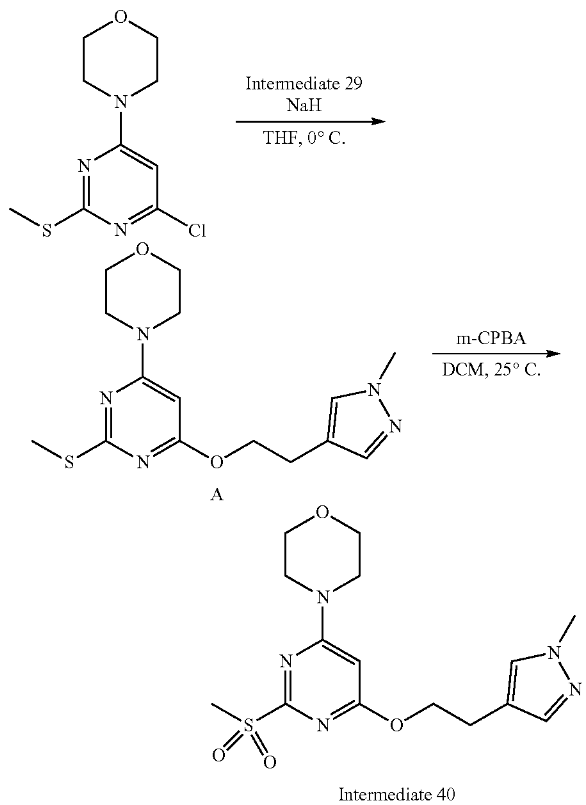

A

Intermediate 40

Preparation of A

To the solution of compound Intermediate 29 (2.6 g, 20.4 mmol) in N,N-dimethylformamide (30 mL) was added sodium hydride (60% in mineral oil, 0.98 g, 24.5 mmol) at 0° C. under nitrogen, and then the mixture was stirred for another 30 min. After which period, the solution of 4-(6-chloro-2-(methylthio)pyrimidin-4-yl)morpholine (4.0 g, 20.4 mmol) in N,N-dimethylformamide (100 mL) was added dropwise to above system. The mixture was stirred at room temperature overnight and poured into water, extracted with ethyl acetate (50 mL×3). The combined organic layers were dried over $Na_2SO_4$, filtered and concentrated to dryness. The resulting crude product was purified by chromatography on silica gel eluting with dichloromethane:methanol=50:1-20:1 to give the product A (4.66 g, 85.4%) as a colorless oil.

Preparation of Intermediate 40

To the solution of A (4.66 g, 14.1 mmol) in dichloromethane (100 mL) was added 3-chlorobenzoperoxoic acid (85% purity, 6.2 g, 30.8 mmol). The mixture was stirred at room temperature overnight and poured into water, extracted with ethyl acetate (50 mL×3). The combined organic layers were dried over $Na_2SO_4$, filtered and concentrated to dryness. The resulting crude product was purified by chromatography on silica gel eluting with petroleum ether:EtOAc=2:1-1:1 to give the desired product Intermediate 40 (3.72 g, 72.9%) as a pale solid.

MS (ESI+APCI; multimode): 368 $[M+H]^+$.

Synthesis of Tert-butyl 2-chloro-4-morpholino-5,7-dihydro-6H-pyrrolo[3,4-d]pyrimidine-6-carboxylate (Intermediate 41)

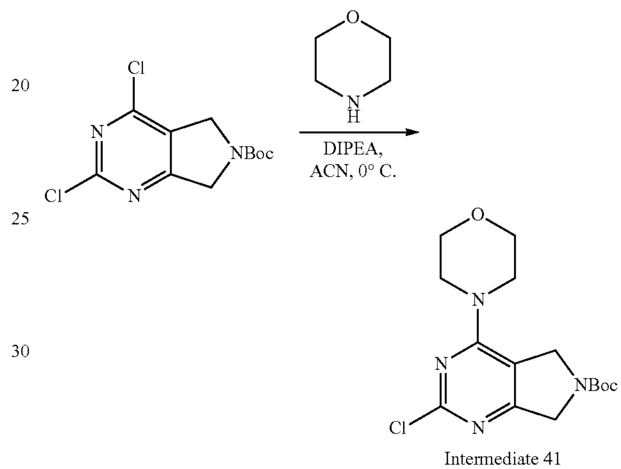

Intermediate 41

To a solution of tert-butyl 2,4-dichloro-5,7-dihydro-6H-pyrrolo[3,4-d]pyrimidine-6-carboxylate (3.0 g, 10.34 mmol) and DIPEA (1.60 g, 12.4 mmol) in acetonitrile (50 mL) was added morpholine (990 mg, 11.38 mmol) dropwise at 0° C. The resulting mixture was stirred for 30 min at 0° C. and then concentrated to dryness under high reduced pressure. The residue was re-dissolved in DCM (50 mL), washed with brine (30 ml×2), dried over anhydrous $Na_2SO_4$, filtered and concentrated. The crude product was purified with silica gel column (eluting with petroleum ether:ethyl acetate=10:1 to 2:1) to give the Intermediate 41 (3.4 g, 96%) as a white solid.

MS (ESI+APCI; multimode): 341$[M+H]^+$.

Synthesis of 4-(5-chloro-1H-pyrrolo[3,2-b]pyridin-7-yl)morpholine (Intermediate 42)

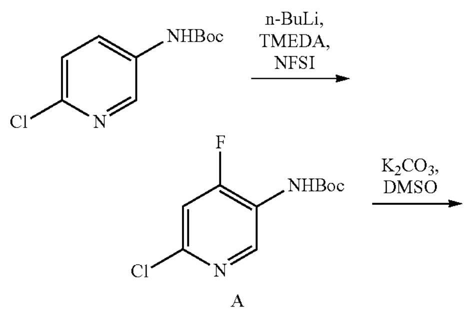

A

-continued

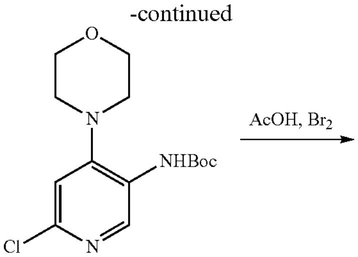

B

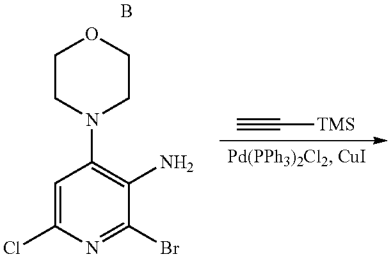

C

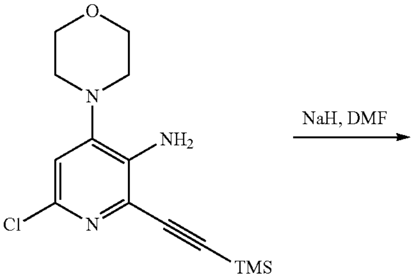

D

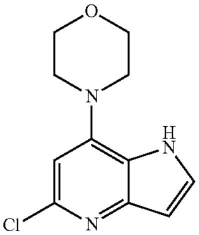

Intermediate 42

Preparation of A

To a solution of tert-butyl (6-chloropyridin-3-yl)carbamate (24 g, 104.94 mmol) and TMEDA (28.65 mL, 251.86 mmol) in diethyl ether (700 mL) was added n-BuLi (119.6 mL, 2.5M, 293.8 mmol) dropwise below −60° C. The reaction was stirred at this temperature for an additional 10 minutes after the addition, and then continued to stir for 2 hrs between −25° C. to −10° C. The reaction was cooled to −60° C. again, and a solution of NFSI (52.94 g, 167.76 mmol) in THF (120 mL) was added while keeping the temperature below −50° C. The precipitate formed on addition impeded the stirring. The reaction was allowed to slowly warm to 0° C. over 1 hour and then quenched with saturated ammonium chloride solution (20 mL). The layers were separated and the aqueous layer was extracted with EA (150 mL×3). The combined organic layers were washed with brine, dried over magnesium sulfate, and concentrated under reduced pressure. The crude compound A was obtained without further purification for the next step.

Preparation of B

To a solution of crude A in DMSO (300 mL) was added morpholine (8.1 g, 93.03 mmol) and $K_2CO_3$ (25.7 g, 186.06 mmol). The resulting mixture was stirred at 100° C. for 30 min and then poured into water (600 mL). The resulting mixture was extracted with EtOAc (150 mL×3). The combined organic layers were washed with $H_2O$, brine (50 mL), dried over $Na_2SO_4$, filtered, and concentrated to dryness. The resulting crude product was purified by chromatography on silica gel eluting with petroleum ether:EtOAc=5:1 to get the desired product B (4.4 g, yield) as yellow solid.

Preparation of C

To a solution of compound B (4.4 g, 14.02 mmol) in AcOH (180 mL) was added $Br_2$ (12 mL) at rt. The mixture was stirred overnight and concentrated under reduced pressure. The residue was basified with sat. $NaHCO_3$ to pH>7, and then extracted with DCM (60 mL×3). The combined organic layers were washed with brine (30 mL), dried over $Na_2SO_4$, filtered, concentrated to dryness. The resulting crude product was purified by chromatography on silica gel eluting with petroleum ether:EtOAc=3:1 to get the desired product C (2.7 g, 66% yield) as a brown solid Preparation of D To the mixture of compound C (2.7 g, 9.23 mmol), $Pd(PPh_3)_2Cl_2$ (648 mg, 0.923 mmol), CuI (176 mg, mmol) in THF:TEA=1:1 (80 ml) was added ethynyltrimethylsilane (2.72 g, 27.69 mmol). The resulting mixture was stirred at 50° C. under nitrogen for 3 hrs and then concentrated under reduced pressure. The residue was purified by chromatography on silica gel eluting with petroleum ether:EtOAc=3:1 to give the desired product D (2.1 g, 73% yield) as a white solid.

Preparation of Intermediate 42

To a solution of compound D (2.1 g, 6.78 mol) in dry DMF (50 mL) was added NaH (651 mg, 27.12 mmol) at 0° C. under nitrogen atmosphere. The resulting mixture was poured into iced water (100 ml) after stirring at room temperature for 5 hrs, and then extracted with EtOAc (60 mL×3). The organic phase was washed with water, brine, dried over $Na_2SO_4$, and concentrated to dryness. The residue was purified by chromatography on silica gel eluting with petroleum ether:EtOAc=2:1 to give Intermediate 42 (1.1 g, 68% yield) as a yellow solid.

$^1$H NMR (400 MHz, DMSO-$d_6$) δ 11.42 (s, 1H), 7.54 (t, J=3.0 Hz, 1H), 6.52 (s, 1H), 6.45 (dd, J=3.1, 1.8 Hz, 1H), 3.88-3.70 (m, 4H), 3.27-3.14 (m, 4H).

Synthesis of ethyl 3-oxo-3-phenylpropanoate (Intermediate 43)

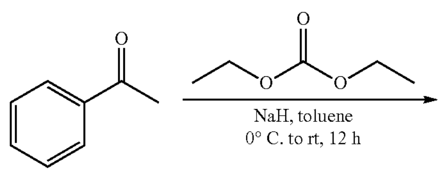

-continued

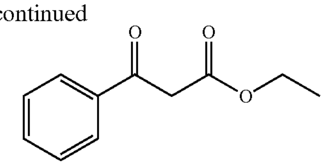

Intermediate 43

To a suspension of acetophenone 1 (1.25 g, 10.4 mmol) in anhydrous Toluene (12.5 ml), at 0° C. under $N_2$ atmosphere, was added NaH (50%, 0.59 g, 24.9 mmol) at same temperature and stirred for 15 min. Diethyl carbonate (2.45 g, 20.8 mmol) was added at 0° C. The reaction mixture was gradually warmed to room temperature and stirred for 12 h. The reaction mixture was cooled to 0° C., quenched with ice cold water (5 mL), diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes to afford Intermediate 43 (1.50 g, 75% yield) as a brown liquid.

LCMS (ESI): m/z=193 $[M+H]^+$.

$^1H$ NMR (400 MHz, DMSO-$d_6$) δ: 7.96-7.94 (m, 2H), 7.68-7.66 (m, 1H), 7.57-7.53 (m, 2H), 4.19 (s, 2H), 4.11 (q, J=7.2 Hz, 2H), 1.17 (t, J=7.2 Hz, 3H).

Synthesis of 3-phenyl-1H-pyrazol-5-ol (Intermediate 44)

Intermediate 43

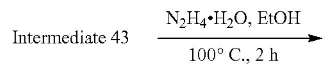

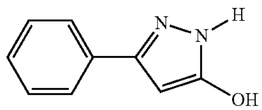

Intermediate 44

To a suspension of Intermediate 43 (1.50 g, 7.80 mmol) in anhydrous Ethanol (15 ml), at room temperature, under $N_2$ atmosphere, was added hydrazine monohydrate (0.24 ml, 7.80 mmol). The reaction mixture was gradually heated to 100° C. and stirred for 2 h. The reaction mixture was cooled to room temperature, diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes to afford 3-phenyl-1H-pyrazol-5-ol (Intermediate 44) (650 mg, 52.0% yield) as an off-white solid.

LCMS (ESI): m/z=161 $[M+H]^+$.

$^1H$ NMR (400 MHz, DMSO-$d_6$) δ: 7.67-7.65 (m, 2H), 7.42-7.38 (m, 2H), 7.31-7.27 (m, 1H), 5.89 (s, 1H), 1.75 (s, 2H).

Synthesis of 2-(1-methyl-1H-pyrazol-3-yl)ethyl methanesulfonate (Intermediate 45)

Intermediate 29

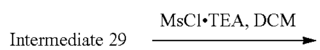

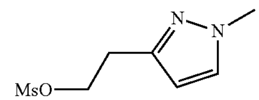

Intermediate 45

To a solution of Intermediate 29 (1.0 g, 7.94 mmol) and triethylamine (1.2 g, 11.9 mmol) in DCM (40 mL) was added methanesulfonyl chloride (1.09 g, 9.53 mmol) at 0° C. under nitrogen atmosphere. The resulting mixture was stirred at 0° C. for 1 h and then concentrated to dryness in vacuo. The residue was purified by flash silica gel column (petroleum ether:THF=5:1 to 1:1) to afford Intermediate 45 (1.57 g, 97%) as yellow oil, which was used without further purification.

Synthesis of (3aR,6aR)-4-(2-((tetrahydrofuran-2-yl)methoxy)-6-(4-(m-tolyl)thiazol-2-yl)pyrimidin-4-yl)hexahydro-2H-furo[3,2-b]pyrrole (Compound 11)

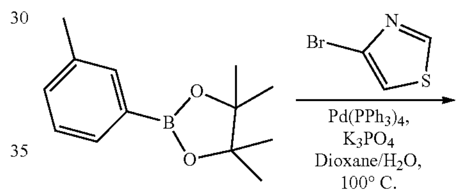

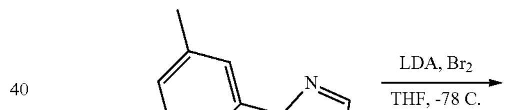

A

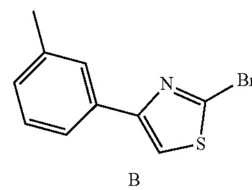

B

Intermediate 1

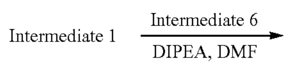

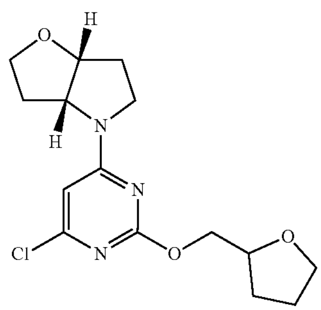

C

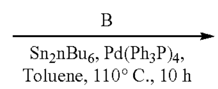

-continued

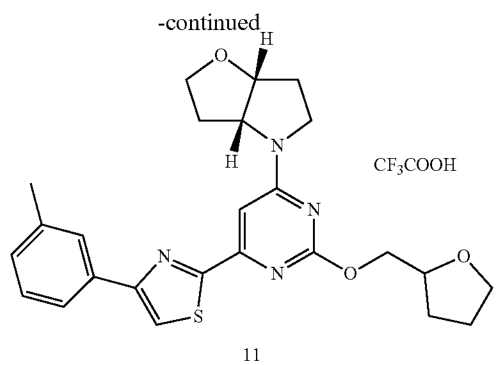

11

Preparation of A

A mixture of 4,4,5,5-tetramethyl-2-(3-methylphenyl)-1,3,2-dioxaborolane (2.6 g, 11.921 mmol, 1 equiv), 4-bromo-1,3-thiazole (1.96 g, 11.950 mmol, 1.00 equiv), $Pd(PPh_3)_4$ (275.51 mg, 0.238 mmol, 0.02 equiv), $K_3PO_4$ (7.59 g, 35.757 mmol, 3.00 equiv), dioxane (100 mL) and $H_2O$ (10 mL) was stirred over night at 100° C. under $N_2$. The resulting suspension was concentrated and purified by flash chromatography on silica gel eluting with DCM/PE (0-100%) to provide 4-(3-methylphenyl)-1,3-thiazole (A) (1.64 g, 75.59%) as a light yellow oil.

Preparation of B

To a solution of 4-(3-methylphenyl)-1,3-thiazole (A) (400 mg, 2.282 mmol, 1 equiv) in THF (10 mL, 0.139 mmol, 0.06 equiv) was added LDA (733.51 mg, 6.847 mmol, 3 equiv) and the mixture was stirred for 30 min at −78° C. under $N_2$. $Br_2$ (0.18 mL, 3.513 mmol, 1.54 equiv) was added and the mixture was stirred for 30 min. The resulting suspension was diluted with EA (100 mL) and washed with $H_2O$ (20 mL), brine (20 mL). The combined organic layers were dried over $Na_2SO_4$, concentrated and purified by flash chromatography on silica gel eluting with DCM/PE (0-100%) to provide 2-bromo-4-(3-methylphenyl)-1,3-thiazole (B) (425 mg, 73.27%) as a light yellow oil.

Preparation of C

A mixture of Intermediate 6 (0.7 g, 4.679 mmol, 1 equiv), Intermediate 1 (1.40 g, 5.614 mmol, 1.20 equiv) and DIEA (1.81 g, 14.036 mmol, 3.00 equiv) in DMF (3 mL) was stirred for 3 h at 100° C. under $N_2$ atmosphere. The mixture was purified by reverse phase chromatography to afford 4-[(3aR,6aR)-hexahydro-2H-furo[3,2-b]pyrrol-4-yl]-6-chloro-2-[(oxolan-2-yl)methoxy]pyrimidin C (1.1 g, 72.17%) as white solid.

LC-MS-PH-ICA-004-0-20: RT=3.356 min, m/z=326.1 $[M+H]^+$

H-NMR-PH-ICA-004-0-20: $^1H$ NMR (300 MHz, Chloroform-d) δ 6.04 (s, 1H), 4.83-4.14 (m, 5H), 4.01-3.35 (m, 6H), 2.48-2.17 (m, 2H), 2.13-2.06 (m, 1H), 2.02-1.74 (m, 5H).

Preparation of Compound 11

Under $N_2$, mixture of 4-[(3aR,6aR)-hexahydro-2H-furo[3,2-b]pyrrol-4-yl]-6-chloro-2-[(oxolan-2-yl)methoxy]pyrimidine (C) (100 mg, 0.307 mmol, 1 equiv), 2-bromo-4-(3-methylphenyl)-1,3-thiazole (B) (400.19 mg, 1.575 mmol, 5.13 equiv), $Sn_2Bu_6$ (356.13 mg, 0.614 mmol, 2.00 equiv), $Pd(PPh_3)_4$ (35.47 mg, 0.031 mmol, 0.10 equiv) and toluene (10 mL) was stirred over night at 110° C. The mixture was concentrated and purified by flash chromatography on silica gel eluting with EA/PE (0-100%) to provide crude product. The crude product was purified by Prep-HPLC with the following conditions (ACN/Water (0.05% TFA), 5%-95%) to afford 4-[(3aR,6aR)-hexahydro-2H-furo[3,2-b]pyrrol-4-yl]-6-[4-(3-methylphenyl)-1,3-thiazol-2-yl]-2-[(oxolan-2-yl)methoxy]pyrimidine (Compound 11) (5.1 mg, 3.54%) as a white solid.

LC-MS RT=3.783 min, m/z=465.20 $[M+H]^+$ $^1H$ NMR (400 MHz, Chloroform-d) δ 7.81 (s, 1H), 7.77 (d, J=7.7 Hz, 1H), 7.65 (s, 1H), 7.36 (t, J=7.6 Hz, 1H), 7.21 (d, J=7.5 Hz, 1H), 7.04 (s, 1H), 4.78-4.26 (m, 5H), 4.04-3.46 (m, 6H), 2.56-2.39 (m, 4H), 2.31-1.95 (m, 6H), 1.85 (s, 1H).

Synthesis of 4-(3-methoxypyrrolidin-1-yl)-2-((tetrahydrofuran-2-yl)methoxy)-6-(3-(m-tolyl)-1H-pyrazol-1-yl)pyrimidine (Compound 15)

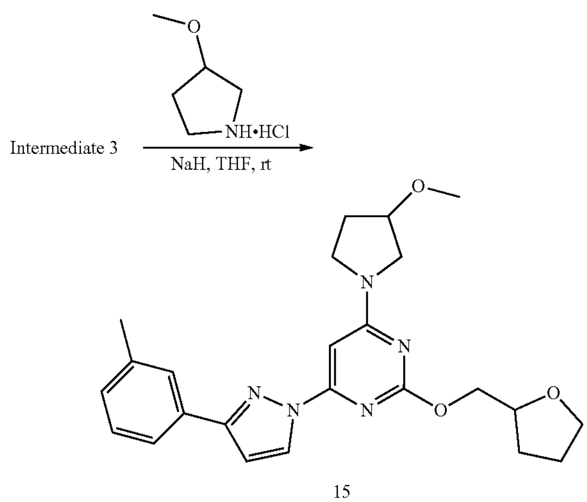

15

To a solution of 4-chloro-6-[3-(3-methylphenyl)-1H-pyrazol-1-yl]-2-[(oxolan-2-yl)methoxy]pyrimidine (Intermediate 3) (40 mg, 0.108 mmol, 1 equiv) in THF (0.5 mL) was successively added 3-methoxypyrrolidine hydrochloride (17.81 mg, 0.129 mmol, 1.20 equiv), NaH (6.47 mg, 0.162 mmol, 1.50 equiv, 60%) and the solution was stirred for 2 h at room temperature. Desired product could be detected by LCMS. Then the mixture was concentrated and purified by prep-HPLC to afford 4-(3-methoxypyrrolidin-1-yl)-6-[3-(3-methylphenyl)-1H-pyrazol-1-yl]-2-[(oxolan-2-yl)methoxy]pyrimidine (Compound 15) (14.1 mg, 30.01%) as a white solid.

LC-MS RT=3.712 min, m/z=436.30 $[M+H]^+$ $^1H$ NMR (400 MHz, Chloroform-d) δ 8.58 (d, J=2.7 Hz, 1H), 7.77 (s, 1H), 7.72 (d, J=7.7 Hz, 1H), 7.35 (t, J=7.6 Hz, 1H), 7.20 (d, J=7.6 Hz, 1H), 6.74 (d, J=2.7 Hz, 1H), 6.71 (s, 1H), 4.50-4.46 (m, 1H), 4.43-4.26 (m, 2H), 4.12 (s, 1H), 4.05-3.78 (m, 3H), 3.68 (s, 3H), 3.40 (s, 3H), 2.45 (s, 3H), 2.17-2.09 (m, 3H), 2.08-1.90 (m, 2H), 1.91-1.77 (m, 1H).

Synthesis of 4-(6-(1H-pyrazol-3-yl)-2-((tetrahydrofuran-2-yl)methoxy)pyrimidin-4-yl)morpholine (Compound 45)

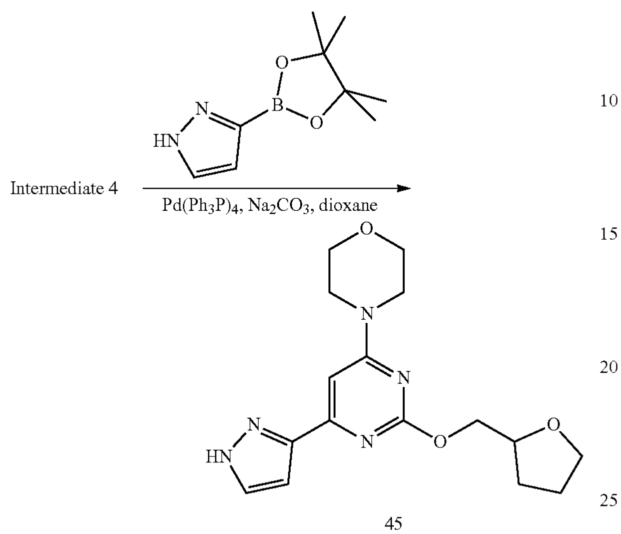

45

Into a 30 mL tube were added 4-[6-chloro-2-[(oxolan-2-yl)methoxy]pyrimidin-4-yl]morpholine (Intermediate 4) (350 mg, 1.168 mmol, 1 equiv), 3-(4,4,5,5-tetramethyl-1,3,2-dioxaborolan-2-yl)-1H-pyrazole (453.12 mg, 2.335 mmol, 2.00 equiv), $Pd(PPh_3)_4$ (134.92 mg, 0.117 mmol, 0.1 equiv) and $Na_2CO_3$ (371.26 mg, 3.503 mmol, 3 equiv). To the mixture was added dioxane (10.5 mL) under an atmosphere of $N_2$. The tube was sealed with a screw cap and stirred at room temperature for 5 minutes. Then the tube was placed into an oil bath and reacted at 100° C. for 2 h. The mixture was purified by silica gel column chromatography to afford 4-[2-[(oxolan-2-yl)methoxy]-6-(1H-pyrazol-3-yl)pyrimidin-4-yl]morpholine (Compound 45) (376 mg, 97.18%) as a white solid.

LC-MS RT=1.621 min, m/z=332.2 $[M+H]^+$ $^1$H NMR (300 MHz, DMSO-$d_6$) δ 13.31 (d, J=101.9 Hz, 1H), 7.69 (d, J=75.4 Hz, 1H), 7.01-6.76 (m, 2H), 4.35-4.09 (m, 3H), 3.89-3.49 (m, 10H), 2.05-1.77 (m, 3H), 1.65 (s, 1H).

Synthesis of 4-(2-(pyridazin-3-ylmethoxy)-6-(3-(m-tolyl)-1H-pyrazol-1-yl)pyrimidin-4-yl)morpholine (Compound 54)

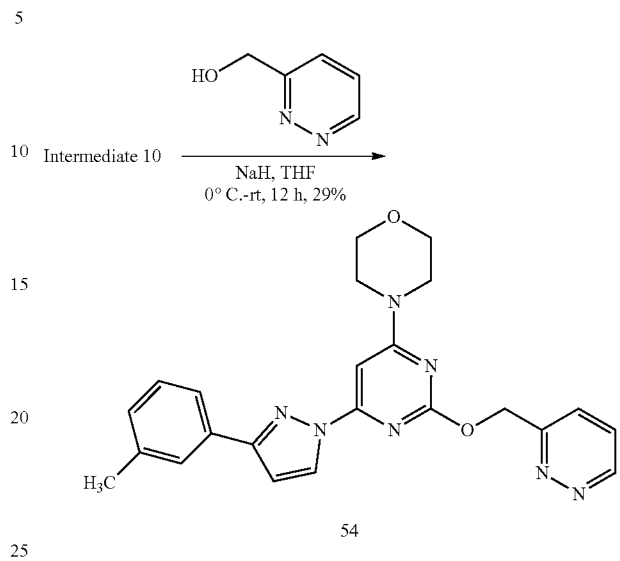

54

To a suspension of 50% NaH (22.4 mg, 0.56 mmol) in anhydrous THF (5 mL) at 0° C., under $N_2$ atmosphere was added pyridazin-3-ylmethanol (30.9 mg, 0.28 mmol) and the reaction mixture was stirred at 0° C. for 15 min. A solution of Intermediate 10 (100 mg, 0.28 mmol) in THF (1.0 mL) was slowly added to the reaction mixture at 0° C. over a period of 2 min. The reaction mixture was stirred at 0° C. to room temperature for 12 h. The reaction mixture was quenched at 0° C. with water (50 mL), and extracted with EtOAc (2×20 mL). The combined organic extracts were washed with brine (20 mL), dried over anhydrous $Na_2SO_4$, filtered and concentrated under vacuum to obtain the crude product. The product was purified by silica-gel chromatography (20-25% EtOAc:Hexanes). Fractions containing the product were combined and concentrated under vacuum to obtain Compound 54 (35.0 mg, 0.08 mmol, 29%) as an off-white solid.

LCMS (ESI): m/z=430 $[M+H]^+$; HPLC: 98.2 (% of AUC).

$^1$H NMR (400 MHz, DMSO-$d_6$) δ: 9.20 (dd J=1.2 Hz, 4.8 Hz, 1H), 8.55 (d, J=2.4 Hz, 1H), 7.81-7.71 (m, 4H), 7.35 (t, J=7.6 Hz, 1H), 7.21 (d, J=7.6 Hz, 1H), 7.06 (d, J=2.8 Hz, 1H), 6.91 (s, 1H), 5.67 (s, 2H), 3.66 (brs, 8H), 2.38 (s, 3H).

The following compounds were synthesized using procedures similar to the one described for Compound 54:

| No. | Structure | Name | LCMS (ESI): m/z $[M + H]^+$ | $^1$H NMR (400 MHz, DMSO-$d_6$) |
|---|---|---|---|---|
| 44 | 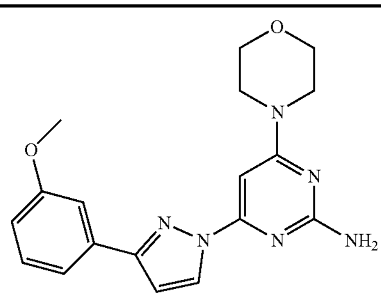 | 4-(3-(3-methoxyphenyl)-1H-pyrazol-1-yl)-6-morpholino-pyrimidin-2-amine | 353 | |

-continued

| No. | Structure | Name | LCMS (ESI): m/z $[M + H]^+$ | $^1H$ NMR (400 MHz, DMSO-$d_6$) |
| --- | --- | --- | --- | --- |
| 46 | 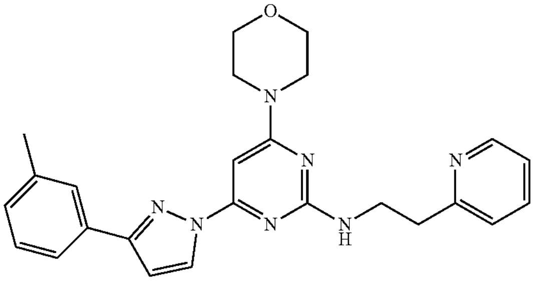 [SMILES: Cc1cccc(-c2ccn(-c3cc(N4CCOCC4)nc(NCCc4ccccn4)n3)n2)c1] | 4-morpholino-N-(2-(pyridin-2-yl)ethyl)-6-(3-(m-tolyl)-1H-pyrazol-1-yl)pyrimidin-2-amine | 442 | |
| 55 | 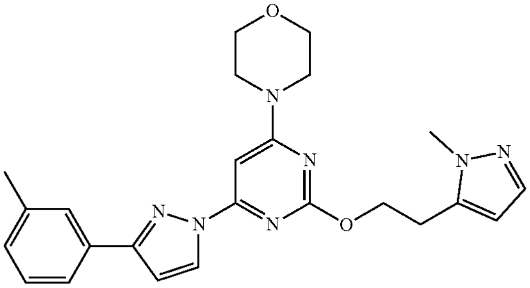 [SMILES: Cc1cccc(-c2ccn(-c3cc(N4CCOCC4)nc(OCCc4ccnn4C)n3)n2)c1] | 4-(2-(2-(1-methyl-1H-pyrazol-5-yl)ethoxy)-6-(3-(m-tolyl)-1H-pyrazol-1-yl)pyrimidin-4-yl)morpholine | 446 | δ: 8.59 (d J = 2.8 Hz, 1H), 7.81 (s, 1H), 7.77 (d, J = 7.6 Hz, 1H), 7.35 (t, J = 7.6 Hz, 1H), 7.30 (d, J = 2.0 Hz, 1H), 7.21 (d, J = 7.6 Hz, 1H), 7.05 (d, J = 2.8 Hz, 1H), 6.90 (s, 1H), 6.15 (d, J = 1.6 Hz, 1H), 4.54 (t, J = 6.8 Hz, 2H), 3.79 (s, 3H), 3.69 (brs, 8H), 3.11 (t, J = 6.8 Hz, 2H), 2.38 (s, 3H) |
| 59 | 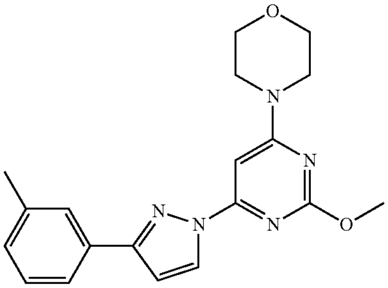 [SMILES: COc1nc(N2CCOCC2)cc(-n2ccc(-c3cccc(C)c3)n2)n1] | 4-(2-methoxy-6-(3-(m-tolyl)-1H-pyrazol-1-yl)pyrimidin-4-yl)morpholine | 352 | δ: 8.59 (d, J = 2.4 Hz, 1H), 7.81 (s, 1H), 7.78 (d, J = 7.6 Hz, 1H), 7.35 (t, J = 7.6 Hz, 1H), 7.21 (d, J = 7.6 Hz, 1H), 7.06 (d, J = 2.8 Hz, 1H), 6.90 (s, 1H), 3.90 (s, 3H), 3.70 (brs, 8H), 2.39 (s, 3H). |
| 61 | 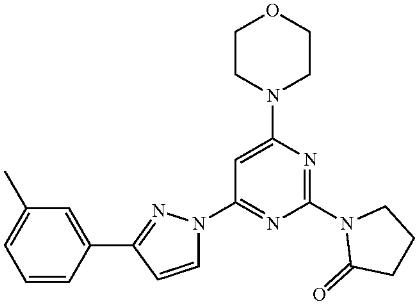 [SMILES: Cc1cccc(-c2ccn(-c3cc(N4CCOCC4)nc(N4CCCC4=O)n3)n2)c1] | 1-(4-morpholino-6-(3-(m-tolyl)-1H-pyrazol-1-yl)pyrimidin-2-yl)pyrrolidin-2-one | 405 | δ: 8.56 (d J = 2.8 Hz, 1H), 7.75 (s, 1H), 7.69 (d, J = 8.0 Hz, 1H), 7.32 (t, J = 7.6 Hz, 1H), 7.18 (d, J = 7.6 Hz, 1H), 6.95 (s, 1H), 6.75 (d, J = 2.8 Hz, 1H), 4.09 (t, J = 7.2 Hz, 2H), 3.80-3.78 (m, 8H), 2.66 (t, J = 8.0 Hz, 2H), 2.42 (s, 3H), 2.15-2.07 (m, 2H). |
| 90 | 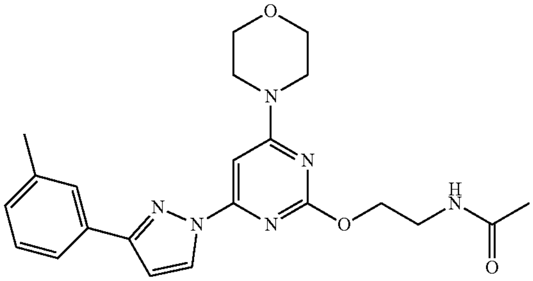 [SMILES: CC(=O)NCCOc1nc(N2CCOCC2)cc(-n2ccc(-c3cccc(C)c3)n2)n1] | N-(2-((4-morpholino-6-(3-(m-tolyl)-1H-pyrazol-1-yl)pyrimidin-2-yl)oxy)ethyl) acetamide | 423 | δ: 8.60 (d, J = 2.4 Hz, 1H), 8.12 (d, J = 4.8 Hz, 1H), 7.81 (s, 1H), 7.77 (d, J = 8.0 Hz, 1H), 7.35 (t, J = 7.6 Hz, 1H), 7.21 (d, J = 7.2 Hz, 1H), 7.06 (d, J = 2.8 Hz, 1H), 6.90 (s, 1H), 4.31 (t, J = 5.6 Hz, 2H), 3.69 (brs, 8H), 3.41 (q, J = 5.2 Hz, 10.8 Hz, 2H), 2.38 (s, 3H), 1.82 (s, 3H). |

-continued

| No. | Structure | Name | LCMS (ESI): m/z $[M + H]^+$ | $^1H$ NMR (400 MHz, DMSO-$d_6$) |
|---|---|---|---|---|
| 91 | 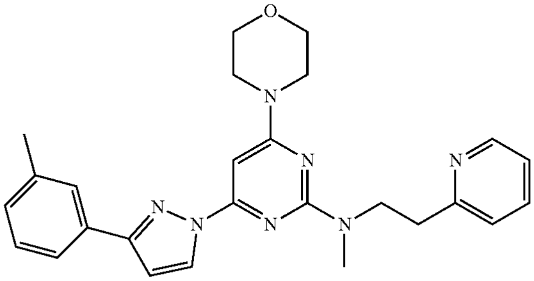 [SMILES: Cc1cccc(-c2ccn(-c3cc(N4CCOCC4)nc(N(C)CCc4ccccn4)n3)n2)c1] | N-methyl-4-morpholino-N-(2-(pyridin-2-yl)ethyl)-6-(3-(m-tolyl)-1H-pyrazol-1-yl)pyrimidin-2-amine | 456 | |
| 92 | 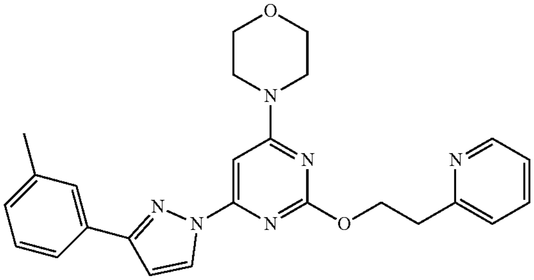 [SMILES: Cc1cccc(-c2ccn(-c3cc(N4CCOCC4)nc(OCCc4ccccn4)n3)n2)c1] | 4-(2-(2-(pyridin-2-yl)ethoxy)-6-(3-(m-tolyl)-1H-pyrazol-1-yl)pyrimidin-4-yl)morpholine | 443 | |
| 93 | 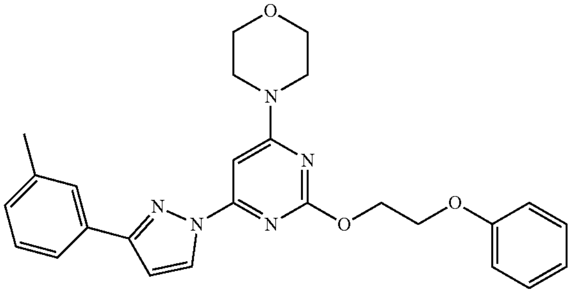 [SMILES: Cc1cccc(-c2ccn(-c3cc(N4CCOCC4)nc(OCCOc4ccccc4)n3)n2)c1] | 4-(2-(2-phenoxyethoxy)-6-(3-(m-tolyl)-1H-pyrazol-1-yl)pyrimidin-4-yl)morpholine | 453 | |
| 94 | 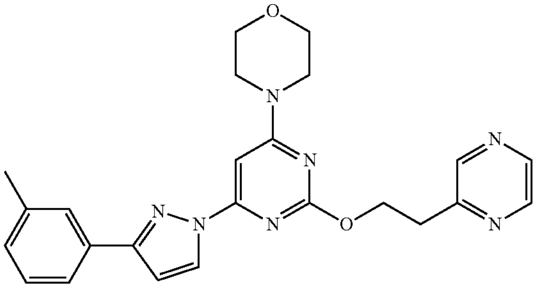 [SMILES: Cc1cccc(-c2ccn(-c3cc(N4CCOCC4)nc(OCCc4cnccn4)n3)n2)c1] | 4-(2-(2-(pyrazin-2-yl)ethoxy)-6-(3-(m-tolyl)-1H-pyrazol-1-yl)pyrimidin-4-yl)morpholine | 444 | |
| 95 | 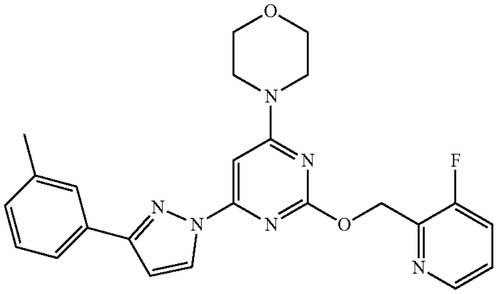 [SMILES: Cc1cccc(-c2ccn(-c3cc(N4CCOCC4)nc(OCc4ncccc4F)n3)n2)c1] | 4-(2-((3-fluoropyridin-2-yl)methoxy)-6-(3-(m-tolyl)-1H-pyrazol-1-yl)pyrimidin-4-yl)morpholine | 447 | |

-continued

| No. | Structure | Name | LCMS (ESI): m/z [M + H]+ | $^1H$ NMR (400 MHz, DMSO-$d_6$) |
|---|---|---|---|---|
| 96 | 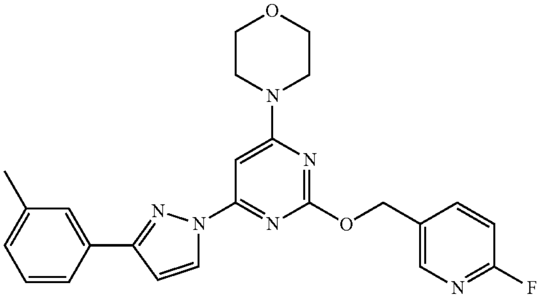 [SMILES: Cc1cccc(-c2ccn(-c3cc(N4CCOCC4)nc(OCc4ccc(F)nc4)n3)n2)c1] | 4-(2-((5-fluoropyridin-2-yl)methoxy)-6-(3-(m-tolyl)-1H-pyrazol-1-yl)pyrimidin-4-yl)morpholine | 447 | |
| 97 | 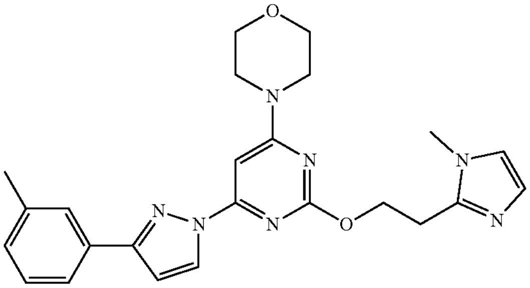 [SMILES: Cc1cccc(-c2ccn(-c3cc(N4CCOCC4)nc(OCCc4nccn4C)n3)n2)c1] | 4-(2-(2-(1-methyl-1H-imidazol-5-yl)ethoxy)-6-(3-(m-tolyl)-1H-pyrazol-1-yl)pyrimidin-4-yl)morpholine | 446 | |
| 98 | 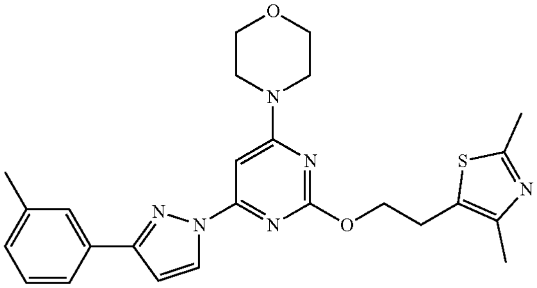 [SMILES: Cc1cccc(-c2ccn(-c3cc(N4CCOCC4)nc(OCCc4sc(C)nc4C)n3)n2)c1] | 4-(2-(2-(2,4-dimethylthiazol-5-yl)ethoxy)-6-(3-(m-tolyl)-1H-pyrazol-1-yl)pyrimidin-4-yl)morpholine | 477 | |
| 99 | 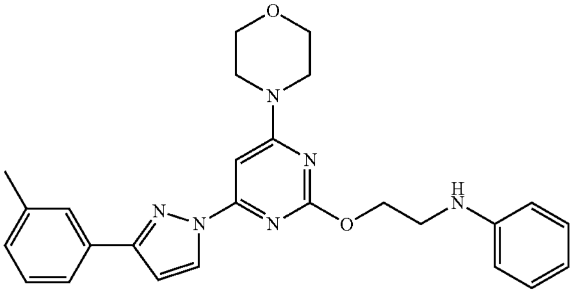 [SMILES: Cc1cccc(-c2ccn(-c3cc(N4CCOCC4)nc(OCCNc4ccccc4)n3)n2)c1] | N-(2-((4-morpholino-6-(3-(m-tolyl)-1H-pyrazol-1-yl)pyrimidin-2-yl)oxy)ethyl)aniline | 457 | |
| 100 | 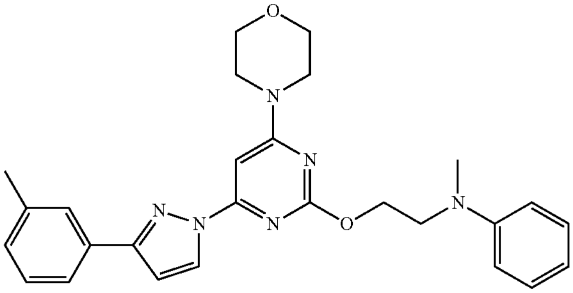 | N-methyl-N-(2-((4-morpholino-6-(3-(m-tolyl)-1H-pyrazol-1-yl)pyrimidin-2-yl)oxy)ethyl)aniline | 471 | |

-continued

| No. | Structure | Name | LCMS (ESI): m/z $[M + H]^+$ | $^1H$ NMR (400 MHz, DMSO-$d_6$) |
|---|---|---|---|---|
| 101 | 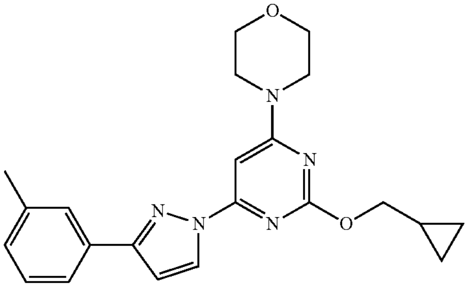 [SMILES: Cc1cccc(-c2ccn(-c3cc(N4CCOCC4)nc(OCC4CC4)n3)n2)c1] | 4-(2-(cyclopropyl-methoxy)-6-(3-(m-tolyl)-1H-pyrazol-1-yl)pyrimidin-4-yl)morpholine | 392 | |
| 102 | 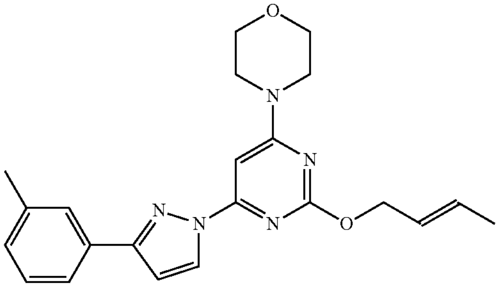 [SMILES: C/C=C/COc1nc(N2CCOCC2)cc(-n2ccc(-c3cccc(C)c3)n2)n1] | (E)-4-(2-(but-2-en-1-yloxy)-6-(3-(m-tolyl)-1H-pyrazol-1-yl)pyrimidin-4-yl)morpholine | 392 | |
| 103 | 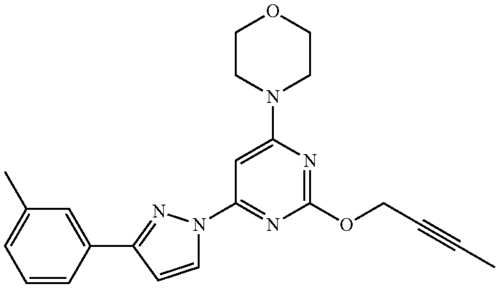 [SMILES: CC#CCOc1nc(N2CCOCC2)cc(-n2ccc(-c3cccc(C)c3)n2)n1] | 4-(2-(but-2-yn-1-yloxy)-6-(3-(m-tolyl)-1H-pyrazol-1-yl)pyrimidin-4-yl)morpholine | 390 | |
| 104 | 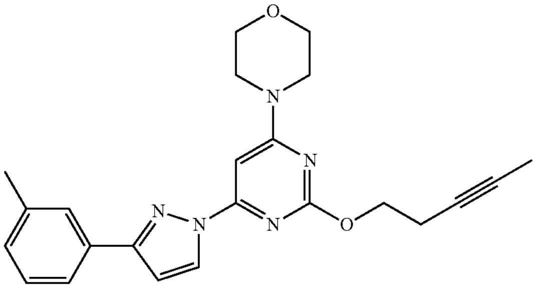 [SMILES: CC#CCCOc1nc(N2CCOCC2)cc(-n2ccc(-c3cccc(C)c3)n2)n1] | 4-(2-(pent-3-yn-1-yloxy)-6-(3-(m-tolyl)-1H-pyrazol-1-yl)pyrimidin-4-yl)morpholine | 404 | |
| 105 | 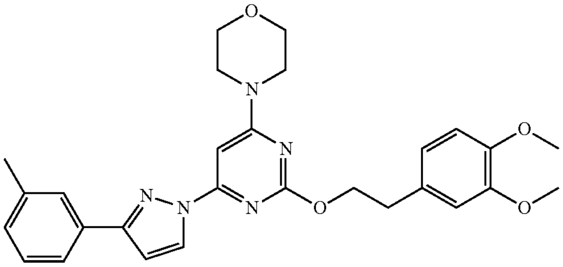 [SMILES: COc1ccc(CCOc2nc(N3CCOCC3)cc(-n3ccc(-c4cccc(C)c4)n3)n2)cc1OC] | 4-(2-(3,4-dimethoxy-phenethoxy)-6-(3-(m-tolyl)-1H-pyrazol-1-yl)pyrimidin-4-yl)morpholine | 503 | |

-continued

| No. | Structure | Name | LCMS (ESI): m/z [M + H]$^+$ | $^1$H NMR (400 MHz, DMSO-$d_6$) |
| --- | --- | --- | --- | --- |
| 106 | 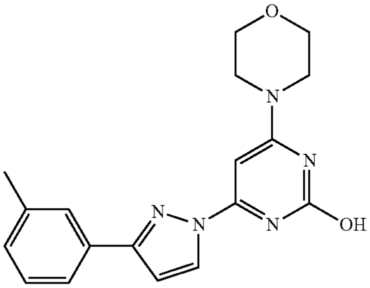 [SMILES: Cc1cccc(-c2ccn(-c3cc(N4CCOCC4)nc(O)n3)n2)c1] | 4-morpholino-6-(3-(m-tolyl)-1H-pyrazol-1-yl)pyrimidin-2-ol | 338 | |
| 107 | 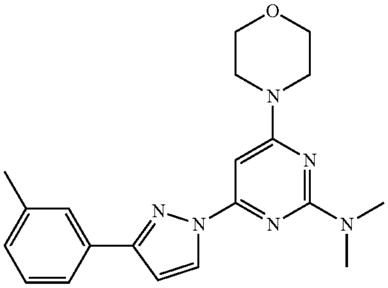 [SMILES: Cc1cccc(-c2ccn(-c3cc(N4CCOCC4)nc(N(C)C)n3)n2)c1] | N,N-dimethyl-4-morpholino-6-(3-(m-tolyl)-1H-pyrazol-1-yl)pyrimidin-2-amine | 365 | |
| 108 | 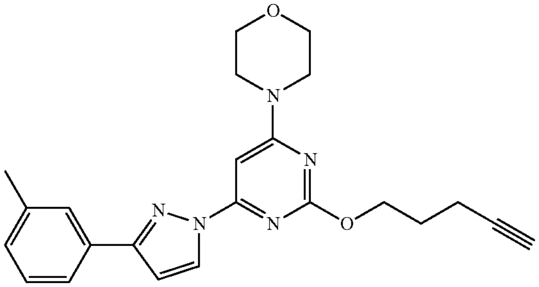 [SMILES: C#CCCCOc1nc(N2CCOCC2)cc(-n2ccc(-c3cccc(C)c3)n2)n1] | 4-(2-(pent-4-yn-1-yloxy)-6-(3-(m-tolyl)-1H-pyrazol-1-yl)pyrimidin-4-yl)morpholine | 404 | |
| 109 | 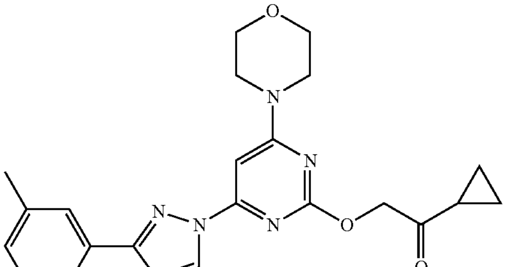 | 1-cyclopropyl-2-((4-morpholino-6-(3-(m-tolyl)-1H-pyrazol-1-yl)pyrimidin-2-yl)oxy)ethan-1-one | 420 | |
| 110 | 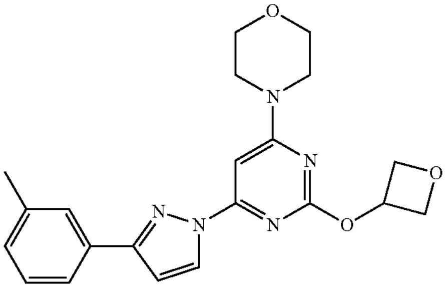 [SMILES: Cc1cccc(-c2ccn(-c3cc(N4CCOCC4)nc(OC4COC4)n3)n2)c1] | 4-(2-(oxetan-3-yloxy)-6-(3-(m-tolyl)-1H-pyrazol-1-yl)pyrimidin-4-yl)morpholine | 394.2 | |

-continued

| No. | Structure | Name | LCMS (ESI): m/z $[M + H]^+$ | $^1H$ NMR (400 MHz, DMSO-$d_6$) |
|---|---|---|---|---|
| 111 | 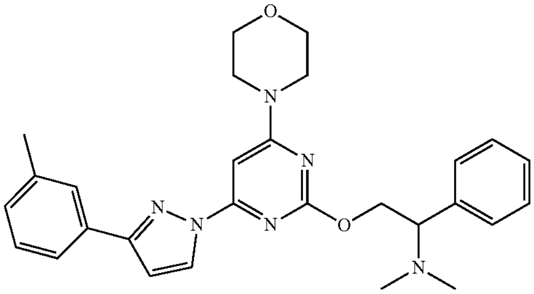 [SMILES: Cc1cccc(-c2ccn(-c3cc(N4CCOCC4)nc(OCC(c4ccccc4)N(C)C)n3)n2)c1] | N,N-dimethyl-2-((4-morpholino-6-(3-(m-tolyl)-1H-pyrazol-1-yl)pyrimidin-2-yl)oxy)-1-phenylethan-1-amine | 485 | |
| 112 | 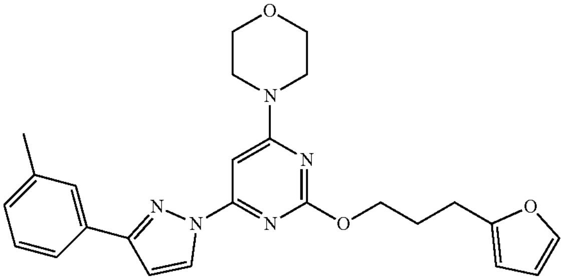 [SMILES: Cc1cccc(-c2ccn(-c3cc(N4CCOCC4)nc(OCCCc4ccco4)n3)n2)c1] | 4-(2-(3-(furan-2-yl)propoxy)-6-(3-(m-tolyl)-1H-pyrazol-1-yl)pyrimidin-4-yl)morpholine | 206 | |
| 113 | 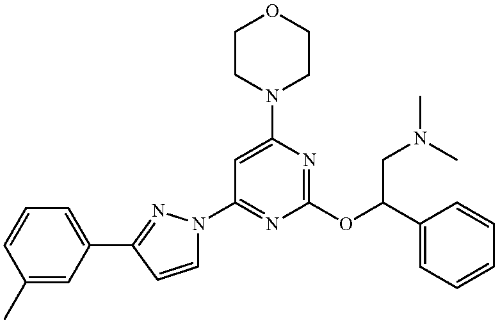 [SMILES: Cc1cccc(-c2ccn(-c3cc(N4CCOCC4)nc(OC(CN(C)C)c4ccccc4)n3)n2)c1] | N,N-dimethyl-2-((4-morpholino-6-(3-(m-tolyl)-1H-pyrazol-1-yl)pyrimidin-2-yl)oxy)-2-phenylethan-1-amine | 485 | |
| 114 | 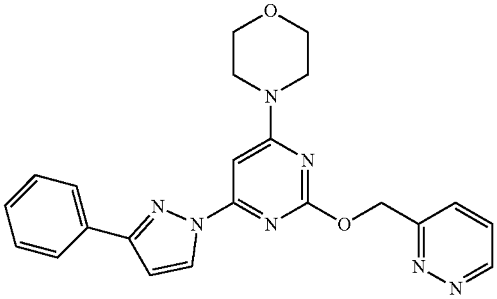 [SMILES: c1ccc(-c2ccn(-c3cc(N4CCOCC4)nc(OCc4cccnn4)n3)n2)cc1] | 4-(6-(3-phenyl-1H-pyrazol-1-yl)-2-(pyridazin-3-ylmethoxy)pyrimidin-4-yl)morpholine | 416 | |
| 115 | 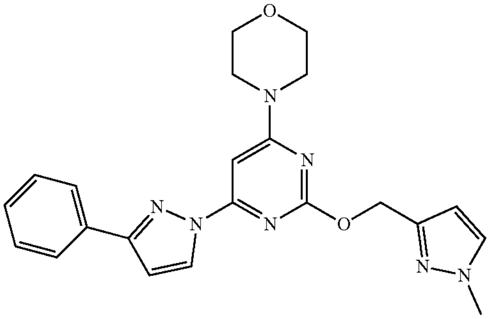 [SMILES: Cn1ccc(COc2nc(N3CCOCC3)cc(-n3ccc(-c4ccccc4)n3)n2)n1] | 4-(2-((1-methyl-1H-pyrazol-3-yl)methoxy)-6-(3-phenyl-1H-pyrazol-1-yl)pyrimidin-4-yl)morpholine | 418 | |

-continued

| No. | Structure | Name | LCMS (ESI): m/z [M + H]+ | $^1$H NMR (400 MHz, DMSO-$d_6$) |
|---|---|---|---|---|
| 116 | 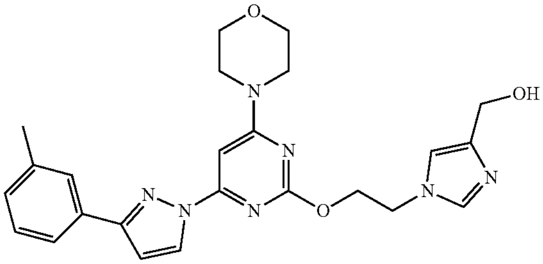 [SMILES: Cc1cccc(-c2ccn(-c3cc(N4CCOCC4)nc(OCCn4cnc(CO)c4)n3)n2)c1] | (1-(2-((4-morpholino-6-(3-(m-tolyl)-1H-pyrazol-1-yl)pyrimidin-2-yl)oxy)ethyl)-1H-imidazol-4-yl)methanol | 462 | |
| 117 | 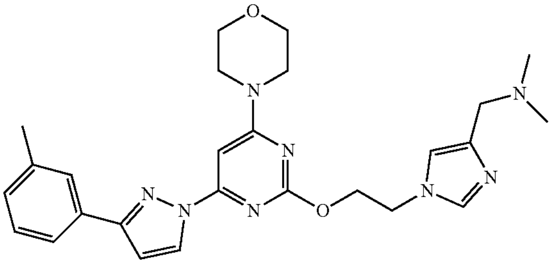 [SMILES: Cc1cccc(-c2ccn(-c3cc(N4CCOCC4)nc(OCCn4cnc(CN(C)C)c4)n3)n2)c1] | N,N-dimethyl-1-(1-(2-((4-morpholino-6-(3-(m-tolyl)-1H-pyrazol-1-yl)pyrimidin-2-yl)oxy)ethyl)-1H-imidazol-4-yl)methanamine | 489 | |
| 118 | 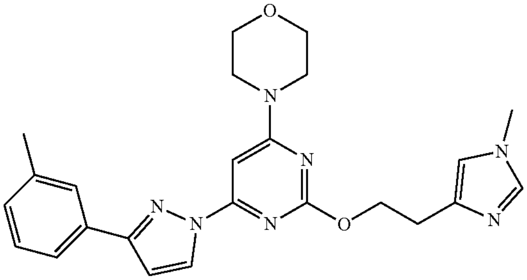 [SMILES: Cc1cccc(-c2ccn(-c3cc(N4CCOCC4)nc(OCCc4cn(C)cn4)n3)n2)c1] | 4-(2-(2-(1-methyl-1H-imidazol-4-yl)ethoxy)-6-(3-(m-tolyl)-1H-pyrazol-1-yl)pyrimidin-4-yl)morpholine | 446 | |
| 119 | 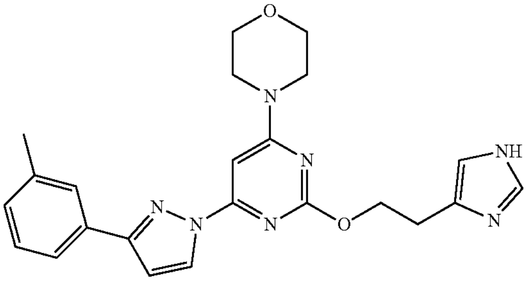 [SMILES: Cc1cccc(-c2ccn(-c3cc(N4CCOCC4)nc(OCCc4c[nH]cn4)n3)n2)c1] | 4-(2-(2-(1H-imidazol-4-yl)ethoxy)-6-(3-(m-tolyl)-1H-pyrazol-1-yl)pyrimidin-4-yl)morpholine | 432 | |

-continued

| No. | Structure | Name | LCMS (ESI): m/z $[M + H]^+$ | $^1$H NMR (400 MHz, DMSO-$d_6$) |
|---|---|---|---|---|
| 120 | 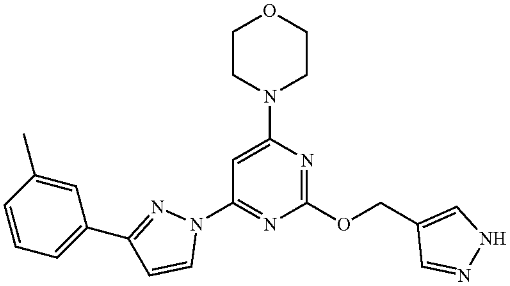 [SMILES: Cc1cccc(-c2ccn(-c3cc(N4CCOCC4)nc(OCc4cn[nH]c4)n3)n2)c1] | 4-(2-((1H-pyrazol-4-yl)methoxy)-6-(3-(m-tolyl)-1H-pyrazol-1-yl)pyrimidin-4-yl)morpholine | 418 | |
| 121 | 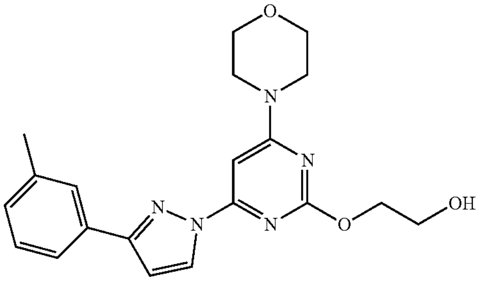 [SMILES: Cc1cccc(-c2ccn(-c3cc(N4CCOCC4)nc(OCCO)n3)n2)c1] | 2-((4-morpholino-6-(3-(m-tolyl)-1H-pyrazol-1-yl)pyrimidin-2-yl)oxy)ethan-1-ol | 382 | |
| 122 | 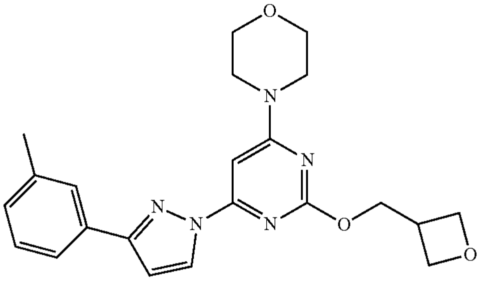 [SMILES: Cc1cccc(-c2ccn(-c3cc(N4CCOCC4)nc(OCC4COC4)n3)n2)c1] | 4-(2-(oxetan-3-ylmethoxy)-6-(3-(m-tolyl)-1H-pyrazol-1-yl)pyrimidin-4-yl)morpholine | 408 | |

Synthesis of 4-(2-(2-(1-methyl-1H-pyrazol-4-yl)ethoxy)-6-(3-(m-tolyl)-1H-pyrazol-1-yl)pyrimidin-4-yl)morpholine (Compound 56)

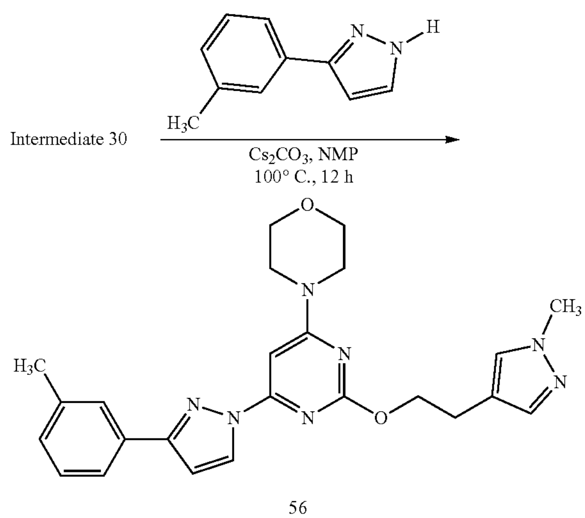

To a stirred solution of Intermediate 30 (300 mg, 0.92 mmol) in NMP (10 mL), placed in a 2 neck round bottom flask, under $N_2$ atmosphere at rt, was added $Cs_2CO_3$ (600 mg, 1.85 mmol), followed with 3-(m-tolyl)-1H-pyrazole (176 mg, 1.11 mmol) and the reaction mixture was gradually heated to 100° C. and stirred for 12 h. The reaction mixture was cooled to rt, diluted with water (200 mL) and extracted with EtOAc (2×40 mL), washed with brine (100 mL). The organic layer was dried over anhydrous $Na_2SO_4$, filtered and concentrated under reduced pressure to afford the crude product. The crude product was purified by silica gel chromatography using 90% EtOAc:Hexanes. Fractions containing the product were combined and concentrated under vacuum to obtain Compound 56 (60.0 mg, 14% yield) as an off-white solid.

MS (ESI+APCI; multimode): 446.2 $[M+H]^+$; HPLC: >99 (% of AUC).

$^1$H NMR (400 MHz, DMSO-$d_6$): δ 8.58 (d, J=2.4 Hz, 1H), 7.81 (s, 1H), 7.77 (d, J=7.6 Hz, 1H), 7.58 (s, 1H), 7.37-7.33 (m, 2H), 7.21 (d, J=7.6 Hz, 1H), 7.05 (d, J=2.8 Hz, 1H), 6.89 (s, 1H), 4.41 (t, J=7.2 Hz, 2H), 3.78 (s, 3H), 3.69 (brs, 8H), 2.86 (t, J=7.2 Hz, 2H), 2.38 (s, 3H).

The following compounds were synthesized using procedures similar to the one described for Compound 56:

| # | Structure | Name | LCMS (ESI): m/z $[M + H]^+$ | $^1H$ NMR (400 MHz, DMSO-$d_6$) |
|---|---|---|---|---|
| 62 | 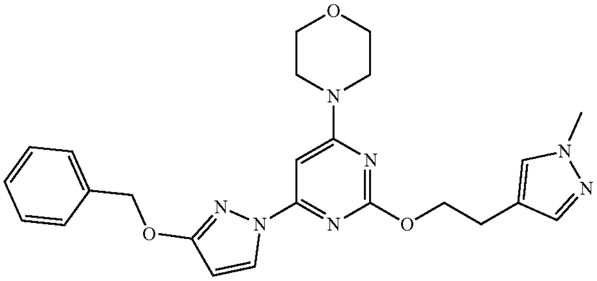 [SMILES: Cn1cc(CCOc2nc(N3CCOCC3)cc(-n3ccc(OCc4ccccc4)n3)n2)cn1] | 4-(6-(3-(benzyloxy)-1H-pyrazol-1-yl)-2-(2-(1-methyl-1H-pyrazol-4-yl)ethoxy) pyrimidin-4-yl)morpholine | 462 | δ: 8.38 (d, J = 2.4 Hz, 1H), 7.56 (s, 1H), 7.49-7.47 (m, 2H), 7.42-7.32 (m, 4H), 6.60 (s, 1H), 6.14 (d, J = 2.4 Hz, 1H), 5.29 (s, 2H), 4.37 (t, J = 7.2 Hz, 2H), 3.77 (s, 3H), 3.68-3.67 (m, 4H), (3.63-3.62 (m, 4H), 2.83 (t, J = 7.2 Hz, 2H). |
| 123 | 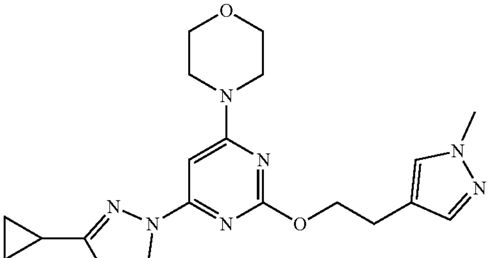 | 4-(6-(3-cyclopropyl-1H-pyrazol-1-yl)-2-(2-(1-methyl-1H-pyrazol-4-yl)ethoxy) pyrimidin-4-yl)morpholine | 396 | |
| 124 | 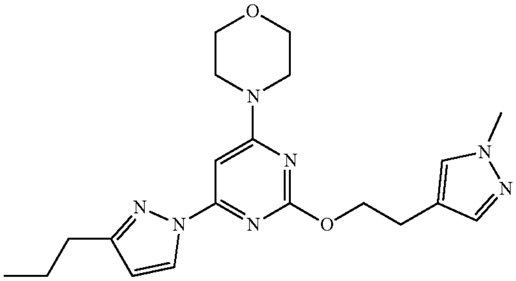 [SMILES: CCCc1ccn(-c2cc(N3CCOCC3)nc(OCCc3cnn(C)c3)n2)n1] | 4-(2-(2-(1-methyl-1H-pyrazol-4-yl)ethoxy)-6-(3-propyl-1H-pyrazol-1-yl)pyrimidin-4-yl)morpholine | 398 | |
| 125 | 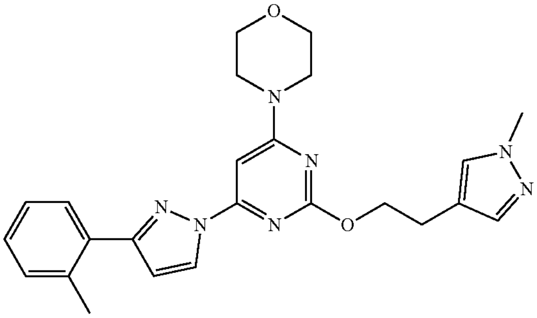 [SMILES: Cc1ccccc1-c1ccn(-c2cc(N3CCOCC3)nc(OCCc3cnn(C)c3)n2)n1] | 4-(2-(2-(1-methyl-1H-pyrazol-4-yl)ethoxy)-6-(3-(o-tolyl)-1H-pyrazol-1-yl)pyrimidin-4-yl)morpholine | 446 | |

-continued

| # | Structure | Name | LCMS (ESI): m/z [M + H]+ | $^1$H NMR (400 MHz, DMSO-$d_6$) |
|---|---|---|---|---|
| 126 | 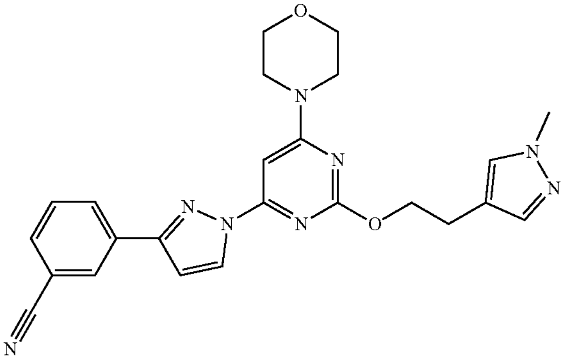 [SMILES: Cn1cc(CCOc2nc(N3CCOCC3)cc(-n3ccc(-c4cccc(C#N)c4)n3)n2)cn1] | 3-(1-(2-(2-(1-methyl-1H-pyrazol-4-yl)ethoxy)-6-morpholino-pyrimidin-4-yl)-1H-pyrazol-3-yl)benzonitrile | 457 | |
| 127 | 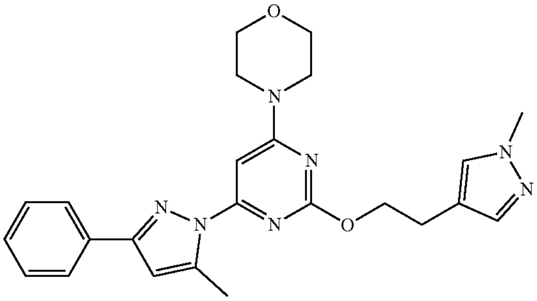 [SMILES: Cc1cc(-c2ccccc2)nn1-c1cc(N2CCOCC2)nc(OCCc2cnn(C)c2)n1] | 4-(2-(2-(1-methyl-1H-pyrazol-4-yl)ethoxy)-6-(5-methyl-3-phenyl-1H-pyrazol-1-yl)pyrimidin-4-yl)morpholine | 446 | |
| 128 | 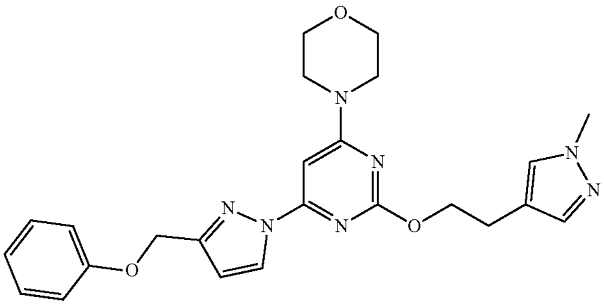 [SMILES: Cn1cc(CCOc2nc(N3CCOCC3)cc(-n3ccc(COc4ccccc4)n3)n2)cn1] | 4-(2-(2-(1-methyl-1H-pyrazol-4-yl)ethoxy)-6-(3-(phenoxymethyl)-1H-pyrazol-1-yl)pyrimidin-4-yl)morpholine | 462 | |
| 129 | 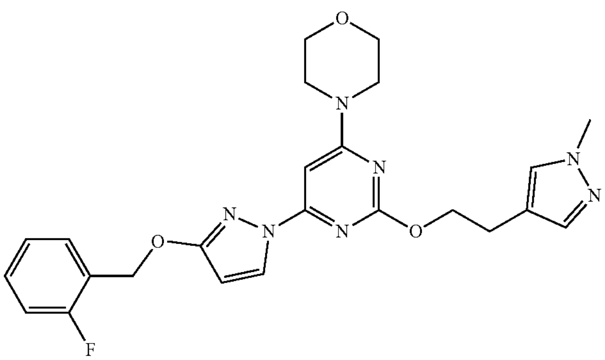 [SMILES: Cn1cc(CCOc2nc(N3CCOCC3)cc(-n3ccc(OCc4ccccc4F)n3)n2)cn1] | 4-(6-(3-((2-fluorobenzyl)oxy)-1H-pyrazol-1-yl)-2-(2-(1-methyl-1H-pyrazol-4-yl)ethoxy)pyrimidin-4-yl)morpholine | 480 | |

Synthesis of (S)-2-((4-morpholino-6-(3-(m-tolyl)-1H-pyrazol-1-yl)pyrimidin-2-yl)oxy)-1-phenylethan-1-ol (Compound 57) and (R)-2-((4-morpholino-6-(3-(m-tolyl)-1H-pyrazol-1-yl)pyrimidin-2-yl)oxy)-1-phenylethan-1-ol (Compound 58)

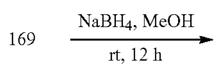

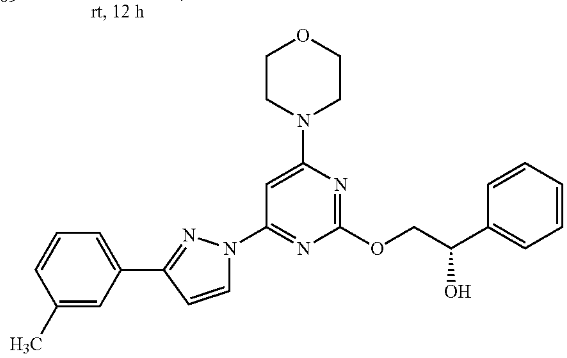

57

Absolute configuration not determined

+

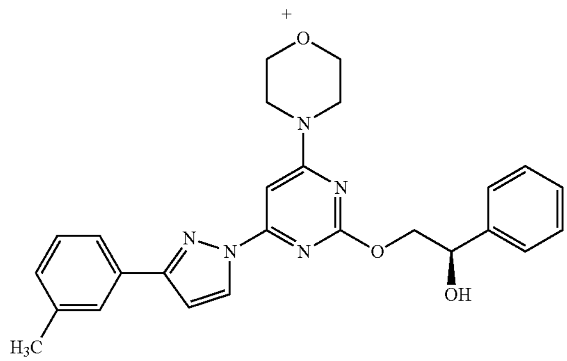

58

To a stirred solution of Compound 169 (300 mg, 0.65 mmol) in $CH_3OH$ (10 mL) at room temperature under $N_2$ atmosphere, was added $NaBH_4$ (74.7 mg, 1.97 mmol) portion wise for 3 min. The reaction mixture was stirred at room temperature for 12 h. $CH_3OH$ was evaporated under reduced pressure, the reaction mixture was diluted with water (50 mL) and extracted with EtOAc (2×50 mL). The combined organic extracts were washed with brine solution (50 mL), dried over anhydrous $Na_2SO_4$ and concentrated under reduced pressure to obtain the crude compound. The crude product was purified by silica-gel column chromatography using 35-40% EtOAc:Hexanes. Fractions containing the product were combined and concentrated under vacuum to obtain Compound 57 and Compound 58 (100 mg, 0.22 mmol, 35% yield, Racemic as an off-white solid. Compound 57 and Compound 58 were separated by chiral HPLC (SFC). Compound 57 (Peak 1 Rt=2.80 min) (15.0 mg, 0.09 mmol, 15% yield, and Compound 58 (Peak 2 Rt=3.60 min) (25.0 mg, 0.16 mmol, 25% yield. The stereochemistry of the enantiomers was not determined.

Racemic:

LCMS (ESI): m/z=458 $[M+H]^+$;

$^1H$ NMR (400 MHz, DMSO-$d_6$) δ: 8.51-8.50 (m, 1H), 7.74 (s, 1H), 7.68 (d, J=7.6 Hz, 1H), 7.49 (d, J=7.6 Hz, 2H), 7.41 (t, J=7.6 Hz, 2H), 7.36-731 (m, 2H), 7.19 (d, J=7.6 Hz, 1H), 6.93 (s, 1H), 6.75-6.74 (m, 1H), 5.21 (d, J=8.4 Hz, 1H), 4.53-4.42 (m, 2H), 3.80-3.79 (m, 4H), 3.75-3.74 (m, 4H), 3.29 (s, 1H), 2.42 (s, 3H).

Compound 57:

LCMS (ESI): m/z=458 $[M+H]^+$; HPLC: >99 (% of AUC)

$^1H$ NMR (400 MHz, DMSO-$d_6$) δ: 8.56 (d, J=2.0 Hz, 1H), 7.81 (s, 1H), 7.77 (d, J=7.6 Hz, 1H), 7.45 (d, J=7.6 Hz, 2H), 7.38-735 (m, 3H), 7.33-7.28 (m, 1H), 7.26-7.20 (m, 1H), 7.05 (d, J=2.0 Hz, 1H), 6.89 (s, 1H), 5.66 (d, J=4.8 Hz, 1H), 4.96-4.95 (m, 1H), 4.39-4.31 (m, 2H), 3.68 (brs, 8H), 2.38 (s, 3H).

Compound 58:

LCMS (ESI): m/z=458 $[M+H]^+$; HPLC: 98.1 (% of AUC).

$^1H$ NMR (400 MHz, DMSO-$d_6$) δ: 8.55 (d J=2.4 Hz, 1H), 7.81 (s, 1H), 7.77 (d, J=7.6 Hz, 1H), 7.45 (d, J=7.6 Hz, 2H), 7.38-7.35 (m, 3H), 7.33-7.28 (m, 1H), 7.26-7.20 (m, 1H), 7.05 (d, J=2.4 Hz, 1H), 6.89 (s, 1H), 5.66 (d, J=4.8 Hz, 1H), 4.97-4.93 (m, 1H), 4.36-4.33 (m, 2H), 3.68-3.67 (m, 8H), 2.38 (s, 3H).

Synthesis of 4-(6-(3-(m-tolyl)-1H-pyrazol-1-yl)pyrimidin-4-yl)morpholine (Compound 60)

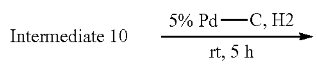

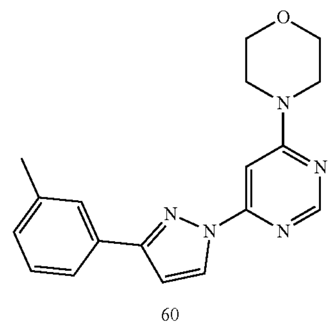

60

Compound 60 was synthesized as shown above using 1 eq Intermediate 10 (100 mg), 10% Pd—C (20 mg) in EtOH/THF (1:1) (5 ml) and $H_2$ (bladder) for 5 h at rt., then purified by silica gel to give Compound 60 (28 mg, 31% yield).

Synthesis of 4-(2-(2-(1-methyl-1H-pyrazol-4-yl)ethoxy)-6-(4-methyl-3-phenyl-1H-pyrazol-1-yl)pyrimidin-4-yl)morpholine (Compound 63)

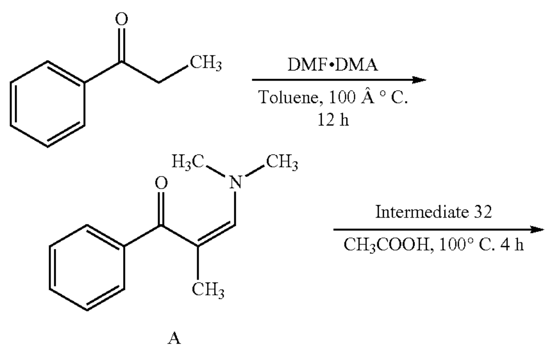

A

-continued

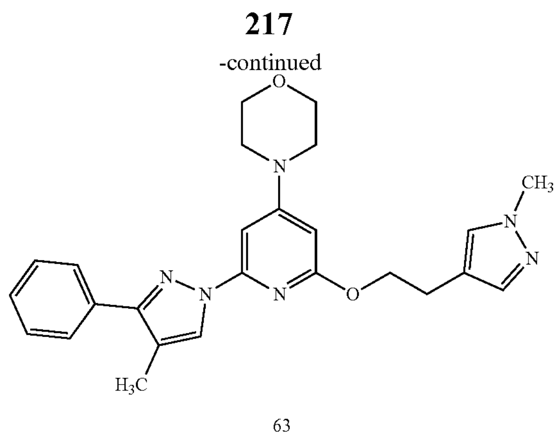

63

Preparation of A

To a stirred solution of propiophenone (1.00 g, 7.45 mmol) in anhydrous toluene (5 mL) at room temperature under $N_2$ atmosphere was added DMF·DMA (4.99 mL, 37.3 mmol). The reaction mixture was gradually warmed to 100° C. and stirred for 12 h. The crude product was purified by silica-gel column chromatography using 50% EtOAc: Hexanes. Fractions containing the product were combined and concentrated under vacuum to obtain A (500 mg, 2.64 mmol, 35% yield) as a yellow liquid.

LCMS (ESI): m/z=190 $[M+H]^+$.

Preparation of Compound 63

To a stirred solution of A (50.0 mg, 0.26 mmol)) in $CH_3COOH$ (50 mL) at room temperature under $N_2$ atmosphere was added Intermediate 30 (84.0 mg, 0.26 mmol). The reaction mixture was gradually heated to 100° C. and stirred for 4 h. The reaction mixture was cooled to room temperature, diluted with water (30 mL), extracted with EtOAc (2×30 mL). The combined organic extracts were washed with brine solution (150 mL), dried over anhydrous $Na_2SO_4$ and concentrated under reduced pressure to obtain the crude product. The crude product was purified by silica-gel column chromatography using 60% EtOAc: Hexanes. Fractions containing the product were combined and concentrated to obtain Compound 63 (40.0 mg, 0.09 mmol, 34% yield) as an off white solid.

LCMS (ESI): m/z=446 $[M+H]^+$; HPLC: >99 (% of AUC).

$^1H$ NMR (400 MHz, DMSO-$d_6$) δ: 7.71 (s, 1H), 7.36-7.34 (m, 3H), 7.32-7.26 (m, 2H), 7.24-7.22 (m, 1H), 7.14 (s, 1H), 6.73 (s, 1H), 3.79 (s, 3H), 3.65-3.63 (m, 4H), 3.57-3.56 (m, 4H), 3.43 (t, J=6.8 Hz, 2H), 2.43 (t, J=6.8 Hz, 2H), 1.94 (s, 3H).

Synthesis of 1-(2-(2-(1-methyl-1H-pyrazol-4-yl)ethoxy)-6-morpholinopyrimidin-4-yl)-N-phenyl-1H-pyrazole-3-carboxamide (Compound 64)

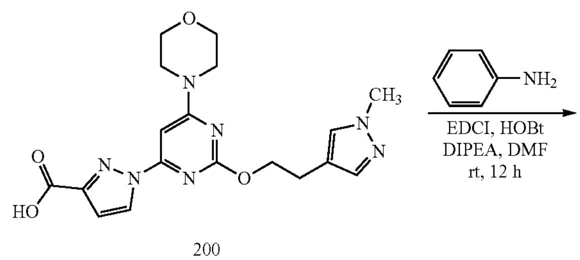

200

-continued

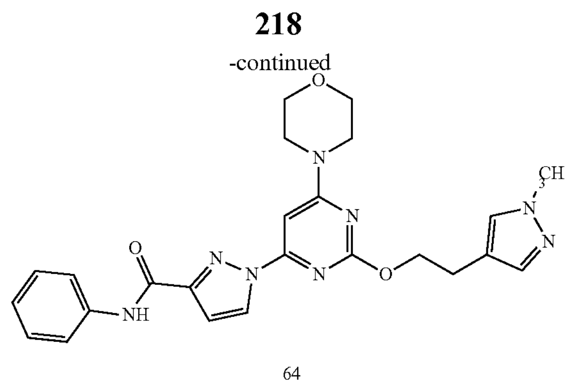

64

To a stirred solution of Compound 200 (35.0 mg, 0.08 mmol) in anhydrous DMF (2.5 mL), at room temperature, under $N_2$ atmosphere, was added aniline (12.2 mg, 0.13 mmol) followed with EDCI (25.2 mg, 0.13 mmol), HOBt (20.1 mg, 0.13 mmol) and DIPEA (0.03 mL, 0.17 mmol). The reaction mixture was stirred at room temperature for 12 h. The reaction mixture was diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 50% EtOAc: Hexanes. Fractions containing the product were combined and concentrated under vacuum to obtain Compound 64 (6.00 mg, 0.01 mmol, 14% yield) as an off-white solid.

MS (ESI+APCI; multimode): 475.0 $[M+H]^+$; HPLC: >99 (% of AUC).

$^1H$ NMR (400 MHz, DMSO-$d_6$): δ: 8.65 (d, J=2.4 Hz, 1H), 7.81 (dd, J=1.2 Hz, 8.8 Hz, 2H), 7.58 (s, 1H), 7.40-7.34 (m, 3H), 7.15-7.11 (m, 2H), 7.01 (d, J=2.4 Hz, 1H), 4.42 (t, J=7.2 Hz, 2H), 3.78 (s, 3H), 3.71 (brs, 8H), 2.86 (t, J=7.2 Hz, 2H).

Synthesis of N-(4-morpholino-6-(3-(m-tolyl)-1H-pyrazol-1-yl)pyrimidin-2-yl)acetamide (Compound 66)

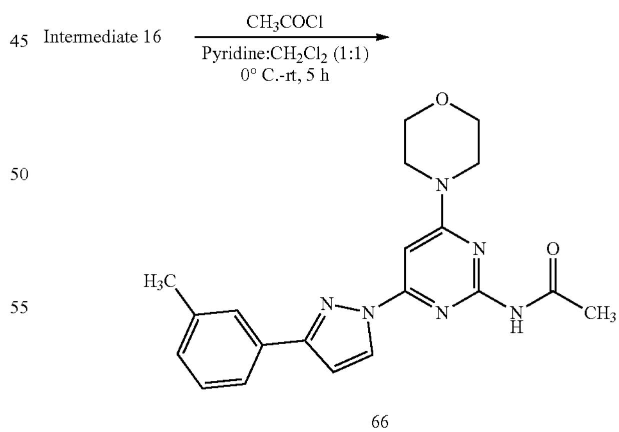

66

To a stirred solution of Intermediate 16 (50.0 mg, 0.14 mmol) in anhydrous $CH_2Cl_2$ (2 mL) and pyridine (2 mL) at 0° C. under $N_2$ atmosphere was added acetyl chloride (11.6 mg, 0.14 mmol) as portion wise over a period of 2 min. The reaction mixture was stirred at room temperature for 5 h. The reaction mixture was diluted with water (20 mL), extracted with $CH_2Cl_2$ (2×30 mL). The combined organic extracts were washed with brine solution (30 mL), dried over anhydrous $Na_2SO_4$ and concentrated under reduced pressure to obtain the crude product. The crude product was purified by silica-gel column chromatography using 30% EtOAc: Hexanes. Fractions containing the product were combined and concentrated under vacuum to obtain Compound 66 (18.0 mg, 0.04 mmol, 32% yield) as an off-white solid.

LCMS (ESI): m/z=379 $[M+H]^+$; HPLC: 96.8 (% of AUC).

$^1$H NMR (400 MHz, DMSO-$d_6$) δ: 10.13 (s, 1H), 8.50 (d, J=2.8 Hz, 1H), 7.81 (s, 1H), 7.77 (d, J=7.6 Hz, 1H), 7.35 (t, J=7.6 Hz, 1H), 7.21 (d, J=7.6 Hz, 1H), 7.07 (d, J=2.8 Hz, 1H), 6.91 (s, 1H), 3.70 (brs, 8H), 2.38 (s, 3H), 2.28 (s, 3H).

Synthesis of 4-(2-(1-methoxy-2-(1-methyl-1H-pyrazol-5-yl)ethyl)-6-(3-phenyl-1H-pyrazol-1-yl)pyrimidin-4-yl)morpholine (Compound 68)

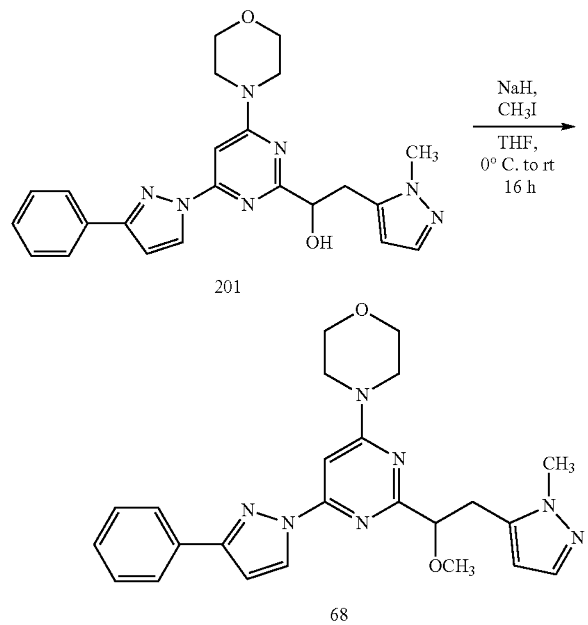

201

68

To a suspension of NaH (50%, 5.01 mg, 0.20 mmol) in anhydrous THF (10 mL) was added Compound 201 (30.0 mg, 0.07 mmol) at 0° C., under $N_2$ atmosphere, and the reaction mixture was stirred at 0° C. for 15 min. $CH_3I$ (0.01 mL, 0.20 mmol) was added 0° C. over a period of 1 min. The reaction mixture was stirred at 0° C. to room temperature for 16 h. The reaction mixture was quenched with water (2 mL) at 0° C., diluted with water (20 mL) and extracted with EtOAc (2×50 mL). The combined organic extracts were washed with brine (50 mL), dried over anhydrous $Na_2SO_4$, filtered and concentrated under vacuum to obtain the crude product. The crude product was purified by silica-gel column chromatography using 80-95% EtOAc:Hexanes to afford Compound 68 (11.0 mg, 0.02 mmol, 35% yield) as an off-white solid.

LCMS (ESI): m/z=446 $[M+H]^+$; HPLC: 95.5 (% of AUC).

$^1$H NMR (400 MHz, DMSO-$d_6$) δ: 8.65 (d, J=2.8 Hz, 1H), 8.01 (dd, J=1.2 Hz, 8.4 Hz, 2H), 7.48 (t, J=7.2 Hz, 2H), 7.41 (d, J=7.2 Hz, 1H), 7.23 (d, J=1.6 Hz, 1H), 7.13 (s, 1H), 7.11 (d, J=2.8 Hz, 1H), 6.01 (d, J=1.6 Hz, 1H), 4.40 (t, J=6.0 Hz, 1H), 3.75 (s, 3H), 3.71 (brs, 8H), 3.22 (s, 3H), 3.21-3.15 (m, 2H).

Synthesis of ethyl 1-(2-(2-(1-methyl-1H-pyrazol-4-yl)ethoxy)-6-morpholinopyrimidin-4-yl)-1H-pyrazole-3-carboxylate (Compound 70)

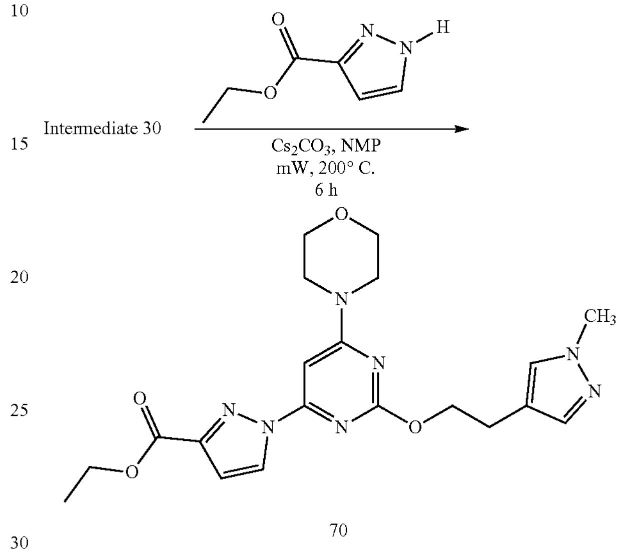

70

To a stirred solution of Intermediate 30 (750 mg, 2.31 mmol) in anhydrous NMP (10 mL), at room temperature, under $N_2$ atmosphere, was added ethyl 1H-pyrazole-3-carboxylate (351 mg, 2.78 mmol) followed with $Cs_2CO_3$ (755 mg, 2.31 mmol). The reaction mixture was irradiated in microwave at 200° C. and stirred for 6 h. The reaction mixture was cooled to room temperature, diluted with water (100 mL), and extracted with EtOAc (2×200 mL). The combined organic extracts were washed with brine (30 mL), dried over anhydrous $Na_2SO_4$, filtered and concentrated under vacuum to obtain the crude product. The crude product was purified by silica-gel column chromatography using 30% EtOAc:Hexanes. Fractions containing the product were combined and concentrated under vacuum to obtain Compound 70 (300 mg, 0.72 mmol, 31% yield) as an off-white solid.

MS (ESI+APCI; multimode): 414.2 $[M+H]^+$; HPLC: 96.3 (% of AUC).

$^1$H NMR (400 MHz, DMSO-$d_6$): δ: 8.66 (d, J=2.8 Hz, 1H), 7.56 (s, 1H), 7.33 (s, 1H), 6.99 (d, J=2.4 Hz, 1H), 6.81 (s, 1H), 4.41 (t, J=7.2 Hz, 2H), 3.86 (s, 3H), 3.77 (s, 3H), 3.67 (brs, 8H), 2.85 (t, J=7.2 Hz, 2H).

Synthesis of 4-(2-(2-(1-methyl-1H-pyrazol-4-yl)ethoxy)-6-(3-(pyridin-3-yl)-1H-pyrazol-1-yl)pyrimidin-4-yl)morpholine (Compound 71)

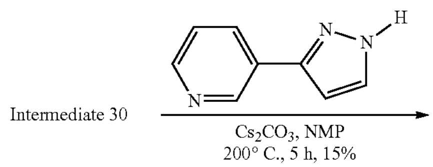

-continued

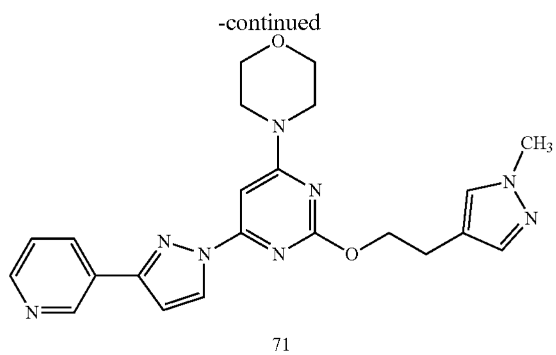

71

To a stirred solution Intermediate 30 (150 mg, 0.46 mmol) in NMP (10 mL), placed in a 2 neck round bottom flask, under $N_2$ atmosphere at rt, was added $Cs_2CO_3$ (300 mg, 0.92 mmol), followed with 3-(1H-pyrazol-3-yl)pyridine (100 mg, 0.69 mmol) and the reaction mixture was gradually heated to 200° C. and stirred for 5 h. The reaction mixture was cooled to rt, diluted with water (100 mL) and extracted with EtOAc (2×20 mL), washed with brine (50 mL). The organic layer was dried over anhydrous $Na_2SO_4$, filtered and concentrated under reduced pressure to afford the crude product. The crude product was purified by silica gel chromatography using 10% $CH_3OH:CH_2Cl_2$. Fractions containing the product were combined and concentrated under vacuum to obtain Compound 71 (30.0 mg, 15% yield) as a light green solid.

MS (ESI+APCI; multimode): 433.3 $[M+H]^+$; HPLC: >99 (% of AUC).

$^1H$ NMR (400 MHz, DMSO-$d_6$): δ: 9.21 (d, J=1.2 Hz, 1H), 8.64 (d, J=2.4 Hz, 1H), 8.59 (dd, J=1.6 Hz, 4.8 Hz, 1H), 8.36-8.33 (m, 1H), 7.57 (s, 1H), 7.52-7.48 (m, 1H), 7.34 (s, 1H), 7.18 (d, J=2.4 Hz, 1H), 6.95 (s, 1H), 4.41 (t, J=7.2 Hz, 2H), 3.78 (s, 3H), 3.69 (brs, 8H), 2.86 (t, J=6.8 Hz, 2H).

Synthesis of 3-methoxy-3-(4-morpholino-6-(3-(m-tolyl)-1H-pyrazol-1-yl)pyrimidin-2-yl)propanenitrile (Compound 72)

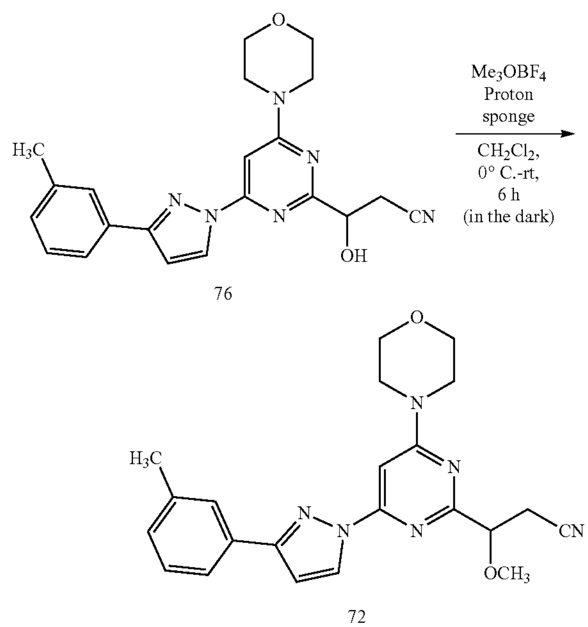

76

72

To a stirred solution of Compound 76 (200 mg, 0.51 mmol) in $CH_2Cl_2$ (15.0 mL), placed in a 2 neck round bottom flask, under $N_2$ atmosphere at 0° C., was added proton sponge (300 mg, 0.51 mmol), $Me_3OBF_4$ (70.0 g, 0.51 mmol) and the reaction mixture was stirred at 0° C. to rt for 6 h (in dark). The reaction mixture was diluted with water (100 mL) and extracted with $CH_2Cl_2$ (2×40 mL), washed with brine (50 mL). The organic layer was dried over anhydrous $Na_2SO_4$, filtered and concentrated under reduced pressure to afford the crude product. The crude product was purified by silica gel chromatography using 50% EtOAc: Hexanes. Fractions containing the product were combined and concentrated under vacuum to obtain Compound 72 (15.0 mg, 7% yield) as an off-white solid.

MS (ESI+APCI; multimode): 405.2 $[M+H]^+$; HPLC: 95.8 (% of AUC).

$^1H$ NMR (400 MHz, DMSO-d6): δ 8.68 (d, J=2.8 Hz, 1H), 7.84 (s, 1H), 7.79 (d, J=7.2 Hz, 1H), 7.36 (t, J=7.6 Hz, 1H), 7.22 (d, J=7.2 Hz, 1H), 7.16 (s, 1H), 7.11 (d, J=2.8 Hz, 1H), 4.45 (t, J=6.0 Hz, 1H), 3.73 (brs, 8H), 3.42 (s, 3H), 3.16-3.14 (m, 2H), 2.39 (s, 3H).

Synthesis of N,N-dimethyl-2-(4-(2-((4-morpholino-6-(3-(m-tolyl)-1H-pyrazol-1-yl)pyrimidin-2-yl)oxy)ethyl)-1H-pyrazol-1-yl)ethan-1-amine (Compound 74)

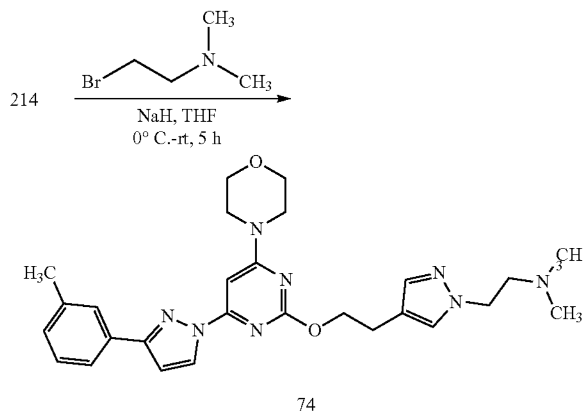

74

To a suspension of 50% NaH (33.4 mg, 1.39 mmol) in anhydrous THF (5 mL) at 0° C., under $N_2$ atmosphere was added Compound 214 (200 mg, 0.46 mmol), and the reaction mixture was stirred at 0° C. for 15 min. A solution of 2-bromo-N,N-dimethylethan-1-amine (108 mg, 0.46 mmol) in THF (1.0 mL) was added to the reaction mixture at 0° C. over a period of 1 min. The reaction mixture was stirred at 0° C. to room temperature for 5 h. The reaction mixture was cooled to 0° C., quenched with water (15 mL), and extracted with EtOAc (2×30 mL). The combined organic extracts were washed with brine (20 mL), dried over anhydrous $Na_2SO_4$, filtered and concentrated under vacuum to obtain the crude product. The crude product was purified by silica-gel column chromatography using 9-10% $CH_3OH$: $CH_2Cl_2$ followed by mass triggered PREP HPLC (0.1% TFA in $CH_3CN:H_2O$) to obtain Compound 74 (125 mg, 0.24 mmol, 53% yield) as an off-white solid.

LCMS (ESI): m/z=503 $[M+H]^+$; HPLC: >99 (% of AUC).

$^1H$ NMR (400 MHz, DMSO-$d_6$) δ: 8.58 (d, J=2.4 Hz, 1H), 7.81 (brs, 1H), 7.77 (d, J=7.2 Hz, 1H), 7.62 (s, 1H), 7.35 (t, J=7.6 Hz, 2H), 7.21 (d, J=7.6 Hz, 1H), 7.05 (d, J=2.4 Hz, 1H), 6.89 (s, 1H), 4.24 (t, J=6.8 Hz, 2H), 4.12 (t, J=6.4 Hz, 2H), 3.69 (brs, 8H), 2.86 (t, J=6.8 Hz, 2H), 2.60 (t, J=6.8 Hz, 2H), 2.38 (s, 3H), 2.14 (s, 6H).

Synthesis of N,N-dimethyl-1-(1-(2-(2-(1-methyl-1H-pyrazol-4-yl)ethoxy)-6-morpholinopyrimidin-4-yl)-3-phenyl-1H-pyrazol-5-yl)methanamine (Compound 75)

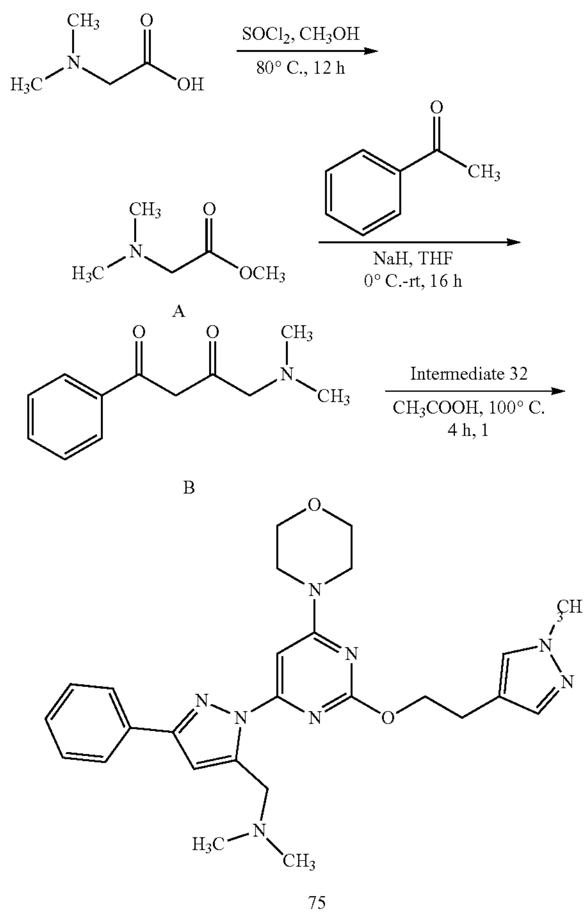

A

B

75

Preparation of A

To a stirred solution of dimethylglycine (1.00 g, 9.70 mmol) in anhydrous $CH_3OH$ (10 mL) at 0° C. under $N_2$ atmosphere was added $SOCl_2$ (3.54 mL, 48.5 mmol). The reaction mixture was gradually heated to 80° C. and stirred for 12 h. The reaction mixture was cooled to 0° C., quenched with sat. $NaHCO_3$ (20 mL) solution, and extracted with $CH_2Cl_2$ (2×50 mL). The combined organic extracts were washed with brine (50 mL), dried over anhydrous $Na_2SO_4$, filtered and concentrated under vacuum to obtain A (700 mg, crude as a colourless liquid. The crude product was used directly in the next step.

LCMS (ESI): m/z=118 $[M+H]^+$.

$^1H$ NMR (400 MHz, $CDCl_3$) δ: 3.77 (s, 3H), 3.17 (s, 2H), 2.35 (s, 6H).

Preparation of B

To a suspension of 50% NaH (899 mg, 37.5 mmol) in anhydrous THF (10 mL) at 0° C., under $N_2$ atmosphere was added acetophenone (1.50 g, 12.4 mmol), and the reaction mixture was stirred at 0° C. for 15 min. A solution of A (1.46 g, 12.4 mmol) in THF (2 mL) was added to the reaction mixture at 0° C. over a period of 1 min. The reaction mixture was stirred at 0° C. to room temperature for 16 h. The reaction mixture was cooled to 0° C., quenched with water (30 mL), and extracted with EtOAc (2×50 mL). The combined organic extracts were washed with brine (50 mL), dried over anhydrous $Na_2SO_4$, filtered and concentrated under vacuum to obtain the crude product. The crude product was purified by silica-gel column chromatography using 5-8% $CH_3OH$:$CH_2Cl_2$. Fractions containing the product were combined and concentrated under vacuum to obtain B (700 mg, 3.41 mmol, 27% yield) as a brown gummy solid.

LCMS (ESI): m/z=206 $[M+H]^+$.

$^1H$ NMR (400 MHz, $CDCl_3$) δ: 7.91 (d, J=7.2 Hz, 2H), 7.50 (t, J=7.2 Hz, 1H), 7.43 (d, J=7.2 Hz, 2H), 6.49 (s, 1H), 3.20 (brs, 2H), 2.36 (brs, 6H).

Preparation of Compound 75

To a stirred solution of B (100 mg, 0.48 mmol) in $CH_3COOH$ (5 mL) at room temperature under $N_2$ atmosphere was added Intermediate 32 (155 mg, 0.48 mmol). The reaction mixture was gradually heated to 100° C. and stirred for 4 h. The reaction mixture was cooled to room temperature, diluted with water (30 mL), and extracted with EtOAc (2×30 mL). The combined organic extracts were washed with brine (50 mL), dried over anhydrous $Na_2SO_4$, filtered and concentrated under vacuum to obtain the crude product. The crude product was purified by silica-gel column chromatography using 10% $CH_3OH$:$CH_2Cl_2$. Fractions containing the product were combined and concentrated under vacuum to obtain Compound 75 (30.0 mg, 0.06 mmol, 12% yield) as an off-white solid.

LCMS (ESI): m/z=489 $[M+H]^+$; HPLC: >99 (% of AUC).

$^1H$ NMR (400 MHz, DMSO-$d_6$) δ: 7.95 (d, J=7.6 Hz, 2H), 7.56 (s, 1H), 7.45 (t, J=7.2 Hz, 2H) 7.38 (d, J=6.8 Hz, 1H), 7.33 (s, 1H), 6.94 (s, 1H), 6.90 (s, 1H), 4.39 (t, J=7.2 Hz, 2H), 3.99 (s, 2H), 3.77 (s, 3H), 3.68-3.66 (m, 8H), 2.86 (t, J=7.2 Hz, 2H), 2.20 (s, 6H).

Synthesis of 3-hydroxy-3-(4-morpholino-6-(3-(m-tolyl)-1H-pyrazol-1-yl)pyrimidin-2-yl)propanenitrile (Compound 76)

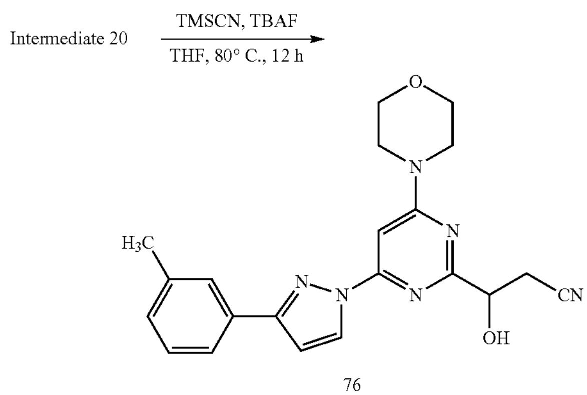

76

To a stirred solution of Intermediate 20 (100 mg, 0.27 mmol) in anhydrous THF (5 ml), at room temperature, under $N_2$ atmosphere, was added TMSCN (0.05 mL, 0.41 mmol)

followed with TBAF (1.0 M in THF, 108 mg, 0.41 mmol). The reaction mixture was gradually heated to 80° C. and stirred for 12 h. The reaction mixture was cooled to room temperature, diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 50% EtOAc:Hexanes. Fractions containing the product were combined and concentrated under vacuum to obtain Compound 76 (50.0 mg, 0.12 mmol, 46% yield) as an off-white solid.

MS (ESI+APCI; multimode): 391.2 $[M+H]^+$; HPLC: >99 (% of AUC).

$^1$H NMR (400 MHz, DMSO-$d_6$): δ: 8.81 (d, J=2.8 Hz, 1H), 7.83 (s, 1H), 7.79 (d, J=7.6 Hz, 1H), 7.35 (t, J=7.6 Hz, 1H), 7.22 (d, J=6.8 Hz, 1H), 7.12 (s, 1H), 7.10 (d, J=2.8 Hz, 1H), 5.84 (d, J=5.6 Hz, 1H), 4.74 (q, J=6.4 Hz, 1H), 3.74-3.72 (m, 8H), 3.13-3.00 (m, 2H), 2.33 (s, 3H).

Synthesis of 4-(6-(3-(methoxymethyl)-5-phenyl-1H-pyrazol-1-yl)-2-(2-(1-methyl-1H-pyrazol-4-yl)ethoxy)pyrimidin-4-yl)morpholine (Compound 77)

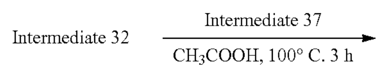

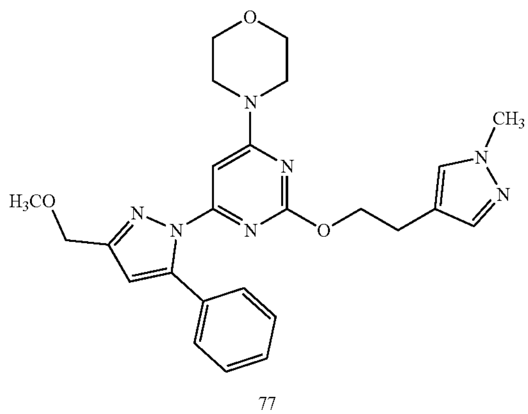

77

To a stirred solution of Intermediate 32 (332 mg, 1.04 mmol) in $CH_3COOH$ (5 mL), at room temperature, under $N_2$ atmosphere, was added Intermediate 37 (100 mg, 0.52 mmol). The reaction mixture was gradually heated to 100° C. and stirred for 3 h. The reaction mixture was cooled to room temperature, diluted with water (100 mL), and extracted with EtOAc (2×100 mL). The combined organic extracts were washed with sat. $NaHCO_3$ (200 mL), brine (20 mL), dried over anhydrous $Na_2SO_4$, filtered and concentrated under vacuum to obtain the crude product. The crude product was purified by silica-gel column chromatography using 60% EtOAc:Hexanes. Fractions containing the product were combined and concentrated under vacuum to obtain Compound 77 (70 mg, 0.14 mmol, 28% yield) as an off-white solid.

MS (ESI+APCI; multimode): 476.3 $[M+H]^+$; HPLC: 97.8 (% of AUC).

$^1$H NMR (400 MHz, MeOD): δ: 7.34-7.30 (m, 6H), 7.25 (s, 1H), 6.65 (s, 1H), 6.53 (s, 1H), 4.53 (s, 2H), 3.83 (s, 3H), 3.77 (t, J=6.8 Hz, 2H), 3.72-3.70 (m, 4H), 3.62-3.60 (m, 4H), 3.44 (s, 3H), 2.60 (t, J=6.8 Hz, 2H). $^1$H NMR (400 MHz, DMSO-$d_6$): δ: 7.34-7.29 (m, 6H), 7.13 (s, 1H), 6.73 (s, 1H), 6.58 (s, 1H), 4.45 (s, 2H), 3.77 (s, 3H), 3.65-3.57 (m, 10H), 3.33 (s, 3H), 2.46-2.44 (m, 2H).

Synthesis of 4-(2-(methoxy(phenyl)methyl)-6-(3-phenyl-1H-pyrazol-1-yl)pyrimidin-4-yl)morpholine (Compound 78)

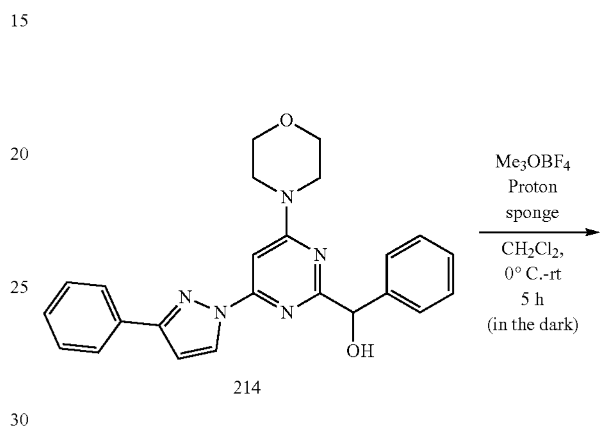

214

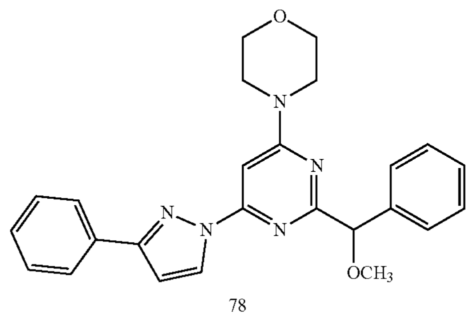

78

To a stirred solution of Compound 214 (85.0 mg, 0.20 mmol) in $CH_2Cl_2$ (10 mL) at 0° C. under $N_2$ atmosphere was added proton sponge (220 mg, 1.02 mmol) and $Me_3OBF_4$ (152 mg, 1.02 mmol). The reaction mixture was stirred in the dark at 0° C. to room temperature for 5 h. The reaction mixture was diluted with water (50 mL), and extracted with EtOAc (2×50 mL). The combined organic extracts were washed with 1N HCl (30 mL), sat $NaHCO_3$ (30 mL) and brine (30 mL), dried over anhydrous $Na_2SO_4$, filtered and concentrated under vacuum to obtain the crude product. The crude product was purified by silica-gel column chromatography using 40% EtOAc:Hexanes. Fractions containing the product were combined and concentrated under vacuum to obtain Compound 78 (25.0 mg, 0.05 mmol, 28% yield) as an off-white solid.

(ESI): m/z=428 $[M+H]^+$; HPLC: >99% (% of AUC).

$^1$H NMR (400 MHz, DMSO-$d_6$) δ: 8.62 (d, J=2.8 Hz, 1H), 7.99 (d, J=7.2 Hz, 2H), 7.54 (d, J=7.2 Hz, 2H), 7.47 (t, J=7.2 Hz, 2H), 7.40 (d, J=7.2 Hz, 1H), 7.38-7.32 (m, 2H), 7.28-7.25 (m, 1H), 7.10 (d, J=2.4 Hz, 1H), 7.08 (s, 1H), 5.23 (s, 1H), 3.70 (brs, 8H), 3.32 (s, 3H)

Synthesis of 1-(1-methyl-1H-pyrazol-4-yl)-3-(4-morpholino-6-(3-phenyl-1H-pyrazol-1-yl)pyrimidin-2-yl)propan-1-ol (Compound 79)

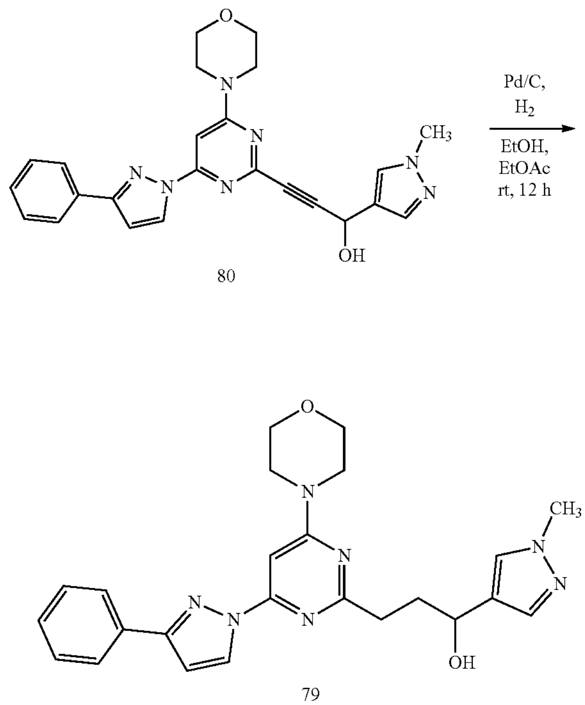

80

79

To a stirred solution of Compound 80 (250 mg, 0.56 mmol) in anhydrous EtOH (20 mL), and EtOAc (10 mL) at room temperature, under $N_2$ atmosphere, was added 10% Pd—C (50 mg, 0.47 mmol). The reaction mixture was stirred under $H_2$ (bladder) at room temperature for 12 h. The reaction mixture was filtered and concentrated under vacuum to obtain the crude product. The crude product was purified by mass triggered PREP HPLC (0.1% TFA in $CH_3CN:H_2O$) to afford Compound 79 (20.0 mg, 0.04 mmol, 8% yield, as an off-white solid.

MS (ESI+APCI; multimode): 446.2 $[M+H]^+$; HPLC: >99 (% of AUC).

$^1H$ NMR (400 MHz, DMSO-$d_6$): δ: 8.62 (d, J=2.8 Hz, 1H), 8.00 (dd, J=1.6 Hz, 8.4 Hz, ×2H), 7.56 (s, 1H), 7.49-7.45 (m, 2H), 7.41-7.38 (m, 1H), 7.34 (s, 1H), 7.08 (d, J=2.8 Hz, 1H), 7.05 (s, 1H), 4.98 (d, J=4.8 Hz, 1H), 4.59 (q, J=6.8 Hz, 12.0 Hz, 1H), 3.78 (s, 3H), 3.70 (brs, 8H), 2.80-2.66 (m, 2H), 2.11-2.05 (m, 2H).

Synthesis of 1-(1-methyl-1H-pyrazol-4-yl)-3-(4-morpholino-6-(3-phenyl-1H-pyrazol-1-yl)pyrimidin-2-yl)prop-2-yn-1-ol (Compound 80)

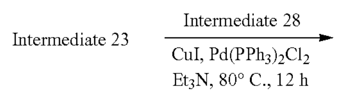

-continued

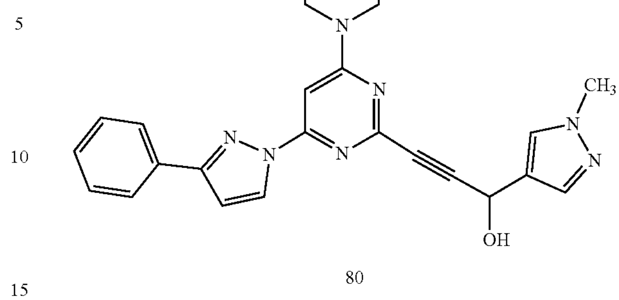

80

To a stirred solution of Intermediate 23 (200 mg, 0.46 mmol) in $Et_3N$ (2.5 mL), at room temperature, under $N_2$ atmosphere, was added Intermediate 28 (82.0 mg, 0.60 mmol) followed with copper (I) iodide (17.5 mg, 0.09 mmol) and bis(triphenylphosphine)palladium(II) chloride (32.4 mg, 0.04 mmol). The reaction mixture was gradually heated to 80° C. and stirred for 12 h. The reaction mixture was cooled to room temperature, diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 80% EtOAc: Hexanes followed with mass triggered PREP HPLC (0.1% TFA in $CH_3CN:H_2O$) to afford Compound 80 (25.0 mg, 0.05 mmol, 12% yield) as an off-white solid.

MS (ESI+APCI; multimode): 442.1 $[M+H]^+$; HPLC: 98.4 (% of AUC).

$^1H$ NMR (400 MHz, DMSO-$d_6$): δ: 8.60 (d, J=2.8 Hz, 1H), 8.01 (dd, J=1.6 Hz, 8.4 Hz, 2H), 7.74 (s, 1H), 7.49-7.41 (m, 3H), 7.40-7.39 (m, 1H), 7.19 (s, 1H), 7.10 (d, J=2.8 Hz, 1H), 6.09 (d, J=6.0 Hz, 1H), 5.60 (d, J=6.0 Hz, 1H), 3.83 (s, 3H), 3.70 (brs, 8H).

Synthesis of 4-(2-methyl-6-(3-(m-tolyl)-1H-pyrazol-1-yl)pyrimidin-4-yl)morpholine (Compound 81)

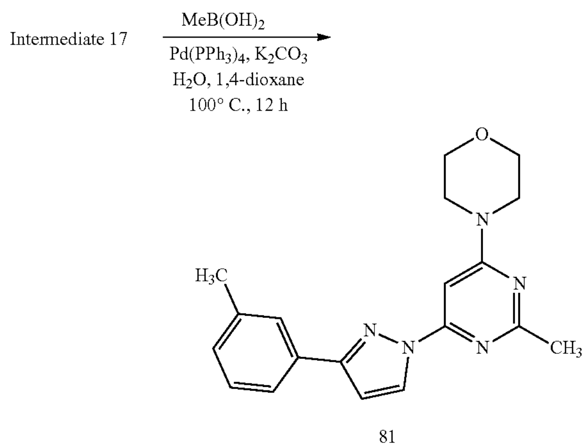

81

To a stirred solution of Intermediate 17 (250 mg, 0.55 mmol) in 1,4 dioxane (15.0 mL), placed in a 2 neck round bottom flask, under $N_2$ atmosphere at rt, was added 2 (40.0 mg, 0.67 mmol) followed with $K_2CO_3$ (154 mg, 1.11 mmol)

in $H_2O$ (5.0 mL). The reaction mixture was de-gassed with Argon for 10 min. $Pd(PPh_3)_4$ (12.0 mg, 0.01 mmol) was added in one lot, and the reaction mixture was gradually heated to 100° C. for 12 h. The reaction mixture was cooled to rt and then concentrated under vacuum to obtain the crude product. The crude product was purified by silica-gel chromatography using (20-25% EtOAc:Hexanes) as eluent to afford Compound 81 (38.0 mg, 20% yield) as an off-white solid.

MS (ESI+APCI; multimode): 336 $[M+H]^+$; HPLC: >99 (% of AUC).

$^1H$ NMR (400 MHz, DMSO-$d_6$): δ: 8.60 (d, J=2.8 Hz, 1H), 7.82 (s, 1H), 7.77 (d, J=7.6 Hz, 1H), 7.35 (t, J=7.6 Hz, 1H), 7.21 (d, J=7.2 Hz, 1H), 7.08-6.98 (m, 2H), 3.70 (brs, 8H), 2.45 (s, 3H), 2.39 (s, 3H).

Synthesis of 4-(2-methoxy-5-methyl-6-(3-(m-tolyl)-1H-pyrazol-1-yl)pyrimidin-4-yl)morpholine (Compound 83)

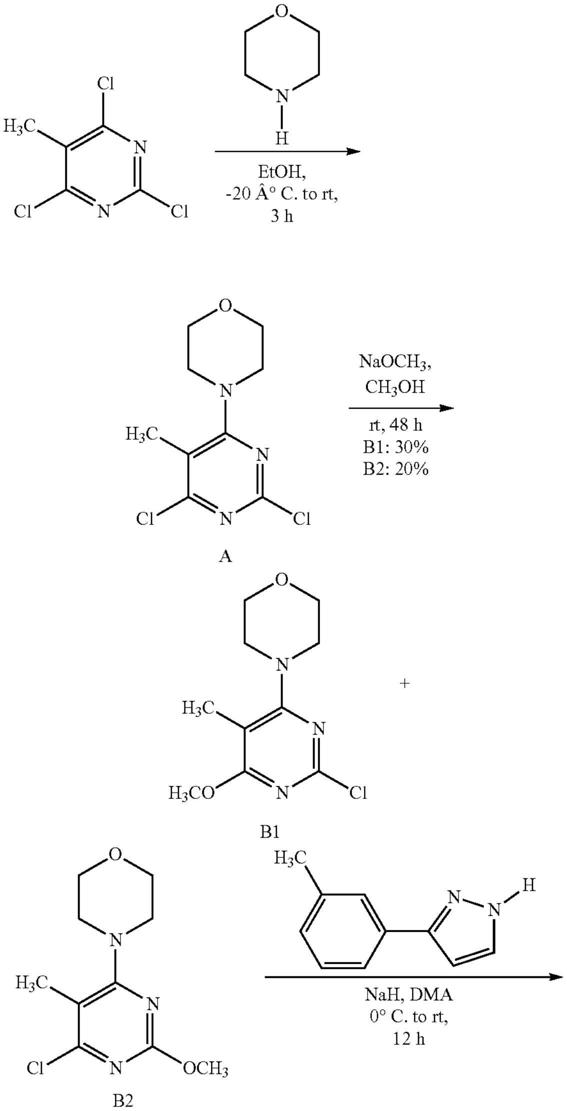

-continued

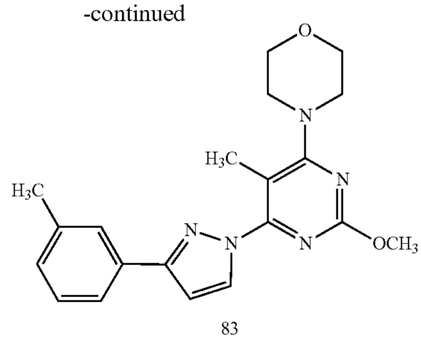

83

Preparation of A

To a stirred solution of 2,4,6-trichloro-5-methylpyrimidine (1.00 g, 5.06 mmol) in anhydrous EtOH (60 mL), at −20° C., under $N_2$ atmosphere, was added morpholine (0.48 mL, 5.57 mmol). The reaction mixture was stirred at −20° C. to room temperature for 3 h. EtOH was evaporated, the reaction mixture was diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc:Hexanes. Fractions containing the product were combined and concentrated under vacuum to obtain A (650 mg, 2.62 mmol, 51% yield) as an off-white solid.

MS (ESI+APCI; multimode): 249 $[M+H]^+$.

$^1H$ NMR (400 MHz, DMSO-$d_6$): δ: 3.78-3.73 (m, 8H), 2.30 (s, 3H).

Preparation of B1 and B2

To a stirred solution of A (500 mg, 2.01 mmol) in anhydrous $CH_3OH$ (50 mL), at room temperature, under $N_2$ atmosphere, was added sodium methoxide (109 mg, 2.01 mmol). The reaction mixture was stirred at room temperature for 48 h. $CH_3OH$ evaporated, the reaction mixture was diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 20% EtOAc:Hexanes. Fractions containing the product were combined and concentrated under vacuum to obtain B1 (150 mg, 0.61 mmol, 30% yield) as an off-white solid, and B2 (100 mg, 0.41 mmol, 20% yield) as an off-white solid B1: MS (ESI+APCI; multimode): 244 $[M+H]^+$ $^1H$ NMR (400 MHz, DMSO-$d_6$): δ: 3.98 (s, 3H), 3.81-3.79 (m, 4H), 3.38-3.35 (m, 4H), 2.02 (s, 3H).

B2: MS (ESI+APCI; multimode): 244 $[M+H]^+$.

$^1H$ NMR (400 MHz, DMSO-$d_6$): δ: 3.94 (s, 3H), 3.82-3.79 (m, 4H), 3.43-3.41 (m, 4H), 2.19 (s, 3H).

Preparation of Compound 83

To a suspension of NaH (50%, 23.6 mg, 0.98 mmol) in anhydrous DMA (5 mL), at 0° C., under $N_2$ atmosphere, was added 3-(m-tolyl)-1H-pyrazole (78 mg, 0.49 mmol) in DMA (5 mL) dropwise over a period of 2 min. The reaction mixture was stirred at 0° C. for 30 min. B1 (100 mg, 0.41 mmol) in DMA (5 mL) was added. The reaction mixture was gradually warmed to room temperature and stirred for 12 h. The reaction mixture was quenched at 0° C. with ice cold water (2 ml), diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc:Hexanes. Fractions containing the product were combined and concentrated under vacuum to obtain Compound 83 (40.0 mg, 0.10 mmol, 26% yield) as an off-white solid.

MS (ESI+APCI; multimode): 366.2 $[M+H]^+$; HPLC: 95.3 (% of AUC).

$^1$H NMR (400 MHz, DMSO-$d_6$): δ: 8.49 (d, J=2.8 Hz, 1H), 7.76 (s, 1H), 7.72 (d, J=8.0 Hz, 1H), 7.34 (t, J=7.6 Hz, 1H), 7.19 (d, J=7.6 Hz, 1H), 7.03 (d, J=2.8 Hz, 1H), 3.90 (s, 3H), 3.73-3.72 (m, 4H), 3.47-3.45 (m, 4H), 2.37 (s, 3H), 2.30 (s, 3H).

Synthesis of N,N-dimethyl-1-(1-(2-(2-(1-methyl-1H-pyrazol-4-yl)ethoxy)-6 -morpholinopyrimidin-4-yl)-3-(m-tolyl)-1H-pyrazol-5-yl)methanamine (Compound 86)

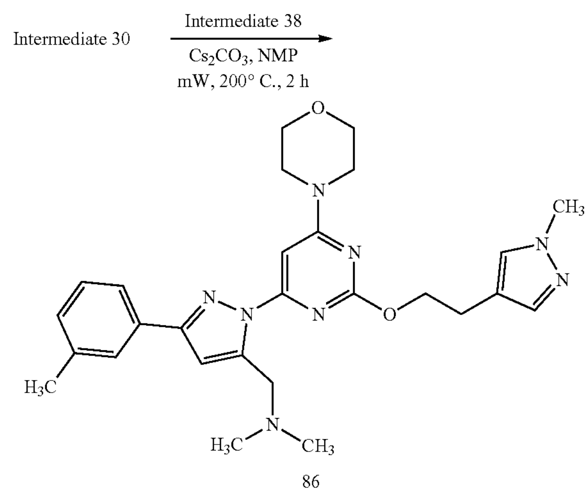

86

To a stirred solution of Intermediate 30 (100 mg, 0.30 mmol) in NMP (5.0 mL), placed in a microwave vial, under $N_2$ atmosphere at rt, was added $Cs_2CO_3$ (300 mg, 0.92 mmol), followed with Intermediate 38 (70.0 mg, 0.30 mmol) and the reaction mixture was irradiated in microwave at 100° C. and stirred for 1 h. The reaction mixture was cooled to rt, diluted with water (100 mL) and extracted with EtOAc (2×40 mL), washed with brine (50 mL). The organic layer was dried over anhydrous $Na_2SO_4$, filtered and concentrated under reduced pressure to afford the crude product. The crude product was purified by silica gel chromatography using 10% $CH_2Cl_2$:$CH_2Cl_2$. Fractions containing the product were combined and concentrated under vacuum to obtain Compound 86 (20.0 mg, 9% yield) as an off-white solid.

MS (ESI+APCI; multimode): 503.3 $[M+H]^+$; HPLC: 98.9 (% of AUC).

$^1$H NMR (400 MHz, DMSO-$d_6$): δ: 7.77 (s, 1H), 7.74 (d, J=7.6 Hz, 1H), 7.56 (s, 1H), 7.33 (brs, 2H), 7.19 (d, J=7.2 Hz, 1H), 6.92 (s, 1H), 6.89 (s, 1H), 4.39 (t, J=6.4 Hz, 2H), 3.99 (s, 2H), 3.78 (s, 3H), 3.68-3.65 (m, 8H), 2.86 (t, J=6.4 Hz, 2H), 2.37 (s, 3H), 2.20 (s, 6H).

Synthesis of 4-(6-methoxy-2-(3-(m-tolyl)-1H-pyrazol-1-yl)pyrimidin-4-yl)morpholine (Compound 87)

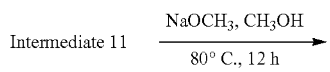

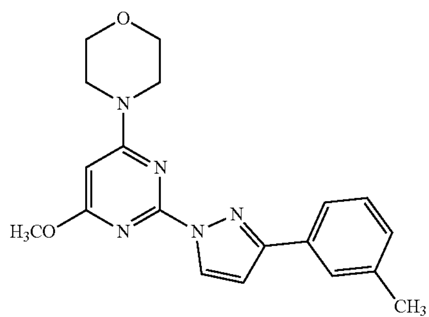

87

To a stirred solution of Intermediate 11 (200 mg, 0.56 mmol) in anhydrous $CH_3OH$ (5 mL) at room temperature under $N_2$ atmosphere was added $NaOCH_3$ (30.4 mg, 0.56 mmol). The reaction mixture was gradually heated to 80° C. and stirred for 12 h. The reaction mixture was diluted with water (20 mL), and extracted with EtOAc (2×30 mL). The combined organic extracts were washed with brine (30 mL), dried over anhydrous $Na_2SO_4$, filtered and concentrated under vacuum to obtain the crude product. The crude product was purified by silica-gel column chromatography using 50-55% EtOAc:Hexanes followed by mass triggered prep HPLC (0.1% TFA in $CH_3CN$:$H_2O$) to obtain Compound 87 (35.0 mg, 0.10 mmol, 17% yield) as an off-white solid.

LCMS (ESI): m/z=352 $[M+H]^+$; HPLC: >99 (% of AUC).

$^1$H NMR (400 MHz, DMSO-$d_6$) δ: 8.67 (d, J=2.8 Hz, 1H), 7.76 (s, 1H), 7.72 (d, J=8.0 Hz, 1H), 7.34 (t, J=7.6 Hz, 1H), 7.19 (d, J=7.6 Hz, 1H), 7.01 (d, J=2.8 Hz, 1H), 6.05 (s, 1H), 3.95 (s, 3H), 3.70-3.69 (m, 8H), 2.38 (s, 3H).

Synthesis of 1-(4-morpholino-6-(3-(m-tolyl)-1H-pyrazol-1-yl)pyrimidin-2-yl)ethan-1-one (Compound 88)

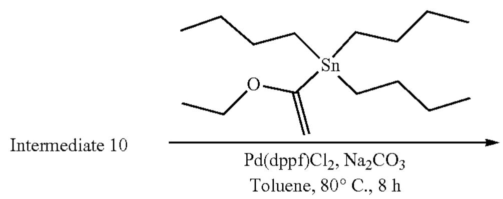

-continued

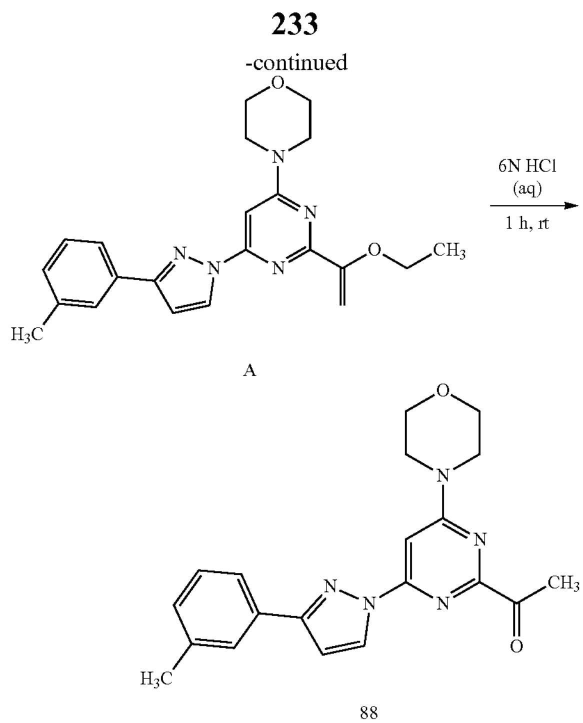

A

88

Preparation of A

To a stirred solution of Intermediate 10 (80.0 mg, 0.22 mmol) in toluene (10 ml) at room temperature, under $N_2$ atmosphere was added tributyl(1-ethoxyvinyl)stannane (81.0 mg, 0.22 mmol) followed with $Na_2CO_3$ (47.7 mg, 0.45 mmol) and $PdCl_2$(dppf) (16.4 mg, 0.02 mmol). The reaction mixture was degassed for 5 min, and gradually heated to 80° C. and stirred for 8 h. The reaction mixture is cooled to room temperature, filtered through celite bed and washed with EtOAc (30 mL). Filtrate was concentrated, diluted with water (20 mL) and extracted with EtOAc (2×30 mL). The combined organic extracts were washed with brine solution (30 mL), dried over anhydrous $Na_2SO_4$ and concentrated under reduced pressure to obtain A (80 mg, crude) as a brown liquid. LCMS (ESI): m/z=392 $[M+H]^+$; crude product directly used in the next step.

Preparation of Compound 88

The crude compound A (80 mg) was dissolved in HCl (6N, 10 mL) at room temperature and stirred for 1 h. The reaction mixture was extracted with EtOAc (2×20 mL). The combined organic extracts were washed with brine solution (20 mL), dried over anhydrous $Na_2SO_4$ and concentrated under reduced pressure to obtain the crude product. The crude product was purified by silica-gel column chromatography using 30% EtOAc:Hexanes. Fractions containing the product were combined and concentrated under vacuum to obtain Compound 88 (25.0 mg, 0.06 mmol, 30% yield) as an off-white solid.

LCMS (ESI): m/z=364 $[M+H]^+$; HPLC: >99 (% of AUC).

$^1$H NMR (400 MHz, DMSO-$d_6$) δ: 8.69 (d J=2.8 Hz, 1H), 7.85 (s, 1H), 7.80 (d, J=7.6 Hz, 1H), 7.36 (t, J=7.6 Hz, 1H), 7.31 (s, 1H), 7.22 (d, J=7.6 Hz, 1H), 7.12 (d, J=2.4 Hz, 1H), 3.76-3.74 (m, 8H), 2.65 (s, 3H), 2.39 (s, 3H).

Synthesis of 4-(2-(2-(pyridin-2-yl)ethoxy)-6-(2-(m-tolyl)thiazol-4-yl)pyrimidin-4-yl)morpholine (Compound 130)

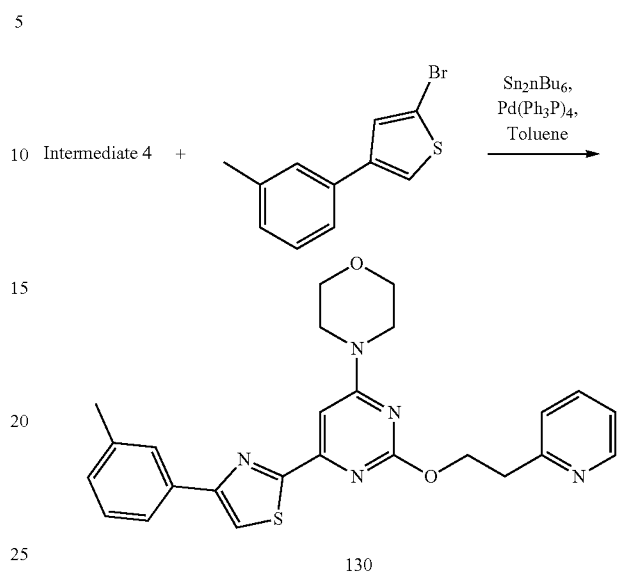

130

LC/MS (mobile phase 5-100% ACN in 3 min), Rt=2.18 min, $(M+H)^+$ 439

$^1$H NMR (300 MHz MeOD): δ 8.26 (s, 1H), 7.86 (m, 2H), 7.38 (m, 2H), 7.24 (s, 1H), 3.35 (m, 3H), 3.94 (m, 1H), 3.80 (m, 9H), 2.47 (s, 3H), 2.01 (m, 4H)

Synthesis of (E)-4-(3-methoxyprop-1-en-1-yl)-2-((tetrahydrofuran-2-yl)methoxy)-6-(3-(m-tolyl)-1H-pyrazol-1-yl)pyrimidine (Compound 131)

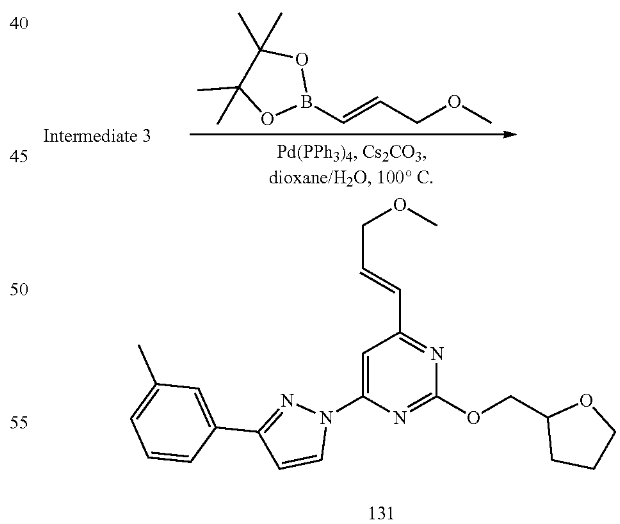

131

A mixture of 4-chloro-6-[3-(3-methylphenyl)-1H-pyrazol-1-yl]-2-[(oxolan-2-yl)methoxy]-pyrimidine (Intermediate 3) (40 mg, 0.108 mmol, 1 equiv), 2-[(1E)-3-methoxy-prop-1-en-1-yl]- 4,4,5,5-tetramethyl-1,3,2 dioxaborolane (42.73 mg, 0.216 mmol, 2 equiv), Pd(PPh3)$_4$ (12.46 mg, 0.011 mmol, 0.1 equiv) and Cs2CO3 (105.43 mg, 0.324 mmol, 3 equiv) in dioxane (4 mL) and $H_2O$ (0.4 mL) was stirred over night at 100° C. under a nitrogen atmosphere. Desired product could be detected by LCMS. Then the mixture was concentrated and purified by flash chromatography on silica gel eluting with EA/PE (0-40%) to afford 4-[(1E)-3-methoxyprop-1-en-1-yl]-6-[3-(3-methylphenyl)-1H-pyrazol-1-yl]-2-[(oxolan-2-yl)methoxy]pyrimidine (Compound 131) (12.6 mg, 27.30%) as a white solid.

LC-MS RT=2.041 min, m/z=407.40 [M+H]$^+$ $^1$H NMR (400 MHz, Chloroform-d) δ 8.62 (d, J=2.7 Hz, 1H), 7.78 (s, 1H), 7.72 (d, J=7.7 Hz, 1H), 7.62 (s, 1H), 7.36 (t, J=7.6 Hz, 1H), 7.26-7.11 (m, 2H), 6.81 (d, J=2.7 Hz, 1H), 6.71 (d, J=15.7 Hz, 1H), 4.54-4.47 (m, 1H), 4.44-4.25 (m, 2H), 4.22 (dd, J=4.9, 1.7 Hz, 2H), 3.98 (q, J=7.0 Hz, 1H), 3.86 (q, J=7.3 Hz, 1H), 3.47 (s, 3H), 2.46 (s, 3H), 2.18-2.10 (m, 1H), 2.09-1.91 (m, 2H), 1.91-1.78 (m, 1H).

Synthesis of 4-(2-((tetrahydrofuran-2-yl)methoxy)-6-(3-(m-tolyl)-1H-pyrazol-1-yl)pyrimidin-4-yl)tetrahydro-2H-pyran-2-one (Compound 132)

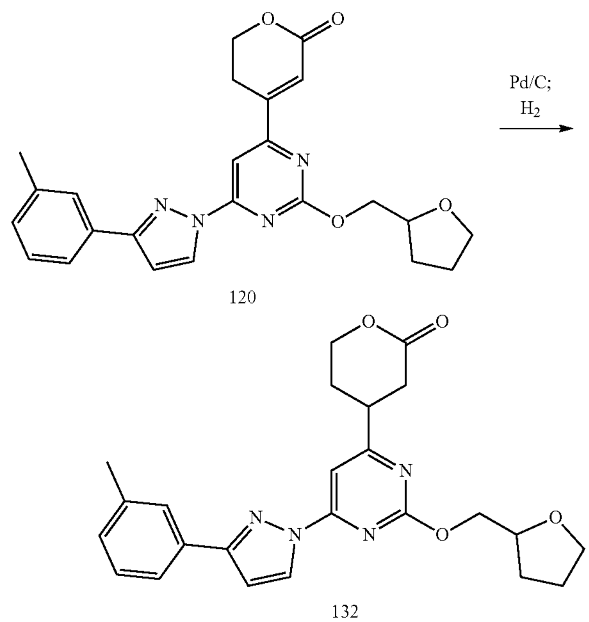

120

132

A mixture of 4-[6-[3-(3-methylphenyl)-1H-pyrazol-1-yl]-2-[(oxolan-2-yl)methoxy]pyrimidin-4-yl]-5,6-dihydro-2H-pyran-2-one (Compound 120) (16 mg, 0.037 mmol, 1 equiv) and Pd/C (4 mg, 0.004 mmol, 0.10 equiv, 10%) in EA (4 mL) was stirred over night at room temperature under a nitrogen atmosphere.

Desired product could be detected by LCMS. Then the mixture was concentrated and purified by flash chromatography on silica gel eluting with EA/PE (0-60%) to afford 4-[6-[3-(3-methylphenyl)-1H-pyrazol-1-yl]-2-[(oxolan-2-yl)methoxy]pyrimidin-4-yl]oxan-2-one (Compound 132) (11.3 mg, 60.34%) as a white solid.

LC-MS: RT=1.370 min, m/z=435.30 [M+H]$^+$ $^1$H NMR (400 MHz, Methanol-$d_4$) δ 8.65 (d, J=2.7 Hz, 1H), 7.81 (s, 1H), 7.75 (d, J=7.7 Hz, 1H), 7.66 (s, 1H), 7.35 (t, J=7.6 Hz, 1H), 7.24 (d, J=7.8 Hz, 1H), 6.98 (d, J=2.7 Hz, 1H), 4.56-4.27 (m, 5H), 3.95 (q, J=6.9 Hz, 1H), 3.84 (q, J=7.5 Hz, 1H), 3.60 (dt, J=13.9, 6.9 Hz, 1H), 2.92 (d, J=7.0 Hz, 2H), 2.44 (s, 3H), 2.38-2.31 (m, 1H), 2.20-2.09 (m, 2H), 2.09-1.92 (m, 2H), 1.89-1.77 (m, 1H).

Synthesis of 4-(2-((tetrahydrofuran-2-yl)methoxy)-6-(3-(m-tolyl)-1H-pyrazol-1-yl)pyrimidin-4-yl)morpholine (Compound 133)

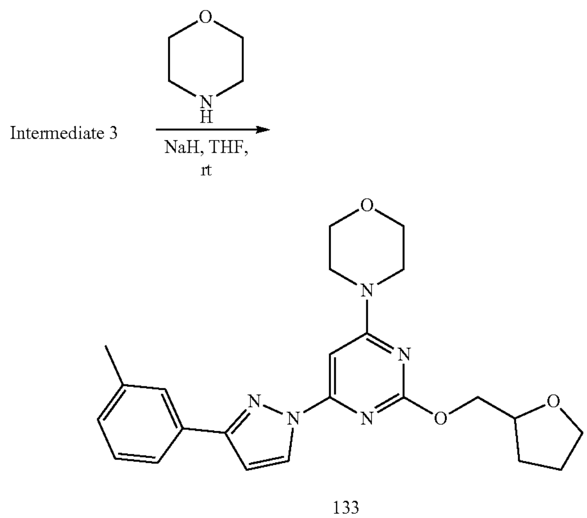

133

To a solution of 4-chloro-6-[3-(3-methylphenyl)-1H-pyrazol-1-yl]-2-[(oxolan-2-yl)methoxy]pyrimidine (Intermediate 3) (40 mg, 0.108 mmol, 1 equiv) in THF (0.5 mL) was successively added morpholine (10.34 mg, 0.119 mmol, 1.10 equiv), NaH (5.18 mg, 0.129 mmol, 1.20 equiv, 60%) and the solution was stirred for 2 h at room temperature. Desired product could be detected by LCMS. Then the mixture was concentrated and purified by prep-HPLC to afford 4-[6-[3-(3-methylphenyl)-1H-pyrazol-1-yl]-2-[(oxolan-2-yl)methoxy]pyrimidin-4-yl]morpholine (Compound 133) (14.7 mg, 31.91%) as a white solid.

LC-MS RT=1.908 min, m/z=422.25 [M+H]$^+$ $^1$H NMR (400 MHz, Chloroform-d) δ 8.59 (d, J=2.6 Hz, 1H), 7.77 (s, 1H), 7.71 (d, J=7.8 Hz, 1H), 7.35 (t, J=7.7 Hz, 1H), 7.21 (d, J=7.7 Hz, 1H), 6.93 (s, 1H), 6.76 (d, J=2.6 Hz, 1H), 4.47-4.43 (m, 1H), 4.39-4.28 (m, 2H), 4.02-3.92 (m, 1H), 3.89-3.70 (m, 9H), 2.45 (s, 3H), 2.08-2.09 (m, 1H), 2.07-1.91 (m, 2H), 1.90-1.76 (m, 1H).

Synthesis of 4-(2-((tetrahydrofuran-2-yl)methoxy)-6-(3-(m-tolyl)-1H-pyrazol-1-yl)pyrimidin-4-yl)tetrahydro-2H-pyran-3-ol (Compound 134)

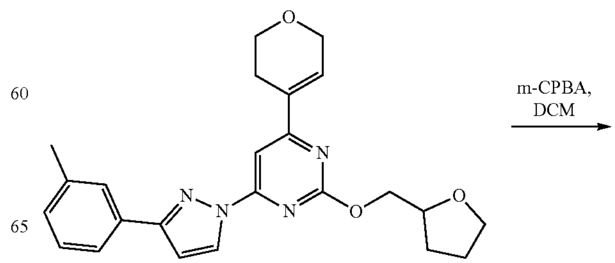

-continued

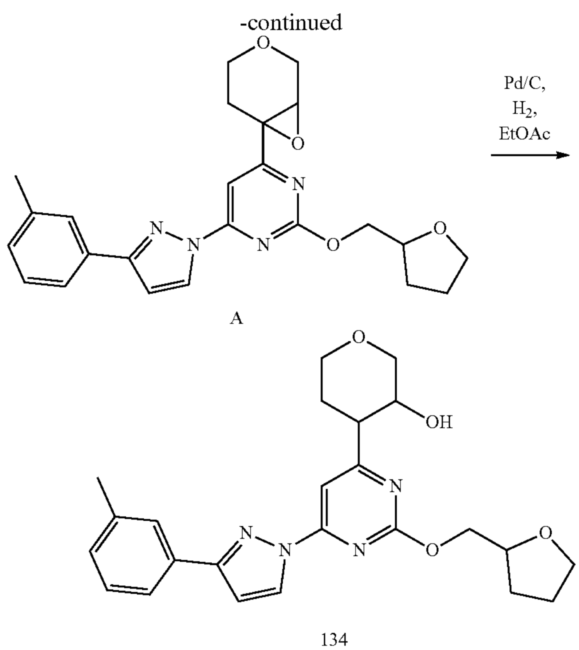

A

134

Preparation of A

A mixture of 4-(3,6-dihydro-2H-pyran-4-yl)-6-[3-(3-methylphenyl)-1H-pyrazol-1-yl]-2-[(oxolan-2-yl)methoxy] pyrimidine (22 mg, 0.053 mmol, 1 equiv) and mCPBA (10.89 mg, 0.063 mmol, 1.20 equiv) in DCE (1 mL) was stirred overnight at room temperature. Desired product could be detected by LCMS. The mixture was concentrated and purified by flash chromatography on silica gel eluting with EA/PE (0-100%) to afford 4-(furan-3-yl)-6-[3-(3-methylphenyl)-1H-pyrazol-1-yl]-2-[(oxolan-2-yl)methoxy]pyrimidine (A) (22 mg, 95.53%) as a light yellow oil.

Preparation of Compound 134

A mixture of 4-[3,7-dioxabicyclo[4.1.0]heptan-6-yl]-6-[3-(3-methylphenyl)-1H-pyrazol-1-yl]-2-[(oxolan-2-yl) methoxy]pyrimidine (A) (22 mg, 0.051 mmol, 1 equiv.) and Pd/C (1.08 mg, 0.010 mmol, 0.20 equiv) in EA (2 mL) was stirred over night at room temperature under a hydrogen atmosphere.

Desired product could be detected by LCMS. Then the mixture was concentrated and purified by flash chromatography on silica gel eluting with EA/PE (0-60%) to afford 4-[6-[3-(3-methylphenyl)-1H-pyrazol-1-yl]-2-[(oxolan-2-yl)methoxy]pyrimidin-4-yl]oxan-3-ol (Compound 134) (4.3 mg, 22.53%) as a light yellow solid.

LC-MS RT=2.074 min, m/z=437.25 $[M+H]^+$ $^1$H NMR (300 MHz, DMSO-$d_6$) δ 8.74 (d, J=2.8 Hz, 1H), 7.83 (s, 1H), 7.79 (d, J=7.5 Hz, 1H), 7.54 (s, 1H), 7.38 (t, J=7.6 Hz, 1H), 7.25 (d, J=7.6 Hz, 1H), 7.16 (d, J=2.8 Hz, 1H), 4.76 (d, J=5.4 Hz, 1H), 4.42-4.31 (m, 2H), 4.22 (p, J=6.6 Hz, 1H), 4.09-3.96 (m, 2H), 3.88-3.77 (m, 2H), 3.70 (q, J=7.5 Hz, 1H), 3.58 (d, J=11.3 Hz, 1H), 3.47 (t, J=10.6 Hz, 1H), 3.05 (dt, J=12.3, 3.0 Hz, 1H), 2.41 (s, 3H), 2.35-2.24 (m, 1H), 2.11-1.81 (m, 3H), 1.76-1.61 (m, 2H).

Synthesis of N-methyl-6-(3-phenyl-1H-pyrazol-1-yl)-2-(2-(tetrahydrofuran-2-yl)ethyl)-N-(tetrahydrofuran-3-yl)pyrimidin-4-amine (Compound 135)

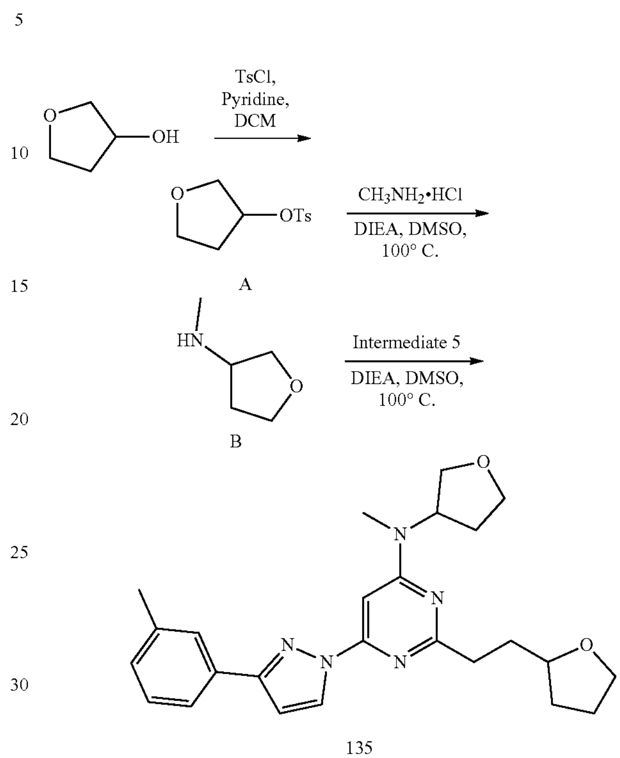

A

B

135

Preparation of A

To a solution of oxolan-3-ol (1 g, 11.350 mmol, 1 equiv) in DCM (30 mL) was successively added Pyridine (2.69 g, 34.008 mmol, 3.00 equiv), 4-methylbenzene-1-sulfonyl chloride (3.03 g, 15.890 mmol, 1.40 equiv) and the mixture was stirred for 2 h at room temperature. Desired product could be detected by LCMS. Then the mixture was concentrated and purified by flash chromatography on silica gel eluting with EA/PE (0-100%) to afford oxolan-3-yl 4-methylbenzene-1-sulfonate (A) (1.2 g, 43.64%) as a light yellow oil.

Preparation of B

A mixture of oxolan-3-yl 4-methylbenzene-1-sulfonate (A) (240 mg, 0.991 mmol, 1 equiv), methanamine hydrochloride (66.88 mg, 0.991 mmol, 1.00 equiv), DIEA (384.06 mg, 2.972 mmol, 3.00 equiv) and DMSO (2 mL) was stirred over night at 100° C. TLC showed oxolan-3-yl 4-methylbenzene-1-sulfonate consumed and the mixture (B) was used directly in the next step.

Preparation of Compound 135

A mixture of 4-chloro-6-[3-(3-methylphenyl)-1H-pyrazol-1-yl]-2-[2-(oxolan-2-yl) ethyl]pyrimidine (Intermediate 5) (200 mg, 0.542 mmol, 1 equiv), N-methyloxolan-3-amine (B) (109.69 mg, 1.084 mmol, 2.00 equiv), DIEA (210.23 mg, 1.627 mmol, 3.00 equiv) and DMSO (2 mL) was stirred for overnight at 100° C.

Desired compound could be detected by LCMS. Then the mixture was concentrated and purified by reverse phase flash chromatography to afford N-methyl-6-[3-(3-methylphenyl)-1H-pyrazol-1-yl]-2-[2-(oxolan-2-yl)ethyl]-N-(oxolan-3-yl) pyrimidin-4-amine (Compound 135) (13.5 mg, 5.74%) as a colorless oil.

LC-MS RT=2.379 min, m/z=434.25 $[M+H]^+$ $^1$H NMR (400 MHz, Methanol-$d_4$) δ 8.62 (d, J=2.7 Hz, 1H), 7.78 (s, 1H), 7.72 (d, J=7.7 Hz, 1H), 7.34 (t, J=7.6 Hz, 1H), 7.22 (d, J=7.1 Hz, 1H), 7.03 (s, 1H), 6.89 (d, J=2.7 Hz, 1H), 4.13 (td, J=8.7, 4.8 Hz, 1H), 4.0-3.85 (m, 4H), 3.82-3.72 (m, 2H), 3.72-3.61 (m, 1H), 3.12 (s, 3H), 2.94-2.76 (m, 2H), 2.44 (s, 3H), 2.42-2.31 (m, 1H), 2.15-1.89 (m, 6H), 1.59 (dq, J=12.3, 7.7 Hz, 1H).

Synthesis of 4-(2-(2-(tetrahyd)rofuran-2-yl)ethyl)-6-(3-(m-tolyl)-1H-pyrazol-1-yl)pyrimidin-4-yl)morpholine (Compound 136)

Intermediate 5

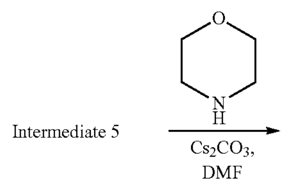

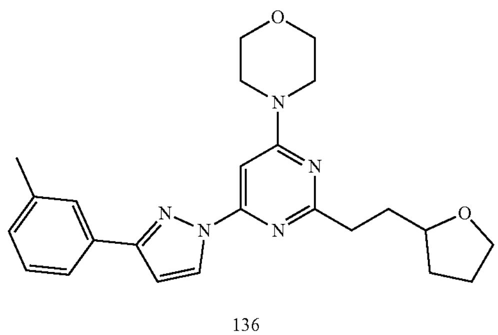

136

To a stirred solution of 4-chloro-6-[3-(3-methylphenyl)-1H-pyrazol-1-yl]-2-[2-(oxolan-2-yl)ethyl]pyrimidine (Intermediate 5) (37 mg, 0.100 mmol, 1 equiv) and morpholine (26.22 mg, 0.301 mmol, 3.00 equiv) in DMF (2 mL) was added $Cs_2CO_3$ (98.05 mg, 0.301 mmol, 3.00 equiv) at 100° C. The mixture was stirred for 5 h. The solvent was evaporated under vacuum. The residue was applied onto a preparative TLC to afford 4-[6-[3-(3-methylphenyl)-1H-pyrazol-1-yl]-2-[2-(oxolan-2-yl)ethyl]pyrimidin-4-yl]morpholine (Compound 136) (25.3 mg, 60.12%) as white solid.

LC-MS RT=2.362 min, m/z=420.1 $[M+H]^+$ $^1$H NMR (400 MHz, Chloroform-d) δ 8.60 (d, J=2.7 Hz, 1H), 7.75 (s, 1H), 7.69 (d, J=7.7 Hz, 1H), 7.32 (t, J=7.6 Hz, 1H), 7.18 (d, J=7.5 Hz, 1H), 7.02 (s, 1H), 6.74 (d, J=2.7 Hz, 1H), 3.97-3.87 (m, 2H), 3.81 (dd, J=5.7, 3.7 Hz, 4H), 3.78-3.69 (m, 5H), 2.96-2.75 (m, 2H), 2.43 (s, 3H), 2.13 (ddt, J=13.1, 9.6, 6.5 Hz, 1H), 2.08-1.98 (m, 2H), 1.91 (dddt, J=18.4, 14.4, 7.6, 5.6 Hz, 2H), 1.60-1.48 (m, 1H).

Synthesis of 4-(2-((tetrahydrofuran-2-yl)methoxy)-6-(2-(m-tolyl)thiazol-4-yl)pyrimidin-4-yl)morpholine (Compound 137)

Intermediate 5 +

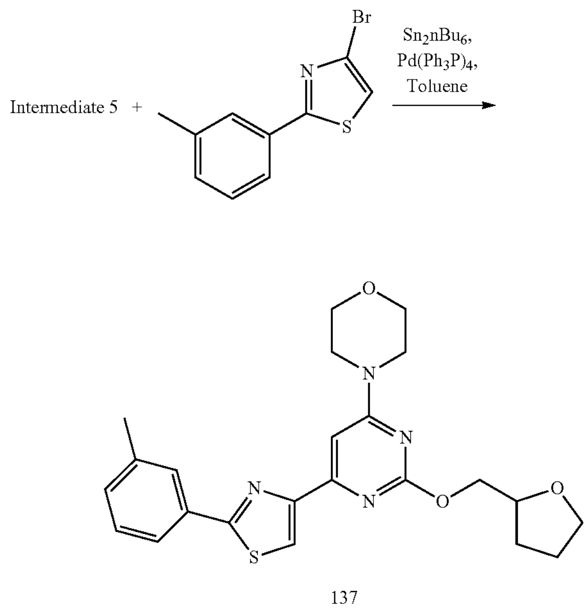

137

Into a 10 mL tube were added 4-[6-chloro-2-[(oxolan-2-yl)methoxy]pyrimidin-4-yl]morpholine (Intermediate 5) (50 mg, 0.167 mmol, 1 equiv), 4-bromo-2-(3-methylphenyl)-1,3-thiazole (84.78 mg, 0.334 mmol, 2.00 equiv), $Sn_2(Bu)_6$ (387.05 mg, 0.667 mmol, 4 equiv) and $Pd(PPh_3)_4$ (57.82 mg, 0.050 mmol, 0.3 equiv). To the mixture was added dioxane (1.5 mL) under an atmosphere of $N_2$. The tube was sealed with a screw cap and stirred in an oil bath and reacted at 110° C. for 15 h. The mixture was purified by preparative HPLC follow by preparative TLC to afford 4-[6-[2-(3-methylphenyl)-1,3-thiazol-4-yl]-2-[(oxolan-2-yl)methoxy]pyrimidin-4-yl]morpholine (Compound 137) (20.9 mg, 28.57%) as a white solid.

LC-MS RT=2.180 min, m/z=439.1 $[M+H]^+$ $^1$H NMR (300 MHz, Methanol-d4) δ 8.24 (s, 1H), 7.87 (s, 1H), 7.81 (d, J=7.6 Hz, 1H), 7.37 (t, J=7.6 Hz, 1H), 7.31 (d, J=7.6 Hz, 1H), 7.24 (s, 1H), 4.43-4.34 (m, 2H), 4.34-4.24 (m, 1H), 3.92 (dt, J=8.1, 6.5 Hz, 1H), 3.77 (tt, J=7.4, 3.8 Hz, 9H), 2.16-1.78 (m, 4H).

Synthesis of 3-(4-morpholino-6-(3-(m-tolyl)-1H-pyrazol-1-yl)pyrimidin-2-yl)propan-1-ol (Compound 138)

Intermediate 10

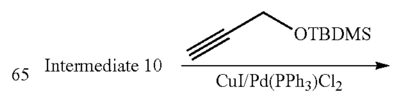

-continued

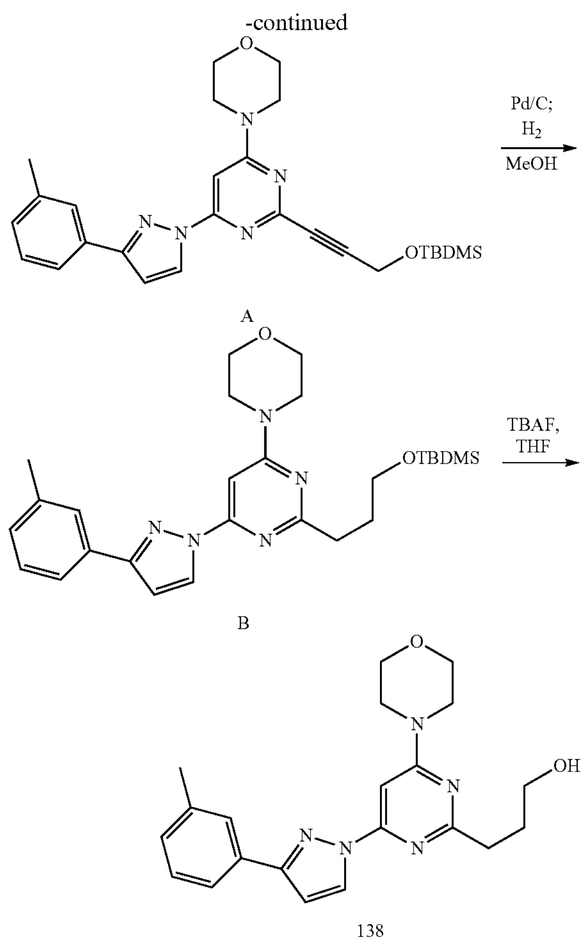

A

B

138

Preparation of A

Into a 25 mL tube were added 4-[2-chloro-6-[3-(3-methylphenyl)-1H-pyrazol-1-yl]pyrimidin-4-yl]morpholine (Intermediate 10) (200 mg, 0.562 mmol, 1 equiv), tert-butyldimethyl(prop-2-yn-1-yloxy)silane (478.68 mg, 2.810 mmol, 5 equiv), $Pd(PPh_3)_2Cl_2$ (39.45 mg, 0.056 mmol, 0.10 equiv) and CuI (32.11 mg, 0.169 mmol, 0.30 equiv). To the mixture was added $Et_3N$ (284.38 mg, 2.810 mmol, 5.00 equiv) and DMF (7 mL) under an atmosphere of $N_2$. The tube was sealed with a screw cap and stirred at room temperature for 5 minutes. Then the tube was placed into an oil bath and reacted at 80° C. overnight. The mixture was purified by Prep-TLC to afford 4-(2-[3-[(tert-butyldimethylsilyl)oxy]prop-1-yn-1-yl]-6-[3-(3-methylphenyl)-1H-pyrazol-1-yl]pyrimidin-4-yl)morpholine (A) (240 mg, 87.20%) as a yellow oil.

Preparation of B

To a solution of 4-(2-[3-[(tert-butyldimethylsilyl)oxy]prop-1-yn-1-yl]-6-[3-(3-methylphenyl)- 1H-pyrazol-1-yl]pyrimidin-4-yl)morpholine (A) (230 mg, 0.470 mmol, 1 equiv) in MeOH (5 mL) was added Pd/C (49.98 mg, 0.047 mmol, 0.1 equiv, 10%) under $N_2$ atmosphere. Then the $N_2$ atmosphere was replaced by $H_2$ atmosphere. The mixture was stirred at room temperature for 5 h. The resulting mixture was filtered and the filtrate was concentrated under reduced pressure. The residue 4-(2-[3-[(tert-butyldimethylsilyl)oxy]propyl]-6-[3-(3-methylphenyl)-1H-pyrazol-1-yl]pyrimidin-4-yl)morpholine (B) (222 mg, 95.73%) can be used for the next step without further purification.

Preparation of Compound 138

To a stirred solution of 4-(2-[3-[(tert-butyldimethylsilyl)oxy]propyl]-6-[3-(3-methylphenyl)-1H-pyrazol-1-yl]pyrimidin-4-yl)morpholine (B) (220 mg, 0.446 mmol, 1 equiv) in THF (5 mL) was added TBAF (349.51 mg, 1.337 mmol, 3.00 equiv). The solution was stirred at room temperature for 5 h. The solution was applied onto a preparative TLC to afford 3-[4-[3-(3-methylphenyl)-1H-pyrazol-1-yl]-6-(morpholin-4-yl)pyrimidin-2-yl]propan-1-ol (Compound 138) (144 mg, 85.16%) as white solid.

LC-MS RT=1.878 min, m/z=380.2 $[M+H]^+$ $^1H$ NMR (300 MHz, DMSO-d6) δ 8.61 (d, J=2.7 Hz, 1H), 7.82 (s, 1H), 7.78 (d, J=7.8 Hz, 1H), 7.35 (t, J=7.6 Hz, 1H), 7.21 (d, J=7.5 Hz, 1H), 7.05 (d, J=2.9 Hz, 2H), 4.48 (t, J=5.2 Hz, 1H), 3.70 (s, 8H), 3.50 (td, J=6.5, 5.2 Hz, 2H), 2.80-2.67 (m, 2H), 2.39 (s, 3H), 1.98-1.85 (m, 2H).

Synthesis of 2-(4-morpholino-6-(3-(m-tolyl)-1H-pyrazol-1-yl)pyrimidin-2-yl)ethan-1-ol (Compound 139)

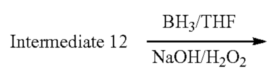

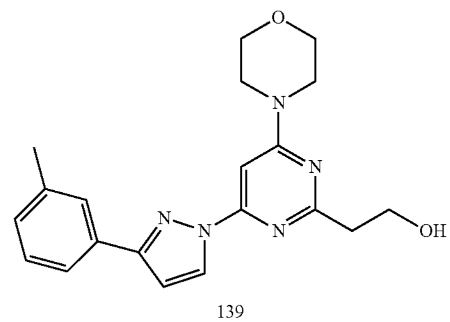

139

Under $N_2$, to a solution of 4-[2-ethenyl-6-[3-(3-methylphenyl)-1H-pyrazol-1-yl]pyrimidin-4-yl]morpholine (Intermediate 12) (80 mg, 0.230 mmol, 1 equiv) in THF (5 mL) was added $BH_3$ -THF (0.46 mL, 0.460 mmol, 2 equiv) and the mixture was stirred for 2 h at 0° C. Then NaOH (0.69 mL, 0.690 mmol, 3.00 equiv) and $H_2O_2$ (1.23 mL, 3.685 mmol, 16.02 equiv) was added. The reaction mixture was stirred at room temperature overnight. The resulting suspension was concentrated and purified by flash chromatography on silica gel eluting with EA/PE (0-100%) to provide 2-[4-[3-(3-methylphenyl)-1H-pyrazol-1-yl]-6-(morpholin-4-yl)pyrimidin-2-yl]ethan-1-ol (Compound 139) (7 mg, 8.32%) as a white solid.

LC-MS RT=4.165 min, m/z=366.20 $[M+H]^+$ $^1H$ NMR (300 MHz, DMSO-$d_6$) δ 8.63 (d, J=2.7 Hz, 1H), 7.83 (s, 1H), 7.78 (d, J=8.1 Hz, 1H), 7.36 (t, J=7.6 Hz, 1H), 7.22 (d, J=7.8 Hz, 1H), 7.07 (s, 1H), 7.06 (s, 1H), 4.59 (t, J=5.5 Hz, 1H), 3.89 (q, J=6.6 Hz, 2H), 3.71 (s, 8H), 2.86 (t, J=6.8 Hz, 2H), 2.39 (s, 3H).

Synthesis of 4-(2-((tetrahydrofuran-2-yl)methoxy)-6-(3-(m-tolyl)-1H-pyrazol-1-yl)pyrimidin-4-yl)-5,6-dihydro-2H-pyran-2-one (Compound 140)

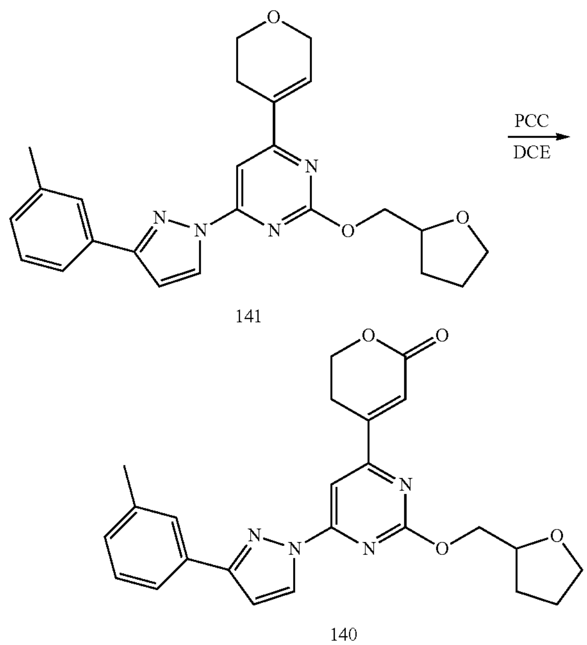

141

140

A mixture of 4-(3,6-dihydro-2H-pyran-4-yl)-6-[3-(3-methylphenyl)-1H-pyrazol-1-yl]-2-[(oxolan-2-yl)methoxy]pyrimidine (Compound 141) (60 mg, 0.143 mmol, 1 equiv), PCC (92.71 mg, 0.430 mmol, 3.00 equiv) and DCE (4 mL) was stirred over night at 50° C. Desired product could be detected by LCMS. Then the mixture was concentrated and purified by flash chromatography on silica gel eluting with EA/PE (0-60%) to afford 4-[6-[3-(3-methylphenyl)-1H-pyrazol-1-yl]-2-[(oxolan-2-yl)methoxy]pyrimidin-4-yl]-5,6-dihydro-2H-pyran-2-one (Compound 140) (28 mg, 45.16%) as a white solid.

LC-MS RT=2.810 min, m/z=433.20 $[M+H]^+$ $^1$H NMR (400 MHz, Chloroform-d) δ 8.64 (d, J=2.8 Hz, 1H), 7.95 (s, 1H), 7.80 (s, 1H), 7.73 (d, J=8.1 Hz, 1H), 7.38 (t, J=7.6 Hz, 1H), 7.25 (d, J=7.7 Hz, 1H), 7.04 (s, 1H), 6.85 (d, J=2.8 Hz, 1H), 4.61 (t, J=6.2 Hz, 2H), 4.56-4.34 (m, 3H), 3.99 (q, J=6.9 Hz, 1H), 3.91-3.82 (m, 1H), 3.06 (t, J=6.9 Hz, 2H), 2.48 (s, 3H), 2.21-2.11 (m, 1H), 2.07-1.96 (m, 2H), 1.88-1.79 (m, 1H).

Synthesis of 4-(3,6-dihydro-2H-pyran-4-yl)-2-((tetrahydrofuran-2-yl)methoxy)-6-(3-(m-tolyl)-1H-pyrazol-1-yl)pyrimidine (Compound 141)

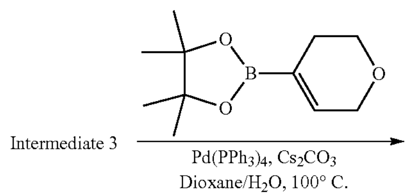

-continued

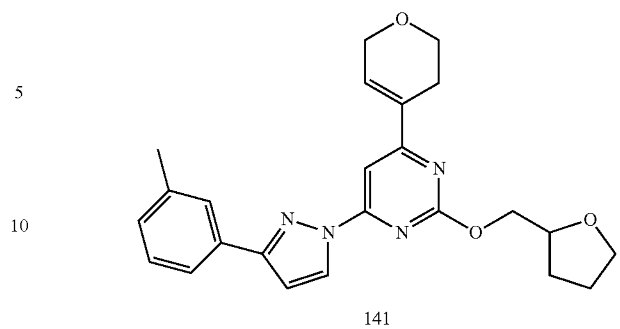

141

A mixture of 4-chloro-6-[3-(3-methylphenyl)-1H-pyrazol-1-yl]-2-[(oxolan-2-yl)methoxy]pyrimidine (100 mg, 0.270 mmol, 1 equiv), 2-(3,6-dihydro-2H-pyran-4-yl)-4,4,5,5-tetramethyl-1,3,2-dioxaborolane (Intermediate 3) (113.30 mg, 0.539 mmol, 2.00 equiv), $Pd(PPh_3)_4$ (31.16 mg, 0.027 mmol, 0.1 equiv) and $Cs_2CO_3$ (263.58 mg, 0.809 mmol, 3.00 equiv) in dioxane (10 mL) and $H_2O$ (1 mL) was stirred over night at 100° C. under a nitrogen atmosphere. Desired product could be detected by LCMS. Then the mixture was concentrated and purified by flash chromatography on silica gel eluting with EA/PE (0-40%) to afford 4-(3,6-dihydro-2H-pyran-4-yl)-6-[3-(3-methylphenyl)-1H-pyrazol-1-yl]-2-[(oxolan-2-yl)methoxy]pyrimidine (Compound 141) (100 mg, 88.61%) as a white solid.

LC-MS RT=3.431 min, m/z=419.15 $[M+H]^+$ $^1$H NMR (400 MHz, Chloroform-d) δ 8.64 (d, J=2.7 Hz, 1H), 7.78 (s, 1H), 7.73 (d, J=7.5 Hz, 1H), 7.70 (s, 1H), 7.37 (t, J=7.6 Hz, 1H), 7.23 (d, J=7.6 Hz, 1H), 7.16 (s, 1H), 6.81 (d, J=2.7 Hz, 1H), 4.57-4.48 (m, 1H), 4.47-4.34 (m, 4H), 4.01-3.96 (m, 3H), 3.86 (q, J=7.4 Hz, 1H), 2.69 (s, 2H), 2.46 (s, 3H), 2.19-2.11 (m, 1H), 2.08-1.94 (m, 2H), 1.91-1.78 (m, 1H).

Synthesis of 4-(2-((tetrahydrofuran-2-yl)methoxy)-6-(1-(m-tolyl)-1H-pyrazol-3-yl)pyrimidin-4-yl)morpholine (Compound 13) and 4-(2-((tetrahydrofuran-2-yl)methoxy)-6-(1-(m-tolyl)-1H-pyrazol-5-yl)pyrimidin-4-yl)morpholine (Compound 142)

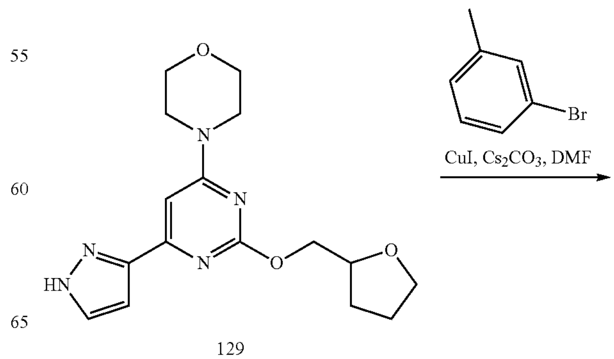

129

-continued

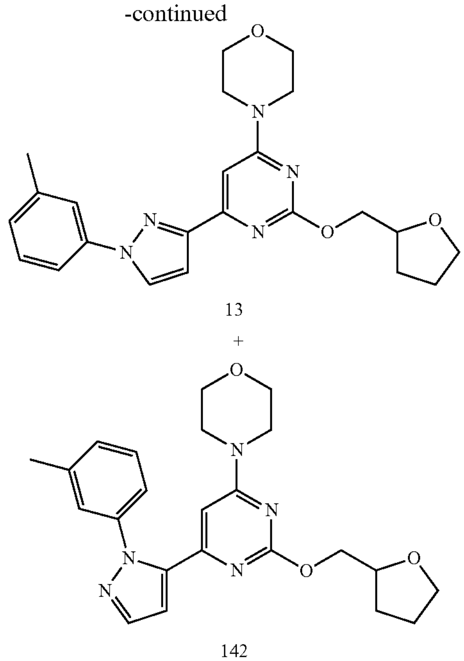

13

+

142

A solution of 4-[2-[(oxolan-2-yl)methoxy]-6-(1H-pyrazol-3-yl)pyrimidin-4-yl]morpholine (Compound 129) (200 mg, 0.604 mmol, 1 equiv), 1-bromo-3-methylbenzene (3096.85 mg, 18.106 mmol, 30 equiv), CuI (57.47 mg, 0.302 mmol, 0.50 equiv) and $Cs_2CO_3$ (589.94 mg, 1.811 mmol, 3 equiv) in DMF (9 mL) was stirred at 160° C. for 4 h under $N_2$ atmosphere. The mixture was diluted with water (50 mL) and extracted with EtOAc (3×50 mL). The combined organic layers were dried over anhydrous $MgSO_4$. After filtration, the filtrate was concentrated under reduced pressure. The residue was applied onto reverse phase chromatography to afford 4-[6-[1-(3-methylphenyl)-1H-pyrazol-3-yl]-2-[(oxolan-2-yl)methoxy]pyrimidin-4-yl]morpholine (Compound 13) (147.3 mg, 57.90%) as white solid and 4-[6-[1-(3-methylphenyl)-1H-pyrazol-5-yl]-2-[(oxolan-2-yl)methoxy]pyrimidin-4-yl]morpholine (Compound 142) (23.7 mg, 9.32%) as white solid.

Compound 13:

LC-MS RT=1.517 min, m/z=422.1 $[M+H]^+$ $^1H$ NMR (300 MHz, Methanol-d4) δ 8.24 (d, J=2.5 Hz, 1H), 7.69 (s, 1H), 7.62 (d, J=8.1 Hz, 1H), 7.38 (t, J=7.8 Hz, 1H), 7.18 (d, J=7.6 Hz, 1H), 7.10 (d, J=2.6 Hz, 1H), 7.08 (s, 1H), 4.43-4.23 (m, 3H), 3.92 (dt, J=8.2, 6.6 Hz, 1H), 3.86-3.65 (m, 9H), 2.44 (s, 3H), 2.15-1.76 (m, 4H).

Compound 142:

LC-MS RT=1.616 min, m/z=422.1 $[M+H]^+$ $^1H$ NMR (300 MHz, Methanol-d4) δ 7.72 (d, J=2.0 Hz, 1H), 7.33 (t, J=7.7 Hz, 1H), 7.25 (d, J=7.5 Hz, 1H), 7.20 (s, 1H), 7.10 (d, J=7.8 Hz, 1H), 6.92 (d, J=2.0 Hz, 1H), 6.42 (s, 1H), 4.03 (td, J=6.7, 4.5 Hz, 1H), 3.91-3.65 (m, 8H), 3.55 (t, J=4.7 Hz, 4H), 2.37 (s, 3H), 2.03-1.81 (m, 3H), 1.65-1.54 (m, 1H).

Synthesis of 4-(oxepan-4-yl)-2-((tetrahydrofuran-2-yl)methoxy)-6-(3-(m-tolyl)-1H-pyrazol-1-yl)pyrimidine (Compound 143)

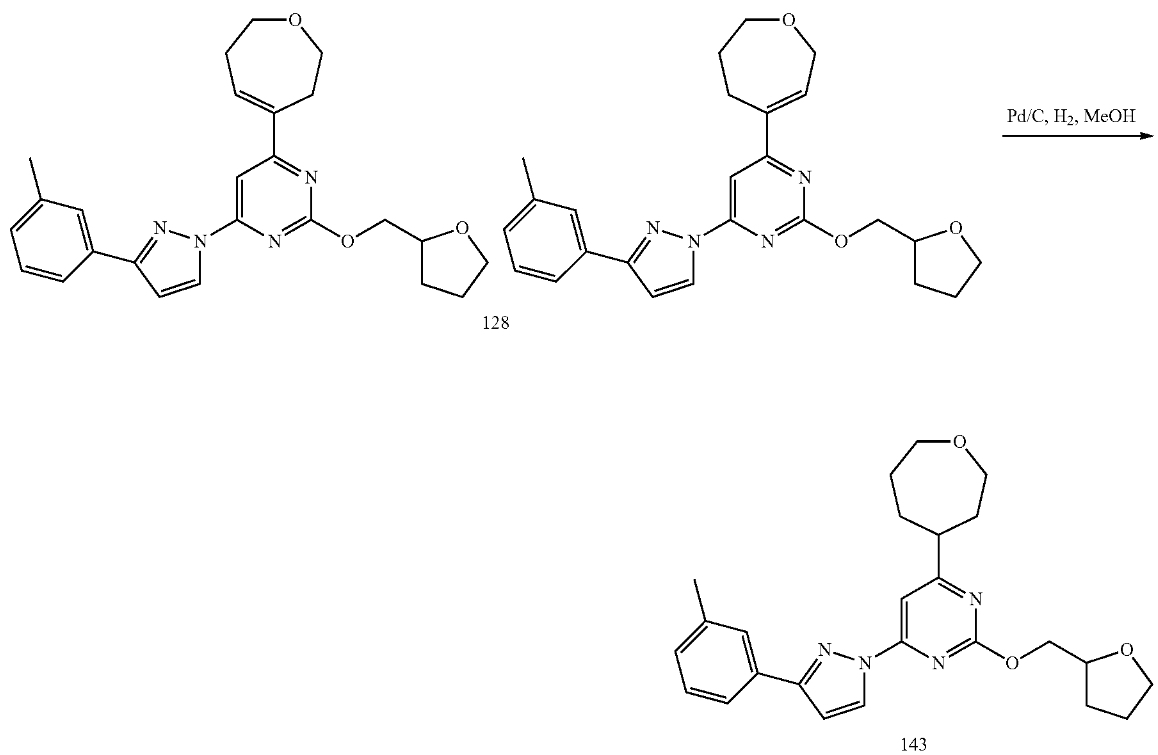

128

143

To a solution of 4-[3-(3-methylphenyl)-1H-pyrazol-1-yl]-2-[(oxolan-2-yl)methoxy]-6-(2,3,6,7-tetrahydrooxepin-4-yl)pyrimidine; 4-[3-(3-methylphenyl)-1H-pyrazol-1-yl]-2-[(oxolan-2-yl)methoxy]-6-(2,5,6,7-tetrahydrooxepin-4-yl) pyrimidine (Compound 128) (40.00 mg, 0.046 mmol, 1.00 equiv) in MeOH (10.00 mL) was added Pd/C (4.92 mg, 0.005 mmol, 0.10 equiv, 10%) under $N_2$ atmosphere. Then the $N_2$ atmosphere was replaced by $H_2$ atmosphere. The mixture was stirred at room temperature for 5 h. The resulting mixture was filtered, the filtrate was concentrated under reduced pressure. The residue was purified by reverse phase chromatography to afford 4-[3-(3-methylphenyl)-1H-pyrazol-1-yl]-6-(oxepan-4-yl)-2-[(oxolan-2-yl)methoxy]pyrimidine (Compound 143) (33.1 mg, 82.37%) as colorless oil.

LC-MS RT=3.606 min, m/z=435.3 $[M+H]^+$ $^1$H NMR (300 MHz, Chloroform-d) δ 8.59 (d, J=2.6 Hz, 1H), 7.77 (s, 1H), 7.70 (d, J=7.7 Hz, 1H), 7.54 (s, 1H), 7.35 (t, J=7.6 Hz, 1H), 7.21 (d, J=7.6 Hz, 1H), 6.79 (d, J=2.3 Hz, 1H), 4.42 (d, J=30.4 Hz, 3H), 4.06-3.66 (m, 6H), 3.03 (s, 1H), 2.44 (s, 3H), 2.05 (d, J=30.2 Hz, 10H).

Synthesis of 4-(2-(3-(1H-1,2,3-triazol-1-yl)propyl)-6-(3-(m-tolyl)-1H-pyrazol-1-yl)pyrimidin-4-yl)morpholine (Compound 144) and 4-(2-(3-(2H-1,2,3-triazol-2-yl)propyl)-6-(3-(m-tolyl)-1H-pyrazol-1-yl) pyrimidin-4-yl)morpholine (Compound 145)

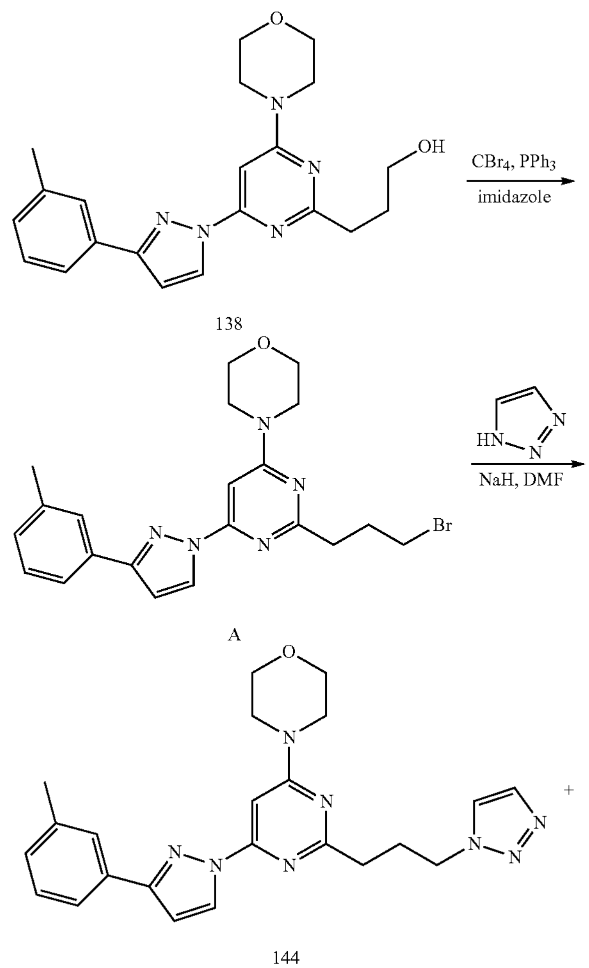

138

A

144

-continued

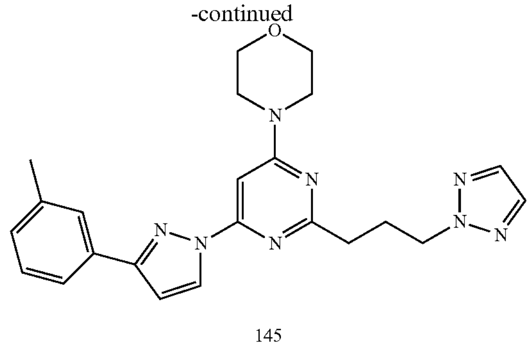

145

Synthesis of A

To a stirred solution of 3-[4-[3-(3-methylphenyl)-1H-pyrazol-1-yl]-6-(morpholin-4-yl)pyrimidin-2-yl]propan-1-ol (Compound 138) (100 mg, 0.264 mmol, 1 equiv), $Ph_3P$ (207.36 mg, 0.791 mmol, 3.00 equiv) and Imidazole (53.82 mg, 0.791 mmol, 3.00 equiv) in DCM (2 mL) was added $CBr_4$ (262.18 mg, 0.791 mmol, 3.00 equiv) at 0° C. under $N_2$ atmosphere. The mixture was stirred for 3 h at room temperature. The solution was applied onto a preparative TLC to afford 4-[2-(3-bromopropyl)-6-[3-(3-methylphenyl)-1H-pyrazol-1-yl]pyrimidin-4-yl]morpholine (A) (42 mg, 36.03%) as white solid. This compound is not stable.

Synthesis of Compound 144 and Compound 145

To a stirred solution of 1H-1,2,3-triazole (19.67 mg, 0.285 mmol, 3.00 equiv) in DMF (0.5 mL) was added NaH (11.39 mg, 0.285 mmol, 3 equiv, 60%) at 0° C. under $N_2$ atmosphere. Half an hour later, the resulting solution was injected into a solution of 4-[2-(3-bromopropyl)-6-[3-(3-methylphenyl)-1H-pyrazol-1-yl]pyrimidin-4-yl]morpholine (A) (42 mg, 0.095 mmol, 1 equiv) in DMF (0.5 mL) under $N_2$ atmosphere. The resulting solution was stirred at room temperature for 3 h. The mixture was applied onto reverse phase chromatography to afford 4-[6-[3-(3-methylphenyl)-1H-pyrazol-1-yl]-2-[3-(1H-1,2,3-triazol-1-yl)propyl]pyrimidin-4-yl]morpholine (Compound 144) (6.4 mg, 15.66%) as white solid and 4-[6-[3-(3-methylphenyl)-1H-pyrazol-1-yl]-2-[3-(2H-1,2,3-triazol-2-yl)propyl]pyrimidin-4-yl]morpholine (Compound 145) (5.9 mg, 14.43%) as white solid.

Compound 144:

LC-MS RT=3.165 min, m/z=431.1 $[M+H]^+$ $^1$H NMR (400 MHz, Methanol-d4) δ 8.60 (d, J=2.8 Hz, 1H), 8.01 (d, J=1.1 Hz, 1H), 7.77 (s, 1H), 7.70 (d, J=8.9 Hz, 2H), 7.32 (t, J=7.6 Hz, 1H), 7.19 (d, J=7.5 Hz, 1H), 7.09 (s, 1H), 6.88 (d, J=2.7 Hz, 1H), 4.58 (t, J=7.0 Hz, 2H), 3.82-3.70 (m, 8H), 2.79 (t, J=7.2 Hz, 2H), 2.46 (p, J=7.1 Hz, 2H), 2.41 (s, 3H).

Compound 145:

LC-MS RT=2.173 min, m/z=431.2 $[M+H]^+$

H-NMR-PH-ICA-005-003-100-1: $^1$H NMR (400 MHz, Chloroform-d) δ 8.61 (d, J=2.7 Hz, 1H), 7.75 (s, 1H), 7.69 (d, J=7.6 Hz, 1H), 7.60 (s, 2H), 7.33 (t, J=7.6 Hz, 1H), 7.18 (d, J=7.5 Hz, 1H), 7.04 (s, 1H), 6.75 (d, J=2.7 Hz, 1H), 4.61 (t, J=7.2 Hz, 2H), 3.86-3.78 (m, 4H), 3.78-3.70 (m, 4H), 2.82 (t, J=7.3 Hz, 2H), 2.51 (p, J=7.3 Hz, 2H), 2.43 (s, 3H).

Synthesis of 2-((tetrahydrofuran-2-yl)methoxy)-4-(2,3,6,7-tetrahydrooxepin-4-yl-6-(3-(m-tolyl)-1H-pyrazol-1-yl)pyrimidine/2-((tetrahydrofuran-2-yl)methoxy)-4-(2,5,6,7-tetrahydrooxepin-4-yl)-6-(3-(m-tolyl)-1H-pyrazol-1-yl)pyrimidine (Compound 146)

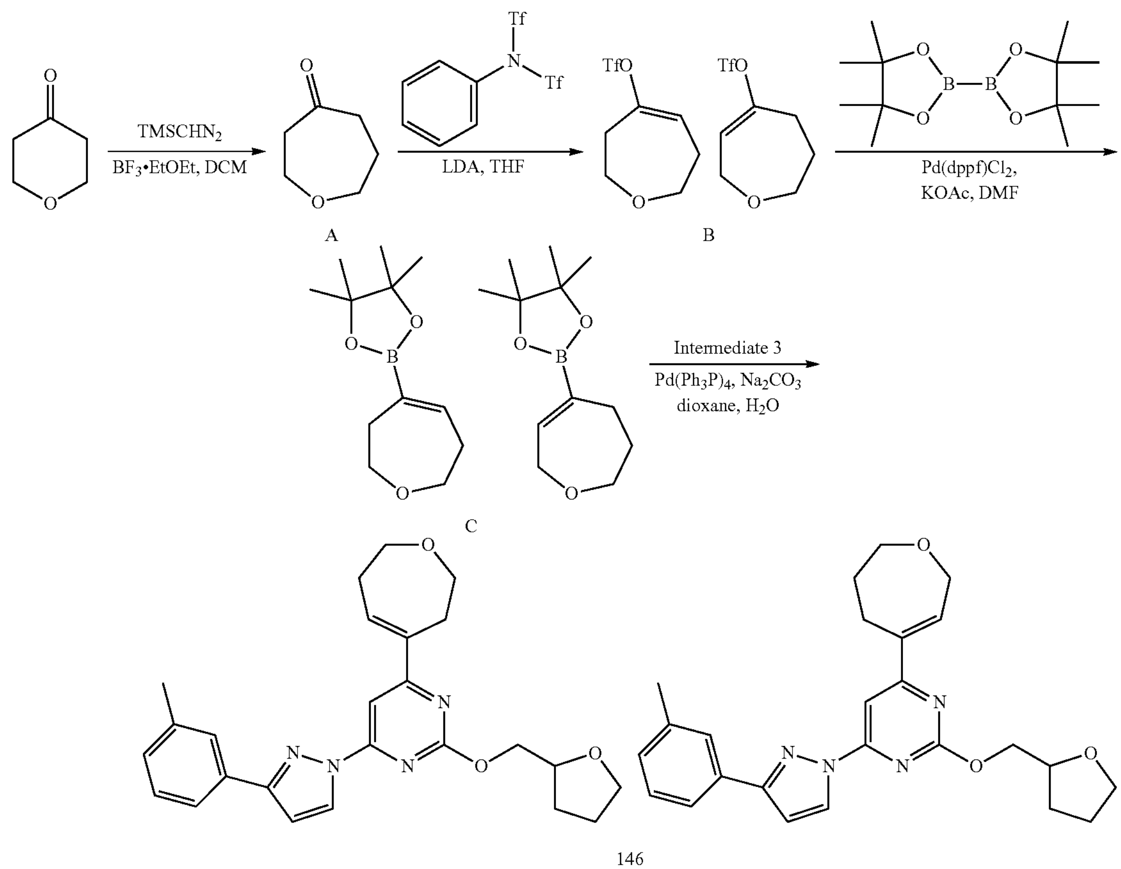

A

B

C

146

Preparation of A

To a stirred solution of oxan-4-one (3.1 g, 30.964 mmol, 1 equiv) in DCM (133 mL) was added $BF_3 \cdot Et_2O$ (4.28 mL) dropwise at −78° C. under $N_2$ atmosphere. After the addition, $TMSCHN_2$ (17.03 mL, 34.060 mmol, 1.10 equiv) was added into the mixture dropwise at −78° C. under $N_2$ atmosphere. The mixture was stirred for 2 h. The mixture was diluted with water and extracted with DCM. The organic layer was separated and dried over $MgSO_4$, filtered, and concentrated in vacuo. The residue was purified by silica gel chromatography to afford oxepan-4-one (A) (1.3 g, 36.78%) as colorless oil.

Preparation of B

To a stirred solution of LDA (10.513 mL, 10.513 mmol, 1.2 equiv) in THF (10 mL) at −78° C. under an $N_2$ atmosphere was added oxepan-4-one (A) (1 g, 8.761 mmol, 1 equiv) slowly via syringe. The mixture was stirred for an additional 30 min at −78° C. before 1,1,1-trifluoro-N-phenyl-N-trifluoromethanesulfonylmethanesulfonamide (3.13 g, 8.761 mmol, 1.00 equiv) in THF (10 mL) was added slowly via syringe. The reaction mixture was then stirred overnight with gradual warming to room temperature. The mixture was partially concentrated in vacuo and then partitioned between 3:1 EtOAc:hexane and water. The organic layer was separated, washed with water, washed once with sat. sodium chloride, dried over magnesium sulfate, and concentrated in vacuo to yield approximately a mixture of (E)-2,3,6,7-tetrahydrooxepin-4-yl trifluoromethanesulfonate:(E)-2,5,6,7-tetrahydrooxepin-4-yl trifluoromethanesulfonate (B). The 1 g crude material was taken on to the next step without further purification.

Preparation of C

A mixture of 2,3,6,7-tetrahydrooxepin-4-yl trifluoromethanesulfonate; 2,5,6,7-tetrahydrooxepin-4-yl trifluoromethanesulfonate (B) (800.00 mg, 1.625 mmol, 1.00 equiv), 4,4,5,5-tetramethyl-2-(4,4,5,5-tetramethyl-1,3,2-dioxaborolan-2-yl)-1,3,2-dioxaborolane (618.86 mg, 2.437 mmol, 1.50 equiv), Pd(dppf)$Cl_2$ (118.88 mg, 0.162 mmol, 0.10 equiv) and KOAc (318.90 mg, 3.249 mmol, 2.00 equiv) in dioxane (8.00 mL) was stirred for 3 h at 80° C. under $N_2$ atmosphere. The solution was applied onto a silica gel column chromatography to afford 4,4,5,5-tetramethyl-2-(2,3,6,7-tetrahydrooxepin-4-yl)-1,3,2-dioxaborolane; 4,4,5,5-tetramethyl-2-(2,5,6,7-tetrahydrooxepin-4-yl)-1,3,2-dioxaborolane (C) (350 mg, 48.06%) as colorless oil, which is a mixture of two isomers.

Preparation of Compound 146

A mixture of 4-chloro-6-[3-(3-methylphenyl)-1H-pyrazol-1-yl]-2-[(oxolan-2-yl)methoxy]-pyrimidine (Intermediate 3) (165.48 mg, 0.446 mmol, 2.00 equiv), 4,4,5,5-tetramethyl-2-(2,3,6,7-tetrahydrooxepin-4-yl)-1,3,2-(C) (100.00 mg, 0.223 mmol, 1.00 equiv), $Pd(PPh_3)_4$ (25.78 mg, 0.022 mmol, 0.10 equiv) and $Na_2CO_3$ (94.59 mg, 0.892 mmol, 4.00 equiv) in $H_2O$ (4.00 mL, 0.000 mmol, 0.00 equiv) and dioxane (4.00 mL) was stirred for 3 h at 110° C. under $N_2$ atmosphere. The mixture was applied onto a reverse phase chromatography to afford 4-[3-(3-methylphenyl)-1H-pyrazol-1-yl]-2-[(oxolan-2-yl)methoxy]-6-(2,3,6,7-tetrahydrooxepin-4-yl)pyrimidine; 4-[3-(3-methylphenyl)-1H-pyrazol-1-yl]-2-[(oxolan-2-yl)methoxy]-6-(2,5,6,7-tetrahydrooxepin-4-yl)pyrimidine (50 mg, 25.91%) as colorless oil, which is a mixture of two isomers.

LC-MS-PH-ICA-001-006-4-1: RT=2.266 min, m/z=433.2 $[M+H]^+$

H-NMR-PH-ICA-001-006-4-1: $^1H$ NMR (300 MHz, Methanol-$d_4$) δ 8.63 (d, J=2.8 Hz, 1H), 7.82-7.68 (m, 3H), 7.33 (t, J=7.6 Hz, 1H), 7.21 (d, J=7.6 Hz, 1H), 7.09 (t, J=6.2 Hz, 1H), 6.94 (d, J=2.8 Hz, 1H), 4.47-4.39 (m, 2H), 4.37-4.26 (m, 1H), 4.01-3.68 (m, 6H), 3.05-2.87 (m, 2H), 2.62 (q, J=5.6 Hz, 2H), 2.42 (s, 3H), 2.18-1.90 (m, 3H), 1.90-1.77 (m, 1H).

Synthesis of 4-chloro-2-(1-(6-morpholino-2-((tetrahydrofuran-2-yl) methoxy) pyrimidin-4-yl)-1H-pyrazol-3-yl)phenol (Compound 147)

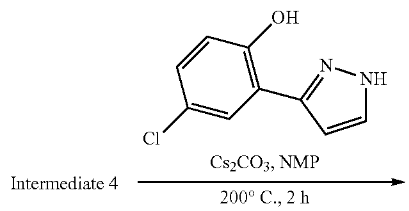

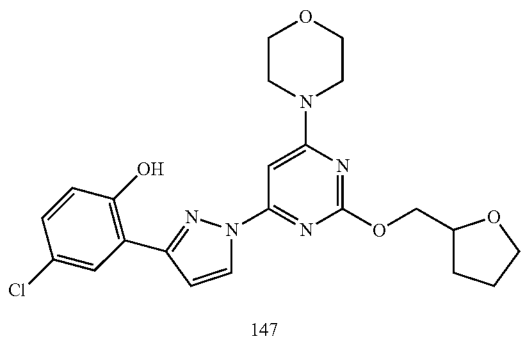

147

Compound 147 was prepared as indicated above, similar to preparation of Compound 137.

LC/MS (mobile phase 5-100% ACN in 5 min), Rt=3.60 min, $(M+H)^+$ 458

Synthesis of 4-(3-methoxypiperidin-1-yl)-2-(2-(tetrahydrofuran-2-yl)ethyl)-6-(3-(m-tolyl)-1H-pyrazol-1-yl)pyrimidine (Compound 148)

148

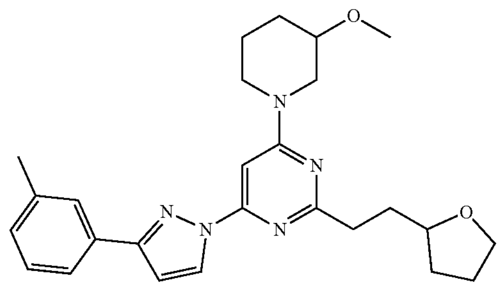

The procedure for the synthesis of Compound 148 is similar to the procedure described for Compound 136.

LC/MS (mobile phase 5-100% ACN in 5 min), Rt=3.70 min, $(M+H)^+$ 448

Synthesis of 4-(6-(3-(3,4-difluorophenyl)-1H-pyrazol-1-yl)-2-((tetrahydrofuran-2-yl)methoxy)pyrimidin-4-yl)morpholine (Compound 149)

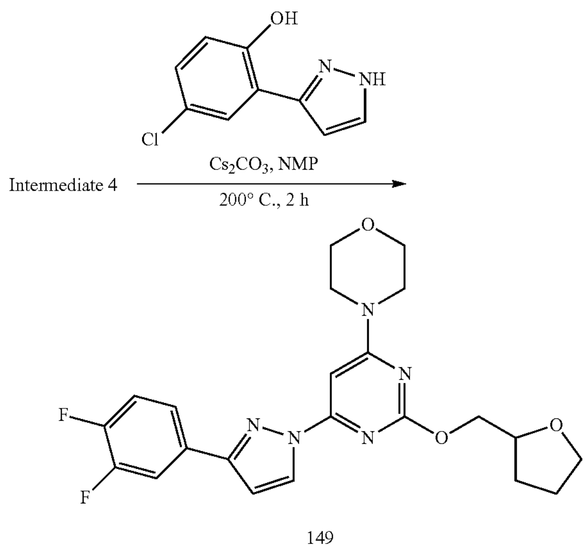

149

Compound 149 was prepared as indicated above, similar to the preparation of Compound 137.

LC/MS (mobile phase 5-100% ACN in 5 min), Rt 4.08 min, $(M+H)^+$ 444

Synthesis of 5-(4-((3aR,6aR)-hexahydro-4H-furo[3,2-b]pyrrol-4-yl)-6-(3-(m-tolyl)-1H-pyrazol-1-yl)pyrimidin-2-yl)pentane-1,2-diol (Compound 150)

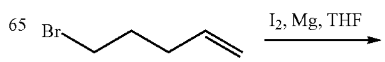

-continued

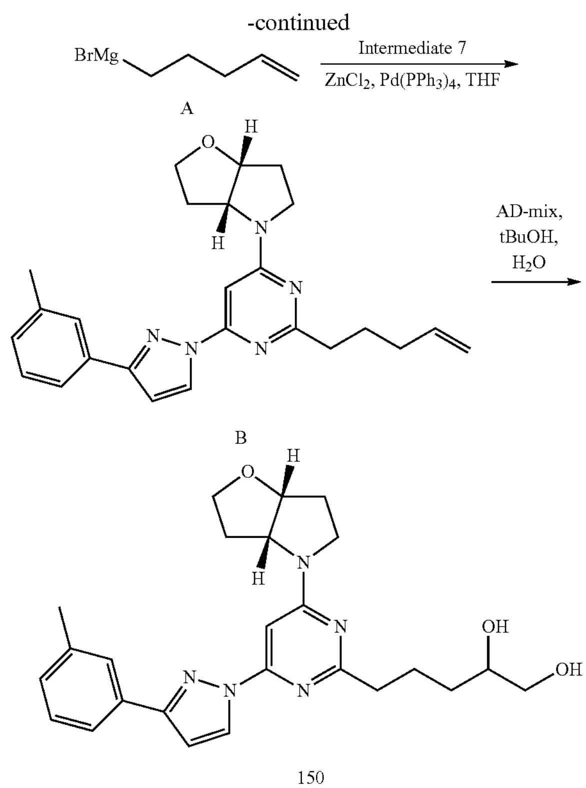

A

B

150

Preparation of A

Into a 100 ml 3-necked round bottom flask, was placed $I_2$ (100.00 mg), Mg (1.00 g, 41.144 mmol, 3.07 equiv) in dry THF (100.00 mL), to this was added 5-bromopent-1-ene (2.00 g, 13.420 mmol, 1.00 equiv) dropwise at reflux, and the yellow system changed to colorless and after stirred for 1 h at reflux, the colorless system changed to grey. The reaction solution (A) was used for next step directly without purification.

Preparation of B

Into 100 ml 3-necked round bottom flask, under $N_2$, to a bromo(pent-4-en-1-yl)magnesium (10.00 mL) (~0.25 mol/L) THF (10.00 mL) solution, was added $ZnCl_2$ (4.00 mL, 0.7 mol/L in THF) dropwise at −20° C., and warmed to room temperature, and stirred for 30 minutes, to this was added 4-[(3aR,6aR)-hexahydro-2H-furo[3,2-b]pyrrol-4-yl]-2-chloro-6-[3-(3-methylphenyl)-1H-pyrazol-1-yl]pyrimidine (Intermediate 7) (20.00 mg, 0.052 mmol, 1.00 equiv) and $Pd(PPh_3)_4$ (20.00 mg, 0.017 mmol, 0.33 equiv) in THF in one batch, warmed to reflux and stirred for 2 h at reflux, monitor by TLC and LCMS, LCSM showed MS as desired product formed, and SM was consumed. This reaction was scale up 100 mg. This two batch was combined and concentration and purified on silica gel column with EA/PA (10%) to afford 60 mg of the desired product (B).

Preparation of Compound 150

Into a 25 mL round bottom flask, was placed 4-[(3aR,6aR)-hexahydro-2H-furo[3,2-b]pyrrol-4-yl]-6-[3-(3-methylphenyl)-1H-pyrazol-1-yl]-2-(pent-4-en-1-yl)pyrimidine (B) (60.00 mg, 0.144 mmol, 1.00 equiv), methanesulfonamide (60.10 mg, 0.632 mmol, 4.38 equiv), AD-mix-alpha (600.00 mg) in t-BuOH (18.00 mL) and $H_2O$ (18.00 mL), and stirred overnight at room temperature monitored by LCMS, LCMS showed desired product was formed, and starting material was consumed. This reaction was extracted with 3×100 ml of EA, and dried over anhydrous $Na_2SO_4$, and concentrated and purified on silica gel column with MeOH/DCM (8%) to afford 5-[4-[(3aR,6aR)-hexahydro-2H-furo[3,2-b]pyrrol-4-yl]-6-[3-(3-methylphenyl)-1H-pyrazol-1-yl]pyrimidin-2-yl]pentane-1,2-diol (Compound 150) (26 mg, 40.05%) as a white solid.

LC-MS RT=1.524 min, m/z=450.2 $[M+H]^+$ $^1H$ NMR (300 MHz, DMSO-$d_6$) δ 8.62 (d, J=2.7 Hz, 1H), 7.77 (d, J=11.7 Hz, 2H), 7.36 (t, J= 7.6 Hz, 1H), 7.21 (d, J=7.6 Hz, 1H), 7.05 (d, J=2.7 Hz, 1H), 6.79 (s, 1H), 4.84-4.51 (m, 2H), 4.50-4.30 (m, 2H), 3.74 (t, J=8.2 Hz, 2H), 3.54-3.37 (m, 2H), 3.26 (q, J=5.2 Hz, 2H), 2.68 (t, J=7.6 Hz, 2H), 2.39 (s, 3H), 2.33-2.20 (m, 1H), 2.08-1.89 (m, 3H), 1.83-1.70 (m, 1H), 1.58-1.46 (m, 1H), 1.39-1.22 (m, 3H).

Synthesis of 1-(4-((3aR,6aR)-hexahydro-4H-furo[3,2-b]pyrrol-4-yl)-6-(3-(m-tolyl)-1H-pyrazol-1-yl)pyrimidin-2-yl)ethane-1,2-diol (Compound 151)

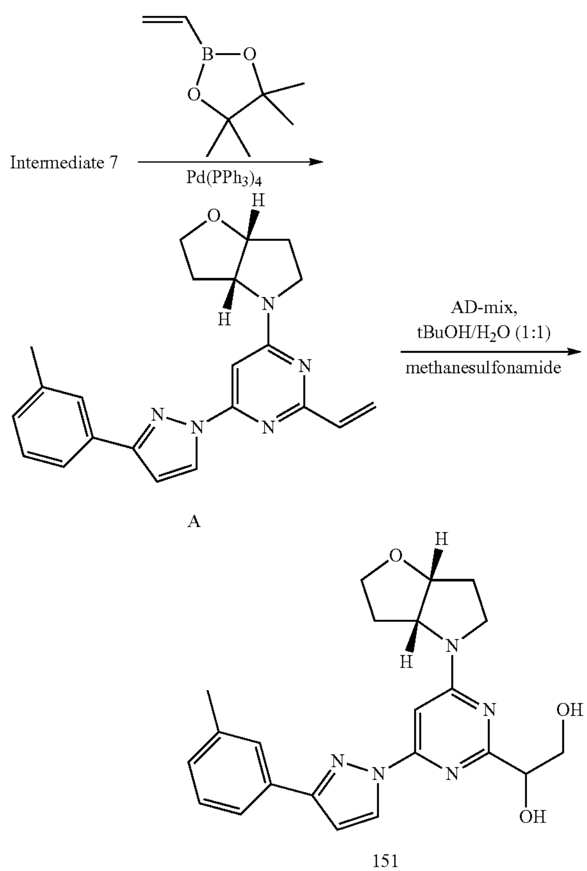

A

151

Preparation of A

Into a 20-mL sealed tube purged and maintained with an inert atmosphere of nitrogen, was placed 4-[(3aR,6aR)-hexahydro-2H-furo[3,2-b]pyrrol-4-yl]-2-chloro-6-[3-(3- methylphenyl)-1H-pyrazol-1-yl]pyrimidine (Intermediate 7) (150.00 mg, 0.393 mmol, 1.00 equiv), dioxane (2.00 mL, 23.608 mmol, 60.10 equiv), $Cs_2CO_3$ (385.15 mg, 1.178 mmol, 3.00 equiv), water (0.20 mL, 0.000 mmol, 0.00 equiv), 2-ethenyl-4,4,5,5-tetramethyl-1,3,2-dioxaborolane (121.00 mg, 0.786 mmol, 2.00 equiv), tetrakis(triphenylphosphane) palladium (45.39 mg, 0.039 mmol, 0.10 equiv). The resulting solution was stirred at 100° C. for 4 h. The resulting mixture was concentrated. The residue was applied onto a silica gel column with ethyl acetate/petroleum ether (1/3). This resulted in 80 mg (54.53%) of 4-[(3aR,6aR)-hexahydro-2H-furo[3,2-b]pyrrol-4-yl]-2-ethenyl-6-[3-(3-methylphenyl)-1H-pyrazol-1-yl]pyrimidine (A) as a white solid.

Preparation of Compound 151

Into a 25-mL vial, was placed 4-[(3aR,6aR)-hexahydro-2H-furo[3,2-b]pyrrol-4-yl]-2-ethenyl-6-[3-(3-methylphenyl)-1H-pyrazol-1-yl]pyrimidine (A) (80.00 mg, 0.214 mmol, 1.00 equiv), AD-mix-alpha (640.00 mg), 2-methylpropan-2-ol (2.00 mL, 0.027 mmol, 0.13 equiv), water (2.00 mL, 0.111 mmol, 0.52 equiv), methanesulfonamide (40.75 mg, 0.428 mmol, 2.00 equiv). The resulting solution was stirred at room temperature for 2 h. The resulting solution was extracted with 3×20 mL of ethyl acetate concentrated. The residue was applied onto a reverse phase chromatography with ACN/$H_2O$ (1/1). This resulted in 21.8 mg (24.98%) of 1-[4-[(3aR,6aR)-hexahydro-2H-furo[3,2-b]pyrrol-4-yl]-6-[3-(3-methylphenyl)-1H-pyrazol-1-yl]pyrimidin-2-yl]ethane-1,2-diol (Compound 151) as a white solid.

LC-MS RT=1.756 min, m/z=408.3 $[M+H]^+$

NMR (400 MHz, DMSO-$d_6$) δ 8.81 (dd, J=13.7, 2.7 Hz, 1H), 7.88-7.71 (m, 2H), 7.37 (t, J=7.6 Hz, 1H), 7.22 (d, J=7.6 Hz, 1H), 7.08 (d, J=2.7 Hz, 1H), 6.84 (s, 1H), 4.98 (t, J=7.2 Hz, 1H), 4.77-4.51 (m, 3H), 4.45 (q, J=5.5 Hz, 1H), 4.15 (s, 1H), 3.84-3.65 (m, 4H), 3.44 (s, 1H), 2.39 (s, 3H), 2.08 (s, 4H).

Synthesis of (4-((3aR,6aR)-hexahydro-4H-furo[3,2-b]pyrrol-4-yl)-6-(3-(m-tolyl)-1H-pyrazol-1-yl)pyrimidin-2-yl)methanol (Compound 152)

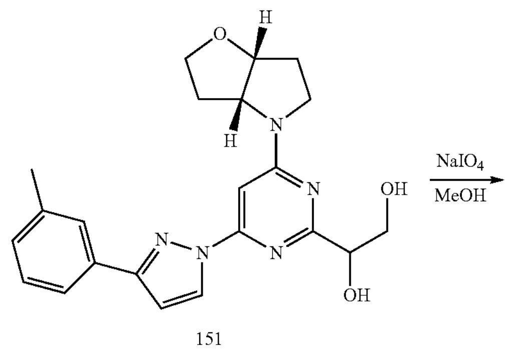

151

-continued

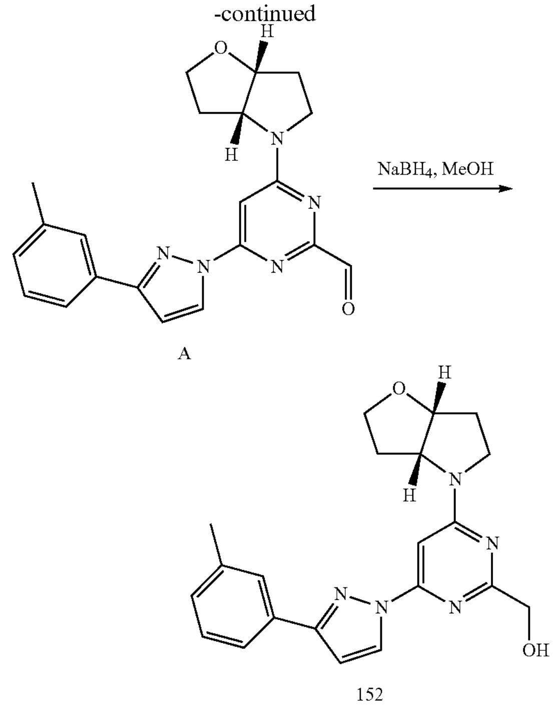

A

152

Preparation of A

Into a 20-mL vial, was placed 1-[4-[(3aR,6aR)-hexahydro-2H-furo[3,2-b]pyrrol-4-yl]-6-[3-(3-methylphenyl)-1H-pyrazol-1-yl]pyrimidin-2-yl]ethane-1,2-diol (Compound 151) (40.00 mg, 0.098 mmol, 1.00 equiv), methanol (2.00 mL, 0.031 mmol, 1.27 equiv), water (0.30 mL, 0.014 mmol, 0.57 equiv), sodium periodate (62.8 mg, 0.294 mmol, 3.00 equiv). The resulting solution was stirred at room temperature for 1 h. The resulting mixture was concentrated. The residue was applied onto a silica gel column with ethyl acetate/petroleum ether (1/1). This resulted in 30 mg (81.39%) of 4-[(3aR,6aR)-hexahydro-2H-furo[3,2-b]pyrrol-4-yl]-6-[3-(3-methylphenyl)-1H-pyrazol-1-yl]pyrimidine-2-carbaldehyde (A) as a white solid.

Preparation of Compound 152

Into a 20-mL vial, was placed 4-[(3aR,6aR)-hexahydro-2H-furo[3,2-b]pyrrol-4-yl]-6-[3-(3-methylphenyl)-1H-pyrazol-1-yl]pyrimidine-2-carbaldehyde (A) (30.00 mg, 0.107 mmol, 1.00 equiv), EtOH (1.00 mL, 24.699 mmol, 231.82 equiv), $NaBH_4$ (8.06 mg, 0.213 mmol, 2.00 equiv). The resulting solution was stirred for 30 min at room temperature. The reaction was then quenched by the addition of MeOH. The resulting solution was extracted with 3×20 ml of ethyl acetate The resulting mixture was concentrated. This resulted in 11 mg (36.47%) of [4-[(3aR,6aR)-hexahydro-2H-furo[3,2-b]pyrrol-4-yl]-6-[3-(3-methylphenyl)-1H-pyrazol-1-yl]pyrimidin-2-yl]methanol (Compound 152) as a white solid.

LCMS-RT=1.821 min, m/z=378.4 $[M+H]^+$ $^1H$ NMR (400 MHz, DMSO-$d_6$) δ 8.77 (d, J=2.7 Hz, 1H), 7.88-7.69 (m, 2H), 7.37 (t, J=7.6 Hz, 1H), 7.22 (d, J=7.6 Hz, 1H), 7.08 (d, J=2.7 Hz, 1H), 6.84 (s, 1H), 4.95 (s, 1H), 4.64 (d, J=41.5 Hz, 2H), 4.45 (d, J=5.9 Hz, 2H), 3.75 (s, 3H), 3.47 (s, 1H), 2.40 (s, 3H), 2.36-2.17 (m, 1H), 2.00 (s, 3H).

Synthesis of 1-(4-morpholino-6-(3-(m-tolyl)-1H-pyrazol-1-yl)pyrimidin-2-yl)ethane-1,2-diol (Compound 153)

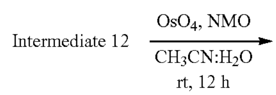

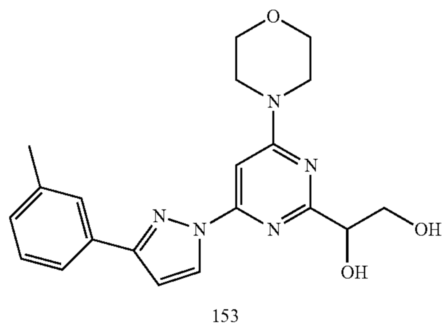

153

Compound 153 was prepared as indicated above LCMS (MM): m/z 382 $[M+H]^+$

Synthesis of 4-[3-(3-methylphenyl)-1H-pyrazol-1-yl]-6-(morpholin-4-yl)pyrimidin-2-yl]methanol (Compound 154)

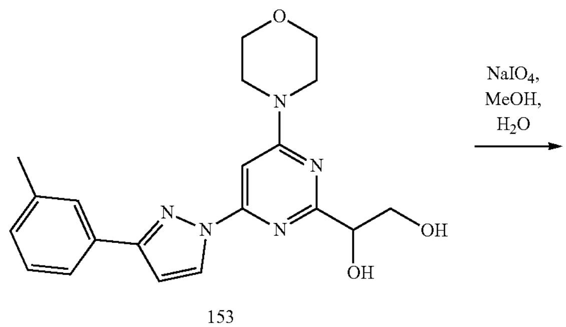

153

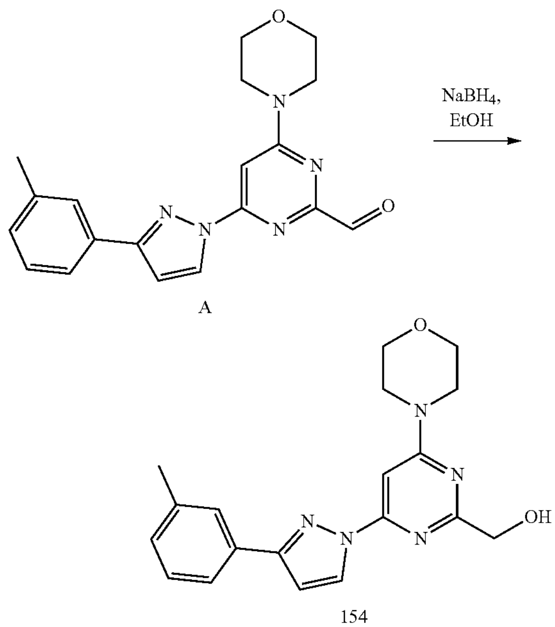

A

154

Preparation of A

A mixture of 1-[4-[3-(3-methylphenyl)-1H-pyrazol-1-yl]-6-(morpholin-4-yl)pyrimidin-2-yl]ethane-1,2-diol (Compound 153) (30 mg, 0.079 mmol, 1 equiv), $NaIO_4$ (33.65 mg, 0.157 mmol, 2.00 equiv), MeOH (2 mL) and $H_2O$ (2 mL) was stirred over night at room temperature. The resulting suspension was concentrated and purified by flash chromatography on silica gel eluting with EA/PE (0-100%) to provide 4-[3-(3-methylphenyl)-1H-pyrazol-1-yl]-6-(morpholin-4-yl)pyrimidine-2-carbaldehyde (A) (13 mg, 47.31%) as a light yellow oil.

Preparation of Compound 154

To a solution of 4-[3-(3-methylphenyl)-1H-pyrazol-1-yl]-6-(morpholin-4-yl)pyrimidine-2-carbaldehyde (A) (13.00 mg, 0.037 mmol, 1.00 equiv) in EtOH (1.00 mL) was added $NaBH_4$ (2.82 mg, 0.075 mmol, 2.00 equiv) and the mixture was stirred over night at room temperature. The resulting suspension was concentrated and purified by flash chromatography on silica gel eluting with EA/PE (0-100%) to provide [4-[3-(3-methylphenyl)-1H-pyrazol-1-yl]-6-(morpholin-4-yl)pyrimidin-2-yl]methanol (Compound 154) (7.6 mg, 58.13%) as a white solid.

LC-MS-RT=1.755 min, m/z=352.4 $[M+H]^+$ $^1$H NMR (400 MHz, DMSO-$d_6$) δ 8.74 (d, J=2.7 Hz, 1H), 7.83 (s, 1H), 7.79 (d, J=7.9 Hz, 1H), 7.36 (t, J=7.5 Hz, 1H), 7.22 (d, J=8.2 Hz, 1H), 7.09 (s, 1H), 7.07 (d, J=2.7 Hz, 1H), 4.98 (t, J=6.1 Hz, 1H), 4.45 (d, J=6.1 Hz, 2H), 3.73 (s, 8H), 2.40 (s, 3H).

Synthesis of 2-methoxy-1-(4-morpholino-6-(3-(m-tolyl)-1H-pyrazol-1-yl)pyrimidin-2-yl)ethan-1-ol (Compound 155) and 2-methoxy-2-(4-morpholino-6-(3-(m-tolyl)-1H-pyrazol-1-yl)pyrimidin-2-yl)ethan-1-ol (Compound 156)

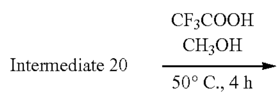

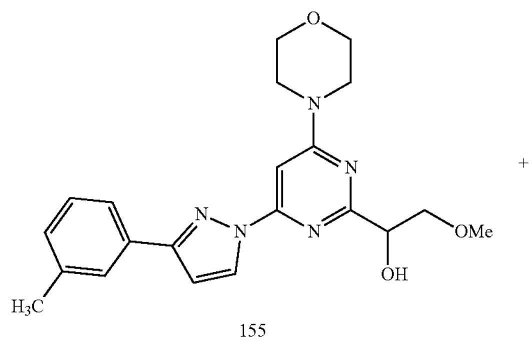

155

+

-continued

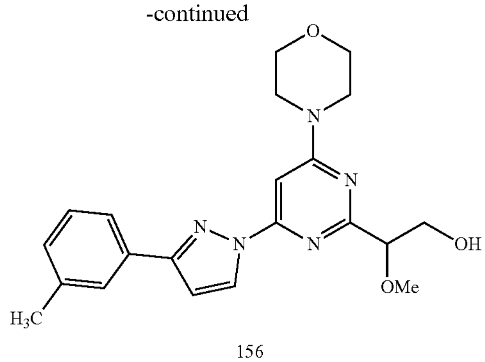

156

To a stirred solution of Intermediate 20 (300 mg, 0.82 mmol) in $CH_3OH$ (5 mL) at room temperature under $N_2$ atmosphere, was added $CF_3COOH$ (0.50 mL, 6.60 mmol). The reaction mixture was gradually heated to 50° C. and stirred for 4 h. $CF_3COOH$ was removed under vacuum, the reaction mixture was diluted with water (20 mL) and extracted with EtOAc (2×25 mL). The combined organic extracts were washed with sat. $NaHCO_3$ (30 mL), brine (30 mL), dried over anhydrous $Na_2SO_4$, filtered and concentrated under vacuum to obtain the crude product. The crude product was purified by silica-gel column chromatography using 10-45% EtOAc:Hexanes. Fractions containing the product were combined and concentrated under vacuum to obtain Compound 155 (55.0 mg, 0.13 mmol, 16% yield) as an off-white solid and Compound 156 (75.0 mg, 0.19 mmol, 22% yield) as an off-white solid.

Compound 155:

LCMS (ESI): m/z=396 $[M+H]^+$;

$^1$H NMR (400 MHz, DMSO-$d_6$) δ: 8.78 (d, J=2.8 Hz, 1H), 7.83 (s, 1H), 7.78 (d, J=7.6 Hz, 1H), 7.35 (t, J=7.6 Hz, 1H), 7.21 (d, J=7.6 Hz, 1H), 7.09 (s, 1H), 7.08 (d, J=2.8 Hz, 1H), 5.17 (d, J=6.4 Hz, 1H), 4.57 (q, J=6.0 Hz, 10.4 Hz, 1H), 3.72 (brs, 10H), 3.27 (s, 3H), 2.38 (s, 3H).

Compound 156:

LCMS (ESI): m/z=396 $[M+H]^+$; HPLC: =98.1 (% of AUC).

$^1$H NMR (400 MHz, DMSO-$d_6$) δ: 8.61 (d, J=2.4 Hz, 1H), 7.83 (s, 1H), 7.78 (d, J=7.6 Hz, 1H), 7.35 (t, J=7.6 Hz, 1H), 7.21 (d, J=7.6 Hz, 1H), 7.12 (s, 1H), 7.07 (d, J=2.4 Hz, 1H), 4.79 (t, J=6.0 Hz, 1H), 4.17 (q, J=5.2 Hz, 6.8 Hz, 1H), 3.77-3.68 (m, 10H), 3.32 (s, 3H), 2.39 (s, 3H).

Synthesis of 4-(2-(2,3-dihydroxypropoxy)-6-(3-(3-methoxyphenyl)-1H-pyrazol-1-yl)pyrimidin-4-yl) thiomorpholine 1,1-dioxide (Compound 157)

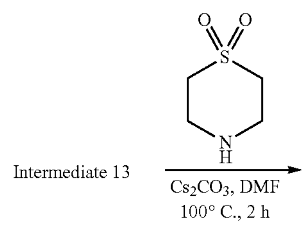

-continued

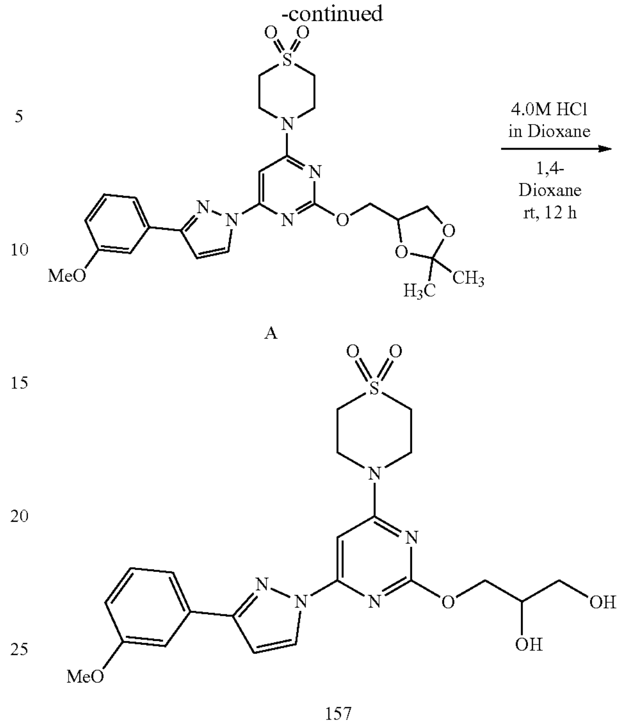

A

157

Preparation of A

To a solution of Intermediate 24 (200 mg, 0.24 mmol) in anhydrous DMF (10 ml) at room temperature under $N_2$ atmosphere was added thiomorpholine 1,1-dioxide (97.0 mg, 0.72 mmol) followed with $Cs_2CO_3$ (234 mg, 0.72 mmol). The reaction mixture was gradually heated to 100° C. and stirred for 2 h. The reaction mixture was diluted with water (50 mL) and extracted with EtOAc (2×100 mL). The combined organic extracts were washed with brine solution (50 mL), dried over anhydrous $Na_2SO_4$ and concentrated under reduced pressure to obtain the crude product. The crude product was purified by silica-gel column chromatography using 15% EtOAc:Hexanes. Fractions containing the product were combined and concentrated under vacuum to obtain A (170 mg, 0.33 mmol, 45%) as an off-white solid.

MS (MM): m/z 516 $[M+H]^+$.

$^1$H NMR (400 MHz, $CDCl_3$): δ 8.54 (d, J=3.2 Hz, 1H), 7.47-7.46 (m, 2H), 7.39-7.35 (m, 1H), 7.03 (s, 1H), 6.95-6.93 (m, 1H), 6.76 (d, J=2.8 Hz, 1H), 4.53-4.46 (m, 2H), 4.34-4.17 (m, 6H), 3.95-3.89 (m, 4H), 3.12 (t, J=4.8 Hz, 4H), 1.48 (s, 3H), 1.40 (s, 3H).

Preparation of Compound 157

To a solution of A (170 mg, 0.33 mmol)) in anhydrous 1,4-Dioxane (5 mL), at room temperature under $N_2$ atmosphere was added HCl (4.0 M HCl in 1,4-Dioxane, 2.0 mL, 65.8 mmol). The reaction mixture was stirred at room temperature for 12 h. The solvent concentrated under reduced pressure to obtain the crude product. The crude product was triturated with MTBE:EtOAc (1:1, 50 mL) to obtain Compound 157 (30.0 mg, 0.06 mmol, 19%) as an off-white solid.

LCMS (MM): m/z 476 $[M+H]^+$; HPLC=98.1 (% of AUC).

$^1H$ NMR (400 MHz, DMSO-$d_6$): δ 8.62 (d, J=2.8 Hz, 1H), 7.60-7.55 (m, 2H), 7.42-7.38 (m, 1H), 7.12-6.97 (m, 3H), 5.00 (d, J=5.2 Hz, 1H), 4.73-4.61 (m, 1H), 4.41-4.37 (m, 1H), 4.22-4.17 (m, 5H), 3.84-3.82 (m, 4H), 3.46-3.44 (m, 2H), 3.31-3.24 (m, 4H).

The following compounds were synthesized using procedures similar to the synthesis of Compound 157:

| # | Structure | Name | LCMS (ESI): m/z $[M + H]^+$ |
|---|---|---|---|
| 158 | 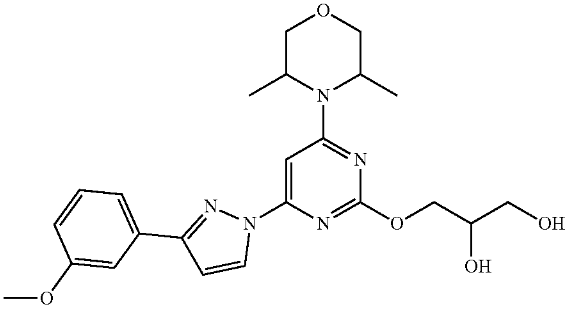 [SMILES: COc1cccc(-c2ccn(-c3cc(N4C(C)COCC4C)nc(OCC(O)CO)n3)n2)c1] | 3-((4-(3,5-dimethylmorpholino)-6-(3-(3-methoxyphenyl)-1H-pyrazol-1-yl)pyrimidin-2-yl)oxy)propane-1,2-diol | 456.2 |
| 159 | 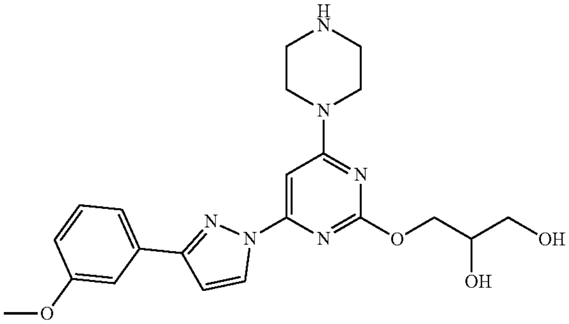 [SMILES: COc1cccc(-c2ccn(-c3cc(N4CCNCC4)nc(OCC(O)CO)n3)n2)c1] | 3-((4-(3-(3-methoxyphenyl)-1H-pyrazol-1-yl)-6-(piperazin-1-yl)pyrimidin-2-yl)oxy)propane-1,2-diol | 427.2 |
| 160 | 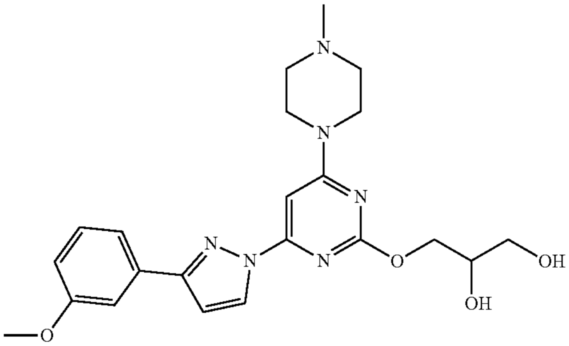 [SMILES: COc1cccc(-c2ccn(-c3cc(N4CCN(C)CC4)nc(OCC(O)CO)n3)n2)c1] | 3-((4-(3-(3-methoxyphenyl)-1H-pyrazol-1-yl)-6-(4-methylpiperazin-1-yl)pyrimidin-2-yl)oxy)propane-1,2-diol | 441.2 |
| 161 | 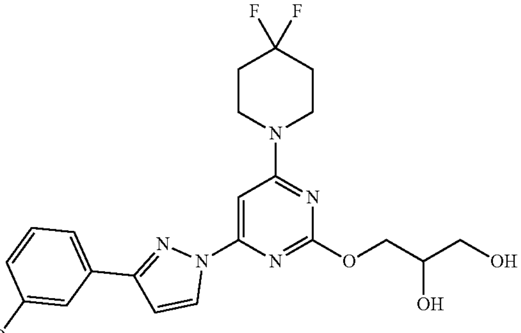 | 3-((4-(4,4-difluoropiperidin-1-yl)-6-(3-(3-methoxyphenyl)-1H-pyrazol-1-yl)pyrimidin-2-yl)oxy)propane-1,2-diol | 462.2 |

-continued

| # | Structure | Name | LCMS (ESI): m/z [M + H]+ |
|---|---|---|---|
| 162 | 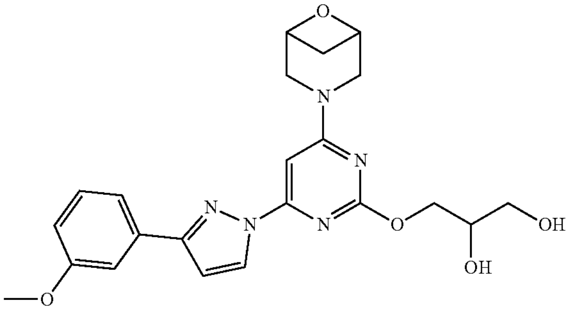 [SMILES: COc1cccc(-c2ccn(-c3cc(N4CC5CC(C4)O5)nc(OCC(O)CO)n3)n2)c1] | 3-((4-(6-oxa-3-azabicyclo[3.1.1]heptan-3-yl)-6-(3-(3-methoxyphenyl)-1H-pyrazol-1-yl)pyrimidin-2-yl)oxy)propane-1,2-diol | 440.2 |
| 163 | 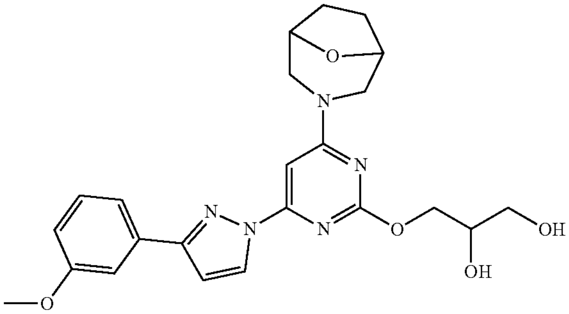 [SMILES: COc1cccc(-c2ccn(-c3cc(N4CC5CCC(C4)O5)nc(OCC(O)CO)n3)n2)c1] | 3-((4-(8-oxa-3-azabicyclo[3.2.1]octan-3-yl)-6-(3-(3-methoxyphenyl)-1H-pyrazol-1-yl)pyrimidin-2-yl)oxy)propane-1,2-diol | 454.2 |

Synthesis of 3-((4-morpholino-6-(3-(3-(trifluoromethyl)phenyl)-1H-pyrazol-1-yl)pyrimidin-2-yl)oxy) propane-1,2-diol (Compound 164)

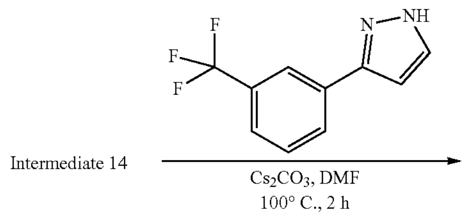

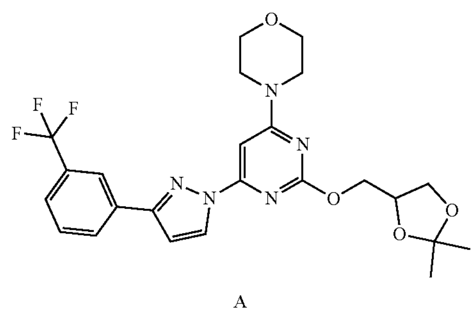

A

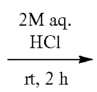

-continued

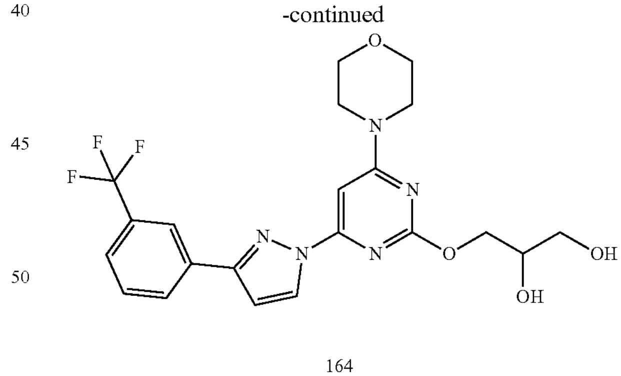

164

Compound 164 was synthesized as illustrated above using 1 eq. of Intermediate 14 (400 mg), 2 eq of Cs2CO3 and 1.2 eq of 3-(3-(trifluoromethyl) phenyl)-1H-pyrazole in 10 ml DMF. Heated at 100° C. for 2 h, purified by silica gel chromatography to give Compound 164 (70% yield)

LC/MS (M+1) 465.2

The following compounds were synthesized using procedures similar to the synthesis of Compound 164:

| # | Structure | Name | LCMS (ESI): m/z [M + H]+ |
|---|---|---|---|
| 165 | 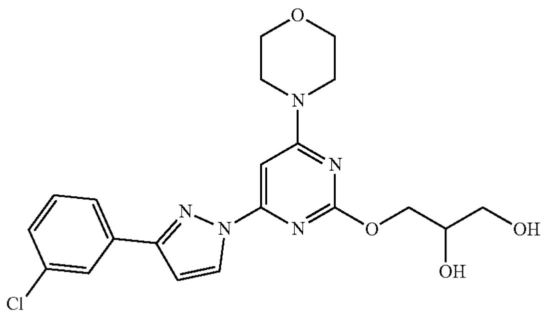 [SMILES: OCC(O)COc1nc(N2CCOCC2)cc(-n2ccc(-c3cccc(Cl)c3)n2)n1] | 3-((4-(3-(3-chlorophenyl)-1H-pyrazol-1-yl)-6-morpholinopyrimidin-2-yl)oxy)propane-1,2-diol | 432 |
| 166 | 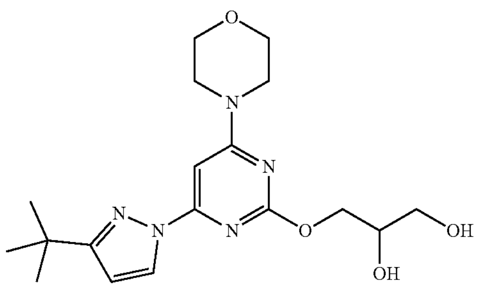 [SMILES: CC(C)(C)c1ccn(-c2cc(N3CCOCC3)nc(OCC(O)CO)n2)n1] | 3-((4-(3-(tert-butyl)-1H-pyrazol-1-yl)-6-morpholinopyrimidin-2-yl)oxy)propane-1,2-diol | 378 |
| 167 | 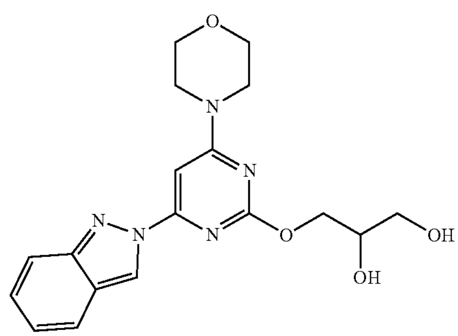 [SMILES: OCC(O)COc1nc(N2CCOCC2)cc(-n2cc3ccccc3n2)n1] | 3-((4-(2H-indazol-2-yl)-6-morpholinopyrimidin-2-yl)oxy)propane-1,2-diol | 372 |
| 168 | 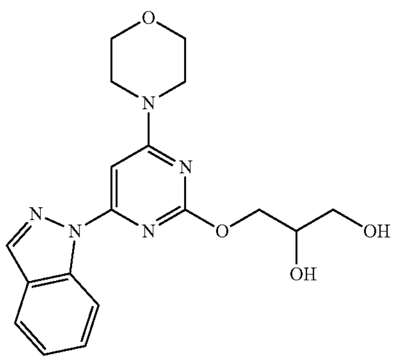 [SMILES: OCC(O)COc1nc(N2CCOCC2)cc(-n2ncc3ccccc32)n1] | 3-((4-(1H-indazol-1-yl)-6-morpholinopyrimidin-2-yl)oxy)propane-1,2-diol | 372 |

Synthesis of 2-((4-morpholino-6-(3-(m-tolyl)-pyrazol-1-yl)pyrimidin-2-yl)oxy-1-phenylethan-1-one (Compound 169)

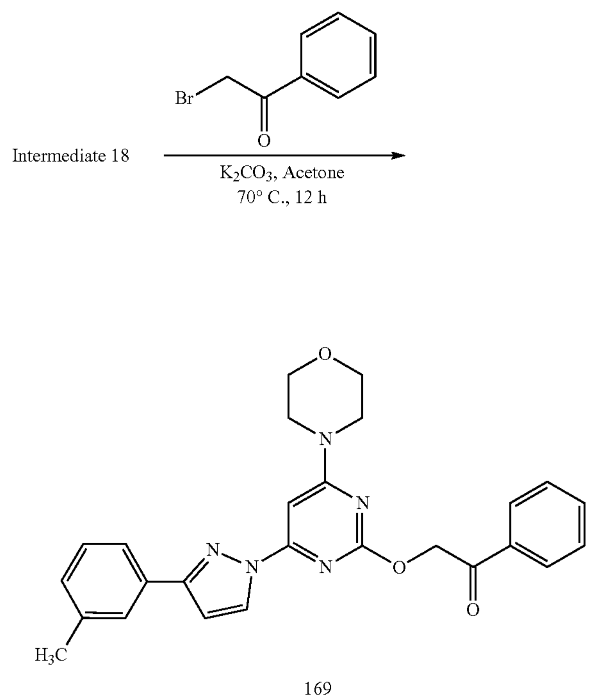

169

To a solution of Intermediate 18 (200 mg, 0.59 mmol) in Acetone (5.0 mL) at room temperature under $N_2$ atmosphere, was added $K_2CO_3$ (164 mg, 1.18 mmol), followed with 2-bromo-1-phenylethan-1-one (118 mg, 0.59 mmol). The reaction mixture was gradually heated to 70° C. and stirred for 12 h. Reaction mixture was cooled to room temperature, acetone evaporated, diluted with water (50 mL), and extracted with EtOAc (2×50 mL). The combined organic extracts were washed with brine solution (50 mL), dried over anhydrous $Na_2SO_4$ and concentrated under reduced pressure to obtain the crude compound. The crude product was purified by silica-gel column chromatography using 40-45% EtOAc:Hexanes. Fractions containing the product were combined and concentrated under vacuum to obtain Compound 169 (100 mg, 0.22 mmol, 37% yield) as an off-white solid.

LCMS (ESI): m/z=456[M+H]$^+$; HPLC: =>99 (% of AUC).

$^1$H NMR (400 MHz, DMSO-$d_6$) δ: 8.40 (d, J=2.8 Hz, 1H), 8.02 (dd, J=1.6 Hz, 8.8 Hz, 2H), 7.79 (s, 1H), 7.73 (d, J=8.0 Hz, 1H), 7.70 (t, J=7.6 Hz, 1H), 7.58 (t, J=7.6 Hz, 2H), 7.34 (t, J=7.6 Hz, 1H), 7.20 (d, J=7.2 Hz, 1H), 7.01 (d, J=2.4 Hz, 1H), 6.88 (s, 1H), 5.69 (s, 2H), 3.59-3.50 (m, 8H), 2.37 (s, 3H).

Synthesis of (S)-2-methoxy-1-(4-morpholino-6-(3-(m-tolyl)-1H-pyrazol-1-yl)pyrimidin-2-yl)ethan-1-ol (Compound 170) and (R)-2-methoxy-1-(4-morpholino-6-(3-(m-tolyl)-1H-pyrazol-1-yl)pyrimidin-2-yl)ethan-1-ol (Compound 171)

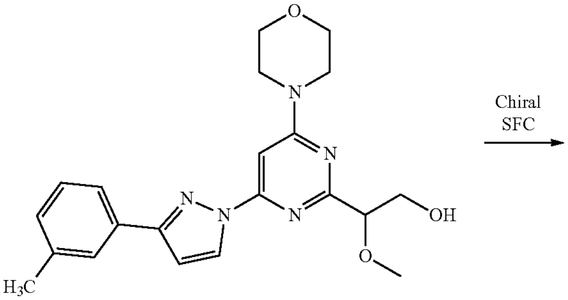

156

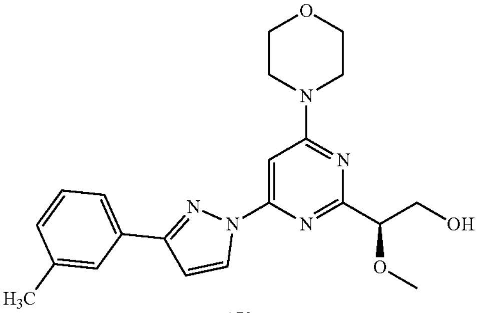

170
1st eluting

+

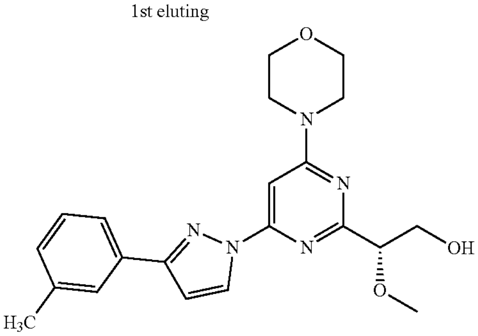

171
2nd eluting
Absolute configuration not determined

The mixture of enantiomers (Compound 156) was separated by chiral HPLC (SFC).

Compound 170 (1$^{st}$ Eluting):

LCMS (ESI): m/z=396 [M+H]$^+$; HPLC: >99 (% of AUC, Rt=4.77 min).

$^1$H NMR (400 MHz, DMSO-$d_6$) δ: 8.61 (d, J=2.8 Hz, 1H), 7.82 (s, 1H), 7.78 (d, J=7.6 Hz, 1H), 7.35 (t, J=7.6 Hz, 1H), 7.21 (d, J=7.6 Hz, 1H), 7.12 (s, 1H), 7.07 (d, J=2.8 Hz, 1H), 4.77 (brs, 1H), 4.18-4.15 (m, 1H), 3.71 (brs, 10H), 3.32 (s, 3H), 2.39 (s, 3H).

Compound 171 (2$^{nd}$ Eluting):

LCMS (ESI): m/z=396 [M+H]$^+$; HPLC: 96.0 (% of AUC, Rt=5.34 min).

$^1$H NMR (400 MHz, DMSO-$d_6$) δ: 8.61 (d, J=2.8 Hz, 1H), 7.82 (s, 1H), 7.78 (d, J=8.0 Hz, 1H), 7.35 (t, J=7.6 Hz, 1H), 7.21 (d, J=7.6 Hz, 1H), 7.12 (s, 1H), 7.07 (d, J=2.8 Hz, 1H), 4.77 (t, J=6.0 Hz, 1H), 4.18-4.15 (m, 1H), 3.76-3.71 (m, 10H), 3.32 (s, 3H), 2.39 (s, 3H).

Synthesis of (1-(2-(2-(1-methyl-1H-pyrazol-4-yl) ethoxy)-6-morpholinopyrimidin-4-yl)-1H-pyrazol-3-yl)(piperidin-1-yl)methanone (Compound 172)

172

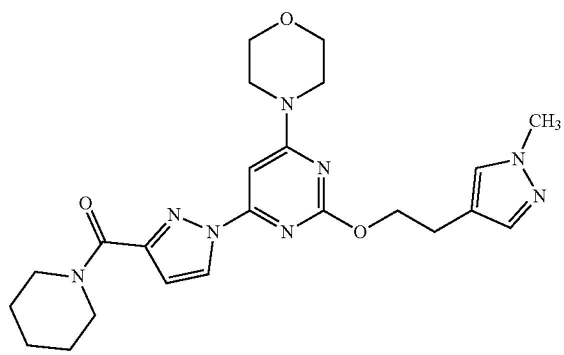

The synthetic procedure for Compound 172 is similar to the procedure for synthesis of Compound 64.

Synthesis of 4-(2-(2-(1-methyl-1H-pyrazol-4-yl) ethoxy)pyrimidin-4-yl)morpholine (Compound 173)

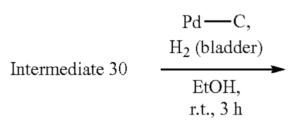

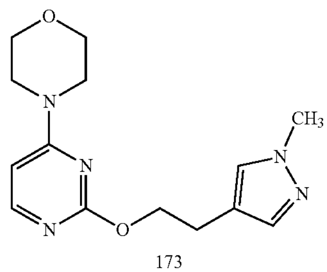

173

Compound 173 was synthesized as shown above using 1 eq of Intermediate 30 (50 mg), 1 eq Pd—C (10%, 5 mg) in EtOH (5 ml) and hydrogen balloon at room temperature for 3 h. Purified by silica gel chromatography to give Compound 173 (92 mg, 27%)

LCMS (ESI): m/z=290[M+H]$^+$;

Synthesis of 2-((4-morpholino-6-(3-(m-tolyl)-1H-pyrazol-1-yl)pyrimidin-2-yl)oxy)acetonitrile (Compound 174)

174

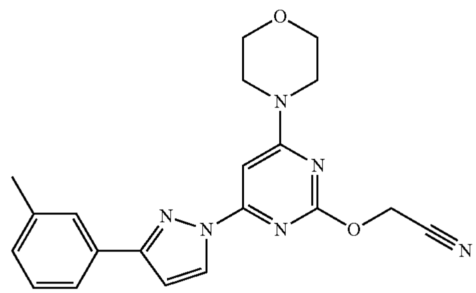

Compound 174 was synthesized in a procedure similar to the procedure described for Compound 176.

LCMS (ESI): m/z=377 [M+H]$^+$;

Synthesis of 4-((4-morpholino-6-(3-(m-tolyl)-1H-pyrazol-1-yl)pyrimidin-2-yl)oxy)butanenitrile (Compound 175)

175

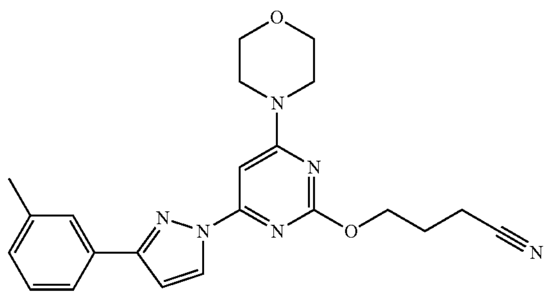

Compound 175 was synthesized in a procedure similar to the procedure described for Compound 176

LCMS (ESI): m/z=405 [M+H]$^+$;

Synthesis of 4-(2-((3-methyloxetan-3-yl)methoxy)-6-(3-(m-tolyl)-1H-pyrazol-1-yl)pyrimidin-4-yl)morpholine (Compound 176)

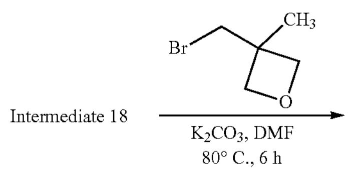

-continued

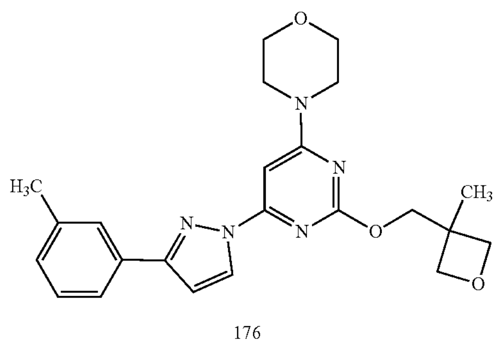

176

To a stirred solution of Intermediate 18 (50.0 mg, 0.14 mmol) in DMF (5 ml) at room temperature under $N_2$ atmosphere, was added $K_2CO_3$ (41.0 mg, 0.29 mmol) followed with 3-(bromomethyl)-3-methyloxetane (29.3 mg, 0.17 mmol). The reaction mixture was gradually heated to 80° C. and stirred for 6 h. The mixture was cooled to room temperature, diluted with water (30 mL), and extracted with EtOAc (2×25 mL). The combined organic extracts were washed with brine solution (25 mL), dried over anhydrous $Na_2SO_4$ and concentrated under reduced pressure to obtain the crude compound. The crude product was purified by silica-gel column chromatography using 30% EtOAc: Hexanes. Fractions containing the product were combined and concentrated under vacuum to obtain Compound 176 (25.0 mg, 0.05 mmol, 40% yield) as an off-white solid.

LCMS (ESI): m/z=422 $[M+H]^+$; HPLC: >99 (% of AUC).

$^1$H NMR (400 MHz, DMSO-$d_6$) δ: 8.63 (d, J=2.8 Hz, 1H), 7.82 (s, 1H), 7.77 (d, J=7.6 Hz, 1H), 7.35 (t, J=7.6 Hz, 1H), 7.21 (d, J=7.6 Hz, 1H), 7.05 (d, J=2.8 Hz, 1H), 6.91 (s, 1H), 4.50 (d, J=5.6 Hz, 2H), 4.42 (s, 2H), 4.31 (d, J=6.0 Hz, 2H), 3.70 (brs, 8H), 2.38 (s, 3H), 1.36 (s, 3H).

Synthesis of 4-(2-(1-methoxy-2-phenylethyl)-6-(3-phenyl-1H-pyrazol-1-yl)pyrimidin-4-yl)morpholine (Compound 177)

177

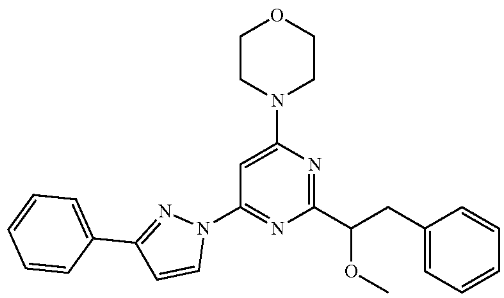

The synthetic procedure for Compound 177 is similar to the procedure described for Compound 68.

LCMS (ESI): m/z=442 $[M+H]^+$

Synthesis of 1-(2-(2-(1-methyl-1H-pyrazol-4-yl)ethoxy)-6-morpholinopyrimidin-4-yl)-1H-pyrazole-3-carboxylic acid (Compound 178)

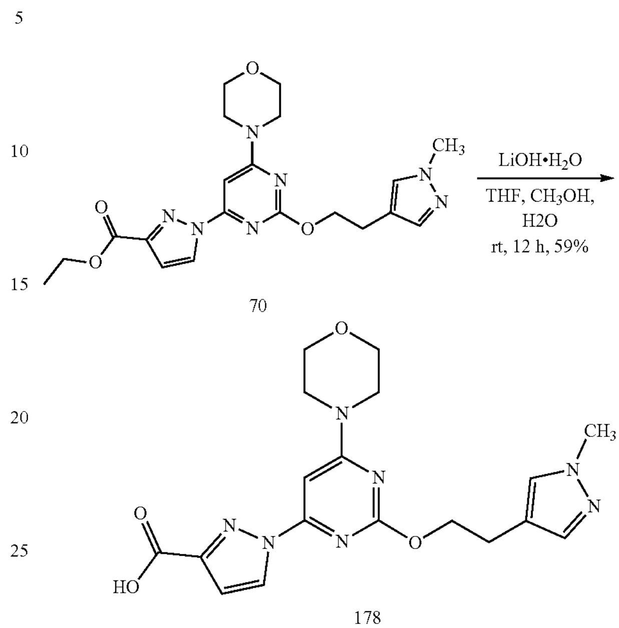

70

178

To a stirred solution of Compound 70 (280 mg, 0.67 mmol) in THF (2.0 mL), $CH_3OH$ (2.0 mL), at rt, was added LiOH·$H_2O$ (48.7 mg, 2.03 mmol) followed with water (2.0 mL). The reaction mixture was stirred at room temperature for 12 h. The solvent was evaporated, and diluted with water (30 mL). The mixture was extracted with EtOAc (25 mL). The aqueous layer was acidified with 2M HCl (5 mL) and extracted with 10% $CH_3OH/CH_2Cl_2$ (2×100 mL). The combined organic extracts were washed with brine (20 mL), dried over anhydrous $Na_2SO_4$, filtered and concentrated under vacuum to obtain the crude product. The crude product was purified by silica-gel column chromatography using 10% $CH_3OH/CH_2Cl_2$. Fractions containing the product were combined and concentrated under vacuum to obtain Compound 178 (160 mg, 0.401 mmol, 59% yield) as an off-white solid.

MS (ESI+APCI; multimode): 400.2 $[M+H]^+$; HPLC: 93.8 (% of AUC).

$^1$H NMR (400 MHz, DMSO-$d_6$): δ: 13.20 (s, 1H), 8.61 (d, J=2.4 Hz, 1H), 7.57 (s, 1H), 7.33 (s, 1H), 6.92 (d, J=2.8 Hz, 1H), 6.81 (s, 1H), 4.41 (t, J=7.2 Hz, 2H), 3.78 (s, 3H), 3.67 (brs, 8H), 2.85 (t, J=7.2 Hz, 2H).

Synthesis of (3-(1-(2-(2-(1-methyl-1H-pyrazol-4-yl)ethoxy)-6-morpholinopyrimidin-4-yl)-1H-pyrazol-3-yl)phenyl)methanol (Compound 179)

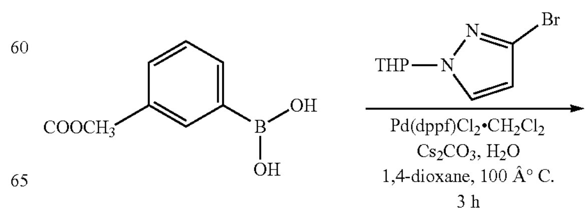

-continued

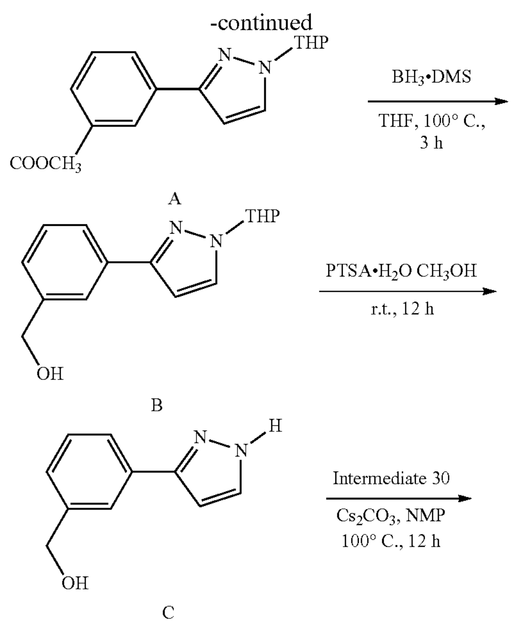

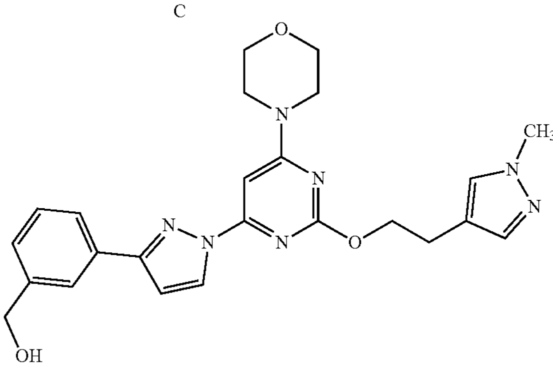

179

Preparation of A

To a stirred solution of 3-bromo-1-(tetrahydro-2H-pyran-2-yl)-1H-pyrazole (1.00 g, 4.33 mmol) in anhydrous dioxane (15 mL), at room temperature, under $N_2$ atmosphere, was added (3-(methoxycarbonyl)phenyl)boronic acid (770 mg, 4.33 mmol) followed with $PdCl_2$(dppf)$\cdot CH_2Cl_2$ (353 mg, 0.43 mmol), $Cs_2CO_3$ (2.82 g, 8.65 mmol) and water (3.0 mL). The reaction mixture was gradually heated to 100° C. and stirred for 3 h. The reaction mixture was cooled to room temperature, diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes. Fractions containing the product were combined and concentrated under vacuum to obtain A (1.10 g, 3.84 mmol, 89% yield) as an off-white solid.

MS (ESI+APCI; multimode): 287.0 $[M+H]^+$.

$^1$H NMR (400 MHz, DMSO-$d_6$): δ: 8.41 (dd, J=1.6 Hz, 1.6 Hz, 1H), 8.09-8.06 (m, 1H), 7.98 (d, J=2.8 Hz, 1H), 7.91-7.88 (m, 1H), 7.57 (t, J=8.0 Hz, 1H), 6.87 (d, J=2.4 Hz, 1H), 5.48-5.45 (m, 1H), 3.97-3.94 (m, 1H), 3.89 (s, 3H), 3.69-3.62 (m, 1H), 2.16-2.08 (m, 1H), 1.99-1.93 (m, 2H), 1.58-1.57 (m, 1H), 1.56-1.54 (m, 2H).

Preparation of B

To a stirred solution of A (1.10 g, 3.84 mmol) in anhydrous THF (15 ml), at room temperature, under $N_2$ atmosphere, was added $BH_3\cdot$DMS (1.0 M in THF, 0.73 mL, 7.68 mmol). The reaction mixture was gradually heated to 80° C. and stirred for 3 h. The reaction mixture was cooled to room temperature, diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 50% EtOAc:Hexanes. Fractions containing the product were combined and concentrated under vacuum to obtain B (800 mg, 3.10 mmol, 81% yield) as an off-white solid.

MS (ESI+APCI; multimode): 258.0 $[M+H]^+$.

$^1$H NMR (400 MHz, DMSO-$d_6$): δ: 7.92 (dd, J=2.8 Hz, 1H), 7.78 (s, 1H), 7.66 (d, J=7.6 Hz, 1H), 7.34 (t, J=7.6 Hz, 1H), 7.24 (d, J=8.0 Hz, 1H), 6.74 (d, J=2.4 Hz, 1H), 5.44-5.41 (m, 1H), 4.53 (s, 2H), 3.96-3.93 (m, 1H), 3.67-3.61 (m, 1H), 3.38-3.35 (m, 1H), 2.15-2.08 (m, 1H), 1.98-1.91 (m, 2H), 1.69-1.66 (m, 1H), 1.57-1.53 (m, 2H).

Preparation of C

To a stirred solution of B (800 mg, 3.10 mmol) in anhydrous $CH_3OH$ (15 mL), at room temperature, under $N_2$ atmosphere, was added PTSA$\cdot H_2O$ (117 mg, 6.19 mmol). The reaction mixture was stirred at room temperature for 12 h. The reaction mixture was diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 80% EtOAc: Hexanes. Fractions containing the product were combined and concentrated under vacuum to obtain C (350 mg, 2.009 mmol, 64% yield) as a brown liquid.

MS (ESI+APCI; multimode): 175.0 $[M+H]^+$.

$^1$H NMR (400 MHz, DMSO-$d_6$): δ: 12.87 (brs, 1H), 7.76 (s, 1H), 7.75 (d, J=2.4 Hz, 1H), 7.66 (d, J=7.6 Hz, 1H), 7.35 (t, J=7.6 Hz, 1H), 7.24 (d, J=7.2 Hz, 1H), 6.68 (d, J=2.0 Hz, 1H), 5.23 (t, J=5.6 Hz, 1H), 4.53 (d, J=6.0 Hz, 2H).

Preparation of Compound 179

To a stirred solution of Intermediate 30 (300 mg, 0.92 mmol) in anhydrous NMP (10 mL), at room temperature, under $N_2$ atmosphere, was added C (161 mg, 0.92 mmol) followed with $Cs_2CO_3$ (604 mg, 1.85 mmol). The reaction mixture was gradually heated to 100° C. and stirred for 12 h. The reaction mixture was cooled to room temperature, diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc:Hexanes. Fractions containing the product were combined and concentrated under vacuum to obtain Compound 179 (190 mg, 0.41 mmol, 44% yield) as an off-white solid.

MS (ESI+APCI; multimode): 462.0 $[M+H]^+$; HPLC: >99 (% of AUC).

$^1$H NMR (400 MHz, DMSO-$d_6$): δ: 8.59 (d, J=2.8 Hz, 1H), 7.92 (s, 1H), 7.84 (d, J=7.6 Hz, 1H), 7.57 (s, 1H), 7.42 (t, J=7.6 Hz, 1H), 7.36-7.34 (m, 2H), 7.05 (d, J=2.8 Hz, 1H), 6.88 (s, 1H), 5.25 (t, J=5.6 Hz, 1H), 4.57 (d, J=5.6 Hz, 2H), 4.41 (t, J=7.2 Hz, 2H), 3.78 (s, 3H), 3.69-3.68 (m, 8H), 2.86 (t, J=7.2 Hz, 2H).

Synthesis of 2-(4-(2-((4-morpholino-6-(3-(m-tolyl)-1H-pyrazol-1-yl)pyrimidin-2-yl)oxy)ethyl)-1H-pyrazol-1-yl)ethan-1-ol (Compound 180)

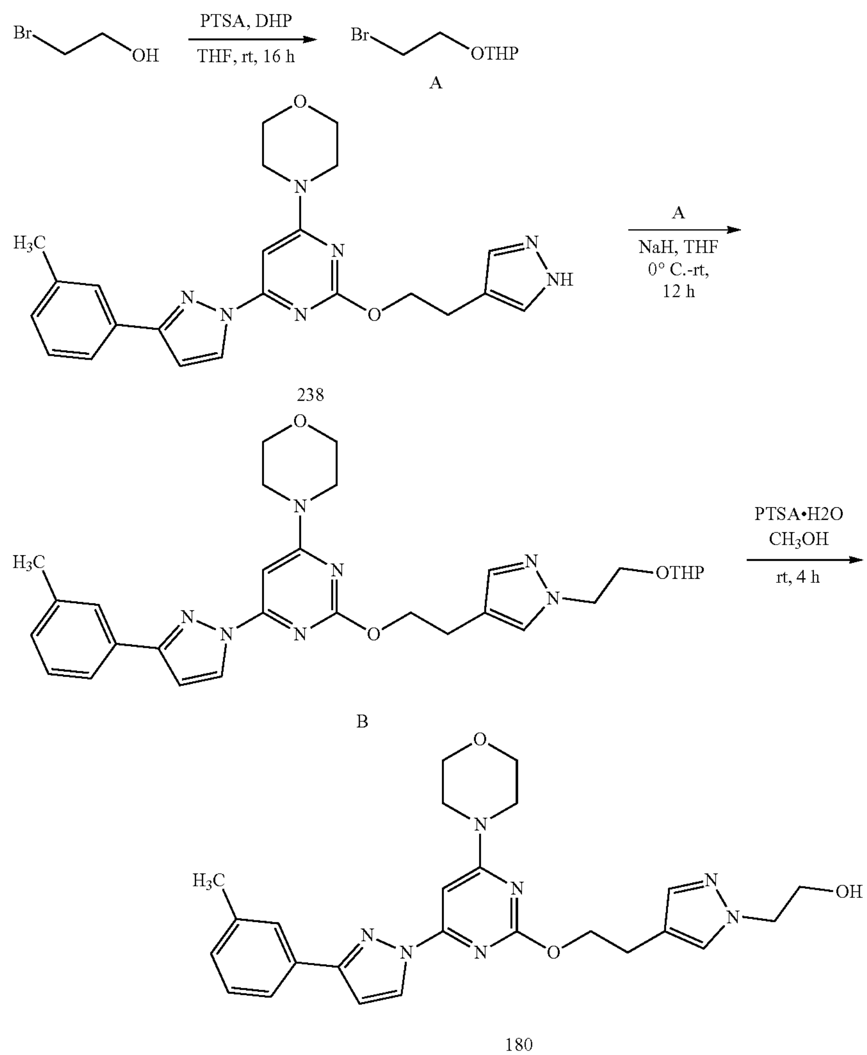

A

238

B

180

Preparation of A 1 g 2-bromoethan-1-oll (1 eq), DHP (1 eq), TPSA $H_2O$ (1 eq) in THF (10 ml), 16 h, rt. Purified by silica gel chromatography (48% yield).

Preparation of B 450 mg Compound 238 (1 eq), A (1 eq) and NaH (50% mineral oil, 3 eq) in 10 ml THF, at 0° C. to rt over 12 h. Purified by silica gel chromatography (51% yield).

Preparation of Compound 180

B (1 eq), PTSA $H_2O$) (1 eq) in MeOH (5 ml), rt for 4 h. Purified by silica gel chromatography (54% yield). LC/MS and NMR consistent.

LCMS (ESI): m/z=476 $[M+H]^+$;

Synthesis of 3-hydroxy-3-(4-morpholino-6-(3-phenyl-1H-pyrazol-1-yl)pyrimidin-2-yl)propanenitrile (Compound 181)

181

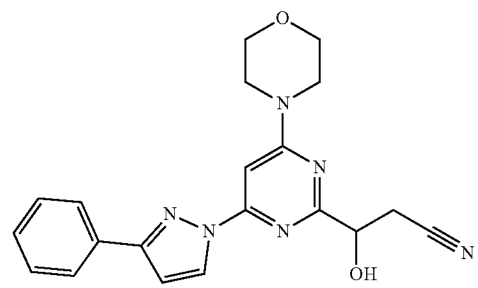

The procedure for Compound 181 is similar to procedure described for Compound 76

MS (ESI+APCI; multimode): 377.2 $[M+H]^+$

Synthesis of 3-methoxy-3-(4-morpholino-6-(3-phenyl-1H-pyrazol-1-yl)pyrimidin-2-yl)propanenitrile (Compound 182)

182

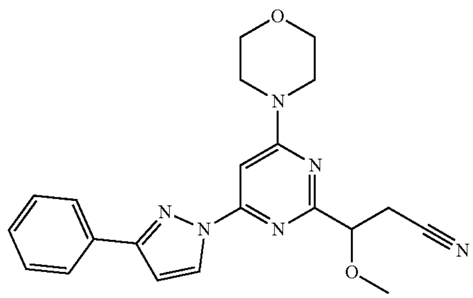

The procedure for Compound 210 is similar to the procedure described for Compound 72.

MS (ESI+APCI; multimode): 391.2 $[M+H]^+$

Synthesis of (4-morpholino-6-(3-phenyl-1H-pyrazol-1-yl)pyrimidin-2-yl)(phenyl)methanol (Compound 183)

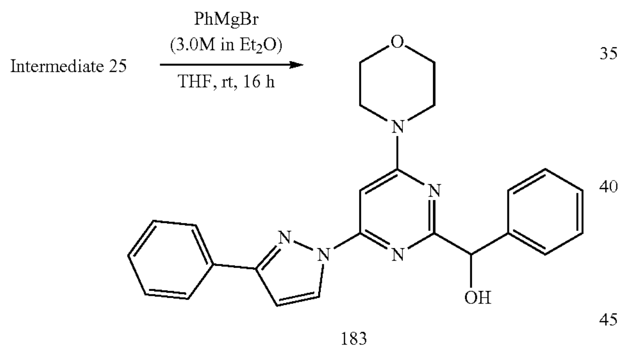

183

To a stirred solution of Intermediate 25 (150 mg, 0.44 mmol) in anhydrous THF (5 mL), was added phenyl magnesium bromide (3.0 M in $Et_2O$, 243 mg, 1.34 mmol) at room temperature, under $N_2$ atmosphere. The reaction mixture was stirred at room temperature for 16 h. The reaction mixture was quenched with sat. $NH_4Cl$ (30 mL) at room temperature, and extracted with EtOAc (2×50 mL). The combined organic extracts were washed with brine (20 mL), dried over anhydrous $Na_2SO_4$, filtered and concentrated under vacuum to obtain the crude product. The crude product was purified by silica-gel column chromatography using 50% EtOAc:Hexanes. Fractions containing the product were combined and concentrated under vacuum to obtain Compound 183 (100 mg, 0.24 mmol, 54% yield) as an off-white solid.

LCMS (ESI): m/z=414 $[M+H]^+$; HPLC: 97.3 (% of AUC).

$^1$H NMR (400 MHz, DMSO-$d_6$) δ: 8.83 (d, J=2.4 Hz, 1H), 8.00 (dd, J=1.2 Hz, 8.4 Hz, 2H), 7.54-7.52 (m, 2H), 7.48-7.45 (m, 2H), 7.41-7.38 (m, 1H), 7.33-7.30 (m, 2H), 7.25-7.21 (m, 1H), 7.10 (d, J=2.8 Hz, 1H), 7.05 (s, 1H), 5.77 (d, J=6.8 Hz, 1H), 5.53 (d, J=6.8 Hz, 1H), 3.70 (brs, 8H).

Synthesis of (1-methyl-1H-pyrazol-4-yl)(4-morpholino-6-(3-phenyl-1H-pyrazol-1-yl)pyrimidin-2-yl)methanol (Compound 184)

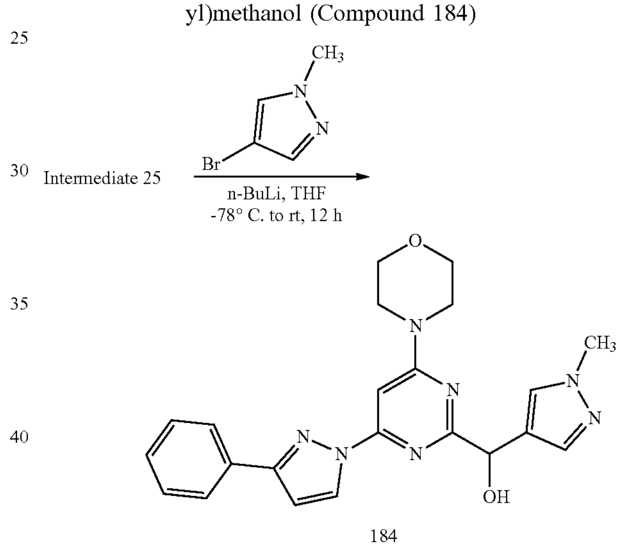

184

Compound 184 was prepared as indicated above.

MS (ESI+APCI; multimode): 418.2 $[M+H]^+$;

The following compounds were synthesized using a procedure similar to the one described for Compound 66.

| # | Structure | Name | LCMS (ESI): m/z [M + H]$^+$ |
|---|---|---|---|
| 185 | 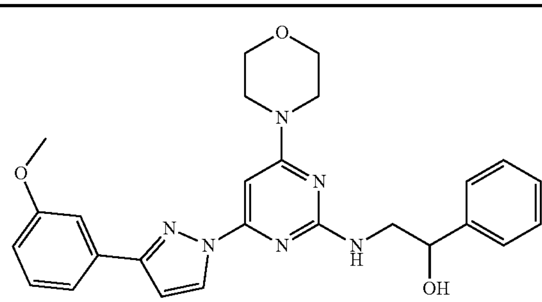 | 2-((4-(3-(3-methoxyphenyl)-1H-pyrazol-1-yl)-6-morpholinopyrimidin-2-yl)amino)-1-phenylethan-1-ol | 473 |

-continued

| # | Structure | Name | LCMS (ESI): m/z $[M + H]^+$ |
|---|---|---|---|
| 186 | 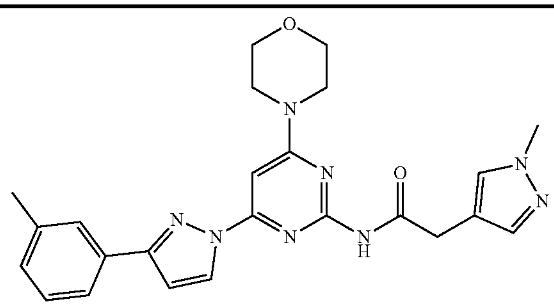 | 2-(1-methyl-1H-pyrazol-4-yl)-N-(4-morpholino-6-(3-(m-tolyl)-1H-pyrazol-1-yl)pyrimidin-2-yl)acetamide | 459 |
| 187 | 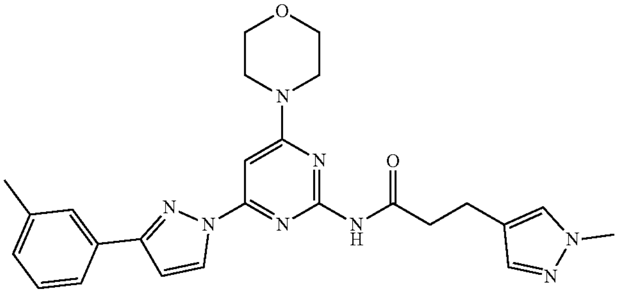 | 3-(1-methyl-1H-pyrazol-4-yl)-N-(4-morpholino-6-(3-(m-tolyl)-1H-pyrazol-1-yl)pyrimidin-2-yl)propenamide | 473 |
| 188 | 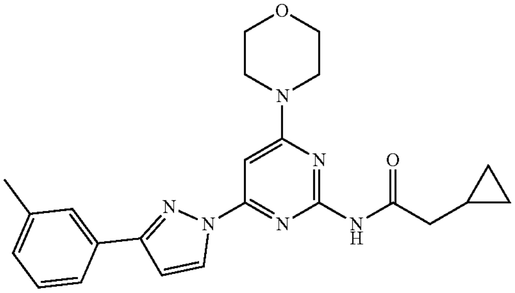 [SMILES: Cc1cccc(-c2ccn(-c3cc(N4CCOCC4)nc(NC(=O)CC4CC4)n3)n2)c1] | 2-cyclopropyl-N-(4-morpholino-6-(3-(m-tolyl)-1H-pyrazol-1-yl)pyrimidin-2-yl)acetamide | 419 |

The following compounds were synthesized using a procedure similar to the one described for Compound 71.

| # | Structure | Name | LCMS (ESI): m/z $[M + H]^+$ |
|---|---|---|---|
| 189 | 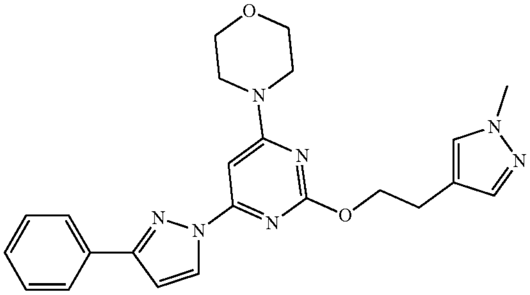 [SMILES: Cn1cc(CCOc2nc(N3CCOCC3)cc(-n3ccc(-c4ccccc4)n3)n2)cn1] | 4-(2-(2-(1-methyl-1H-pyrazol-4-yl)ethoxy)-6-(3-phenyl-1H-pyrazol-1-yl)pyrimidin-4-yl)morpholine | 432 |

-continued

| # | Structure | Name | LCMS (ESI): m/z [M + H]$^+$ |
|---|---|---|---|
| 190 | 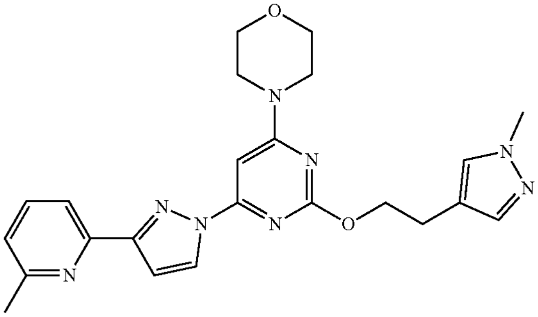 [SMILES: Cc1cccc(-c2ccn(-c3cc(N4CCOCC4)nc(OCCc4cnn(C)c4)n3)n2)n1] | 4-(2-(2-(1-methyl-1H-pyrazol-4-yl)ethoxy)-6-(3-(6-methylpyridin-2-yl)-1H-pyrazol-1-yl)pyrimidin-4-yl)morpholine | 447 |
| 191 | 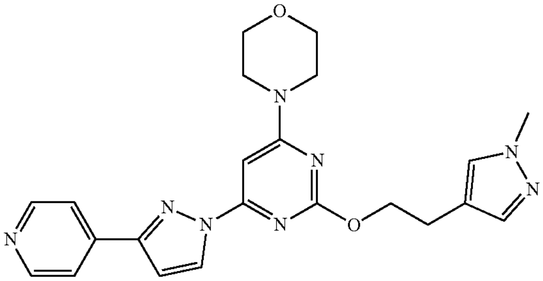 [SMILES: Cn1cc(CCOc2nc(N3CCOCC3)cc(-n3ccc(-c4ccncc4)n3)n2)cn1] | 4-(2-(2-(1-methyl-1H-pyrazol-4-yl)ethoxy)-6-(3-(pyridin-4-yl)-1H-pyrazol-1-yl)pyrimidin-4-yl)morpholine | 433 |
| 192 | 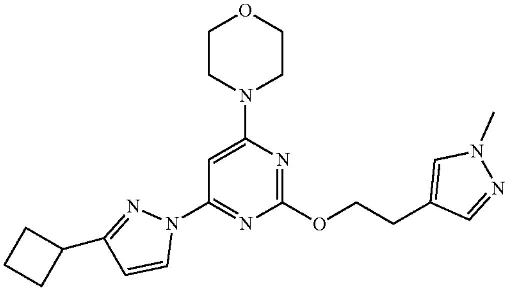 [SMILES: Cn1cc(CCOc2nc(N3CCOCC3)cc(-n3ccc(C4CCC4)n3)n2)cn1] | 4-(6-(3-cyclobutyl-1H-pyrazol-1-yl)-2-(2-(1-methyl-1H-pyrazol-4-yl)ethoxy)pyrimidin-4-yl)morpholine | 410 |
| 193 | 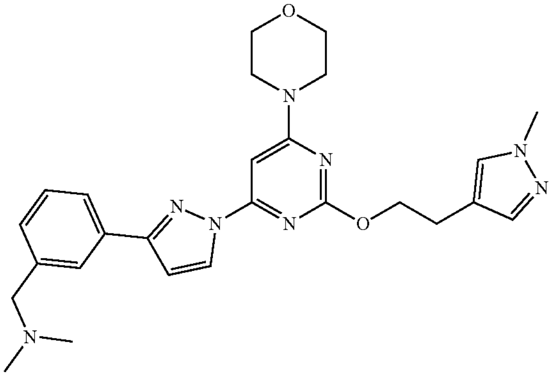 [SMILES: CN(C)Cc1cccc(-c2ccn(-c3cc(N4CCOCC4)nc(OCCc4cnn(C)c4)n3)n2)c1] | N,N-dimethyl-1-(3-(1-(2-(2-(1-methyl-1H-pyrazol-4-yl)ethoxy)-6-morpholinopyrimidin-4-yl)-1H-pyrazol-3-yl)phenyl)methanamine | 489 |

-continued
| # | Structure | Name | LCMS (ESI): m/z [M + H]+ |
|---|---|---|---|
| 194 | 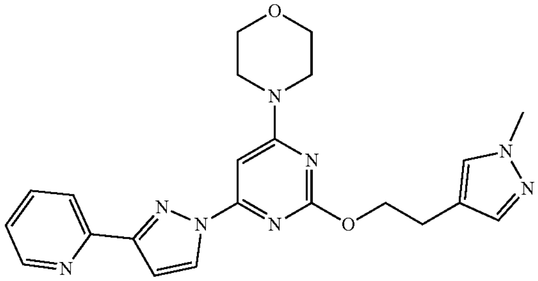 [SMILES: Cn1cc(CCOc2nc(N3CCOCC3)cc(-n3ccc(-c4ccccn4)n3)n2)cn1] | 4-(2-(2-(1-methyl-1H-pyrazol-4-yl)ethoxy)-6-(3-(pyridin-2-yl)-1H-pyrazol-1-yl)pyrimidin-4-yl)morpholine | 433 |
| 195 | 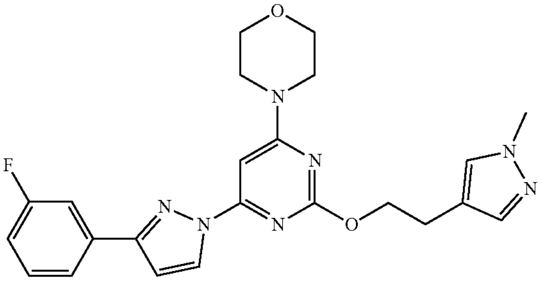 [SMILES: Cn1cc(CCOc2nc(N3CCOCC3)cc(-n3ccc(-c4cccc(F)c4)n3)n2)cn1] | 4-(6-(3-(3-fluorophenyl)-1H-pyrazol-1-yl)-2-(2-(1-methyl-1H-pyrazol-4-yl)ethoxy)pyrimidin-4-yl)morpholine | 450 |
| 196 | 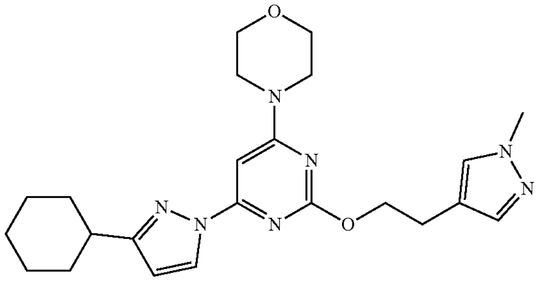 [SMILES: Cn1cc(CCOc2nc(N3CCOCC3)cc(-n3ccc(C4CCCCC4)n3)n2)cn1] | 4-(6-(3-cyclohexyl-1H-pyrazol-1-yl)-2-(2-(1-methyl-1H-pyrazol-4-yl)ethoxy)pyrimidin-4-yl)morpholine | 437 |
| 197 | 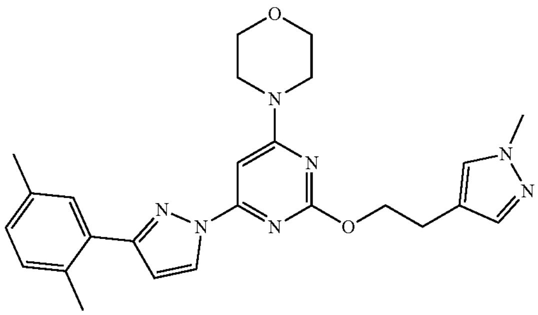 [SMILES: Cc1ccc(C)c(-c2ccn(-c3cc(N4CCOCC4)nc(OCCc4cnn(C)c4)n3)n2)c1] | 4-(6-(3-(2,5-dimethylphenyl)-1H-pyrazol-1-yl)-2-(2-(1-methyl-1H-pyrazol-4-yl)ethoxy)pyrimidin-4-yl)morpholine | 460 |

Synthesis of 4-(2-(2-(1-methyl-1H-pyrazol-5-yl)ethoxy)-6-(5-methyl-3-phenyl-1H-pyrazol-1-yl)pyrimidin-4-yl)morpholine (Compound 198)

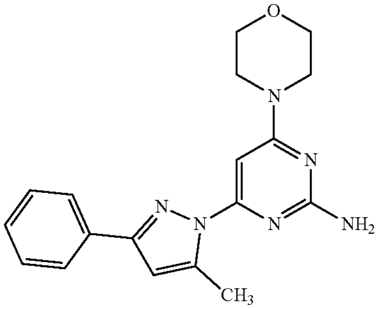

202

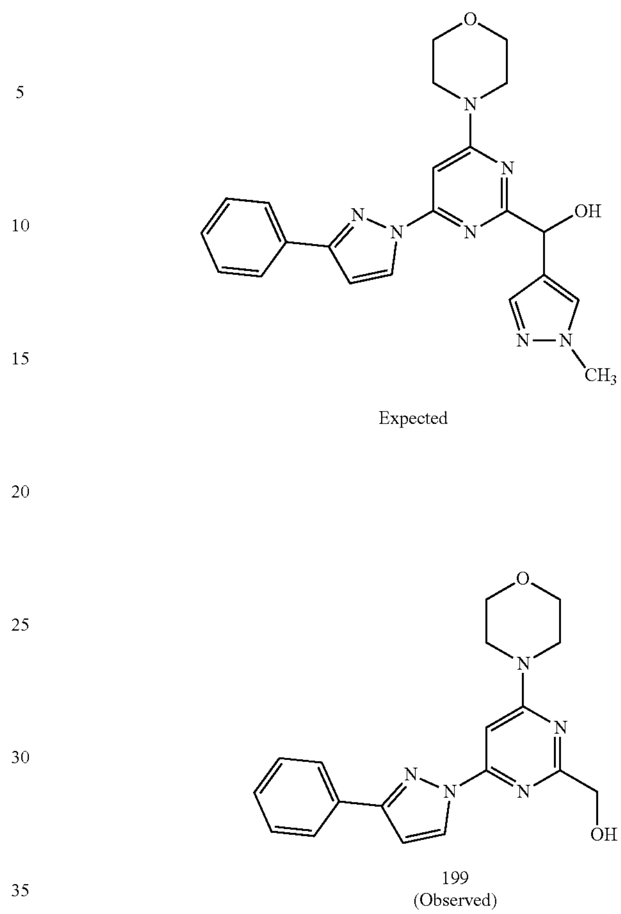

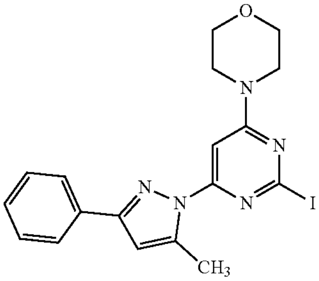

A

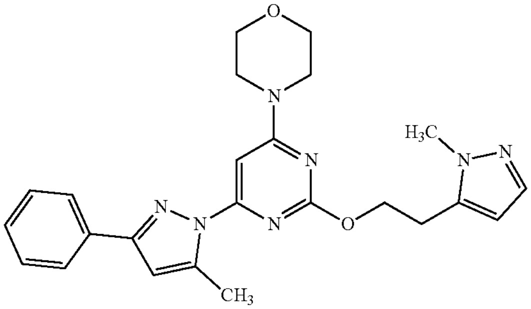

198

Compound 198 was prepared as indicated above. MS (ESI+APCI; multimode): 420 $[M+H]^+$.

Synthesis of (4-morpholino-6-(3-phenyl-1H-pyrazol-1-yl)pyrimidin-2-yl)methanol (Compound 199)

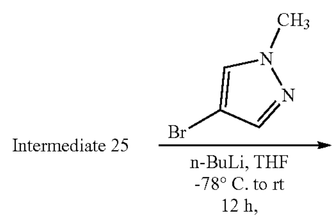

-continued

Expected 199
(Observed)

To a stirred solution of Intermediate 25 (300 mg, 1.86 mmol) in anhydrous THF (10 mL), at −78° C., under $N_2$ atmosphere, was added n-BuLi (1.0 M in Hexanes, 0.13 mL, 2.05 mmol) over a period of 5 min, and the reaction mixture was stirred at −78° C. for 15 min. 4-bromo-1-methyl-1H-pyrazole (750 mg, 2.23 mmol) in THF (2 mL) was added at −78° C. over a period of 5 min. The reaction mixture was stirred at −78° C. to room temperature for 12 h. The reaction mixture was quenched with sat. $NH_4Cl$ (5 mL), diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc:Hexanes. Fractions containing the product were combined and concentrated under vacuum to obtain Compound 199 (350 mg, 1.037 mmol, 55% yield #) as an off-white solid.

MS (ESI+APCI; multimode): 338.2 $[M+H]^+$; HPLC: 98.8 (% of AUC).

$^1H$ NMR (400 MHz, DMSO-$d_6$): δ: 8.74 (d, J=2.4 Hz, 1H), 8.00 (dd, J=1.2 Hz, 8.4 Hz, 2H), 7.49-7.45 (m, 2H), 7.42-7.38 (m, 1H), 7.09 (d, J=2.8 Hz, 2H), 4.99 (t, J=6.0 Hz, 1H), 4.44 (d, J=6.0 Hz, 2H), 3.71 (brs, 8H).

Synthesis of 4-(6-(3-(3-(methoxymethyl)phenyl)-1H-pyrazol-1-yl)-2-(2-(1-methyl-1H-pyrazol-4-yl)ethoxy)pyrimidin-4-yl)morpholine (Compound 200)

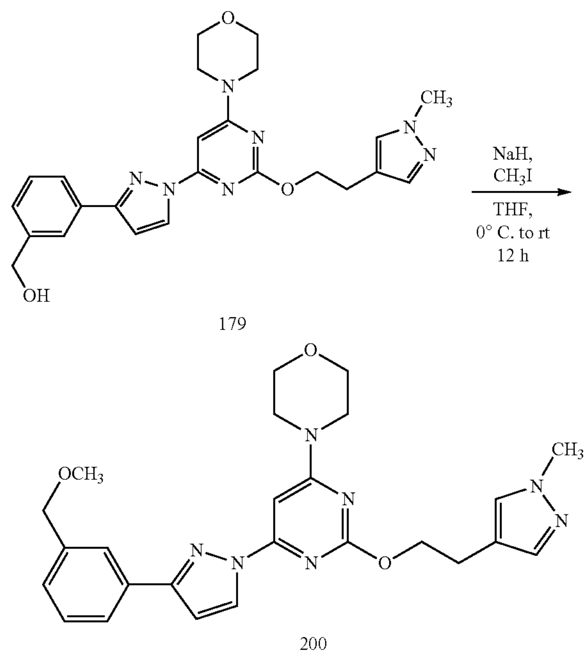 [SMILES: Cn1cc(CCOc2nc(N3CCOCC3)cc(-n3ccc(-c4cccc(CO)c4)n3)n2)cn1 ; COCc1cccc(-c2ccn(-c3cc(N4CCOCC4)nc(OCCc4cnn(C)c4)n3)n2)c1]

179

200

To a suspension of Compound 179 (240 mg, 0.52 mmol) in anhydrous THF (20 ml), at 0° C. under $N_2$ atmosphere, was added NaH (50%, 30.0 mg, 1.24 mmol) and stirred at 0° C. for 30 min. Methyl iodide (0.09 ml, 1.56 mmol) was added at same temperature. The reaction mixture was gradually warmed to room temperature and stirred for 12 h. The reaction mixture was cooled to 0° C., quenched with ice cold water (5 mL), diluted with water (20 mL), and extracted with EtOAc (2×50 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc:Hexanes to afford Compound 200 (124 mg, 50% yield) as an off-white solid.

LCMS (ESI): m/z=476 $[M+H]^+$; HPLC: 98.0% (AUC).

$^1$H NMR (400 MHz, DMSO-$d_6$) δ: 8.60 (d, J=2.4 Hz, 1H), 7.92-7.90 (m, 2H), 7.58 (s, 1H), 7.45 (t, J=8.0 Hz, 1H), 7.36-7.34 (m, 2H), 7.08 (d, J=2.8 Hz, 1H), 6.89 (s, 1H), 4.48 (s, 2H), 4.41 (t, J=7.2 Hz, 2H), 3.78 (s, 3H), 3.69 (brs, 8H), 3.32 (s, 3H), 2.86 (t, J=7.2 Hz, 2H).

Synthesis of 2-(1-methyl-1H-pyrazol-5-yl)-1-(4-morpholino-6-(3-phenyl-1H-pyrazol-1-yl)pyrimidin-2-yl)ethan-1-ol (Compound 201)

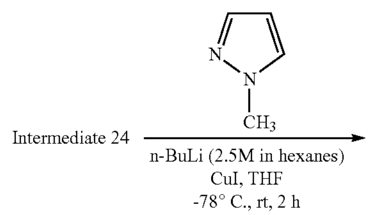

-continued

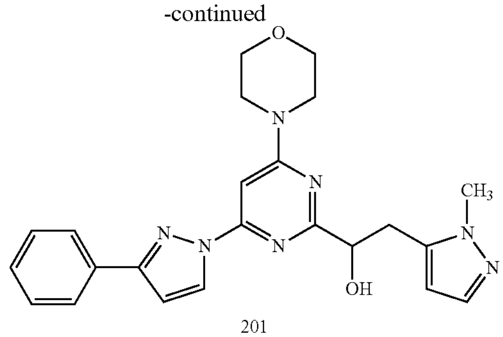

201

To a stirred solution of Intermediate 24 (47.0 mg, 0.57 mmol) in anhydrous THF (10 mL), at −78° C., under $N_2$ atmosphere, was added n-BuLi (2.5 M in Hexanes, 0.22 mL, 0.57 mmol) and the reaction mixture was stirred at −78° C. for 30 min. copper(I) iodide (54.5 mg, 0.28 mmol) and 1 (200 mg, 0.57 mmol) in THF (2 mL) were added at −78° C. over a period of 3 min. The reaction mixture was stirred at −78° C. to room temperature for 2 h. The reaction mixture was quenched with sat. $NH_4Cl$ (20 mL) at 0° C., and extracted with EtOAc (2×30 mL). The combined organic extracts were washed with brine (20 mL), dried over anhydrous $Na_2SO_4$, filtered and concentrated under vacuum to obtain the crude product. The crude compound was purified by C-18 column chromatography using 70% $CH_3CN:H_2O$ to afford Compound 201 (40.0 mg, 0.09 mmol, 16% yield) as an off white solid.

LCMS (ESI): m/z=432 $[M+H]^+$; HPLC: 90.1 (% of AUC).

$^1$H NMR (400 MHz, DMSO-$d_6$) δ: 8.78 (d, J=2.8 Hz, 1H), 8.01 (dd, J=1.6 Hz, 8.4 Hz, 2H), 7.47 (t, J=7.2 Hz, 2H), 7.42-7.38 (m, 1H), 7.22 (d, J=1.6 Hz, 1H), 7.10 (d, J=2.8 Hz, 2H), 6.00 (d, J=1.6 Hz, 1H), 5.31 (d, J=5.6 Hz, 1H), 4.73-4.68 (m, 1H), 3.76 (s, 3H), 3.71 (brs, 8H), 3.29-3.24 (m, 1H), 3.12-3.06 (m, 1H).

Synthesis of 4-(5-methyl-3-phenyl-1H-pyrazol-1-yl)-6-morpholinopyrimidin-2-amine (Compound 202)

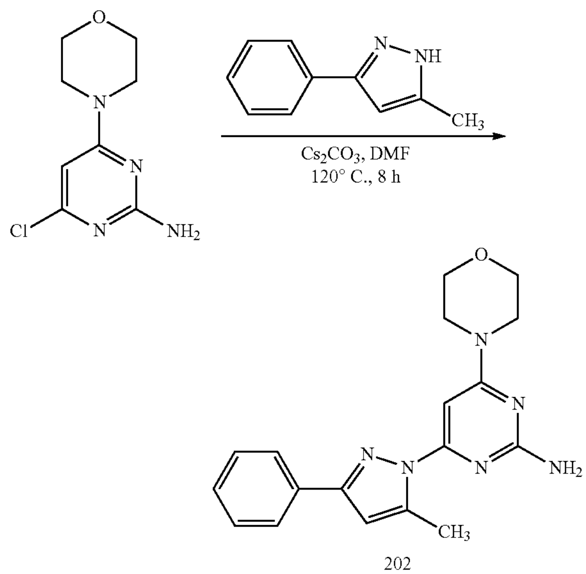 [SMILES: Nc1nc(Cl)cc(N2CCOCC2)n1 ; Cc1cc(-c2ccccc2)n[nH]1 ; Cc1cc(-c2ccccc2)nn1-c1cc(N2CCOCC2)nc(N)n1]

202

Compound 202 was prepared as shown in the scheme above, using 500 mg 4-chloro-6-morpholinopyrimidin-2-amine (1 eq), 5-methyl-3-phenyl-1H-pyrazole (1.5 eq) of $Cs_2CO_3$ (2 eq) in DMF (5 ml) at 120° C. over 8 h. Purified by silica gel chromatography followed by LC MS (5% yield).

LCMS (ESI): m/z=337 $[M+H]^+$;

Synthesis of 4-(6-(3-(1H-indol-3-yl)-1H-pyrazol-1-yl)-2-(2-(1-methyl-1H-pyrazol-4-yl)ethoxy)pyrimidin-4-yl)morpholine (Compound 203)

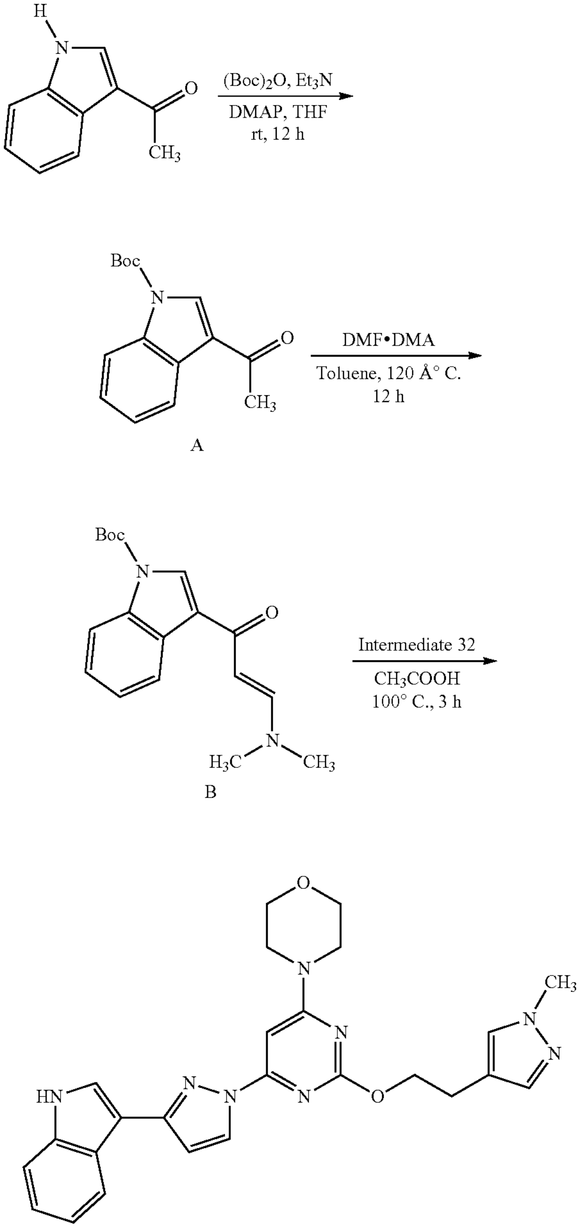

203

Compound 203 was synthesized as indicated above.

LCMS (ESI): m/z=471 $[M+H]^+$;

Synthesis of (R)-2-methoxy-2-(4-(5-methyl-3-phenyl-1H-pyrazol-1-yl)-6-morpholinopyrimidin-2-yl)ethan-1-ol (Compound 204)

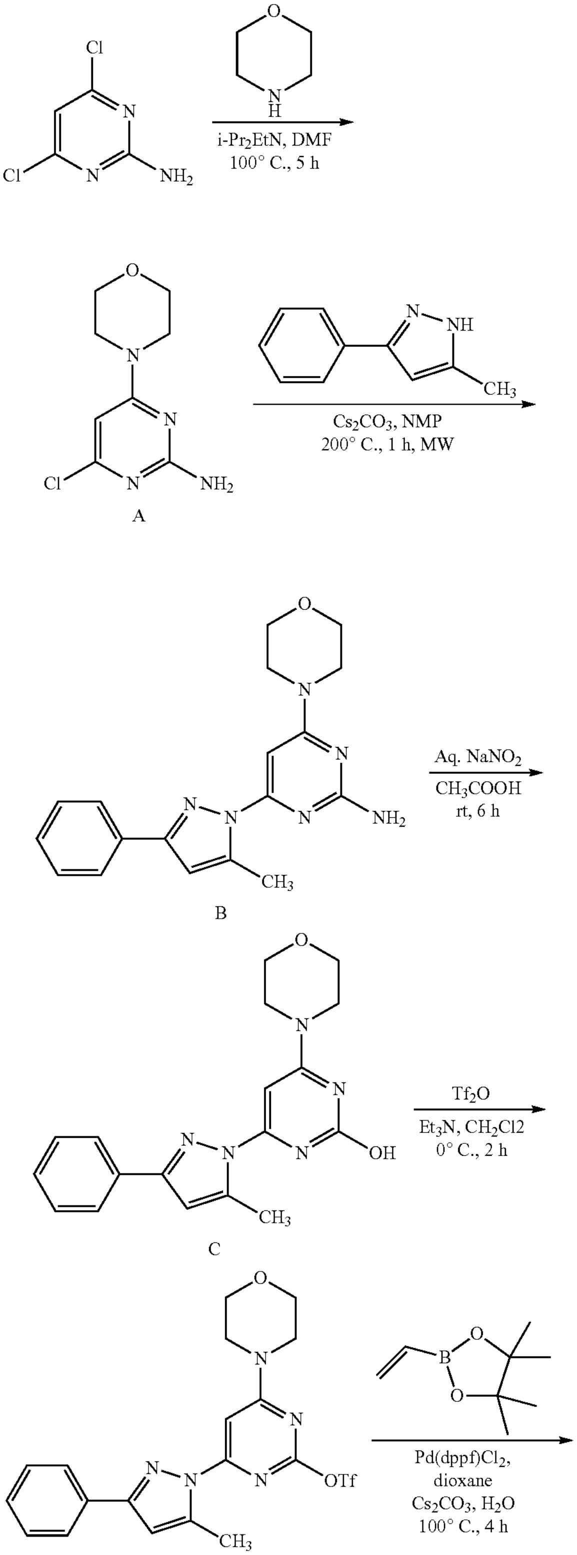

-continued

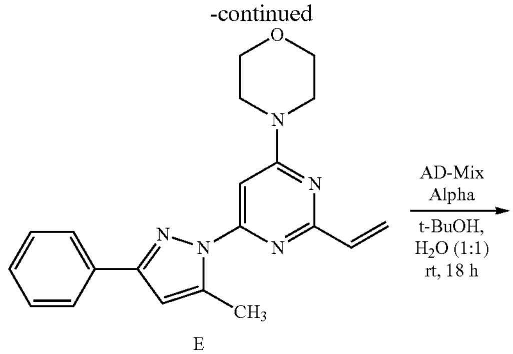

E

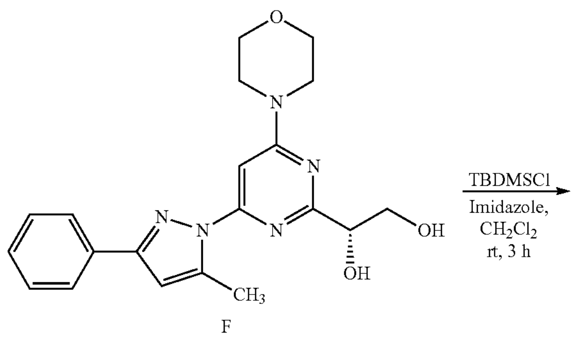

F

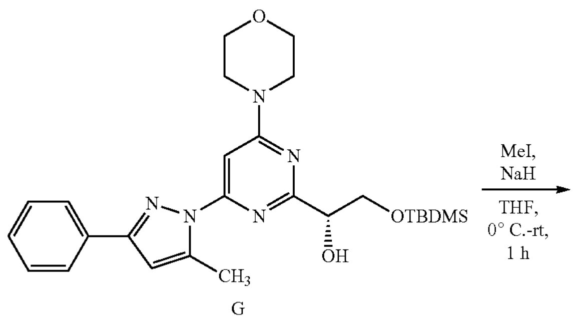

G

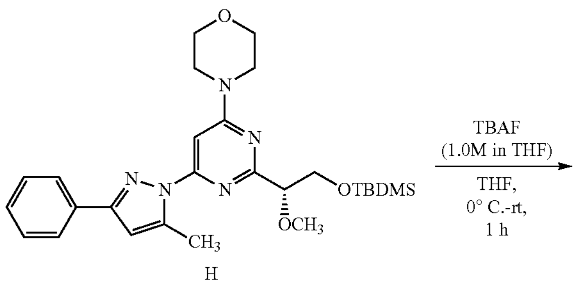

H

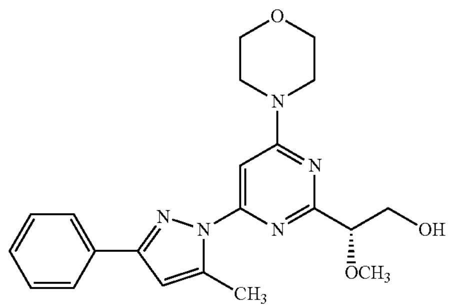

204
(absolute configuration not determined)

Preparation of A

To a stirred solution of 4,6-dichloropyrimidin-2-amine (35.0 g, 0.21 mol) in DMF (110 mL), placed in a 3 neck round bottom flask, under $N_2$ atmosphere at r.t, was added morpholine (20.4 mL, 0.23 mol) and DIPEA (60 mL, 0.31 mol). The reaction mixture was refluxed at 100° C. for 5 h. The reaction mixture was cooled to room temperature, diluted with ice cold water (1.0 L), whereupon the product precipitated. The precipitated product was collected by filtration under vacuum, washed with MTBE (200 mL) and dried under vacuum to obtain A (26.0 g, 87% yield) as a brown solid.

MS (ESI+APCI; multimode): 215 $[M+H]^+$.

Preparation of B

To a stirred solution of A (1.3 g, 6.3 mmol) in NMP (3.0 mL), placed in a microwave vial (G30), was added 5-methyl-3-phenyl-1H-pyrazole (1.0 g, 0.63 mmol), and $Cs_2CO_3$ (6.2 g, 18.96 mmol) at r.t., the reaction mixture was heated to 200° C. for 1 h in microwave. The reaction mixture was cooled to room temperature, and the reaction mixture was diluted with water (100 mL) and extracted with EtOAc (3×50 mL). The combined organic extracts were washed with brine (100 mL), dried over anhydrous $Na_2SO_4$, filtered and concentrated under vacuum to obtain the crude product. The product was purified by silica-gel chromatography using (30-35% EtOAc:Hexanes). The fractions containing the product were combined and concentrated under vacuum to obtain B (1.0 g, 32% yield) as a brown solid.

MS (ESI+APCI; multimode): 337 $[M+H]^+$.

$^1$H NMR (400 MHz, DMSO-$d_6$): δ: 7.86 (d, J=7.6 Hz, 2H), 7.43 (t, J=7.2 Hz, 2H), 7.35 (t, J=7.6 Hz, 1H), 6.73 (s, 1H), 6.50 (s, 1H), 6.33 (s, 2H) 3.71-3.51 (m, 8H), 2.67 (s, 3H);

Preparation of C

To a stirred solution of B (1.0 g, 2.97 mmol) in $CH_3COOH$ (20 mL) placed in a 3 neck round bottom flask, at 0° C. under $N_2$ atmosphere, was added $NaNO_2$ (1.0 g, 14.86 mmol) in $H_2O$ (20 mL) slowly by dropping funnel. The reaction mixture was stirred at room temperature for 6 h. After completion of reaction, the reaction mixture was diluted with ice cold water (100 mL), whereupon the product precipitated. The precipitated product was collected by filtration under vacuum, washed with MTBE (20 mL), hexane (20 mL) and dried under vacuum to obtain C (0.82 g, 82% yield) as a brown solid.

MS (ESI+APCI; multimode): 338 $[M+H]^+$.

$^1$H NMR (400 MHz, DMSO-$d_6$): δ: 7.91 (d, J=7.6 Hz, 2H), 7.45 (t, J=7.6 Hz, 2H), 7.43 (t, J=7.6 Hz, 1H), 6.83 (s, 1H), 6.63 (s, 1H), 3.79-3.58 (m, 8H), 2.64 (s, 3H0

Preparation of D

To a stirred solution of C (0.82 g, 2.43 mmol) in $CH_2Cl_2$ (15 mL), placed in a 3 neck round bottom flask, under $N_2$ atmosphere at r.t, was added $Et_3N$ (3.4 mL, 24.30 mmol) followed with $Tf_2O$ (2.1 mL, 14.15 mmol) by dropping funnel at 0° C. The reaction mixture was stirred at 0° C. for 2 h. After completion of reaction, the reaction mixture was quenched with saturated $NaHCO_3$ at 0° C., and extracted with $CH_2Cl_2$ (3×50 mL). The combined organic extracts were washed with brine (100 mL), dried over anhydrous $Na_2SO_4$, filtered and concentrated under vacuum to obtain the crude product. The crude product washed with hexane (50 mL) and dried under vacuum to obtain D (1.0 g, crude) as a brown solid.

MS (ESI+APCI; multimode): 470 $[M+H]^+$.

Preparation of E

To a stirred solution of D (1.0 g, 2.12 mmol) in 1,4-Dioxane (15 ml) at room temperature under $N_2$ atmosphere was added 4,4,5,5-tetramethyl-2-vinyl-1,3,2-dioxaborolane (0.39 g, 2.55 mmol) followed with $Cs_2CO_3$ (1.4 g, 4.26 mmol), Pd(dppf)$Cl_2$ (0.15 g, 0.21 mmol) and Water (3 mL). The reaction mixture was degassed for 10 min, gradually heated to 100° C. and stirred for 4 h. The reaction mixture is cooled to room temperature, filtered through celite bed and washed with EtOAc (50 mL). Filtrate is concentrated, diluted with water (50 mL) and extracted with EtOAc (2×50 mL). The combined organic extracts were washed with brine solution (100 mL), dried over anhydrous $Na_2SO_4$ and concentrated under reduced pressure to obtain the crude product. The crude compound was purified by silica-gel column chromatography using 10-12% EtOAc:Hexane to obtain E (330 mg, 30% yield) as a brown solid.

MS (ESI+APCI; multimode): 348 $[M+H]^+$.

$^1$H NMR (400 MHz, DMSO-$d_6$): δ: 7.93 (d, J=7.2 Hz, 2H), 7.45 (t, J=7.2 Hz, 2H), 7.38 (t, J=7.2 Hz, 1H), 7.11 (s, 1H), 6.83 (s, 1H), 6.69-6.60 (m, 1H), 6.49 (dd, J=17.2 Hz, J=17.2 Hz, 1H), 5.71 (dd, J=17.2 Hz, J=17.2 Hz, 1H), 3.70 (brs, 8H), 2.74 (s, 3H).

Preparation of F

To a stirred solution of E (250 mg, 0.69 mmol) in t-butanol:$H_2O$ (1:1, 5 mL), placed in 2 neck round bottom flask at r.t, were added AD-mix Alpha (1.1 g, 1.38 mmol) and the mixture was stirred at r.t for 18 h. After completion of reaction, the reaction mixture was quenched with Sodium thiosulfate solution (50 mL) and extracted with EtOAc (2×50 mL). The combined organic extracts were washed with brine solution (100 mL), dried over anhydrous $Na_2SO_4$ and concentrated under reduced pressure to obtain the crude product. The crude compound was purified by silica-gel column chromatography using 55-60% EtOAc:Hexane to obtain F (200 mg, 72% yield) as an off-white solid.

MS (ESI+APCI; multimode): 382 $[M+H]^+$.

$^1$H NMR (400 MHz, DMSO-$d_6$): δ: 7.92 (d, J=7.2 Hz, 2H), 7.45 (t, J=7.2 Hz, 2H), 7.37 (t, J=7.2 Hz, 1H), 7.09 (s, 1H), 6.82 (s, 1H), 4.93 (d, J=6.0 Hz, 1H), 4.61 (t, J=6.0 Hz, 1H), 4.44 (q, J=6.0 Hz, 1H), 3.83-3.75 (m, 1H), 3.74-3.63 (m, 9H), 2.72 (s, 3H);

Preparation of G

To a stirred solution of F (200 mg, 0.34 mmol) in $CH_2Cl_2$ (10 mL), placed in 2 neck round bottom flask at r.t, were added Imidazole (142 mg, 2.09 mmol) followed by TBDMSCl (94 mg, 0.62 mmol) and the mixture was stirred at r.t for 3 h. After completion of reaction, the reaction mixture was quenched with ice water (50 mL) and extracted with DCM (2×50 mL). The combined organic extracts were washed with brine solution (100 mL), dried over anhydrous $Na_2SO_4$ and concentrated under reduced pressure to obtain the crude product. The crude compound was purified by silica-gel column chromatography using 5-10% EtOAc: Hexane to obtain G (190 mg, 73% yield) as a brown solid.

MS (ESI+APCI; multimode): 496 $[M+H]^+$.

Preparation of H

To a stirred suspension of NaH (18.0 mg of a 60% suspension, 0.76 mmol) in THF (10.0 mL) under $N_2$ atmosphere at 0° C., was added G (190 mg, 0.38 mmol). The suspension was stirred at 0° C. for 30 min, and then Iodomethane (109 mg, 0.76 mmol) was added to the reaction mixture. The ice bath was removed, and the mixture was allowed to attain r.t. and was stirred for 1 h. The reaction was quenched by addition of saturated $NH_4Cl$ (aq), extracted with EtOAc (1×50 mL). The combined organic phases were dried over $Na_2SO_4$, filtered, and concentrated. The crude material was washed with hexane (15 mL) to obtained H (160 mg, crude) as a brown solid. MS (ESI+APCI; multimode): 510 $[M+H]^+$.

Preparation of Compound 204

To a stirred solution of H (160 mg, 0.31 mmol) in THF (10 mL) at 0° C. under $N_2$ atmosphere was added 1.0 M TBAF in THF (1.4 mL, 2.82 mmol) The reaction mixture was stirred at 0° C. to room temperature for 1 h. The reaction mixture was diluted with water (50 mL), and extracted with EtOAc (2×50 mL). The combined organic extracts were washed with sat $NaHCO_3$ (50 mL) and brine (50 mL), dried over anhydrous $Na_2SO_4$, filtered and concentrated under vacuum to obtain the crude product. The crude product was purified by silica-gel column chromatography using 40-45% EtOAc:Hexane. Fractions containing the product were combined and concentrated under vacuum to obtain Compound 204 (30 mg, 35% yield) as an off-white solid.

MS (ESI+APCI; multimode): 396 $[M+H]^+$. Chiral HPLC: 91.8 (% of AUC).

$^1$H NMR (400 MHz, DMSO-$d_6$): δ: 7.93 (d, J=7.6 Hz, 2H), 7.45 (t, J=7.6 Hz, 2H), 7.37 (t, J=7.6 Hz, 1H), 7.12 (s, 1H), 6.83 (s, 1H), 4.80 (t, J=6.0 Hz, 1H), 4.16 (t, J=4.8 Hz, 1H), 3.76-3.66 (m, 10H), 3.31 (s, 3H), 2.71 (s, 3H);

Synthesis of (S)-2-methoxy-2-(4-(5-methyl-3-phenyl-1H-pyrazol-1-yl)-6-morpholinopyrimidin-2-yl) ethan-1-ol (Compound 205)

205

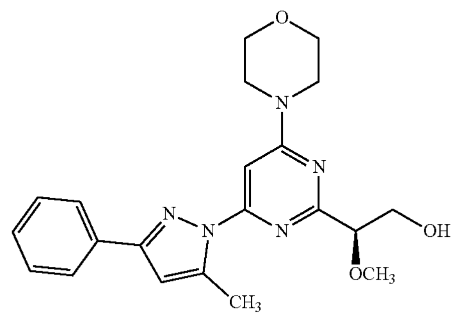

(absolute configuration not determined)

As described for the Synthesis of Compound 204 using AD-mix beta for the corresponding Intermediate F.

MS (ESI+APCI; multimode): 396 $[M+H]^+$. Chiral HPLC: 91.0 (% of AUC).

$^1$H NMR (400 MHz, DMSO-$d_6$): δ: 7.92 (d, J=7.2 Hz, 2H), 7.45 (t, J=7.2 Hz, 2H), 7.37 (t, J=7.2 Hz, 1H), 7.11 (s, 1H), 6.82 (s, 1H), 4.77 (t, J=4.0 Hz, 1H), 4.16 (t, J=5.2 Hz, 1H), 3.76-3.66 (m, 10H), 3.31 (s, 3H), 2.72 (s, 3H)

Synthesis of N,N-dimethyl-1-(1-(2-((3-methyloxetan-3-yl)methoxy)-6-morpholinopyrimidin-4-yl)-3-(m-tolyl)-1H-pyrazol-5-yl)methanamine (Compound 206) and N,N-dimethyl-1-(1-(2-((3-methyloxetan-3-yl)methoxy)-6-morpholinopyrimidin-4-yl)-3-phenyl-1H-pyrazol-5-yl)methanamine (Compound 207)

To a suspension of NaH (71.5 mg, 1.78 mmol) in anhydrous THF (10 ml) at 0° C. under $N_2$ atmosphere, was added N-(2-hydroxyethyl)acetamide (92.0 mg, 0.89 mmol) and the reaction mixture was stirred at same temperature for 15 min. Intermediate 17 (400 mg, 0.89 mmol) in THF (10 ml) was slowly added to the reaction mixture at 0° C. over a period of 5 min. The reaction mixture was gradually warmed to room temperature for 12 h. The reaction mixture was cooled

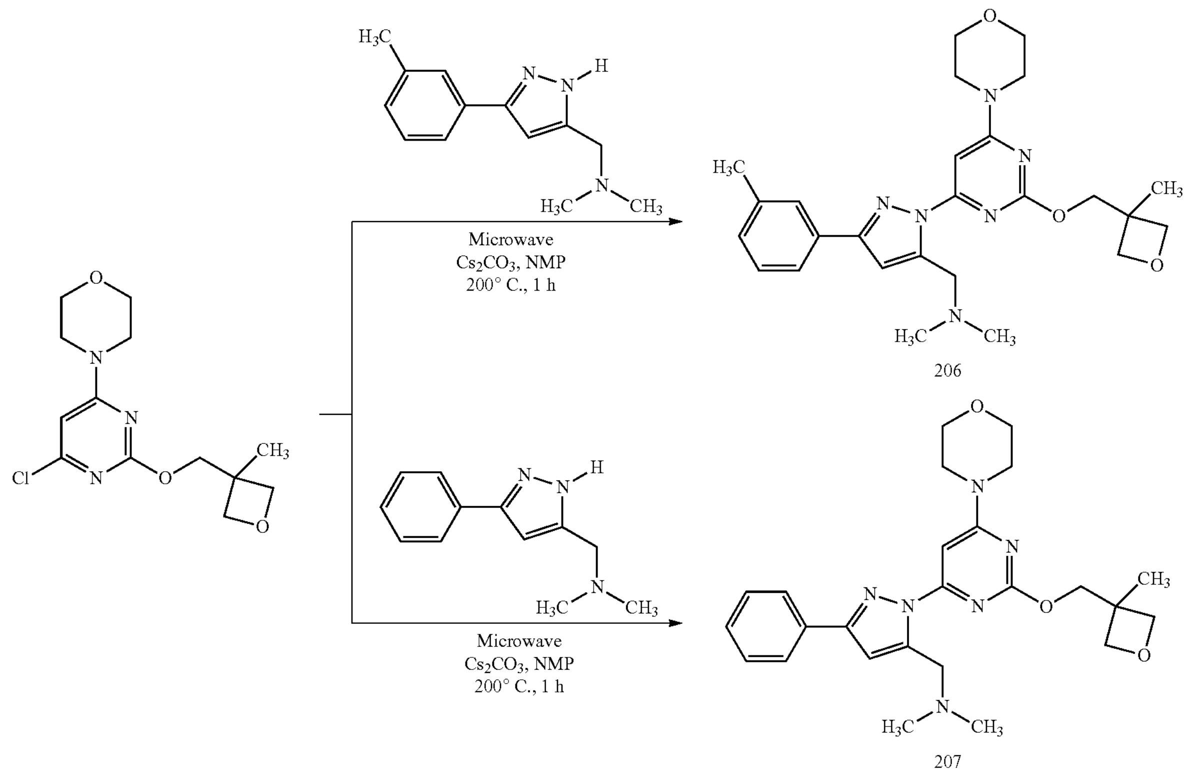 [SMILES: CC1(COc2nc(Cl)cc(N3CCOCC3)n2)COC1 ; CN(C)Cc1cc(-c2ccccc2)n[nH]1 ; Cc1cccc(-c2cc(CN(C)C)[nH]n2)c1 ; CN(C)Cc1cc(-c2ccccc2)nn1-c1cc(N2CCOCC2)nc(OCC2(C)COC2)n1 ; Cc1cccc(-c2cc(CN(C)C)n(-c3cc(N4CCOCC4)nc(OCC4(C)COC4)n3)n2)c1]

206

207

Synthesis of 2-((4-morpholino-6-(3-(m-tolyl)-1H-pyrazol-1-yl)pyrimidin-2-yl)amino)ethan-1-ol (Compound 208)

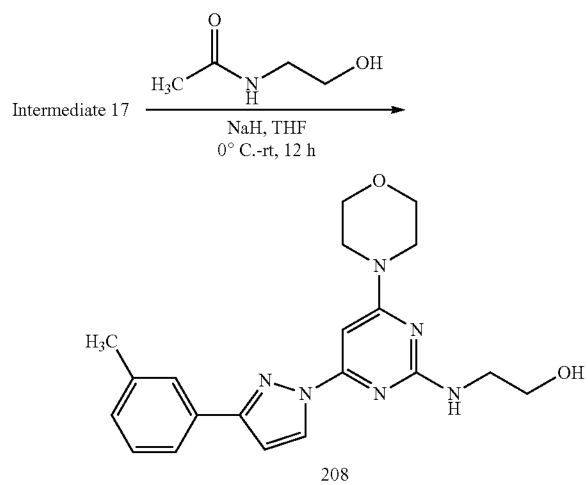

208 to 0° C., quenched with water (20 mL), and extracted with EtOAc (2×50 mL). The combined organic extracts were washed with brine (50 mL), dried over anhydrous $Na_2SO_4$, filtered and concentrated under vacuum to obtain the crude product. The crude product was purified by silica-gel column chromatography using 50-80% EtOAc:Hexanes to afford Compound 208 (30.0 mg, 8.82% yield) as an off-white solid.

LCMS (ESI): m/z=381 $[M+H]^+$; HPLC: 96.9% (AUC). $^1H$ NMR (400 MHz, DMSO-$d_6$) δ: 8.55-8.47 (m, 1H), 7.79 (s, 1H), 7.74 (d, J=7.6 Hz, 1H), 7.34 (t, J=7.6 Hz, 1H), 7.19 (d, J=7.2 Hz, 1H), 7.01 (d, J=1.6 Hz, 1H), 6.74 (brs, 1H), 6.54 (s, 1H), 4.66 (t, J=5.6 Hz, 1H), 3.68 (brs, 4H), 3.60 (brs, 4H), 3.55-3.52 (m, 2H), 3.51-3.41 (m, 2H), 2.38 (s, 3H).

Synthesis of 2-((4-morpholino-6-(3-(m-tolyl)-1H-pyrazol-1-yl)pyrimidin-2-yl)oxy)ethan-1-amine (Compound 209)

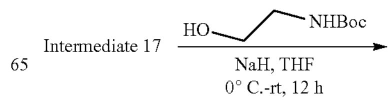

-continued

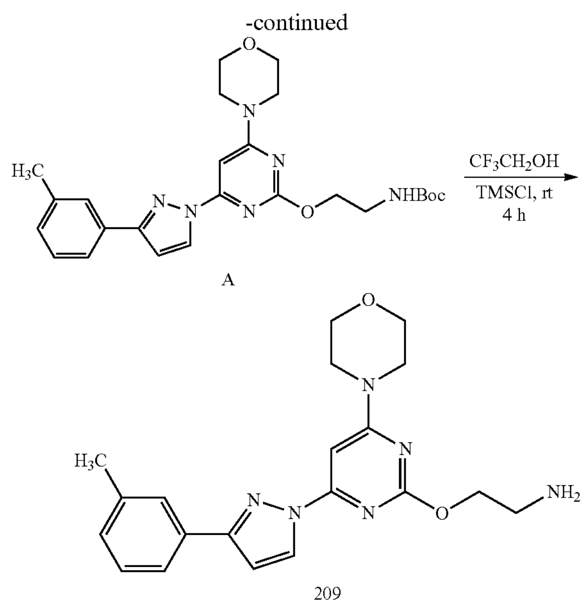

A

209

Preparation of A

To a suspension of 50% NaH (89.0 mg, 2.23 mmol) in anhydrous THF (10 mL) was added tert-butyl (2-hydroxyethyl)carbamate (180 mg, 1.11 mmol) at 0° C., under $N_2$ atmosphere, and the reaction mixture was stirred at 0° C. for 15 min. Intermediate 17 (500 mg, 1.118 mmol) in THF (2 mL) was added to the reaction mixture at 0° C. over a period of 2 min. The reaction mixture was stirred at 0° C. to room temperature for 12 h. The reaction mixture was quenched with water (20 mL) at 0° C., and extracted with EtOAc (2×100 mL). The combined organic extracts were washed with brine (100 mL), dried over anhydrous $Na_2SO_4$, filtered and concentrated under vacuum to obtain the crude product. The crude product was purified by silica-gel column chromatography using 50-55% EtOAc:Hexanes. Fractions containing the product were combined and concentrated under vacuum to obtain A (280 mg, 0.58 mmol, 52% yield) as an off-white solid.

LCMS (ESI): m/z=481 $[M+H]^+$.

$^1$H NMR (400 MHz, $CDCl_3$) δ: 8.53 (d, J=2.8 Hz, 1H), 7.74 (s, 1H), 7.69 (d, J=8.0 Hz, 1H), 7.33 (t, J=7.6 Hz, 1H), 7.19 (d J=7.6 Hz, 1H), 6.91 (s, 1H), 6.75 (d, J=2.4 Hz, 1H), 5.12 (brs, 1H), 4.43 (t, J=5.2 Hz, 2H), 3.82-3.79 (m, 4H), 3.75-3.74 (m, 4H), 3.57 (t, J=4.8 Hz, 2H), 2.43 (s, 3H), 1.44 (s, 9H).

Preparation of Compound 209

To a stirred solution of A (270 mg, 0.56 mmol) in anhydrous Trifluroethanol (5 mL) at 0° C., under $N_2$ atmosphere was added TMSCl (0.07 mL, 0.56 mmol). The reaction mixture was stirred at 0° C. to room temperature for 4 h. $CF_3CH_2OH$ was removed under vacuum. The residue was dissolved in water (25 mL), and extract with EtOAc (2×20 mL). The aqueous layer was basified with sat. $NaHCO_3$ and extracted with EtOAc (2×20 mL). The combined organic extracts were dried over anhydrous $Na_2SO_4$, filtered and concentrated under vacuum to obtain Compound 209 (60.0 mg, 0.15 mmol, 28% yield) as an off white solid.

LCMS (ESI): m/z=381 $[M+H]^+$; HPLC: =95.1 (% of AUC).

$^1$H NMR (400 MHz, DMSO-$d_6$) δ: 8.59 (d, J=2.8 Hz, 1H), 7.82 (s, 1H), 7.77 (d, J=7.6 Hz, 1H), 7.35 (t, J=7.6 Hz, 1H), 7.21 (d, J=7.6 Hz, 1H), 7.06 (d, J=2.4 Hz, 1H), 6.89 (s, 1H), 4.25 (t, J=6.0 Hz, 2H), 3.69 (brs, 8H), 2.87 (t, J=6.0 Hz, 2H), 2.38 (s, 3H).

Synthesis of 1-(2-(2-(1-methyl-1H-pyrazol-4-yl)ethoxy)-6-morpholinopyrimidin-4-yl)-3-phenyl-1H-pyrazol-5-ol (Compound 210) and 1-(2-(2-(1-methyl-1H-pyrazol-4-yl)ethoxy)-6-morpholinopyrimidin-4-yl)-5-phenyl-1H-pyrazol-3-ol (Compound 211)

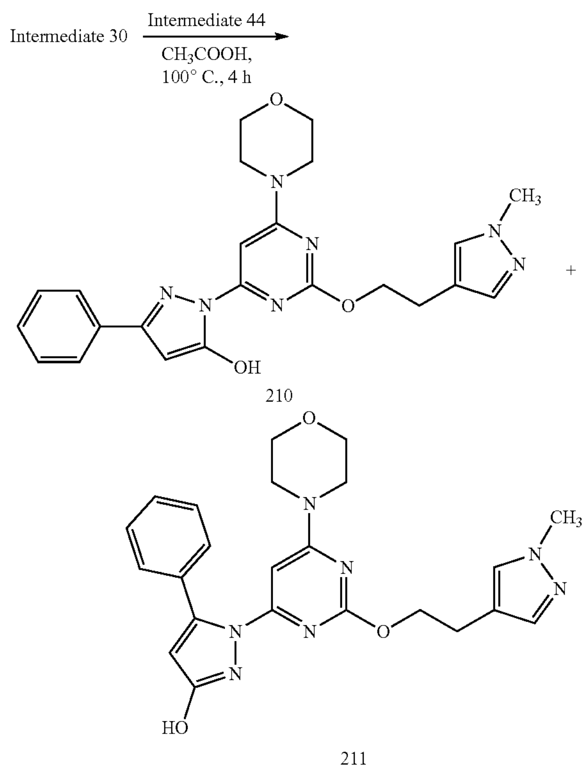 [SMILES: Cn1cc(CCOc2nc(N3CCOCC3)cc(-n3nc(-c4ccccc4)cc3O)n2)cn1 ; Cn1cc(CCOc2nc(N3CCOCC3)cc(-n3nc(O)cc3-c3ccccc3)n2)cn1]

210

+

211

To a suspension of Intermediate 30 (300 mg, 0.93 mmol) in anhydrous acetic acid (15 ml), at room temperature, under $N_2$ atmosphere, was added Intermediate 44 (181 mg, 0.93 mmol). The reaction mixture was gradually heated to 100° C. and stirred for 4 h. The reaction mixture was cooled to room temperature, diluted with water (50 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 40% EtOAc: Hexanes to afford Compound 210 (20 mg, 4.76% yield) as an off-white solid, and a mixture of Compound 211 and Compound 210 120 mg, 14.27% yield).

LCMS (ESI): m/z=448 $[M+H]^+$; HPLC: 98.2% (AUC).

$^1$H NMR (400 MHz, DMSO-$d_6$) δ: 12.70 (s, 1H), 7.89 (d, J=7.6 Hz, 2H), 7.56 (s, 1H), 7.46-7.38 (m, 3H), 7.33 (s, 1H), 6.73 (s, 1H), 6.18 (s, 1H), 4.39 (t, J=6.8 Hz, 2H), 3.78 (s, 3H), 3.70 (s, 8H), 2.87 (t, J=6.8 Hz, 2H).

Synthesis of 4-(2-(2-(1-methyl-1H-pyrazol-4-yl)ethoxy)-6-((1-methyl-3-phenyl-1H-pyrazol-5-yl)oxy)pyrimidin-4-yl)morpholine (Compound 212) and 4-(2-(2-(1-methyl-1H-pyrazol-4-yl)ethoxy)-6-((1-methyl-5-phenyl-1H-pyrazol-3-yl)oxy)pyrimidin-4-yl)morpholine (Compound 213)

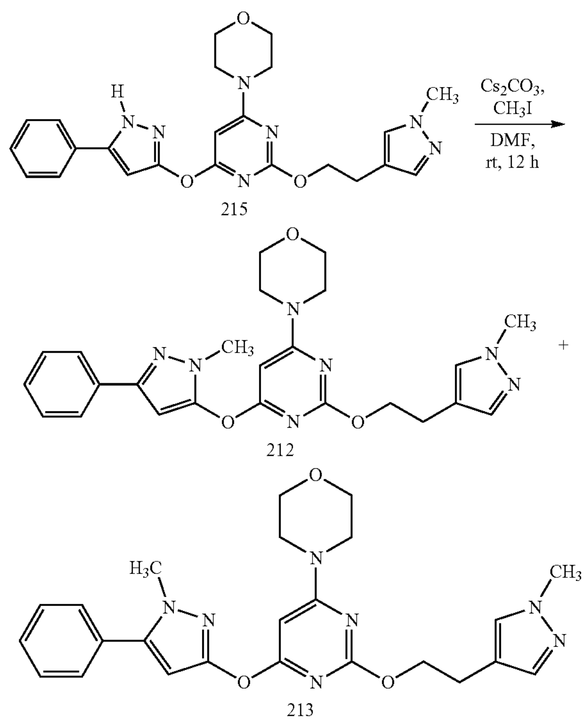 [SMILES: Cn1cc(CCOc2nc(Oc3cc(-c4ccccc4)[nH]n3)cc(N3CCOCC3)n2)cn1 ; Cn1cc(CCOc2nc(Oc3cc(-c4ccccc4)nn3C)cc(N3CCOCC3)n2)cn1 ; Cn1cc(CCOc2nc(Oc3cc(-c4ccccc4)n(C)n3)cc(N3CCOCC3)n2)cn1]

215

212

+

213

To a suspension of Compound 215 (100 mg, 0.22 mmol) in anhydrous DMF (10 ml), at room temperature, under $N_2$ atmosphere, was added methyl iodide (0.01 ml, 0.22 mmol) followed with $Cs_2CO_3$ (109 mg, 0.33 mmol). The reaction mixture was stirred at room temperature for 12 h. The reaction mixture was diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes followed with Mass Triggered PREP HPLC to afford Compound 212 (25 mg, 24.24% yield) as an off-white solid, and Compound 213 (15 mg, 14.54% yield) as an off-white solid.

Compound 212

LCMS (ESI): m/z=462 $[M+H]^+$; HPLC: 98.4% (AUC).

$^1H$ NMR (400 MHz, DMSO-$d_6$) δ: 7.57-7.48 (m, 6H), 7.27 (s, 1H), 6.24 (s, 1H), 6.03 (s, 1H), 4.28 (t, J=7.2 Hz, 2H), 3.79 (s, 3H), 3.75 (s, 3H), 3.68-3.65 (m, 4H), 3.58-3.57 (m, 4H), 2.79 (t, J=7.2 Hz, 2H).

Compound 213

LCMS (ESI): m/z=462 $[M+H]^+$; HPLC: 99.1% (AUC).

$^1H$ NMR (400 MHz, DMSO-$d_6$) δ: 7.78-7.76 (m, 2H), 7.41-7.37 (m, 3H), 7.32-7.28 (m, 1H), 7.23 (s, 1H), 6.53 (s, 1H), 6.16 (s, 1H), 4.22 (t, J=7.2 Hz, 2H), 3.69 (s, 3H), 3.66-3.64 (m, 7H), 3.60-3.59 (m, 4H), 2.74 (t, J=7.2 Hz, 2H).

Synthesis of 4-(2-(2-(1H-pyrazol-4-yl)ethoxy)-6-(3-(m-tolyl)-1H-pyrazol-1-yl)pyrimidin-4-yl)morpholine (Compound 214)

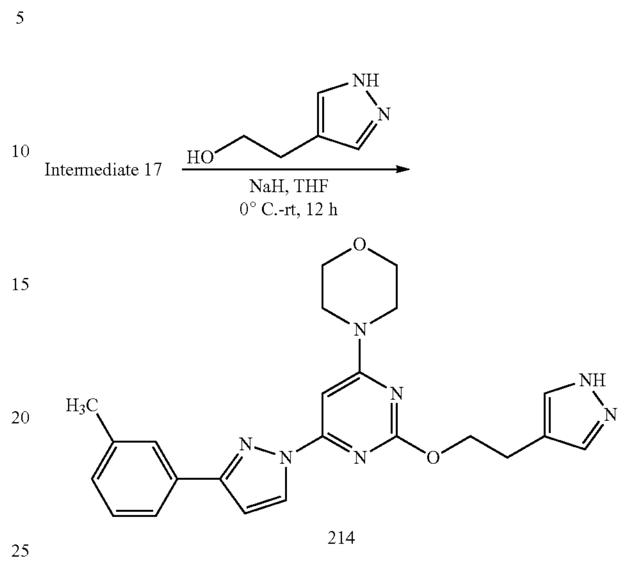

214

To a suspension of 50% NaH (258 mg, 10.7 mmol) in anhydrous THF (20 mL) was added Intermediate 17 (600 mg, 1.34 mmol) at 0° C., under N2 atmosphere, and the reaction mixture was stirred at 0° C. for 15 min. A solution of 2-(1H-pyrazol-4-yl)ethan-1-oll (600 mg, 1.34 mmol) in THF (3 mL) was added to the reaction mixture at 0° C. over a period of 1 min. The reaction mixture was stirred at 0° C. to room temperature for 12 h. The reaction mixture was cooled to 0° C., quenched with water (30 mL), and extracted with EtOAc (2×50 mL). The combined organic extracts were washed with brine (50 mL), dried over anhydrous Na2SO4, filtered and concentrated under vacuum to obtain the crude product. The crude product was purified by silica-gel column chromatography using 5-8% CH3OH: CH2Cl2. Fractions containing the product were combined and concentrated under vacuum to obtain Compound 214 (250 mg, 0.57 mmol, 43% yield) as an off-white solid.

LCMS (ESI): m/z=432 $[M+H]^+$; HPLC: 96.0 (% of AUC).

$^1H$ NMR (400 MHz, DMSO-d6) δ: 12.59 (brs, 1H), 8.58 (d, J=2.4 Hz, 1H), 7.81 (s, 1H), 7.77 (d, J=7.6 Hz, 1H), 7.62 (brs, 1H), 7.42 (brs, 1H), 7.35 (t, J=7.6 Hz, 1H), 7.21 (d, J=7.6 Hz, 1H), 7.04 (d, J=2.4 Hz, 1H), 6.89 (s, 1H), 4.43 (t, J=7.2 Hz, 2H), 3.69 (brs, 8H), 2.89 (t, J=7.2 Hz, 2H), 2.38 (s, 3H).

Synthesis of 4-(2-(2-(1-methyl-1H-pyrazol-4-yl)ethoxy)-6-((5-phenyl-1H-pyrazol-3-yl)oxy)pyrimidin-4-yl)morpholine (Compound 215)

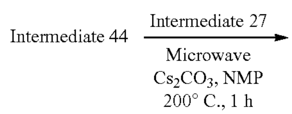

-continued

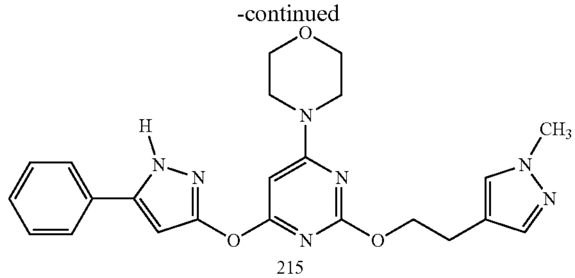

215

To a suspension of Intermediate 44 (74.2 mg, 0.46 mmol) in anhydrous NMP (5 ml), at room temperature under $N_2$ atmosphere, was added Intermediate 27 (150 mg, 0.46 mmol) followed with $Cs_2CO_3$ (151 mg, 0.46 mmol). The reaction mixture was gradually heated to 100° C. and stirred for 12 h. The reaction mixture was cooled to room temperature, diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc:Hexanes to afford Compound 215 (120 mg, 57.9% yield) as an off-white solid.

LCMS (ESI): m/z=448 $[M+H]^+$; HPLC: 96.4% (AUC).

$^1$H NMR (400 MHz, DMSO-$d_6$) δ: 12.96 (s, 1H), 7.74 (d, J=7.6 Hz, 2H), 7.48-7.44 (m, 3H), 7.38-7.35 (m, 1H), 7.24 (s, 1H), 6.52 (d, J=2.0 Hz, 1H), 5.99 (s, 1H), 4.24 (t, J=7.2 Hz, 2H), 3.70 (s, 3H), 3.64-3.63 (m, 4H), 3.54 (brs, 4H), 2.75 (t, J=7.2 Hz, 2H)

The following compounds were synthesized using procedures similar to procedures described for Compound 75 and Compound 86.

| # | Structure | Name | LCMS (ESI): m/z $[M + H]^+$ |
| --- | --- | --- | --- |
| 216 | 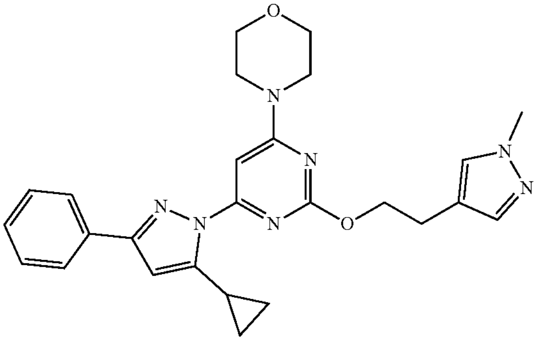 [SMILES: Cn1cc(CCOc2nc(N3CCOCC3)cc(-n3nc(-c4ccccc4)cc3C3CC3)n2)cn1] | 4-(6-(5-cyclopropyl-3-phenyl-1H-pyrazol-1-yl)-2-(2-(1-methyl-1H-pyrazol-4-yl)ethoxy)pyrimidin-4-yl)morpholine | 472 |
| 217 | 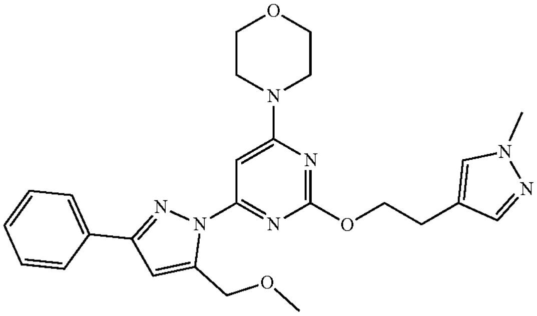 [SMILES: COCc1cc(-c2ccccc2)nn1-c1cc(N2CCOCC2)nc(OCCc2cnn(C)c2)n1] | 4-(6-(5-(methoxymethyl)-3-phenyl-1H-pyrazol-1-yl)-2-(2-(1-methyl-1H-pyrazol-4-yl)ethoxy)pyrimidin-4-yl)morpholine | 476 |
| 218 | 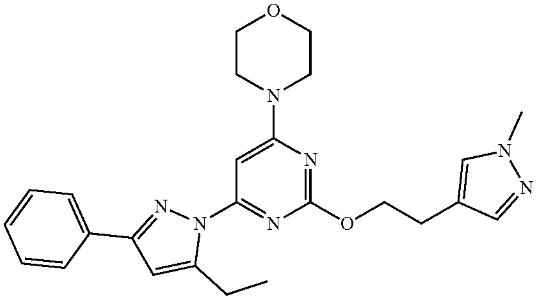 [SMILES: CCc1cc(-c2ccccc2)nn1-c1cc(N2CCOCC2)nc(OCCc2cnn(C)c2)n1] | 4-(6-(5-ethyl-3-phenyl-1H-pyrazol-1-yl)-2-(2-(1-methyl-1H-pyrazol-4-yl)ethoxy)pyrimidin-4-yl)morpholine | 460 |

-continued

| # | Structure | Name | LCMS (ESI): m/z $[M + H]^+$ |
|---|---|---|---|
| 219 | 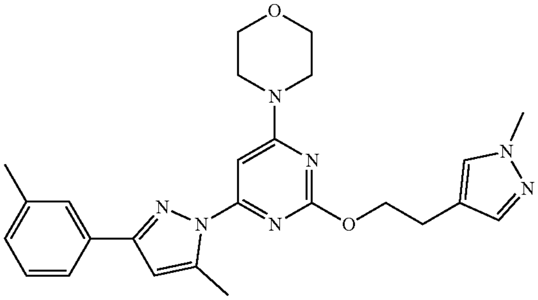 [SMILES: Cc1cccc(-c2cc(C)n(-c3cc(N4CCOCC4)nc(OCCc4cnn(C)c4)n3)n2)c1] | 4-(2-(2-(1-methyl-1H-pyrazol-4-yl)ethoxy)-6-(5-methyl-3-(m-tolyl)-1H-pyrazol-1-yl)pyrimidin-4-yl)morpholine | 460 |
| 220 | 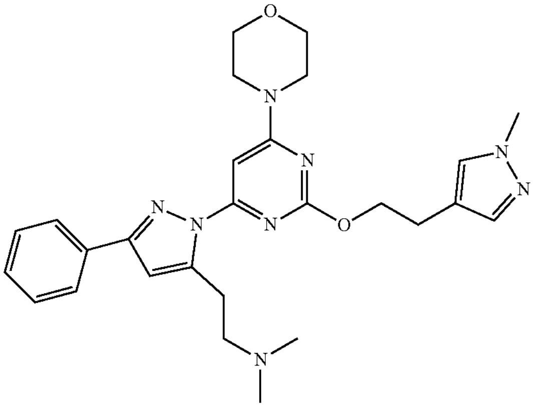 [SMILES: CN(C)CCc1cc(-c2ccccc2)nn1-c1cc(N2CCOCC2)nc(OCCc2cnn(C)c2)n1] | N,N-dimethyl-2-(1-(2-(2-(1-methyl-1H-pyrazol-4-yl)ethoxy)-6-morpholinopyrimidin-4-yl)-3-phenyl-1H-pyrazol-5-yl)ethan-1-amine | 503 |
| 221 | 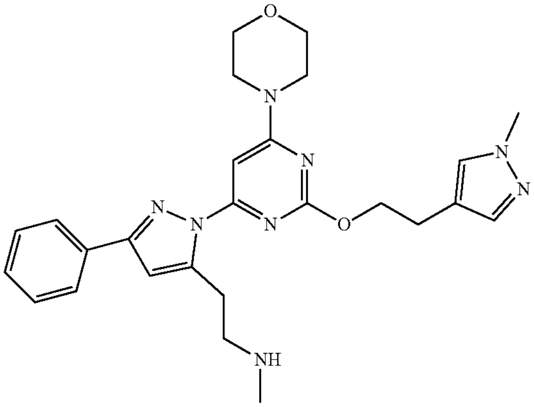 [SMILES: CNCCc1cc(-c2ccccc2)nn1-c1cc(N2CCOCC2)nc(OCCc2cnn(C)c2)n1] | N-methyl-2-(1-(2-(2-(1-methyl-1H-pyrazol-4-yl)ethoxy)-6-morpholinopyrimidin-4-yl)-3-phenyl-1H-pyrazol-5-yl)ethan-1-amine | 489 |
| 222 | 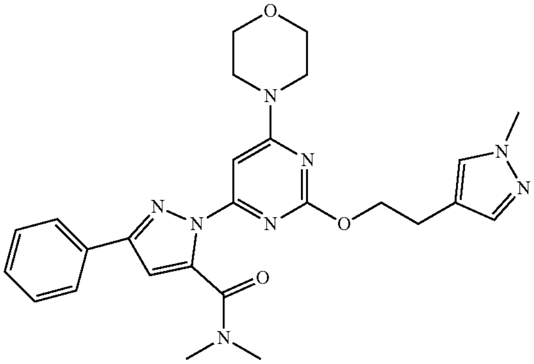 [SMILES: CN(C)C(=O)c1cc(-c2ccccc2)nn1-c1cc(N2CCOCC2)nc(OCCc2cnn(C)c2)n1] | N,N-dimethyl-1-(2-(2-(1-methyl-1H-pyrazol-4-yl)ethoxy)-6-morpholinopyrimidin-4-yl)-3-phenyl-1H-pyrazole-5-carboxamide | 503 |

Synthesis of 4-(2-(2-(1-methyl-1H-pyrazol-4-yl)ethyl)-6-(3-(m-tolyl)-1H-pyrazol-1-yl)pyrimidin-4-yl)morpholine (Compound 223)
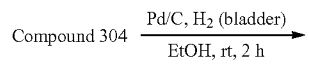
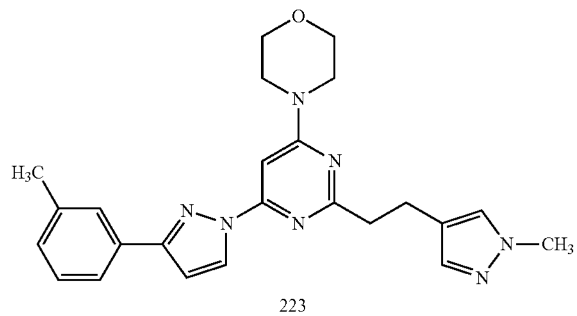
223
Compound 223 was obtained by hydrogenation of Compound 304 as indicated above.
LCMS (ESI): m/z=430 $[M+H]^+$;
Synthesis of (S)-2-methoxy-2-(4-(5-methyl-3-(m-tolyl)-1H-pyrazol-1-yl)-6-morpholinopyrimidin-2-yl)ethan-1-ol (Compound 224)
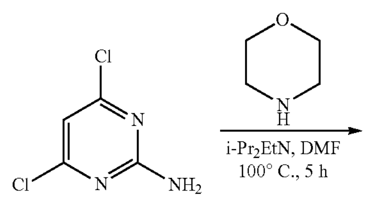
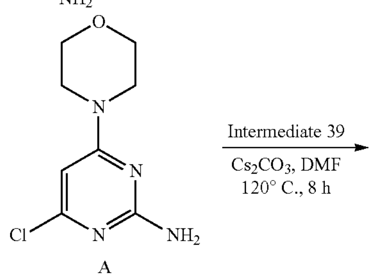
A
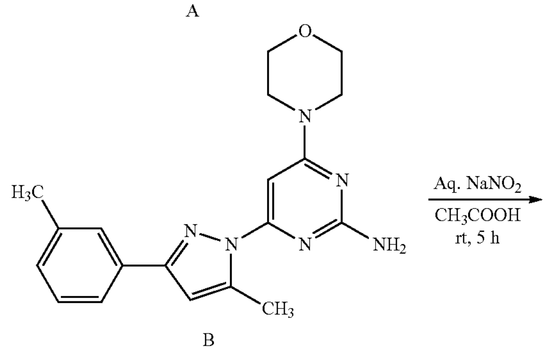
B
-continued
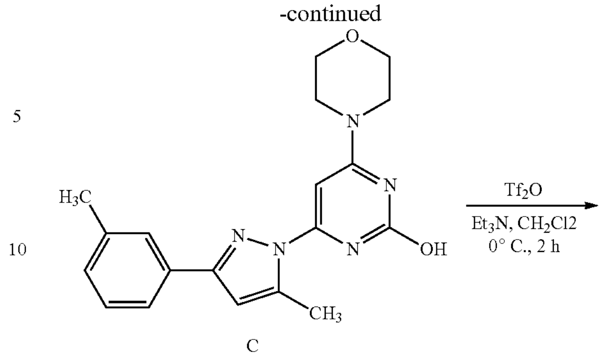
C
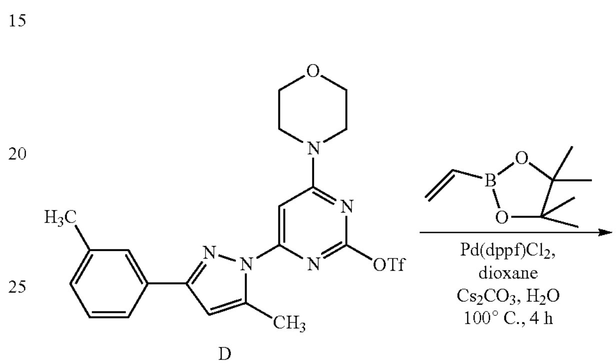
D
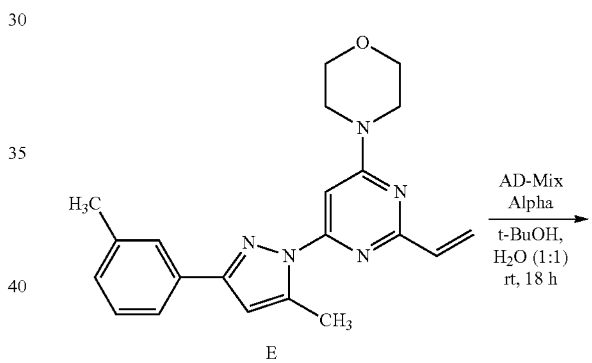
E
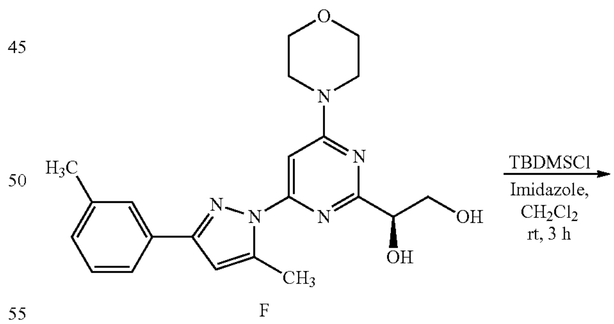
F
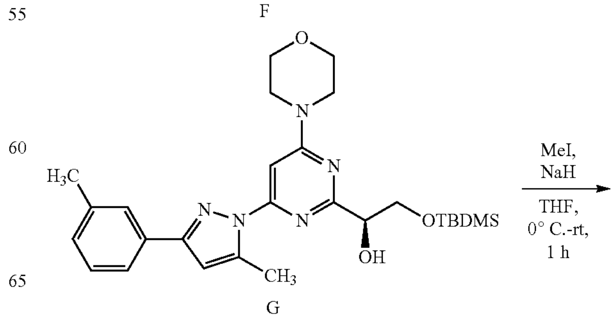
G -continued

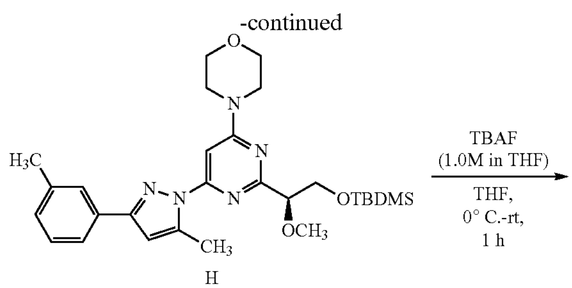

H

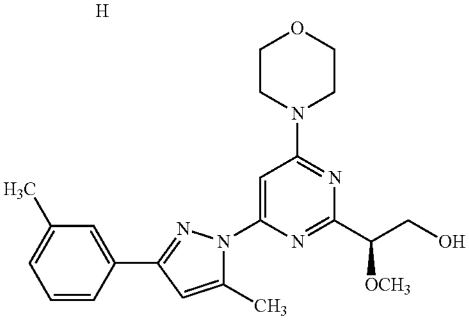

224

Absolute configuration not determined

Preparation of A

To a stirred solution of 4,6-dichloropyrimidin-2-amine (35.0 g, 0.21 mol) in DMF (110 mL), placed in a 3 neck round bottom flask, under $N_2$ atmosphere at r.t, was added morpholine (20.4 mL, 0.23 mol) and DIPEA (60 mL, 0.31 mol). The reaction mixture was refluxed at 100° C. for 5 h. The reaction mixture was cooled to room temperature, diluted with ice cold water (1.0 L), whereupon the product precipitated. The precipitated product was collected by filtration under vacuum, washed with MTBE (200 mL) and dried under vacuum to obtain A (26.0 g, 87% yield) as a brown solid.

MS (ESI+APCI; multimode): 215 $[M+H]^+$.

$^1H$ NMR (400 MHz, DMSO-d6): δ 6.53 (brs, 2H), 6.09 (s, 1H), 3.65-3.44 (m, 8H);

Preparation of B

To a stirred solution of A (3.4.0 g, 15.96 mmol) in DMF (30 mL), placed in a 3 neck round bottom flask, under $N_2$ atmosphere at r.t, was added Intermediate 39 (2.5 g, 14.51 mmol) followed with $Cs_2CO_3$ (9.4 g, 29.03 mmol). The reaction mixture was refluxed at 160° C. for 8 h. After completion of reaction, the reaction mixture cooled to r.t. and diluted with ice cold water (1 L), whereupon the product precipitated. The precipitated product was collected by filtration under vacuum, washed with MTBE (500 mL) and dried under vacuum to obtain B (4.0 g, 80% yield) as a brown solid.

MS (ESI+APCI; multimode): 351 $[M+H]^+$;

$^1H$ NMR (400 MHz, DMSO-$d_6$): δ: 7.70 (s, 1H), 7.66 (d, J=7.6 Hz, 1H), 7.31 (t, J=7.6 Hz, 1H), 7.16 (d, J=7.6 Hz, 1H), 6.71 (s, 1H), 6.49 (s, 1H), 6.34 (brs, 2H), 3.69-3.55 (m, 8H), 2.67 (s, 3H), 2.36 (s, 3H);

Preparation of C

To a stirred solution of B (4.5 g, 12.83 mmol) in $CH_3COOH$ (90 mL) placed in a 3 neck round bottom flask, at 0° C. under $N_2$ atmosphere, was added $NaNO_2$ (4.4 g, 64.19 mmol) in $H_2O$ (90 mL) slowly by dropping funnel. The reaction mixture was stirred at room temperature for 5 h. After completion of reaction, the reaction mixture was diluted with ice cold water (500 mL), whereupon the product precipitated. The precipitated product was collected by filtration under vacuum, washed with MTBE (50 mL), hexane (50 mL) and dried under vacuum to obtain C (3.0 g, 67% yield) as an off-white solid.

MS (ESI+APCI; multimode): 352 [M+H]+

Preparation of D

To a stirred solution of C (4.0 g, 11.38 mmol) in $CH_2Cl_2$ (40 mL), placed in a 3 neck round bottom flask, under $N_2$ atmosphere at r.t, was added $Et_3N$ (15.8 mL, 113.83 mmol) followed with $Tf_2O$ (9.5 mL, 56.91 mmol) by dropping funnel at 0° C. The reaction mixture was stirred at 0° C. for 2 h. After completion of reaction, the reaction mixture was quenched with saturated $NaHCO_3$ at 0° C., and extracted with $CH_2Cl_2$ (3×100 mL). The combined organic extracts were washed with brine (150 mL), dried over anhydrous $Na_2SO_4$, filtered and concentrated under vacuum to obtain the crude product. The crude product washed with MTBE (50 mL), hexane (50 mL) and dried under vacuum to obtain D (2.7 g, crude) as a brown solid.

MS (ESI+APCI; multimode): 484 $[M+H]^+$.

Preparation of E

To a stirred solution of D (2.7 g, 5.58 mmol) in 1,4-Dioxane (25 ml) at room temperature under $N_2$ atmosphere was added 4,4,5,5-tetramethyl-2-vinyl-1,3,2-dioxaborolane (1.0 g, 6.70 mmol) followed with $Cs_2CO_3$ (3.6 g, 6.70 mmol), Pd(dppf)$Cl_2$-DCM (0.45 g, 0.55 mmol) and Water (5 mL). The reaction mixture was degassed for 10 min, gradually heated to 100° C. and stirred for 4 h. The reaction mixture is cooled to room temperature, filtered through celite bed and washed with EtOAc (50 mL). Filtrate is concentrated, diluted with water (50 mL) and extracted with EtOAc (2×50 mL). The combined organic extracts were washed with brine solution (100 mL), dried over anhydrous $Na_2SO_4$ and concentrated under reduced pressure to obtain the crude product. The crude compound was purified by silica-gel column chromatography using 10-12% EtOAc: Hexane to obtain E (0.6 g, 30% yield) as a brown solid.

MS (ESI+APCI; multimode): 362 $[M+H]^+$.

Preparation of F

To a stirred solution of E (250 mg, 0.69 mmol) in t-butanol:$H_2O$ (1:1, 10 mL), placed in 2 neck round bottom flask at r.t, were added AD-mix Alpha (1.0 g, 1.38 mmol) and the mixture was stirred at r.t for 18 h. After completion of reaction, the reaction mixture was quenched with Sodium thiosulfate solution (100 mL) and extracted with EtOAc (2×100 mL). The combined organic extracts were washed with brine solution (100 mL), dried over anhydrous $Na_2SO_4$ and concentrated under reduced pressure to obtain the crude product. The crude compound was purified by silica-gel column chromatography using 55-60% EtOAc:Hexane to obtain F (120 mg, 44% yield) as an off-white solid.

MS (ESI+APCI; multimode): 396 $[M+H]^+$.

$^1H$ NMR (400 MHz, DMSO-$d_6$): δ: 7.69 (s, 1H), 7.64 (d, J=7.8 Hz, 1H), 7.31 (t, J=7.6 Hz, 1H), 7.18 (d, J=7.6 Hz, 1H), 7.14 (s, 1H), 6.51 (s, 1H), 4.71-4.65 (m, 1H), 4.31 (d,

J=3.8 Hz, 1H), 4.01-3.92 (m, 2H), 3.87-3.69 (m, 8H), 2.75 (s, 3H), 2.65 (brs, 1H), 2.42 (s, 3H);

Preparation of G

To a stirred solution of F (120 mg, 0.30 mmol) in $CH_2Cl_2$ (15 mL), placed in 2 neck round bottom flask at r.t, were added Imidazole (83 mg, 1.21 mmol) followed by TBDMSCl (54 mg, 0.36 mmol) and the mixture was stirred at r.t for 3 h. After completion of reaction, the reaction mixture was quenched with ice water (50 mL) and extracted with DCM (2×50 mL). The combined organic extracts were washed with brine solution (100 mL), dried over anhydrous $Na_2SO_4$ and concentrated under reduced pressure to obtain the crude product. The crude compound was purified by silica-gel column chromatography using 5-10% EtOAc: Hexane to obtain G (120 mg, 78% yield) as an off-white solid.

MS (ESI+APCI; multimode): 510 $[M+H]^+$.

Preparation of H

To a stirred suspension of NaH (9.5 mg of a 60% suspension, 0.39 mmol) in THF (10.0 mL) under $N_2$ atmosphere at 0° C., was added G (100 mg, 0.19 mmol). The suspension was stirred at 0° C. for 30 min and then Iodomethane (55 mg, 0.39 mmol) was added to the reaction mixture. The ice bath was removed, and the mixture was allowed to attain r.t. and was stirred for 1 h. The reaction was quenched by addition of saturated $NH_4Cl$ (aq), extracted with EtOAc (1×50 mL). The combined organic phases were dried over $Na_2SO_4$, filtered, and concentrated. The crude material was washed with hexane to obtained H (80 mg, crude) as a brown solid.

MS (ESI+APCI; multimode): 524 $[M+H]^+$.

Preparation of Compound 224

To a stirred solution of H (100 mg, 0.19 mmol) in THF (10 mL) at 0° C. under $N_2$ atmosphere was added 1.0 M TBAF in THF (0.9 mL, 0.95 mmol) The reaction mixture was stirred at 0° C. to room temperature for 1 h. The reaction mixture was diluted with water (50 mL), and extracted with EtOAc (2×50 mL). The combined organic extracts were washed with sat $NaHCO_3$ (50 mL) and brine (50 mL), dried over anhydrous $Na_2SO_4$, filtered and concentrated under vacuum to obtain the crude product. The crude product was purified by silica-gel column chromatography using 40-45% EtOAc:Hexane. Fractions containing the product were combined and concentrated under vacuum to obtain Compound 224 (50 mg, 65% yield) as an off-white solid.

MS (ESI+APCI; multimode): 410 $[M+H]^+$. Chiral HPLC: 92.4 (% of AUC).

$^1$H NMR (400 MHz, DMSO-$d_6$): δ: 7.74 (s, 1H), 7.70 (d, J=7.6 Hz, 1H), 7.33 (t, J=7.6 Hz, 1H), 7.19 (d, J=7.6 Hz, 1H), 7.10 (s, 1H), 6.80 (s, 1H), 4.77 (t, J=6.0 Hz, 1H), 4.15 (t, J=6.0 Hz, 1H), 3.77-3.65 (m, 10H), 3.31 (s, 3H), 2.71 (s, 3H), 2.37 (s, 3H)

Synthesis of (S)-2-methoxy-2-(4-(5-methyl-3-(m-tolyl)-1H-pyrazol-1-yl)-6-morpholinopyrimidin-2-yl)ethan-1-ol (Compound 225)

225

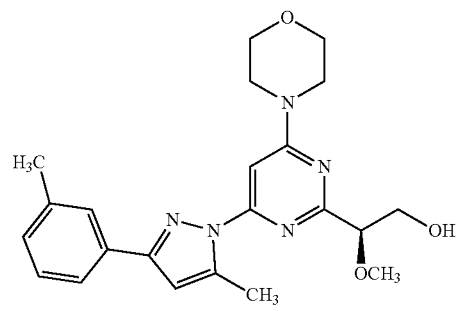

*Absolute configuration not determined*

As described for Compound 224 using AD-mix beta for the preparation of the corresponding MS (ESI+APCI; multimode): 410 $[M+H]^+$. Chiral HPLC: 91.9 (% of AUC).

$^1$H NMR (400 MHz, DMSO-$d_6$): δ: 7.74 (s, 1H), 7.71 (d, J=7.6 Hz, 1H), 7.33 (t, J=7.6 Hz, 1H), 7.19 (d, J=7.6 Hz, 1H), 7.10 (s, 1H), 6.81 (s, 1H), 4.80 (t, J=6.0 Hz, 1H), 4.15 (t, J=6.0 Hz, 1H), 3.77-3.64 (m, 10H), 3.33 (s, 3H), 2.71 (s, 3H), 2.37 (s, 3H)

Synthesis of 2-methoxy-2-(4-morpholino-6-(3-(m-tolyl)-1H-pyrazol-1-yl)pyrimidin-2-yl)propan-1-ol (Compound 226)

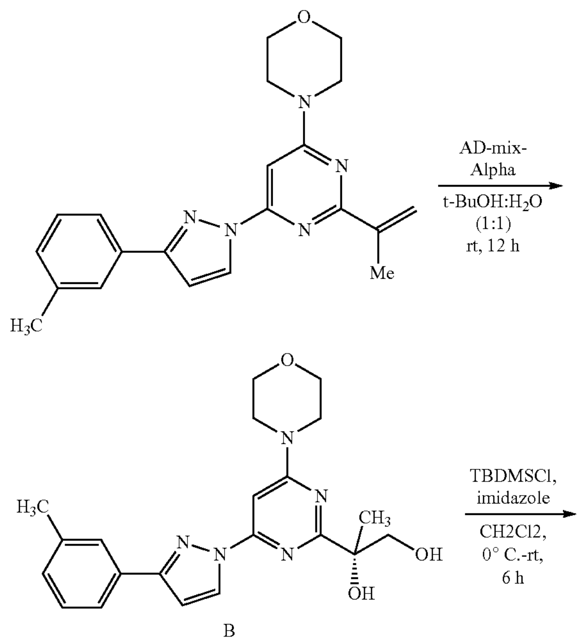

B

-continued

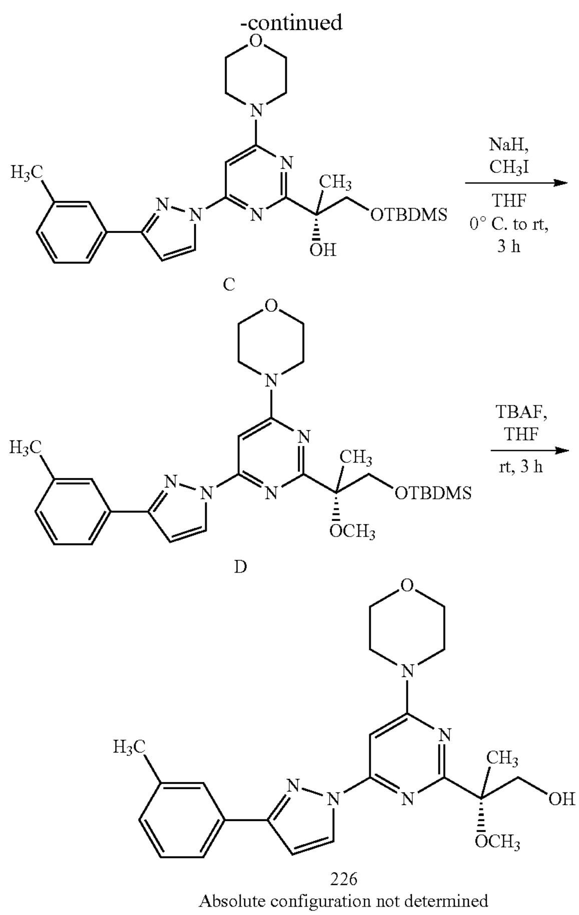

C

D

226

Absolute configuration not determined

Preparation of B

To a suspension of A (200 mg, 0.55 mmol) in t-BuOH (10 ml) and Water (10 mL) at room temperature under $N_2$ atmosphere, was added AD-mix-alpha (652 mg, 0.82 mmol). The reaction mixture was stirred at room temperature for 12 h. The reaction mixture was diluted with water (50 mL), and extracted with EtOAc (2×50 mL). The combined organic extracts were washed with brine solution (50 mL), dried over anhydrous $Na_2SO_4$ and concentrated under reduced pressure to obtain the crude compound. The crude compound was washed with MTBE to afford 4 (125 mg, 57.1% yield) as an off white solid.

LCMS (ESI): m/z=396 $[M+H]^+$.

$^1$H NMR (400 MHz, DMSO-$d_6$) δ: 8.85 (d, J=2.4 Hz, 1H), 7.83 (s, 1H), 7.78 (d, J=7.6 Hz, 1H), 7.35 (t, J=7.6 Hz, 1H), 7.21 (d, J=7.6 Hz, 1H), 7.19-7.15 (m, 2H), 4.90 (s, 1H), 4.50 (t, J=6.0 Hz, 1H), 3.72-3.66 (m, 9H), 3.59-3.55 (m, 1H), 2.39 (s, 3H), 1.39 (s, 3H).

Preparation of C

To a suspension of B (250 mg, 0.63 mmol) in $CH_2Cl_2$ (10 mL) at 0° C. under $N_2$ atmosphere, was added imidazole (129 mg, 1.89 mmol) followed with TBDMSCl (96 mg, 0.63 mmol) over a period of 2 min. The reaction mixture was gradually warmed to room temperature and stirred for 6 h. The reaction mixture was diluted with water (50 mL), and extracted with $CH_2Cl_2$ (2×100 mL). The combined organic extracts were washed with brine solution (50 mL), dried over anhydrous $Na_2SO_4$ and concentrated under reduced pressure to obtain the crude compound. The crude compound was purified by silica-gel column chromatography using 20-25% EtOAc:Hexanes to afford C (193 mg, 59.7% yield) as a light brown gummy liquid.

LCMS (ESI): m/z=510 $[M+H]^+$.

$^1$H NMR (400 MHz, $CDCl_3$) δ: 8.62 (d, J=2.8 Hz, 1H), 7.80 (s, 1H), 7.75 (d, J=7.6 Hz, 1H), 7.38 (t, J=7.6 Hz, 1H), 7.24 (d, J=7.6 Hz, 1H), 7.12 (s, 1H), 6.81 (d, J=2.8 Hz, 1H), 4.67 (brs, 1H), 4.00-3.98 (m, 1H), 3.87-3.85 (m, 5H), 3.82-3.77 (m, 4H), 2.48 (s, 3H), 1.63 (s, 3H), 0.79 (s, 9H), −0.000 (s, 3H), −0.099 (s, 3H).

Preparation of D

To a suspension of C (200 mg, 0.39 mmol) in anhydrous Tetrahydrofuran (10 ml), at 0° C. under $N_2$ atmosphere, was added NaH (50%, 28.2 mg, 1.17 mmol) and the mixture was stirred at same temperature for 30 min, methyl iodide (0.03 ml, 0.58 mmol) was added. The reaction mixture was gradually warmed to room temperature and stirred for 3 h. The reaction mixture was cooled to 0° C., quenched with water (5 mL), diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes to afford D (150 mg, 73.0% yield) as an off-white solid.

LCMS (ESI): m/z=524 $[M+H]^+$.

$^1$H NMR (400 MHz, $CDCl_3$) δ: 8.56 (d, J=2.8 Hz, 1H), 7.69 (s, 1H), 7.63 (d, J=7.6 Hz, 1H), 7.26 (t, J=7.6 Hz, 1H), 7.11 (d, J=7.6 Hz, 1H), 7.00 (s, 1H), 6.68 (d, J=2.8 Hz, 1H), 4.06-3.97 (m, 1H), 3.84-3.81 (m, 1H), 3.75-3.73 (m, 4H), 3.70-3.68 (m, 4H), 3.20 (s, 3H), 2.36 (s, 3H), 1.56 (s, 3H), 0.73 (s, 9H), −0.074 (s, 3H), −0.140 (s, 3H).

Preparation of Compound 226

To a suspension of D (150 mg, 0.28 mmol) in anhydrous THF (10 ml), at room temperature under $N_2$ atmosphere, was added TBAF (1.0 M in THF, 150 mg, 0.57 mmol). The reaction mixture was stirred at room temperature for 3 h. The reaction mixture was diluted with water (50 mL), and extracted with EtOAc (2×100 mL). The combined organic extracts were washed with Sat. $NaHCO_3$ (150 mL), brine (20 mL), dried over anhydrous $Na_2SO_4$, filtered and concentrated under vacuum to obtain the crude product. The crude product was purified by silica-gel column chromatography using 40% EtOAc:Hexanes to afford Compound 226 (30.0 mg, 25.6% yield) as an off-white solid.

LCMS (ESI): m/z=410 $[M+H]^+$; HPLC: 97.1% (AUC). CHIRAL HPLC: 98.9% (AUC).

$^1$H NMR (400 MHz, DMSO-$d_6$) δ: 8.63 (d, J=2.4 Hz, 1H), 7.83 (s, 1H), 7.79 (d, J=7.6 Hz, 1H), 7.36 (d, J=8.0 Hz, 1H), 7.22 (d, J=8.0 Hz, 1H), 7.10 (s, 1H), 7.08 (d, J=2.8 Hz, 1H), 4.62 (t, J=6.4 Hz, 1H), 3.82-3.78 (m, 1H), 3.74-3.72 (m, 9H), 3.13 (s, 3H), 2.39 (s, 3H), 1.52 (s, 3H).

Synthesis of 2-methoxy-2-(4-morpholino-6-(3-(m-tolyl)-1H-pyrazol-1-yl)pyrimidin-2-yl)propan-1-ol (Compound 227)

227

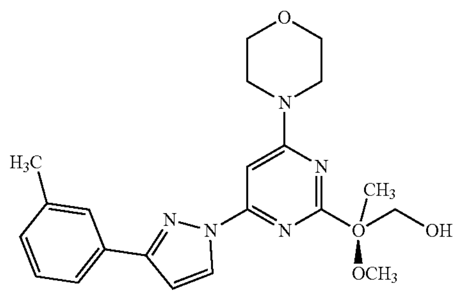

*Absolute configuration not determined*

As described for the synthesis of Compound 243 using AD-Mix-Beta for the preparation of the corresponding Intermediate B.

LCMS (ESI): m/z=410 $[M+H]^+$; HPLC: 99.0% (AUC). CHIRAL HPLC: 99.3% (AUC).

$^1$H NMR (400 MHz, DMSO-$d_6$) δ: 8.63 (d, J=2.4 Hz, 1H), 7.83-7.78 (m, 2H), 7.38-7.34 (m, 1H), 7.22 (d, J=7.6 Hz, 1H), 7.10 (s, 1H), 7.08 (d, J=2.8 Hz, 1H), 4.61 (t, J=6.4 Hz, 1H), 3.83-3.78 (m, 1H), 3.74-3.72 (m, 9H), 3.13 (s, 3H), 2.39 (s, 3H), 1.52 (s, 3H).

Synthesis of 2-methoxy-2-(4-morpholino-6-(3-(m-tolyl)-1H-pyrazol-1-yl)pyrimidin-2-yl)-2-phenylethan-1-ol (Compound 228)

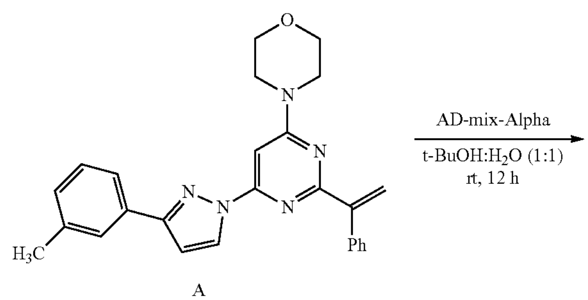

A

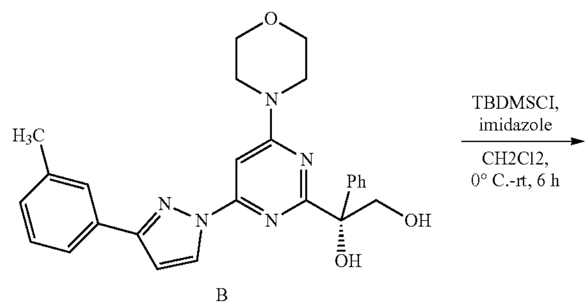

B

-continued

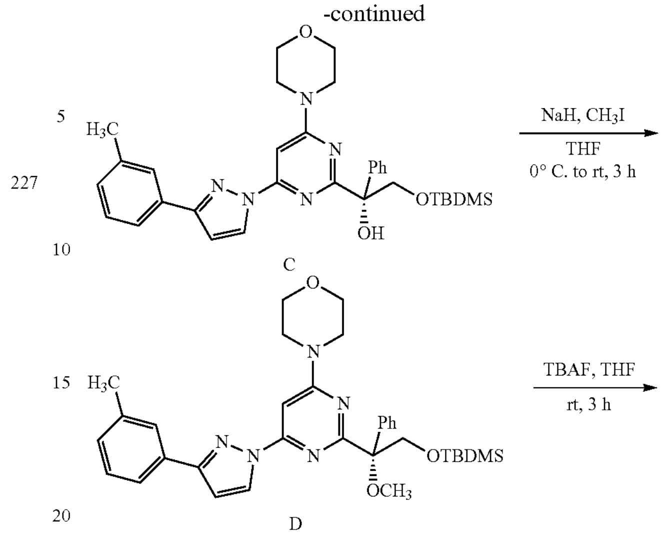

C

D

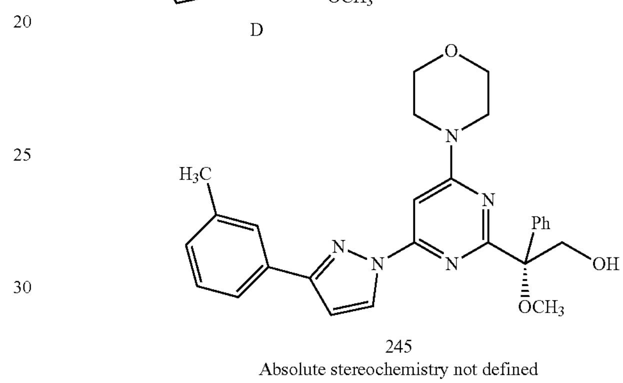

245

Absolute stereochemistry not defined

Preparation of B

To a suspension of A (800 mg, 1.88 mmol) in anhydrous t-BuOH (20 ml) and Water (20.00 ml), at room temperature under $N_2$ atmosphere, was added AD-mix-beta (2.20 g, 2.82 mmol). The reaction mixture was stirred at room temperature for 12 h. The reaction mixture was diluted with water (100 mL), and extracted with EtOAc (2×150 mL). The combined organic extracts were washed with brine (50 mL), dried over anhydrous $Na_2SO_4$ and concentrated under reduced pressure to obtain the crude compound. The crude compound was washed with MTBE to afford B (600 mg, 69.4% yield) as an off-white solid.

LCMS (ESI): m/z=458 $[M+H]^+$.

$^1$H NMR (400 MHz, DMSO-$d_6$) δ: 8.96 (d, J=2.4 Hz, 1H), 7.82 (s, 1H), 7.78 (d, J=8.0 Hz, 1H), 7.73 (d, J=7.2 Hz, 2H), 7.37-7.28 (m, 3H), 7.23-7.20 (m, 2H), 7.09 (d, J=2.8 Hz, 1H), 7.06 (s, 1H), 5.64 (s, 1H), 4.67-4.64 (m, 1H), 4.36-4.31 (m, 1H), 3.77-3.73 (m, 9H), 2.38 (s, 3H).

Preparation of C

To a suspension of B (600 mg, 1.30 mmol) in anhydrous dichloromethane (20 ml), at 0° C. under $N_2$ atmosphere, was added TBDMSCl (400 mg, 2.62 mmol) followed with imidazole (360 mg, 5.24 mmol). The reaction mixture was gradually warmed to room temperature and stirred for 3 h. The reaction mixture was diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 20% EtOAc: Hexanes to afford C (430 mg, 57.3% yield) as an off-white solid.

LCMS (ESI): m/z=572 $[M+H]^+$.

$^1$H NMR (400 MHz, $CDCl_3$) δ: 8.59 (d, J=2.4 Hz, 1H), 7.86 (d, J=7.6 Hz, 2H), 7.75 (s, 1H), 7.69 (d, J=7.6 Hz, 1H), 7.35-7.27 (m, 3H), 7.20-7.18 (m, 2H), 7.06 (s, 1H), 6.77 (d, J=2.8 Hz, 1H), 5.28 (s, 1H), 4.54 (d, J=10.0 Hz, 1H), 3.96 (d, J=9.6 Hz, 1H), 3.77-3.76 (m, 8H), 2.43 (s, 3H), 0.74 (s, 9H), −0.005 (s, 3H), −0.082 (s, 3H).

Preparation of D

To a suspension of C (430 mg, 0.74 mmol) in anhydrous Tetrahydrofuran (20 ml), at 0° C. under $N_2$ atmosphere, was added NaH (50%, 56.0 mg, 2.24 mmol), and the mixture was stirred at same temperature for 10 min, methyl iodide (0.06 ml, 1.12 mmol) was added. The reaction mixture was gradually warmed to room temperature and stirred for 3 h. The reaction mixture was cooled to 0° C., quenched with water (10 mL), diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 30% EtOAc: Hexanes to afford D (280 mg, 63.6% yield) as an off-white solid.

LCMS (ESI): m/z=586 $[M+H]^+$.

$^1$H NMR (400 MHz, $CDCl_3$) δ: 8.66 (d, J=2.0 Hz, 1H), 7.86 (s, 1H), 7.81 (d, J=8.0 Hz, 1H), 7.62 (d, J=7.6 Hz, 2H), 7.46-7.41 (m, 3H), 7.35-7.29 (m, 2H), 7.19 (s, 1H), 6.84 (d, J=2.4 Hz, 1H), 4.62-4.53 (m, 2H), 3.92-3.91 (m, 4H), 3.84-3.83 (m, 4H), 3.53 (s, 3H), 2.55 (s, 3H), 0.90 (s, 9H), −0.017 (s, 3H), −0.000 (s, 3H).

Preparation of Compound 228

To a suspension of D (140 mg, 0.23 mmol) in anhydrous THF (10 ml), at room temperature, under $N_2$ atmosphere, was added TBAF (1.0 M in THF, 94 mg, 0.35 mmol). The reaction mixture was stirred at room temperature for 3 h. The reaction mixture was diluted with water (50 mL) at room temperature, and extracted with EtOAc (2×100 mL). The combined organic extracts were washed with Sat. $NaHCO_3$ (50 mL), brine (20 mL), dried over anhydrous $Na_2SO_4$, filtered and concentrated under vacuum to obtain the crude product. The crude product was purified by silica-gel column chromatography using 80% EtOAc:Hexanes to afford Compound 228 (30 mg, 26.6% yield) as an off-white solid.

LCMS (ESI): m/z=472 $[M+H]^+$; HPLC: 97.8% (AUC). CHIRAL HPLC: 90.7% (AUC).

$^1$H NMR (400 MHz, DMSO-$d_6$) δ: 8.59 (d, J=2.8 Hz, 1H), 7.83 (s, 1H), 7.79 (d, J=7.6 Hz, 1H), 7.50 (d, J=7.2 Hz, 2H), 7.37 (t, J=8.0 Hz, 1H), 7.31 (t, J=7.2 Hz, 2H), 7.23 (d, J=7.2 Hz, 2H), 7.08 (s, 1H), 7.07 (d, J=2.8 Hz, 1H), 4.55 (t, J=6.4 Hz, 1H), 4.37-4.33 (m, 2H), 3.72-3.71 (m, 8H), 3.31 (s, 3H), 2.40 (s, 3H).

Synthesis of 2-methoxy-2-(4-morpholino-6-(3-(m-tolyl)-1H-pyrazol-1-yl)pyrimidin-2-yl)-2-phenylethan-1-ol (Compound 229)

229

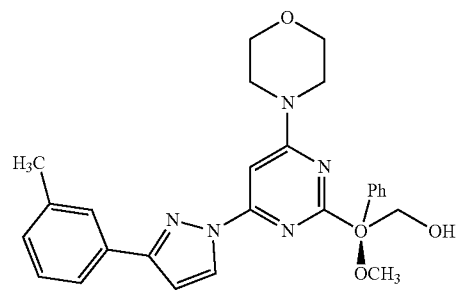

*Absolute configuration not determined*

As described for the synthesis of Compound 228 using AD-Mix-Beta for the preparation of the corresponding Intermediate B LCMS (ESI): m/z=472 $[M+H]^+$; HPLC: 92.7% (AUC). CHIRAL HPLC: 92.1% (AUC).

$^1$H NMR (400 MHz, DMSO-$d_6$) δ: 8.57 (d, J=2.8 Hz, 1H), 7.81-7.76 (m, 2H), 7.48 (d, J=7.2 Hz, 2H), 7.34 (t, J=7.6 Hz, 1H), 7.30-7.20 (m, 4H), 7.06 (d, J=4.4 Hz, 2H), 4.53 (t, J=6.0 Hz, 1H), 4.38-4.28 (m, 2H), 3.70-3.68 (m, 8H), 3.31 (s, 3H), 2.38 (s, 3H).

Synthesis of 1-(1-methyl-1H-pyrazol-4-yl)-3-(4-morpholino-6-(3-(m-tolyl)-1H-pyrazol-1-yl)pyrimidin-2-yl)prop-2-yn-1-ol (Compound 230)

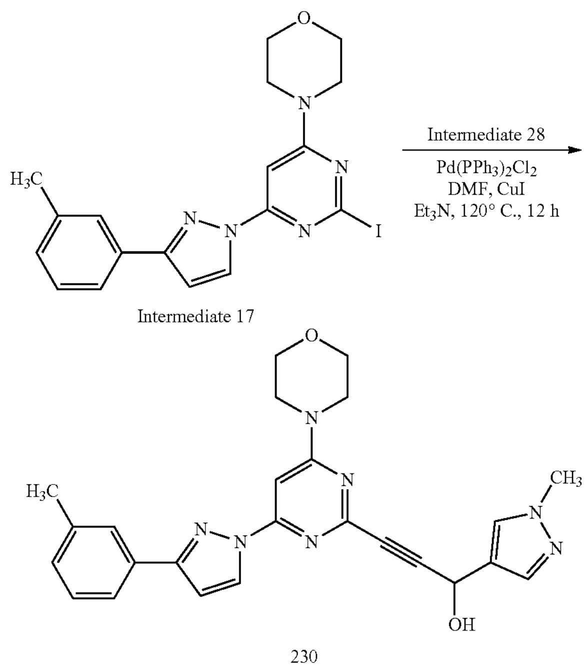

Intermediate 17

230

To a suspension of Intermediate 17 (1314 mg, 2.94 mmol) in anhydrous triethylamine (15 ml) and DMF (6.00 ml), at room temperature under $N_2$ atmosphere, was added Intermediate 28 (200 mg, 1.469 mmol) followed with copper(I) iodide (56.0 mg, 0.29 mmol) and bis(triphenylphosphine) palladium(II) chloride (103 mg, 0.14 mmol). The reaction mixture was gradually heated to 120° C. and stirred for 12 h. The reaction mixture was cooled to room temperature, diluted with water (100 mL), and extracted with EtOAc (2×100 mL). The combined organic extracts were washed with brine (20 mL), dried over anhydrous $Na_2SO_4$, filtered and concentrated under vacuum to obtain the crude product. The crude product was purified by silica-gel column chromatography using 80% EtOAc:Hexanes to afford Compound 230 (29.0 mg, 4.33% yield) as an off-white solid.

LCMS (ESI): m/z=456 $[M+H]^+$; HPLC: 97.5% (AUC).

$^1$H NMR (400 MHz, DMSO-$d_6$) δ: 8.58 (d, J=2.8 Hz, 1H), 7.83 (s, 1H), 7.79 (d, J=8.0 Hz, 1H), 7.74 (s, 1H), 7.46 (s, 1H), 7.35 (t, J=7.6 Hz, 1H), 7.22 (d, J=7.6 Hz, 1H), 7.18 (s, 1H), 7.08 (d, J=2.4 Hz, 1H), 6.08 (d, J=6.0 Hz, 1H), 5.59 (d, J=6.4 Hz, 1H), 3.83 (s, 3H), 3.70 (s, 8H), 2.38 (s, 3H).

Synthesis of 1-(1-methyl-1H-pyrazol-4-yl)-3-(4-morpholino-6-(3-(m-tolyl)-1H-pyrazol-1-yl)pyrimidin-2-yl)propan-1-ol (Compound 231)

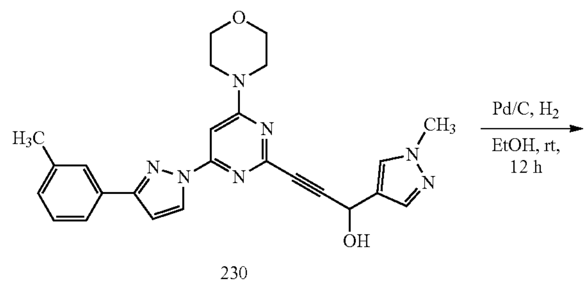

230

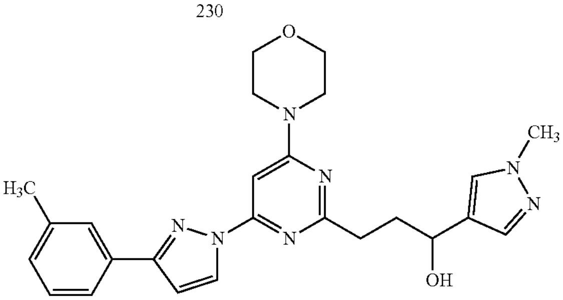

231

To a suspension of Compound 230 (250 mg, 0.54 mmol) in anhydrous Ethanol (25 ml), at room temperature, under $N_2$ atmosphere was added Pd/C (58.4 mg). The reaction mixture was stirred under Hydrogen gas (bladder) at room temperature for 12 h. The reaction mixture was filtered through celite, washed with EtOAc (100 mL), and concentrated under vacuum to obtain the crude product. The crude product was purified by silica-gel column chromatography using 80% EtOAc:Hexanes followed with mass triggered PREP HPLC to afford Compound 231 (60.0 mg, 23.79% yield) as an off-white solid.

LCMS (ESI): m/z=460 $[M+H]^+$; HPLC: 96.3% (AUC).

$^1$H NMR (400 MHz, DMSO-$d_6$) δ: 8.61 (d, J=2.8 Hz, 1H), 7.81 (s, 1H), 7.77 (d, J=8.0 Hz, 1H), 7.55 (s, 1H), 7.37-7.33 (m, 2H), 7.21 (d, J=6.8 Hz, 1H), 7.05-7.04 (m, 2H), 4.96 (d, J=5.2 Hz, 1H), 4.61-4.57 (m, 1H), 3.78 (s, 3H), 3.70 (s, 8H), 2.78-2.66 (m, 2H), 2.38 (s, 3H), 2.12-2.06 (m, 2H).

Synthesis of 4-(6-(3-(1-methyl-1H-indol-3-yl)-1H-pyrazol-1-yl)-2-(2-(1-methyl-1H-pyrazol-4-yl)ethoxy)pyrimidin-4-yl)morpholine (Compound 232)

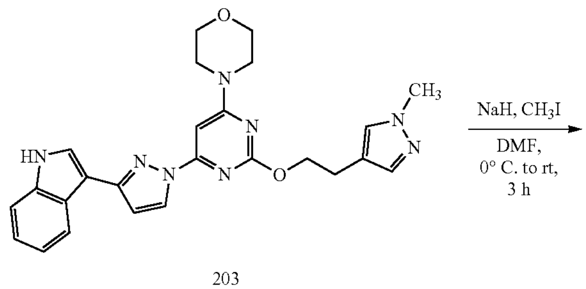

203

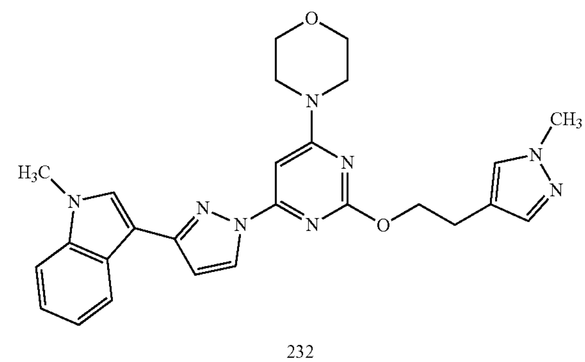

232

Compound 232 was prepared as indicated above, using 1.5 eq of NaH and 1.5 eq of NaH (50% in mineral oil).

LCMS (ESI): m/z=485 $[M+H]^+$;

Synthesis of (1-(2-(2-(1-methyl-1H-pyrazol-4-yl)ethoxy)-6-morpholinopyrimidin-4-yl)-3-phenyl-1H-pyrazol-5-yl)methanol (Compound 233)

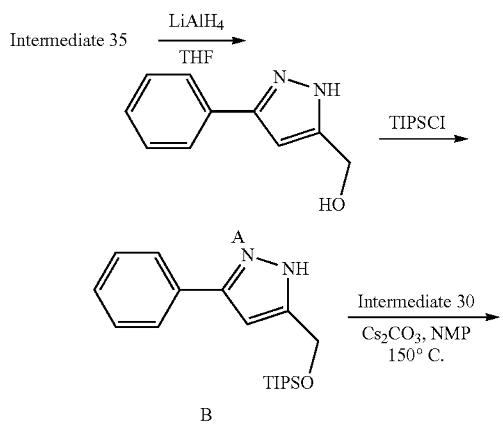

-continued

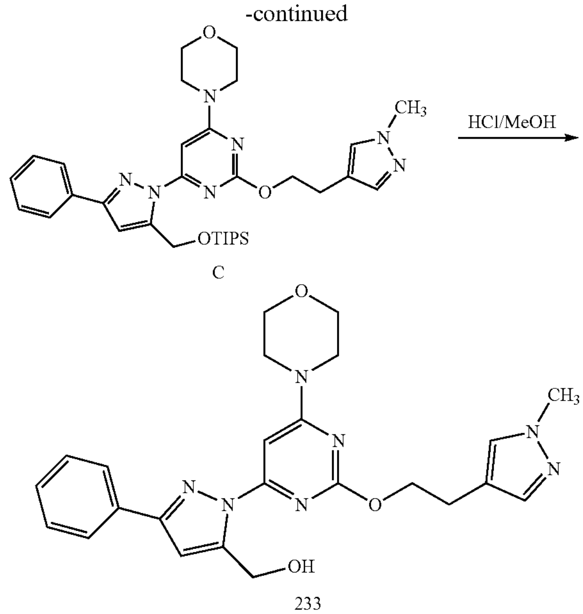

C

233

Preparation of A

To a solution of Intermediate 35 (1.0 g, 4.6 mmol) in THF (10 mL) was added $LiAlH_4$ (1.85 mL, 2.5 M, 4.6 mmol) dropwise at 0° C. The resulting mixture was stirred for 2.5 hrs and then quenched with $Na_2SO_4 \cdot 10\ H_2O$. The precipitate was filtered and washed with THF (10 mL).

The filtrate was dried over $Na_2SO_4$, filtered, concentrated to dryness. The crude product was purified by chromatography on silica gel eluting with petroleum ether:EtOAc=1:1 to EtOAc, and to EtOAc:MeOH=20:1 to get the desired product A (350 mg, 43%) as a light-yellow solid.

Preparation of B

To a solution of A (300 mg, 1.7 mmol) and imidazole (176 mg, 2.6 mmol) in DMF (5 mL) was added TIPSCl (500 mg, 2.6 mmol) at room temperature. The mixture was poured into water (20 mL) after stirring overnight and then extracted with EtOAc (20 mL×2). The combined organic layers were washed with brine (20 mL×2), dried over $Na_2SO_4$, filtered, concentrated to dryness. The crude product was purified by chromatography on silica gel eluting with petroleum ether:EtOAc=5:1 to get the desired product B (530, 93%) as yellow oil.

Preparation of C

The mixture of compound B (400 mg, 1.2 mmol), Intermediate 30 (392 mg, 1.2 mmol) and $Cs_2CO_3$ (588 mg, 1.8 mmol) in NMP (8 mL) was stirred at 150° C. overnight. After cooling to room temperature, water (30 mL) was added and the mixture was extracted with EtOAc (30 mL×2). The combined organic layers were washed with brine (20 mL×3), dried over $Na_2SO_4$, filtered, concentrated to dryness. The resulting crude product was purified by chromatography on silica gel eluting with petroleum ether: EtOAc=5:1 to petroleum ether:EtOAc=1:1 to get the desired product C (270 mg, 37%) as light-yellow oil.

Preparation of Compound 233

To a solution of compound C (270 mg, 0.44 mmol) in MeOH (5 mL) was added HCl/MeOH (2 mL, 4 M). The mixture was stirred overnight at room temperature and then concentrated to dryness under reduced pressure. The residue was purified by Prep-HPLC (TFA method) to get Compound 233 (120 mg, 60%) as a white solid.

MS: m/z 462 $[M+1]^+$.

$^1H$ NMR (400 MHz, $CDCl_3$) δ: 7.86 (dd, J=8.4 Hz, J=1.2 Hz, 1H), 7.55 (s, 1H), 7.46-7.37 (m, 4H), 6.93 (s, 1H), 6.70 (s, 1H), 4.81 (s, 2H), 4.43 (t, J=6.4 Hz, 2H), 3.96 (s, 3H), 3.83-3.74 (m, 8H), 2.97 (t, J=6.4 Hz, 2H).

Synthesis of (1-(2-(2-(1-methyl-1H-pyrazol-4-yl) ethoxy)-6-morpholinopyrimidin-4-yl)-3-(m-tolyl)-1H-pyrazol-5-yl)methanol (Compound 234)

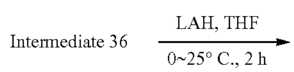

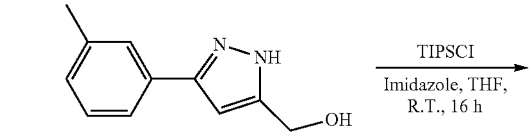

TIPSCl
Imidazole, THF,
R.T., 16 h

A

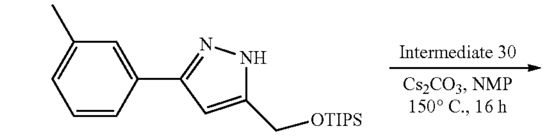

Intermediate 30
$Cs_2CO_3$, NMP
150° C., 16 h

B

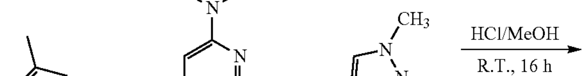

HCl/MeOH
R.T., 16 h

C

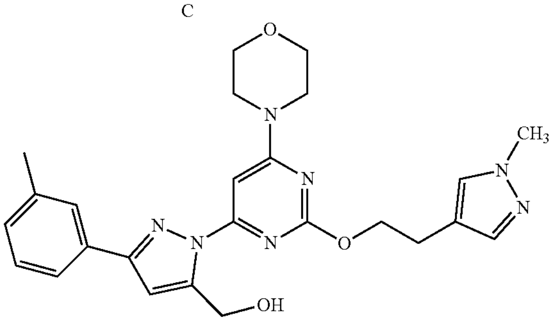

234

Preparation of A

To a solution of compound Intermediate 36 (3.0 g, 13.1 mmol) in THF (30 mL) was added $LiAlH_4$ (2.5 M, 15.65 mL, 39.1 mmol) dropwise at 0° C. under $N_2$ atmosphere. The resulting mixture was allowed to warm to room temperature and stirred for 4 hours. After which period, water (1 mL) was added carefully followed by NaOH (Wt=15%, 1 mL) solution and water (3 mL). The resulting system was dried over $Na_2SO_4$, filtered and concentrated under reduced pressure. The residue, A, was purified by chromatography on silica gel eluting with Petroleum ether:Ethyl acetate=10:1-0:1 to the desired product (2 g, 81.2%) as a white solid.

Preparation of B

A mixture of compound A (1.88 g, 10.0 mmol), imidazole (1.02 g, 15.0 mmol) and triisopropylsilyl chloride (2.90 g, 15.0 mmol) in THF (40 mL) was stirred at room temperature overnight. The mixture was concentrated, and the residue B was purified by chromatography on silica gel eluting with petroleum ether:ethyl acetate=10:1-5:1 to get the desired product (3.3 g, 95.6%) as colorless oil.

Preparation of C

A mixture of compound B (159.1 mg, 0.461 mmol), Intermediate 30 (149.3 mg, 0.461 mmol) and $Cs_2CO_3$ (224.7 mg, 0.691 mmol) in NMP (3 mL) was stirred at 150° C. for 16 hours. After which period, the mixture was cooled down to room temperature and diluted with ethyl acetate (20 mL). The resulting mixture was washed with water (10 mL) and brine (10 mL×4), dried over $Na_2SO_4$, filtered and concentrated to dryness under reduced pressure. The residue was purified by chromatography on silica gel eluting with petroleum ether:ethyl acetate=5:1-1:1 to get the desired product, C (80 mg, 27.5%) as clear oil.

Preparation of Compound 234

To a solution of compound C (80.0 mg, 0.127 mmol) in MeOH (2 mL) was added HCl/MeOH solution (2 mL) at room temperature, and then the mixture was stirred at room temperature for 16 hours. After which period, the mixture was concentrated to dryness under reduced pressure, which was then purified by Prep-HPLC to get Compound 234 (25.5 mg, 42.3%) as a white solid.

$^1H$ NMR (400 MHz, $CDCl_3$) δ 7.70 (s, 1H), 7.64 (d, J=7.6 Hz, 1H), 7.48 (s, 1H), 7.36 (s, 1H), 7.33 (t, J=7.6 Hz, 1H), 7.18 (d, J=7.6 Hz, 1H), 5.30 (s, 1H), 4.80 (s, 2H), 4.41 (t, J=6.4 Hz, 2H), 3.92 (s, 3H), 3.81-3.45 (m, 8H), 2.95 (t, J=6.4 Hz, 2H), 2.42 (s, 3H).

Synthesis of 4-(2-(2-(1-methyl-1H-pyrazol-4-yl)ethoxy)-6-(5-(morpholinomethyl)-3-(m-tolyl)-1H-pyrazol-1-yl)pyrimidin-4-yl)morpholine (Compound 235)

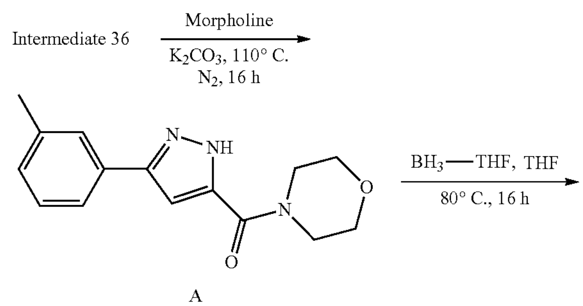

A

-continued

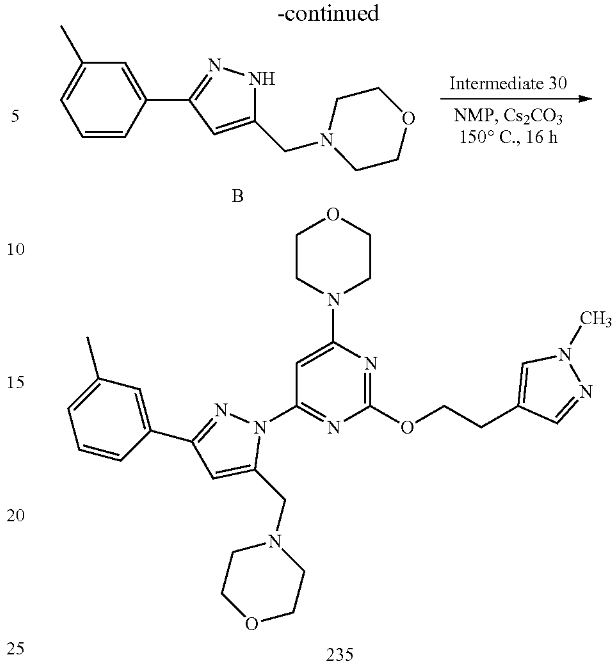

B

235

Preparation of A

A mixture of compound Intermediate 36 (2.0 g, 8.7 mmol) and $K_2CO_3$ (3.6 g, 26.1 mmol) in morpholine (8 mL) was stirred at 110° C. for 16 hours. After which period, the mixture was cooled down to room temperature and diluted with ethyl acetate. The resulting system was washed with brine (30 mL×4), dried over $Na_2SO_4$, filtered and concentrated under reduced pressure. The residue purified by chromatography on silica gel eluting with petroleum ether: ethyl acetate=5:1-0:1 to get the desired product A (1.7 g, 72.1%) as a white solid.

Preparation of B

To a solution of A (1.58 g, 5.83 mmol) in THF (10 mL) at 0° C. under $N_2$ atmosphere, $BH_3$/THF (1M, 17.49 mL, 17.49 mmol) was dropped into it slowly. The solution was stirred at 80° C. for 16 hours and then cooled down to room temperature. MeOH (10 mL) was added into above solution carefully. The resulting mixture was stirred at 80° C. for another 8 hours. After which period, the mixture was cooled down to room temperature again and concentrated to dryness. The residue was purified by chromatography on silica gel eluting with petroleum ether:ethyl acetate=5:1-1:1 to get the desired product B (1.0 g, 66.7%) as a white solid.

Preparation of Compound 235

A mixture of compound B (400.1 mg, 1.55 mmol), compound Intermediate 30 (502.2 mg, 1.55 mmol) and $Cs_2CO_3$ (755.8 mg, 2.325 mmol) in NMP (3 mL) was stirred at 150° C. for 16 hours. After which period, the mixture was cooled down to room temperature and diluted with ethyl acetate (20 mL). The resulting system was washed with water (10 mL) and brine (10 mL×4), dried over $Na_2SO_4$, filtered and concentrated under reduced pressure. The residue was purified by Prep-HPLC to get Compound 235 (120 mg, 14.2%) as a white solid.

$^1$H NMR (400 MHz, $CDCl_3$) δ: 7.66 (s, 1H), 7.65 (d, J=8.0 Hz, 1H), 7.56 (s, 1H), 7.45 (s, 1H), 7.32 (t, J=7.6 Hz, 1H), 7.22 (d, J=7.6 Hz, 1H), 7.04 (s, 1H), 6.85 (s, 1H), 4.76 (s, 2H), 4.52 (t, J=6.4 Hz, 2H), 4.01 (d, J=13.2 Hz, 2H), 3.96 (s, 3H), 3.83-3.68 (m, 10H), 3.50-3.46 (m, 2H), 3.27 (t, J=10.8 Hz, 2H), 2.98 (t, J=6.4 Hz, 2H), 2.42 (s, 3H).

Synthesis of 4-(2-methoxy-6-(5-(morpholinomethyl)-3-(m-tolyl)-1H-pyrazol-1-yl)pyrimidin-4-yl)morpholine (Compound 236)

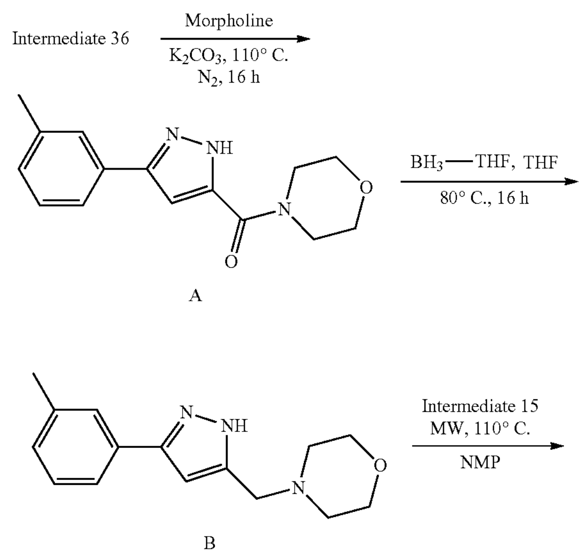

A

B

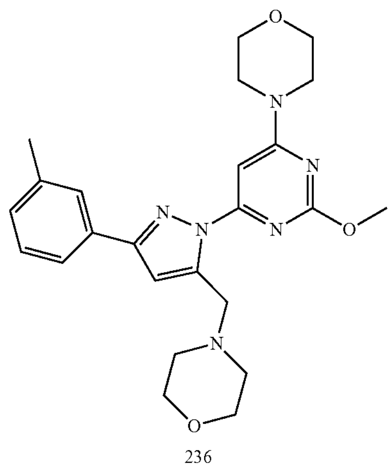

236

Preparation of A

A mixture of Intermediate 36 (2.0 g, 8.7 mmol) and $K_2CO_3$ (3.6 g, 26.1 mmol) in morpholine (8 mL) was stirred at 110° C. for 16 hours. After which period, the mixture was cooled down to room temperature and diluted with ethyl acetate. The resulting system was washed with brine (30 mL×4), dried over $Na_2SO_4$, filtered, and concentrated under reduced pressure. The residue was purified by chromatography on silica gel eluting with petroleum ether:ethyl acetate=5:1-0:1 to get the desired product A (1.7 g, 72.1%) as a white solid.

Preparation of B

To a solution of A (1.58 g, 5.83 mmol) in THF (10 mL) at 0° C. under $N_2$ atmosphere, $BH_3$/THF (1M, 17.49 mL, 17.49 mmol) was dropped into it slowly. The solution was stirred at 80° C. for 16 hours and then cooled down to room temperature. MeOH (10 mL) was added into above solution carefully. The resulting mixture was stirred at 80° C. for another 8 hours. After which period, the mixture was cooled down to room temperature again and concentrated to dryness. The residue was purified by chromatography on silica gel eluting with petroleum ether:ethyl acetate=5:1-1:1 to get the desired product B (1.0 g, 66.7%) as a white solid.

Preparation of Compound 236

A solution of B (520 mg, 2.0 mmol), Intermediate 15 (510 mg, 2.23 mmol), $Pd_2(dba)_3$ (559 mg, 0.6 mmol), Xantphos (353 mg, 0.6 mmol) and t-BuOK (68 mg, 0.6 mmol) in NMP (13 mL) was stirred at 110° C. in a sealed tube for 2 hours. The mixture was cooled down to room temperature and poured into water, extracted with ethyl acetate (50 mL×2). The combined organic layers were dried over sodium sulfate, filtered and concentrated to dryness. The residue was purified by flash column eluting with hexane:ethyl acetate=1:1 to 1:0 to obtain the desired product Compound 236 (45 mg, 50%) as a yellow solid. ESI: $[M+H]^+$=451.20 $^1$H NMR (400 MHz, DMSO-$d_6$): δ 7.81-7.72 (m, 2H), 7.33-7.31 (m, 1H), 7.20-7.19 (m, 1H), 6.94-6.91 (m, 2H), 4.10 (s, 2H), 3.88 (s, 3H), 3.76-3.55 (m, 13H), 3.32 (s, 3H), 2.38 (s, 3H).

Synthesis of 4-(2-(2-(1-methyl-1H-pyrazol-4-yl)ethoxy)-6-(5-morpholino-3-(m-tolyl)-1H-pyrazol-1-yl)pyrimidin-4-yl)morpholine (Compound 237)

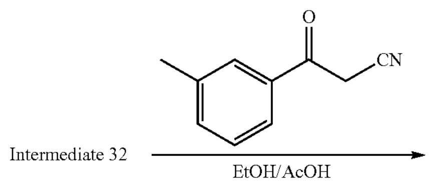

-continued

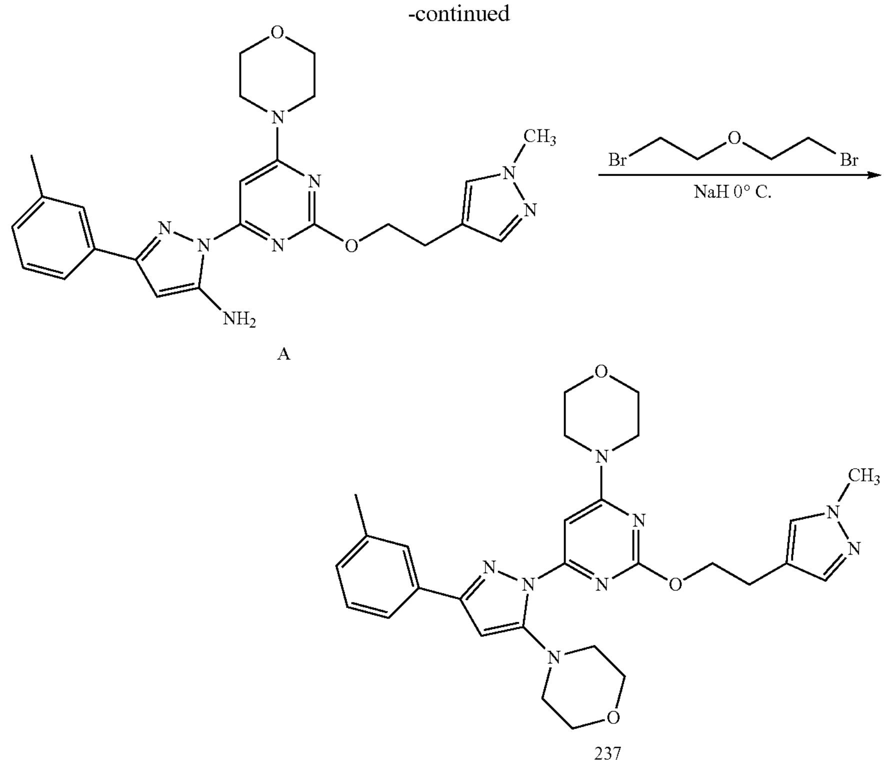

A

237

Preparation of A

The mixture of Intermediate 32 (200 mg, 0.6 mmol) and 3-oxo-3-(m-tolyl)propanenitrile (100 mg, 0.6 mmol) in EtOH:AcOH=5:1 (5 mL) was stirred at 80° C. for 3 hrs. After cooling to room temperature, the mixture was concentrated and purified by chromatography on silica gel eluting with petroleum ether:EtOAc=1:1 to EtOAc to get the desired compound A (220 mg, 76%) as a white solid.

Preparation of Compound 237

To a solution of A (220 mg, 0.48 mmol) in DMF (4 mL) was added NaH (57.6 mg, 1.44 mmol) at 0° C. After stirring for 20 min, 1-bromo-2-(2-bromoethoxy) ethane (111 mg, 0.48 mmol) was added to above system. The mixture was allowed to stir at 60° C. overnight. After cooling to room temperature, the mixture was poured into water (15 mL) and extracted with EtOAc (20 mL×2). The combined organic layers were washed with brine (20 mL×2), dried over $Na_2SO_4$, filtered, concentrated to dryness. The crude product was purified by chromatography on silica gel eluting with DCM:MeOH=20:1 to get the crude product (150 mg), which was then further purified by Prep-HPLC (base method) to Compound 237 (80 mg, 32%) as a white solid.

ESI: $[M+1]^+$=531

$^1$H NMR (400 MHz, $CDCl_3$): δ 7.69 (s, 1H), 7.64 (d, J=7.6 Hz, 1H), 7.48 (s, 1H), 7.42 (s, 1H), 7.30 (t, J=7.6 Hz, 1H), 7.17 (d, J=7.6 Hz, 1H), 6.84 (s, 1H), 6.18 (s, 1H), 4.46 (t, J=6.8 Hz, 2H), 3.93 (s, 3H), 3.85-3.79 (m, 8H), 3.71-3.70 (m, 4H), 3.13-3.11 (m, 4H), 2.98 (t, J=6.8 Hz, 2H), 2.41 (s, 1H).

Synthesis of N,N-dimethyl-2-(3-(((4-morpholino-6-(3-(m-tolyl)-1H-pyrazol-1-yl)pyrimidin-2-yl)oxy)methyl)-1H-pyrazol-1-yl)ethan-1-amine (Compound 238)

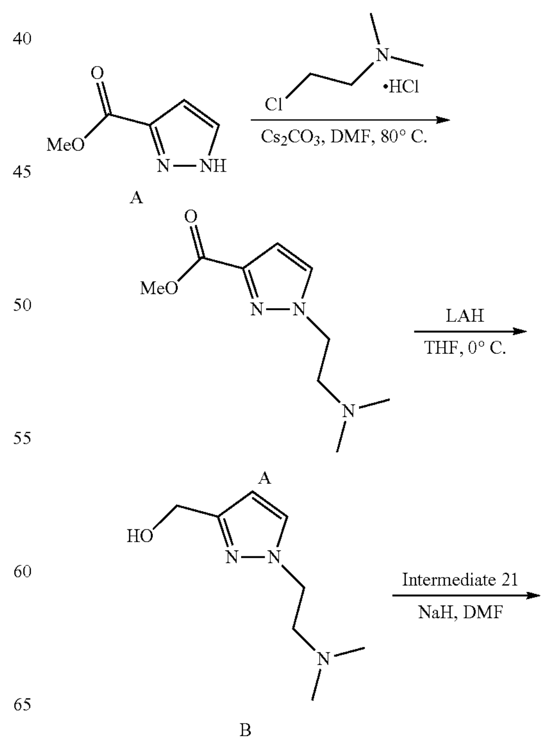

A

A

B

-continued

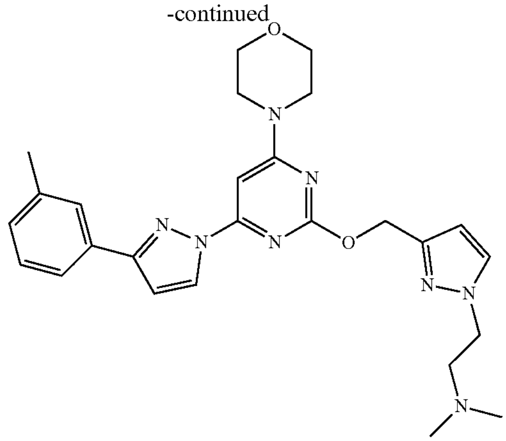

238

Preparation of A

A solution of methyl 1H-pyrazole-3-carboxylate (10.0 g, 79.3 mmol), 2-chloro-N,N-dimethylethanamine hydrochloride (17.0 g, 118.0 mmol) and $Cs_2CO_3$ (77.5 g, 212.3 mmol) in anhydrous DMF (200 mL) was heated at 80° C. overnight under $N_2$ atmosphere. After cooling to room temperature, the reaction mixture was diluted with water/DCM. The organic layer was separated and washed with brine, dried over $Na_2SO_4$, filtered and concentrated to dryness under reduced pressure. The residue was purified by chromatography on silica gel eluting with methanol:ethyl acetate=1:20-1:10 to get the desired product A (2.57 g, 15.2%) as colourless oil.

Preparation of B

To a solution of compound 36 (2.57 g, 13.0 mmol) in anhydrous THF (28 mL) was added $LiAlH_4$ (2.5 M, 7.8 mL, 19.5 mmol) dropwise at 0° C. under $N_2$ atmosphere. The resulting mixture was stirred at room temperature for 2 hours and then quenched with $Na_2SO_4$—$H_2O$. After filtration, the organic solution was concentrated under reduced pressure to give crude product B as brown oil (1.08 g, 43.2%), which was used in the next run directly.

Preparation of Compound 238

To a solution of B (141 mg, 0.83 mmol) in DMF (5 mL) was added 60% NaH at 0° C. under nitrogen. The resulting mixture was stirred for 1 h at this temperature, Intermediate 21 (500 mg, 1.25 mmol) was added to above reaction mixture. After stirring at rt for another 1 h, the mixture was diluted with EA and washed with water and brine, dried over $Na_2SO_4$, filtered and concentrated. The residue was purified by Prep-HPLC to get the desired product Compound 238 (160 mg, 40%) as colorless syrup.

$^1H$ NMR (400 MHz, $CDCl_3$) δ 8.58 (d, J=2.7 Hz, 1H), 7.74 (s, 1H), 7.69 (d, J=7.7 Hz, 1H), 7.41 (d, J=2.2 Hz, 1H), 7.32 (t, J=7.6 Hz, 1H), 7.18 (d, J=7.5 Hz, 1H), 6.90 (s, 1H), 6.73 (d, J=2.7 Hz, 1H), 6.38 (d, J=2.2 Hz, 1H), 5.44 (s, 2H), 4.21 (t, J=6.8 Hz, 2H), 3.78 (dd, J=8.4, 5.5 Hz, 8H), 2.76 (t, J=6.8 Hz, 2H), 2.43 (s, 3H), 2.27 (s, 6H).

Synthesis of 4-(6-(2-(1-methyl-1H-pyrazol-3-yl)ethyl)-2-(3-(m-tolyl)-1H-pyrazol-1-yl)-6,7-dihydro-5H-pyrrolo[3,4-d]pyrimidin-4-yl)morpholine hydrochloride (Compound 239)

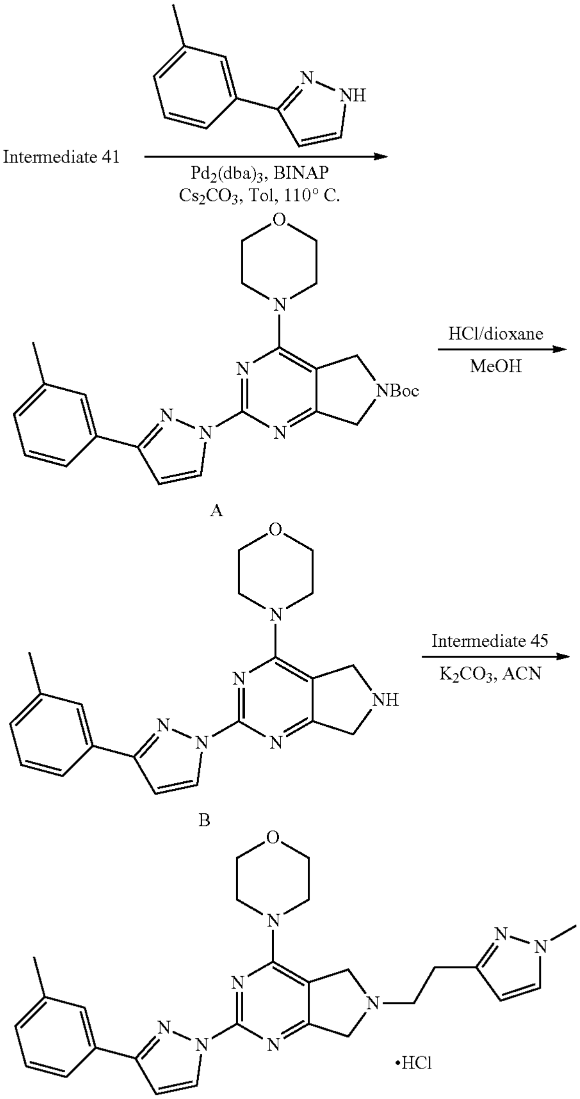

239

Preparation of A

A mixture of Intermediate 41 (700 mg, 2.06 mmol), 3-(m-tolyl)-1H-pyrazole (272 mg, 1.72 mmol), $Cs_2CO_3$ (1.12 g, 3.44 mmol), $Pd_2(dba)_3$ (158 mg, 0.172 mmol) and BINAP (214 mg, 0.344 mmol) in toluene (20 mL) was stirred at 110° C. overnight under nitrogen atmosphere. After cooling down to room temperature, the mixture was filtered; and the filtrate was concentrated to dryness. The residue was purified by column on silica gel (eluting with DCM:MeOH=20:1) to give A (500 mg, 63%) as a yellow solid.

Preparation of B

A mixture of A (500 mg, 1.08 mmol) in HCl/dioxane (10 mL, 4M) and MeOH (5 mL) was stirred at room temperature for 2 hrs. After which period, the mixture was concentrated and neutralized with saturated aq. $K_2CO_3$ solution to pH=8, then concentrated in vacuum. The residue was purified by column on silica gel (eluting with DCM:MeOH=10:1) to give the B (300 mg, 77%) as a yellow solid.

Preparation of Compound 239

A mixture of B (300 mg, 0.83 mmol), Intermediate 45 (254 mg, 1.24 mmol) and $K_2CO_3$ (229 mg, 1.66 mmol) in acetonitrile (5 mL) was stirred overnight at 75° C. The reaction mixture was concentrated and then diluted with DCM (60 mL), the resulting solution was washed with brine (20 mL×2), dried over anhydrous $Na_2SO_4$, filtered and concentrated to dryness. The residue was purified by chromatography on silica gel (DCM:MeOH=100:1-20:1) to give the crude product, which was purified further by Prep-HPLC (HCl) to give Compound 239 (19.6 mg, 5% yield) as the hydrochloride salt.

MS: m/z 471.7 $[M+H]^+$.

$^1$H NMR (400 MHz, $D_2O$) δ 8.18-8.17 (m, 1H), 7.60 (brs, 1H), 7.59 (d, J=2.4 Hz, 1H), 7.55 (d, J=7.6 Hz, 1H), 7.30 (t, J=7.6 Hz, 1H), 7.17 (t, J=7.2 Hz, 1H), 6.78-6.71 (m, 1H), 6.26 (d, J=2.0 Hz, 1H), 4.46-4.36 (m, 4H), 3.83 (s, 3H), 3.71-3.69 (m, 4H), 3.47-3.44 (m, 6H), 3.04 (t, J=7.2 Hz, 2H), 2.30 (s, 3H).

Synthesis of 4-(6-(2-(1-methyl-1H-pyrazol-3-yl)ethyl)-2-(5-methyl-3-phenyl-1H-pyrazol-1-yl)-6,7-dihydro-5H-pyrrolo[3,4-d]pyrimidin-4-yl)morpholine (Compound 240)

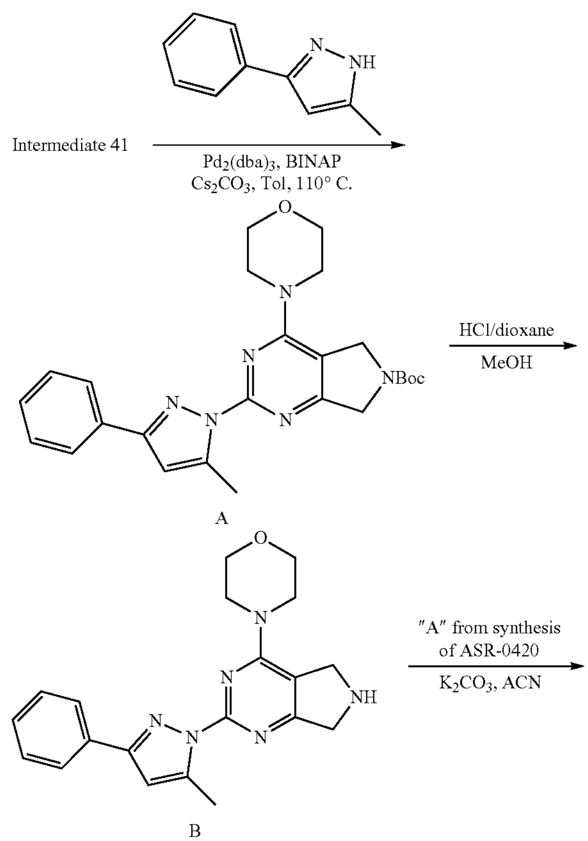

A

B

-continued

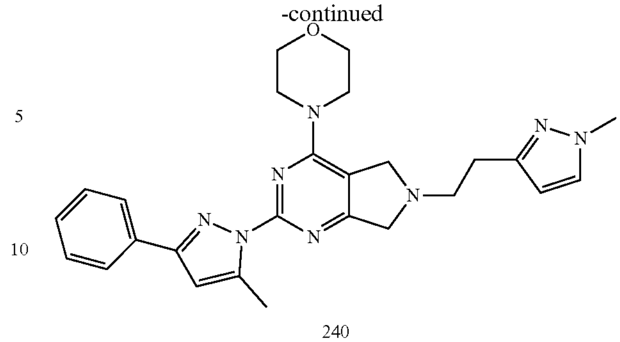

240

From 5-methyl-3-phenyl-1H-pyrazole, Compound 240 was prepared according to a similar procedure to that of Compound 239. (26.2 mg, 3%).

MS: m/z 471.5 $[M+H]^+$ $^1$H NMR (400 MHz, $D_2O$) δ 7.62-7.58 (m, 3H), 7.34 (brs, 3H), 6.39-6.37 (m, 1H), 6.35-6.33 (m, 1H), 4.53-4.48 (m, 4H), 3.85 (s, 3H), 3.70-3.62 (m, 6H), 3.36 (brs, 4H), 3.14 (t, J=7.2 Hz, 2H), 2.29-2.26 (m, 3H).

Synthesis of 4-(5-(3-(m-tolyl)-1H-pyrazol-1-yl)-1H-pyrrolo[3,2-b]pyridin-7-yl)morpholine (Compound 241)

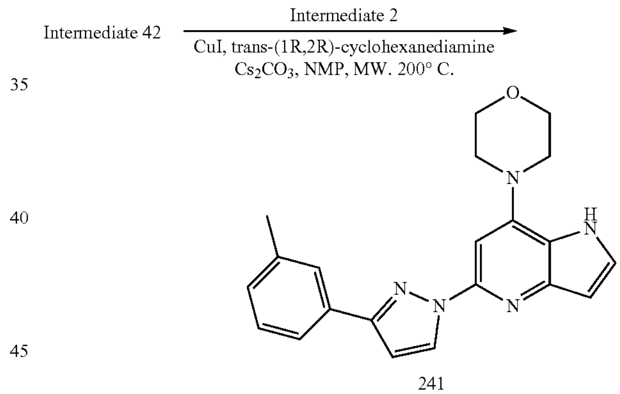

241

The mixture of Intermediate 2 (103 mg, 0.653 mmol), Intermediate 42 (200 mg, 0.841 mmol), CuI (80 mg, 0.421 mmol), trans-(1R,2R)-cyclohexanediamine (48 mg, 0.421 mmol) and $Cs_2CO_3$ (386 mg, 1.187 mmol) in NMP (4 mL) was stirred at 200° C. for 2 hrs in microwave reactor. After cooling to room temperature, the reaction mixture was diluted with water (30 mL) and then extracted with EtOAc (20 mL×3). The combined organic layers were washed with water (30 mL×3), brine (20 mL×3), dried over $Na_2SO_4$, filtered, and concentrated to dryness. The residue obtained was purified by Prep-HPLC (FA) to get the desired product Compound 241 (25 mg, 11% yield) as white solid.

MS: m/z 360 $[M+H]^+$.

$^1$H NMR (400 MHz, DMSO-$d_6$) δ: 11.39 (s, 1H), 8.64 (d, J=2.5 Hz, 1H), 7.77 (d, J=11.9 Hz, 2H), 7.57 (t, J=2.8 Hz, 1H), 7.35 (dd, J=14.5, 6.9 Hz, 2H), 7.19 (d, J=7.5 Hz, 1H), 6.99 (d, J=2.5 Hz, 1H), 6.54 (s, 1H), 3.87 (d, J=4.4 Hz, 4H), 3.32 (d, J=4.4 Hz, 4H), 2.40 (s, 3H).

Synthesis of N,N-dimethyl-1-(1-(7-morpholino-1H-pyrrolo[3,2-b]pyridin-5-yl)-3-(m-tolyl)-1H-pyrazol-5-yl) (Compound 242)

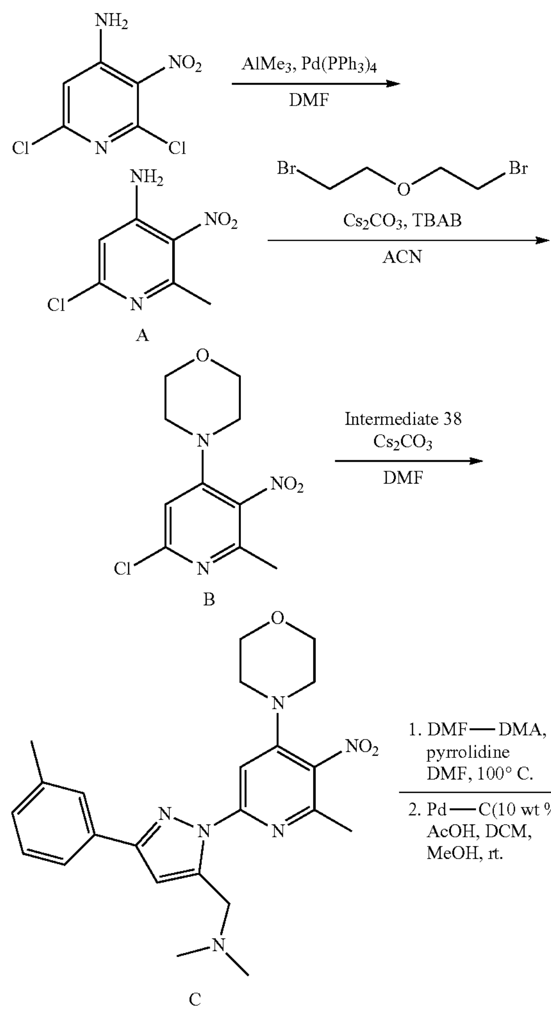

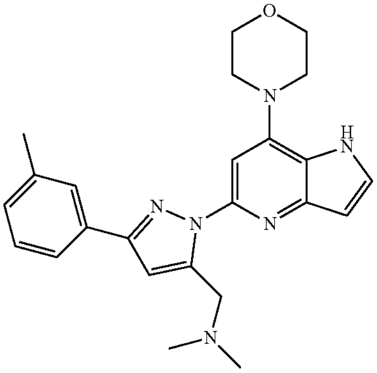

242

Preparation of A

To a pressure vessel, a degassed solution of 2,6-dichloro-3-nitropyridin-4-amine (5.0 g, 24 mmol) and tetrakis (triphenylphosphine) palladium (2.78 g, 2.4 mmol) in DMF (50 mL) was added dropwise a solution of trimethylaluminium (12.6 mL, 2 M, 25.2 mmol). The resulting solution was stirred at 70° C. for 2 h under nitrogen and cooled down to room temperature before pouring into iced water (100 mL). The resulting mixture was extracted with EtOAc (50 mL×3). The combined organic layers were dried over $Na_2SO_4$ and concentrated to dryness under reduced pressure. The crude product was purified by chromatography on silica gel eluting with petroleum ether:EtOAc=5:1 to get the desired product A (3.1 g, 68% yield) as yellow solid.

Preparation of B

The mixture of A (3.44 g, 18.34 mmol), $Cs_2CO_3$ (17.93 g, 55.02 mmol), TBAB (0.6 g, 1.83 mmol) and 2,2'-dibromodiethyl ether (6.38 g, 27.51 mmol) in acetonitrile (120 mL) was stirred at 90° C. overnight. After which period, the mixture was cooled down to room temperature and concentrated to dryness. The residue was diluted with water (50 mL) and extracted with EtOAc (20 mL×3). The combined organic layers were washed with brine (20 mL), dried over $Na_2SO_4$, filtered, concentrated to dryness. The resulting crude product was purified by chromatography on silica gel eluting with petroleum ether:EtOAc=4:1 to get the desired compound B (2.8 g, 60% yield) as yellow solid.

Preparation of C

The mixture of B (0.42 g, 1.63 mmol), Intermediate 38 (0.27 g, 1.25 mmol) and $Cs_2CO_3$ (1.23 g, 3.76 mmol) in DMF (8 mL) was stirred at 100° C. overnight. After cooling to room temperature, the mixture was poured into water (20 mL) and extracted with EtOAc (10 mL×2). The combined organic layers were washed with brine (10 mL×2), dried over $Na_2SO_4$ and filtered. The filtrate was concentrated to dryness. The crude product was purified by chromatography on silica gel eluting with EtOAc to get the desired compound C (0.20 g, 37%) as yellow solid.

Preparation of Compound 242

To a solution of compound C (0.20 g, 0.46 mmol) and DMF-DMA (0.17 g, 1.38 mmol) in DMF (10 mL) was added pyrrolidine (0.49 g, 0.69 mmol). The mixture was stirred at 100° C. for 6 hrs, and then concentrated under reduced pressure. The residue was dissolved in methanol (25 mL) and dichloromethane (5 mL), and then acetic acid (2.5 ml) was added. To above solution was added Pd/C (10 wt %) (0.05 g, 0.046 mmol). The resulting mixture was stirred for 4 hours under $H_2$ at rt. After which period, the reaction mixture was filtered through a short pad of celite. The filtrate was concentrated and purified by Prep-HPLC to get the desired product Compound 242 (22.3 mg, 12% yield) as off-white solid. MS: $[M+H]^+$=417

$^1H$ NMR (400 MHz, DMSO-$d_6$) δ 11.76 (s, 1H), 10.26 (s, 1H), 7.78 (s, 1H), 7.75 (s, 1H), 7.69 (t, J=2.9 Hz, 1H), 7.39 (t, J=7.5 Hz, 1H), 7.29 (s, 1H), 7.27 (s, 1H), 7.24 (d, J=7.5 Hz, 1H), 6.66 (dd, J=2.9, 1.7 Hz, 1H), 4.65 (s, 2H), 3.88 (m, 4H), 3.40 (m, 4H), 2.99 (s, 6H), 2.40 (s, 3H).

Synthesis of 4-(5-(5-methyl-3-phenyl-1H-pyrazol-1-yl)-1H-pyrrolo[3,2-b]pyridin-7-yl)morpholine (Compound 243)

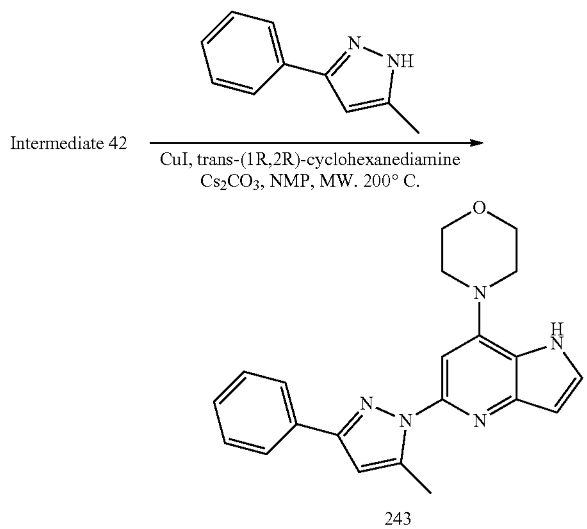

243

Compound 243 was synthesized by following a similar procedure to that of Compound 241, using the reagents illustrated above.

MS: m/z 360 $[M+H]^+$.

$^1H$ NMR (400 MHz, DMSO-$d_6$) δ 11.42 (s, 1H), 7.88 (d, J=7.2 Hz, 2H), 7.58 (t, J=2.9 Hz, 1H), 7.44 (t, J=7.6 Hz, 2H), 7.35 (d, J=7.3 Hz, 1H), 7.08 (s, 1H), 6.74 (s, 1H), 6.57-6.50 (m, 1H), 3.91-3.77 (m, 4H), 3.33-3.21 (m, 4H), 2.62 (s, 3H).

Synthesis of 8-(1-(2-(2-(1-methyl-1H-pyrazol-4-yl)ethoxy)-6-morpholinopyrimidin-4-yl)-1H-pyrazol-3-yl)-3,4-dihydro-2H-benzo[b][1,4]oxazine (Compound 244)

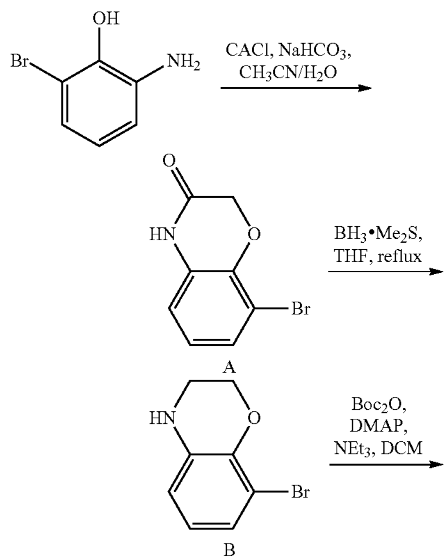

-continued

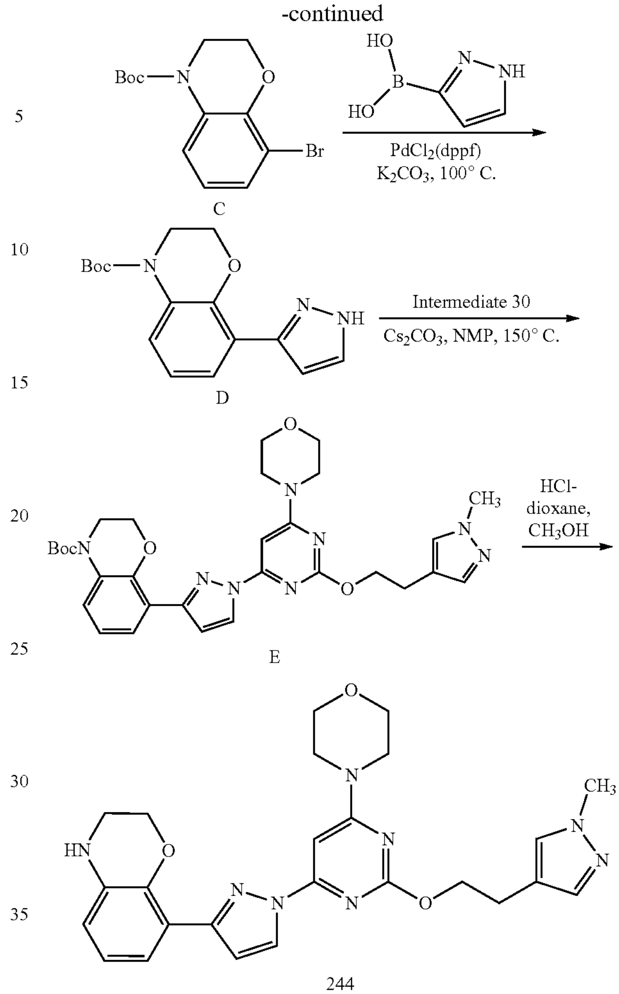

244

Preparation of A

To a mixture of 2-amino-6-bromophenol (10.0 g, 53.2 mmol) and $NaHCO_3$ (13.4 g, 159.5 mmol) in $CH_3CN$ (260 mL)/$H_2O$ (130 mL), 2-chloroacetyl chloride (5.5 mL, 69.1 mmol) was added dropwise at 0° C. The mixture was refluxed for 3 h. After which period, the mixture was diluted with ethyl acetate and washed by brine, dried over $Na_2SO_4$, filtered and concentrated under reduced pressure to give the desired product A (11.7 g, 96.4%) as a pink solid, which was used in next step without purification.

Preparation of B

To a solution of A (11.7 g, 51.3 mmol) in THF (150 mL) was cooled down to 0° C. under $N_2$ atmosphere, then $BH_3$-$Me_2S$ (24.3 mL, 256.2 mmol) was dropped into it slowly. The resulting mixture was refluxed for 1.5 h and then cooled down to room temperature, MeOH (10 mL) was added into above solution carefully. The mixture was stirred for another hour and concentrated to dryness under reduced pressure. The residue was purified by chromatography on silica gel eluting with petroleum ether:ethyl acetate=15:1-4:1 to get the desired product B (10.5 g, 95.6%) as brown oil.

Preparation of C

A mixture of B (4.13 g, 19.3 mmol), $Boc_2O$ (8.41 g, 38.5 mmol), TEA (8.0 mL, 61.1 mmol) and DMAP (471 mg, 3.86 mmol) in dry DCM (20 mL) was stirred at room temperature for 24 h. After which period, the mixture was diluted with ethyl acetate and washed with water and brine, dried over $Na_2SO_4$. After filtration and concentration under reduced pressure, the residue was purified by chromatography on silica gel eluting with petroleum ether:ethyl acetate=20:1-10:1 to get the desired product D (4.77 g, 78.8%) as brown oil.

Preparation of D

A mixture of C (1.08 g, 3.43 mmol), (1H-pyrazol-3-yl) boronic acid (768 mg, 6.86 mmol), $PdCl_2$(dppf) (250 mg, 0.34 mmol) and $K_2CO_3$ (1.19 mg, 8.57 mmol) in 1,4-dioxane (28 mL)/$H_2O$ (7 mL) was stirred at 100° C. under nitrogen atmosphere overnight. After which period, the mixture was cooled down to room temperature and filtered through a pad of silica gel. The filtrate was diluted with ethyl acetate, washed with brine, dried over $Na_2SO_4$, filtered and concentrated under reduced pressure. The residue purified by chromatography on silica gel eluting with petroleum ether:ethyl acetate=10:1-1:1 to get the desired product D (567 mg, 54.8%) as a pink solid.

Preparation of E

A mixture of D (102 mg, 0.34 mmol), compound Intermediate 30 (110 mg, 0.34 mmol) and $Cs_2CO_3$ (165 mg, 0.51 mmol) in NMP (2 mL) was stirred at 150° C. overnight. After which period, the mixture was cooled down to room temperature and diluted with ethyl acetate. The resulting system was washed by water and brine, dried over $Na_2SO_4$, filtered and concentrated under reduced pressure. The residue was purified by chromatography on silica gel eluting with petroleum ether:ethyl acetate=1:1 to get the desired product E (94 mg, 47.2%) as a white solid.

Preparation of Compound 244

To a solution of E (94 mg, 0.16 mmol) in $CH_3OH$ (2.5 mL) was added 4 N HCl/dioxane (2.5 mL) and the mixture was stirred at rt for 2 h. After which period, the reaction was quench by addition of 1 N NaOH aqueous solution; and the resulting mixture was extracted by ethyl acetate. The combined organic layers were washed by water and brine, dried over $Na_2SO_4$, filtered and concentrated under reduced pressure. The residue was purified by Prep-HPLC to get the desired product Compound 244 (58 mg, 74.3%) as a white solid.

$^1$H NMR (400 MHz, $CDCl_3$) δ 8.51 (d, J=2.7 Hz, 1H), 7.44-7.39 (m, 2H), 7.30 (s, 1H), 6.96 (d, J=2.7 Hz, 1H), 6.90 (s, 1H), 6.83 (t, J=7.8 Hz, 1H), 6.62 (dd, J=7.8, 1.5 Hz, 1H), 4.46 (t, J=7.3 Hz, 2H), 4.39-4.33 (m, 2H), 3.87 (s, 3H), 3.80-3.76 (m, 4H), 3.75-3.68 (m, 4H), 3.51-3.46 (m, 2H), 2.99 (t, J=7.2 Hz, 2H).

Synthesis of 8-(5-methyl-1-(2-(2-(1-methyl-1H-pyrazol-4-yl)ethoxy)-6-morpholinopyrimidin-4-yl)-1H-pyrazol-3-yl)-3,4-dihydro-2H-benzo[b][1,4]oxazine (Compound 245)

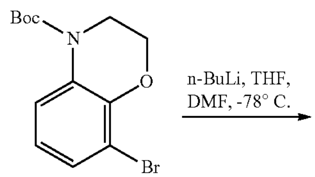

C
(see synthesis of 261)

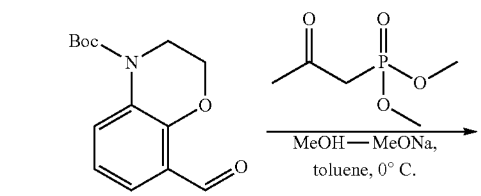

A

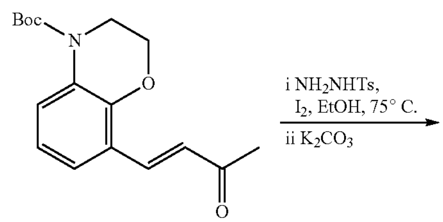

B

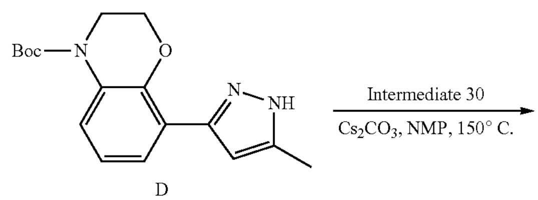

D

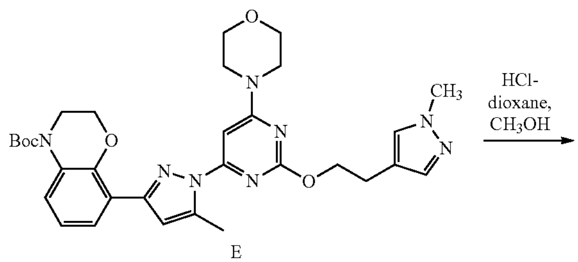

E

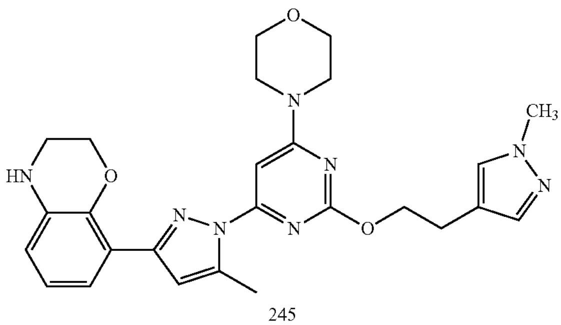

245

Preparation of A

To a solution of C (see synthesis of Compound 244) (5.80 g, 18.5 mmol) in THF (60 mL) was added n-BuLi in THF (2.5M, 8.13 mL, 20.3 mmol) dropwise at −78° C. under $N_2$ atmosphere. The resulting solution was stirred for 0.5 h, and then anhydrous DMF (2.87 mL, 36.9 mmol) was added carefully at this temperature. The reaction mixture was stirred for another 0.5 h and quenched by addition of saturated $NH_4Cl$ (aq). After it was allowed to warm to rt gradually, the mixture was diluted with EtOAc, and washed with brine. The organic layer was dried over $Na_2SO_4$ and concentrated under reduced pressure. The residue was purified by chromatography on silica gel eluting with petroleum ether:ethyl acetate=10:1-8:1 to get the desired product A (2.10 g, 43.1%) as a white solid.

Preparation of B

To a solution of A (2.10 g, 7.98 mmol) and dimethyl (2-oxopropyl)phosphonate (2.01 g, 12.0 mmol) in toluene (30 mL) was added 30% (w %) MeONa/MeOH (2.16 g, 12.0 mmol) at 0° C. under $N_2$ atmosphere, and the mixture was stirred for 1 h. After which period, the reaction was quenched by addition of saturated $NH_4Cl$ (aq) and allowed to warm to rt gradually. The mixture was diluted with EtOAc, and washed with brine. The organic layer was dried over $Na_2SO_4$ and concentrated under reduced pressure. The residue was purified by chromatography on silica gel eluting with petroleum ether:ethyl acetate=10:1 to get the desired product B (2.40 g, 99.1%) as a white solid.

Preparation of D

To a solution of B (316 mg, 1.04 mmol) and $NH_2NHTs$ (234 mg, 1.26 mmol) in EtOH (20 mL) was added $I_2$ (37 mg, 0.145 mmol) and the mixture was heated to 75° C. and stirred for 10 min. Then $K_2CO_3$ (215 mg, 1.56 mmol) was added to above solution in one portion and the resulting system was stirred at 75° C. overnight. The reaction was cooled down to rt and quenched by saturated $Na_2SO_3$ (aq). The mixture was diluted with EtOAc, and washed saturated $NaHCO_3$ (aq) and brine. The organic layer was dried over $Na_2SO_4$ and concentrated under reduced pressure. The residue was purified by chromatography on silica gel eluting with petroleum ether:ethyl acetate=3:1-1.5:1 to get the desired product D (2.88 g, 87.8%) as a white solid.

Preparation of E

A mixture of D (288 mg, 0.914 mmol), Intermediate 30 (326 mg, 1.01 mmol) and $Cs_2CO_3$ (447 mg, 1.37 mmol) in NMP (3 mL) was stirred at 150° C. overnight. After which period, the mixture was cooled down to room temperature and diluted with ethyl acetate. The resulting system was washed by water and brine, dried over $Na_2SO_4$, filtered and concentrated under reduced pressure. The crude product E (obtained as syrup) was used in next step directly without further purification.

Preparation of Compound 245

To a solution of the above crude compound E in $CH_3OH$ (6 mL) was added 4 N HCl/1,4-dioxane (6 mL) and the mixture was stirred at rt for 2 h. After which period, the reaction was quench by addition of 1 N NaOH(aq), and the resulting mixture was extracted by ethyl acetate. The organic layers were washed by water and brine, dried over $Na_2SO_4$, filtered and concentrated under reduced pressure. The residue purified by Prep-HPLC to get the desired compound Compound 245 (92 mg, 20.0% for two steps) as a white solid.

$^1$H NMR (400 MHz, $CDCl_3$) δ 7.39 (s, 1H), 7.36 (dd, J=7.8, 1.5 Hz, 1H), 7.28 (s, 1H), 6.92 (s, 1H), 6.81 (t, J=7.8 Hz, 1H), 6.70 (s, 1H), 6.60 (dd, J=7.8, 1.5 Hz, 1H), 4.44 (t, J=7.2 Hz, 2H), 4.38-4.33 (m, 2H), 3.87 (s, 3H), 3.80-3.74 (m, 4H), 3.73-3.67 (m, 4H), 3.50-3.44 (m, 2H), 2.98 (t, J=7.2 Hz, 2H), 2.75 (s, 3H).

Synthesis of 4-methyl-3-(2-(2-(1-methyl-1H-pyrazol-4-yl)ethoxy)-6-morpholinopyrimidin-4-yl)-1-(m-tolyl)imidazolidin-2-one (Compound 246)

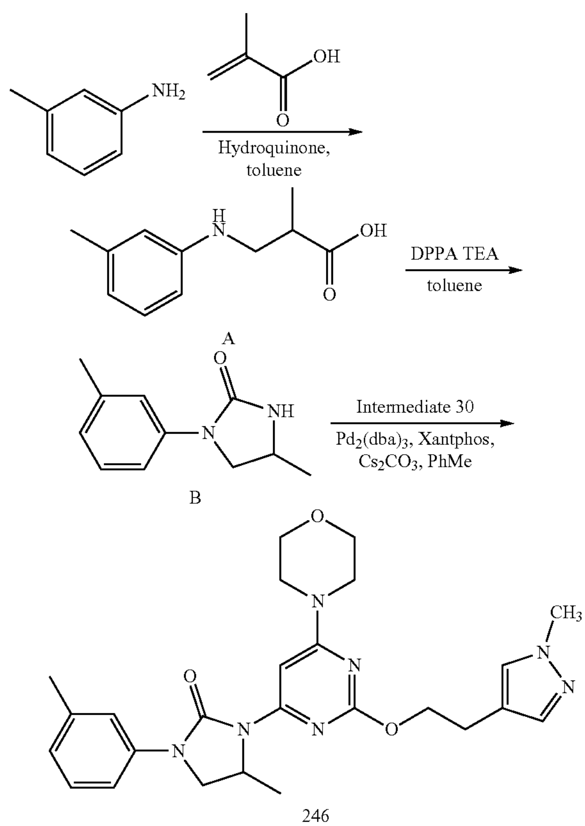

A

B

246

Preparation of A

To a solution of m-toluidine (10 g, 93.46 mmol) in toluene (25 mL) was added methacrylic acid (9.6 g, 112.15 mmol) and hydroquinone (500 mg, 4.67 mmol) at room temperature. After addition, the resulting mixture was stirred at 70° C. for 24 hrs. After which period, the mixture was cooled down to room temperature, then diluted with water (100 mL) and extracted with EtOAc (100 mL×3). The combined organic layers were washed with water (100 mL×3) and brine (100 mL), dried over anhydrous $Na_2SO_4$, filtered and concentrated under reduced pressure. The residue was purified by flash silica gel chromatography eluting with DCM: MeOH=24:1 to give the desired compound A (6.9 g, yield 38%) as yellow oil.

Preparation of B

To a solution of A (6.9 mg, 35.7 mmol) in toluene (140 mL) was added triethylamine (12.6 g, 124.95 mmol), DPPA (29.49 g, 107.1 mmol) at room temperature. After addition, the resulting mixture was stirred at 120° C. overnight. Then the reaction mixture was poured into water (100 mL) and extracted with dichloromethane (100 mL×3). The combined organic layers were washed with water (100 mL×3) and brine (100 mL×1), dried over anhydrous $Na_2SO_4$, filtered and concentrated under reduced pressure. The residue was purified by flash silica gel chromatography eluting with petroleum ether:EtOAc=4:1 to give the desired compound B (6.3 g, yield 92.8%) as a white solid.

Preparation of Compound 246

To a solution of B (76.5 mg, 0.4 mmol) in toluene (7 mL) was added Intermediate 30 (100 mg, 0.3095 mmol), $Pd_2(dba)_3$ (56 mg, 0.062 mmol), xantphos (71 mg, 0.12 mmol) and $Cs_2CO_3$ (301 mg, 0.93 mmol) at rt under $N_2$ atmosphere. After addition, the resulting mixture was stirred at 110° C. overnight. After cooling to room temperature, the reaction mixture was diluted with water (10 mL) and extracted with ethyl acetate (10 mL×3). The combined organic layers were washed with water (10 mL×3) and brine (10 mL), dried over anhydrous $Na_2SO_4$, filtered and concentrated under reduced pressure. The residue was purified by Prep-HPLC to give compound Compound 246 (40 mg, yield 27%) as a white solid.

$^1$H NMR (400 MHz, DMSO-$d_6$): δ 7.55 (s, 1H), 7.48 (s, 1H), 7.37 (d, J=8.0 Hz, 1H), 7.31 (s, 1H), 7.25 (t, J=8.0 Hz, 1H), 7.19 (s, 1H), 6.93 (d, J=8.0 Hz, 1H), 4.79-4.67 (m, 1H), 4.33-4.28 (m, J=7.7, 4.0 Hz, 2H), 4.10 (t, J=8.0 Hz, 1H), 3.78 (s, 3H), 3.71-3.59 (m, 4H), 3.54-3.49 (m, 5H), 2.83 (t, J=4.0 Hz, 2H), 2.32 (s, 3H), 1.38 (d, J=8.0 Hz, 3H). MS: m/z 478 [M+1]$^+$.

Synthesis of 1-methyl-2-(2-(2-(1-methyl-1H-pyrazol-4-yl)ethoxy)-6-morpholinopyrimidin-4-yl)-4-(m-tolyl)-1,2-dihydro-3H-pyrazol-3-one (Compound 247)

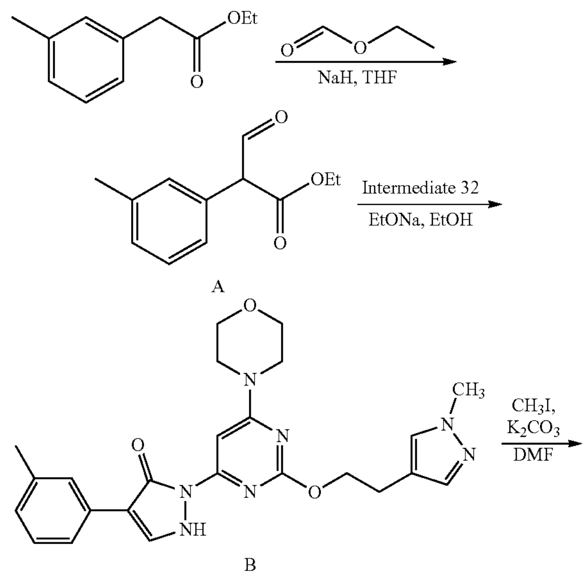

A

B

-continued

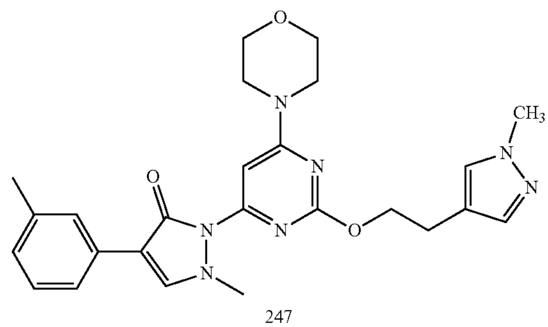

247

Preparation of A

To a solution of ethyl 2-(m-tolyl)acetate (3.0 g, 16.83 mmol) and ethyl formate (1.87 g, 25.25 mmol) in anhydrous THF (30 mL) was added NaH (60% dispersion in oil, 1.35 g, 33.66 mmol) in portions at 0° C. The reaction mixture was stirred at room temperature for 2 h. The mixture was quenched with $NH_4Cl$ (aq.) at 0° C. and extracted with EA (3×50 mL). The combined organic layers were washed with brine, dried over anhydrous $Na_2SO_4$, filtered and concentrated. The residue was purified by flash silica gel chromatography eluting with petroleum ether:EtOAc=24:1 to afford the desired product A 2.67 g, yield: 76.9%) as colorless oil.

Preparation of B

To a solution of Intermediate 32 (130 mg, 0.407 mmol) in EtOH (2 mL) was added A (88 mg, 0.427 mmol). The reaction mixture was stirred at room temperature for 2 hrs. After which period, the reaction mixture was added EtONa (27.7 mg, 0.407 mmol) at 0° C., and continued to stir at room temperature for another 0.5 h. The mixture was adjusted to pH=5 with a solution of 2 N HCl at 0° C. before the extraction with EtOAc (20 mL×3). The combined organic layers were dried over anhydrous $Na_2SO_4$, concentrated. The residue was purified by flash silica gel chromatography eluting with DCM:MeOH=10:1 to afford the desired compound B (120 mg, yield: 64.2%) as light yellow solid.

Preparation of Compound 247

To a solution of B (110 mg, 0.238 mmol) and $K_2CO_3$ (65.8 mg, 0.476 mmol) in anhydrous DMF (3 mL) was added $CH_3I$ (50.7 mg, 0.357 mmol) at 0° C. The reaction mixture was stirred at room temperature for 1 h. After completion of the reaction, the mixture was extracted with EtOAc (5 mL×3). The combined organic layers were washed with brine, dried over anhydrous $Na_2SO_4$ and concentrated. The residue was purified by Prep-HPLC to afford Compound 247 (50 mg, yield: 44.2%) as a white solid.

MS: m/z 476 [M+1]$^+$.

$^1$H NMR (400 MHz, DMSO-$d_6$): δ 8.50 (s, 1H), 7.72 (s, 1H), 7.63 (d, J=7.6 Hz, 1H), 7.55 (s, 1H), 7.32 (s, 1H), 7.24 (t, J=7.6 Hz, 1H), 7.02 (d, J=7.6 Hz, 1H), 6.97 (s, 1H), 4.34 (t, J=6.8 Hz, 2H), 3.77 (s, 3H), 3.70-3.3.59 (m, 8H), 3.54 (s, 3H), 2.83 (t, J=7.2 Hz, 2H), 2.31 (s, 3H).

Synthesis of N-(4-(2-(1-methyl-1H-pyrazol-4-yl) ethoxy)-6-morpholinopyrimidin-2-yl)-2-(m-tolyl) acetamide (Compound 248)

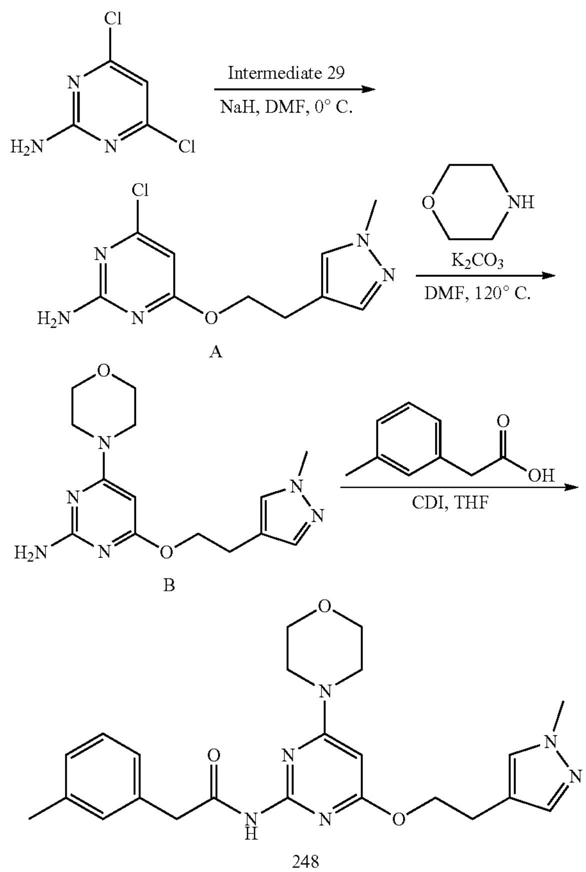

A

B

248

Preparation of A

To the solution of compound Intermediate 29 (3.8 g, 30.5 mmol) in N,N-dimethylformamide (6.0 mL) was added sodium hydride (60% in mineral oil, 1.46 g, 36.6 mmol) at 0° C., and the mixture was stirred for another 30 min. After which period, the solution of 4,6-dichloropyrimidin-2-amine (5.0 g, 30.5 mmol) in N,N-dimethylformamide (60 mL) was added to above system dropwise. After stirring at room temperature at room temperature overnight, the resulting mixture was poured into water and extracted with ethyl acetate (80 mL×3). The combined organic layers were dried over $Na_2SO_4$, filtered and concentrated to dryness. The resulting crude product was purified by chromatography on silica gel eluting with petroleum ether:EtOAc=10:1-1:1 to give the desired product A (5.4 g, 69.3%) as a white solid.

Preparation of B

To the solution of A (5.4 g, 21.2 mmol) in N,N-dimethylformamide (120 mL) was added morpholine (5.54 g, 63.70 mmol) and potassium carbonate (8.8 g, 63.7 mmol). And the resulting mixture was stirred at 120° C. overnight. After which period, the mixture was cooled to room temperature and poured into water, extracted with ethyl acetate (50 mL×2). The combined organic layers were dried over $Na_2SO_4$, filtered and concentrated to dryness. The resulting crude product was purified by chromatography on silica gel eluting with petroleum ether:EtOAc=1:1 to EtOAc to give the desired product B (6.0 g, 92.9%) as a white solid.

Preparation of Compound 248

To a solution of B (2.0 g, 6.6 mmol) in tetrahydrofuran (50 mL) was added 2-(m-tolyl)acetic acid (2.0 g, 13.2 mmol) and N,N'-carbonyldiimidazole (2.13 g, 13.2 mmol). And the resulting mixture was stirred at reflux for 19 hrs. After cooling down to room temperature, the mixture was poured into water and extracted with ethyl acetate (50 mL×3). The combined organic layers were dried over $Na_2SO_4$, filtered and concentrated to dryness. The resulting crude product was purified by chromatography on silica gel eluting with petroleum ether:EtOAc=5:1-1:1 to give Compound 248 (0.53 g, 18.5%) as a white solid.

$^1$H NMR (400 MHz, DMSO-$d_6$): δ 10.11 (s, 1H), 7.51 (s, 1H), 7.29 (s, 1H), 7.18 (m, 1H), 7.11-6.96 (m, 3H), 5.79 (s, 1H), 4.31 (t, J=6.9 Hz, 2H), 3.76 (m, 5H), 3.61 (m, 4H), 3.52 (m, 4H), 2.79 (t, J=6.9 Hz, 2H), 2.28 (s, 3H).

Synthesis of N-(2-(2-(1-methyl-1H-pyrazol-4-yl) ethoxy)-6-morpholinopyrimidin-4-yl)-2-(m-tolyl) acetamide (Compound 249)

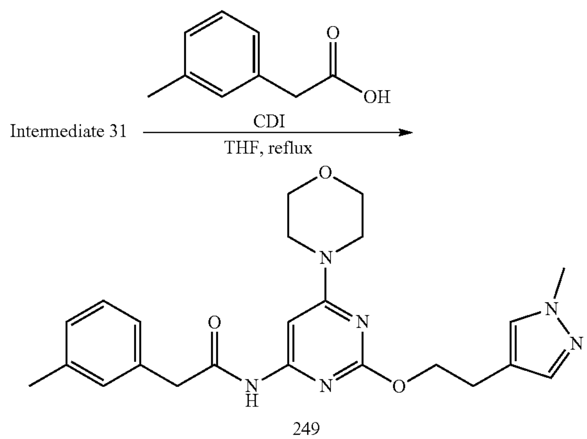

249

To the solution of Intermediate 31 (0.25 g, 0.82 mmol) in tetrahydrofuran (15 mL) was added 2-(m-tolyl)acetic acid (0.19 g, 1.23 mmol) and N,N'-carbonyldiimidazole (0.2 g, 1.23 mmol). The resulting mixture was stirred at reflux for 19 hours in a sealed tube. After which period, the mixture was cooled down to room temperature and poured into water. The system was extracted with ethyl acetate (15 mL×3), the combined organic layers were dried over $Na_2SO_4$, filtered and concentrated to dryness. The resulting crude product was purified by chromatography on silica gel eluting with petroleum ether:EtOAc=5:1-1:1 to give the Compound 249 (30 mg, 8.4%) as a white solid.

$^1$H NMR (400 MHz, Methanol-$d_4$): δ 7.47 (s, 1H), 7.37 (s, 1H), 7.20 (t, J=7.5 Hz, 1H), 7.14 (s, 1H), 7.13-7.04 (m, 3H), 4.38 (t, J=6.7 Hz, 2H), 3.82 (s, 3H), 3.74-3.68 (m, 4H), 3.66 (s, 2H), 3.61-3.53 (m)

Synthesis of N-methyl-N-(4-(2-(1-methyl-1H-pyrazol-4-yl)ethoxy)-6-morpholinopyrimidin-2-yl)-2-(m-tolyl)acetamide (Compound 250)

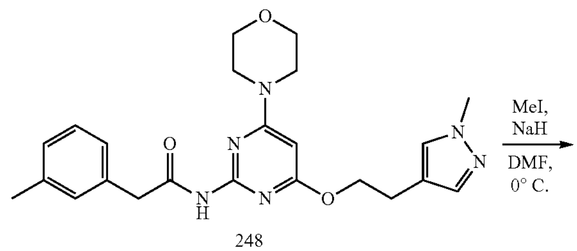

248

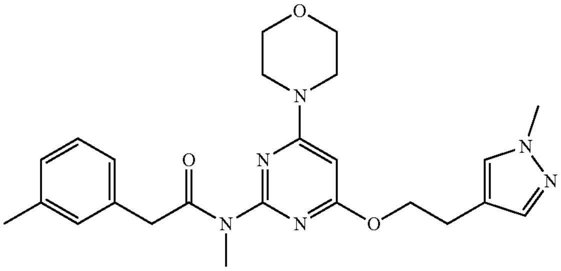

250

To the solution of Compound 248 (0.20 g, 0.46 mmol) in N,N-dimethylformamide (3.0 mL) was added sodium hydride (60% in mineral oil, 36.8 mg, 0.92 mmol) at 0° C., and then the mixture was stirred for another 30 min. After which period, the solution of iodomethane (78 mg, 0.55 mmol) in N,N-dimethylformamide (2.0 mL) was added to above mixture dropwise. The mixture was stirred at room temperature for 2 hours before pouring into water, and extracted with ethyl acetate (15 mL×3). The combined organic layers were dried over sodium sulphate and concentrated under vacuum to dryness. The crude product was purified with Prep-HPLC (basic condition) to give the desired product Compound 250 (80 mg, 38.8%) as a white solid.

LC-MS: Calculated Exact Mass=450.2, Found $[M+H]^+$=451.2.

$^1$H NMR (400 MHz, DMSO-$d_6$) δ 7.41 (s, 1H), 7.32 (s, 1H), 7.10-7.06 (m, 1H), 6.96-6.95 (m, 1H), 6.87-6.85 (m, 2H), 5.80 (s, 1H), 4.32-4.28 (t, J=6.9 Hz, 2H), 4.06 (s, 2H), 3.81 (s, 3H), 3.69-3.66 (m, 4H), 3.50-3.48 (m, 4H), 3.35 (s, 1H), 2.84-2.81 (t, J=6.9 Hz, 2H), 2.23 (s, 3H).

Synthesis of 4-(6-(2-(1-methyl-1H-pyrazol-4-yl)ethoxy)-2-(3-(m-tolyl)-1H-pyrazol-1-yl)pyrimidin-4-yl)morpholine (Compound 251)

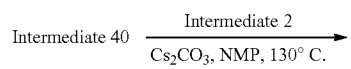

-continued

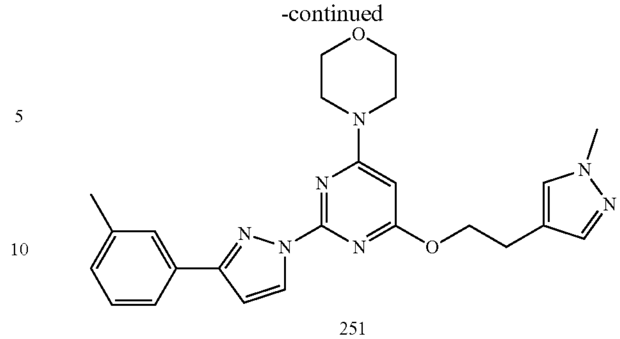

251

To the solution of Intermediate 40 (0.15 g, 0.41 mmol) in 1-methylpyrrolidin-2-one (5.0 mL) was added Intermediate 2 (77.5 mg, 0.49 mmol) and cesium carbonate (0.20 g, 0.61 mmol). The resulting mixture was stirred at 130° C. overnight in a sealed tube. After which period, the mixture was cooled down to room temperature, poured into water and extracted with ethyl acetate (15 mL×3). The combined organic layers were dried over $Na_2SO_4$, filtered and concentrated to dryness. The resulting crude product was purified by chromatography on silica gel eluting with petroleum ether:EtOAc=8:1-1:1 to give the desired product Compound 251 (0.13 g, 71.5%) as a white solid.

LC-MS: Calculated Exact Mass=445.2, Found $[M+H]^+$=446.2.

1H NMR (400 MHz, DMSO-$d_6$) δ 8.66 (d, J=2.7 Hz, 1H), 7.77 (s, 1H), 7.74 (d, J=7.8 Hz, 1H), 7.59 (s, 1H), 7.38 (s, 1H), 7.35 (t, J=7.6 Hz, 1H), 7.19 (d, J=7.5 Hz, 1H), 7.01 (d, J=2.7 Hz, 1H), 6.06 (s, 1H), 4.46 (t, J=6.9 Hz, 2H), 3.78 (s, 3H), 3.68 (m, 8H), 2.88 (t, J=6.8 Hz, 2H), 2.38 (s, 3H).

Synthesis of N-methyl-N-(4-(2-(1-methyl-1H-pyrazol-4-yl)ethoxy)-6-morpholinopyrimidin-2-yl)quinazolin-2-amine (Compound 252)

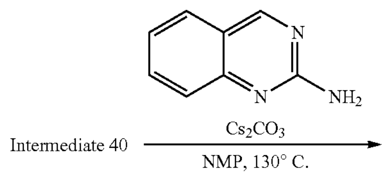

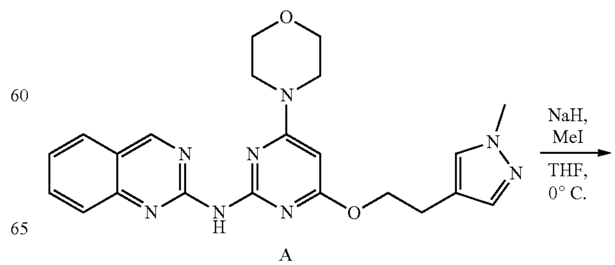

A

-continued

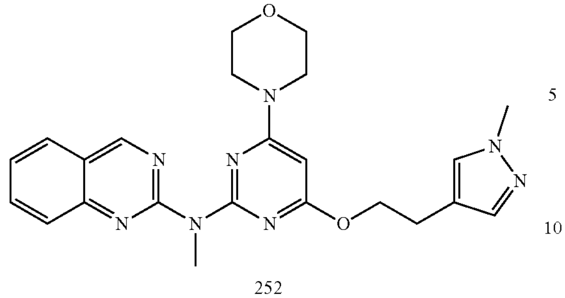

252

Preparation of A

To the solution of Intermediate 40 (0.5 g, 1.4 mmol) in 1-methylpyrrolidin-2-one (15 mL) was added quinazolin-2-amine (0.3 g, 2.0 mmol) and cesium carbonate (0.9 g, 2.7 mmol). The mixture was stirred at 130° C. for 19 hours. After which period, the mixture was cooled down to room temperature, poured into water and extracted with ethyl acetate (15.00 mL×3). The combined organic layers were dried over $Na_2SO_4$, filtered and concentrated to dryness. The resulting crude product was purified by chromatography on silica gel eluting with petroleum ether:EtOAc=5:1 to ethyl acetate to give the desired product A (0.3 g, 50.1%) as a white solid.

Preparation of Compound 252

To the solution of A (0.2 g, 0.46 mmol) in N,N-dimethylformamide (5.0 mL) was added sodium hydride (60% in mineral oil, 37.0 mg, 0.92 mmol) at 0° C., and the mixture was stirred for another 30 min. Then the solution of iodomethane (66.0 mg, 0.46 mmol) in N,N-dimethylformamide (2.0 mL) was added to above mixture dropwise. The resulting mixture was stirred at room temperature for 2 hours and poured into water, extracted with ethyl acetate (15 mL×3). The combined organic layers were dried over sodium sulphate and concentrated to dryness under vacuum. The residue was further purified with Prep-HPLC (basic) to give the desired product Compound 252 (80.0 mg, 38.8%) as a white solid.

LC-MS: Calculated Exact Mass=446.2, Found $[M+H]^+$=447.2.

$^1$H NMR (400 MHz, DMSO-$d_6$) δ 9.37 (d, J=0.4 Hz, 1H), 8.03-8.01 (d, J=8.1 Hz, 1H), 7.90-7.86 (m, 1H), 7.76-7.74 (d, J=8.1 Hz, 1H), 7.54 (s, 1H), 7.39 (s, 1H), 7.19 (s, 1H), 5.78 (s, 1H), 4.24-4.21 (t, J=7.0 Hz, 2H), 3.73 (s, 3H), 3.70-3.56 (m, 7H), 3.54-3.40 (m, 4H), 2.78-2.75 (t, J=6.9 Hz, 2H).

Synthesis of N,N-dimethyl-1-(2-(2-(2-(1-methyl-1H-pyrazol-4-yl)ethoxy)-6-morpholinopyrimidin-4-yl)-2H-indazol-5-yl)methanamine (Compound 253)

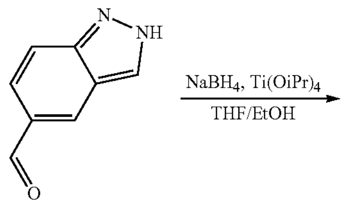

-continued

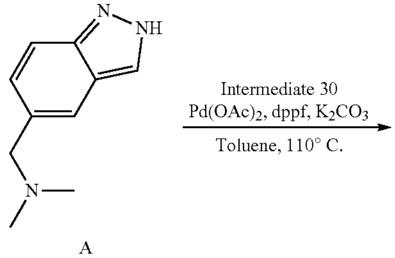

A

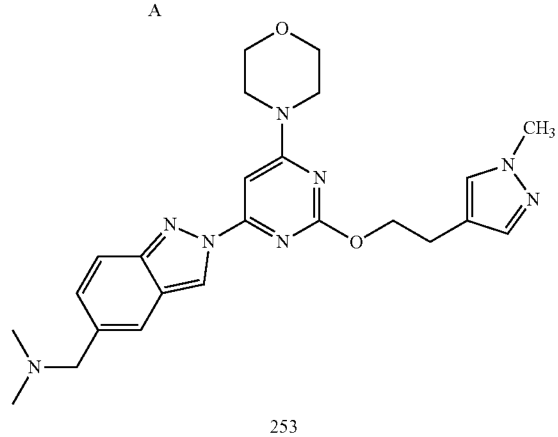

253

Preparation of A

To a solution of 1H-indazole-5-carbaldehyde (515 mg, 3.52 mmol) and dimethylamine (3.6 mL, 2N in THF) in EtOH (5 mL) was added titanium(IV) isopropoxide (2.0 g, 7.04 mmol). The resulting mixture was stirred at room temperature overnight. After then, $NaBH_4$ (200 mg, 5.28 mmol) was added to above system, the resulting mixture was further stirred for another 1 hrs at room temperature. After which period, the reaction mixture was poured into aqueous ammonia solution (30 mL, 2 N). The resulting precipitate was filtered out and washed with dichloromethane (100 mL). The filtrate was separated. The aqueous phase was extracted with dichloromethane (100 mL×2), The combined dichloromethane extracts were dried over $K_2CO_3$ and concentrated in vacuo and purified by chromatography on silica gel eluting with DCM:MeOH=9:1 to get the desired product A (524 mg, 85%) as a white solid.

Preparation of Compound 253

The mixture of Intermediate 30 (150 mg, 0.46 mmol), a (175 mg, 0.92 mmol), dppf (153 mg, 0.28 mmol), $Pd(OAc)_2$ (31 mg, 0.14 mmol) and $K_2CO_3$ (159 mg, 1.15 mmol) in Toluene (5 mL) was stirred at 110° C. for 3 hrs under nitrogen atmosphere in microwave reactor. After which period, the mixture was cooled down to room temperature and filtered through a pad of Celite. The filtrate was purified by Prep-HPLC to give the desired product Compound 253 (35 mg, yield: 16%) as a brown solid.

$^1$HNMR (400 MHz, DMSO-$d_6$): δ 8.63 (d, J=8.0 Hz, 1H), 8.43 (s, 1H), 7.75 (s, 1H), 7.60 (s, 1H), 7.50 (d, J=8.0 Hz, 1H), 7.37 (s, 1H), 6.88 (s, 1H), 4.47 (t, J=8.0 Hz, 2H), 3.80 (s, 3H), 3.71-3.66 (m, 4H), 3.65-3.60 (m, 4H), 3.53 (s, 2H), 2.92 (t, J=8.0 Hz, 2H), 2.19 (s, 6H).

Synthesis of N,N-dimethyl-1-(3-methyl-2-(2-(2-(1-methyl-1H-pyrazol-4-yl)ethoxy)-6-morpholinopyrimidin-4-yl)-2H-indazol-5-yl)methanamine (Compound 254)

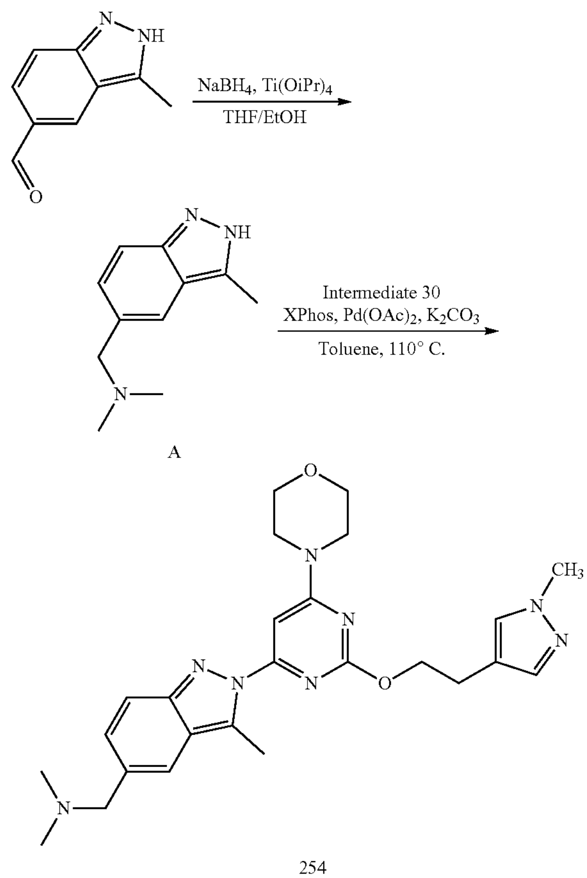

A

254

The synthesis of Compound 254 is similar to that of Compound 253, using the reagents illustrated above.

$^1$HNMR (400 MHz, DMSO-$d_6$): δ 8.58 (d, J=8.0 Hz, 1H), 7.71 (s, 1H), 7.59 (s, 1H), 7.50 (d, J=8.0 Hz, 1H), 7.37 (s, 1H), 6.76 (s, 1H), 4.45 (t, J=8.0 Hz, 2H), 3.80 (s, 3H), 3.71-3.65 (m, 4H), 3.64-3.58 (m, 6H), 2.91 (t, J=8.0 Hz, 2H), 2.56 (s, 3H), 2.23 (s, 6H).

Synthesis of (3-methyl-2-(2-(2-(1-methyl-1H-pyrazol-4-yl)ethoxy)-6-morpholinopyrimidin-4-yl)-2H-indazol-6-yl)methanol (Compound 255)

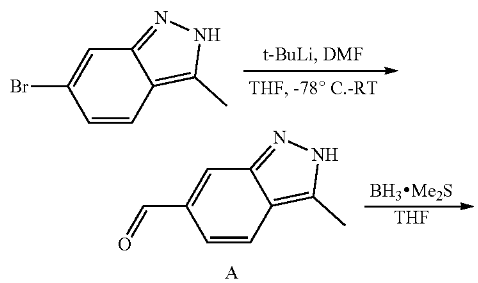

A

-continued

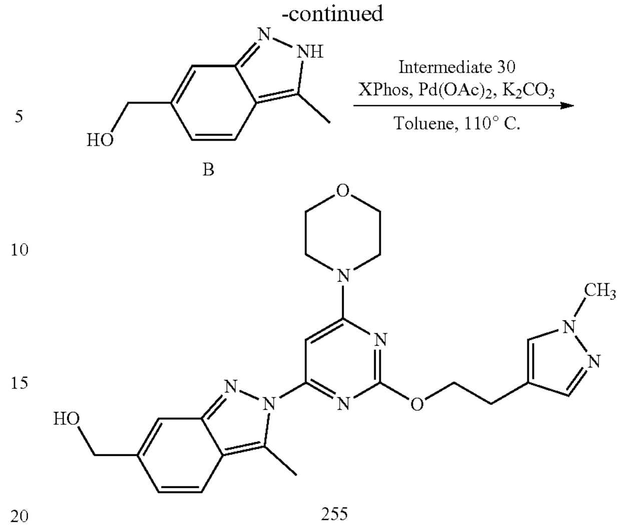

B

255

Preparation of A

To argon flushed flask of anhydrous THF (15 mL) was added dropwise t-BuLi (9 mL, 11.8 mmol) at −78° C. After stirring at −78° C. for 15 min, a solution of 6-bromo-3-methyl-2H-indazole (500 mg, 2.36 mmol) in anhydrous THF (5 mL) was added dropwise such that the temperature of the solution no exceed −70° C. After stirring at −78° C. for another 1 h, to the above solution was added anhydrous DMF (525 mg, 7.19 mmol) dropwise. The resulting system was stirred at −78° C. for another 1 hrs and then allowed to warm to room temperature overnight. After which period, the system was quenched by addition of water at 0° C. and then extracted with EA (50 mL×3). The combined organic layers were washed with brine (60 mL), dried over $Na_2SO_4$, filtered, and concentrated to dryness. The resulting crude product was purified by chromatography on silica gel eluting with petroleum ether:MTBE=3:2 to get the desired product A (285 mg, 75%) as colorless oil.

Preparation of B $BH_3$-$Me_2S$ (2.3 mL, 4.62 mmol) was added to a solution of A (275 mg, 1.71 mmol) in THF (15 mL) at 0° C. The resulting mixture was stirred at rt for 2 hrs, TLC showed the total consumption of A. The system was poured into water (20 mL) and extracted with EtOAc (30 mL×3). The combined organic layers were washed with brine (30 mL), dried over $Na_2SO_4$, filtered and concentrated to dryness to get the desired compound B (255 mg, 91%) as a white solid, which was used in next step without further purification.

Preparation of Compound 255

The mixture of Intermediate 30 (200 mg, 0.62 mmol), B (150 mg, 0.92 mmol), XPhos (177 mg, 0.37 mmol), $Pd(OAc)_2$ (28 mg, 0.12 mmol) and $K_2CO_3$ (256 mg, 1.85 mmol) in Toluene (5 mL), was stirred at 110° C. for 3 hrs under nitrogen in microwave reactor. After which period, the mixture was cooled down to room temperature and filtered through a pad of Celite. The filtrate was concentrated and purified by Prep-HPLC to give the desired product Compound 255 (30 mg, yield: 7%) as a white solid.

$^1$HNMR (400 MHz, DMSO-$d_6$): δ 8.68 (s, 1H), 7.76 (d, J=8.0 Hz, 1H), 7.61 (s, 1H), 7.36 (s, 1H), 7.27 (d, J=8.0 Hz, 1H), 6.79 (s, 1H), 5.42 (t, J=4.0 Hz, 1H), 4.66 (d, J=8.0 Hz, 2H), 4.50 (t, J=4.0 Hz, 2H), 3.80 (s, 3H), 3.72-3.67 (m, 4H), 3.65-3.60 (m, 4H), 2.92 (t, J=8.0 Hz, 2H), 2.57 (s, 3H).

Synthesis of (S)-2-(4-(5-cyclopropyl-3-phenyl-1H-pyrazol-1-yl)-6-morpholinopyrimidin-2-yl)-2-methoxyethan-1-ol (Compound 256) and (R)-2-(4-(5-cyclopropyl-3-phenyl-1H-pyrazol-1-yl)-6-morpholinopyrimidin-2-yl)-2-methoxyethan-1-ol (Compound 257)

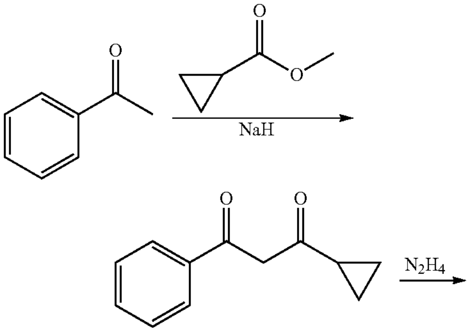

A

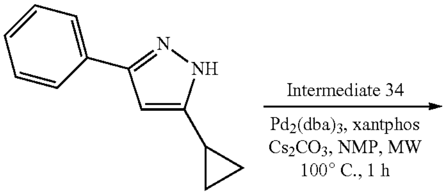

B

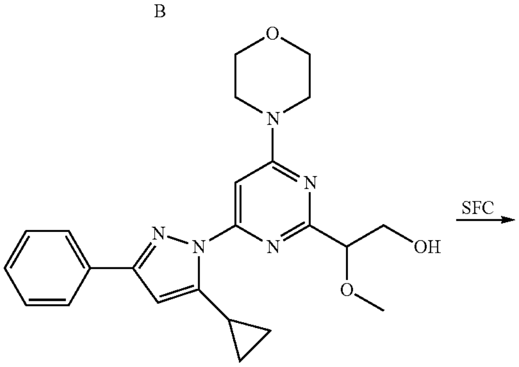

C

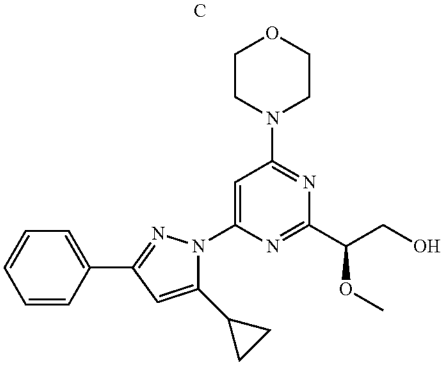

+

256

-continued

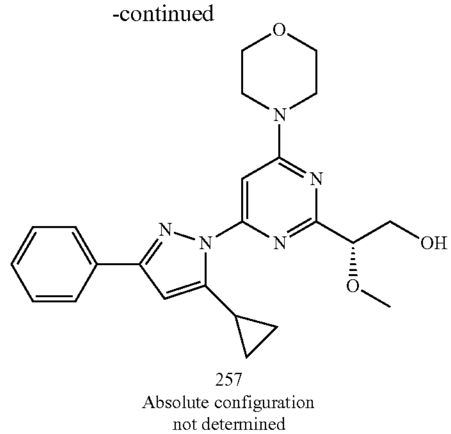

257
Absolute configuration not determined

Preparation of A

To a suspension of NaH (2.4 g, 60 mmol) and methyl cyclopropane carboxylate (6.0 g, 60 mmol) in dry THF (40 mL) was added the solution of acetophenone (3.6 g, 30 mmol) in THF (10 mL) dropwise over 0.5 h. The mixture was stirred under reflux until TLC indicated the total consumption of the ketone. After cooling, the reaction mixture was poured into ice-water (100 mL), acidified to pH=6 with aqueous HCl. The resulting mixture was extracted with ethyl acetate (50 mL×3). The combined organic layers were washed with brine (50 mL×3), dried over anhydrous $Na_2SO_4$, filtrated, and concentrated to dryness. The resulting crude product was purified by chromatography on silica gel eluting with petroleum ether:EtOAc=10:1 to get A (5.2 g, 92%) as light yellow oil.

Preparation of B

To a solution of A (5.2 g, 27.6 mmol) in EtOH (30 mL) and AcOH (3 mL) was added $NH_2NH_2$—$H_2O$ (1.6 g, 33.1 mmol) at 60° C., and the solution was stirred for 50 min. The mixture was concentrated and diluted with EtOAc (80 mL). The resulting solution was washed with brine (50 mL×3), dried over $Na_2SO_4$, filtered and concentrated to dryness. The resulting crude product was purified by chromatography on silica gel eluting with petroleum ether:EtOAc=10:1-3:1 to get B (4.3 g, 85%) as a white solid.

Preparation of C

A mixture of B (134 mg, 0.73 mmol), Intermediate 34 (200 mg, 0.73 mmol), $Pd_2(dba)_3$ (134 mg, 0.147 mmol), Xant-phos (85 mg, 0.147 mmol) and $Cs_2CO_3$ (477 mg, 1.47 mmol) in NMP (5 mL) was placed at 100° C. in a microwave reactor under nitrogen atmosphere for 1 hour. After which period, the mixture was diluted with EtOAc (80 mL) and washed with brine (30 mL×4), dried over $Na_2SO_4$, filtered and concentrated to dryness. The resulting crude product was purified by chromatography on silica gel eluting with petroleum ether:EtOAc=5:1-1:1 to get C (50 mg, 16%) as a white solid.

Preparation of Compound 256 and Compound 257

C was separated by chiral HPLC (SFC) to get to Compound 256 (18 mg, 1$^{st}$ peak) and Compound 257 (18 mg, 2$^{nd}$ peak). The stereochemistry of the enantiomers was not determined.

Compound 256 (1st Peak)

$^1H$ NMR (600 MHz, $CDCl_3$) δ 8.08-7.78 (m, 2H), 7.41 (dd, J=8.3, 6.9 Hz, 2H), 7.38-7.31 (m, 1H), 7.13 (s, 1H), 6.33 (s, 1H), 4.40 (m, 1H), 3.98-3.92 (m, 2H), 3.86-3.74 (m, 8H), 3.52 (s, 3H), 2.94-2.91 (m, 1H), 1.11-1.00 (m, 2H), 0.77-0.75 (m, 2H).

Compound 257 (2nd Peak $^1H$ NMR (600 MHz, $CDCl_3$) δ 7.86-7.81 (m, 2H), 7.41 (dd, J=8.3, 6.9 Hz, 2H), 7.38-7.32 (m, 1H), 7.11 (s, 1H), 6.33 (s, 1H), 4.33 (m, 1H), 4.06-3.89 (m, 2H), 3.85-3.71 (m, 8H), 3.52 (s, 3H), 2.94-2.91 (m, 1H), 1.12-0.98 (m, 2H), 0.77-0.75 (m, 2H).

Synthesis of (S)-2-(4-(3-(benzo[b]thiophen-3-yl)-1H-pyrazol-1-yl)-6-morpholinopyrimidin-2-yl)-2-methoxyethan-1-ol (Compound 258) and (R)-2-(4-(3-(benzo[b]thiophen-3-yl)-1H-pyrazol-1-yl)-6-morpholinopyrimidin-2-yl)-2-methoxyethan-1-ol (Compound 259)

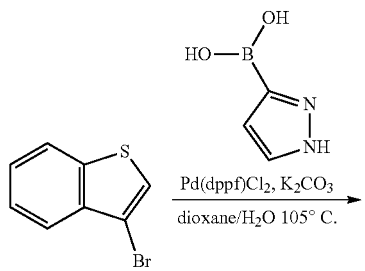

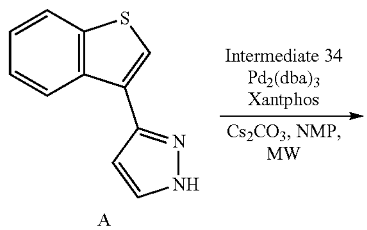

A

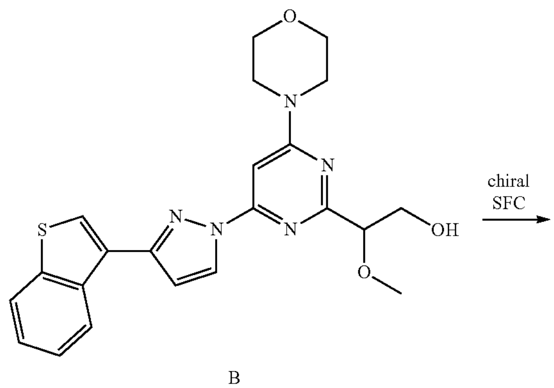

B

-continued

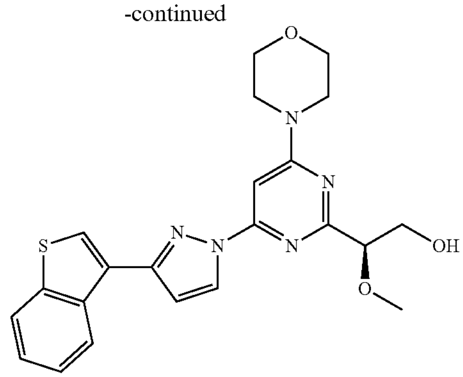

258

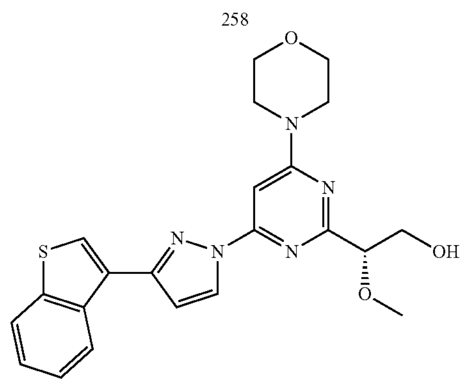

259
Absolute stereochemistry not defined

Preparation of A

The mixture of 3-bromobenzo[b]thiophene (500 mg, 2.35 mmol), (1H-pyrazol-3-yl)boronic acid (279 mg, 2.35 mmol), $K_2CO_3$ (1.1 g, 7.04 mmol) and Pd(dppf)$Cl_2$ (172 mg, 0.235 mmol) in dioxane:water=5:1 (12 mL) under an atmosphere of nitrogen was stirred at 105° C. for 12 hrs. After which period, the reaction mixture was cooled down to room temperature and diluted with EtOAc. The separated organic phase was washed with water, brine, dried over $Na_2SO_4$ and concentrated to dryness. The resulting crude product was purified by chromatography on silica gel eluting with petroleum ether:EtOAc=3:1 to give the A (80 mg, 17%) as brown oil.

Preparation of B

The mixture of Intermediate 34 100 mg, 0.365 mmol), compound A (88 mg, 0.44 mmol), $Pd_2(dba)_3$ (66 mg, 0.072 mmol), Xantphos (42 mg, 0.072 mmol) and $Cs_2CO_3$ (236 mg, 0.72 mmol) in NMP (4 mL) was warmed up to 110° C. in a microwave reactor for 1.5 hrs. After cooling to room temperature, the reaction mixture was diluted with water (12 mL) and then extracted with EtOAc (30 mL×2). The combined organic layers were washed with brine (20 mL×3), dried over $Na_2SO_4$, filtered, concentrated to dryness. The resulting crude product was purified by chromatography on silica gel eluting with petroleum ether:EtOAc=5:1 to petroleum ether:EtOAc=1:1 to get the desired product B (60 mg, 37.9%) as light-yellow oil.

Preparation of Compound 258 and Compound 259

B was separated by chiral SFC to give to get Compound 258 and Compound 259. The stereochemistry of the enantiomers was not determined.

Compound 258 (1st Peak)

$^1$H NMR (400 MHz, $CDCl_3$) δ 8.80 (d, J=4.0 Hz, 1H), 8.56 (d, J=8.0 Hz, 1H), 7.93 (d, J=8.0 Hz, 1H), 7.83 (s, 1H), 7.52-7.41 (m, 2H), 7.19 (s, 1H), 6.84 (d, J=4.0 Hz, 1H), 4.60 (t, J=4.0 Hz, 1H), 4.05-3.95 (m, 2H), 3.87-3.84 (m, 8H), 3.56 (s, 3H).

Compound 259 (2nd Peak)

$^1$H NMR (400 MHz, $CDCl_3$) δ 8.80 (d, J=4.0 Hz, 1H), 8.56 (d, J=8.0 Hz, 1H), 7.93 (d, J=8.0 Hz, 1H), 7.83 (s, 1H), 7.52-7.41 (m, 2H), 7.19 (s, 1H), 6.84 (d, J=4.0 Hz, 1H), 4.60 (t, J=4.0 Hz, 1H), 4.05-3.95 (m, 2H), 3.87-3.84 (m, 8H), 3.56 (s, 3H).

Synthesis of 2-(4-(3-(1H-indol-3-yl)-5-methyl-1H-pyrazol-1-yl)-6-morpholinopyrimidin-2-yl)-2-methoxyethan-1-ol (Compound 260) and (R)-2-(4-(3-(1H-indol-3-yl)-5-methyl-1H-pyrazol-1-yl)-6-morpholinopyrimidin-2-yl)-2-methoxyethan-1-ol (Compound 261)

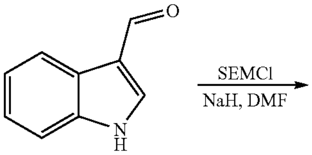

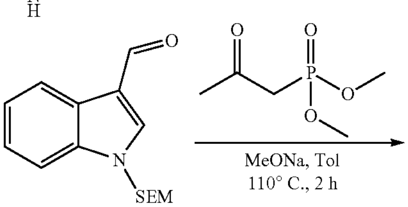

A

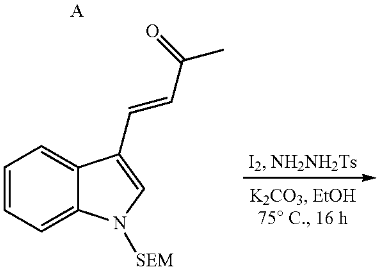

B

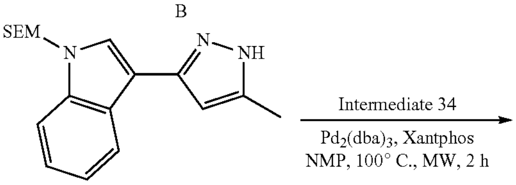

C

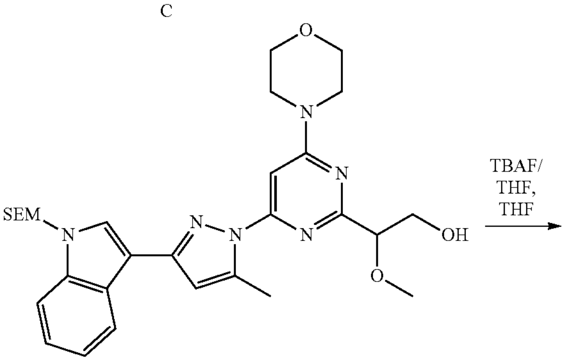

D

-continued

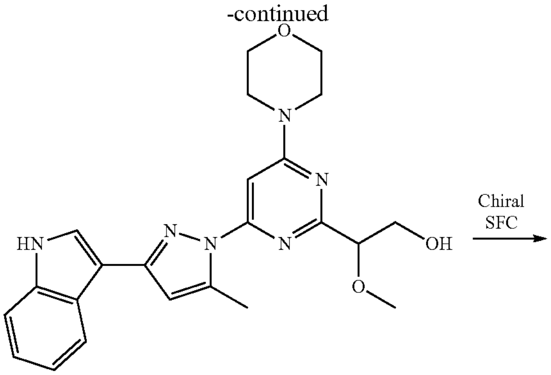

E

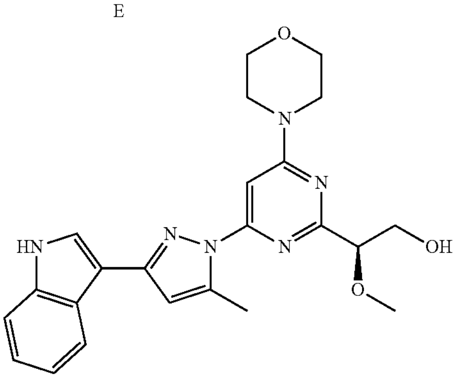

260

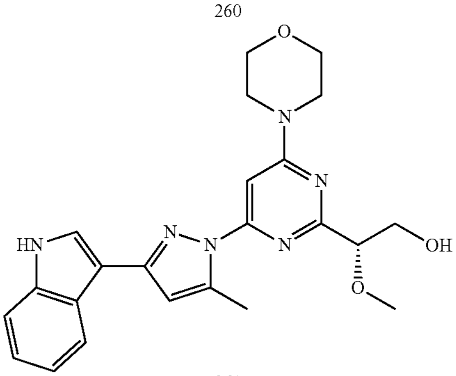

261

Absolute stereochemistry not determined

Preparation of A

To a solution of compound 1H-indole-3-carbaldehyde (2.9 g, 20 mmol) in DMF (30 mL) was added NaH (1.2 g, 30 mmol) at 0° C., the mixture was stirred at room temperature for 30 minutes before cooling to 0° C. again, and SEMCl (4.0 g, 24 mmol) was added slowly. The mixture was stirred at room temperature for another 2 hours before pouring into water (100 mL) and extracted with EtOAc (80 mL×3). The combined organic layers were washed with brine (80 mL×4), dried over $Na_2SO_4$, filtered and concentrated to dryness. The resulting crude product A was used without further purification (4.8 g, 87%) as colorless oil.

Preparation of B

To the mixture of compound A (4.8 g, 17.5 mmol) and dimethyl (2-oxopropyl)phosphonate (2.9 g, 17.5 mmol) in toluene (100 mL) was added MeONa/MeOH (30%, 3.2 g, 17.5 mmol). The mixture was stirred at 110° C. under nitrogen atmosphere for 2 hours. After which period, the mixture was diluted with EtOAc (100 mL) after cooling to room temperature and washed by brine (60 mL×3), dried over $Na_2SO_4$, filtered, concentrated to dryness. The resulting crude product was purified by chromatography on silica gel eluting with petroleum ether:EtOAc=10:1-3:1 to get the desired compound B (4.6 g, 84%) as a slight yellow solid.

Preparation of C

A mixture of compound B (4.6 g, 14.6 mmol), $I_2$ (164 mg, 1.5 mmol) and $NH_2NH_2Ts$ (3.28 g, 17.6 mmol) in EtOH (100 mL) was stirred at 75° C. under nitrogen atmosphere for 0.5 hour. Then $K_2CO_3$ (2.44 mg, 17.6 mmol) was added into it, the resulting mixture was stirred at 75° C. under nitrogen atmosphere for 16 hours. After cooling to room temperature, the mixture was concentrated under reduced pressure and diluted with EtOAc (100 mL). The separated organic phase was washed by brine (50 mL×5), dried over $Na_2SO_4$, filtered, concentrated to dryness. The resulting crude product was purified by chromatography on silica gel eluting with petroleum ether:EtOAc=5:1-1:1 to get the desired compound C (1.76 g, 37%) as yellow oil.

Preparation of D

A mixture of compound C (273 mg, 0.83 mmol), Intermediate 34 (228 mg, 0.83 mmol), $Pd_2(dba)_3$ (152 mg, 0.166 mmol), Xantphos (96 mg, 0.166 mmol) and $Cs_2CO_3$ (541 mg, 1.66 mmol) in NMP (5 mL) was heated up to 100° C. in a microwave reactor under nitrogen atmosphere for 2 hours. After which period, the mixture was cooled down to room temperature and diluted with EtOAc (50 mL). The resulting mixture was washed by brine (30 mL×4), dried over $Na_2SO_4$, filtered, concentrated to dryness. The residue was purified by chromatography on silica gel eluting with petroleum ether:EtOAc=5:1-1:1 to get compound D (145 mg, 31%) as yellow oil.

Preparation of E

A mixture of compound D (145 mg, 0.31 mmol), TBAF/THF (1.86 mL, 1.86 mmol) and ethylenediamine (56 mg, 0.93 mmol) in THF (1 mL) was stirred at 80° C. under nitrogen atmosphere for 16 hours. After cooling to room temperature, the mixture was diluted with EtOAc (40 mL) and washed by brine (30 mL×4), dried over $Na_2SO_4$, filtered, concentrated to dryness. The resulting crude product was purified by Prep-HPLC to get the desired product E (65 mg, 48%) as a white solid.

Synthesis of Compound 260 and Compound 261

Compound E was separated by chiral HPLC (SFC) to get to Compound 260 (25 mg) and Compound 261 (25 mg). The stereochemistry of the enantiomers was not determined.

Compound 260 ($1^{st}$ Peak):

$^1H$ NMR (400 MHz, $CDCl_3$) δ 8.36 (s, 1H), 8.29-8.17 (m, 1H), 7.61 (d, J=2.6 Hz, 1H), 7.46-7.40 (m, 1H), 7.30-7.22 (m, 2H), 7.18 (s, 1H), 6.49 (d, J=1.0 Hz, 1H), 4.34 (dd, J=6.4, 4.4 Hz, 1H), 4.05-3.90 (m, 2H), 3.86-3.68 (m, 8H), 3.54 (s, 3H), 2.80 (d, J=0.8 Hz, 3H).

Compound 261 ($2^{nd}$ Peak):

$^1H$ NMR (400 MHz, $CDCl_3$) δ 8.36 (s, 1H), 8.29-8.17 (m, 1H), 7.61 (d, J=2.6 Hz, 1H), 7.46-7.40 (m, 1H), 7.30-7.22 (m, 2H), 7.18 (s, 1H), 6.49 (d, J=1.0 Hz, 1H), 4.34 (dd, J=6.4, 4.4 Hz, 1H), 4.05-3.90 (m, 2H), 3.86-3.68 (m, 8H), 3.54 (s, 3H), 2.80 (d, J=0.8 Hz, 3H).

The following compounds were prepared using procedures similar to the preparation of Compounds 256/257, 261/262 and 300/301:

| # | Structure | Name | LCMS (ESI): m/z [M + H]+ | 1H NMR |
|---|---|---|---|---|
| 262 | 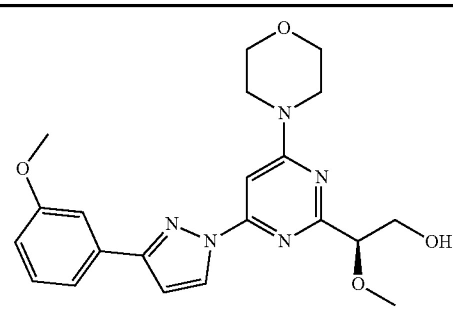 | (S)-2-methoxy-2-(4-(3-(3-methoxyphenyl)-1H-pyrazol-1-yl)-6-morpholinopyrimidin-2-yl)ethan-1-ol | 412 | |
| 263 | 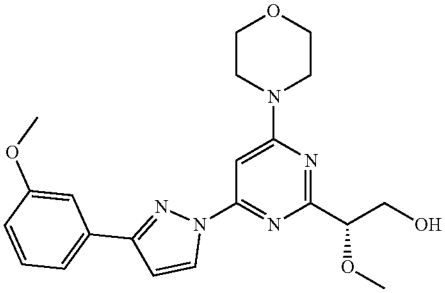 [SMILES: COc1cccc(-c2ccn(-c3cc(N4CCOCC4)nc([C@H](CO)OC)n3)n2)c1] | (R)-2-methoxy-2-(4-(3-(3-methoxyphenyl)-1H-pyrazol-1-yl)-6-morpholinopyrimidin-2-yl)ethan-1-ol | 412 | |

-continued

| # | Structure | Name | LCMS (ESI): m/z $[M + H]^+$ | 1H NMR |
|---|---|---|---|---|
| 264 | 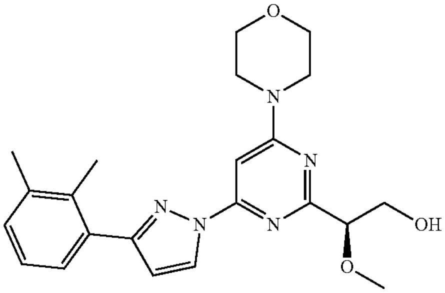 [SMILES: CO[C@H](CO)c1nc(N2CCOCC2)cc(-n2ccc(-c3cccc(C)c3C)n2)n1] | (S)-2-(4-(3-(2,3-dimethylphenyl)-1H-pyrazol-1-yl)-6-morpholinopyrimidin-2-yl)-2-methoxyethan-1-ol | 410 | |
| 265 | 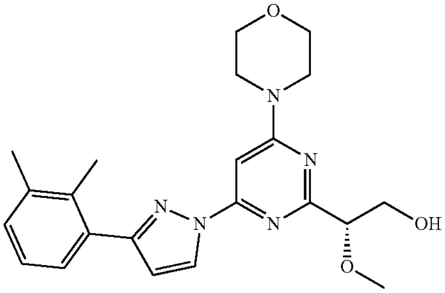 [SMILES: CO[C@@H](CO)c1nc(N2CCOCC2)cc(-n2ccc(-c3cccc(C)c3C)n2)n1] | (R)-2-(4-(3-(2,3-dimethylphenyl)-1H-pyrazol-1-yl)-6-morpholinopyrimidin-2-yl)-2-methoxyethan-1-ol | 410 | |
| 266 | 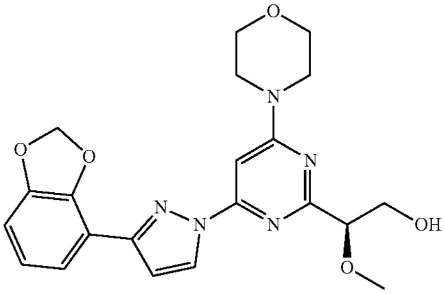 [SMILES: CO[C@H](CO)c1nc(N2CCOCC2)cc(-n2ccc(-c3cccc4c3OCO4)n2)n1] | (S)-2-(4-(3-(benzo[d][1,3]dioxol-4-yl)-1H-pyrazol-1-yl)-6-morpholinopyrimidin-2-yl)-2-methoxyethan-1-ol | 426 | |
| 267 | 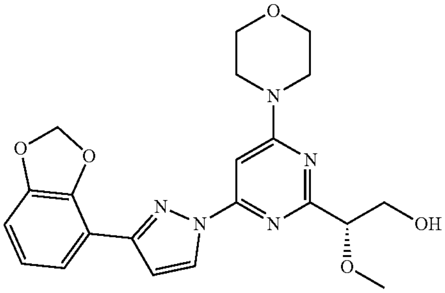 [SMILES: CO[C@@H](CO)c1nc(N2CCOCC2)cc(-n2ccc(-c3cccc4c3OCO4)n2)n1] | (R)-2-(4-(3-(benzo[d][1,3]dioxol-4-yl)-1H-pyrazol-1-yl)-6-morpholinopyrimidin-2-yl)-2-methoxyethan-1-ol | 426 | |
| 268 | 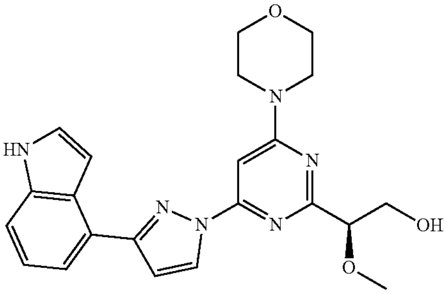 [SMILES: CO[C@H](CO)c1nc(N2CCOCC2)cc(-n2ccc(-c3cccc4[nH]ccc34)n2)n1] | (S)-2-(4-(3-(1H-indol-4-yl)-1H-pyrazol-1-yl)-6-morpholinopyrimidin-2-yl)-2-methoxyethan-1-ol | 421 | |

-continued

| # | Structure | Name | LCMS (ESI): m/z [M + H]+ | 1H NMR |
|---|---|---|---|---|
| 269 | 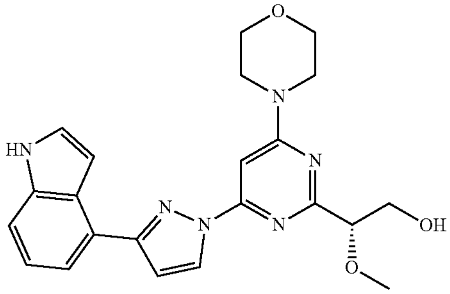 [SMILES: CO[C@@H](CO)c1nc(N2CCOCC2)cc(-n2ccc(-c3cccc4[nH]ccc34)n2)n1] | (R)-2-(4-(3-(1H-indol-4-yl)-1H-pyrazol-1-yl)-6-morpholinopyrimidin-2-yl)-2-methoxyethan-1-ol | 421 | |
| 270 | 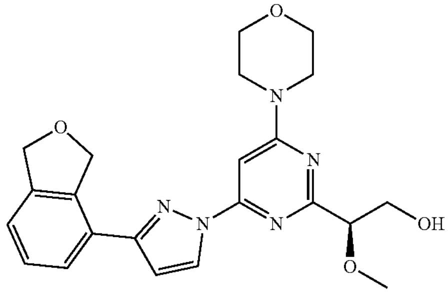 [SMILES: CO[C@H](CO)c1nc(N2CCOCC2)cc(-n2ccc(-c3cccc4c3COC4)n2)n1] | (S)-2-(4-(3-(1,3-dihydroisobenzofuran-4-yl)-1H-pyrazol-1-yl)-6-morpholinopyrimidin-2-yl)-2-methoxyethan-1-ol | 424 | |
| 271 | 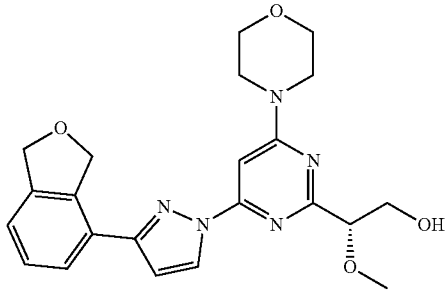 [SMILES: CO[C@@H](CO)c1nc(N2CCOCC2)cc(-n2ccc(-c3cccc4c3COC4)n2)n1] | (R)-2-(4-(3-(1,3-dihydroisobenzofuran-4-yl)-1H-pyrazol-1-yl)-6-morpholinopyrimidin-2-yl)-2-methoxyethan-1-ol | 424 | |
| 272 | 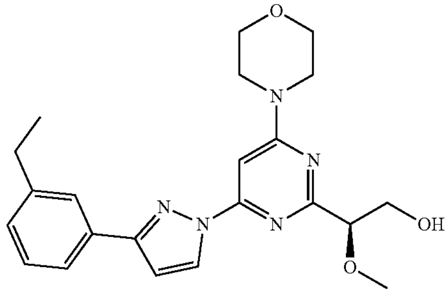 [SMILES: CCc1cccc(-c2ccn(-c3cc(N4CCOCC4)nc([C@@H](CO)OC)n3)n2)c1] | (S)-2-(4-(3-(3-ethylphenyl)-1H-pyrazol-1-yl)-6-morpholinopyrimidin-2-yl)-2-methoxyethan-1-ol | 410 | |
| 273 | 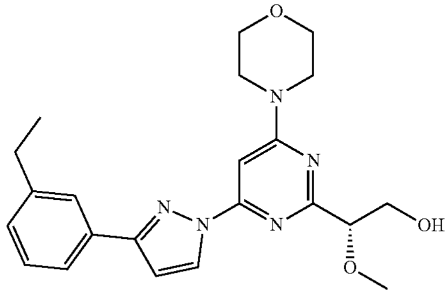 [SMILES: CCc1cccc(-c2ccn(-c3cc(N4CCOCC4)nc([C@H](CO)OC)n3)n2)c1] | (R)-2-(4-(3-(3-ethylphenyl)-1H-pyrazol-1-yl)-6-morpholinopyrimidin-2-yl)-2-methoxyethan-1-ol | 410 | |

-continued

| # | Structure | Name | LCMS (ESI): m/z [M + H]+ | 1H NMR |
| --- | --- | --- | --- | --- |
| 274 | 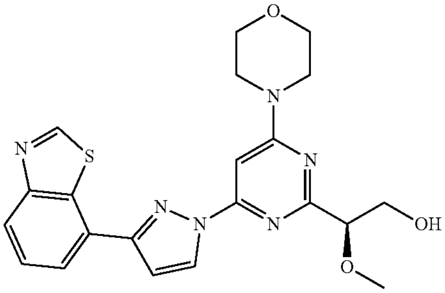 [SMILES: CO[C@H](CO)c1nc(N2CCOCC2)cc(-n2ccc(-c3cccc4ncsc34)n2)n1] | (S)-2-(4-(3-(benzo[d]thiazol-7-yl)-1H-pyrazol-1-yl)-6-morpholinopyrimidin-2-yl)-2-methoxyethan-1-ol | 439 | |
| 275 | 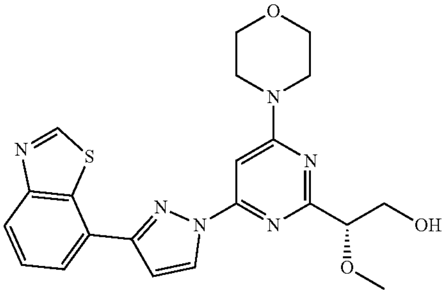 [SMILES: CO[C@@H](CO)c1nc(N2CCOCC2)cc(-n2ccc(-c3cccc4ncsc34)n2)n1] | (R)-2-(4-(3-(benzo[d]thiazol-7-yl)-1H-pyrazol-1-yl)-6-morpholinopyrimidin-2-yl)-2-methoxyethan-1-ol | 439 | |
| 276 | 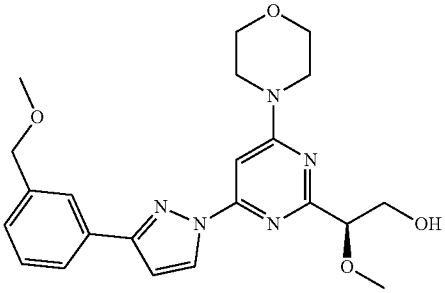 [SMILES: COCc1cccc(-c2ccn(-c3cc(N4CCOCC4)nc([C@@H](CO)OC)n3)n2)c1] | (S)-2-methoxy-2-(4-(3-(3-(methoxymethyl)phenyl)-1H-pyrazol-1-yl)-6-morpholinopyrimidin-2-yl)ethan-1-ol | 426 | |
| 277 | 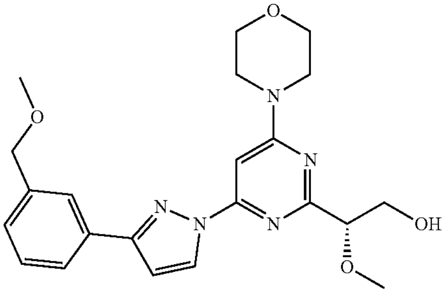 [SMILES: COCc1cccc(-c2ccn(-c3cc(N4CCOCC4)nc([C@H](CO)OC)n3)n2)c1] | (R)-2-methoxy-2-(4-(3-(3-(methoxymethyl)phenyl)-1H-pyrazol-1-yl)-6-morpholinopyrimidin-2-yl)ethan-1-ol | 426 | |
| 278 | 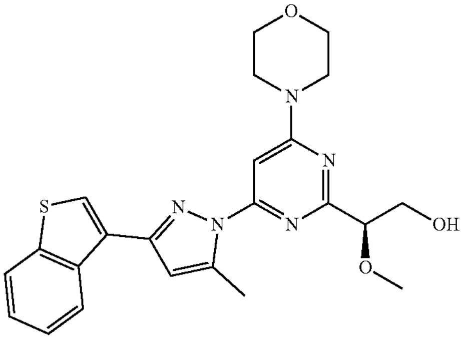 [SMILES: CO[C@H](CO)c1nc(N2CCOCC2)cc(-n2nc(-c3csc4ccccc34)cc2C)n1] | (S)-2-(4-(3-(benzo[b]thiophen-3-yl)-5-methyl-1H-pyrazol-1-yl)-6-morpholinopyrimidin-2-yl)-2-methoxyethan-1-ol | 452 | |

-continued

| # | Structure | Name | LCMS (ESI): m/z [M + H]+ | 1H NMR |
|---|---|---|---|---|
| 279 | 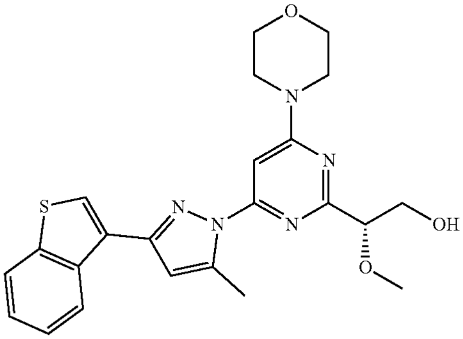 [SMILES: CO[C@@H](CO)c1nc(N2CCOCC2)cc(-n2nc(-c3csc4ccccc34)cc2C)n1] | (R)-2-(4-(3-(benzo[b]thiophen-3-yl)-5-methyl-1H-pyrazol-1-yl)-6-morpholinopyrimidin-2-yl)-2-methoxyethan-1-ol | 452 | |
| 280 | 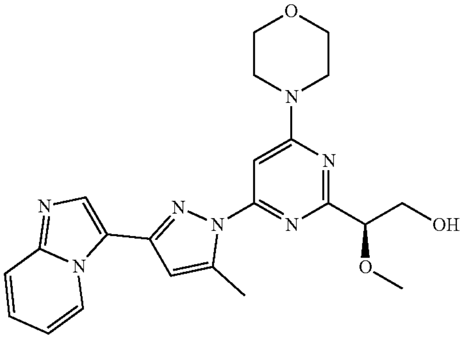 [SMILES: CO[C@H](CO)c1nc(N2CCOCC2)cc(-n2nc(-c3cnc4ccccn34)cc2C)n1] | (S)-2-(4-(3-(imidazo[1,2-a]pyridin-3-yl)-5-methyl-1H-pyrazol-1-yl)-6-morpholinopyrimidin-2-yl)-2-methoxyethan-1-ol | 436 | |
| 281 | 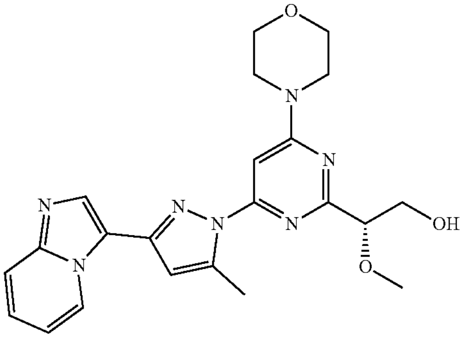 [SMILES: CO[C@@H](CO)c1nc(N2CCOCC2)cc(-n2nc(-c3cnc4ccccn34)cc2C)n1] | (R)-2-(4-(3-(imidazo[1,2-a]pyridin-3-yl)-5-methyl-1H-pyrazol-1-yl)-6-morpholinopyrimidin-2-yl)-2-methoxyethan-1-ol | 436 | |
| 282 | 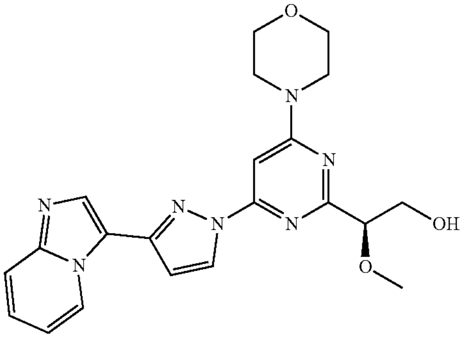 [SMILES: CO[C@H](CO)c1nc(N2CCOCC2)cc(-n2ccc(-c3cnc4ccccn34)n2)n1] | (S)-2-(4-(3-(imidazo[1,2-a]pyridin-3-yl)-1H-pyrazol-1-yl)-6-morpholinopyrimidin-2-yl)-2-methoxyethan-1-ol | 422 | δ 9.38 (d, J = 6.9 Hz, 1H), 8.66 (d, J = 2.7 Hz, 1H), 8.05 (s, 1H), 7.73 (d, J = 9.0 Hz, 1H), 7.33-7.27 (m, 1H), 7.08-6.93 (m, 2H), 6.81 (d, J = 2.7 Hz, 1H), 4.35 (dd, J = 6.1, 4.5 Hz, 1H), 4.01-3.94 (m, 2H), 3.89-3.72 (m, 8H), 3.57 (s, 3H). |

-continued

| # | Structure | Name | LCMS (ESI): m/z [M + H]+ | 1H NMR |
|---|---|---|---|---|
| 283 | 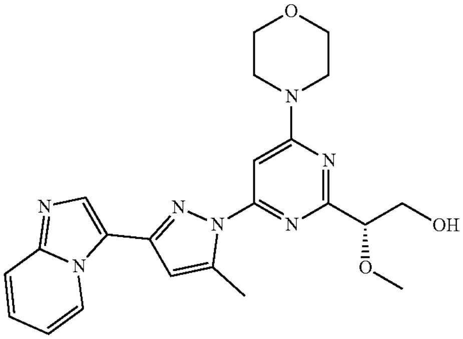 [SMILES: CO[C@@H](CO)c1nc(N2CCOCC2)cc(-n2nc(-c3cnc4ccccn34)cc2C)n1] | (R)-2-(4-(3-(imidazo[1,2-a]pyridin-3-yl)-1H-pyrazol-1-yl)-6-morpholinopyrimidin-2-yl)-2-methoxyethan-1-ol | 422 | δ 9.39 (d, J = 6.9 Hz, 1H), 8.67 (d, J = 2.8 Hz, 1H), 8.06 (s, 1H), 7.78 (d, J = 9.1 Hz, 1H), 7.46-7.27 (m, 1H), 7.13-6.94 (m, 2H), 6.81 (d, J = 2.8 Hz, 1H), 4.35 (dd, J = 6.2, 4.4 Hz, 1H), 4.09-3.85 (m, 2H), 3.86-3.70 (m, 8H), 3.57 (s, 3H). |
| 284 | 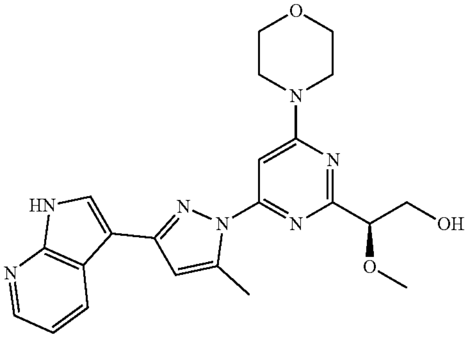 [SMILES: CO[C@H](CO)c1nc(N2CCOCC2)cc(-n2nc(-c3c[nH]c4ncccc34)cc2C)n1] | (S)-2-methoxy-2-(4-(5-methyl-3-(1H-pyrrolo[2,3-b]pyridin-3-yl)-1H-pyrazol-1-yl)-6-morpholinopyrimidin-2-yl)ethan-1-ol | 436 | |
| 285 | 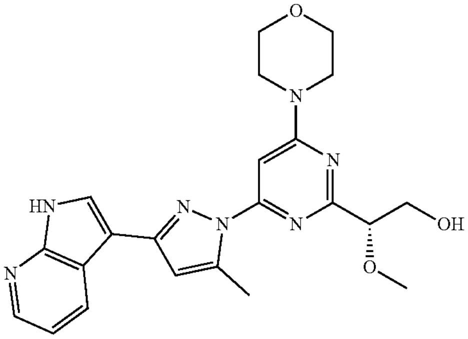 [SMILES: CO[C@@H](CO)c1nc(N2CCOCC2)cc(-n2nc(-c3c[nH]c4ncccc34)cc2C)n1] | (R)-2-methoxy-2-(4-(5-methyl-3-(1H-pyrrolo[2,3-b]pyridin-3-yl)-1H-pyrazol-1-yl)-6-morpholinopyrimidin-2-yl)ethan-1-ol | 436 | |
| 286 | 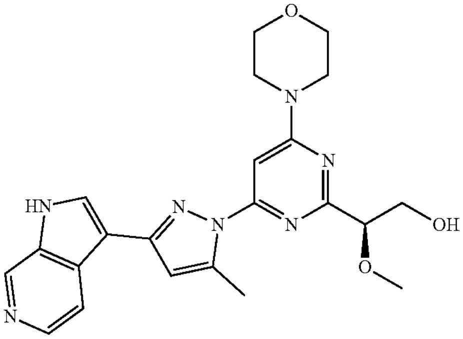 | (S)-2-methoxy-2-(4-(5-methyl-3-(1H-pyrrolo[2,3-c]pyridin-3-yl)-1H-pyrazol-1-yl)-6-morpholinopyrimidin-2-yl)ethan-1-ol | 436 | |

-continued

| # | Structure | Name | LCMS (ESI): m/z [M + H]+ | 1H NMR |
|---|---|---|---|---|
| 287 | 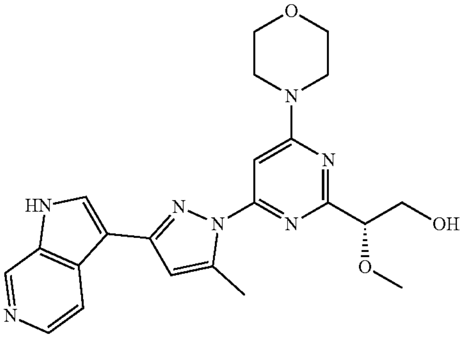 | (R)-2-methoxy-2-(4-(5-methyl-3-(1H-pyrrolo[2,3-c]pyridin-3-yl)-1H-pyrazol-1-yl)-6-morpholinopyrimidin-2-yl)ethan-1-ol | 436 | |
| 288 | 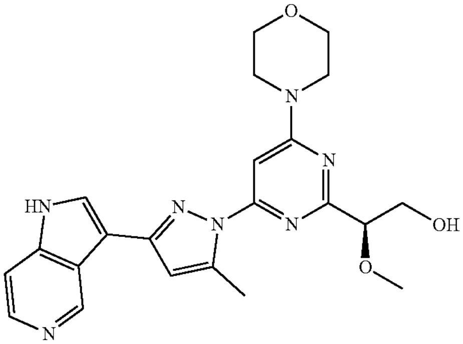 | (S)-2-methoxy-2-(4-(5-methyl-3-(1H-pyrrolo[3,2-c]pyridin-3-yl)-1H-pyrazol-1-yl)-6-morpholinopyrimidin-2-yl)ethan-1-ol | 436 | |
| 289 | 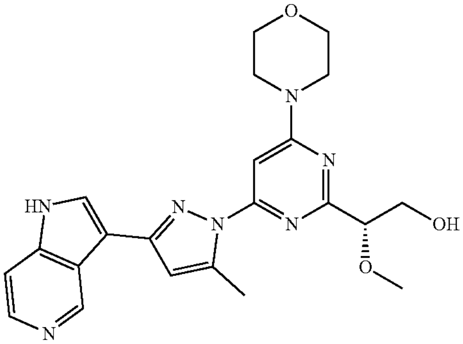 | (R)-2-methoxy-2-(4-(5-methyl-3-(1H-pyrrolo[3,2-c]pyridin-3-yl)-1H-pyrazol-1-yl)-6-morpholinopyrimidin-2-yl)ethan-1-ol | 436 | |
| 290 | 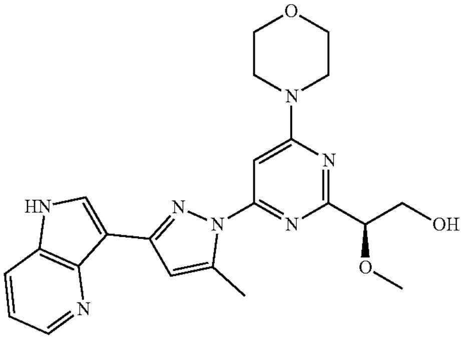 | (S)-2-methoxy-2-(4-(5-methyl-3-(1H-pyrrolo[3,2-b]pyridin-3-yl)-1H-pyrazol-1-yl)-6-morpholinopyrimidin-2-yl)ethan-1-ol | 436 | |

-continued
| # | Structure | Name | LCMS (ESI): m/z [M + H]$^+$ | 1H NMR |
|---|---|---|---|---|
| 291 | 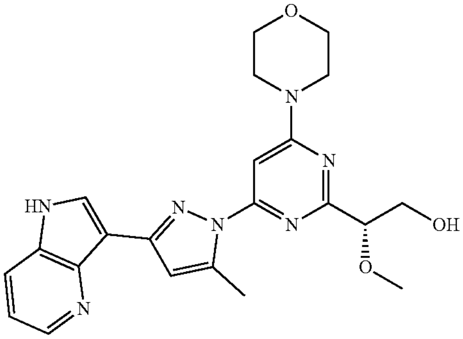 | (R)-2-methoxy-2-(4-(5-methyl-3-(1H-pyrrolo[3,2-b]pyridin-3-yl)-1H-pyrazol-1-yl)-6-morpholinopyrimidin-2-yl)ethan-1-ol | 436 | |
| 292 | 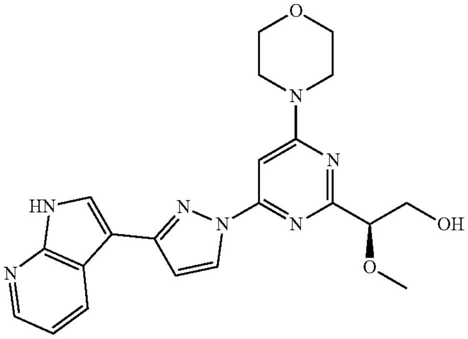 | (S)-2-(4-(3-(1H-pyrrolo[2,3-b]pyridin-3-yl)-1H-pyrazol-1-yl)-6-morpholinopyrimidin-2-yl)-2-methoxyethan-1-ol | 422 | |
| 293 | 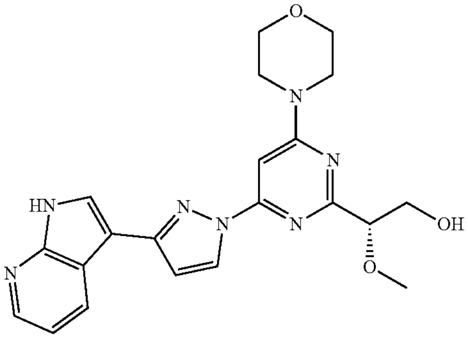 | (R)-2-(4-(3-(1H-pyrrolo[2,3-b]pyridin-3-yl)-1H-pyrazol-1-yl)-6-morpholinopyrimidin-2-yl)-2-methoxyethan-1-ol | 422 | |
| 294 | 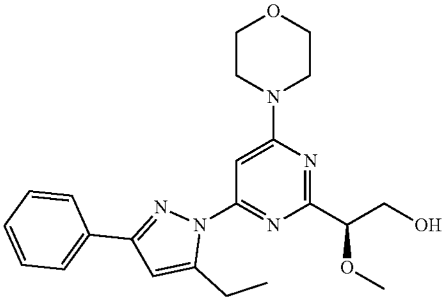 | (S)-2-(4-(5-ethyl-3-phenyl-1H-pyrazol-1-yl)-6-morpholinopyrimidin-2-yl)-2-methoxyethan-1-ol | 410 | |

-continued

| # | Structure | Name | LCMS (ESI): m/z $[M + H]^+$ | 1H NMR |
| --- | --- | --- | --- | --- |
| 295 | 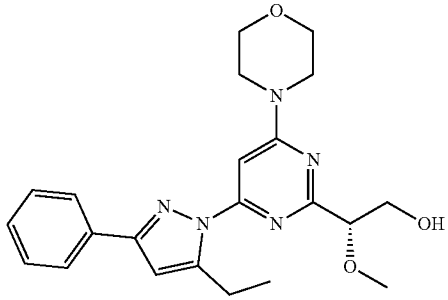 | (R)-2-(4-(5-ethyl-3-phenyl-1H-pyrazol-1-yl)-6-morpholinopyrimidin-2-yl)-2-methoxyethan-1-ol | 410 | |

Synthesis of 4-(6-(3-(3,3-dimethylcyclohexa-1,5-dien-1-yl)-1H-pyrazol-1-yl)-2-(2-(1-methyl-1H-pyrazol-4-yl)ethoxy)pyrimidin-4-yl)morpholine (Compound 296)

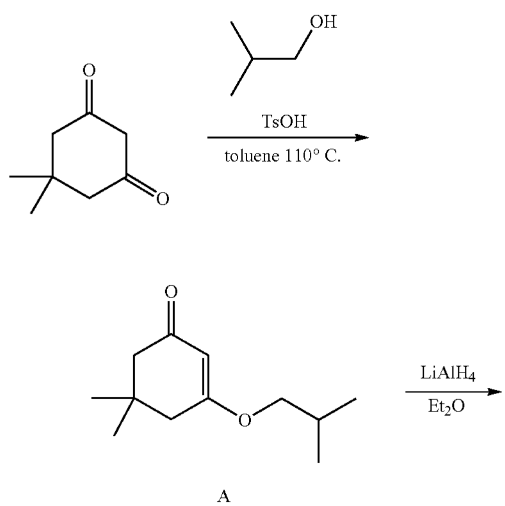

A

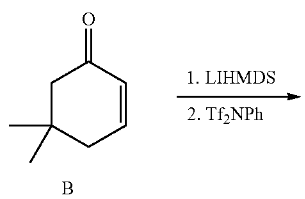

B

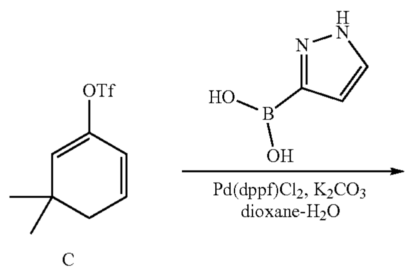

C

-continued

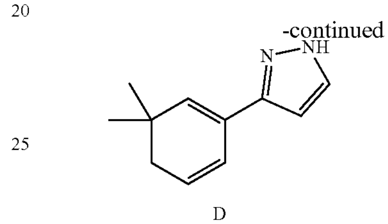

Intermediate 30

$Cs_2CO_3$, NMP, 150° C.

D

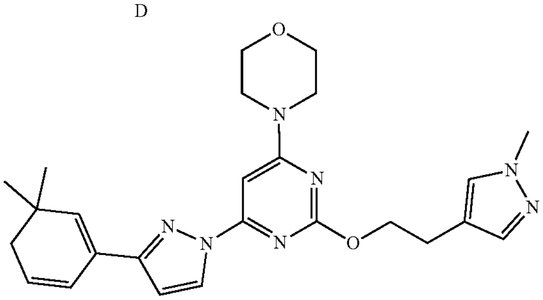

296

Preparation of A

The mixture of 5,5-dimethylcyclohexane-1,3-dione (6.0 g, 42.6 mmol), 2-methylpropan-1-ol (4.1 g, 55.7 mmol), TsOH (1.47 g, 8.5 mmol) and molecular sieve (3 g) in toluene (100 mL) was stirred at 120° C. for 16 hrs under $N_2$ atmosphere. The reaction mixture was filtered and water (100 mL) was added and then extracted with EtOAc (50 mL×2). The combined organic layers were washed with brine (30 mL×3), dried over $Na_2SO_4$, filtered and concentrated to dryness. The crude product was purified by chromatography on silica gel eluting with petroleum ether: EtOAc=20:1-10:1 to get A (6.8 g, 81%) as yellow oil.

Preparation of B

To a solution of $LiAlH_4$ (2 M, 2 mL) in $Et_2O$ (20 mL) was added a solution of A (2.0 g, 10.2 mmol) in $Et_2O$ (2 mL) at 0° C. The mixture was stirred at room temperature for 1 h. then HCl (2 N, 30 mL) was added and then extracted with ether (20 mL×2). The combined organic layers were washed with brine (10 mL×3), dried over $Na_2SO_4$, filtered and concentrated to get crude B (980 mg, 77%) as yellow oil.

Preparation of C

To a solution of B (775 mg, 6.3 mmol) in THF (10 mL) was added LiHMDS (11.3 mL) at −70° C. The mixture was stirred for 0.5 h at this temperature, a solution of $Tf_2NPh$ (2.9 g, 8.19 mmol) in THF (8 mL) was added to above solution. and the resulting solution was allowed to stirred at 0° C. for 2 hrs. Ice-water (10 mL) was added and the resulting mixture was extracted with EtOAc (10 mL×2). The combined organic layers were washed with brine (10 mL×3), dried over $Na_2SO_4$, filtered and concentrated to dryness. The crude product was purified by chromatography on silica gel eluting with petroleum ether:EtOAc=1:0 to get C (1.0 g, 63%) as yellow oil.

Preparation of D

The mixture of C (1.0 g, 3.9 mmol), (1H-pyrazol-3-yl) boronic acid (660 mg, 5.9 mmol), Pd(dppf)$Cl_2$ (850 mg, 1.2 mmol) and $K_2CO_3$ (1.1 g, 7.8 mmol) in dioxane/$H_2O$ (15 mL/3 mL) was stirred at 105° C. for 1 h under microwave in $N_2$. After which period, water (15 mL) was added to above reaction system and the resulting mixture was extracted with EtOAc (10 mL×2). The combined organic layers were washed with brine (10 mL×3), dried over $Na_2SO_4$, filtered and concentrated to dryness. The crude product was purified by chromatography on silica gel eluting with petroleum ether:EtOAc=10:1 to get D (180 mg, 27%) as yellow oil.

Preparation of Compound 296

The mixture of D (150 mg, 0.86 mmol), Intermediate 30 (278 mg, 0.86 mmol) and $Cs_2CO_3$ (560 mg, 1.72 mmol) in NMP (3 mL) was stirred at 150° C. for 3 hrs. After cooling to room temperature, water (10 mL) was added to above solution, and the resulting mixture was extracted with EtOAc (10 mL×2). The combined organic layers were washed with brine (10 mL×3), dried over $Na_2SO_4$, filtered and concentrated to dryness. The crude product was purified by Prep-HPLC to get Compound 296 (50 mg, 16%) as colorless oil.

$^1$H NMR (400 MHz, $CDCl_3$): δ 8.44 (d, J=2.7 Hz, 1H), 7.40 (s, 1H), 7.29 (s, 1H), 6.80 (s, 1H), 6.68-6.60 (m, 1H), 6.53 (d, J=2.7 Hz, 1H), 6.10 (s, 1H), 6.00-5.89 (m, 1H), 4.45 (t, J=7.2 Hz, 2H), 3.87 (s, 3H), 3.82-3.65 (m, 8H), 2.98 (t, J=7.2 Hz, 2H), 2.25-2.14 (m, 2H), 1.11 (s, 6H).

Synthesis of 4-(2-(((1-methyl-1H-imidazol-4-yl) methoxy)methyl)-6-(3-(m-tolyl)-1H-pyrazol-1-yl) pyrimidin-4-yl)morpholine (Compound 297)

154

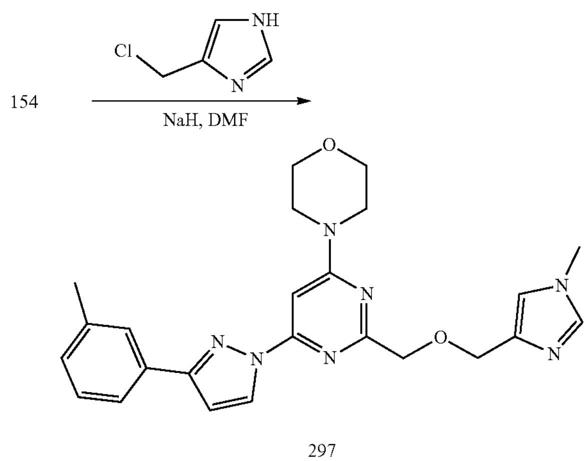

297

To a solution of Compound 154 (120 mg, 0.57 mmol) in DMF (3 mL) was added NaH (109 mg, 4.5 mmol) and stirred at 0° C. for 0.5 h. then 4-(chloromethyl)-1H-imidazole (115 mg, 1.14 mmol) was added to above system. The reaction mixture was stirred at room temperature for 2 hrs before the addition of water (10 mL), which was then extracted with EtOAc (10 mL×2). The combined organic layers were washed with brine (10 mL×3), dried over $Na_2SO_4$, filtered, concentrated to dryness. The residue was purified by Prep-HPLC to give Compound 297 (80 mg, 53%) as off-white oil.

$^1$H NMR (400 MHz, $CDCl_3$) δ 8.64 (d, J=2.7 Hz, 1H), 7.75 (s, 1H), 7.69 (d, J=7.7 Hz, 1H), 7.44 (s, 1H), 7.33 (t, J=7.6 Hz, 1H), 7.18 (d, J=7.5 Hz, 1H), 7.08 (s, 1H), 6.95 (s, 1H), 6.74 (d, J=2.7 Hz, 1H), 4.75 (s, 2H), 4.64 (s, 2H), 3.82-3.76 (m, 8H), 3.68 (s, 3H), 2.43 (s, 3H).

The following compounds were prepared using procedures similar to the one described for Compound 297:

| # | Structure | Name | LCMS (ESI): m/z [M + H]$^+$ |
|---|---|---|---|
| 298 | 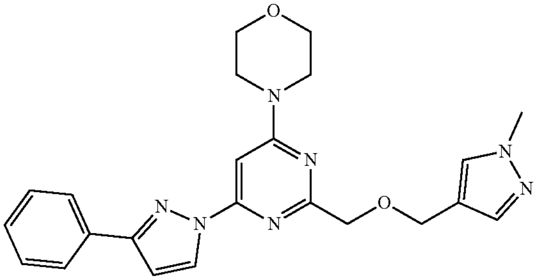 | 4-(2-(((1-methyl-1H-pyrazol-4-yl)methoxy)methyl)-6-(3-phenyl-1H-pyrazol-1-yl)pyrimidin-4-yl)morpholine | 432 |

-continued

| # | Structure | Name | LCMS (ESI): m/z [M + H]$^+$ |
|---|---|---|---|
| 299 | 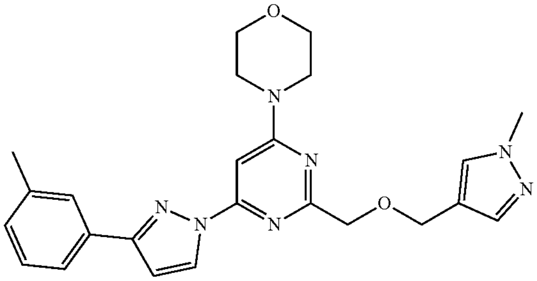 | 4-(2-(((1-methyl-1H-pyrazol-4-yl)methoxy)methyl)-6-(3-(m-tolyl)-1H-pyrazol-1-yl)pyrimidin-4-yl)morpholine | 446 |
| 300 | 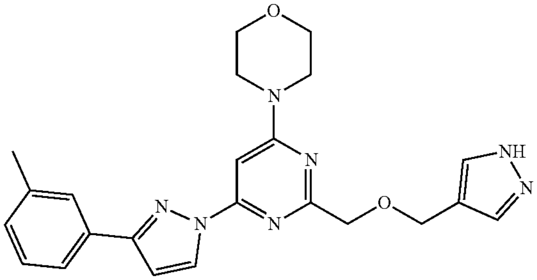 | 4-(2-(((1H-pyrazol-4-yl)methoxy)methyl)-6-(3-(m-tolyl)-1H-pyrazol-1-yl)pyrimidin-4-yl)morpholine | 432 |
| 301 | 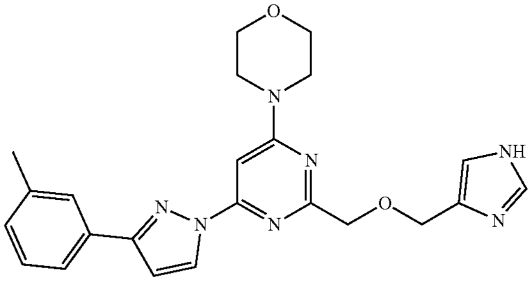 | 4-(2-(((1H-imidazol-4-yl)methoxy)methyl)-6-(3-(m-tolyl)-1H-pyrazol-1-yl)pyrimidin-4-yl)morpholine | 432 |

Synthesis of 4-(2-(2-(1-methyl-1H-pyrazol-4-yl)ethoxy)-6-(3-((2-methylpyridin-4-yl)ox)-1H-pyrazol-1-yl)pyrimidin-4-yl)morpholine (Compound 302)

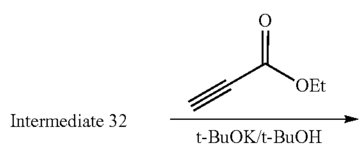

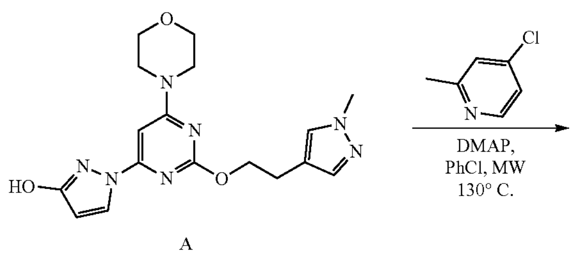

A

-continued

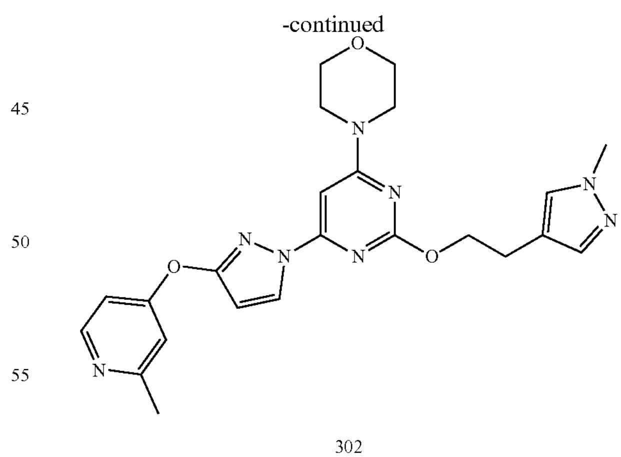

302

Preparation of A

To a mixture of Intermediate 32 (0.36 g, 1.13 mmol) in t-BuOH (8.0 mL) was added ethyl propiolate (0.15 mL, 1.48 mmol) dropwise at 30° C. under $N_2$ atmosphere. Then t-BuOK (266 mg, 2.37 mmol) was added into the mixture at 0° C. The reaction mixture was stirred at rt for 2 days. After the reaction was completed, the mixture was concentrated and diluted with ethyl acetate/water. The pH was adjusted to 2-3 by 1M HCl. The organic phase was separated, and water phase was extracted with DCM three times. The combined organic layers were washed with brine, dried over $Na_2SO_4$, filtered and concentrated under reduced pressure to give the crude A (200 mg) as brown oil.

Preparation of Compound 302

A mixture of A (123 mg, 0.33 mmol), 4-chloro-2-methylpyridine (120 mg, 0.94 mmol) and DMAP (111 mg, 0.91 mmol) in dry PhCl (3.0 mL) was heated at 130° C. under microwave for 12 hrs. The mixture was diluted with ethyl acetate and washed with water and brine, dried over $Na_2SO_4$, filtered and concentrated under reduced pressure. The residue was purified by Prep-HPLC to get Compound 302 (32 mg, 10%) as a brown oil.

$^1$H NMR (400 MHz, $CDCl_3$): δ 8.50 (d, J=2.8 Hz, 1H), 8.42 (dd, J=4.4, 2.2 Hz, 1H), 7.41 (s, 1H), 7.29 (s, 1H), 6.93-6.89 (m, 2H), 6.64 (s, 1H), 6.12 (d, J=2.8 Hz, 1H), 4.46 (t, J=7.2 Hz, 2H), 3.88 (s, 3H), 3.81-3.73 (m, 4H), 3.72-3.65 (m, 4H), 2.99 (t, J=7.2 Hz, 2H), 2.55 (s, 3H).

Synthesis of 4-(2-(2-(1-methyl-1H-pyrazol-4-yl)ethoxy)-6-(3-(pyridin-4-yloxy)-1H-pyrazol-1-yl)pyrimidin-4-yl)morpholine (Compound 303)

303

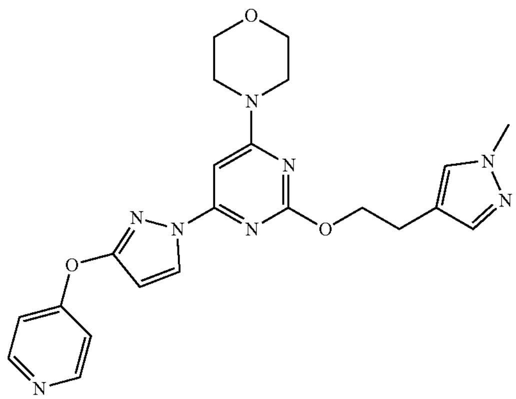

Compound 303 was synthesized by a similar procedure as Compound 302.

LCMS (ESI): m/z=449 [M+H]$^+$

Synthesis of (E)-4-(2-(2-(1-methyl-1H-pyrazol-4-yl)vinyl)-6-(3-(m-tolyl)-1H-pyrazol-1-yl)pyrimidin-4-yl)morpholine (Compound 304)

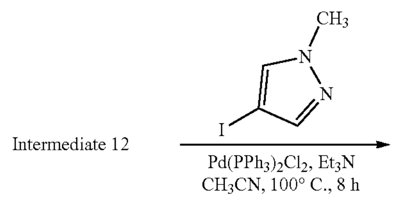

-continued

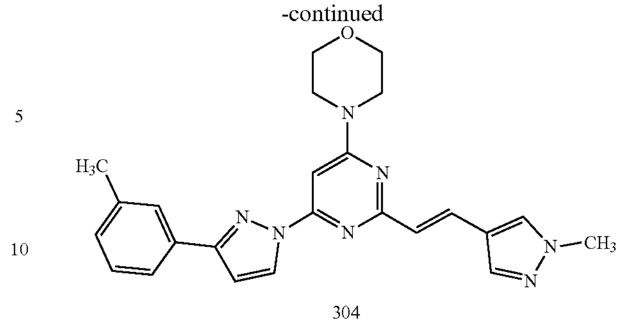

304

Compound 304 was prepared as follows: 190 mg Intermediate 12 (1 eq.), 4-iodo-1-methyl-1H-pyrazole (1.5 eq.), $Pd(PPh_3)_2Cl_2$ (0.1 eq.), triethylamine (4 eq.) in acetonitrile (10 ml), heated at 100° C. for 6 h, purified by silica gel chromatography. Yield 25%. $^1$H NMR and LC/MS consistent with the structure of Compound 304.

LCMS (ESI): m/z=428[M+H]$^+$

Synthesis of (S)-2-methoxy-2-(4-((S)-2-methylmorpholino)-6-(3-(m-tolyl)-1H-pyrazol-1-yl)pyrimidin-2-yl)ethan-1-ol (Compound 305) and (R)-2-methoxy-2-(4-((S)-2-methylmorpholino)-6-(3-(m-tolyl)-1H-pyrazol-1-yl)pyrimidin-2-yl)ethan-1-ol (Compound 306)

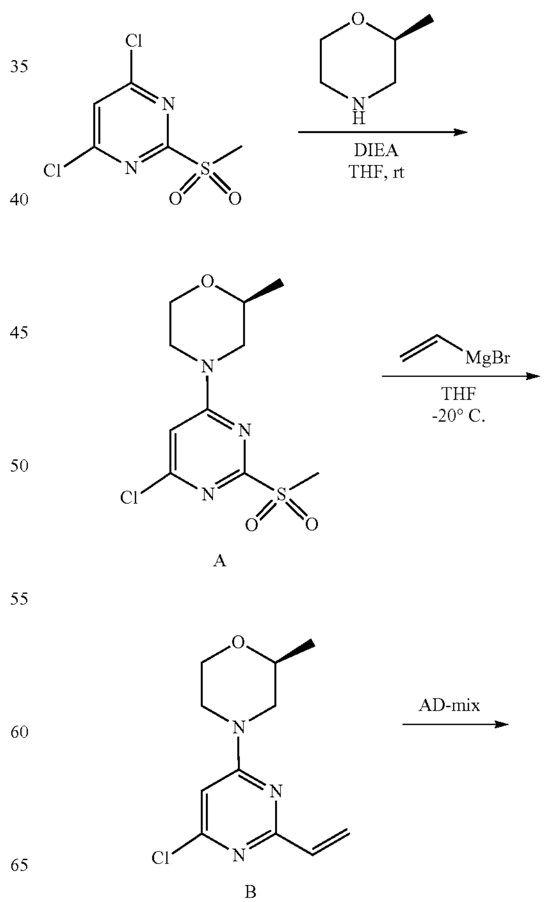

-continued

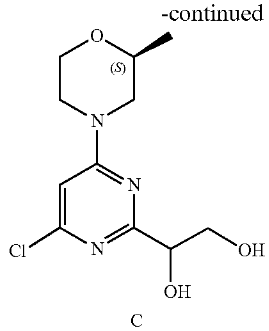

C

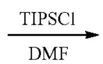

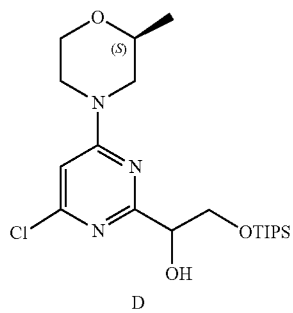

D

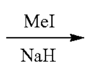

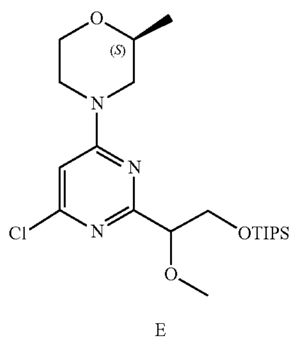

E

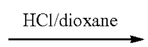

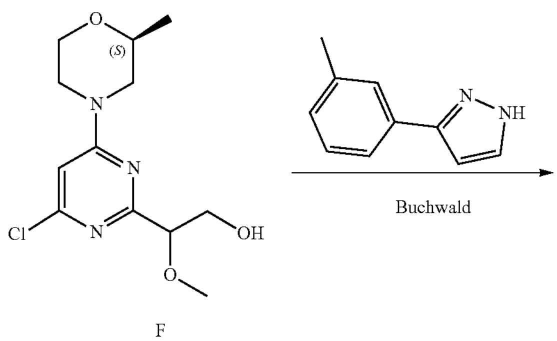

F

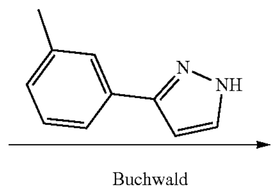

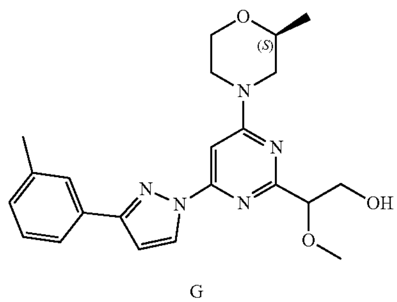

G

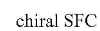

-continued

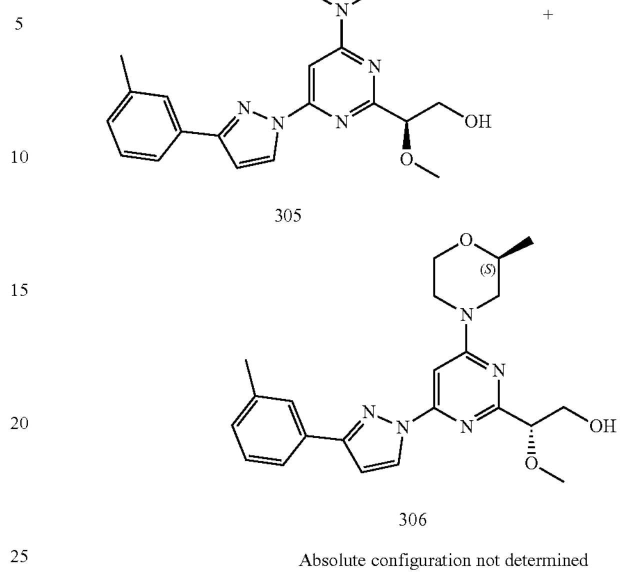

305

+

306

Absolute configuration not determined

Preparation of A

To a solution of 4,6-dichloro-2-(methylsulfonyl)pyrimidine (2.13 g, 9.4 mmol) in THF (20 mL) was added (S)-2-methylmorpholine (950 mg, 9.4 mmol) and DIEA (1.8 g, 14.1 mmol) at 0° C. The mixture was stirred at room temperature overnight, then poured into water (60 mL) and extracted with EtOAc (20 mL×2). The combined organic layers were washed with brine (200 mL), dried over $Na_2SO_4$, filtered, concentrated to dryness. The resulting crude product was purified by chromatography on silica gel eluting with petroleum ether:EtOAc=2:1 to 1:1 to get the desired product A (2.1 g, 77%) as yellow oil.

Preparation of B

To a solution of A (2.2 g, 75 mmol) in THF (20 mL) was added vinyl magnesium bromide (18.9 mL, 18.9 mmol, 1M in THF) slowly at −10° C. The resulting system was stirred for 1 h at 0° C., and then quenched with sat. $NH_4Cl$ solution (20 mL). The mixture was extracted with EtOAc (20 mL×2). The combined organic layers were washed with brine (50 mL), dried over $Na_2SO_4$, filtered and concentrated to dryness. The resulting crude product was purified by chromatography on silica gel eluting with petroleum ether: EtOAc=5:1 to get the desired product B (1.5 g, 83%) as yellow oil.

Preparation of C

To a solution of compound B (200 mg, 0.84 mmol) in acetone:$H_2O$=1:1 (16 mL) was added AD-mix-α/AD-mix-β (1 g) at room temperature. The mixture was stirred for 4 hrs. Then quenched with sat. $Na_2SO_3$ solution (20 mL). The mixture was extracted with EtOAc (20 mL×3). The combined organic layers were washed with brine (20 mL), dried over $Na_2SO_4$, filtered and concentrated to get the desired product C (280 mg, crude) as a white solid, which was used for next step directly.

Preparation of D

To a solution of C (220 mg, 0.8 mmol) in DMF (5 mL) was added imidazole (81.6 mg, 1.2 mmol) and TIPSCl (156 mg, 0.8 mmol). The mixture was stirred at rt overnight, then poured into water (15 mL) and extracted with EtOAc (20 mL×2). The combined organic layers were washed with brine (10 mL×3), dried over $Na_2SO_4$, filtered, concentrated to dryness. The resulting crude product was purified by chromatography on silica gel eluting with petroleum ether: EtOAc=10:1 to 5:1 to get the desired product D (230 mg, 53%) as colorless oil.

Preparation of E

To a solution of D (230 mg, 0.53 mmol) in DMF (5 mL) was added NaH (43 mg, 1.07 mmol) at −10° C. and stirred for 10 min, Then MeI (75 mg, 0.53 mmol) was added and the mixture was stirred at −10° C. for 30 min. Water (15 mL) was added and the resulting mixture was extracted with EtOAc (10 mL×2). The combined organic layers were washed with brine (10 mL×3), dried over $Na_2SO_4$, filtered and concentrated to dryness. The crude product was purified by chromatography on silica gel eluting with petroleum ether:EtOAc=5:1 to get the desired product E (207 mg, 87%) as light yellow oil.

Preparation of F

To a solution of compound E (207 mg, 0.47 mmol) in MeOH (5 mL) was added HCl/dioxane (5 mL, 4 M). The mixture was stirred at rt for 3 hours and then concentrated to dryness. The crude product was re-dissolved in MeOH (10 mL) and basified to pH=9-10 using basic resin and then filtered. The filtrate was concentrated to get the desired product F (120 mg, 90%) as light yellow oil, which was used for next step directly.

Preparation of G

The mixture of compound F (120 mg, 0.42 mmol), 3-(m-tolyl)-1H-pyrazole (67 mg, 0.42 mmol), $Pd_2(dba)_3$ (76 mg, 0.08 mmol), Xant-phose (48 mg, 0.08 mmol) and $Cs_2CO_3$ (266 mg, 0.8 mmol) in NMP (5 mL) was stirred at 100° C. under microwave and nitrogen atmosphere for 1.2 hour. The mixture was diluted with EtOAc (20 mL) and washed by brine (10 mL×4), dried over $Na_2SO_4$, filtered and concentrated to dryness. The resulting crude product was purified by chromatography on silica gel eluting with petroleum ether:EtOAc=2:1-1:1 to get the desired product G (73 mg, 51%).

Preparation Compound 305 and Compound 306

G was separated by chiral HPLC (SFC) to get to Compound 305 (30 mg, $1^{st}$ Peak) and Compound 306 (30 mg, $2^{nd}$ Peak). The stereochemistry of the enantiomers was not determined.

Compound 305 ($1^{st}$ Peak)

$^1$H NMR (400 MHz, $CDCl_3$): δ 8.60 (d, J=2.8 Hz, 1H), 7.75 (s, 1H), 7.70 (d, J=7.6 Hz, 1H), 7.34 (t, J=7.6 Hz, 1H), 7.19 (d, J=7.6 Hz, 1H), 7.12 (s, 1H), 6.76 (d, J=2.8 Hz, 1H), 4.37-4.34 (m, 3H), 4.05-3.96 (m, 3H), 3.69-3.65 (m, 3H), 3.55 (s, 3H), 2.77 (t, J=7.6 Hz, 1H), 2.70 (t, J=7.6 Hz, 1H), 2.44 (s, 3H), 1.29 (d, J=6.4 Hz, 3H).

Compound 306 $2^{nd}$ Peak)

$^1$H NMR (400 MHz, $CDCl_3$): δ 8.60 (d, J=2.8 Hz, 1H), 7.75 (s, 1H), 7.70 (d, J=7.6 Hz, 1H), 7.34 (t, J=7.6 Hz, 1H), 7.19 (d, J=7.6 Hz, 1H), 7.12 (s, 1H), 6.76 (d, J=2.8 Hz, 1H), 4.37-4.34 (m, 3H), 4.05-3.96 (m, 3H), 3.69-3.65 (m, 3H), 3.55 (s, 3H), 2.77 (t, J=7.6 Hz, 1H), 2.70 (t, J=7.6 Hz, 1H), 2.44 (s, 3H), 1.29 (d, J=6.4 Hz, 3H).

Synthesis of (S)-2-methoxy-2-(4-((R)-2-methylmorpholino)-6-(3-(m-tolyl)-1H-pyrazol-1-yl)pyrimidin-2-yl)ethan-1-ol (Compound 307) and (R)-2-methoxy-2-(4-((R)-2-methylmorpholino)-6-(3-(m-tolyl)-1H-pyrazol-1-yl)pyrimidin-2-yl)ethan-1-ol (Compound 308)

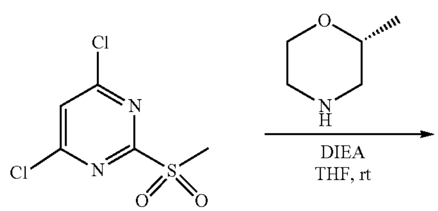

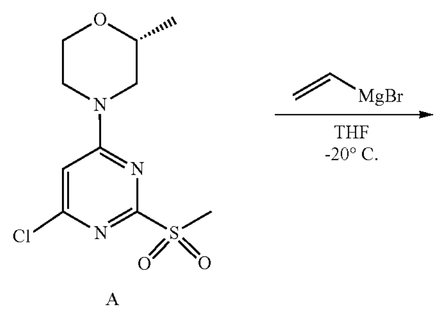

A

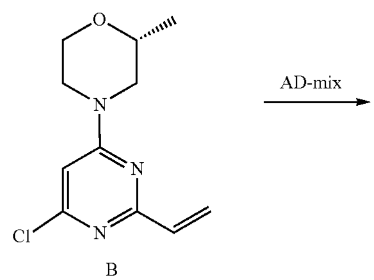

B

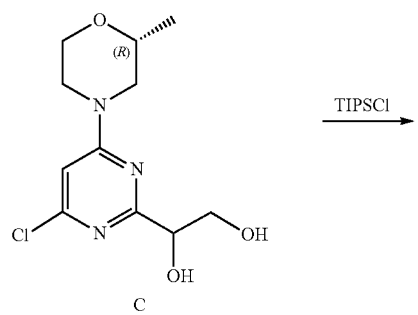

C

-continued

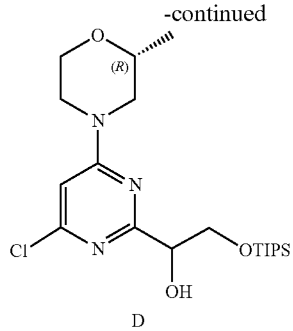

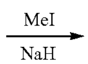

D

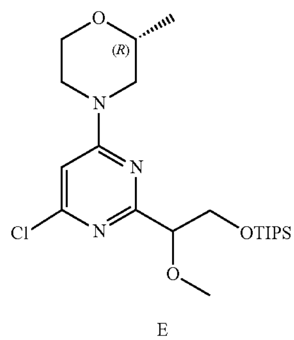

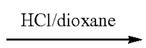

E

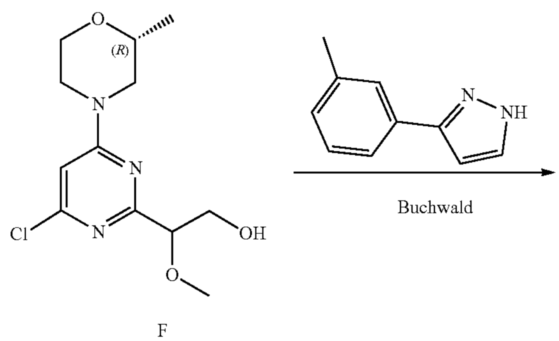

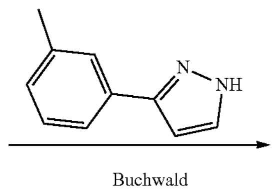

F

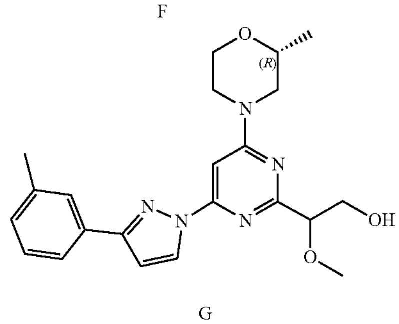

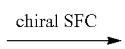

G

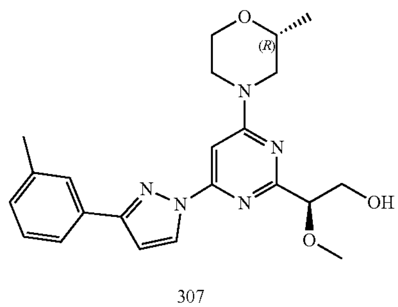

307

-continued

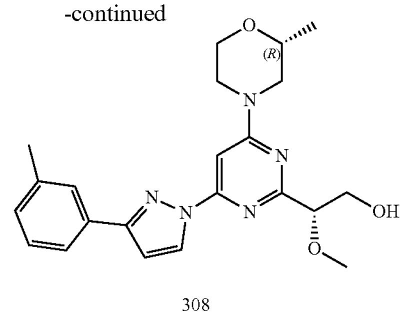

308

Absolute configuration not determined

Using a similar procedure as for compounds Compound 305 and 306, Compound 307 and Compound 308 were synthesized (scheme above).

Compound 307 (1st Peak)

$^1$H NMR (400 MHz, $CDCl_3$): δ 8.60 (d, J=4.0 Hz, 1H), 7.75 (s, 1H), 7.70 (d, J=8.0 Hz, 1H), 7.34 (t, J=8.0 Hz, 1H), 7.20 (d, J=8.0 Hz, 1H), 7.12 (s, 1H), 6.77 (d, J=4.0 Hz, 1H), 4.36-4.34 (m, 3H), 3.99-3.96 (m, 3H), 3.71-3.63 (m, 2H), 3.55 (s, 3H), 3.17-3.10 (m, 1H), 2.85-2.72 (m, 1H), 2.44 (s, 3H), 1.30 (d, J=12 Hz, 3H).

Compound 308 (2nd Peak)

$^1$H NMR (400 MHz, $CDCl_3$): δ 8.60 (d, J=4.0 Hz, 1H), 7.75 (s, 1H), 7.70 (d, J=8.0 Hz, 1H), 7.34 (t, J=8.0 Hz, 1H), 7.20 (d, J=8.0 Hz, 1H), 7.12 (s, 1H), 6.77 (d, J=4.0 Hz, 1H), 4.36-4.34 (m, 3H), 3.99-3.96 (m, 3H), 3.71-3.63 (m, 2H), 3.55 (s, 3H), 3.17-3.10 (m, 1H), 2.85-2.72 (m, 1H), 2.44 (s, 3H), 1.30 (d, J=12 Hz, 3H)

Synthesis of (S)-2-(difluoromethoxy)-2-(4-morpholino-6-(3-(m-tolyl)-1H-pyrazol-1-yl)pyrimidin-2-yl)ethan-1-ol (Compound 309) and (R)-2-(difluoromethoxy)-2-(4-morpholino-6-(3-(m-tolyl)-1H-pyrazol-1-yl)pyrimidin-2-yl)ethan-1-ol (Compound 310)

Intermediate 33

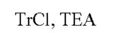

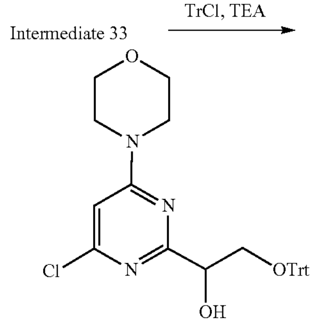

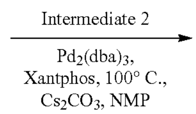

A

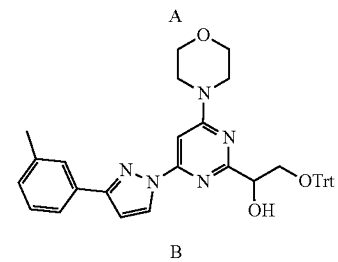

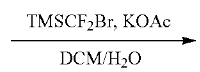

B

-continued

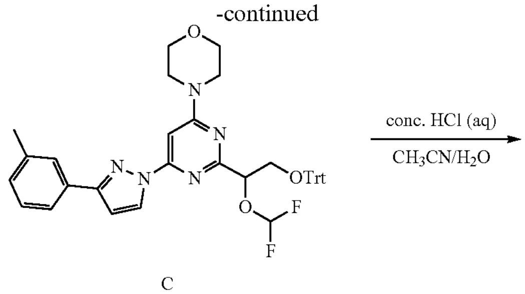

C

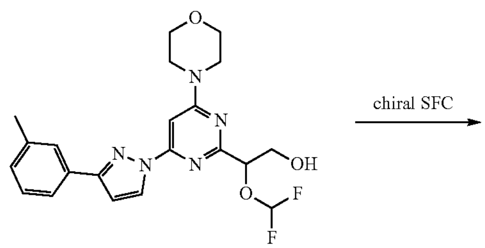

D

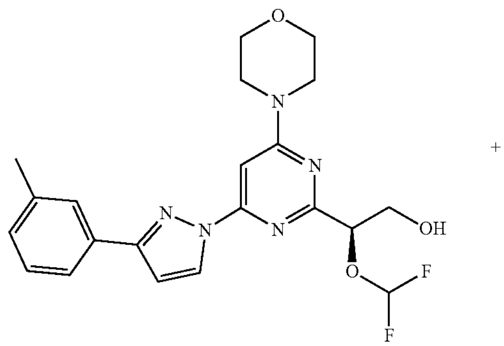

+

309

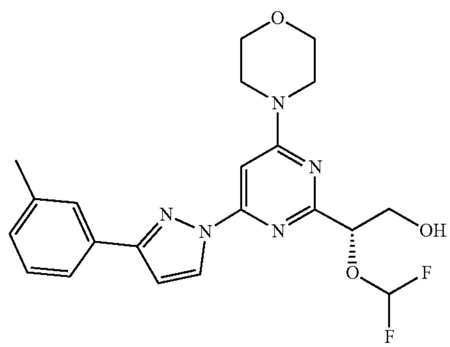

310

Absolute configuration not determined

Preparation of A

To a solution Intermediate 33 (610 mg, 2.36 mmol) in DCM (25 mL) was added TEA (0.61 mL, 4.70 mmol) and TrCl (985 mg, 3.53 mmol) at 0° C. The reaction mixture was warmed to room temperature and stirred overnight. The reaction was quenched by addition of MeOH, and the mixture was concentrated. The resulting crude product was purified by chromatography on silica gel eluting with petroleum ether:EtOAc=5:1-3:1 to get A (970 mg, 82%) as a white solid.

Preparation of B

A mixture of A (780 mg, 1.55 mmol), Intermediate 2 (245 mg, 1.55 mmol), $Pd_2(dba)_3$ (283 mg, 0.31 mmol), Xantphos (179 mg, 0.31 mmol) and $Cs_2CO_3$ (1.01 g, 3.10 mmol) in NMP (15 mL) was placed in a microwave reactor at 100° C. under nitrogen atmosphere for 1 hour. The mixture was diluted with EtOAc (80 mL) and washed by brine (30 mL×4), dried over $Na_2SO_4$, filtered and concentrated to dryness. The resulting crude product was purified by chromatography on silica gel eluting with petroleum ether:EtOAc=7:1-6:1 to get B (970 mg, >99%) as yellow foam.

Preparation of C

To a solution of B (960 mg, 1.54 mmol) in DCM (3.0 mL)/$H_2O$ (3.0 mL) was added KOAc (1.21 g, 12.30 mmol) and $TMSCF_2Br$ (0.96 mL, 6.16 mmol) under nitrogen atmosphere in a plastic bottle. The reaction mixture was stirred overnight at room temperature. The mixture was diluted with DCM and washed by brine, dried over $Na_2SO_4$, filtered and concentrated to dryness. The resulting crude product was purified by chromatography on silica gel eluting with petroleum ether:EtOAc=10:1-8:1 to get C (201 mg, 19%) as yellow oil.

Preparation of D

To a solution of C (194 mg, 0.29 mmol) in $CH_3CN$ (11.8 mL)/$H_2O$ (1.1 mL) was added conc. HCl (aq) (0.7 mL) dropwise. The reaction mixture was stirred at room temperature for 2.5 h. The reaction was quenched by saturated $NaHCO_3$ (aq) carefully. The mixture was diluted with EtOAc and washed by brine, dried over $Na_2SO_4$, filtered and concentrated to dryness. The resulting crude product was purified by chromatography on silica gel eluting with petroleum ether:EtOAc=3:1-2.5:1 to get D (100 mg, 81%) as a yellow solid.

Preparation of Compound 309 and Compound 310

D was separated by chiral HPLC (SFC) to get to Compound 309 (40 mg, $1^{st}$ peak) and Compound 310 (40 mg, $2^{nd}$ Peak). The stereochemistry of the enantiomers was not determined.

Compound 309 $1^{st}$ Peak)

$^1H$ NMR (400 MHz, $CDCl_3$): δ 8.54 (d, J=2.7 Hz, 1H), 7.74 (s, 1H), 7.69 (d, J=7.7 Hz, 1H), 7.34 (t, J=7.6 Hz, 1H), 7.20 (d, J=7.6 Hz, 1H), 7.14 (s, 1H), 6.77 (d, J=2.7 Hz, 1H), 6.55 (dd, J=77.7, 73.0 Hz, 1H), 5.08 (t, J=5.2 Hz, 1H), 4.14-4.05 (m, 2H), 3.89-3.72 (m, 8H), 2.43 (s, 3H).

Compound 310 ($2^{nd}$ Peak)

$^1H$ NMR (400 MHz, $CDCl_3$): δ 8.54 (d, J=2.7 Hz, 1H), 7.74 (s, 1H), 7.69 (d, J=7.7 Hz, 1H), 7.34 (t, J=7.6 Hz, 1H), 7.20 (d, J=7.6 Hz, 1H), 7.14 (s, 1H), 6.77 (d, J=2.7 Hz, 1H), 6.55 (dd, J=77.7, 73.0 Hz, 1H), 5.08 (t, J=5.2 Hz, 1H), 4.14-4.05 (m, 2H), 3.89-3.72 (m, 8H), 2.43 (s, 3H).

Synthesis of (S)-2-ethoxy-2-(4-morpholino-6-(3-(m-tolyl)-1H-pyrazol-1-yl)pyrimidin-2-yl)ethan-1-ol (Compound 311) and (R)-2-ethoxy-2-(4-morpholino-6-(3-(m-tolyl)-1H-pyrazol-1-yl)pyrimidin-2-yl)ethan-1-ol (Compound 312)

Intermediate 33

Imidazole, TIPSCl

DMF

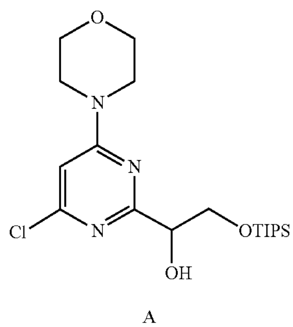

A

EtI, NaH

DMF

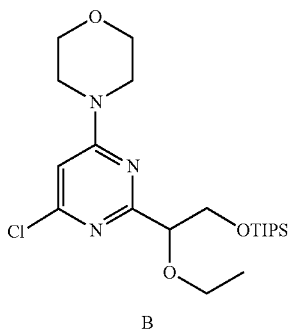

B

HCl/dioxane

MeOH

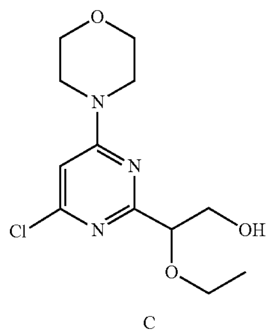

C

Intermediate 2

$Pd_2(dba)_3$, Xantphos, $Cs_2CO_3$, NMP

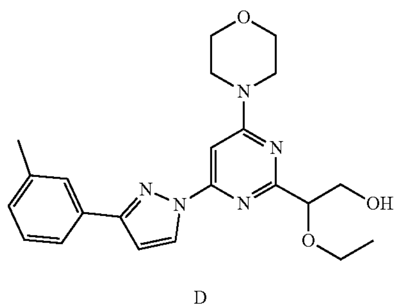

D chiral SFC

-continued

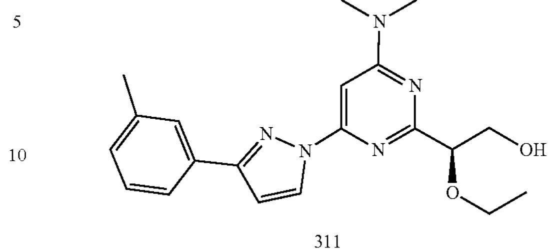

311

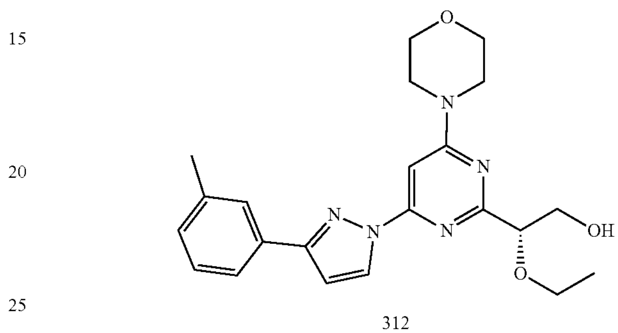

312

Absolute configuration not determined

Preparation of A

A mixture of Intermediate 33 (400 mg, 1.54 mmol), imidazole (157 mg, 2.31 mmol), and TIPSCl (328 mg, 1.70 mmol) in DMF (10 mL) was stirred at room temperature overnight. The mixture was diluted with EtOAc (80 mL) and washed with brine (30 mL×4), dried over $Na_2SO_4$, filtered and concentrated to dryness. The resulting crude product was purified by chromatography on silica gel eluting with petroleum ether:EtOAc=15:1-9:1 to get A (480 mg, 75%) as a white solid.

Preparation of B

To a solution A (480 mg, 1.15 mmol) in DMF (10 mL) was added NaH (60% in oil, 92 mg, 2.30 mmol) at 0° C. The mixture was stirred at 0° C. for 10 minutes, and then EtI (270 mg, 1.73 mmol) was added into it slowly. The reaction mixture was stirred at room temperature for 1 hour, quenched with water (50 mL) and extracted with EtOAc (20 mL×3). The combined organic layers were washed with brine (80 mL×4), dried over $Na_2SO_4$, filtered and concentrated to dryness. The resulting crude product was purified by chromatography on silica gel eluting with petroleum ether:EtOAc=10:1-5:1 to get B (411 mg, 80%) as yellow oil.

Preparation of C

To a solution of B (411 mg, 0.93 mmol) in MeOH (5 mL) was added 4 N HCl/dioxane (5 mL) at room temperature, the mixture was stirred at room temperature overnight. The solvent was removed under reduced pressure, the residue was re-dissolved in methanol (5 mL) and adjusted PH=8-9 with Ambersep® 900 (OH), and filtered. The filtrate was concentrated to dryness and then purified by chromatography on silica gel eluting with petroleum ether:EtOAc=10:1-3:1 to get C (231 mg, 87%) as yellow oil.

Preparation of D

A mixture of C (210 mg, 0.73 mmol), Intermediate 2 (115 mg, 0.73 mmol), $Pd_2(dba)_3$ (137 mg, 0.15 mmol), Xantphos (87 mg, 0.15 mmol) and $Cs_2CO_3$ (476 mg, 1.46 mmol) in NMP (4 mL) was microwaved at 100° C. under nitrogen atmosphere for 1 hour. The mixture was then cooled down to room temperature and diluted with EtOAc (80 mL). The resulting mixture was washed by brine (30 mL×4), dried over $Na_2SO_4$, filtered and concentrated to dryness. The resulting crude product was purified by chromatography on silica gel eluting with petroleum ether:EtOAc=5:1-1:1 to get D (93 mg, 31%) as a yellow solid.

Preparation of Compound 311 and Compound 312 was separated by chiral HPLC (SFC) to get compounds Compound 311 (40 mg, $1^{st}$ peak) and Compound 312 ($2^{nd}$ peak). The stereochemistry of the enantiomers was not determined.

Compound 311 ($1^{st}$ Peak)

$^1$H NMR (400 MHz, DMSO-$d_6$): δ 8.61 (d, J=2.8 Hz, 1H), 7.83 (s, 1H), 7.78 (d, J=7.6 Hz, 1H), 7.36 (t, J=7.6 Hz, 1H), 7.21 (d, J=7.2 Hz, 1H), 7.11 (s, 1H), 7.07 (d, J=2.8 Hz, 1H), 5.76 (s, 1H), 4.73 (t, J=5.9 Hz, 1H), 4.27 (dd, J=6.7, 5.3 Hz, 1H), 3.79-3.72 (m, 1H), 3.68 (s, 8H), 3.53 (tdd, J=9.3, 7.1, 2.3 Hz, 2H), 2.39 (s, 3H), 1.14 (t, J=7.0 Hz, 3H).

Compound 312 ($2^{nd}$ Peak)

$^1$H NMR (400 MHz, DMSO-$d_6$): δ 8.61 (d, J=2.8 Hz, 1H), 7.83 (s, 1H), 7.78 (d, J=7.6 Hz, 1H), 7.36 (t, J=7.6 Hz, 1H), 7.21 (d, J=7.2 Hz, 1H), 7.11 (s, 1H), 7.07 (d, J=2.8 Hz, 1H), 5.76 (s, 1H), 4.73 (t, J=5.9 Hz, 1H), 4.27 (dd, J=6.7, 5.3 Hz, 1H), 3.79-3.70 (m, 1H), 3.68 (s, 8H), 3.53 (tdd, J=9.3, 7.1, 2.3 Hz, 2H), 2.39 (s, 3H), 1.14 (t, J=7.0 Hz, 3H).

Synthesis of (S)-1-(1-(2-(2-(1-methyl-1H-pyrazol-4-yl)ethoxy)-6-morpholinopyrimidin-4-yl)-3-(m-tolyl)-1H-pyrazol-5-yl)ethan-1-ol (Compound 313) and (R)-1-(1-(2-(2-(1-methyl-1H-pyrazol-4-yl)ethoxy)-6-morpholinopyrimidin-4-yl)-3-(m-tolyl)-1H-pyrazol-5-yl)ethan-1-ol (Compound 314)

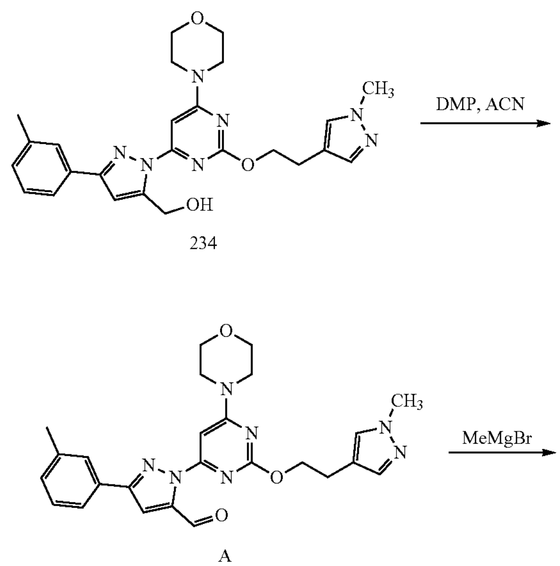

234

A

-continued

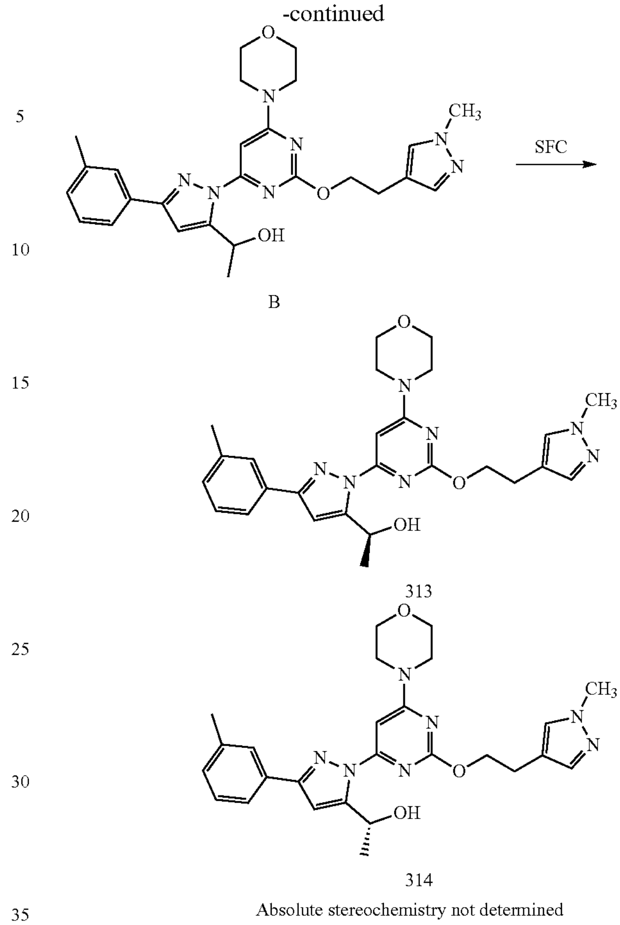

B

313

314

Absolute stereochemistry not determined

Preparation of A

Dess-Martin periodinane (202 mg, 0.476 mmol) was added to the solution of Compound 234 (160 mg, 0.317 mmol) in ACN (5 mL). The resulting reaction mixture was stirred at room temperature for 2 hours. After which period, the mixture was diluted with EtOAc (80 mL) and washed by brine (30 mL×2), dried over $Na_2SO_4$, filtered, concentrated to dryness. The residue was purified by chromatography on silica gel eluting with petroleum ether:EtOAc=5:1-1:1 to give desired compound A (140 mg, 93%) as a white solid.

Preparation of B

To a solution of A (120 mg, 0.254 mmol) in THF (5 mL) was added $CH_3MgBr$ (0.3 mL, 0.3 mmol) at 0° C. The resulting solution was allowed to warm to room temperature and stirred for 2 hours, and then quenched with sat. $NH_4Cl$ (10 mL) and diluted with EtOAc (20 mL). The separated organic phase was washed with brine (20 mL×3), dried over $Na_2SO_4$, filtered and concentrated to dryness. The residue was purified by chromatography on silica gel eluting with petroleum ether:EtOAc=3:1-1:2 to give the desired compound B (80 mg, 65%) as a white solid.

Preparation of Compound 313 and Compound 314

B was separated by chiral HPLC (SFC) to get to Compound 313 (30 mg, $1^{st}$ peak) and Compound 314 (30 mg, $2^{nd}$ peak). The stereochemistry of the enantiomers was not determined.

Compound 313 1$^{st}$ Peak):

$^1$H NMR (400 MHz, $CDCl_3$) δ 7.78-7.60 (m, 2H), 7.40 (s, 1H), 7.35-7.28 (m, 2H), 7.19 (d, J=7.5 Hz, 1H), 6.92 (s, 1H), 6.68 (s, 1H), 5.14 (q, J=6.6 Hz, 1H), 4.57-4.32 (m, 2H), 3.87 (s, 3H), 3.84-3.66 (m, 8H), 2.96 (t, J=6.9 Hz, 2H), 2.42 (s, 3H), 1.70 (d, J=6.6 Hz, 3H).

Compound 314 (2n peak):

$^1$H NMR (400 MHz, $CDCl_3$) δ 7.72-7.61 (m, 2H), 7.40 (s, 1H), 7.34-7.27 (m, 2H), 7.19 (d, J=7.5 Hz, 1H), 6.92 (s, 1H), 6.68 (s, 1H), 5.14 (q, J=6.6 Hz, 1H), 4.50-4.32 (m, 2H), 3.87 (s, 3H), 3.84-3.66 (m, 8H), 2.96 (t, J=6.9 Hz, 2H), 2.42 (s, 3H), 1.70 (d, J=6.6 Hz, 3H).

Synthesis of (R)-1-(3-(1-(2-(2-(1-methyl-1H-pyrazol-4-yl)ethoxy)-6-morpholinopyrimidin-4-yl)-1H-pyrazol-3-yl)phenyl)ethan-1-ol (Compound 315) and (S)-1-(3-(1-(2-(2-(1-methyl-1H-pyrazol-4-yl)ethoxy)-6-morpholinopyrimidin-4-yl)-1H-pyrazol-3-yl)phenyl)ethan-1-ol (Compound 316)

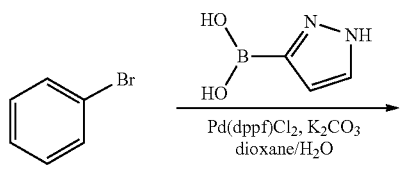

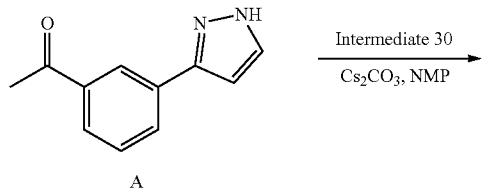

A

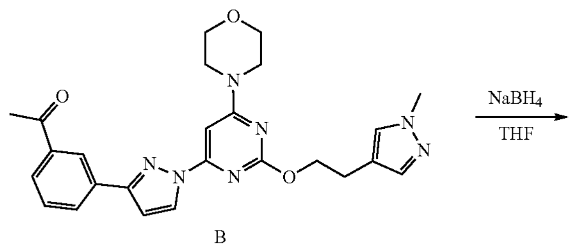

B

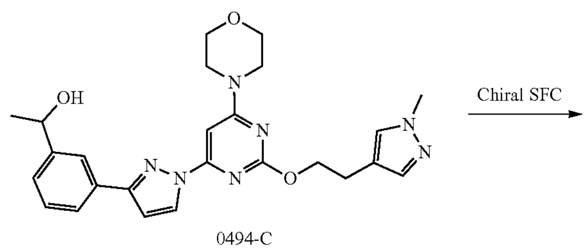

0494-C

-continued

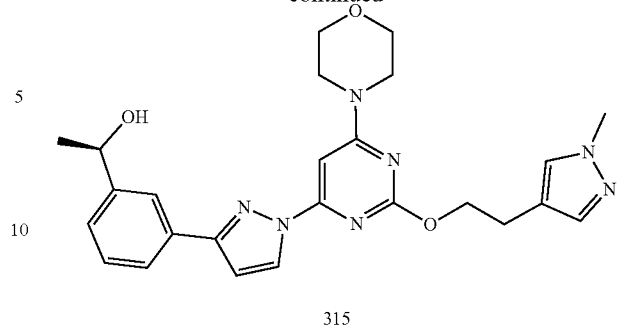

315

Absolute configuration not determined

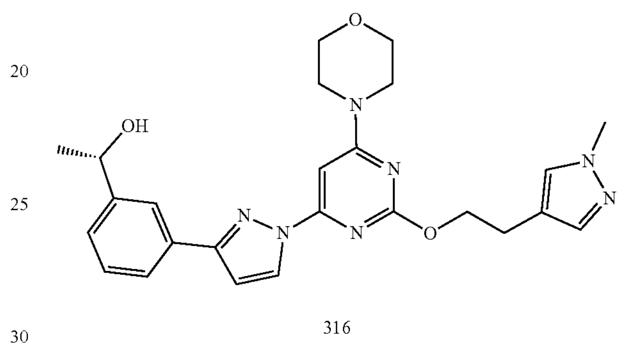

316

Preparation of A

A mixture of 1-(3-bromophenyl)ethan-1-one (600 mg, 3.02 mmol), (1H-pyrazol-3-yl)boronic acid (507 mg, 4.53 mmol), $Pd(dppf)Cl_2$ (439 mg, 0.60 mmol) and $K_2CO_3$ (834 mg, 6.04 mmol) in 1,4-dioxane (24 mL) and $H_2O$ (6 mL) was stirred at 100° C. under nitrogen atmosphere for 16 hours. After cooling to room temperature, the mixture was diluted with EtOAc (50 mL) and washed with brine (30 mL×2), dried over $Na_2SO_4$, filtered and concentrated to dryness. The resulting crude product was purified by chromatography on silica gel eluting with petroleum ether: EtOAc=5:1-2:1 to get A (472 mg, 84%) as yellow oil.

Preparation of B

A mixture of A (472 mg, 2.54 mmol), Intermediate 30 (904 mg, 2.80 mmol) and $Cs_2CO_3$ (1656 mg, 5.08 mmol) in NMP (15 mL) was stirred at 150° C. overnight under nitrogen atmosphere. After cooling to room temperature, the mixture was diluted with EtOAc (50 mL) and washed with brine (30 mL×4), dried over $Na_2SO_4$, filtered and concentrated to dryness. The resulting crude product was purified by chromatography on silica gel eluting with petroleum ether:EtOAc= 4:1-1:1 to get B (740 mg, 62%) as a light yellow solid.

Preparation of C

To a solution of B (740 mg, 1.56 mmol) in THF (10 mL) was added $NaBH_4$ (119 mg, 3.12 mmol) at 0° C. The mixture was stirred at room temperature for 5 hours under nitrogen atmosphere and quenched with water (60 mL) at 0° C. The mixture was then extracted with EtOAc (20 mL×3). The combined organic layers were washed with brine (40 mL×4), dried over $Na_2SO_4$, filtered and concentrated to dryness. The resulting crude product was purified by chromatography on silica gel eluting with petroleum ether: EtOAc=2:1-1:2 to get C (470 mg, 63%) as light yellow oil.

Preparation of Compound 315 and Compound 316

C (220 mg) was separated by chiral HPLC (SFC) to get compounds Compound 315 (100 mg, 1st peak) and Compound 316 (100 mg, 2nd peak). The stereochemistry of the enantiomers was not determined.

Compound 315 (1st Peak)

$^1$H NMR (400 MHz, DMSO-$d_6$): δ 8.60 (d, J=2.7 Hz, 1H), 7.93 (s, 1H), 7.86-7.80 (m, 1H), 7.58 (s, 1H), 7.44-7.36 (m, 2H), 7.34 (s, 1H), 7.06 (d, J=2.7 Hz, 1H), 6.89 (s, 1H), 5.25 (d, J=4.2 Hz, 1H), 4.80 (dd, J=6.3, 4.4 Hz, 1H), 4.42 (t, J=7.0 Hz, 2H), 3.79 (s, 3H), 3.69 (d, J=5.4 Hz, 8H), 2.86 (t, J=7.0 Hz, 2H), 1.38 (d, J=6.4 Hz, 3H).

Compound 316 (2nd Peak)

$^1$H NMR (400 MHz, DMSO-d6): δ 8.60 (d, J=2.7 Hz, 1H), 7.94 (s, 1H), 7.84 (d, J=7.2 Hz, 1H), 7.58 (s, 1H), 7.44-7.36 (m, 2H), 7.35 (s, 1H), 7.06 (d, J=2.7 Hz, 1H), 6.89 (s, 1H), 5.24 (d, J=4.2 Hz, 1H), 4.80 (dd, J=6.2, 4.5 Hz, 1H), 4.42 (t, J=7.0 Hz, 2H), 3.79 (s, 3H), 3.69 (d, J=5.7 Hz, 8H), 2.86 (t, J=7.0 Hz, 2H), 1.38 (d, J=6.4 Hz, 3H).

Synthesis of 4-(2-(2-(pyridazin-3-yl)ethyl)-6-(3-(m-tolyl)-1H-pyrazol-1-yl)pyrimidin-4-yl)morpholine (Compound 317)

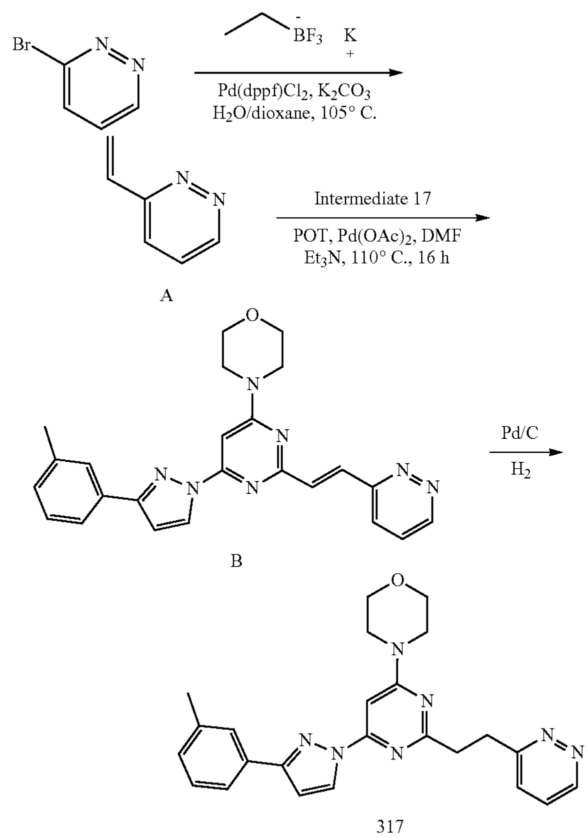

A

B

317

Preparation of A

A mixture of 3-bromopyridazine (500 mg, 3.14 mmol), vinyl trifluoropotassium borate (640 mg, 4.7 mmol), $Pd(dppf)Cl_2$ (460 mg, 0.63 mmol) and $K_2CO_3$ (870 mg, 6.28 mmol) in 1,4-dioxane (12 mL) and $H_2O$ (3 mL) was stirred at 105° C. under nitrogen atmosphere for 16 hours. After cooling to the room temperature, the mixture was diluted with EtOAc (50 mL) and washed by brine (30 mL×2), dried over $Na_2SO_4$, filtered and concentrated to dryness. The resulting crude product was purified by chromatography on silica gel eluting with petroleum ether:EtOAc=3:1-1:1 to get A (110 mg, 33%) as brown oil.

Preparation of B

A mixture of A (110 mg, 1.04 mmol), tri(o-tolyl)phosphine (61 mg, 0.2), $Pd(OAc)_2$ (34 mg, 0.15 mmol), Intermediate 17 (224 mg, 0.5 mmol) and triethylamine (150 mg, 1.5 mmol) in DMF (5 mL) was stirred at 105° C. under nitrogen atmosphere for 16 hours. The mixture was then diluted with EtOAc (40 mL) and washed by brine (30 mL×3), dried over $Na_2SO_4$, filtered and concentrated to dryness. The resulting crude product was purified by chromatography on silica gel eluting with petroleum ether: EtOAc=3:1-1:1 to get B (130 mg, 29.4%) as a slight yellow solid.

Preparation of Compound 317

To a solution of B (50 mg, 0.118 mmol) in MeOH was added Pd/C (10%, 10 mg) and stirred at room temperature under hydrogen atmosphere for 16 hours. The solution was filtered, and the filtrate was concentrated to dryness. The resulting crude product was purified by Prep-HPLC to get Compound 317 (5 mg, 10%) as a white solid.

$^1$H NMR (400 MHz, $CDCl_3$): δ 9.06 (dd, J=4.4, 2.1 Hz, 1H), 8.53 (d, J=2.7 Hz, 1H), 7.82-7.65 (m, 2H), 7.44-7.27 (m, 3H), 7.18 (d, J=7.6 Hz, 1H), 7.02 (s, 1H), 6.74 (d, J=2.7 Hz, 1H), 3.75 (dt, J=9.1, 4.2 Hz, 8H), 3.55 (t, J=7.6 Hz, 2H), 3.31 (t, J=7.6 Hz, 2H), 2.43 (s, 3H).

Synthesis of (S)-2-(4-(3-(1H-indol-3-yl)-1H-pyrazol-1-yl)-6-morpholinopyrimidin-2-yl)-2-methoxyethan-1-ol (Compound 318) and (R)-2-(4-(3-(1H-indol-3-yl)-1H-pyrazol-1-yl)-6-morpholinopyrimidin-2-yl)-2-methoxyethan-1-ol (Compound 319)

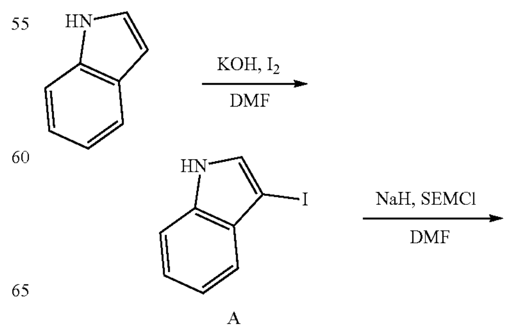

A

-continued

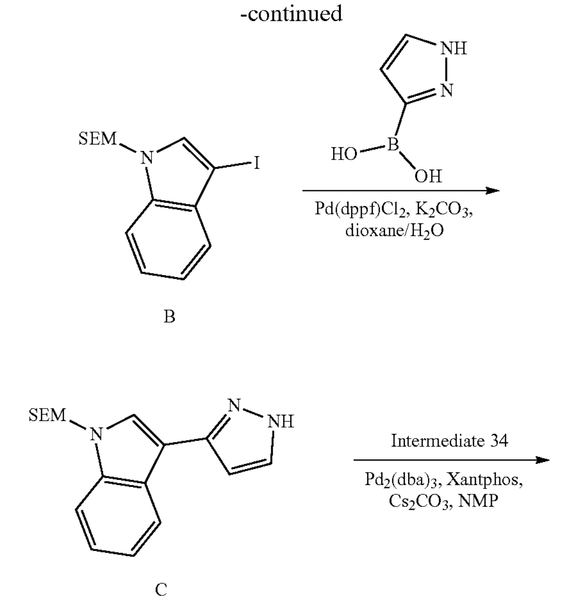

B

C

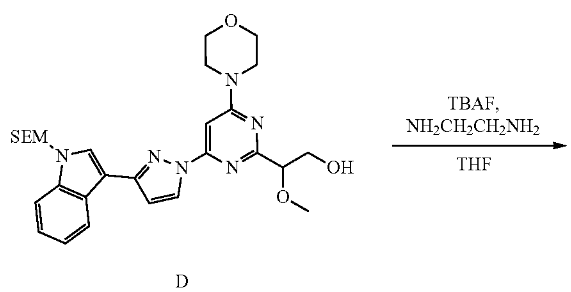

D

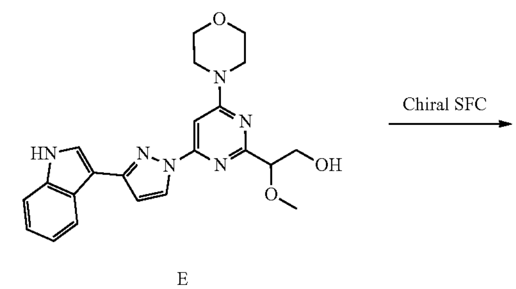

E

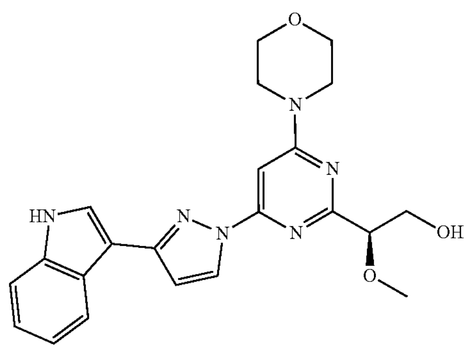

318

+

-continued

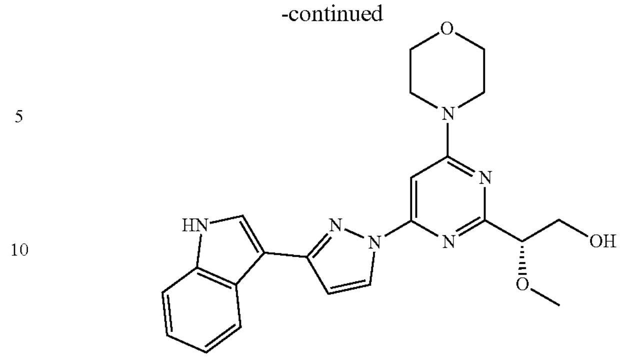

319

Absolute stereochemistry not determined

Preparation of A

A solution of indole (1.0 g, 8.55 mmol) in DMF (15 mL) was treated with KOH (1.20 g, 21.38 mmol) at room temperature for 20 minutes. $I_2$ (2.17 g, 8.55 mmol) was dissolved in 3 mL of DMF and was added to above reaction mixture. The resulting solution was stirred for an additional 1 hour, and then poured into 200 mL of ice-water. The precipitate was collected by filtration, washed with water and dried to give the desired product A (1.7 g, 82%) as reddish brown solid.

Preparation of B

To a solution of compound A (400 mg, 1.65 mmol) in DMF (8 mL) was added NaH (60% in oil, 132 mg, 3.30 mmol) at −10° C., the mixture was stirred at room temperature for 15 minutes, then cooled to −10° C. and SEMCl (412 mg, 2.48 mmol) was added slowly. The mixture was stirred at room temperature for 1 hour. Poured into water (50 mL) and extracted with EtOAc (20 mL×3). The combined organic layer was washed with brine (50 mL×4), dried over $Na_2SO_4$, filtered and concentrated to dryness. The resulting crude product was purified by chromatography on silica gel eluting with petroleum ether:EtOAc=20:1-10:1 to get compound B (550 mg, 90%) as clear oil.

Preparation of C

The mixture of compound B (550 mg, 1.47 mmol), (1H-pyrazol-3-yl)boronic acid (248 mg, 2.21 mmol), $Pd(dppf)Cl_2$ (322 mg, 0.44 mmol) and $K_2CO_3$ (609 mg, 4.41 mmol) in 1,4-dioxane (20 mL) and $H_2O$ (5 mL) was stirred at 100° C. under nitrogen atmosphere for 16 hours. After which period, the mixture was cooled down to room temperature and diluted with EtOAc (40 mL), which was then washed by brine (30 mL×2), dried over $Na_2SO_4$, filtered and concentrated to dryness. The resulting crude product was purified by chromatography on silica gel eluting with petroleum ether:EtOAc=5:1-2:1 to get the desired product C (180 mg, 39%) as brown oil.

Preparation of D

A mixture of compound C (180 mg, 0.58 mmol), Intermediate 34 (185 mg, 0.58 mmol), $Pd_2(dba)_3$ (110 mg, 0.12 mmol), Xant-phos (69 mg, 0.12 mmol) and $Cs_2CO_3$ (378 mg, 1.16 mmol) in NMP (4 mL) was heated to 100° C. in a microwave reactor under nitrogen atmosphere for 1.5 hour. After which period, the mixture was diluted with EtOAc (80 mL) and washed by brine (30 mL×4), dried over $Na_2SO_4$, filtered and concentrated to dryness. The resulting crude product was purified by chromatography on silica gel eluting with petroleum ether:EtOAc=4:1- 1:1 to give the desired compound D (238 mg, 75%) as brown oil.

Preparation of E

A mixture of compound D (238 mg, 0.43 mmol), TBAF (1.0M in THF, 2.6 mL, 2.58 mmol) and ethylenediamine (77 mg, 1.29 mmol) in THF (2 mL) was stirred at 80° C. under nitrogen atmosphere for 16 hours. After cooling down to room temperature, the mixture was diluted with EtOAc (40 mL) and washed with brine (30 mL×4). The combined organic solvents were dried over $Na_2SO_4$, filtered and concentrated to dryness. The resulting residue was purified by chromatography on silica gel eluting with petroleum ether: EtOAc=3:1-1:1 to giver desired compound E (238 mg, 75%) as a yellow solid.

Preparation of Compound 318 and Compound 319

Compound E was separated by chiral HPLC (SFC) to give to Compound 318 (45 mg, 1$^{st}$ peak) and Compound 319 (40 mg, 2$^{nd}$ peak). The stereochemistry of the enantiomers was not determined.

Compound 318 (1$^{st}$ Peak):

$^1$NMR (400 MHz, $CDCl_3$) δ 8.62 (d, J=2.7 Hz, 1H), 8.30 (dd, J=15.2, 9.0 Hz, 2H), 7.67 (d, J=2.6 Hz, 1H), 7.47-7.40 (m, 1H), 7.32-7.27 (m, 2H), 7.15 (s, 1H), 6.75 (d, J=2.7 Hz, 1H), 4.39-4.33 (m, 1H), 4.03-3.94 (m, 2H), 3.85-3.76 (m, 8H), 3.56 (s, 3H).

Compound 319 (2$^{nd}$ Peak):

$^1$NMR (400 MHz, $CDCl_3$) δ 8.62 (d, J=2.7 Hz, 1H), 8.30 (dd, J=15.2, 9.0 Hz, 2H), 7.67 (d, J=2.6 Hz, 1H), 7.47-7.40 (m, 1H), 7.32-7.27 (m, 2H), 7.15 (s, 1H), 6.75 (d, J=2.7 Hz, 1H), 4.38-4.36 (m, 1H), 4.02-3.94 (m, 2H), 3.85-3.76 (m, 8H), 3.56 (s, 3H).

Synthesis of (S)-2-methoxy-2-(4-(3-(1-methyl-1H-indol-3-yl)-1H-pyrazol-1-yl)-6-morpholinopyrimidin-2-yl)ethan-1-ol (Compound 320) and (R)-2-methoxy-2-(4-(3-(1-methyl-1H-indol-3-yl)-1H-pyrazol-1-yl)-6-morpholinopyrimidin-2-yl)ethan-1-ol (Compound 321)

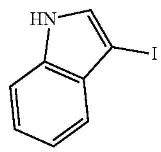

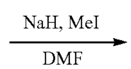

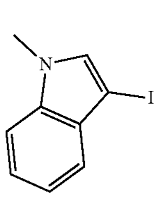

A

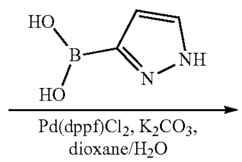

-continued

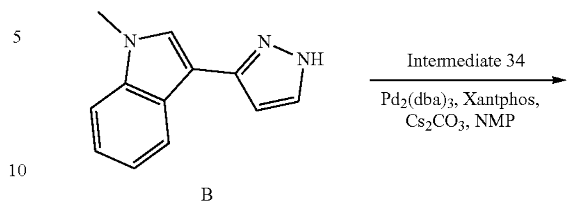

B

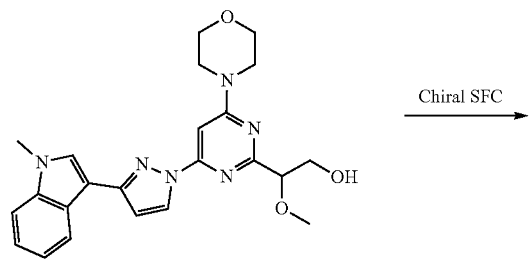

C

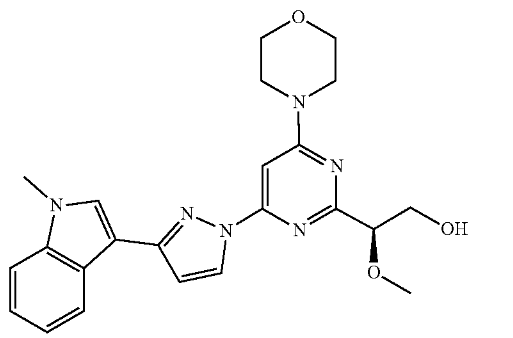

320

+

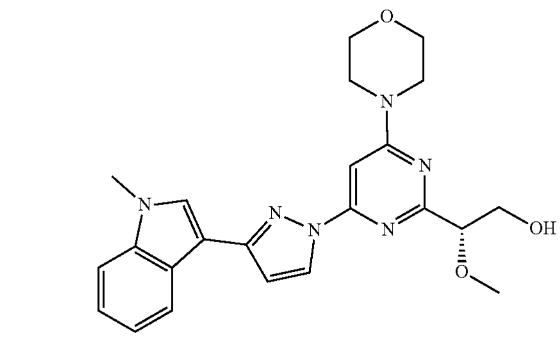

321

Absolute stereochemistry not determined

Preparation of A

To a solution of compound 3-iodoindole (900 mg, 3.70 mmol) in DMF (20 mL) was added NaH (296 mg, 7.40 mmol) at −10° C. The resulting mixture was stirred at room temperature for 15 minutes, and then cooled down to −10° C. again. MeI (788 mg, 5.55 mmol) was added to above solution slowly. The reaction mixture was stirred at room temperature for another 1 hour before pouring into water (100 mL), which was then extracted with EtOAc (50 mL×3). The combined organic layers were washed with brine (80 mL×4), dried over $Na_2SO_4$, filtered and concentrated to dryness. The resulting crude product was purified by chromatography on silica gel eluting with petroleum ether: EtOAc=20:1-10:1 to give the desired compound A (790 mg, 83%) as clear oil.

Preparation of B

A mixture of compound B (790 mg, 3.07 mmol), (1H-pyrazol-3-yl)boronic acid (447 mg, 3.99 mmol), Pd(dppf)$Cl_2$ (446 mg, 0.61 mmol) and $K_2CO_3$ (847 mg, 6.14 mmol) in 1,4-dioxane (24 mL) and $H_2O$ (6 mL) was stirred at 100° C. under nitrogen atmosphere for 16 hours. After which period, the mixture was cooled down to room temperature and diluted with EtOAc (50 mL), which was then washed with brine (30 mL×2), dried over $Na_2SO_4$, filtered and concentrated to dryness. The resulting residue was purified by chromatography on silica gel eluting with petroleum ether:EtOAc=20:1-10:1 to give the desired compound B (102 mg, 17%) as a yellow oil.

Preparation of C

A mixture of compound B (102 mg, 0.52 mmol), Intermediate 34 (142 mg, 0.52 mmol), $Pd_2(dba)_3$ (92 mg, 0.10 mmol), Xant-phos (58 mg, 0.10 mmol) and $Cs_2CO_3$ (339 mg, 1.04 mmol) in NMP (3 mL) was heated to 100° C. in a microwave reactor at under nitrogen atmosphere for 1.5 hour. After which period, the mixture was diluted with EtOAc (80 mL) and washed by brine (30 mL×4), dried over $Na_2SO_4$, filtered and concentrated to dryness. The resulting residue was purified by chromatography on silica gel eluting with petroleum ether:EtOAc=4:1-1:1 to give the desired compound C (144 mg, 64%) as a light yellow solid.

Preparation Compound 320 and Compound 321

C was separated by chiral HPLC (SFC) to give to Compound 320 (60 mg, 1st peak) and Compound 321 (50 mg, 2nd peak). The stereochemistry of the enantiomers was not determined.

Compound 320 (1st Peak):

$^1$NMR (400 MHz, $CDCl_3$) δ 8.72 (d, J=2.6 Hz, 1H), 8.25 (d, J=7.4 Hz, 1H), 7.56 (s, 1H), 7.38 (d, J=7.7 Hz, 1H), 7.35-7.26 (m, 2H), 7.20 (s, 1H), 6.74 (d, J=2.8 Hz, 1H), 4.53 (t, J=5.4 Hz, 1H), 4.03-3.95 (m, 2H), 3.87-3.80 (m, 11H), 3.55 (s, 3H).

Compound 321 (2nd peak):

$^1$NMR (400 MHz, $CDCl_3$) δ 8.72 (d, J=2.6 Hz, 1H), 8.25 (d, J=7.4 Hz, 1H), 7.56 (s, 1H), 7.38 (d, J=7.8 Hz, 1H), 7.35-7.27 (m, 2H), 7.20 (s, 1H), 6.74 (d, J=2.7 Hz, 1H), 4.54 (t, J=5.4 Hz, 1H), 4.03-3.95 (m, 2H), 3.87-3.81 (m, 11H), 3.55 (s, 3H).

Synthesis of (R)-4-(2-(1-methoxypropyl)-6-(3-(m-tolyl)-1H-pyrazol-1-yl)pyrimidin-4-yl)morpholine (Compound 322) and (S)-4-(2-(1-methoxypropyl)-6-(3-(m-tolyl)-1H-pyrazol-1-yl)pyrimidin-4-yl)morpholine (Compound 323)

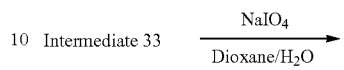

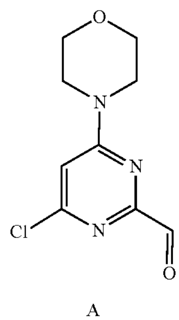

A

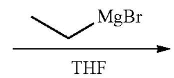

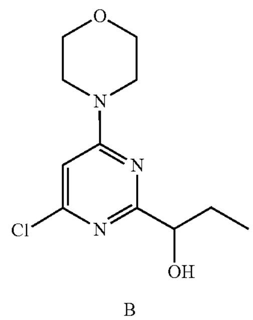

B

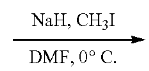

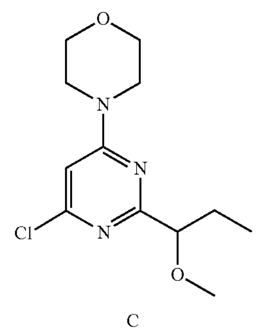

C

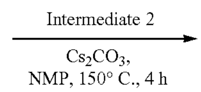

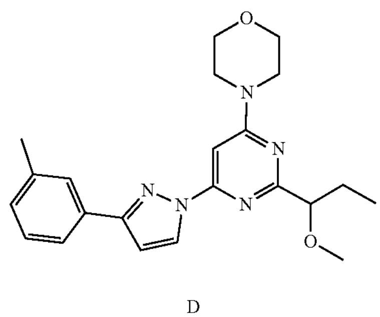

D

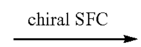

-continued

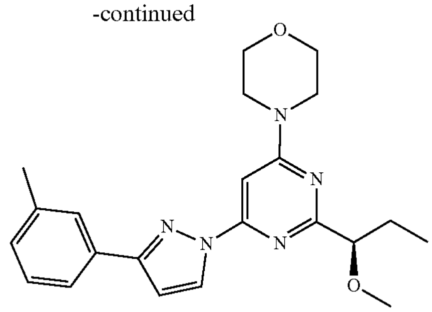

322

Absoluteconfiguration not determined

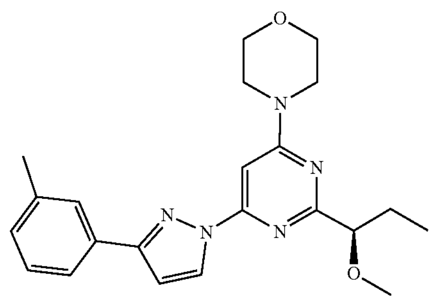

323

Preparation of A

To a solution of Intermediate 33 (800 mg, 3.1 mmol) in dioxane/$H_2O$ (15 mL/4 mL) was added $NaIO_4$ (1.32 g, 6.2 mmol), then stirred at room temperature for 2 hrs. Water (30 mL) was added and the resulting mixture was extracted with DCM (20 mL×3). The combined organic layer was dried over $Na_2SO_4$, filtered, concentrated to give crude A (580 mg, 83%) as off white solid.

Preparation of B

To a solution of crude A (580 mg, 2.6 mmol) in THF (8 mL) was added dropwise $CH_3CH_2MgBr$ (2M, 3 mL, 6.4 mmol) at 0° C., then stirred at 0° C. for 1 h. Ice-water (10 mL) and $NH_4Cl$ (aq) was added and the resulting mixture was extracted with EtOAc (20 mL×2). The combined organic layers were washed with brine (10 mL×3), dried over $Na_2SO_4$, filtered and concentrated to dryness. The crude product was purified by chromatography on silica gel eluting with petroleum ether:EtOAc=8:1 to 5:1 to get B (230 mg, 35%) as yellow oil.

Preparation of C

To a solution of crude B (200 mg, 0.7 mmol) in DMF (5 mL) was added NaH (85 mg, 1.9 mmol) at 0° C. After stirring for 10 min. MeI (170 mg, 0.98 mmol) was added to above solution, the resulting solution was then stirred at 0° C. for 1 h. Water (10 mL) was added and the resulting mixture was extracted with EtOAc (20 mL×2). The combined organic layers were washed with brine (10 mL×3), dried over $Na_2SO_4$, filtered, concentrated to dryness. The crude product was purified by chromatography on silica gel eluting with petroleum ether:EtOAc=8:1 to 5:1 to get Preparation of D The mixture of C (170 mg, 0.63 mmol), Intermediate 2 (110 mg, 0.69 mmol), and $Cs_2CO_3$ (410 mg, 1.26 mmol) in NMP (5 mL) was sealed and stirred at 150° C. for 4 hrs. Water (10 mL) was added and the resulting mixture was extracted with EtOAc (20 mL×2). The combined organic layer was washed with brine (10 mL×3), dried over $Na_2SO_4$, filtered, concentrated to dryness. The crude product was purified by chromatography on silica gel eluting with petroleum ether:EtOAc=10:1 to 5:1 to get D (200 mg, 81.3%) as a white solid.

Synthesis of Compound 322 and Compound 323

D (200 mg) was separated by chiral SFC to give to get Compound 322 (80 mg, 40%, $1^{st}$ Peak) and Compound 323 (80 mg, 40%, $2^{nd}$ peak). The stereochemistry of the enantiomers was not determined.

Compound 322 ($1^{st}$ Peak)

$^1$H NMR (400 MHz, $CDCl_3$) δ: 8.74 (d, J=2.3 Hz, 1H), 7.75 (s, 1H), 7.70 (d, J=7.7 Hz, 1H), 7.33 (t, J=7.6 Hz, 1H), 7.19 (d, J=7.5 Hz, 1H), 7.15 (s, 1H), 6.76 (d, J=2.6 Hz, 1H), 4.22 (t, J=6.6 Hz, 1H), 3.88-3.76 (m, 8H), 3.42 (s, 3H), 2.43 (s, 3H), 1.96-1.85 (m, 2H), 0.99 (t, J=7.4 Hz, 3H).

Compound 323 ($2^{nd}$ Peak)

$^1$H NMR (400 MHz, $CDCl_3$): δ 8.74 (d, J=2.3 Hz, 1H), 7.75 (s, 1H), 7.70 (d, J=7.7 Hz, 1H), 7.33 (t, J=7.6 Hz, 1H), 7.19 (d, J=7.5 Hz, 1H), 7.15 (s, 1H), 6.76 (d, J=2.6 Hz, 1H), 4.22 (t, J=6.6 Hz, 1H), 3.88-3.76 (m, 8H), 3.42 (s, 3H), 2.43 (s, 3H), 1.96-1.85 (m, 2H), 0.99 (t, J=7.4 Hz, 3H).

Synthesis of (R)-4-(2-(1,4-dioxan-2-yl)-6-(3-(m-tolyl)-1H-pyrazol-1-yl)pyrimidin-4-yl)morpholine (Compound 324) and (S)-4-(2-(1,4-dioxan-2-yl)-6-(3-(m-tolyl)-1H-pyrazol-1-yl)pyrimidin-4-yl)morpholine (Compound 325)

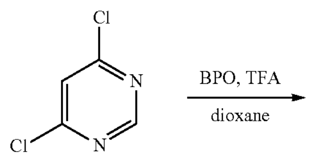

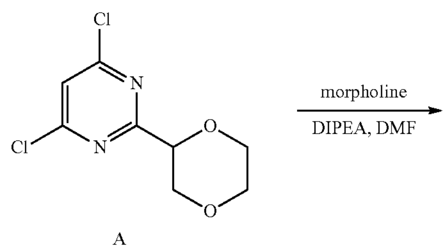

A

-continued

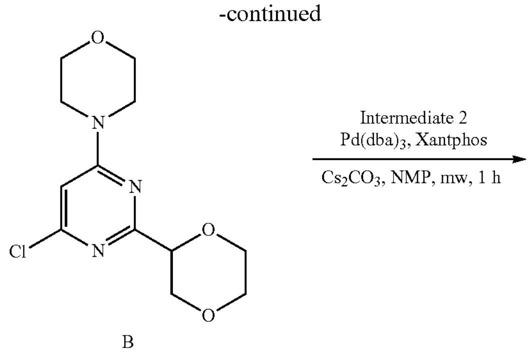

B

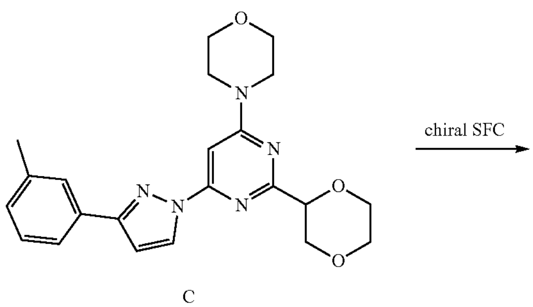

C

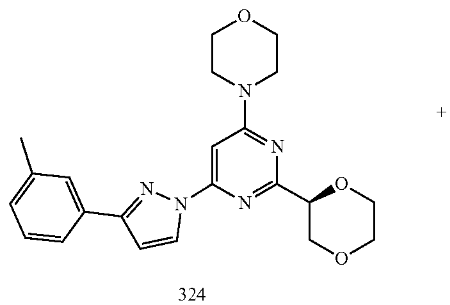

+

324

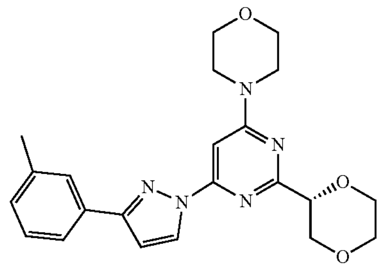

325

Absolute stereochemistry not determined

Preparation of A

To a solution of 4,6-dichloropyrimidine (1.0 g, 6.7 mmol) and TFA (995 mg, 8.7 mmol) in dioxane (15 mL) was added BPO (2.1 g, 8.7 mmol) and the reaction mixture was stirred at 80° C. under $N_2$ for 4 hrs. After which period, the mixture was concentrated to remove dioxane, water (20 mL) was added and the resulting mixture was extracted with EtOAc (20 mL×2). The combined organic layers were washed with brine (30 mL×3), dried over $Na_2SO_4$, filtered and concentrated to dryness. The crude product was purified by chromatography on silica gel eluting with petroleum ether: EtOAc=20:1 to 10:1 to get A (250 mg, 16%) as colorless oil.

Preparation of B

The mixture of A (220 mg, 0.94 mmol), morpholine (123 mg, 1.41 mmol), and DIPEA (363 mg, 2.82 mmol)) in DMF (5 mL) was stirred at room temperature for 30 min. Water (10 mL) was added to above solution and the resulting mixture was extracted with EtOAc (10 mL×2). The combined organic layers were washed with brine (10 mL×3), dried over $Na_2SO_4$, filtered and concentrated to dryness. The crude product was purified by chromatography on silica gel eluting with petroleum ether:EtOAc=8:1 to 3:1 to get B (180 mg, 70%) as colorless oil.

Preparation of C

The mixture of B (180 mg, 0.63 mmol), Intermediate 2 (100 mg, 0.63 mmol), $Pd_2(dba)_3$ (116 mg, 0.12 mmol), Xantphos (73 mg, 0.12 mmol) and $Cs_2CO_3$ (412 mg, 1.26 mmol) in NMP (5 mL) was sealed and stirred at 110° C. under microwave for 2 hrs. After cooling to room temperature, water (10 mL) was added to above solution and the resulting mixture was extracted with EtOAc (20 mL×2). The combined organic layers were washed with brine (10 mL×3), dried over $Na_2SO_4$, filtered and concentrated to dryness. The crude product was purified by chromatography on silica gel eluting with petroleum ether:EtOAc=10:1 to 5:1 to get C (180 mg, 70%) as a white solid.

Preparation of Compound 324 and Compound 325

C was separated by chiral SFC to give Compound 324 (65 mg, 36%, $1^{st}$ peak) and Compound 325 (60 mg, 33%, $2^{nd}$ peak). The stereochemistry of the enantiomers was not determined.

Compound 324 ($1^{st}$ Peak)

$^1H$ NMR (400 MHz, $CDCl_3$): δ 8.63 (d, J=2.7 Hz, 1H), 7.75 (s, 1H), 7.69 (d, J=7.7 Hz, 1H), 7.33 (t, J=7.6 Hz, 1H), 7.19 (d, J=7.6 Hz, 1H), 7.13 (s, 1H), 6.75 (d, J=2.7 Hz, 1H). 4.68 (dd, J=9.5, 2.9 Hz, 1H), 4.19 (dd, J=11.6, 2.9 Hz, 1H), 3.98-3.85 (m, 2H), 3.84-3.74 (m, 10H). 2.43 (s, 3H)

Compound 325 ($2^{nd}$ Peak)

$^1H$ NMR (400 MHz, $CDCl_3$): δ 8.63 (d, J=2.7 Hz, 1H), 7.75 (s, 1H), 7.69 (d, J=7.7 Hz, 1H), 7.33 (t, J=7.6 Hz, 1H), 7.19 (d, J=7.6 Hz, 1H), 7.13 (s, 1H), 6.75 (d, J=2.7 Hz, 1H). 4.68 (dd, J=9.5, 2.9 Hz, 1H), 4.19 (dd, J=11.6, 2.9 Hz, 1H), 3.98-3.85 (m, 2H), 3.84-3.74 (m, 10H). 2.43 (s, 3H)

Synthesis of 4-(2-(tetrahydro-2H-pyran-4-yl)-6-(3-(m-tolyl)-1H-pyrazol-1-yl)pyrimidin-4-yl)morpholine (Compound 326)

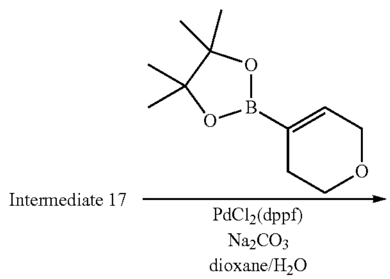

-continued

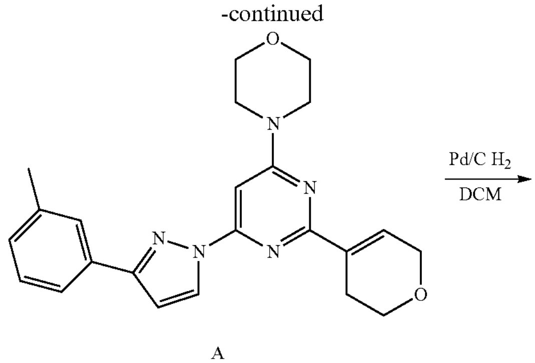

A

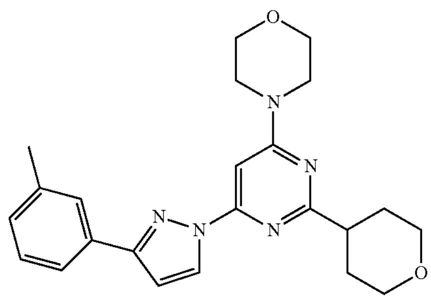

326

Preparation of A

The mixture of compound Intermediate 17 (50 mg, 0.1 mmol), 2-(3,6-dihydro-2H-pyran-4-yl)-4,4,5,5-tetramethyl-1,3,2-dioxaborolane (26 mg, 0.12 mmol), $Pd(dppf)Cl_2$ (20 mg, 0.027 mmol) and $Na_2CO_3$ (24 mg, 0.2 mmol) in dioxane and water (5:1, 12 mL) was stirred under an atmosphere of nitrogen at 100° C. for 12 hrs. After cooling to room temperature, the mixture was poured into water (30 mL) and extracted with EtOAc (30 mL×2). The combined organic layers were washed with brine (20 mL×2), dried over $Na_2SO_4$, filtered and concentrated to dryness. The crude product was purified by chromatography on silica gel eluting with petroleum ether:EtOAc=3:1 to get the desired product A (35 mg, 77.8%) as a withe solid.

Preparation of Compound 326

The mixture of A (35 mg, 0.086 mmol) and palladium on charcoal (10%) (20 mg, 0.189 mmoL) in dichloromethane (10 mL) was stirred under hydrogen atmosphere at 40° C. for 12 hours. The mixture was filtered through a pad of celite, and the filtrated was concentrated to dryness. The crude compound was purified by chromatography on silica gel eluting with petroleum ether:EtOAc=3:1 to get the desired product Compound 326 (30 mg, 85.7%) as a withe solid.

$^1$H NMR (400 MHz, $CDCl_3$): δ 8.66 (s, 1H), 7.75 (s, 1H), 7.70 (d, J=8.0 Hz, 1H), 7.33 (t, J=8.0 Hz, 1H), 7.19 (d, J=8.0 Hz, 1H), 7.05 (s, 1H), 6.76 (d, J=4.0 Hz, 1H), 4.10-4.06 (m, 2H), 3.84-3.77 (m, 8H), 3.60-3.54 (m, 2H), 2.43 (s, 3H), 2.00-1.96 (m, 4H).

Synthesis of (R)-4-(2-(tetrahydrofuran-2-yl)-6-(3-(m-tolyl)-1H-pyrazol-1-yl)pyrimidin-4-yl)morpholine (Compound 327) and (S)-4-(2-(tetrahydrofuran-2-yl)-6-(3-(m-tolyl)-1H-pyrazol-1-yl)pyrimidin-4-yl) morpholine (Compound 328)

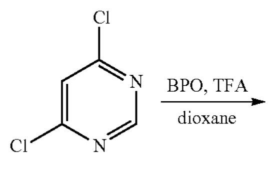

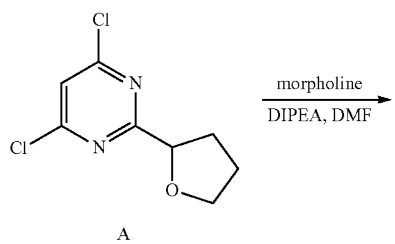

A

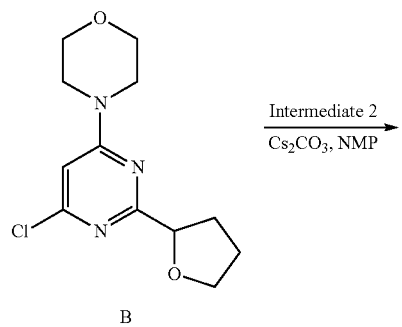

B

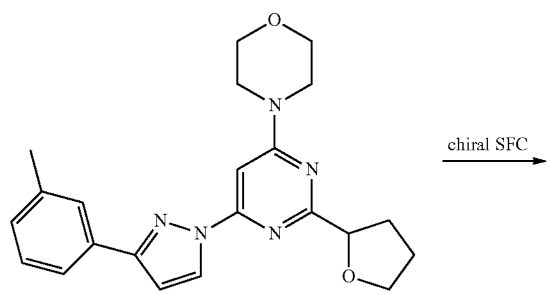

C

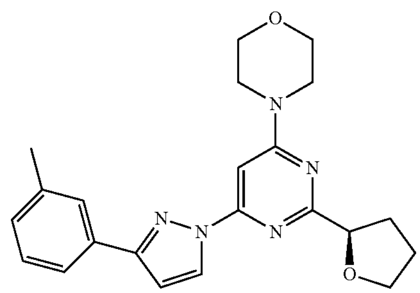

+

327

-continued

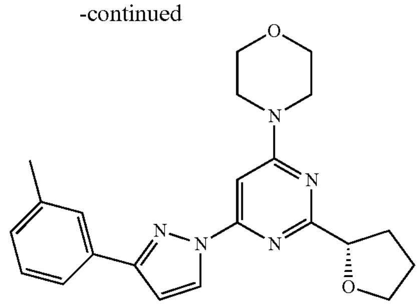

328
Absolute configuration not determined

Preparation of A

To a solution of 4,6-dichloropyrimidine (2.0 g, 13.4 mmol) and TFA (1.99 mg, 17.4 mmol in THF (30 mL) was added BPO (4.2 g, 17.4 mmol). The reaction mixture was stirred at 80° C. under $N_2$ for 16 hrs. After which period, the solution was concentrated to remove THF, and the residue was diluted with water (20 mL). The resulting mixture was extracted with EtOAc (20 mL×2). The combined organic layer s were washed with brine (30 mL×3), dried over $Na_2SO_4$, filtered and concentrated to dryness. The crude product was purified by Prep-TLC to get A (190 mg, 6.5%) as yellow oil.

Preparation of B

The mixture of A (180 mg g, 0.83 mmol), morpholine (108 mg, 1.24 mmol), and DIPEA (268 mg, 2.07 mmol) in DMF (5 mL) was stirred at room temperature for 30 min. Water (10 mL) was added to above solution, and the resulting mixture was extracted with EtOAc (10 mL×2). The combined organic layers were washed with brine (10 mL×3), dried over $Na_2SO_4$, filtered and concentrated to get crude B (350 mg) as yellow oil.

Preparation of C

The mixture of B (140 mg, 0.52 mmol), Intermediate 2 (82 mg, 0.52 mmol) and $Cs_2CO_3$ (340 mg, 1.04 mmol) in NMP (5 mL) was stirred at 150° C. for 4 hrs in sealed tube. After cooling to room temperature, water (10 mL) was added to above reaction system, and the resulting mixture was extracted with EtOAc (20 mL×2). The combined organic layers were washed with brine (10 mL×3), dried over $Na_2SO_4$, filtered and concentrated to dryness. The crude product was purified by chromatography on silica gel eluting with petroleum ether:EtOAc=10:1 to get crude C (140 mg, 67%) as a white solid.

Preparation of Compound 327 and Compound 3208

C (140 mg) was separated by chiral SFC to give compounds Compound 327 (50 mg, 35.7%, $1^{st}$ peak) and Compound 328 (52 mg, 37.1%, $2^{nd}$ Peak)

Compound 327 ($1^{st}$ Peak)

$^1$H NMR (400 MHz, $CDCl_3$): δ 8.63 (d, J=2.6 Hz, 1H), 7.75 (s, 1H), 7.69 (d, J=7.7 Hz, 1H), 7.37-7.28 (m, 1H), 7.18 (d, J=7.6 Hz, 1H), 7.09 (s, 1H), 6.75 (d, J=2.6 Hz, 1H), 4.96 (dd, J=7.7, 5.5 Hz, 1H), 4.20 (dd, J=14.2, 7.3 Hz, 1H), 4.02 (td, J=7.7, 5.7 Hz, 1H), 3.87-3.70 (m, 8H), 2.43 (s, 3H), 2.38-2.26 (m, 1H), 2.26-2.06 (m, 2H), 2.08-1.89 (m, 1H).

Compound 328 ($2^{nd}$ Peak)

$^1$H NMR (400 MHz, $CDCl_3$): δ 8.63 (d, J=2.6 Hz, 1H), 7.75 (s, 1H), 7.69 (d, J=7.7 Hz, 1H), 7.37-7.28 (m, 1H), 7.18 (d, J=7.6 Hz, 1H), 7.09 (s, 1H), 6.75 (d, J=2.6 Hz, 1H), 4.96 (dd, J=7.7, 5.5 Hz, 1H), 4.20 (dd, J=14.2, 7.3 Hz, 1H), 4.02 (td, J=7.7, 5.7 Hz, 1H), 3.87-3.70 (m, 8H), 2.43 (s, 3H), 2.38-2.26 (m, 1H), 2.26-2.06 (m, 2H), 2.08-1.89 (m, 1H).

Synthesis of (R)-4-(2-(tetrahydrofuran-3-yl)-6-(3-(m-tolyl)-1H-pyrazol-1-yl)pyrimidin-4-yl)morpholine (Compound 329) and (S)-4-(2-(tetrahydrofuran-3-yl)-6-(3-(m-tolyl)-1H-pyrazol-1-yl)pyrimidin-4-yl) morpholine (Compound 330)

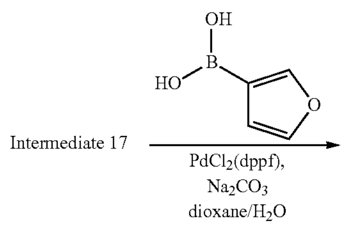

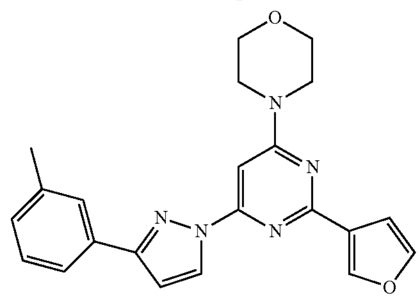

Pd/C, $H_2$
DCM

A

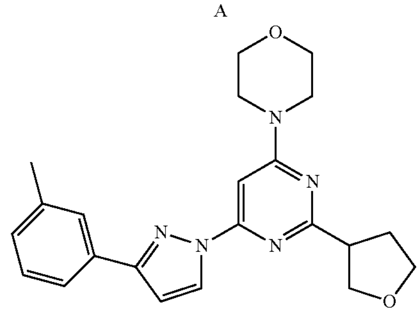

chiral SFC

B

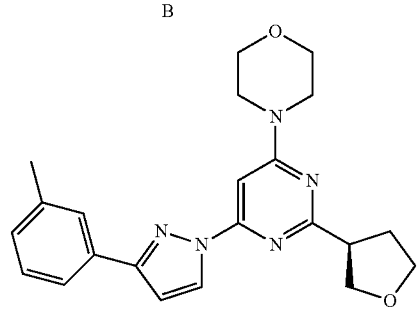

+

329

-continued

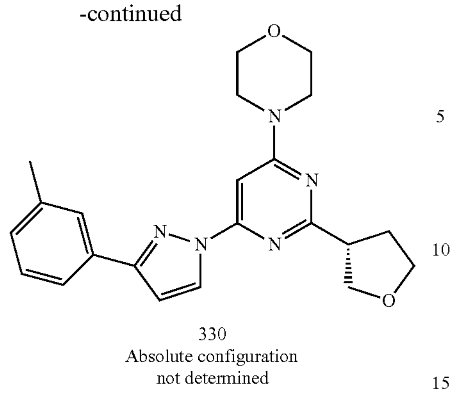

330
Absolute configuration
not determined

Preparation of A

The mixture of Intermediate 17 (120 mg, 0.27 mmol), furan-3-ylboronic acid (33 mg, 0.297 mmol), Pd(dppf)$Cl_2$ (20 mg, 0.027 mmol) and $Na_2CO_3$ (57 mg, 0.54 mmol) in dioxane and water (5:1, 12 mL) under an atmosphere of nitrogen was stirred at 100° C. for 12 hrs. After cooling to room temperature, the mixture was poured into water (30 mL) and extracted with EtOAc (30 mL×2). The combined organic layers were washed with brine (20 mL×3), dried over $Na_2SO_4$, filtered and concentrated to dryness. The crude product was purified by chromatography on silica gel eluting with petroleum ether:EtOAc=3:1 to get the desired product A (90 mg, 86.5%) as a withe solid.

Preparation of B

The mixture of A (90 mg, 0.23 mmol) and Pd/C (10 wt %) (0.05 g, 0.046 mmol) in DCM (10 mL) was stirred under $H_2$ at room temperature overnight. The reaction mixture was filtered, concentrated and purified by Prep-HPLC to get the desired product B (80 mg, 88.8%) as a white solid.

Preparation of Compound 329 and Compound 330

B (80 mg) was separated by chiral SFC to give Compound 329 (35 mg, 44%, 1st Peak) and Compound 330 (35 mg, 44%, 2nd Peak). The stereochemistry of the enantiomers was not determined.

Compound 329 (1st Peak)

$^1$H NMR (600 MHz, $CDCl_3$): δ 8.62 (d, J=6.0 Hz, 1H), 7.75 (s, 1H), 7.70 (d, J=6.0 Hz, 1H), 7.33 (t, J=6.0 Hz, 1H), 7.20 (d, J=6.0 Hz, 1H), 7.05 (s, 1H), 6.75 (d, J=6.0 Hz, 1H, 4.21 (t, J=6.0 Hz, 1H), 4.09-4.02 (m, 2H), 3.96-3.92 (m, 1H), 3.83-3.76 (m, 8H), 3.64-3.56 (m, 1H), 2.43 (s, 3H), 2.40-2.29 (m, 2H).

Compound 330 (2nd Peak)

$^1$H NMR (600 MHz, $CDCl_3$): δ 8.62 (d, J=6.0 Hz, 1H), 7.75 (s, 1H), 7.70 (d, J=6.0 Hz, 1H), 7.33 (t, J=6.0 Hz, 1H), 7.20 (d, J=6.0 Hz, 1H), 7.05 (s, 1H), 6.75 (d, J=6.0 Hz, 1H, 4.21 (t, J=6.0 Hz, 1H), 4.09-4.02 (m, 2H), 3.96-3.92 (m, 1H), 3.83-3.76 (m, 8H), 3.64-3.56 (m, 1H), 2.43 (s, 3H), 2.40-2.29 (m, 2H).

Synthesis of (3R,5R)-5-(4-morpholino-6-(3-(m-tolyl)-1H-pyrazol-1-yl)pyrimidin-2-yl)tetrahydrofuran-3-ol (Compound 331) and (3S,5R)-5-(4-morpholino-6-(3-(m-tolyl)-1H-pyrazol-1-yl)pyrimidin-2-yl)tetrahydrofuran-3-ol (Compound 332)

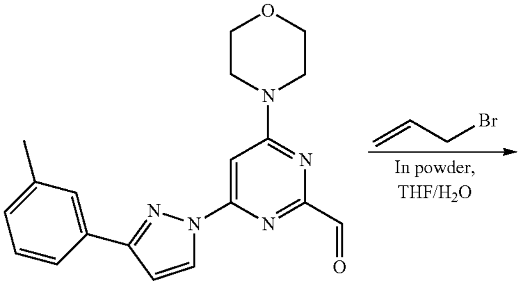

4-morpholino-6-(3-(m-tolyl)-1H-pyrazol-1-yl)pyrimidine-2-carbaldehyde

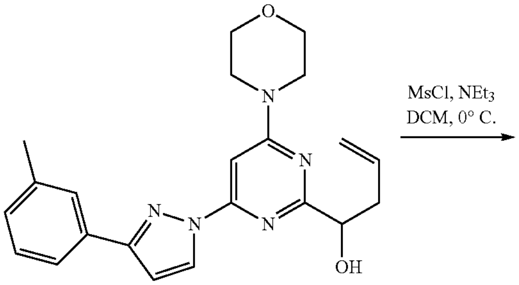

A

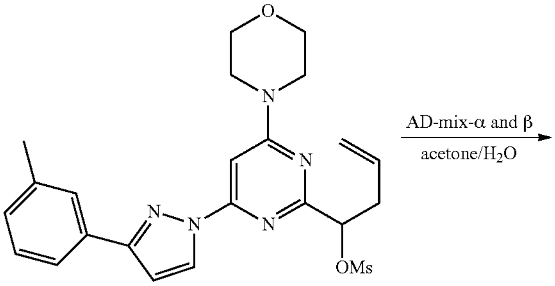

B

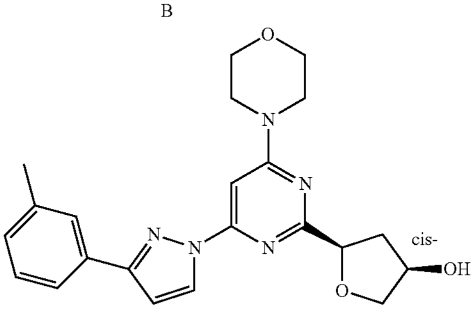

+

331

-continued

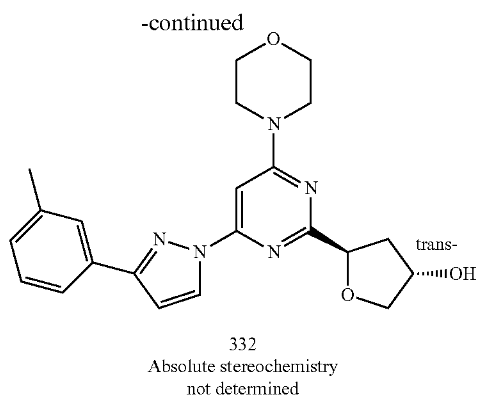

332
Absolute stereochemistry not determined

Preparation of A

To a mixture of 4-morpholino-6-(3-(m-tolyl)-1H-pyrazol-1-yl)pyrimidine-2-carbaldehyde (0.50 g, 1.43 mmol) (synthetic procedure as described for Intermediate 25) in THF (20 mL)/$H_2O$ (10 mL) was added In powder (247 mg, 2.15 mmol) and allyl bromide (0.19 mL, 2.20 mmol) at rt and the reaction mixture was stirred for 2.5 hrs. After the reaction was completed, the mixture was diluted with ethyl acetate/water. The water phase was extracted with DCM three times, and the combined organic layers were washed with brine, dried over $Na_2SO_4$, filtered and concentrated under reduced pressure. The resulting crude product was purified by chromatography on silica gel eluting with petroleum ether: EtOAc=8:1-7:1 to get A (500 mg, 90%) as a yellow solid.

Preparation of B

To a mixture of A (0.50 g, 1.28 mmol) in dry DCM (12 mL) was $NEt_3$ (0.44 mL, 3.17 mmol) and MsCl (0.12 mL, 1.55 mmol) at 0° C. under $N_2$ atmosphere and the reaction mixture was stirred for 1 h. After the reaction was completed, the mixture was diluted with ethyl acetate/water. The organic layer was washed with saturated $NaHCO_3$ (aq) and brine, dried over $Na_2SO_4$, filtered and concentrated to crude B without further purification.

Preparation of Compound 331 and Compound 332

To a mixture of B in acetone (20 mL)/$H_2O$ (20 mL) was added AD-mix (5 g) and the reaction mixture was stirred overnight. The mixture was then diluted with ethyl acetate and washed by water and brine, dried over $Na_2SO_4$, filtered and concentrated under reduced pressure. The resulting crude product was purified by chromatography on silica gel eluting with petroleum ether:EtOAc=1.5:1-1:1 to get Compound 331 (180 mg) as a white foam and Compound 332 (310 mg) as a white solid.

Compound 331:

$^1$H NMR (400 MHz, $CDCl_3$): δ 8.49 (s, 1H), 7.74 (s, 1H), 7.69 (d, J=7.7 Hz, 1H), 7.33 (t, J=7.6 Hz, 1H), 7.20 (d, J=7.5 Hz, 1H), 7.13 (s, 1H), 6.77 (d, J=2.7 Hz, 1H), 5.08 (dd, J=10.0, 1.8 Hz, 1H), 4.50-4.46 (m, 1H), 4.23 (d, J=9.1 Hz, 1H), 3.93 (dd, J=9.3, 2.8 Hz, 1H), 3.86-3.69 (m, 8H), 2.57-2.47 (m, 1H), 2.43 (s, 3H), 2.31-2.24 (m, 1H).

Compound 332:

$^1$H NMR (400 MHz, $CDCl_3$): 8.62 (d, J=2.5 Hz, 1H), 7.75 (s, 1H), 7.69 (d, J=7.7 Hz, 1H), 7.33 (t, J=7.6 Hz, 1H), 7.19 (d, J=7.5 Hz, 1H), 7.11 (s, 1H), 6.75 (d, J=2.5 Hz, 1H), 5.20 (t, J=7.6 Hz, 1H), 4.72-4.68 (m, 1H), 4.29 (dd, J=9.6, 3.9 Hz, 1H), 3.98 (d, J=9.6 Hz, 1H), 3.86-3.69 (m, 8H), 2.54-2.32 (m, 5H).

Synthesis of 4-(1-methyl-5-(3-(m-tolyl)-1H-pyrazol-1-yl)-1H-pyrrolo[3,2-b]pyridin-7-yl)morpholine (Compound 333)

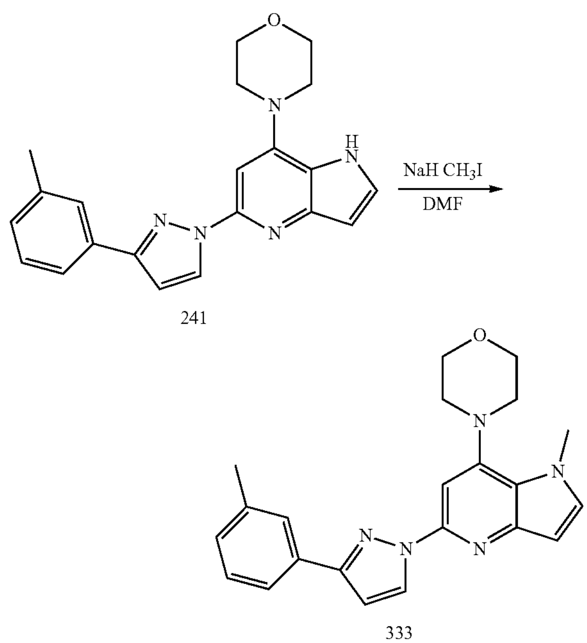

241

333

To a solution of Compound 241 (40 mg, 0.11 mmol) in DMF (5 mL) was added NaH (20 mg, 0.5 mmol) at −10° C. and stirred for 10 min, then MeI (20 mg, 0.12 mmol) was added to above solution. The resulting mixture was stirred at −10° C. for 30 min. After which period, the reaction was quenched by the addition of water (15 mL); and the mixture extracted was extracted with EtOAc (10 mL×2). The combined organic layers were washed with brine (10 mL×3), dried over $Na_2SO_4$, filtered, concentrated to dryness. The crude residue was purified by chromatography on silica gel eluting with petroleum ether:EtOAc=1:1 to give Compound 333 (16 mg, 39.0%) as light white solid.

$^1$H NMR (400 MHz, $CDCl_3$) δ 8.72 (s, 1H), 7.79 (s, 2H), 7.74 (d, J=8 Hz, 1H), 7.68 (s, 1H), 7.33 (t, J=6 Hz, 1H), 7.20-7.16 (m, 2H), 6.78 (d, J=4 Hz, 1H), 6.68 (s, 1H), 4.07 (s, 3H), 3.97 (t, J=4 Hz, 4H), 3.25 (t, J=4 Hz, 4H), 2.44 (s, 3H).

Synthesis of 4-(2-methyl-5-(3-(m-tolyl)-1H-pyrazol-1-yl)-1H-pyrrolo[3,2-b]pyridin-7-yl)morpholine (Compound 334)

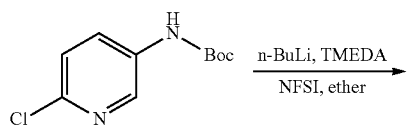

-continued

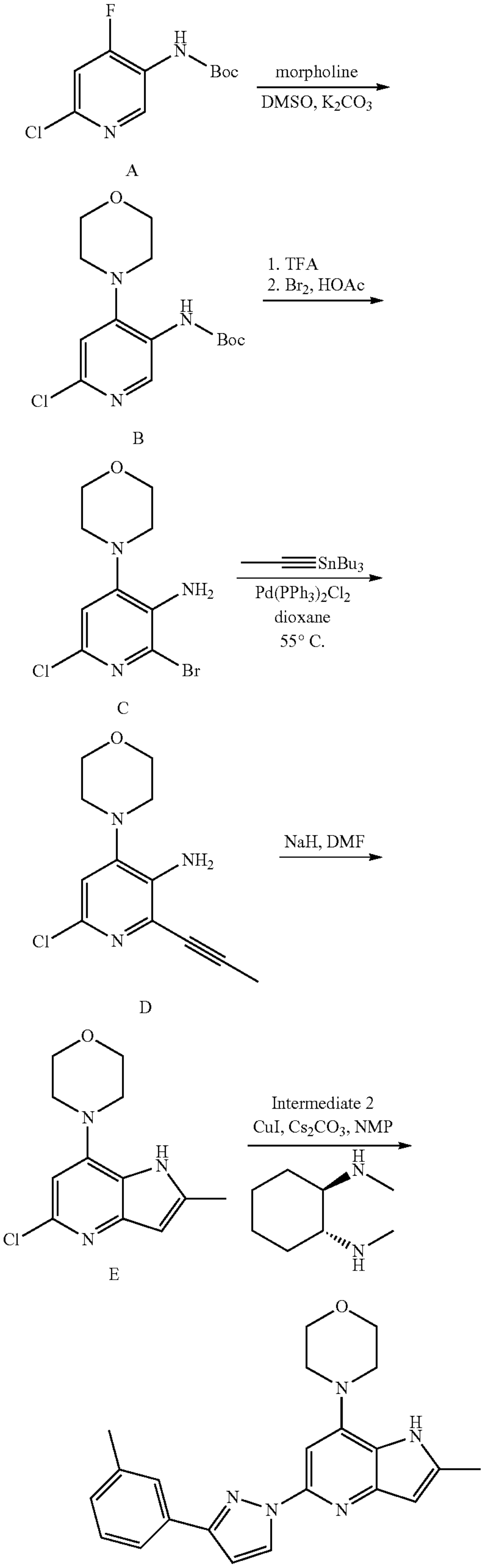

A

B

C

D

E

334

Preparation of A

To a solution of tert-butyl (6-chloropyridin-3-yl)carbamate (7.0 g, 30.6 mmol) and TMEDA (8.5 g, 73.5 mmol) in anhydrous $Et_2O$ (140 mL) was added n-BuLi (34 mL, 85.7 mmol) dropwise below −60° C. The reaction solution was then stirred at −60° C. for an additional 10 minutes before warming up between −25° C. to −10° C. for 2 hrs. After then, the reaction solution was cooled down to −60° C. again, and a solution of NFSI (15.5 g, 48.9 mmol) in THF (30 mL) was added while keeping the temperature below −50° C. It precipitated on addition and stirring became difficult. The reaction mixture was then allowed to slowly warm to 0° C. over 1 hour and then quenched with saturated ammonium chloride solution (20 mL). The biphasic layers were separated and the aqueous layer was extracted with EA (50 mL×3). The combined organic layers were washed with brine, dried over anhydrous $Na_2SO_4$, filtered, concentrated to dryness. The residue was purified by chromatography on silica gel eluting with petroleum ether:EtOAc=100:1 to 10:1 to give the desired compound A (3.7 g, 49.3%) as yellow oil.

Preparation of B

To a solution of crude A (3.5 g, 93.03 mmol) and morpholine (2.5 g, 28.4 mmol) in DMSO (60 mL) was added $K_2CO_3$ (4.9 g, 35.5 mmol). The resulting reaction mixture was stirred at room temperature for 20 h before the addition of water (30 mL), which was then extracted with EtOAc (30 mL×2). The combined organic layers were washed with brine (20 mL×3), dried over $Na_2SO_4$, filtered, concentrated to dryness. The residue was purified by chromatography on silica gel eluting with petroleum ether:EtOAc=8:1 to 4:1 to give the desired compound B (3 g, 67%) as an off-white solid.

Preparation of C

To a solution of B (2.0 g, 6.4 mmol) in AcOH (30 mL) was added $Br_2$ (6 mL) at room temperature. The resulting mixture was stirred overnight and concentrated under reduced pressure. Water (30 mL) was added to above residue before it was extracted with EtOAc (30 mL×2). The combined organic layer was dried over $Na_2SO_4$, filtered, concentrated to dryness. The residue was purified by chromatography on silica gel eluting with petroleum ether:EtOAc=8:1 to 4:1 to give the desired compound C (500 mg, 27%) as a brown solid.

Preparation of D

The mixture of C (400 mg, 1.4 mmol), tributyl(prop-1-yn-1-yl)stannane (814 mg, 2.4 mmol), $(Ph_3P)_2PdCl_2$ (290 mg, 0.42 mmol) in dioxane (10 mL) was sealed and stirred at 60° C. for 4 hrs under $N_2$. After which period, water (10 mL) was added to above reaction solution, and the resulting mixture was extracted with EtOAc (20 mL×2). The combined organic layers were washed with brine (10 mL×3), dried over $Na_2SO_4$, filtered, concentrated to dryness. The crude residue was purified by chromatography on silica gel eluting with petroleum ether:EtOAc=10:1 to 5:1 to give the desired compound D (120 mg, 34.7%) as a white solid.

Preparation of E

To a solution of D (130 mg, 0.52 mmol) in DMF (5 mL) was added NaH (100 mg, 2.59 mmol) at room temperature.

The resulting solution was stirred at 60° C. for 2 hrs. After cooling down to the room temperature, the reaction mixture was extracted with EtOAc (20 mL×2) after the addition of water (20 mL). The combined organic layers were washed with brine (20 mL×3), dried over $Na_2SO_4$, filtered, concentrated to dryness. The crude product was purified by chromatography on silica gel eluting with petroleum ether: EtOAc=8:1 to 3:1 to give the desired compound E (60 mg, 46%) as an off-white solid.

Compound 334:

The mixture of -E (65 mg, 0.26 mmol), Intermediate 2 (45 mg, 0.28 mmol), CuI (20 mg, 0.10 mmol), trans-$N_1$,$N_2$-dimethylcyclohexane-1,2-diamine (15 mg, 0.10 mmol) and $Cs_2CO_3$ (169 mg, 0.52 mmol) in NMP (5 mL) was sealed and placed in a microwave reactor at 200° C. for 4 hrs. After which period, water (10 mL) was added to above reaction system and the resulting mixture was extracted with EtOAc (20 mL×2). The combined organic layers were washed with brine (10 mL×3), dried over $Na_2SO_4$, filtered, concentrated to dryness. The crude product was purified by Prep-TLC to get Compound 334 (11 mg, 11.5%) as an off-white solid.

$^1$H NMR (400 MHz, $CDCl_3$) δ 8.63 (s, 1H), 8.04 (s, 1H), 7.78 (s, 1H), 7.73 (d, J=7.3 Hz, 1H), 7.45 (s, 1H), 7.32 (t, J=7.5 Hz, 1H), 7.15 (d, J=7.3 Hz, 1H), 6.75 (d, J=1.9 Hz, 1H), 6.37 (s, 1H), 3.98-3.90 (m, 4H), 3.41-3.31 (m, 4H), 2.50 (s, 3H), 2.43 (s, 3H).

Synthesis of 4-(3-methyl-5-(3-(m-tolyl)-1H-pyrazol-1-yl)-1H-pyrrolo[3,2-b]pyridin-7-yl)morpholine (Compound 335)

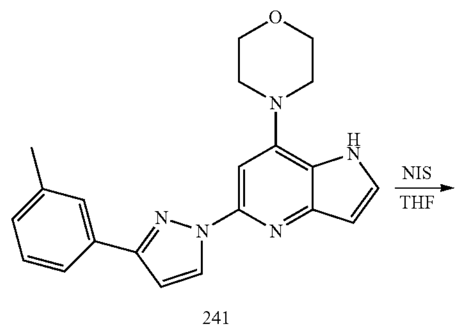

241

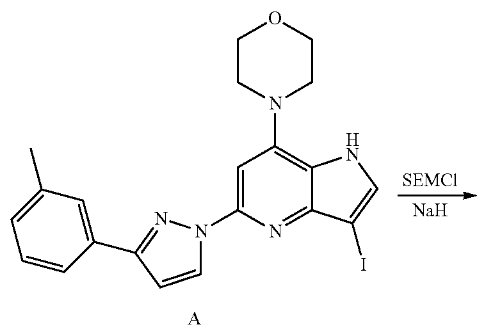

A

-continued

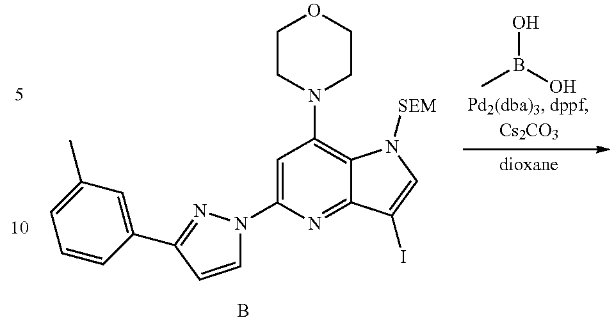

B

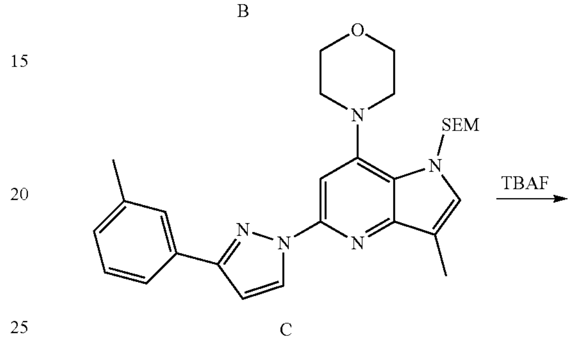

C

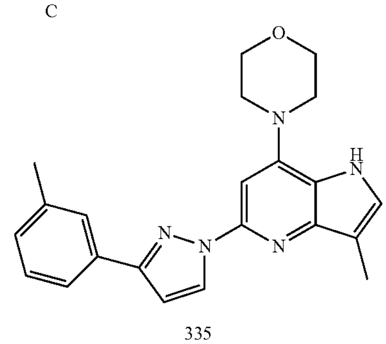

335

Preparation of A

To a solution of Compound 241 (440 mg, 1.2 mmol) in tetrahydrofuran (6 mL) was added N-Iodosuccinimide (176 mg, 2.6 mmol) at room temperature. The resulting mixture was stirred for 15 mins at 25° C. The mixture was poured into water (20 mL) after stirring overnight and then extracted with EtOAc (20 mL×2). The combined organic layers were washed with brine (20 mL×2), dried over $Na_2SO_4$, filtered, concentrated to dryness. The residue was purified by chromatography on silica gel eluting with petroleum ether:EtOAc=3:1 to get the desired product A (284 mg, 48.0%) as a yellow solid.

Preparation of B

To a solution of A (284 mg, 0.585 mmol) in DMF (5 mL) was added NaH (80 mg, 2 mmol) at −10° C. and stirred for 10 min. Then SEMCl (154 mg, 0.928 mmol) was added to above solution and the resulting mixture was stirred at −10° C. for 30 min. Water (15 mL) was added to quench the reaction, and the resulting mixture was extracted with EtOAc (10 mL×2). The combined organic layers were washed with brine (10 mL×3), dried over $Na_2SO_4$, filtered, concentrated to dryness. The crude product was purified by chromatography on silica gel eluting with petroleum ether: EtOAc=3:1 to give the desired product B (255 mg, 70.8%) as light yellow solid.

Preparation of C

To a solution of B (255 mg, 0.415 mmol) in dioxane (5 mL) was added methylboronic acid (55 mg, 0.916 mmol), $Pd_2(dba)_3$ (90 mg, 0.098 mmol), $Cs_2CO_3$ (318 mg, 0.975 mmol) and DPPF (44 mg, 0.079 mmol) under an atmosphere of nitrogen and the reaction mixture was stirred at 100° C. for 12 h. After which period, the mixture was cooled down to room temperature, poured into water (30 mL) and then extracted with EtOAc (30 mL×2). The combined organic layers were washed with brine (20 mL×2), dried over $Na_2SO_4$, filtered, concentrated to dryness. The residue was purified by chromatography on silica gel eluting with petroleum ether:EtOAc=3:1 to give the desired product C (80 mg, 39.4%) as a withe solid.

Preparation Compound 335

To a solution of C (80 mg, 0.159 mmol) in tetrahydrofuran (5 mL) was added TBAF trihydrate (69 mg, 0.264 mmol) and ethylenediamine monohydrate (1.5 mL) at room temperature. The resulting mixture was stirred at 80° C. for 15 hrs before pouring into water (20 mL), and then extracted with EtOAc (20 mL×2). The combined organic layers were washed with brine (20 mL×2), dried over $Na_2SO_4$, filtered, concentrated to dryness. The residue was purified by chromatography on silica gel eluting with petroleum ether: EtOAc=1:1 to get the desired product Compound 335 (36 mg, 64.4%) as a white solid.

$^1H$ NMR (400 MHz, $CDCl_3$) δ 8.73 (d, J=4.0 Hz, 1H), 7.78 (s, 1H), 7.74 (d, J=4.0 Hz, 1H), 7.46 (s, 1H), 7.33 (t, J=8.0 Hz, 1H), 7.17 (d, J=4.0 Hz, 2H), 6.78 (d, J=4.0 Hz, 1H), 3.96-3.94 (m, 4H), 3.42-3.40 (m, 4H), 2.44 (s, 3H), 2.39 (s, 3H).

Synthesis of 4-(2-methyl-5-(3-(m-tolyl)-1H-pyrazol-1-yl)pyrazolo[1,5-a]pyrimidin-7-yl)morpholine (Compound 336)

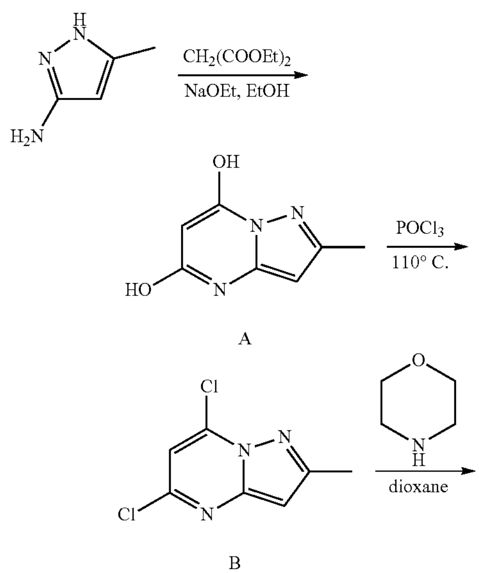

A

B

-continued

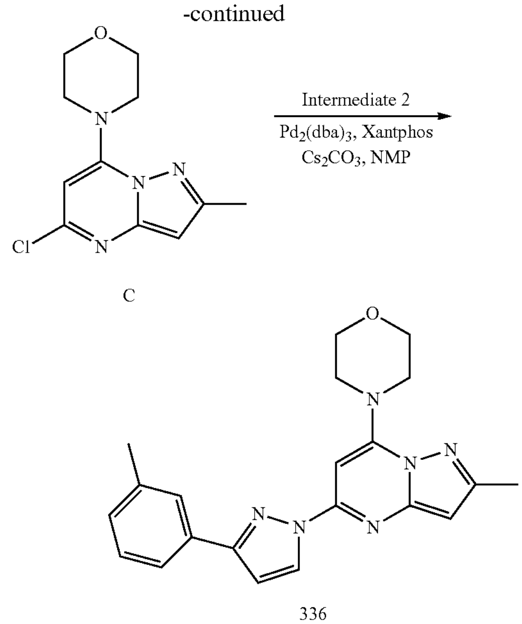

C

336

Preparation of A

To a solution of 5-methyl-1H-pyrazol-3-amine (5.0 g, 51.5 mmol) and diethylmalonate (9.5 mL, 103 mmol) in EtOH (150 mL) was added NaOEt (7.0 g, 103 mmol). The mixture was stirred at 80° C. overnight and then cooled down to room temperature. The formed solid was collected by filtration, which was washed with EtOAc and dried to get desired compound B (17.7 g, >100%, sodium salt) as a brown solid.

Preparation of B

The mixture of A (1.0 g, 6.1 mmol) and $POCl_3$ (5 mL) was stirred at 110° C. for 4 hrs and then concentrated under reduced pressure. The residue was poured into iced water (10 mL) and extracted with EtOAc (20 mL). The organic phase was washed with brine (10 mL), dried over $Na_2SO_4$, filtered and concentrated to dryness. The resulting residue was purified by chromatography on silica gel eluting with petroleum ether:EtOAc=10:1 to give the desired compound B (230 mg, 19%) as a white solid.

Preparation of C

To a solution of B (230 mg, 1.1 mmol) in dioxane (5 mL) was added morpholine (198 mg, 2.2 mmol). The mixture was stirred at room temperature for 2 hrs and then concentrated to dryness under reduced pressure. The resulting crude product was purified by chromatography on silica gel eluting with petroleum ether:EtOAc=5:1-2:1 to give the desired compound C (230 mg, 80%) as a white solid.

Preparation of Compound 336

The mixture of C (100 mg, 0.4 mmol), Intermediate 2 (63 mg, 0.4 mmol), $Pd_2(dba)_3$ (37 mg, 0.04 mmol), Xantphos (23 mg, 0.04 mmol) and $Cs_2CO_3$ (260 mg, 0.8 mmol) in NMP (3 mL) was placed in a microwave reactor at 100° C. under nitrogen atmosphere for 1.2 hours. After which period, the mixture was diluted with EtOAc (20 mL) and washed by brine (10 mL×5), dried over $Na_2SO_4$, filtered, concentrated to dryness. The resulting residue was purified by chromatography on silica gel eluting with petroleum ether:EtOAc=5:1 to give the desired product Compound 336 (80 mg, 54%) as a white solid.

$^1H$ NMR (400 MHz, $CDCl_3$) δ 8.66 (d, J=2.8 Hz, 1H), 7.76 (s, 1H), 7.71 (d, J=7.6 Hz, 1H), 7.34 (t, J=7.6 Hz, 1H), 7.19 (d, J=7.6 Hz, 1H), 6.99 (s, 1H), 6.80 (d, J=2.8 Hz, 1H), 4.02-4.00 (m, 4H), 3.89-3.86 (m, 4H), 2.49 (s, 3H), 2.44 (s, 3H).

Synthesis of 4-(3-methyl-5-(3-(m-tolyl)-1H-pyrazol-1-yl)pyrazolo[1,5-a]pyrimidin-7-yl)morpholine (Compound 337)

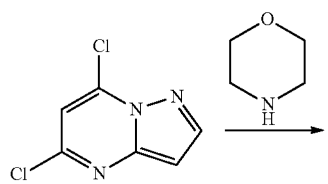

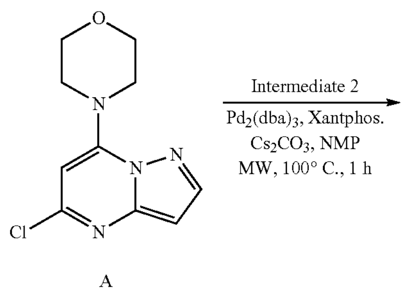

A

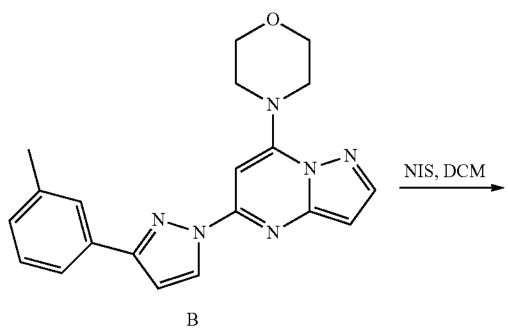

B

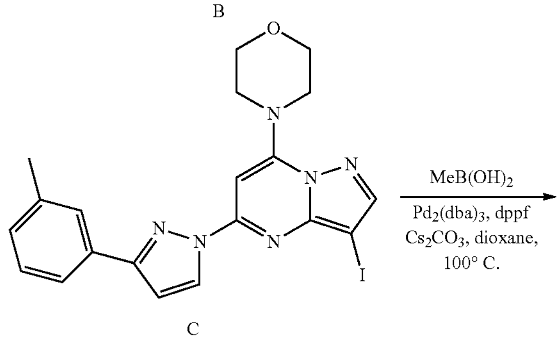

C

-continued

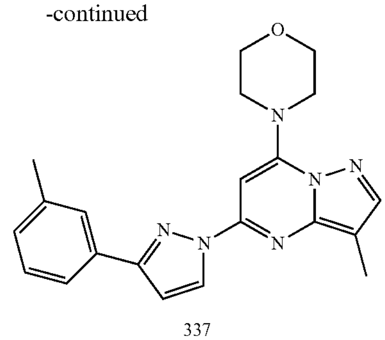

337

Preparation of A

To a solution of 5,7-dichloropyrazolo[1,5-a]pyrimidine (820 mg, 4.36 mmol) in dioxane (20 mL) was added morpholine (759 mg, 8.72 mmol) at room temperature. The solution was stirred at room temperature for 30 minutes before the dilution with water. The resulting mixture was extracted with EtOAc (50 mL×3). The combined organic layers were washed with brine (50 mL×3), dried over $Na_2SO_4$, filtered and concentrated to dryness. The residue was purified by chromatography on silica gel eluting with petroleum ether:EtOAc=5:1-3:1 to give desired compound A (958 mg, 92%) as yellow oil.

Preparation of B

A mixture of A (800 mg, 3.4 mmol), Intermediate 2 (532 mg, 3.4 mmol), $Pd_2(dba)_3$ (616 mg, 0.67 mmol), Xantphos (388 mg, 0.67 mmol) and $Cs_2CO_3$ (2.19 g, 6.7 mmol) in NMP (10 mL) was placed in a microwave reactor at 120° C. under and nitrogen atmosphere for 1 hour. After which period, the mixture was diluted with EtOAc (50 mL) and washed by brine (30 mL×5), dried over $Na_2SO_4$, filtered and concentrated to dryness. The residue was purified by chromatography on silica gel eluting with petroleum ether:EtOAc=10:1 to get compound B (365 mg, 30%) as yellow oil.

Preparation of C

To a solution of B (365 mg, 1 mmol) in DCM (3 mL) was added NIS (247.5 mg, 1.1 mmol) and 1 mL THF to dissolve NIS. The mixture was stirred at room temperature for 2 hours. After then, the mixture was diluted with DCM (50 mL) and washed by brine (30 mL×3), dried over $Na_2SO_4$, filtered, concentrated to dryness. The resulting crude product was purified by chromatography on silica gel eluting with petroleum ether:EtOAc=10:1-3:1 to give the desired compound C (400 mg, 82%) as yellow oil.

Preparation of Compound 337

A mixture of C (400 mg, 0.82 mmol), $MeB(OH)_2$ (59 mg, 0.98 mmol), dppf (90.8 mg, 0.164 mmol), $Pd_2(dba)_3$ (150 mg, 0.164 mmol) and $Cs_2CO_3$ (534.6 mg, 1.64 mmol) in dioxane (4 mL) was stirred at 100° C. under nitrogen atmosphere overnight. After cooling to the room temperature, the mixture was diluted with EtOAc (50 mL) and washed with brine (50 mL×3), dried over $Na_2SO_4$, filtered and concentrated to dryness. The residue was purified by Prep-HPLC to get the desired product Compound 337 (14 mg, 4.6%) as a white solid.

$^1H$ NMR (400 MHz, $CDCl_3$) δ 8.71 (d, J=2.8 Hz, 1H), 7.89 (s, 1H), 7.77 (s, 1H), 7.73 (d, J= 7.6 Hz, 1H), 7.35 (t, J=7.6 Hz, 1H), 7.20 (d, J=7.6 Hz, 1H), 7.02 (s, 1H), 6.81 (d, J=2.8 Hz, 1H), 4.02-4.00 (m, 4H), 3.86-3.83 (m, 4H), 2.45 (s, 3H), 2.34 (s, 3H).

Synthesis of 4-(2-(2-(1-methyl-1H-pyrazol-5-yl)ethyl)-6-(3-(m-tolyl)-1H-pyrazol-1-yl)pyrimidin-4-yl)morpholine (Compound 338)

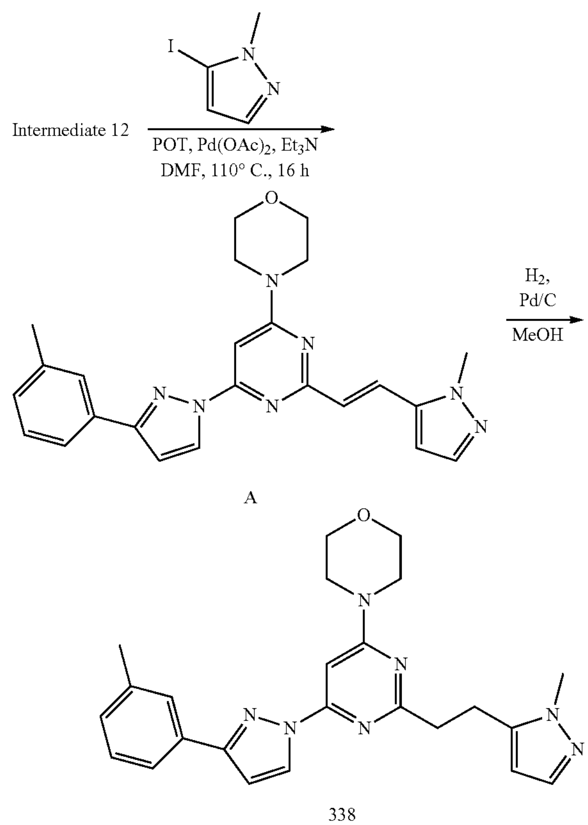

A

338

Preparation of A

A mixture of Intermediate 12 (85 mg, 0.245 mmol), 5-iodo-1-methyl-1H-pyrazole (87 mg, 0.42 mmol), tri(o-tolyl)phosphine (30 mg, 0.098 mmol), $Pd(OAc)_2$ (17 mg, 0.074 mmol) and triethylamine (74 mg, 0.735 mmol) in DMF (2 mL) was stirred at 105° C. under nitrogen atmosphere for 16 hours. After cooling to the room temperature, the mixture was diluted with EtOAc (40 mL), washed with brine (30 mL×4), dried over $Na_2SO_4$, filtered and concentrated to dryness. The resulting crude product was purified by chromatography on silica gel eluting with petroleum ether:EtOAc=3:1-1:2 to get A (43 mg, 41%) as a white solid.

Preparation of Compound 338

To a solution of A (43 mg, 0.100 mmol) in MeOH was added Pd/C (10%, 10 mg). The mixture stirred at room temperature under hydrogen atmosphere for 16 hours, filtered and concentrated to dryness. The resulting crude product was purified by chromatography on silica gel eluting with petroleum ether:EtOAc=10:1-3:1 to get Compound 338 (35 mg, 82%) as a white solid.

$^1H$ NMR (400 MHz, $CDCl_3$): δ 8.57 (d, J=2.7 Hz, 1H), 7.80-7.65 (m, 2H), 7.44-7.28 (m, 2H), 7.19 (d, J=7.6 Hz, 1H), 7.05 (s, 1H), 6.76 (d, J=2.7 Hz, 1H), 6.08 (d, J=1.4 Hz, 1H), 3.86-3.71 (m, 11H), 3.19-3.03 (m, 4H), 2.43 (s, 3H).

Synthesis of 2-(1-(4-morpholino-6-(3-(m-tolyl)-1H-pyrazol-1-yl)pyrimidin-2-yl)-1H-imidazol-4-yl)ethan-1-ol (Compound 339)

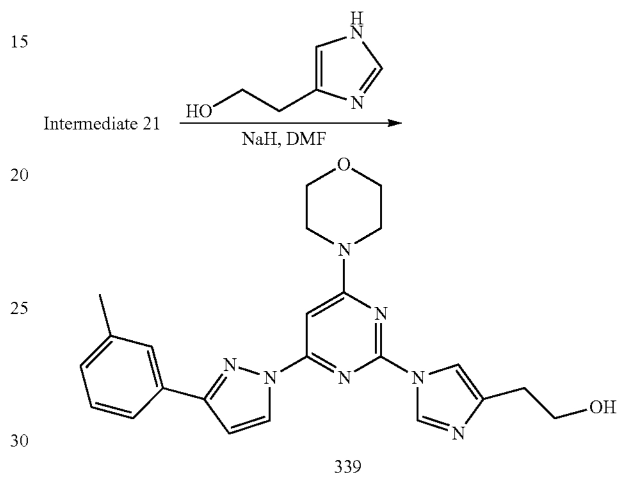

339

To a solution of 2-(1H-imidazol-4-yl)ethan-1-ol (50 mg, 0.446 mmol) in DMF (5 mL) was added NaH (35 mg, 0.892 mmol) at −10° C. and the mixture was stirred for 10 min at this temperature, then Intermediate 21 (178 mg, 0.446 mmol) was added. The resulting mixture was stirred at −10° C.-0° C. for 3 hrs before the addition of ice-water, and then extracted with EtOAc (10 mL×2). The combined organic layers were washed with brine (10 mL×3), dried with $Na_2SO_4$, filtered, concentrated and purified by chromatography on silica gel eluting with DCM:MeOH=50:1-20:1 to give the compound Compound 339 (42 mg, 22%) as a white powder.

$^1H$ NMR (400 MHz, DMSO-$d_6$): δ 8.92 (d, J=2.7 Hz, 1H), 8.65 (d, J=1.2 Hz, 1H), 7.85 (s, 1H), 7.81 (d, J=6.4 Hz, 2H), 7.37 (t, J=7.6 Hz, 1H), 7.23 (d, J=7.5 Hz, 1H), 7.14 (d, J=2.7 Hz, 1H), 7.08 (s, 1H), 3.82-3.72 (m, 8H), 3.70-3.65 (m, 2H), 2.70 (t, J=7.0 Hz, 2H), 2.40 (s, 3H).

Synthesis of (R)-4-(6-(3-(3-(1-methoxyethyl)phenyl)-1H-pyrazol-1-yl)-2-(2-(1-methyl-1H-pyrazol-4-yl)ethoxy)pyrimidin-4-yl)morpholine (Compound 340) and (S)-4-(6-(3-(3-(1-methoxyethyl)phenyl)-1H-pyrazol-1-yl)-2-(2-(1-methyl-1H-pyrazol-4-yl)ethoxy)pyrimidin-4-yl)morpholine (Compound 341)

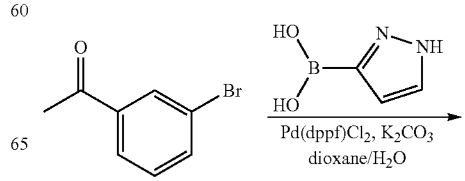

-continued

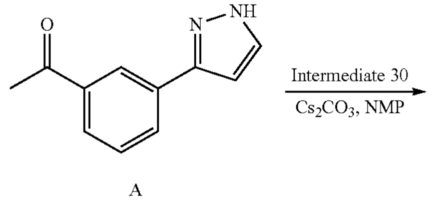

A

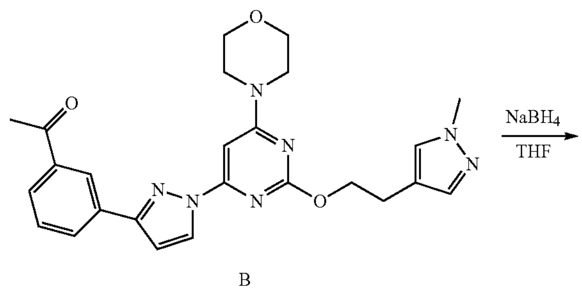

B

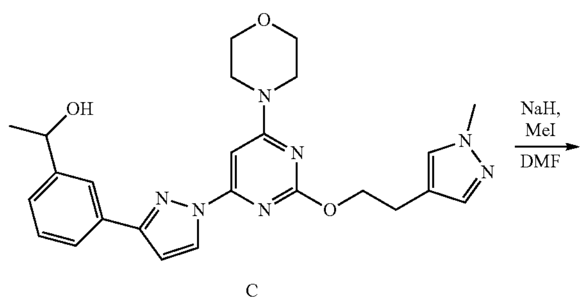

C

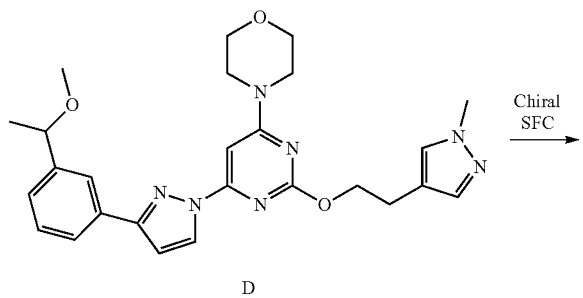

D

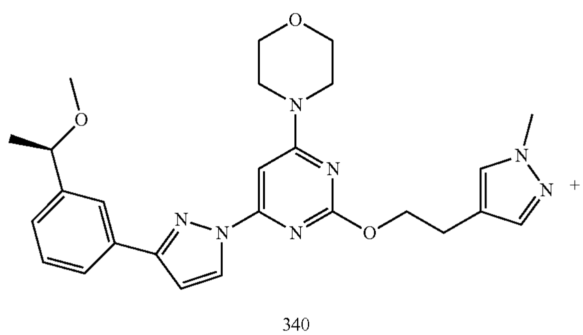

340

+

-continued

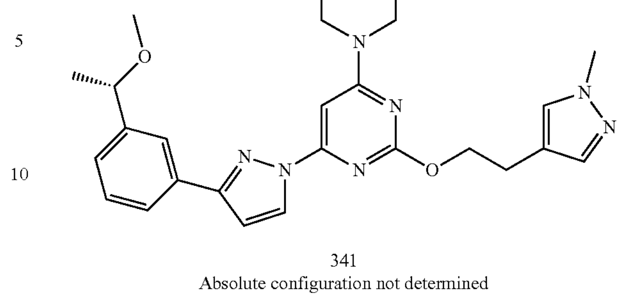

341
Absolute configuration not determined

Preparation of A

A mixture of 1-(3-bromophenyl)ethan-1-one (600 mg, 3.02 mmol), (1H-pyrazol-3-yl)boronic acid (507 mg, 4.53 mmol), Pd(dppf)$Cl_2$ (439 mg, 0.60 mmol) and $K_2CO_3$ (834 mg, 6.04 mmol) in 1,4-dioxane (24 mL) and $H_2O$ (6 mL) was stirred at 100° C. under nitrogen atmosphere for 16 hours. After cooling to the room temperature, the mixture was diluted with EtOAc (50 mL) and washed by brine (30 mL×2), dried over $Na_2SO_4$, filtered and concentrated to dryness. The resulting crude product was purified by chromatography on silica gel eluting with petroleum ether: EtOAc=5:1-2:1 to get the desired compound A (472 mg, 84%) as yellow oil.

Preparation of B

A mixture of A (472 mg, 2.54 mmol), Intermediate 30 (904 mg, 2.80 mmol) and $Cs_2CO_3$ (1.6 g, 5.08 mmol) in NMP (15 mL) was stirred at 150° C. overnight under nitrogen atmosphere. After cooling to the room temperature, the mixture was diluted with EtOAc (50 mL) and washed by brine (30 mL×4), dried over $Na_2SO_4$, filtered and concentrated to dryness. The residue was purified by chromatography on silica gel eluting with petroleum ether:EtOAc=4:1-1:1 to give the desired compound B (740 mg, 62%) as a light yellow solid.

Preparation of C

To a solution of B (740 mg, 1.56 mmol) in THF (10 mL) was added $NaBH_4$ (119 mg, 3.12 mmol) at 0° C., the mixture was stirred at room temperature for 5 hours under nitrogen atmosphere, Then the reaction was quenched with addition of water (60 mL) at 0° C., and the resulting mixture was extracted with EtOAc (20 mL×3). The combined organic layers were washed with brine (40 mL×4), dried over $Na_2SO_4$, filtered and concentrated to dryness. The residue was purified by chromatography on silica gel eluting with petroleum ether:EtOAc=2:1-1:2 to give desired product C (470 mg, 63%) as light yellow oil.

Preparation of D

To a solution of C (250 mg, 0.53 mmol) in DMF (6 mL) was added NaH (42 mg, 1.06 mmol) at −10° C., the mixture was stirred at room temperature for 15 minutes before cooling down to −10° C. again. MeI (114 mg, 0.80 mmol) was added slowly to above solution, the reaction mixture was stirred at room temperature for another 1 hour. After which period, the reaction mixture was poured into water (50 mL) and extracted with EtOAc (20 mL×3). The combined organic layers were washed with brine (40 mL×4), dried over $Na_2SO_4$, filtered and concentrated to dryness. The resulting crude product was purified by chromatography on silica gel eluting with petroleum ether:EtOAc=4:1-1:1 to get the desired compound D (200 mg, 78%) as light-yellow oil.

Preparation Compound 340 and Compound 341

D was separated by chiral HPLC (SFC) to get targets Compound 340 (80 mg, $1^{st}$ peak) and Compound 341 (80 mg, $2^{nd}$ peak). The stereochemistry of the enantiomers was not determined.

Compound 340 ($1^{st}$ Peak):

$^1H$ NMR (400 MHz, DMSO-d6) δ 8.61 (d, J=2.7 Hz, 1H), 7.90 (d, J=1.8 Hz, 2H), 7.58 (s, 1H), 7.46 (t, J=7.9 Hz, 1H), 7.34 (d, J=5.7 Hz, 2H), 7.09 (d, J=2.7 Hz, 1H), 6.90 (s, 1H), 4.41 (dd, J=13.8, 6.8 Hz, 3H), 3.79 (s, 3H), 3.69 (d, J=3.7 Hz, 8H), 3.16 (s, 3H), 2.86 (t, J=7.0 Hz, 2H), 1.39 (d, J=6.3 Hz, 3H).

Compound 341 ($2^{nd}$ Peak):

$^1H$ NMR (400 MHz, DMSO-$d_6$) δ 8.60 (d, J=2.5 Hz, 1H), 7.90 (d, J=5.8 Hz, 2H), 7.58 (s, 1H), 7.46 (t, J=7.9 Hz, 1H), 7.35 (s, 2H), 7.09 (d, J=2.4 Hz, 1H), 6.90 (s, 1H), 4.41 (dd, J=12.2, 6.2 Hz, 3H), 3.79 (s, 3H), 3.70 (s, 8H), 3.16 (s, 3H), 2.86 (t, J=6.9 Hz, 2H), 1.39 (d, J=6.4 Hz, 3H).

Synthesis of (R)-2-(4-(3-(2,5-dimethylphenyl)-1H-pyrazol-1-yl)-6-morpholinopyrimidin-2-yl)-2-methoxyethan-1-ol (Compound 342) and (S)-2-(4-(3-(2,5-dimethylphenyl)-1H-pyrazol-1-yl)-6-morpholinopyrimidin-2-yl)-2-methoxyethan-1-ol (Compound 343)

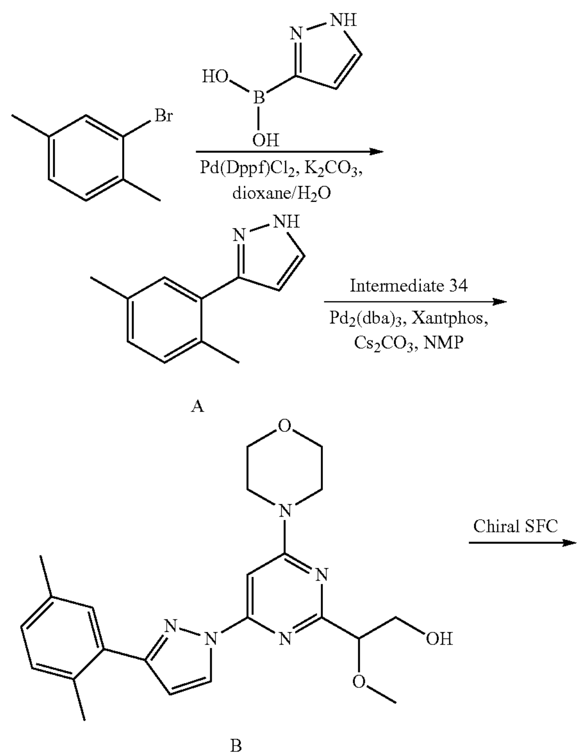

A

B

-continued

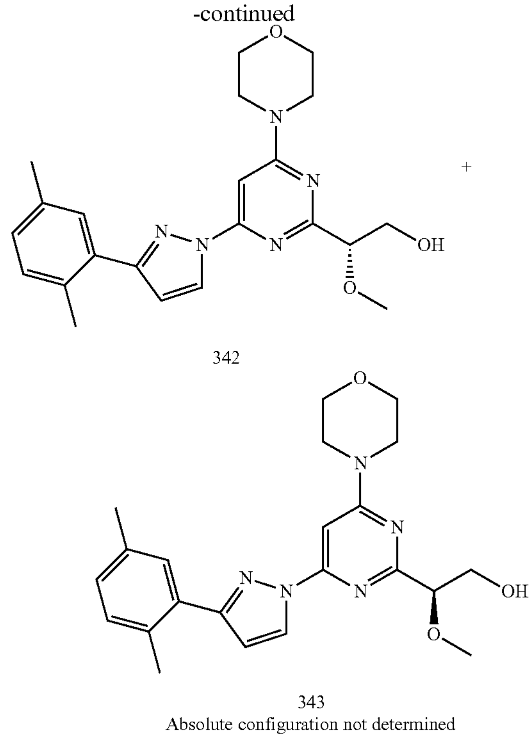

342

+

343

Absolute configuration not determined

Preparation of A

The mixture of 2-bromo-1,4-dimethylbenzene (300 mg, 1.62 mmol), (1H-pyrazol-3-yl)boronic acid (236 mg, 2.11 mmol), Pd(dppf)$Cl_2$ (234 mg, 0.32 mmol) and $K_2CO_3$ (447 mg, 3.24 mmol) in 1,4-dioxane (12 mL) and $H_2O$ (3 mL) was stirred at 100° C. under nitrogen atmosphere for 16 hours. The mixture was diluted with EtOAc (40 mL) and washed by brine (30 mL×2), dried over $Na_2SO_4$, filtered and concentrated to dryness. The resulting crude product was purified by chromatography on silica gel eluting with petroleum ether:EtOAc=20:1-10:1 to get A (158 mg, 57%) as yellow oil.

Preparation of B

A mixture of A (108 mg, 0.63 mmol), Intermediate 34 (172 mg, 0.63 mmol), $Pd_2(dba)_3$ (119 mg, 0.13 mmol), Xantphos (75 mg, 0.13 mmol) and $Cs_2CO_3$ (411 mg, 1.26 mmol) in NMP (4 mL) was microwaved at 100° C. under nitrogen atmosphere for 1 hour. After cooling to room temperature, the mixture was diluted with EtOAc (60 mL). The combined organic layers were washed with brine (30 mL×4), dried over $Na_2SO_4$, filtered and concentrated to dryness. The resulting crude product was purified by chromatography on silica gel eluting with petroleum ether: EtOAc=5:1-1:1 to get B (140 mg, 54%) as yellow oil.

Preparation Compound 342 and Compound 343

B was separated by chiral HPLC (SFC) to get to Compound 342 (60 mg, $1^{st}$ peak) and Compound 343 (50 mg, $2^{nd}$ Peak). The stereochemistry of the enantiomers was not determined.

Compound 342 ($1^{st}$ Peak):

$^1H$ NMR (400 MHz, $CDCl_3$) δ: 8.69 (d, J=2.7 Hz, 1H), 7.42 (s, 1H), 7.18 (d, J=7.8 Hz, 1H), 7.14-7.09 (m, 2H), 6.63

(d, J=2.7 Hz, 1H), 4.51 (t, J=5.5 Hz, 1H), 4.01-3.94 (m, 2H), 3.83-3.74 (m, 8H), 3.55 (s, 3H), 2.46 (s, 3H), 2.37 (s, 3H).

Compound 343 (2nd Peak):

$^1$H NMR (400 MHz, $CDCl_3$) δ 8.62 (d, J=2.7 Hz, 1H), 7.42 (s, 1H), 7.18 (d, J=7.8 Hz, 1H), 7.13-7.07 (m, 2H), 6.62 (d, J=2.7 Hz, 1H), 4.38 (dd, J=6.0, 4.6 Hz, 1H), 4.02-3.92 (m, 2H), 3.83-3.71 (m, 8H), 3.55 (s, 3H), 2.46 (s, 3H), 2.37 (s, 3H).

Synthesis of (S)-4-(6-(3-(1H-indol-3-yl)-5-methyl-1H-pyrazol-1-yl)-2-(1,4-dioxan-2-yl)pyrimidin-4-yl)morpholine (Compound 344) and (R)-4-(6-(3-(1H-indol-3-yl)-5-methyl-1H-pyrazol-1-yl)-2-(1,4-dioxan-2-yl)pyrimidin-4-yl)morpholine (Compound 345)

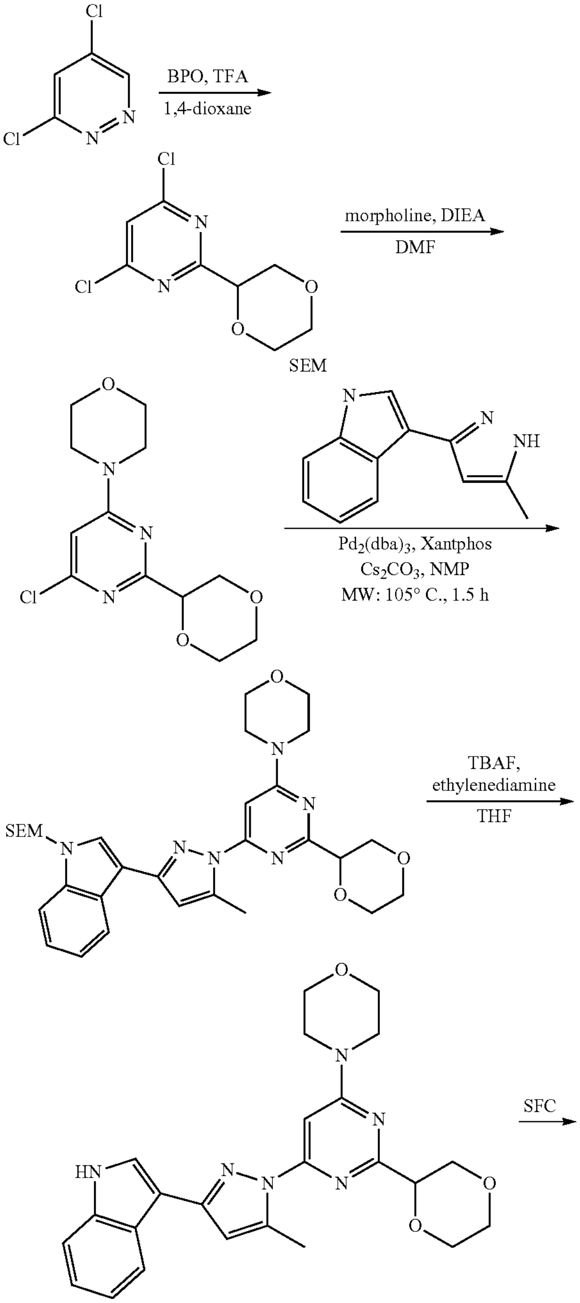

-continued

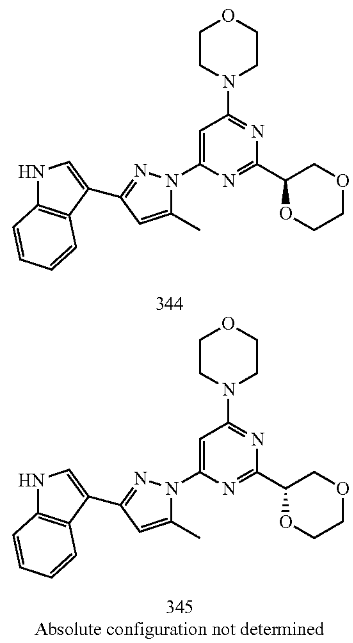

344

345

Absolute configuration not determined

Compound 344 and Compound 345 were synthesized according to the scheme above.

LCMS (ESI): m/z=447 $[M+H]^+$.

Synthesis of 4-(2-(2-(1-methyl-H-pyrazol-4-ylethoxy)-6-(3-(m-tolyloxy)-1H-pyrazol-1-yl)pyrimidin-4-yl)morpholine (Compound 346)

346

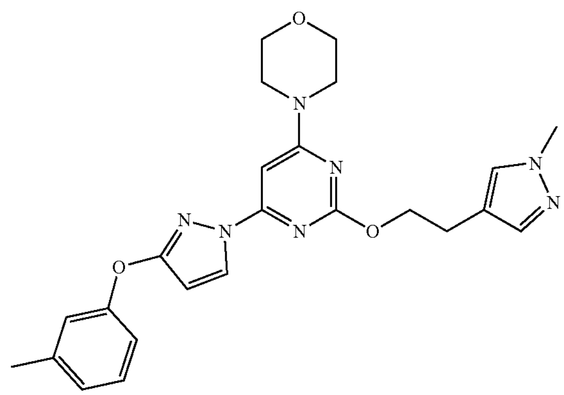

Compound 346 was synthesized using a procedure similar to Compound 302

LCMS (ESI): m/z=462 $[M+H]^+$

Synthesis of 4-(2-(2-methoxypropan-2-yl)-6-(3-(m-tolyl)-1H-pyrazol-1-yl)pyrimidin-4-yl)morpholine (Compound 347)

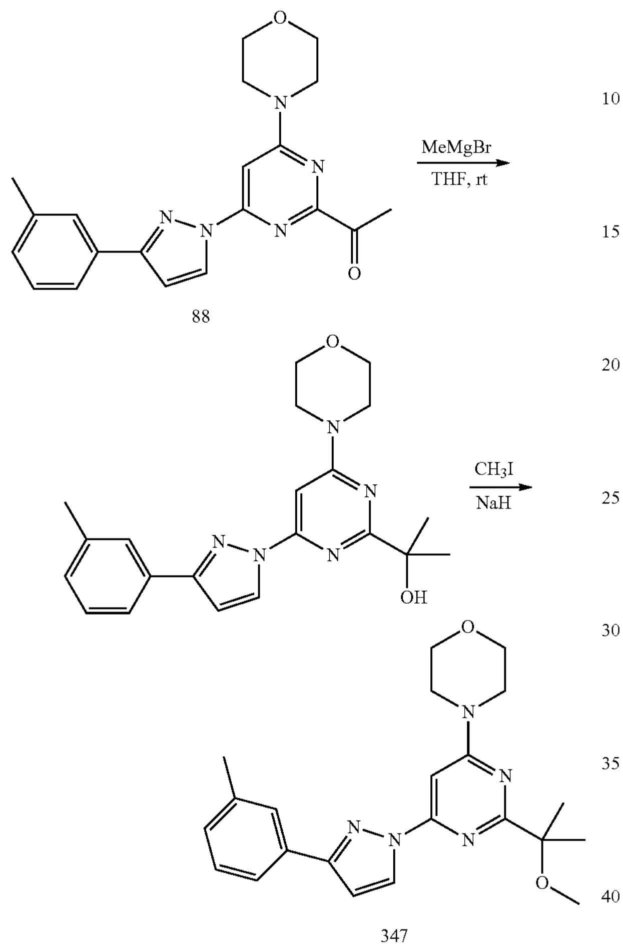

88

347

Compound 347 was prepared as shown in the scheme above.

LCMS (ESI): m/z=394 $[M+H]^+$

Biological Activity

The activity of Compounds 1-20 was measured using a PIKFYVE assay (luciferase ADP-Glo kinase assay available from Promega Corp. of Madison, WI). The activity for each compound is provided in Table 1 below ("A" refers to an $IC_{50}$ of less than 5 nM, "B" refers to an $IC_{50}$ of 5-100 nM, "C" refers to an $IC_{50}$ of 101-1,000 nM, and "D" refers to an $IC_{50}$ of 1,001-10,000 nM).

TABLE 1

| Compound No. | PIKFYVE Activity ($IC_{50}$ in nM) |
|---|---|
| 1 | B |
| 2 | A |
| 3 | A |
| 4 | C |
| 5 | C |
| 6 | B |
| 7 | A |
| 8 | B |
| 9 | A |
| 10 | D |
| 11 | C |
| 12 | B |
| 13 | B |
| 14 | C |
| 15 | D |
| 16 | C |
| 17 | B |
| 18 | D |
| 19 | B |
| 20 | B |

The activity of Compounds 39-90 was also measured using a PIKFYVE assay (luciferase ADP-Glo kinase assay available from Promega Corp. of Madison, WI). The activity for each compound is provided in Table 2 below A" refers to an $IC_{50}$ of less than 5 nM, "B" refers to an $IC_{50}$ of 5-100 nM, "C" refers to an $IC_{50}$ of 101-1,000 nM, and "D" refers to an $IC_{50}$ of 1,001-10,000 nM).

TABLE 2

| Compound No. | PIKFYVE Activity ($IC_{50}$ in nM) |
|---|---|
| 39 | D |
| 40 | C |
| 41 | D |
| 42 | C |
| 43 | A |
| 44 | A |
| 45 | C |
| 46 | B |
| 47 | B |
| 48 | C |
| 49 | B |
| 50 | A |
| 51 | D |
| 52 | C |
| 53 | C |
| 54 | A |
| 55 | A |
| 56 | A |
| 57 | A |
| 58 | A |
| 59 | B |
| 60 | C |
| 61 | B |
| 62 | A |
| 63 | C |
| 64 | A |
| 65 | A |
| 66 | A |
| 67 | A |
| 68 | A |
| 69 | B |
| 70 | B |
| 71 | A |
| 72 | A |
| 73 | A |
| 74 | A |
| 75 | B |
| 76 | A |
| 77 | B |
| 78 | B |
| 79 | A |
| 80 | A |
| 81 | A |
| 82 | B |
| 83 | C |
| 84 | B |
| 85 | C |
| 86 | A |

TABLE 2-continued

| Compound No. | PIKFYVE Activity ($IC_{50}$ in nM) |
|---|---|
| 87 | C |
| 88 | A |
| 89 | A |
| 90 | A |

The activity of Compounds 93-347 was also measured using a PIKFYVE assay (luciferase ADP-Glo kinase assay available from Promega Corp. of Madison, WI). The activity for each compound is provided in Table 3 below ("A" refers to an $IC_{50}$ of less than 3 nM, "B" refers to an $IC_{50}$ of >3 and <10 nM, "C" refers to an $IC_{50}$ of >10 and <100 nM, "D" refers to an $IC_{50}$ of >100 and <5,000 nM), and "E" refers to a $IC_{50}$ of >5000 nm.

TABLE 3

| Compound No. | PIKFYVE Activity ($IC_{50}$ in nM) |
|---|---|
| 91 | B |
| 92 | B |
| 93 | C |
| 94 | A |
| 95 | B |
| 96 | C |
| 97 | B |
| 98 | B |
| 99 | C |
| 100 | B |
| 101 | B |
| 102 | A |
| 103 | B |
| 104 | A |
| 105 | A |
| 106 | C |
| 107 | C |
| 108 | B |
| 109 | B |
| 110 | A |
| 111 | B |
| 112 | C |
| 113 | A |
| 114 | B |
| 115 | A |
| 116 | A |
| 117 | C |
| 118 | A |
| 119 | B |
| 120 | C |
| 121 | B |
| 122 | B |
| 123 | C |
| 124 | E |
| 125 | C |
| 126 | C |
| 127 | A |
| 128 | B |
| 129 | B |
| 151 | C |
| 155 | B |
| 156 | B |
| 169 | C |
| 170 | B |
| 171 | B |
| 172 | D |
| 173 | E |
| 174 | B |
| 175 | A |
| 176 | A |
| 177 | C |
| 178 | D |
| 179 | A |
| 180 | A |
| 181 | C |

TABLE 3-continued

| Compound No. | PIKFYVE Activity ($IC_{50}$ in nM) |
|---|---|
| 182 | C |
| 183 | C |
| 184 | C |
| 186 | A |
| 187 | A |
| 188 | A |
| 189 | A |
| 190 | B |
| 191 | C |
| 192 | D |
| 193 | A |
| 194 | B |
| 195 | A |
| 196 | E |
| 197 | B |
| 198 | C |
| 200 | A |
| 201 | C |
| 202 | D |
| 203 | C |
| 204 | C |
| 205 | C |
| 206 | B |
| 207 | C |
| 208 | B |
| 209 | C |
| 211 | A |
| 212 | B |
| 213 | D |
| 214 | A |
| 215 | C |
| 216 | A |
| 217 | A |
| 218 | A |
| 219 | A |
| 220 | A |
| 221 | A |
| 222 | D |
| 223 | A |
| 224 | B |
| 225 | B |
| 226 | B |
| 227 | A |
| 228 | A |
| 229 | B |
| 230 | A |
| 231 | A |
| 232 | D |
| 233 | A |
| 234 | A |
| 235 | A |
| 236 | A |
| 237 | A |
| 238 | A |
| 239 | C |
| 240 | D |
| 241 | B |
| 242 | B |
| 243 | D |
| 244 | C |
| 245 | C |
| 246 | D |
| 247 | D |
| 248 | E |
| 249 | D |
| 250 | E |
| 251 | B |
| 252 | E |
| 253 | C |
| 254 | D |
| 255 | C |
| 256 | C |
| 257 | C |
| 258 | A |
| 259 | B |
| 260 | A |
| 261 | A |

TABLE 3-continued

| Compound No. | PIKFYVE Activity ($IC_{50}$ in nM) |
|---|---|
| 262 | C |
| 263 | C |
| 264 | D |
| 265 | D |
| 266 | D |
| 267 | C |
| 268 | C |
| 269 | C |
| 270 | D |
| 271 | D |
| 272 | B |
| 273 | B |
| 274 | D |
| 275 | D |
| 276 | B |
| 277 | B |
| 278 | A |
| 279 | B |
| 280 | D |
| 281 | D |
| 282 | D |
| 283 | D |
| 284 | C |
| 285 | C |
| 286 | D |
| 287 | D |
| 288 | D |
| 289 | D |
| 290 | D |
| 291 | D |
| 292 | C |
| 293 | C |
| 294 | C |
| 295 | C |
| 296 | D |
| 297 | B |
| 298 | B |
| 299 | A |
| 300 | A |
| 302 | C |
| 303 | D |
| 304 | B |
| 305 | C |
| 306 | D |
| 307 | C |
| 308 | C |
| 309 | B |
| 310 | C |
| 311 | B |
| 312 | B |
| 313 | A |
| 314 | A |
| 315 | A |
| 316 | B |
| 317 | B |
| 318 | A |
| 319 | A |
| 320 | B |
| 321 | B |
| 322 | B |
| 323 | C |
| 324 | C |
| 325 | C |
| 326 | C |
| 327 | B |
| 328 | B |
| 329 | B |
| 330 | B |
| 331 | B |
| 332 | B |
| 333 | D |
| 334 | C |
| 335 | C |
| 336 | C |
| 337 | C |
| 338 | B |
| 339 | B |

TABLE 3-continued

| Compound No. | PIKFYVE Activity ($IC_{50}$ in nM) |
|---|---|
| 340 | C |
| 341 | A |
| 342 | C |
| 343 | C |
| 344 | A |
| 345 | A |
| 346 | A |
| 347 | B |

Cell-Based Pikfyve Inhibition Activity Assay

Cell Culture and Drug Treatment

BJ fibroblast cells were obtained from American Type Cell Culture (ATCC, CRL-2522). The cells were maintained in DMEM (Genesee Scientific, 25-500) supplemented with 10% fetal bovine serum (Genesee Scientific, 25-514) and 1% penicillin-streptomycin (Genesee Scientific, 25-512) at 37° C. in the atmosphere 5% CO2. BJ fibroblasts were plated into black flat clear bottom 96-well plates (Grenier, 655090) at a density of $3\times10^3$ per well and were allowed to attach in culture for 8-10 hours before drug treatment. Drugs were tested at eleven doses separated by 3 fold from 0.03 nM to 3000 nM in triplicates for 4 hours at 37° C. After 4 hours, treatment media was aspirated and replaced with 4% Paraformaldehyde (Electron Microscopy Science, 15714-S) and cells were fixed at room temperature for 5 minutes. 4% PFA in wells were then discarded and replaced with a blocking buffer consisting of 1×PBS with 0.1% Tween (Sigma-Aldrich, P1754-500), 5% Donkey Serum (Jackson ImmunoResearch, 017-000-121), and 1% BSA (Caisson Labs, B005-50GM) and incubated at room temperature for 30 minutes. Blocking buffer was then discarded and replaced with a primary EEA1 antibody (Fisher Scientific, BD610457) in a 1:1000 dilution and incubated at 4° C. overnight. Following overnight incubation, plates were washed with 1×PBS three times and incubated with secondary antibody Donkey anti-Mouse IgG, Alexa Fluor 555 (Invitrogen, A31570) (1:1000 dilution) for 1 hour at room temperature in the dark. Subsequently cell plates were washed with 1×PBS three times and can be stored at 4° C. if not being proceeding with imaging procedure.

Imaging and Data Analysis

Images were acquired with 20× objective (ImageXpress MicroConfocal, Molecular Devices) creating z-series of 5 planes (5 steps, 3 μm each step), 16 tiles per well. Images were then analyzed using a custom CellProfiler protocol to obtain mean vesicle size. The mean vesicle size from 16 images was used as the output for each well. The mean vesicle size from 0.5% DMSO treated condition was considered as having no Pikfyve inhibition activity and the 3 μM Apilimod treated condition was considered as having 100% inhibition activity. The mean vesicle size was converted to % inhibition activity and the data was fitted to a dose-response curve using log(inhibitor) vs normalized response-variable slope using GraphPad Prism.

The activity for some compounds described herein is provided in Table 4 below ("A" refers to an EEA1 $EC_{50}$ of less than 20 nM, "B" refers to an EEA1 $EC_{50}$ of >20 and <100 nM, "C" refers to an EEA1 $EC_{50}$ of >100 and <500 nM, "D" refers to an EEA1 $EC_{50}$ of >500 and <5,000 nM), and "E" refers to a EEA1 $EC_{50}$ of >5000 nm.

TABLE 4

| Compound | EEA1 $EC_{50}$ |
|---|---|
| 43 | B |
| 44 | C |
| 54 | B |
| 55 | B |
| 56 | A |
| 57 | B |
| 58 | B |
| 59 | B |
| 60 | D |
| 61 | C |
| 62 | B |
| 64 | B |
| 66 | C |
| 68 | C |
| 69 | D |
| 70 | E |
| 71 | D |
| 72 | C |
| 74 | B |
| 75 | C |
| 76 | B |
| 77 | D |
| 78 | D |
| 79 | C |
| 80 | B |
| 81 | C |
| 82 | D |
| 83 | E |
| 85 | D |
| 86 | B |
| 87 | C |
| 88 | C |
| 90 | A |
| 93 | C |
| 94 | A |
| 95 | B |
| 96 | C |
| 97 | B |
| 98 | A |
| 99 | C |
| 100 | C |
| 101 | C |
| 102 | A |
| 103 | C |
| 104 | B |
| 105 | A |
| 106 | D |
| 107 | D |
| 108 | B |
| 109 | B |
| 110 | C |
| 111 | E |
| 112 | D |
| 113 | C |
| 114 | C |
| 115 | C |
| 116 | C |
| 117 | D |
| 118 | B |
| 119 | B |
| 120 | C |
| 121 | C |
| 122 | C |
| 123 | D |
| 124 | E |
| 125 | C |
| 126 | C |
| 127 | B |
| 128 | D |
| 129 | C |
| 155 | C |
| 156 | C |
| 169 | C |
| 170 | C |
| 171 | C |
| 172 | E |
| 173 | E |
| 174 | C |

TABLE 4-continued

| Compound | EEA1 $EC_{50}$ |
|---|---|
| 175 | B |
| 176 | C |
| 177 | D |
| 178 | E |
| 179 | A |
| 180 | B |
| 181 | D |
| 182 | D |
| 183 | C |
| 184 | C |
| 186 | C |
| 187 | B |
| 188 | C |
| 189 | B |
| 190 | C |
| 191 | E |
| 193 | C |
| 194 | C |
| 195 | B |
| 197 | C |
| 198 | D |
| 200 | A |
| 201 | D |
| 202 | D |
| 203 | C |
| 204 | D |
| 205 | D |
| 206 | D |
| 208 | B |
| 209 | C |
| 211 | C |
| 212 | D |
| 214 | A |
| 215 | D |
| 216 | B |
| 217 | B |
| 218 | B |
| 219 | B |
| 220 | A |
| 221 | B |
| 223 | C |
| 224 | C |
| 225 | C |
| 226 | D |
| 227 | C |
| 228 | C |
| 229 | C |
| 230 | B |
| 231 | B |
| 232 | E |
| 233 | B |
| 234 | A |
| 235 | B |
| 236 | E |
| 237 | A |
| 238 | C |
| 241 | D |
| 242 | D |
| 245 | E |
| 258 | C |
| 259 | C |
| 260 | A |
| 261 | A |
| 262 | C |
| 263 | C |
| 268 | D |
| 269 | D |
| 272 | C |
| 273 | C |
| 274 | E |
| 275 | E |
| 276 | C |
| 277 | C |
| 278 | D |
| 279 | D |
| 292 | B |
| 293 | C |
| 297 | C |

TABLE 4-continued

| Compound | EEA1 $EC_{50}$ |
|---|---|
| 298 | D |
| 299 | B |
| 300 | B |
| 302 | E |
| 303 | E |
| 304 | B |
| 305 | D |
| 306 | E |
| 307 | E |
| 308 | D |
| 309 | D |
| 310 | D |
| 311 | C |
| 312 | C |
| 313 | A |
| 314 | A |
| 315 | A |
| 316 | B |
| 317 | C |
| 318 | A |
| 319 | A |
| 320 | B |
| 321 | D |
| 322 | D |
| 323 | D |
| 324 | D |
| 325 | D |
| 326 | D |
| 327 | D |
| 328 | E |
| 329 | E |
| 330 | E |
| 331 | C |
| 332 | D |
| 334 | D |
| 335 | D |
| 336 | D |
| 337 | D |
| 338 | E |
| 339 | C |
| 341 | A |
| 344 | A |
| 345 | A |
| 346 | B |
| 347 | C |

All references cited herein are incorporated by reference.

What is claimed is:

1. A compound of the formula (I)

(I)

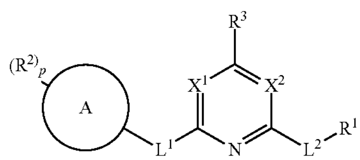

or a pharmaceutically acceptable salt thereof, wherein each occurrence of $R^2$ is independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocyclyl;

$R^3$ is a nitrogen- or oxygen-containing moiety;

Ring A is (i) a 5 or 6-membered heteroaryl, a 5-6, 6-5 or 6-6 membered bicyclic heteroaryl, or a heterocyclyl, each having at least one nitrogen or oxygen ring atom, or (ii) phenyl;

$L^1$ is absent, $C_1$-$C_2$ alkylene, —$NR^c$—, —O—, —S—, —C(O)—, —NHC(O)—, —C(O)NH—, —$NR^c$C(O)—, or —$NR^c$C(O)$(CR^aR^b)_m$—;

wherein -$L^2$-R' is

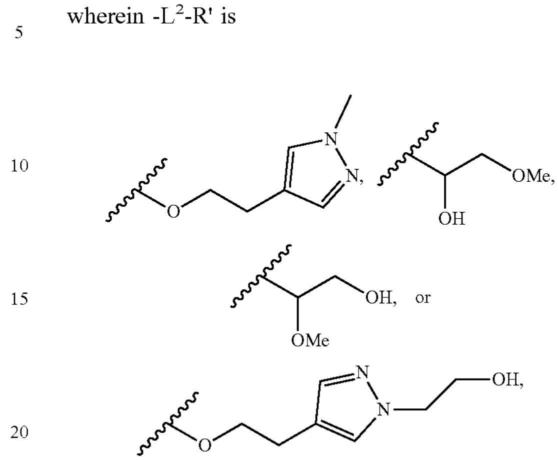

(i) $X^1$ is CH or $CR^c$ and $X^2$ is N, or (ii) $X^1$ is N and $X^2$ is N, CH, or $CR^c$;

each occurrence of $R^a$ and $R^b$ are independently hydrogen, hydroxy, hydroxy$(C_{1-4})$alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —C(O)$R^d$, —C(S)$R^d$, —OC(O)$R^d$, —SC(O)$R^d$, OC(S)$R^d$, SC(S)$R^d$, —$NR^c$C(O)$R^d$, —$NR^c$C(S)$R^d$, —$SO_2R^c$, —S(O)$R^e$, —$NR^cSO_2R^d$, —$OS(O)_2R^d$, —OP(O)$R^dR^c$, or —P(O)$R^dR^e$;

each occurrence of $R^c$ is independently a hydrogen or $C_1$-6 alkyl;

each occurrence of $R^d$ and $R^c$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

m is 1-4; and p is 1 or 2.

2. The compound of claim 1, wherein -$L^2$-$R^1$ is

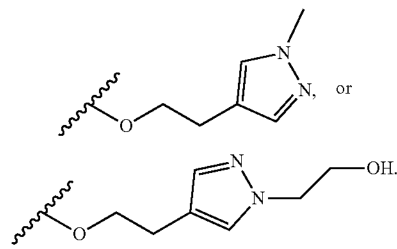

3. The compound of claim 1, wherein $-L^2-R^1$ is
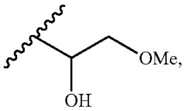
or
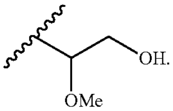
4. The compound of claim 1, wherein $R^2$ is phenyl, 3-methoxyphenyl, 3-methylphenyl, 3-trifluoromethylphenyl, or 3-chlorophenyl.
5. The compound of claim 1, wherein $R^3$ is
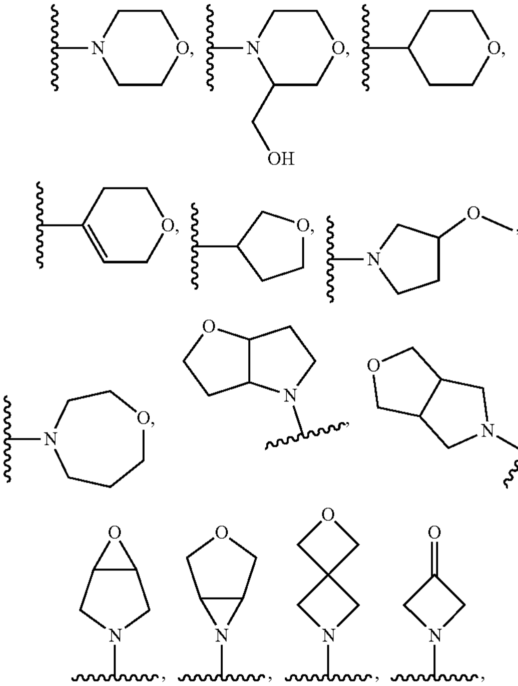
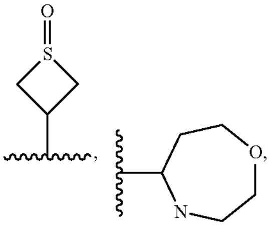
or
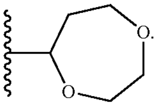
6. The compound of claim 1, wherein ring A is
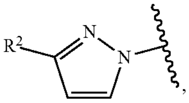
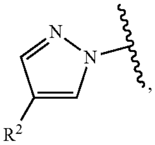
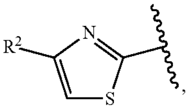
or
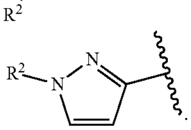
7. The compound of claim 1, wherein the moiety
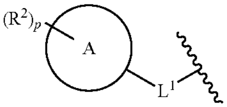
is
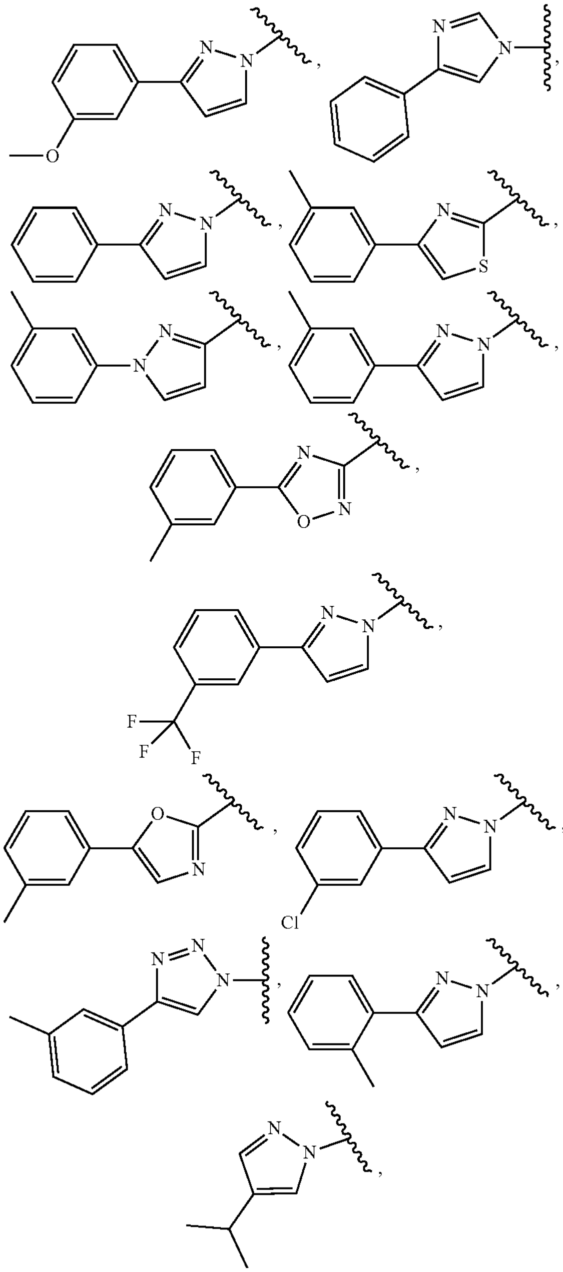
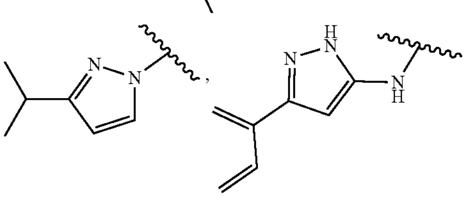
, or -continued

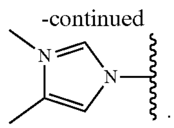

8. A compound of the formula (XIII):

(XIII)

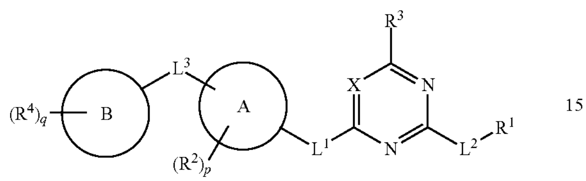

or a tautomer or pharmaceutically acceptable salt thereof, wherein each occurrence of $R^2$ is, independently, hydrogen, nitro, cyano, hydroxyl, halogen, substituted or unsubstituted amino, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy, substituted or unsubstituted mercaptane, or substituted or unsubstituted heterocyclyl;

$R^3$ is a nitrogen- and/or oxygen-containing moiety;

each occurrence of $R^4$ is, independently, hydrogen, nitro, hydroxyl, halogen, cyano, substituted or unsubstituted amino, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy, substituted or unsubstituted mercaptane, or substituted or unsubstituted heterocyclyl;

$L^1$ is absent, $C_1$-$C_4$ alkylene, —$NR^c$—, —O—, —S—, —C(O)—, —$NR^cC(O)$—, —$C(O)NR^c$—, or —$NR^cC(O)(CR^aR^b)_m$—;

-$L_2$-R is

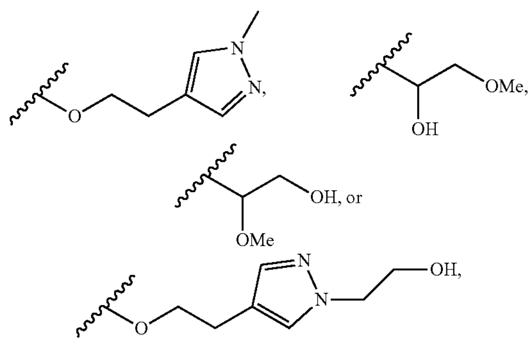

$L^3$ is absent, optionally substituted $C_1$-$C_7$ alkylene, —$NR^c$—, —O—, —S—, —C(O)—, —$NR^cC(O)$—, —$C(O)NR^c$—, —$NR^cC(O)$—, or —$NR^cC(O)(CR^aR^b)_m$—;

X is N or $CR^c$;

Ring A is (i) a 5 or 6-membered heteroaryl, a 5-6, 6-5 or 6-6 membered bicyclic heteroaryl, or a heterocyclyl, each having at least one nitrogen or oxygen ring atom, or (ii) aryl;

Ring B is absent, or (i) a 5 or 6-membered heteroaryl, a 5-6, 6-5 or 6-6 membered bicyclic heteroaryl or a heterocyclyl, each having at least one nitrogen, oxygen or sulfur ring atom, or (ii) aryl;

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, —$OR^d$, —$SR^d$, —$NR^dR^e$, —$C(O)R^d$, —$C(S)R^d$, —$OC(O)R^d$, —$SC(O)R^d$, $OC(S)R^d$, $SC(S)R^d$, —$NR^cC(O)R^d$, —$NR^cC(S)R^d$, —$SO_2R^c$, —$S(O)R^e$, —$NR^cSO_2R^d$, —$OS(O)_2R^d$, —$OP(O)R^dR^c$, or —$P(O)R^dR^e$;

$R^c$ is hydrogen or $C_{1-6}$ alkyl;

each occurrence of $R^d$ and $R^c$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

each occurrence of m is independently 0, 1, 2, 3, 4, 5, 6 or 7;

p is 0, 1, 2, 3 or 4; and q is 0, 1, or 2.

9. The compound of claim 8, wherein -$L^2$-$R^1$ is a

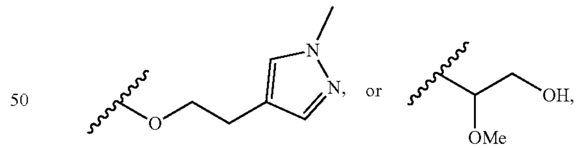

10. The compound of claim 8, wherein Ring A is unsubstituted pyrazolyl.

11. The compound of claim 8, wherein Ring B is substituted-er unsubstituted phenyl, indole, azaindole, or benzothiophene.

12. The compound of claim 8, wherein $R^3$ is

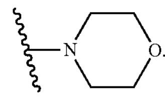

13. A compound of the formula (XIII-A):

(XIII-A)

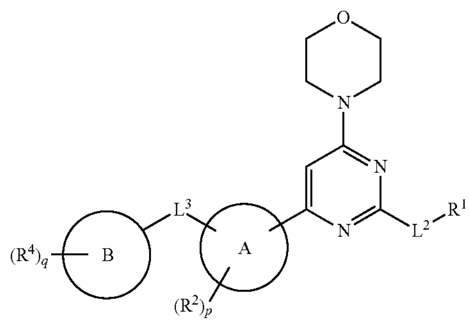

or a tautomer or pharmaceutically acceptable salt thereof, wherein

Ring A is a 5 or 6-membered heteroaryl, a 5-6, 6-5 or 6-6 membered bicyclic heteroaryl, or a heterocyclyl, each having at least one nitrogen or oxygen ring atom;

Ring B is (i) a 5 or 6-membered heteroaryl, a 5-6, 6-5 or 6-6 membered bicyclic heteroaryl or a heterocyclyl, each having at least one nitrogen, oxygen or sulfur ring atom, or (ii) aryl;

each occurrence of $R^2$ is, independently, hydrogen, nitro, cyano, hydroxyl, halogen, substituted or unsubstituted amino, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy, substituted or unsubstituted mercaptane, or substituted or unsubstituted heterocyclyl;

each occurrence of $R^4$ is, independently, hydrogen, nitro, hydroxyl, halogen, cyano, substituted or unsubstituted amino, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, substituted or unsubstituted carboxy, substituted or unsubstituted mercaptane, or substituted or unsubstituted heterocyclyl;

$-L^2-R'$ is

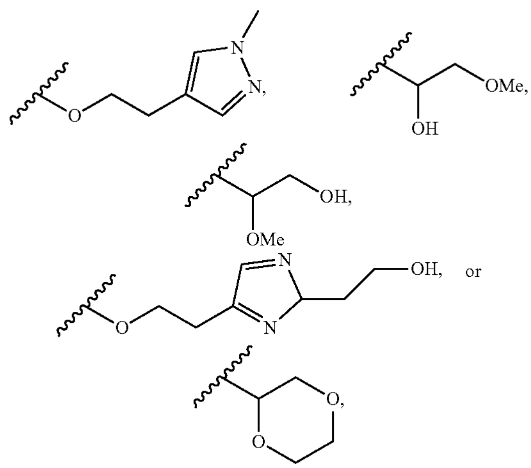

$L^3$ is absent, optionally substituted $C_1$-$C_7$ alkylene, $—NR^c—$, $—O—$, $—S—$, $—C(O)—$, $—NR^cC(O)—$, $—C(O)NR^c—$, $—NR^cC(O)—$, or $—NR^cC(O)(CR^aR^b)_m—$;

each occurrence of $R^a$ and $R^b$ are independently hydrogen, hydroxy, hydroxy($C_{1-4}$)alkyl, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl, halogen, nitro, $—OR^d$, $—SR^d$, $—NR^dR^e$, $—C(O)R^d$, $—C(S)R^d$, $—OC(O)R^d$, $—SC(O)R^d$, $OC(S)R^d$, $SC(S)R^d$, $—NR^cC(O)R^d$, $—NR^cC(S)R^d$, $—SO_2R^c$, $—S(O)R^e$, $—NR^cSO_2R^d$, $—OS(O)_2R^d$, $—OP(O)R^dR^c$, or $—P(O)R^dR^e$;

$R^c$ is hydrogen or $C_{1-6}$ alkyl;

each occurrence of $R^d$ and $R^c$ are independently hydrogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heteroaryl, substituted or unsubstituted cycloalkyl, or substituted or unsubstituted heterocyclyl;

m is 0, 1, 2, 3, 4, 5, 6 or 7;

p is 0, 1, 2, 3 or 4; and q is 0, 1, or 2.

14. A compound of the formula (XVII):

(XVII)

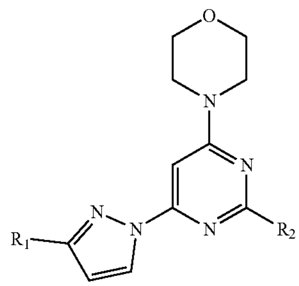

or a tautomer or pharmaceutically acceptable salt thereof, wherein $R^1$ is

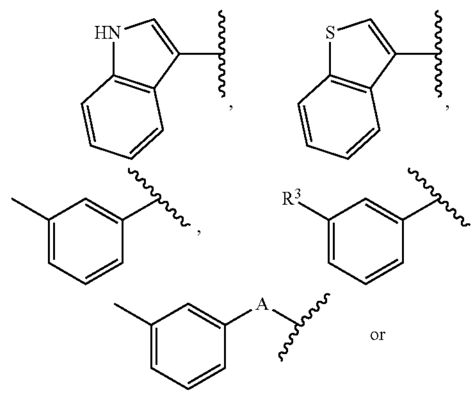

-continued
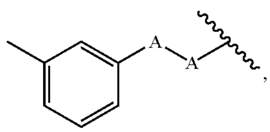
wherein $R^3$ is $C_{1-6}$ alkyl, optionally containing one or more heteroatoms, and A is —$CH_2$—, —CHMe-, —C($Me_2$)-, —O—, —S—, —NH—, or —N($C_{1-4}$ alkyl)-; and
$R^2$ is
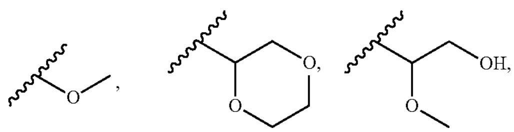
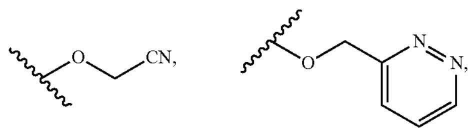
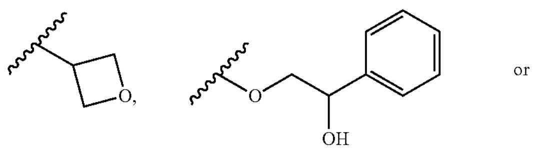
or
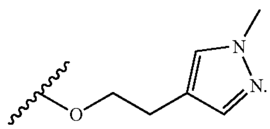
15. A compound that is
21
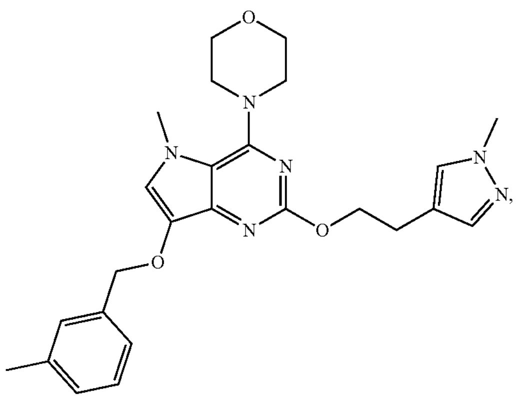
-continued
22
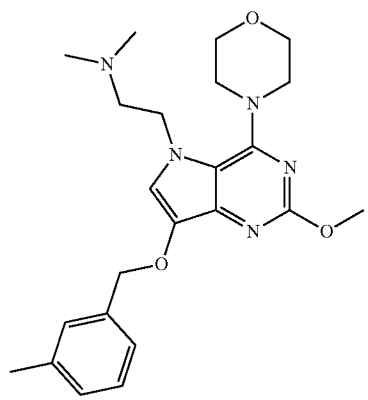
,
23
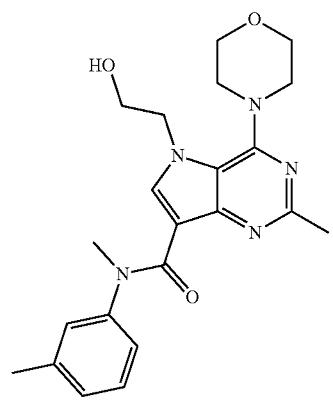
,
24
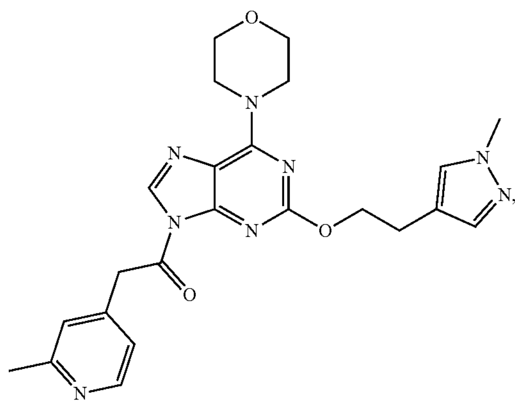
25
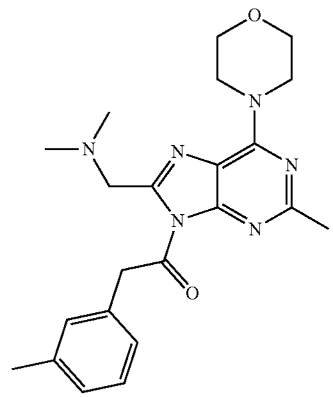
, -continued
26
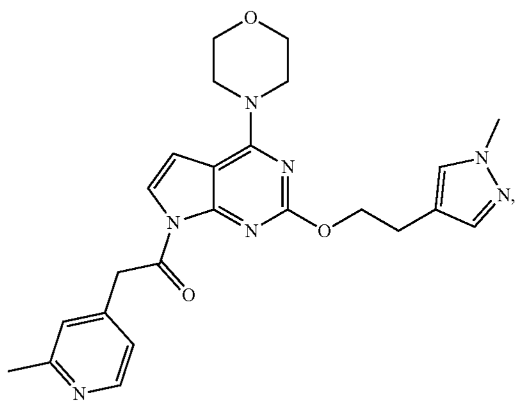
27
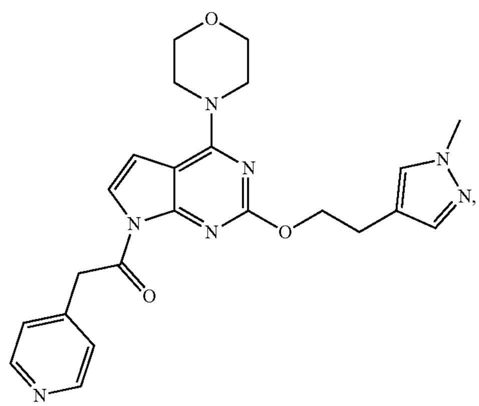
28
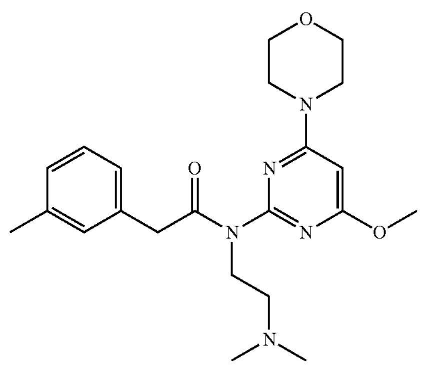
,
29
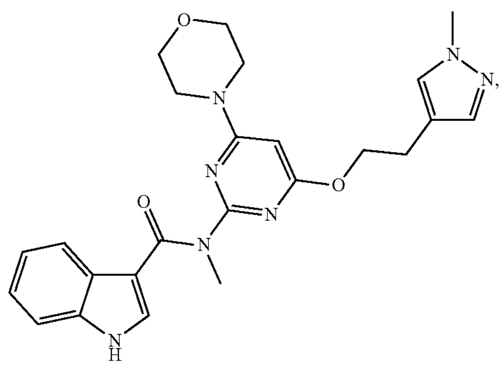
-continued
30
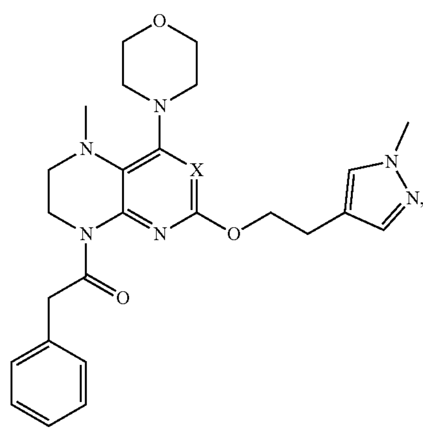
31
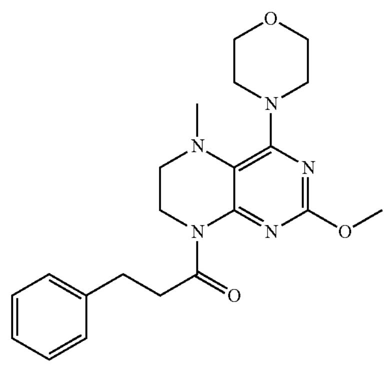
,
32
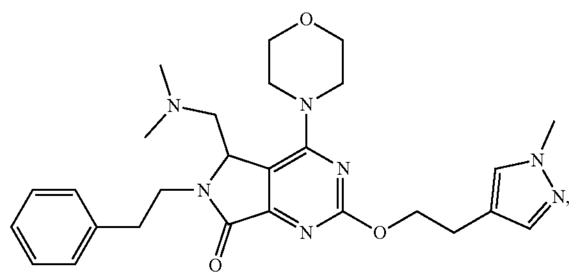
33
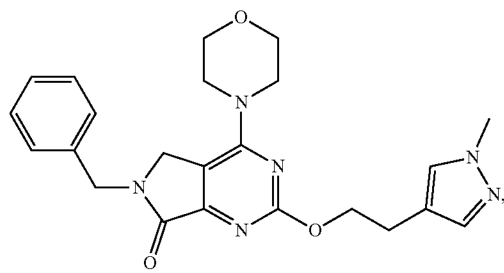

-continued
34
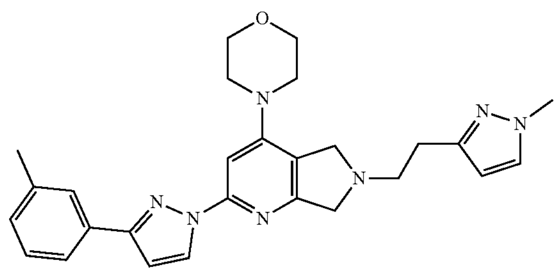
,
35
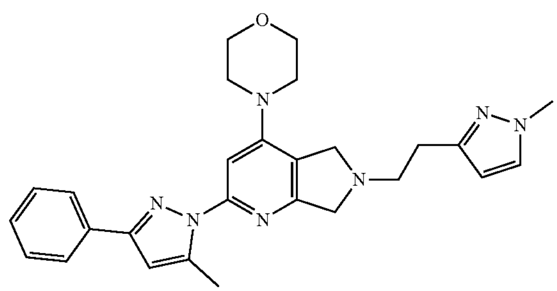
,
36
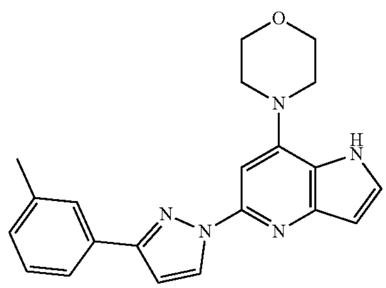
,
37
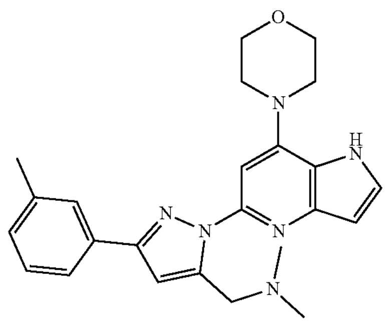
,
38
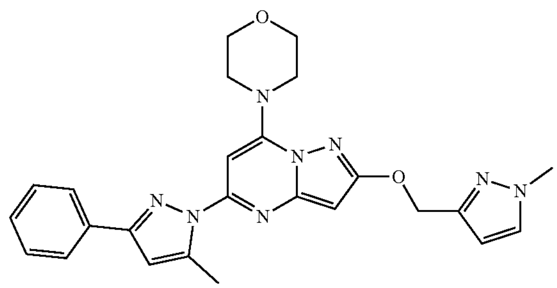
,
-continued
40
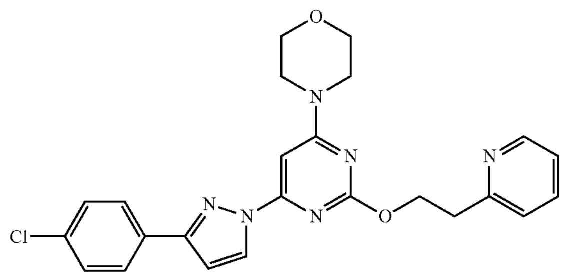
,
41
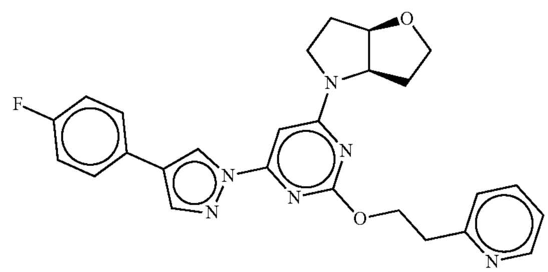
,
42
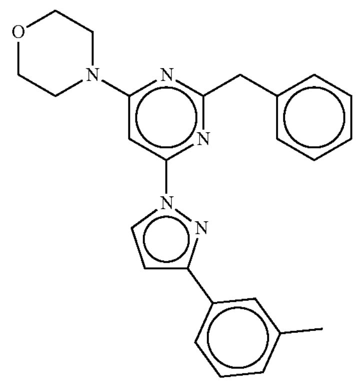
,
43
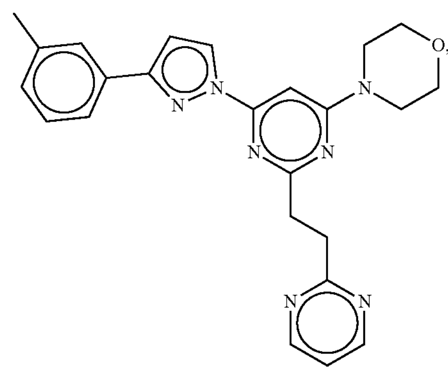
44
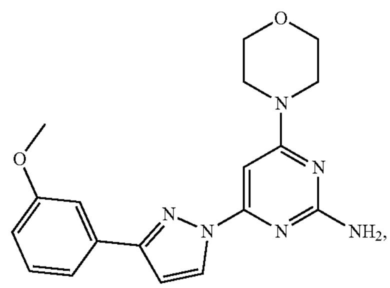

-continued
45
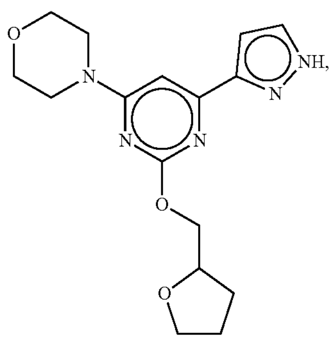
46
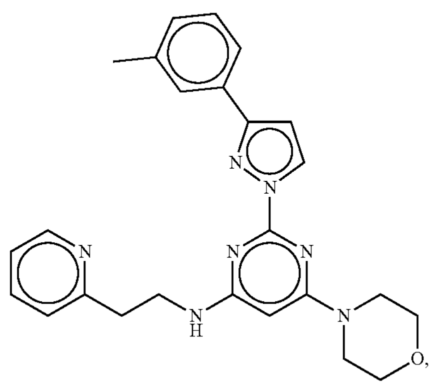
47
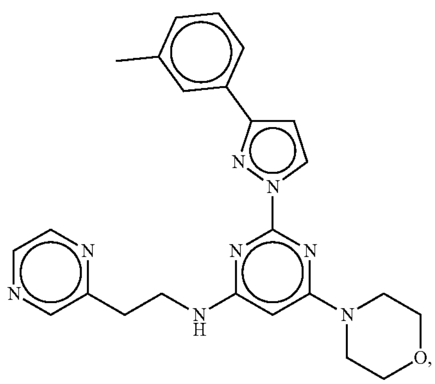
48
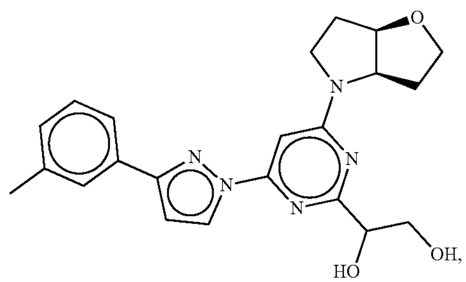
-continued
49
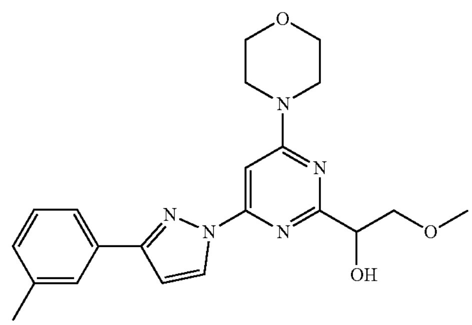
50
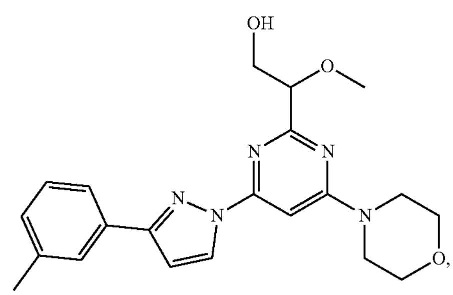
51
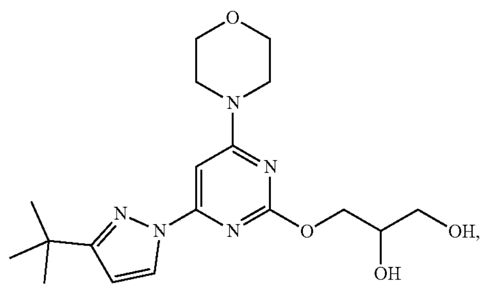
52
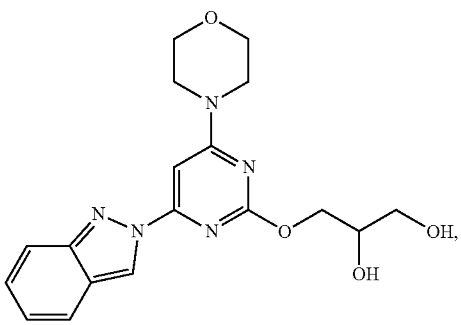

-continued
53
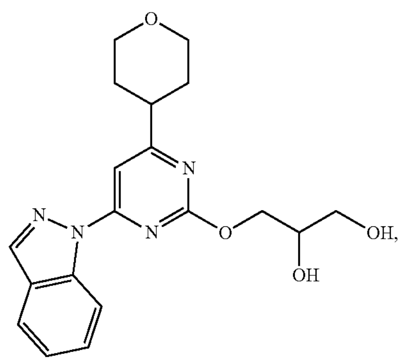
54
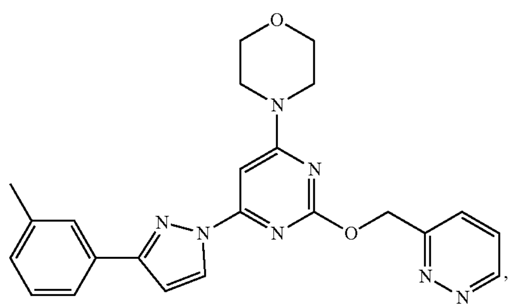
55
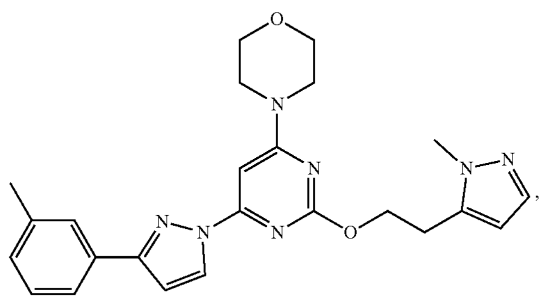
56
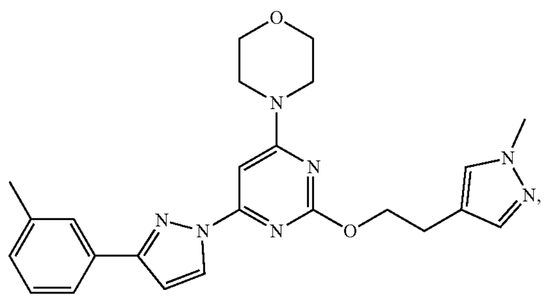
57
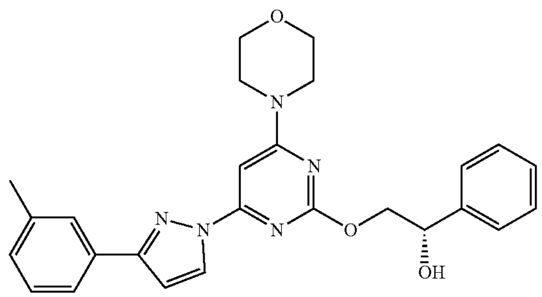
58
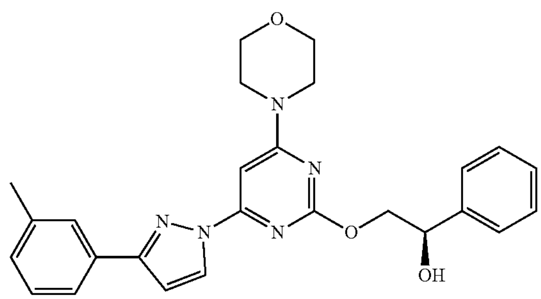
59
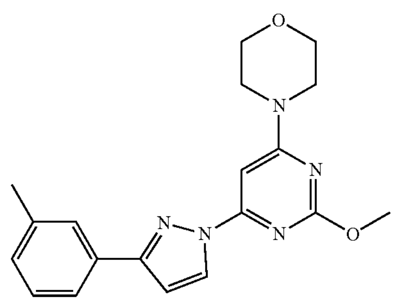
60
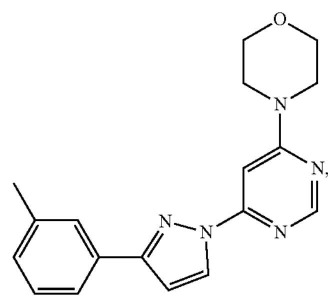
61
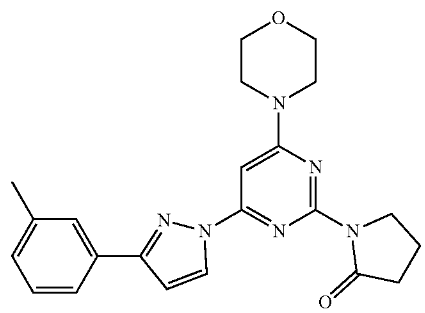
62
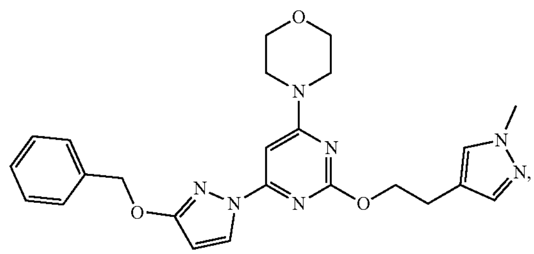

63
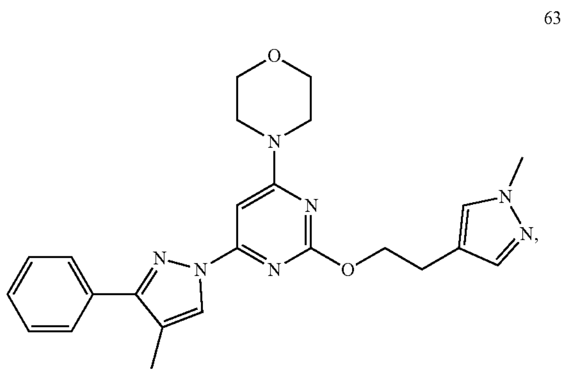
64
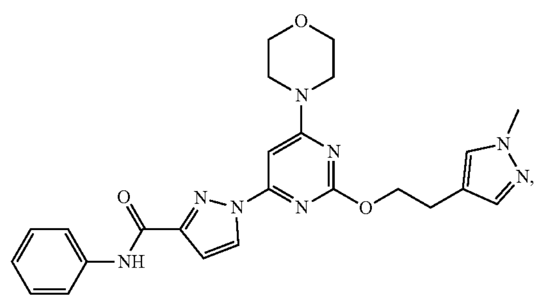
65
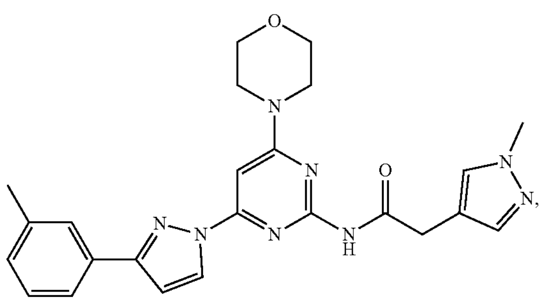
66
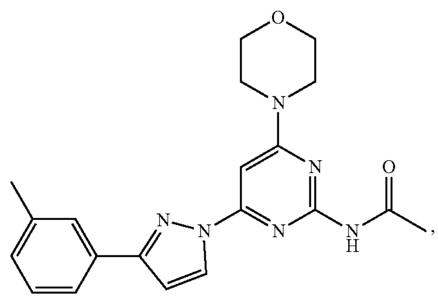
67
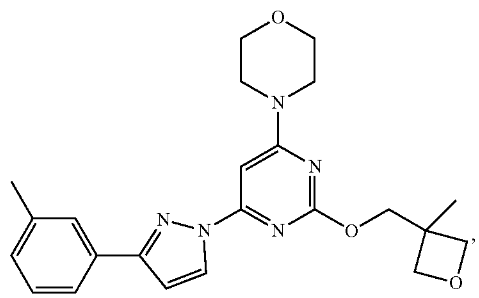
68
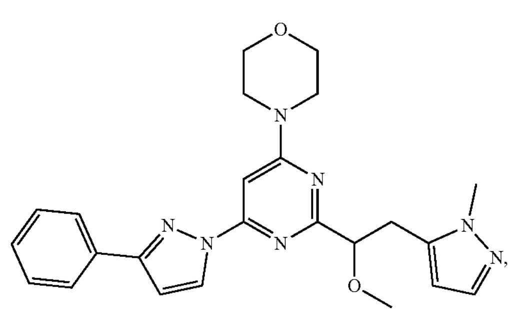
69
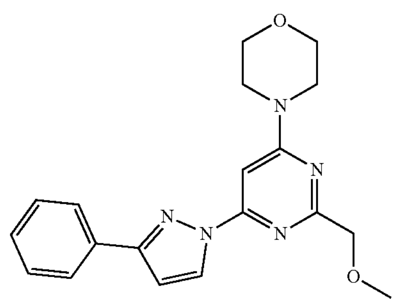
70
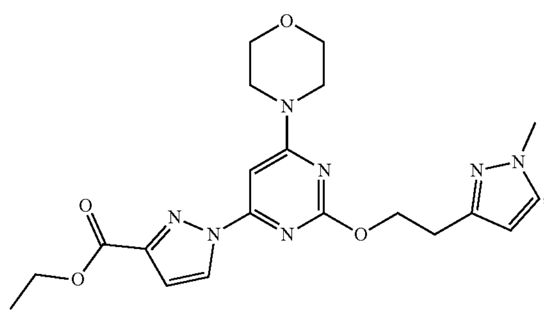
71
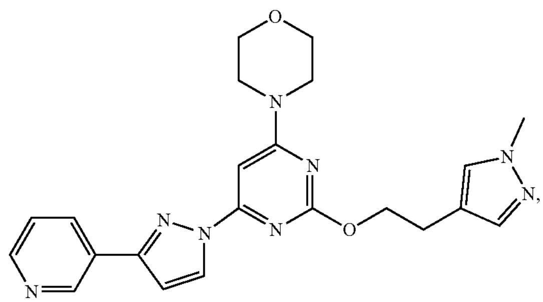
72
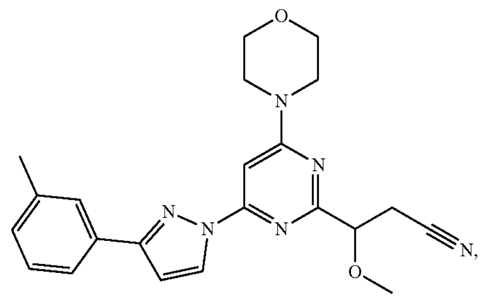

73
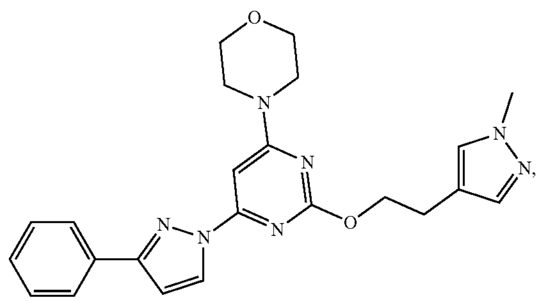
74
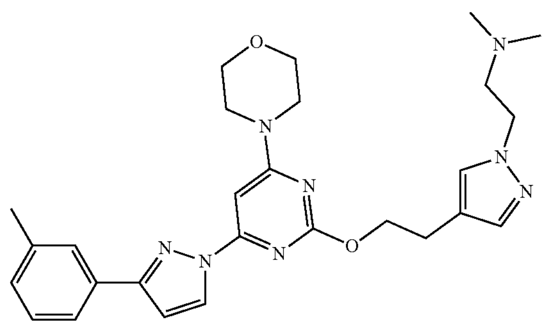
,
75
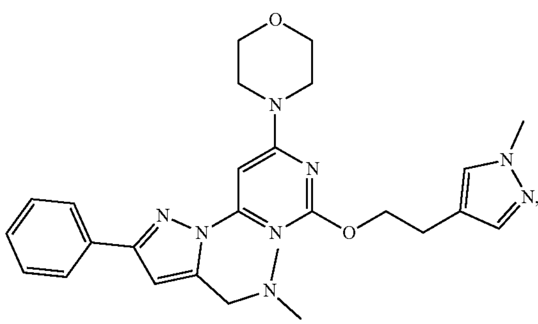
76
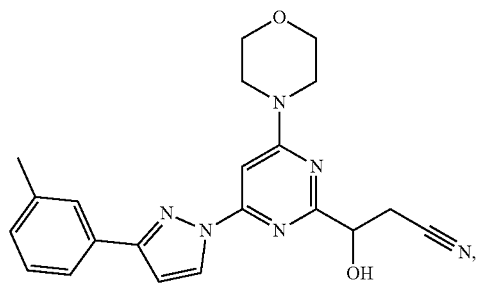
77
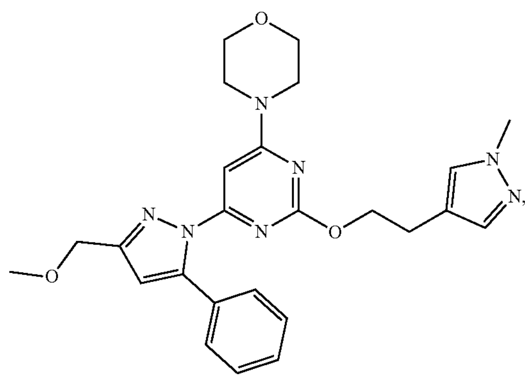
78
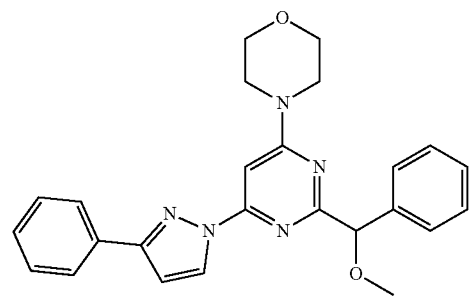
,
79
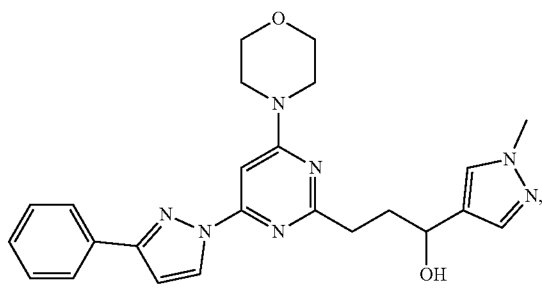
80
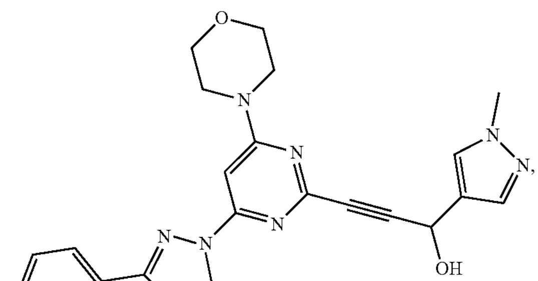
81
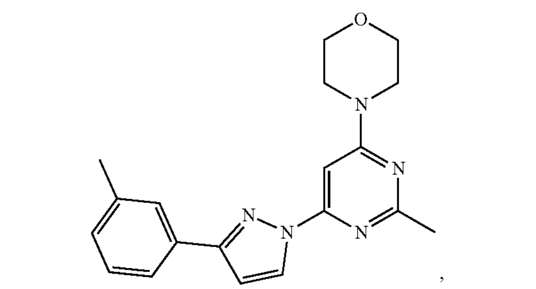
, 82
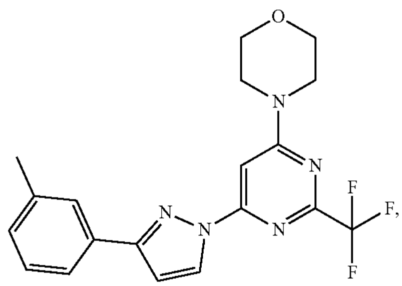
83
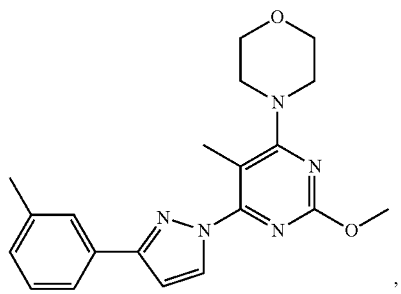
,
84
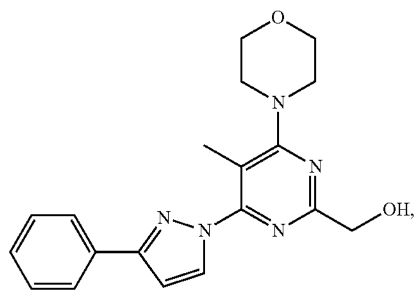
85
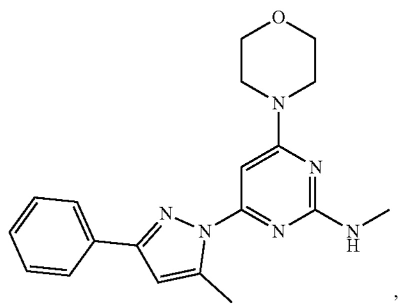
,
86
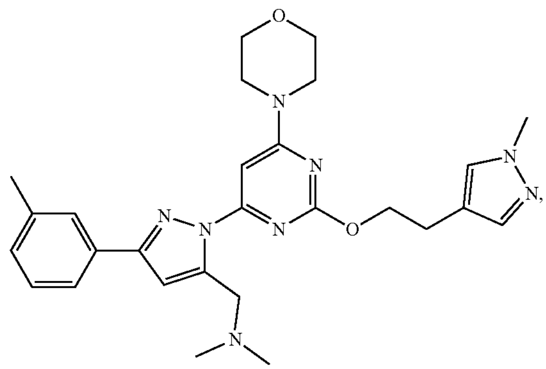
87
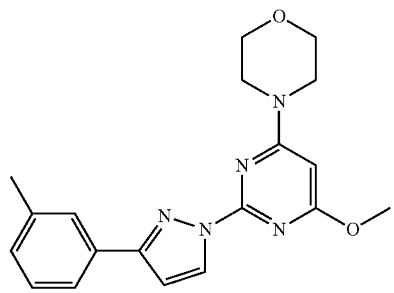
,
88
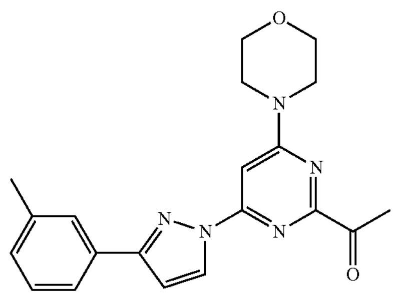
,
89
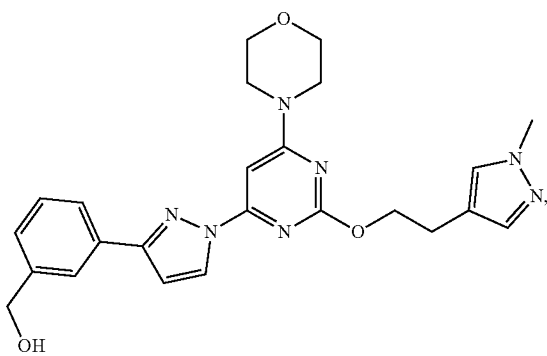
90
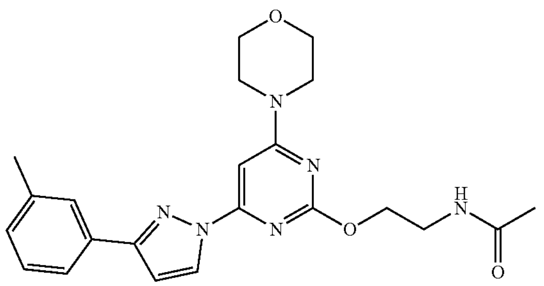
, -continued
91
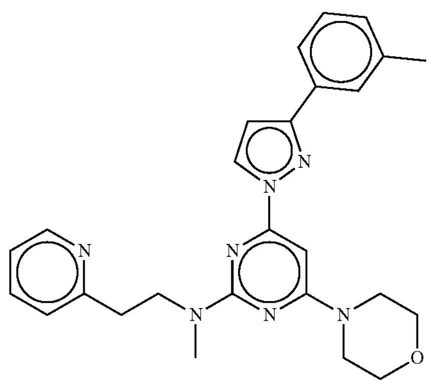
220
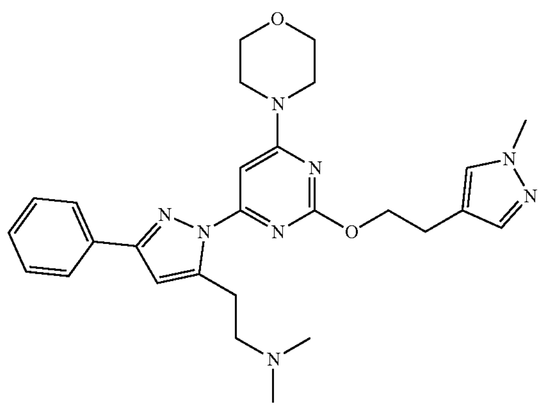
91
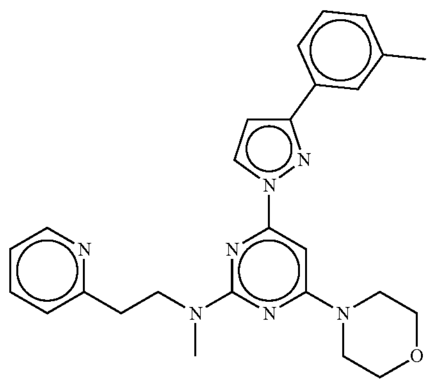
-continued
220
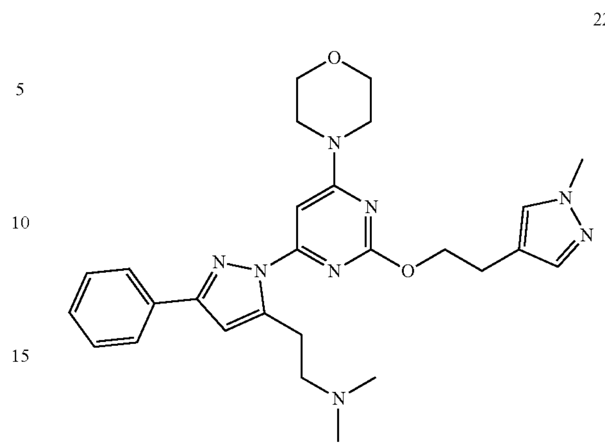
92
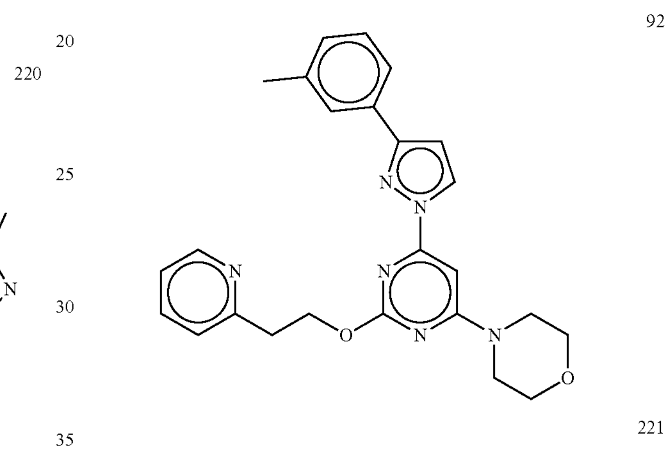
221
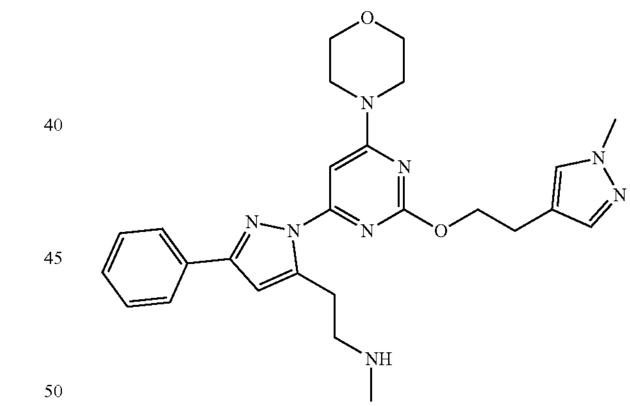
93
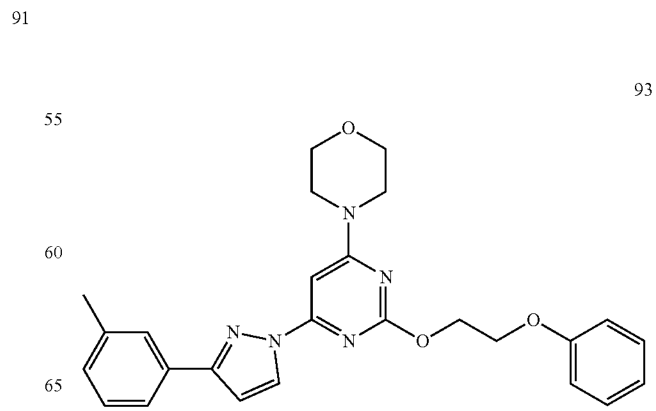

-continued
222
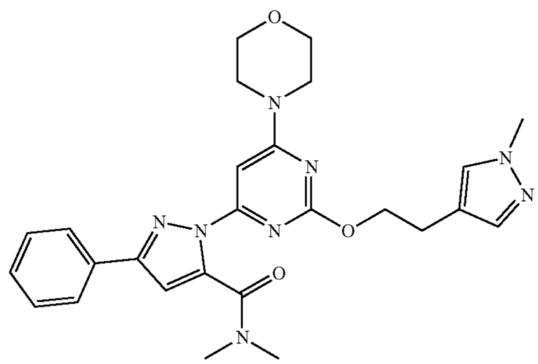
94
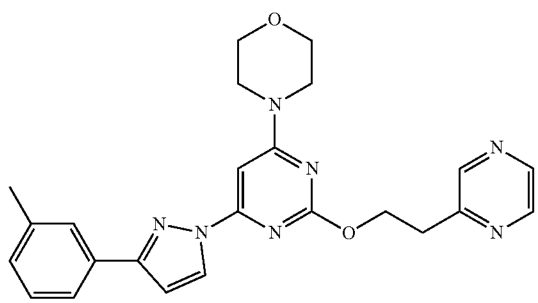
223
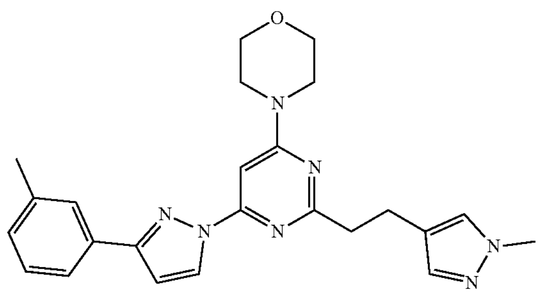
95
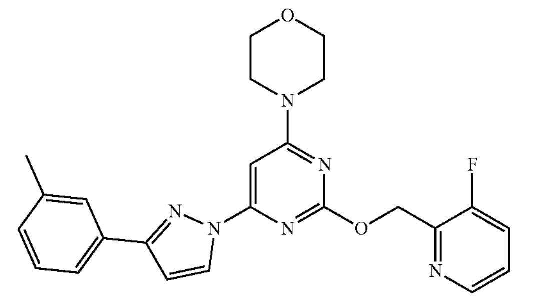
224
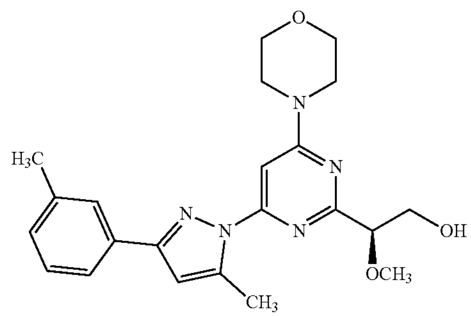
-continued
96
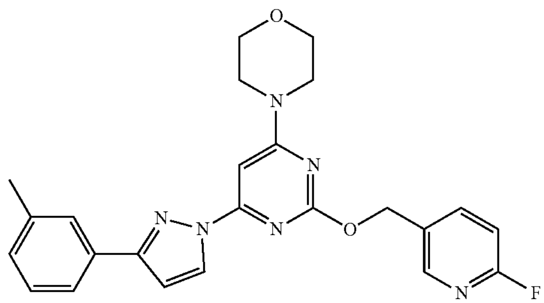
225
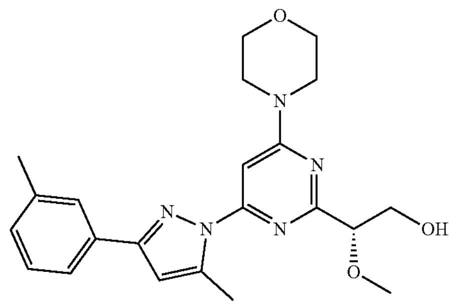
97
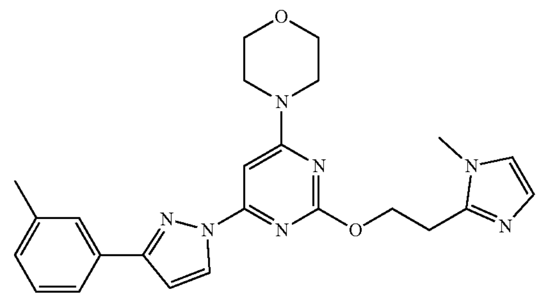
226
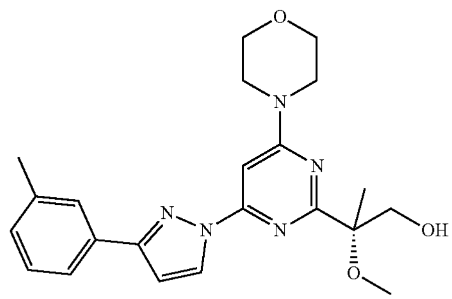
98
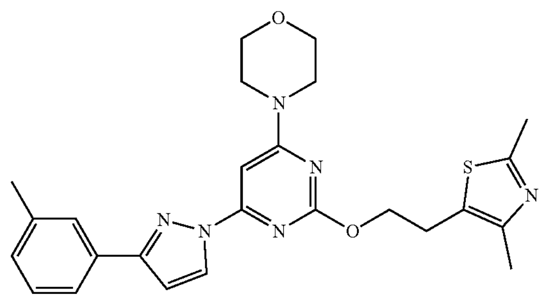

-continued
227
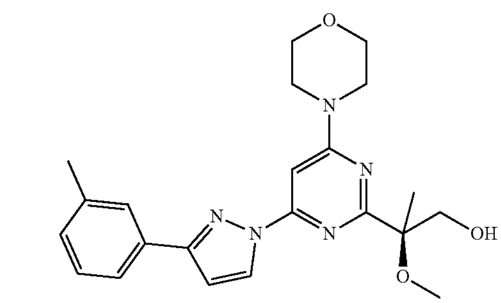
99
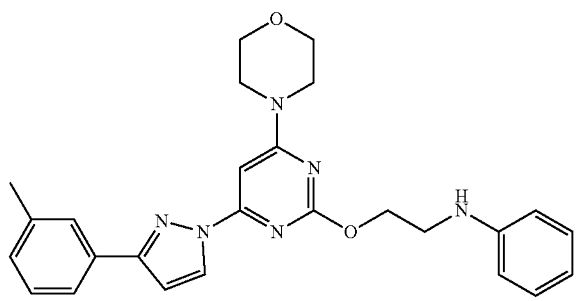
228
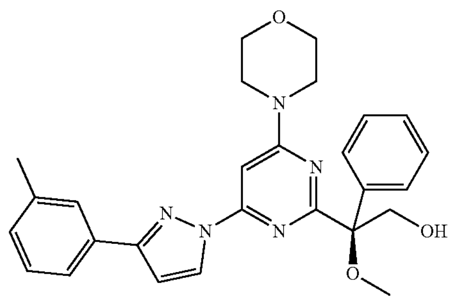
100
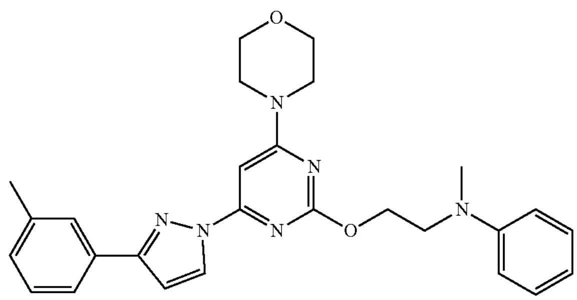
229
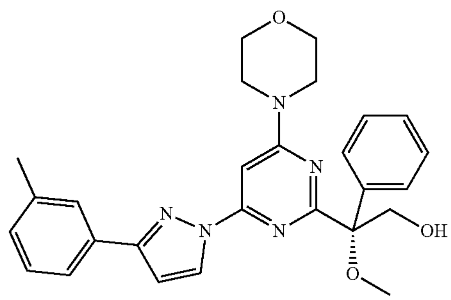
-continued
101
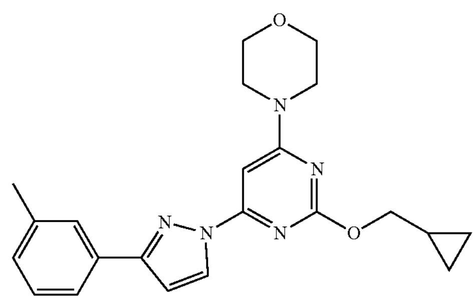
230
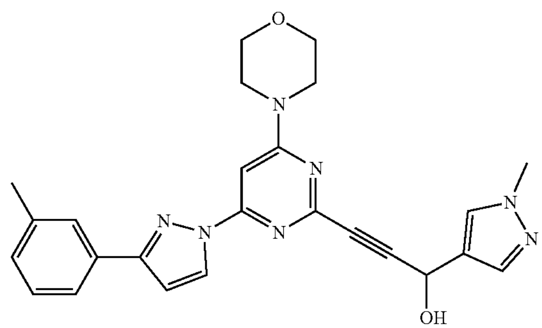
102
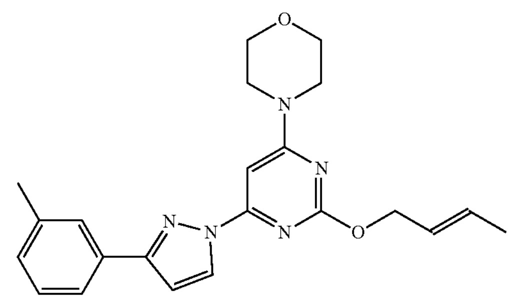
231
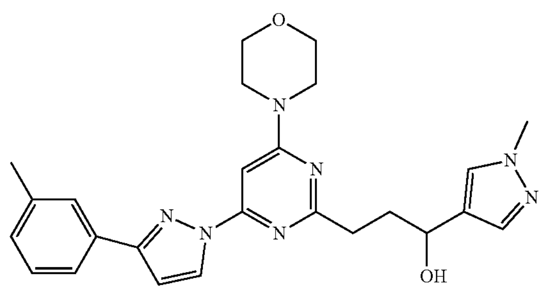
103
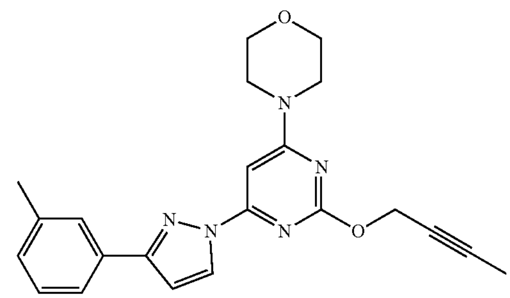

-continued
232
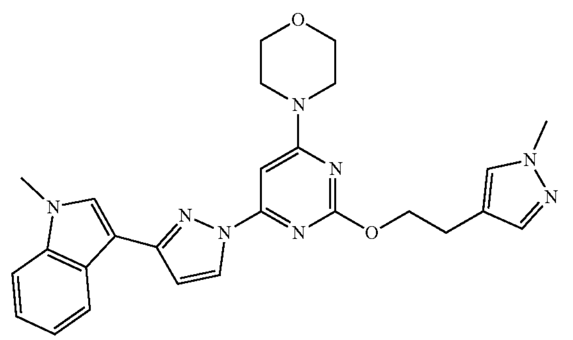
104
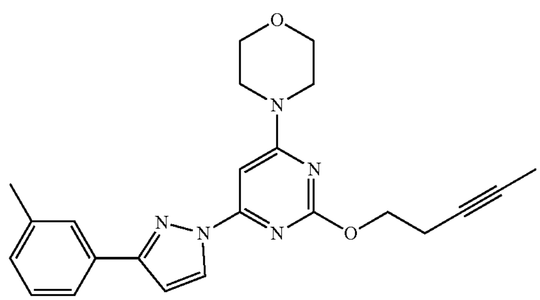
233
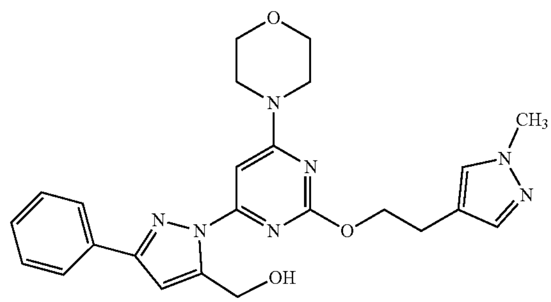
105
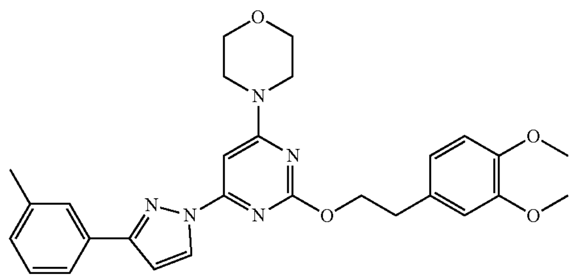
234
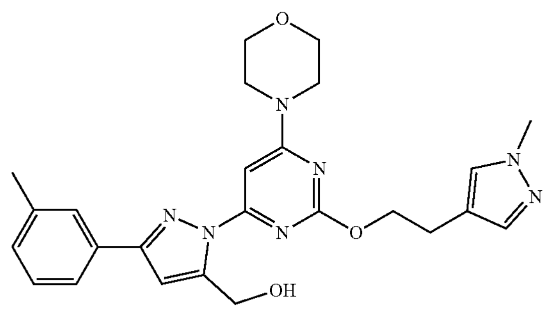
-continued
106
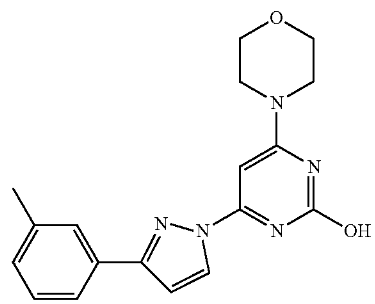
235
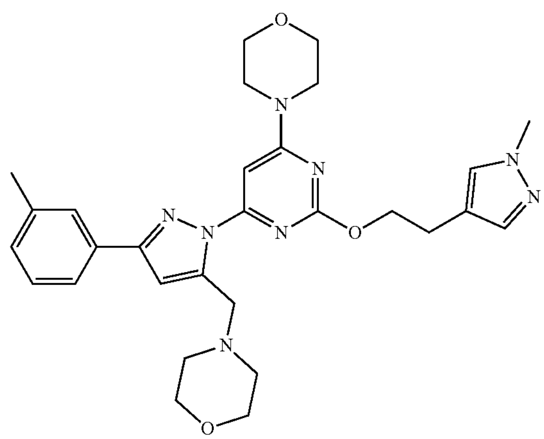
107
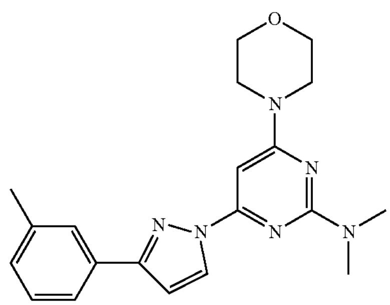
236
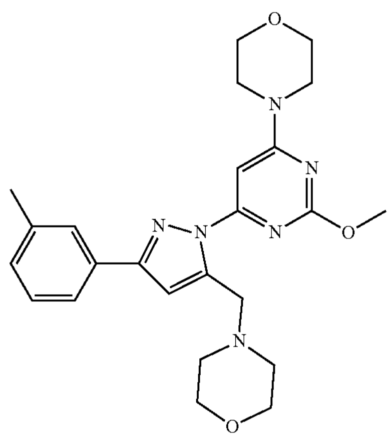

-continued
108
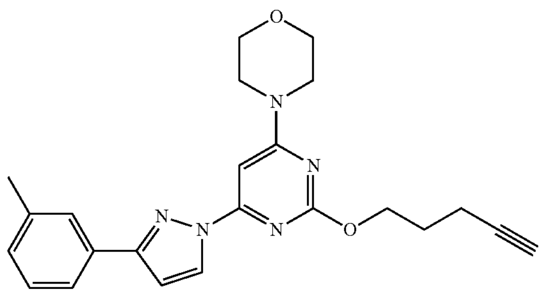
237
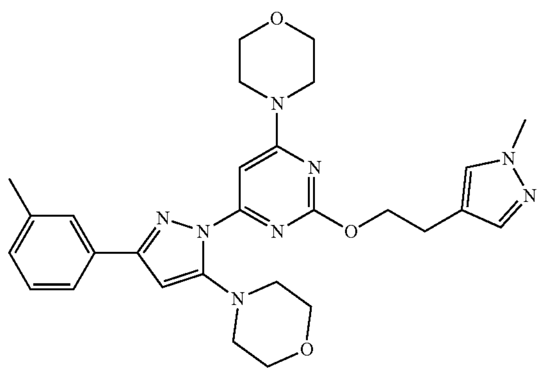
109
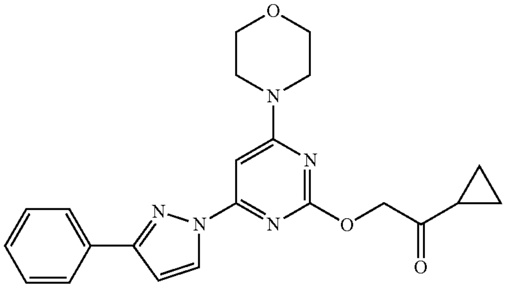
238
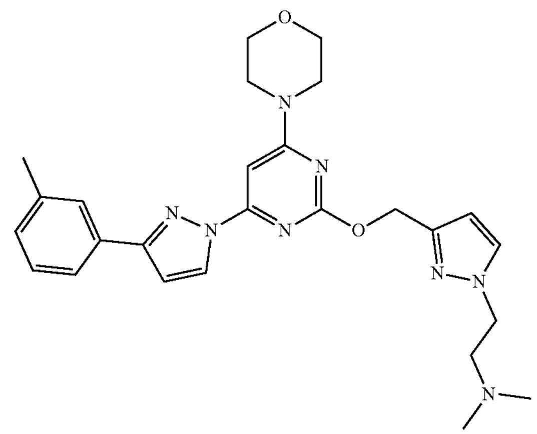
-continued
110
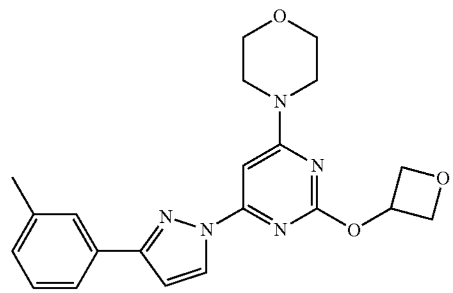
239
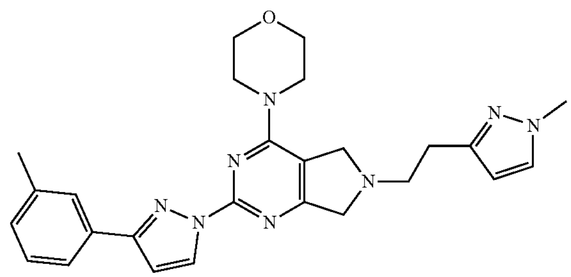
111
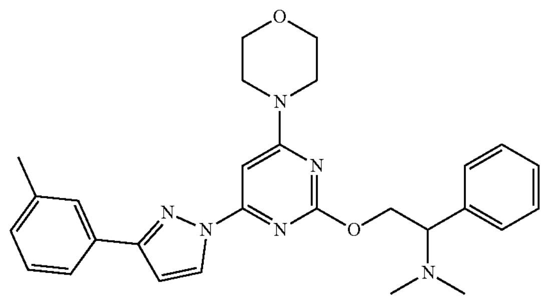
240
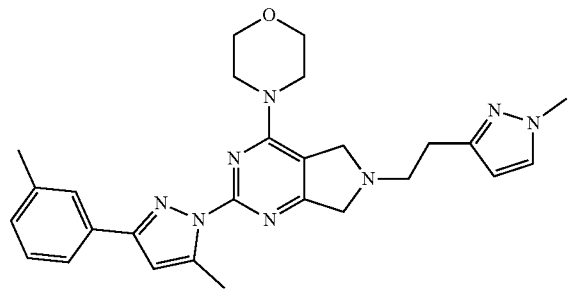
112
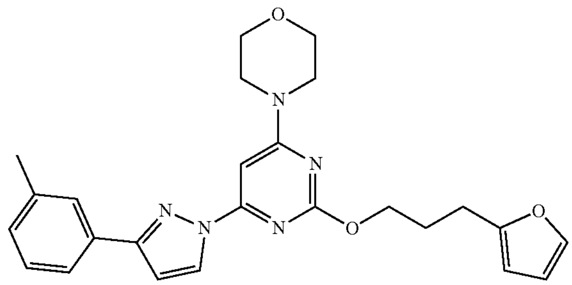

-continued
241
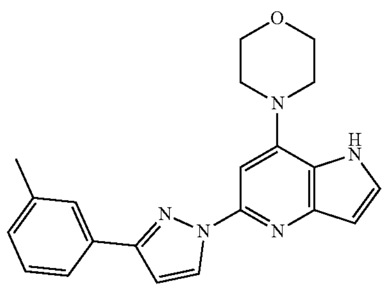
113
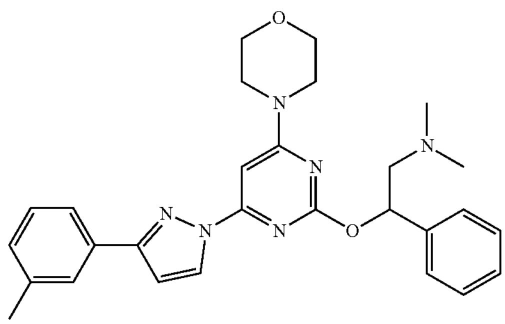
242
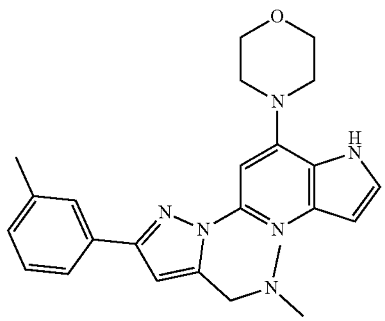
114
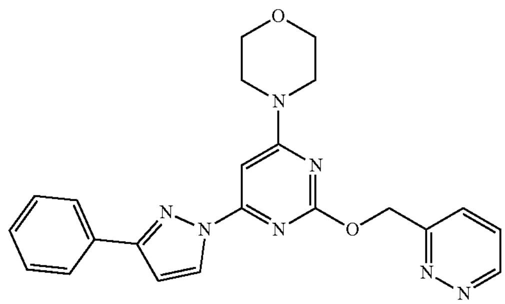
243
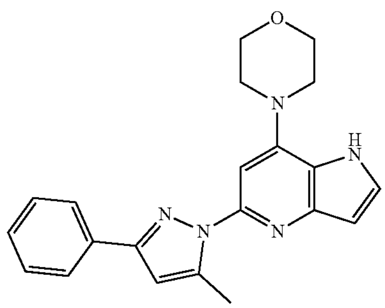
-continued
115
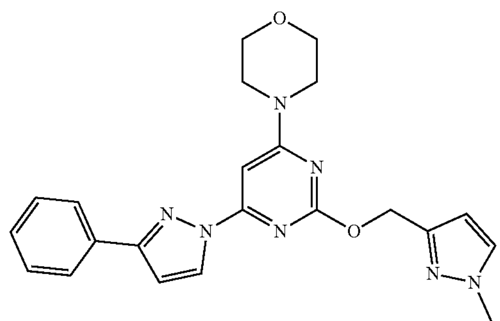
244
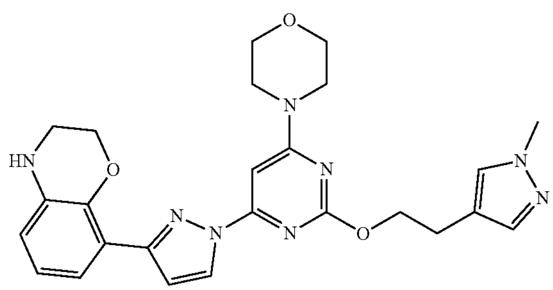
116
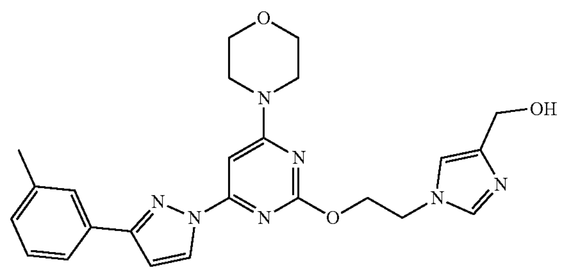
245
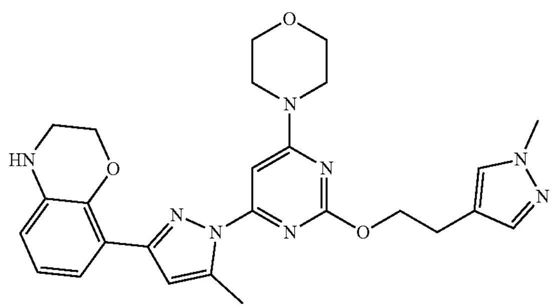
117
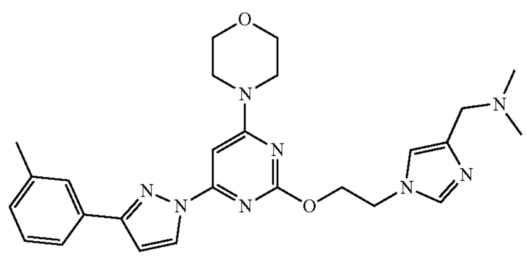

-continued
246
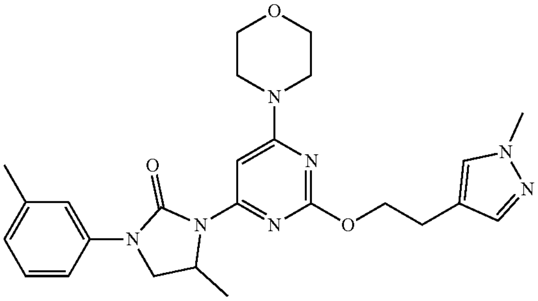
118
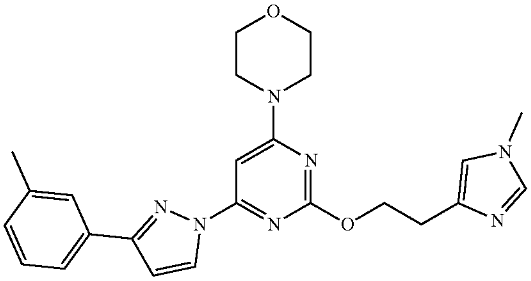
247
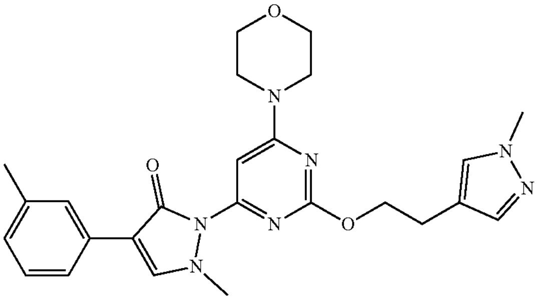
119
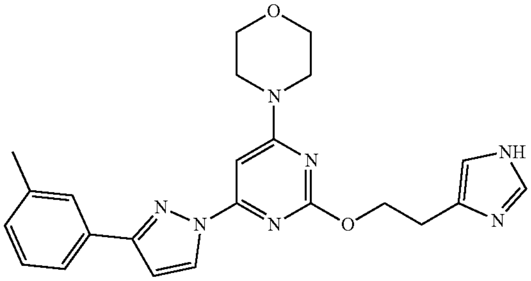
248
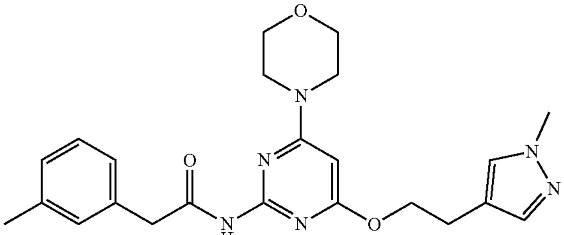
-continued
120
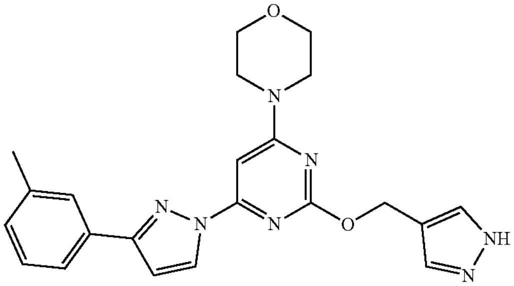
249
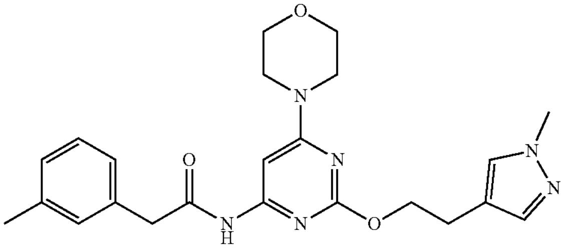
121
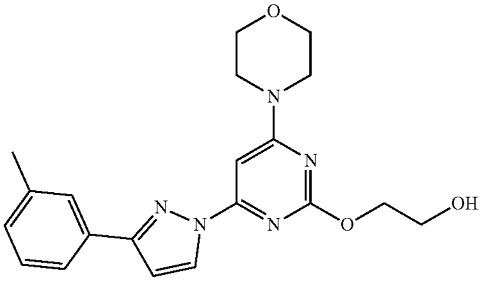
250
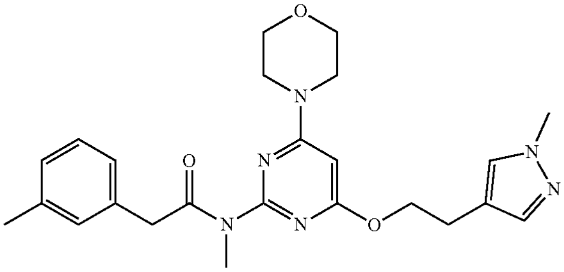
122
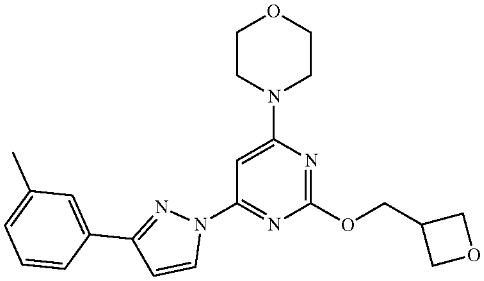

-continued
251
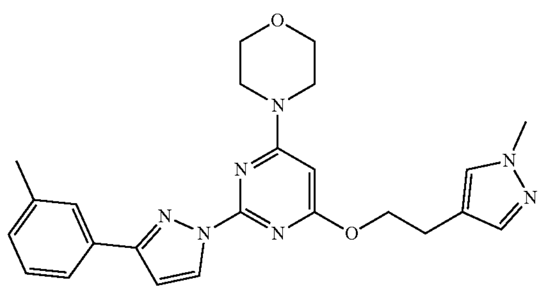
123
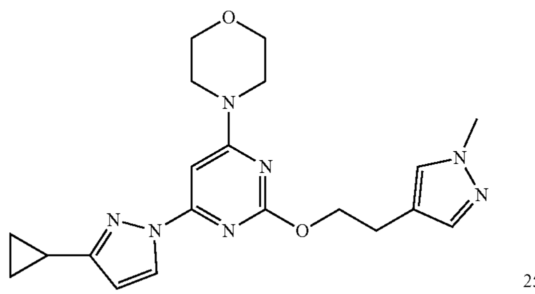
252
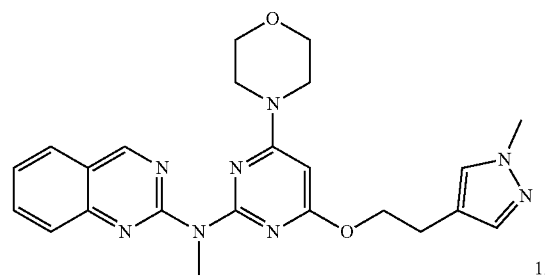
124
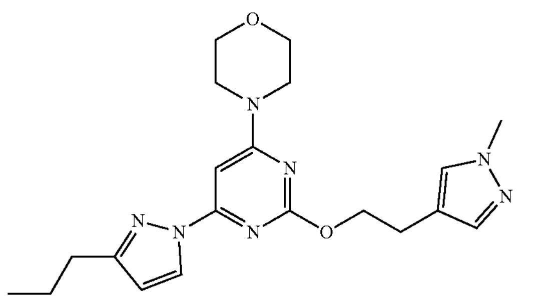
253
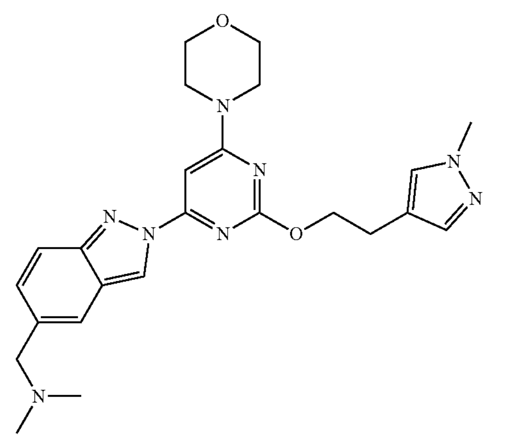
-continued
125
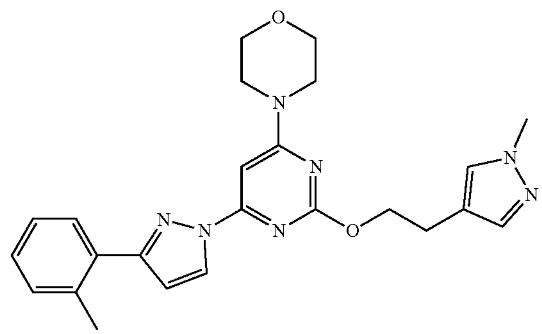
254
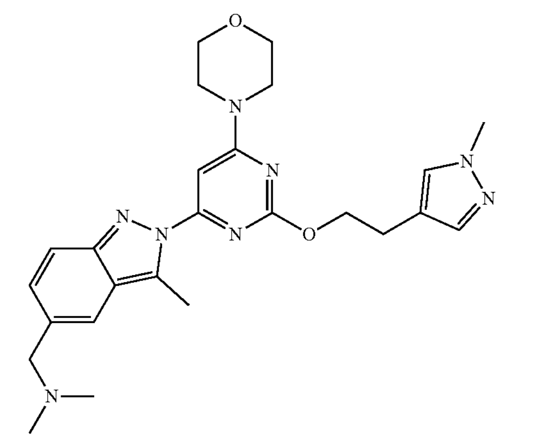
126
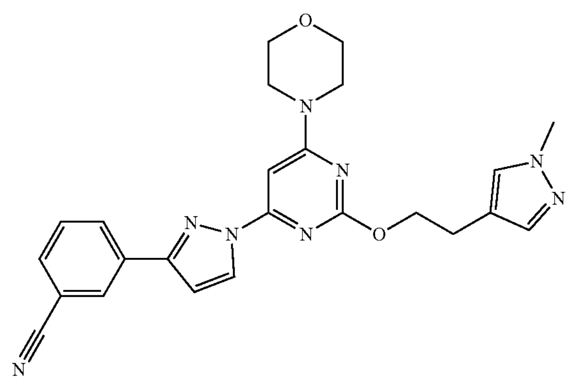
255
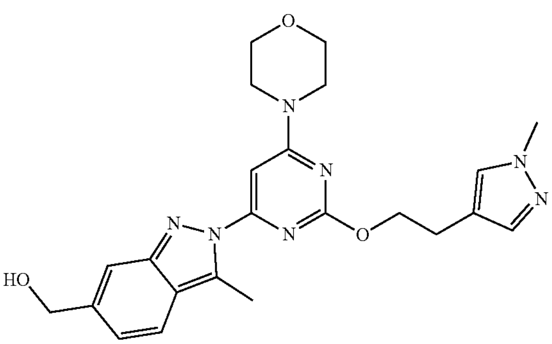

-continued
127
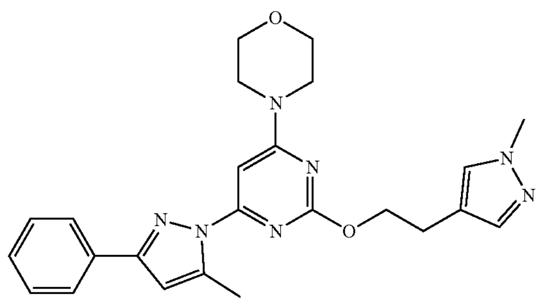
256
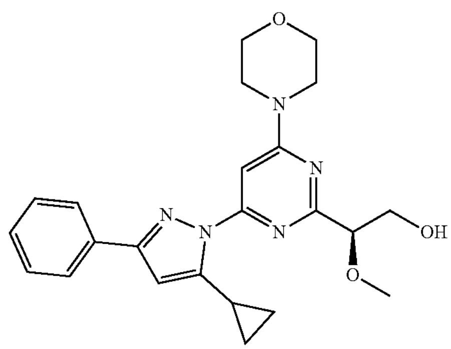
128
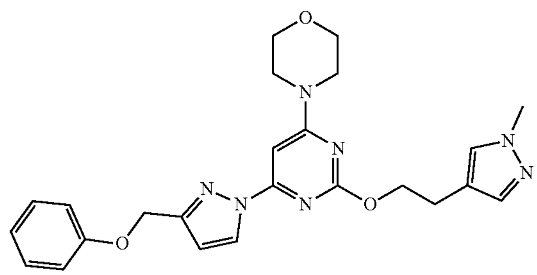
257
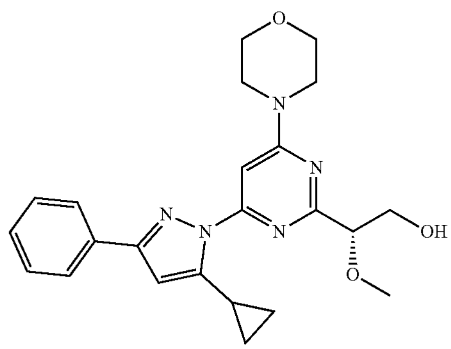
129
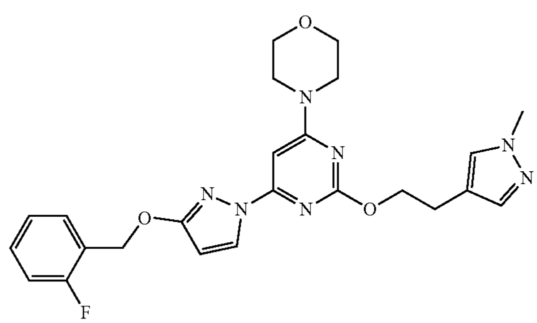
-continued
258
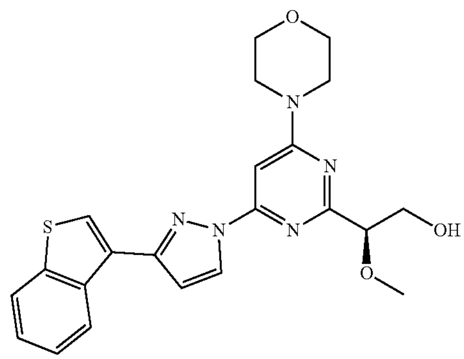
130
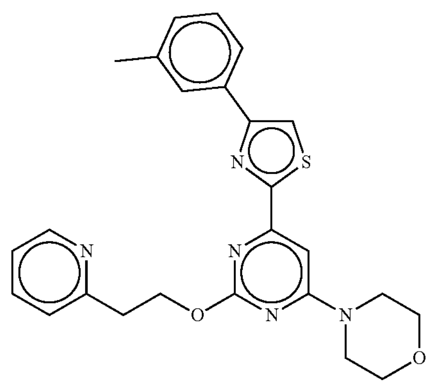
259
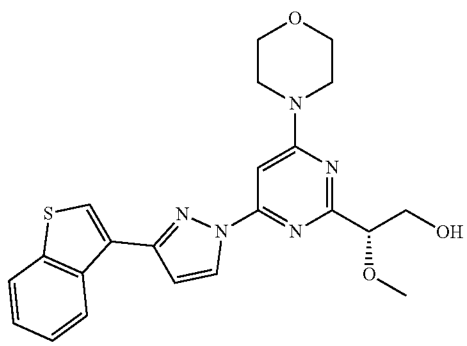
131
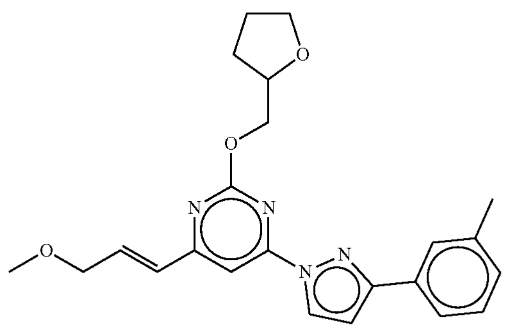

-continued
260
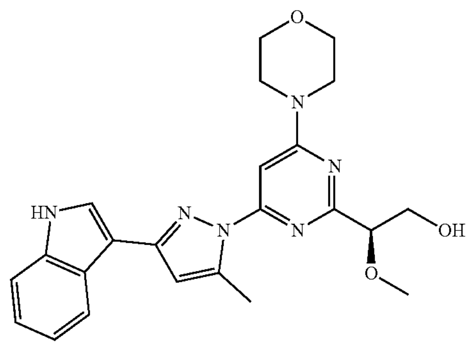
132
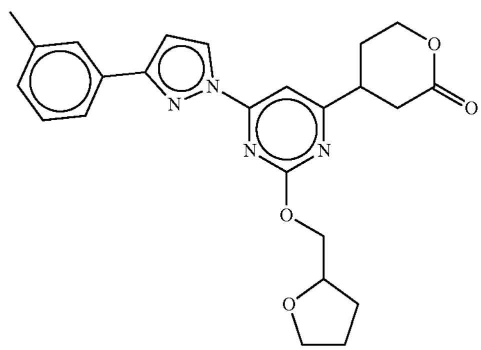
261
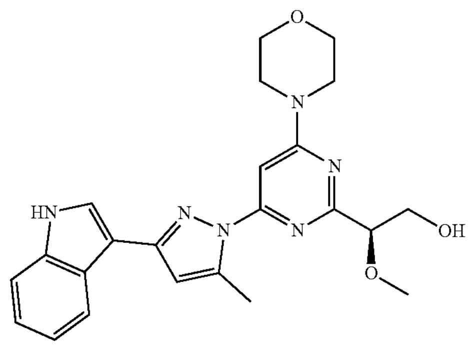
-continued
133
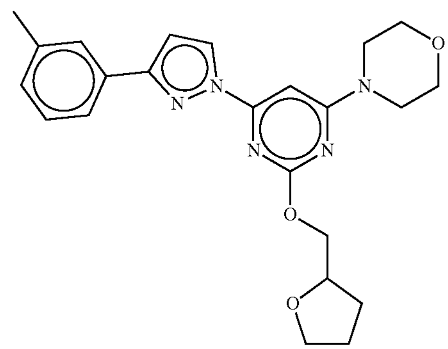
262
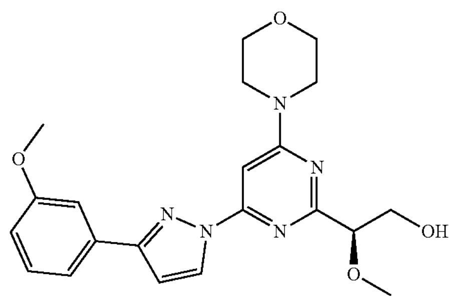
134
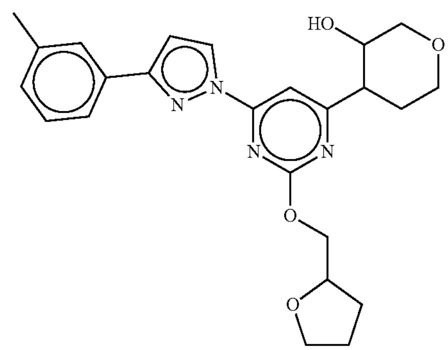
263
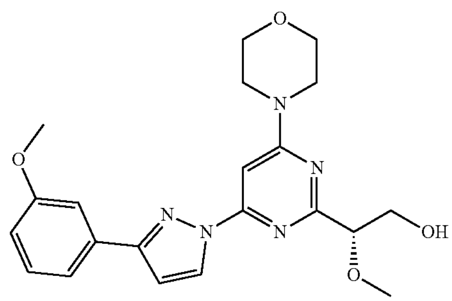

135
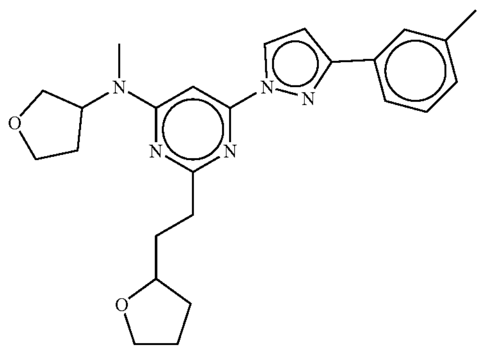
136
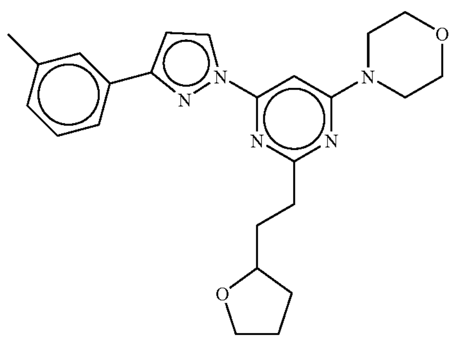
137
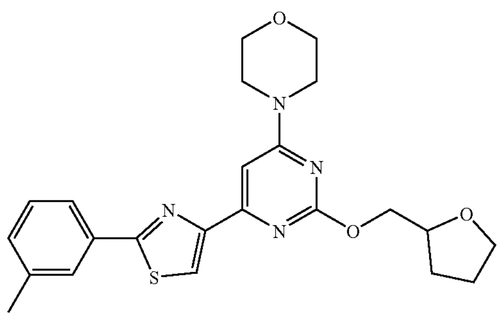
138
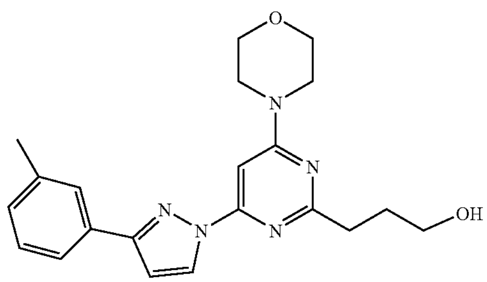
139
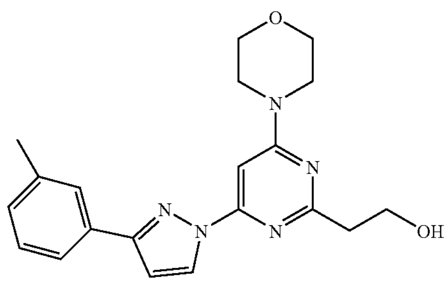
264
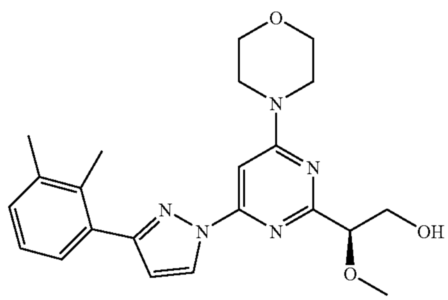
265
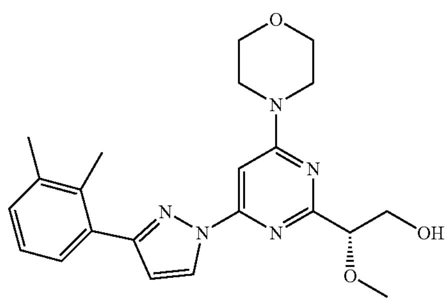
266
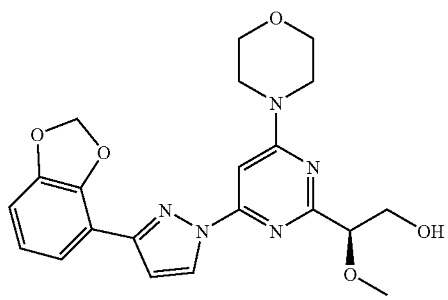
267
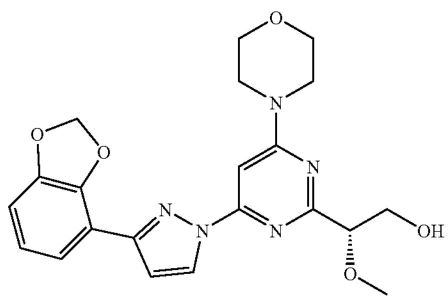
268
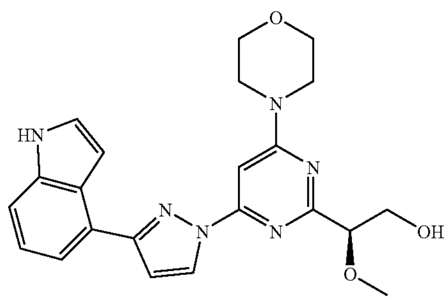

-continued
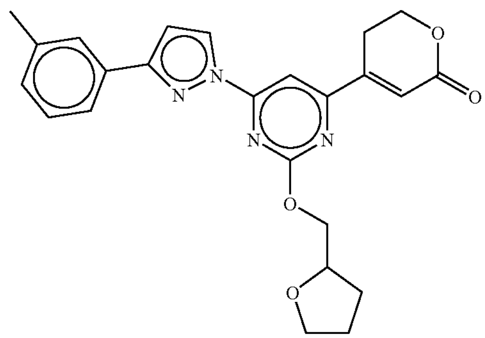
140
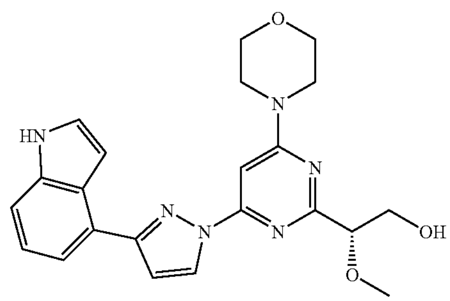
269
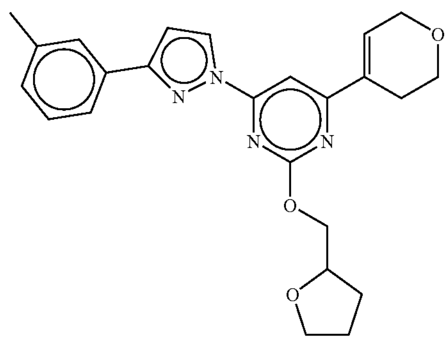
141
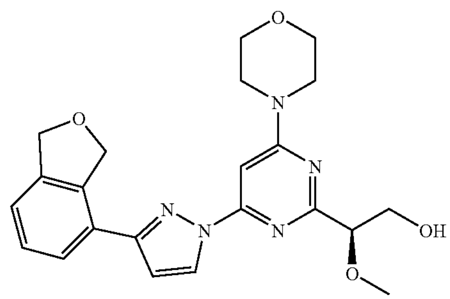
270
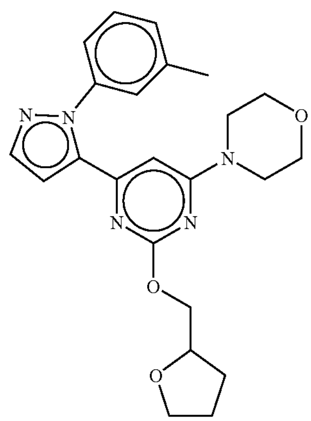
142
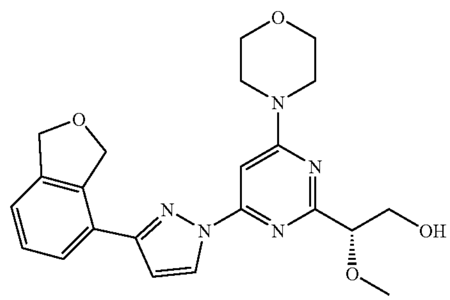
271
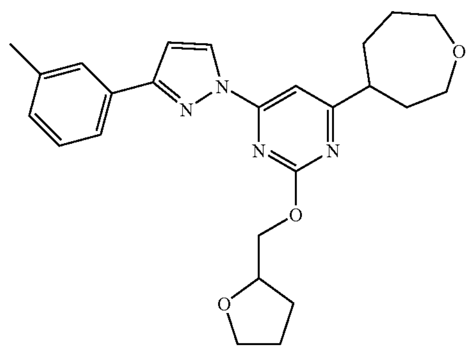
143
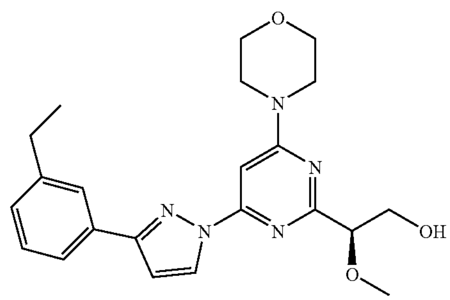
272

-continued
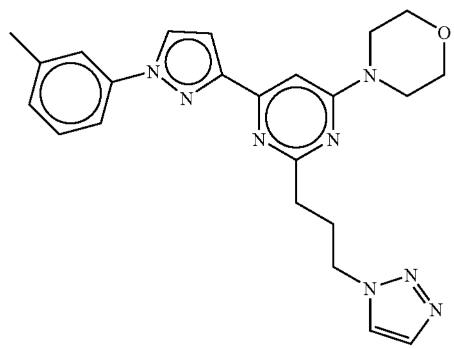
144
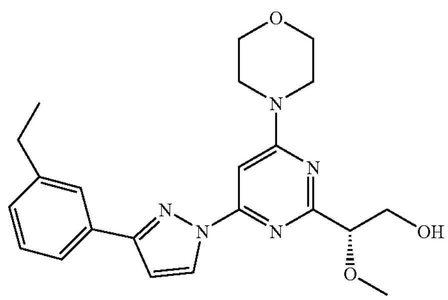
273
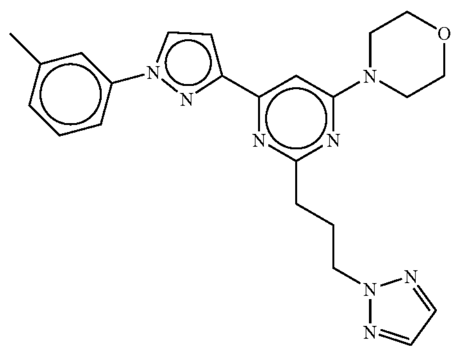
145
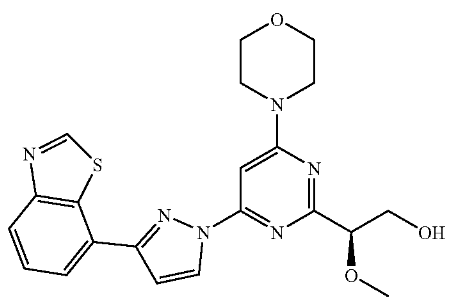
274
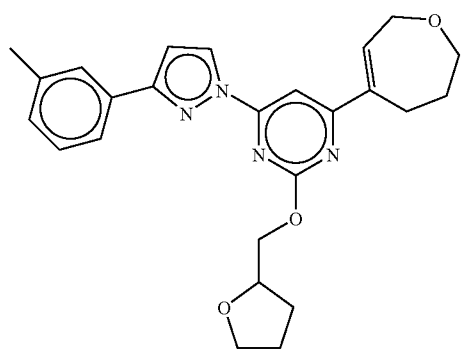
146
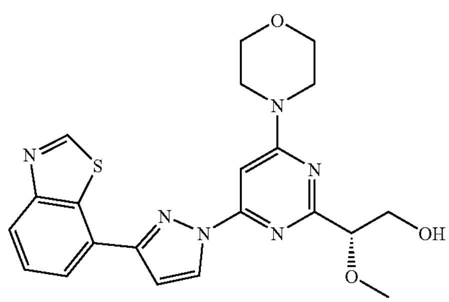
275
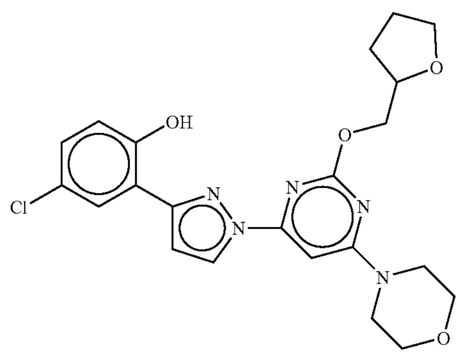
147
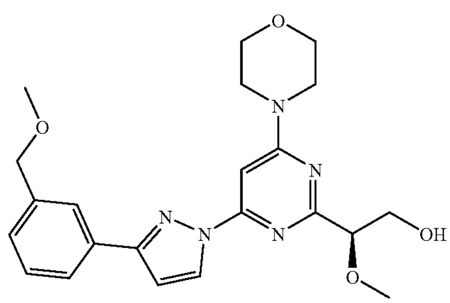
276

-continued
148
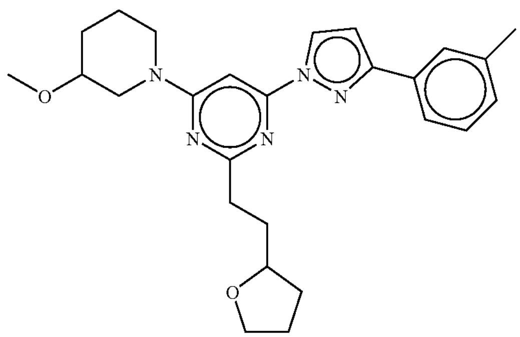
277
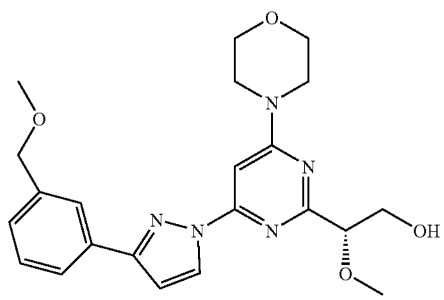
149
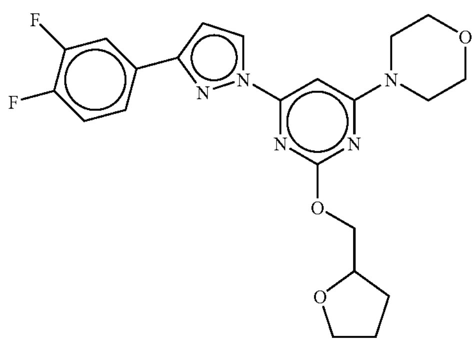
278
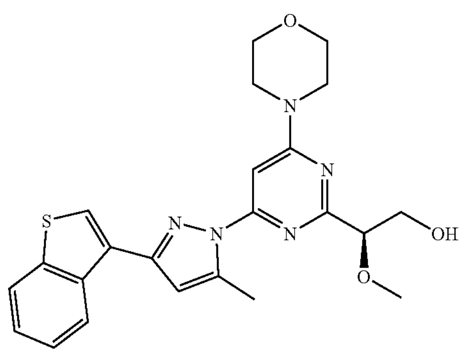
150
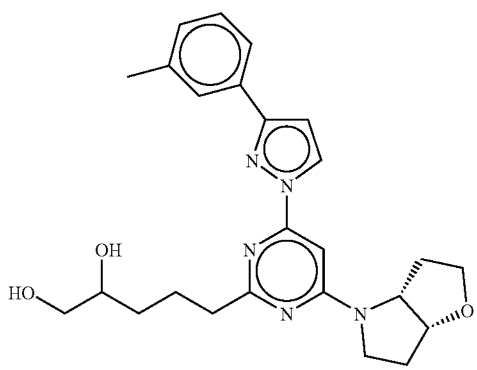
279
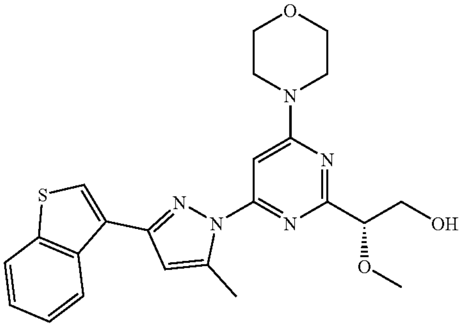
151
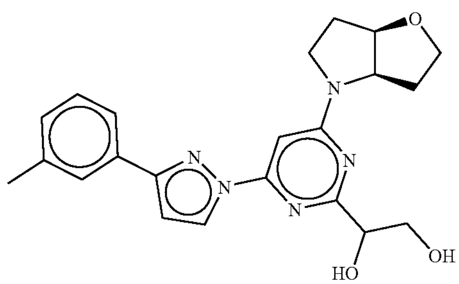
280
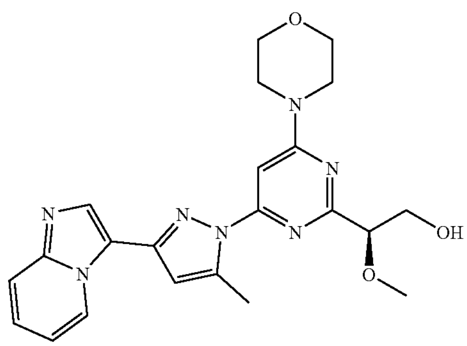

-continued
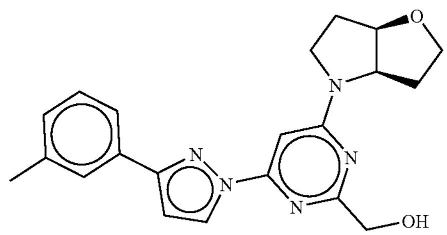
152
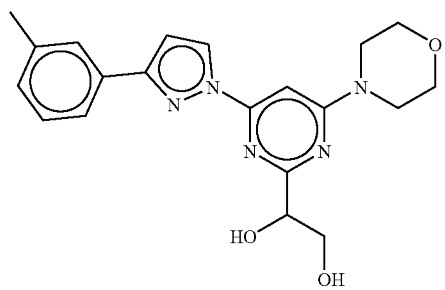
153
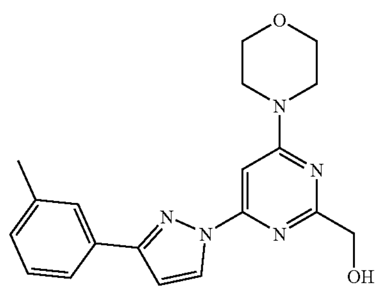
154
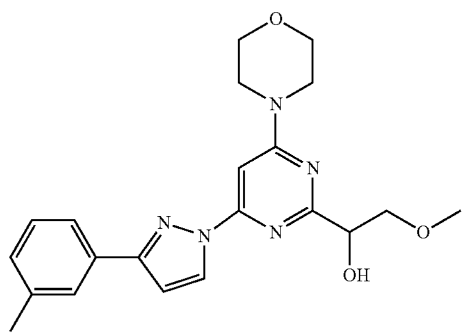
155
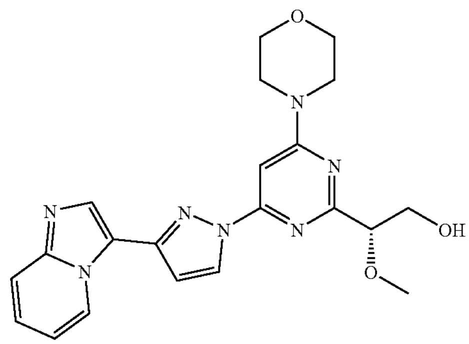
281
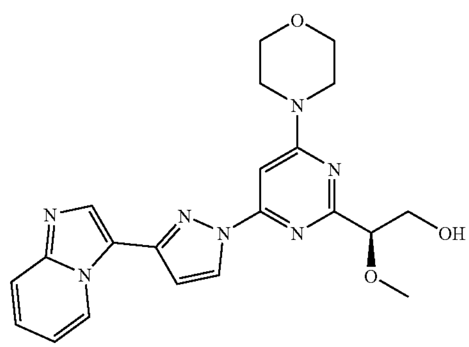
282
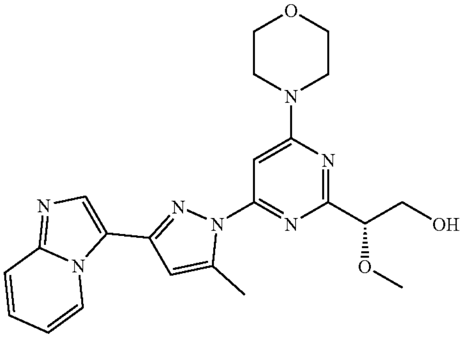
283
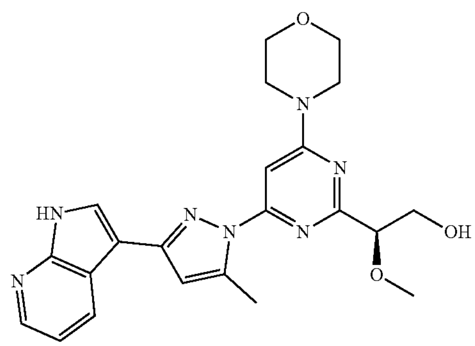
284

-continued
156
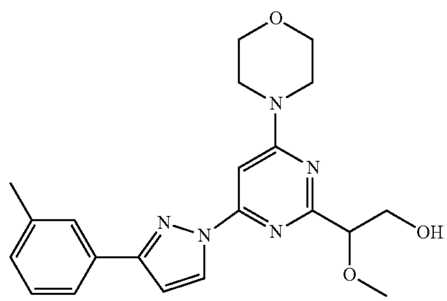
157
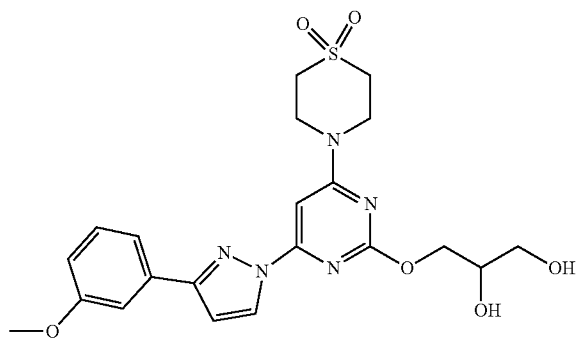
158
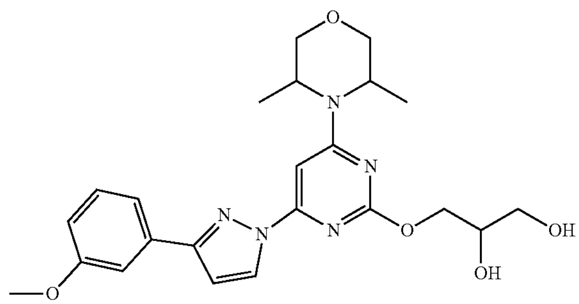
159
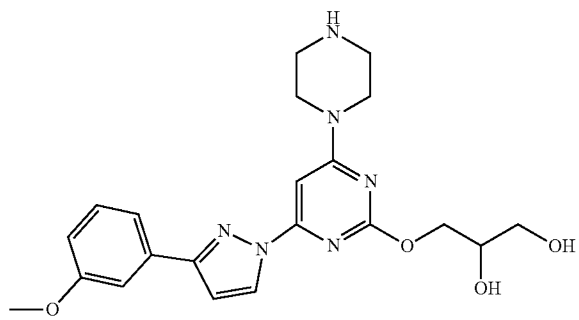
285
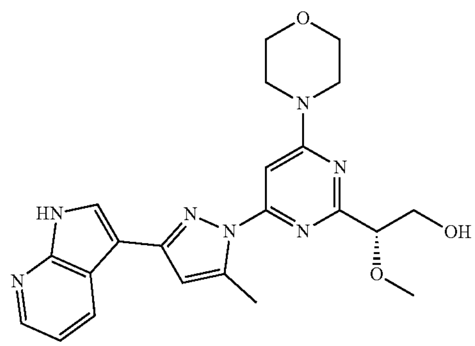
286
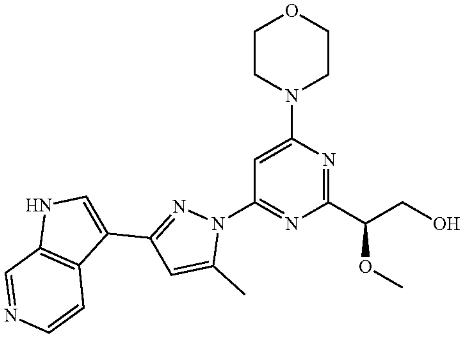 [SMILES: CO[C@H](CO)c1nc(N2CCOCC2)cc(-n2nc(-c3c[nH]c4cnccc34)cc2C)n1]
287
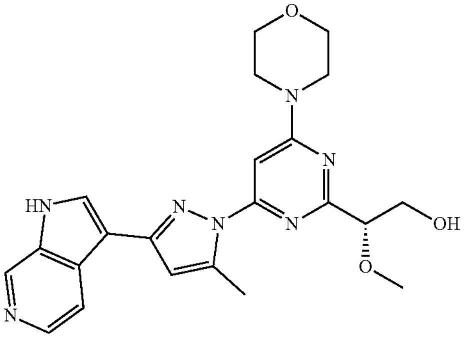 [SMILES: CO[C@@H](CO)c1nc(N2CCOCC2)cc(-n2nc(-c3c[nH]c4cnccc34)cc2C)n1]
288
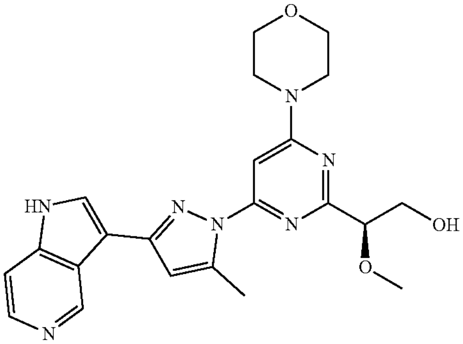 [SMILES: CO[C@H](CO)c1nc(N2CCOCC2)cc(-n2nc(-c3c[nH]c4ccncc34)cc2C)n1]

-continued
160
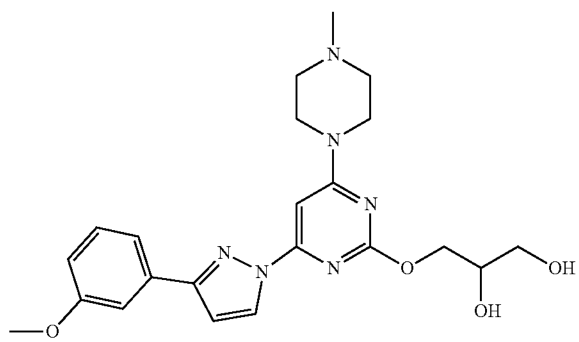
289
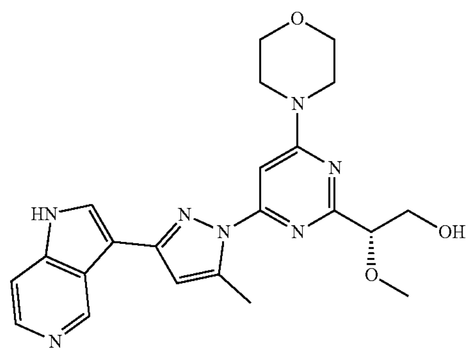 [SMILES: CO[C@@H](CO)c1nc(N2CCOCC2)cc(-n2nc(-c3c[nH]c4ccncc34)cc2C)n1]
161
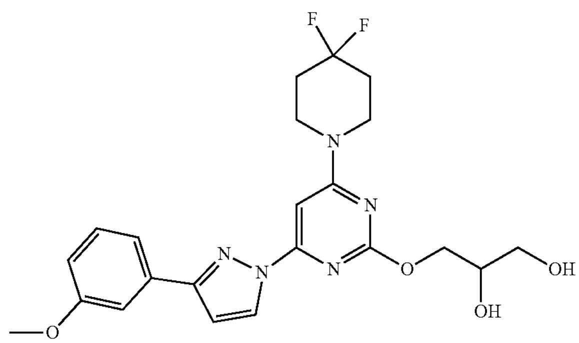
290
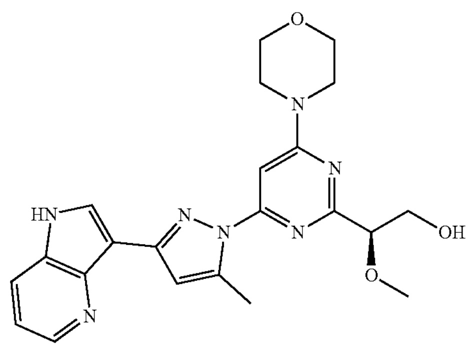 [SMILES: CO[C@H](CO)c1nc(N2CCOCC2)cc(-n2nc(-c3c[nH]c4cccnc34)cc2C)n1]
162
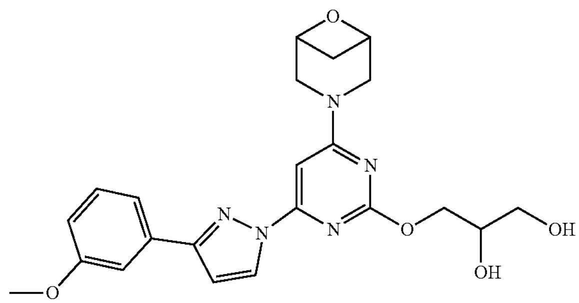
291
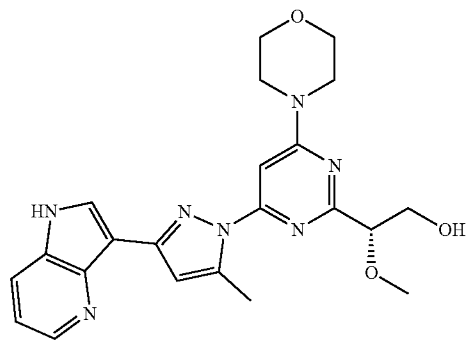 [SMILES: CO[C@@H](CO)c1nc(N2CCOCC2)cc(-n2nc(-c3c[nH]c4cccnc34)cc2C)n1]
163
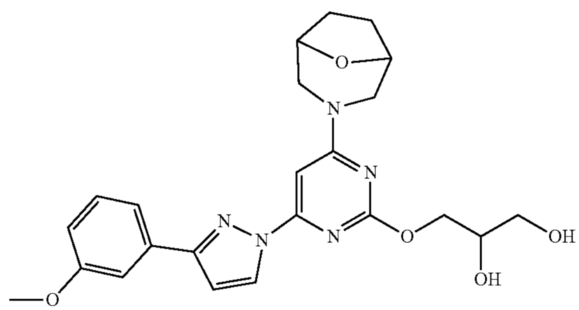
292
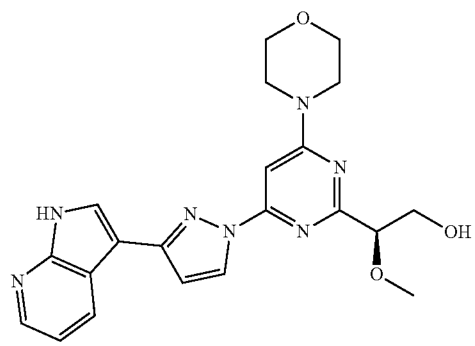 [SMILES: CO[C@H](CO)c1nc(N2CCOCC2)cc(-n2ccc(-c3c[nH]c4ncccc34)n2)n1]

-continued
164
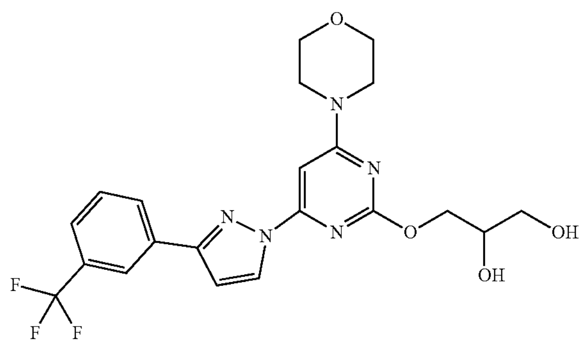
293
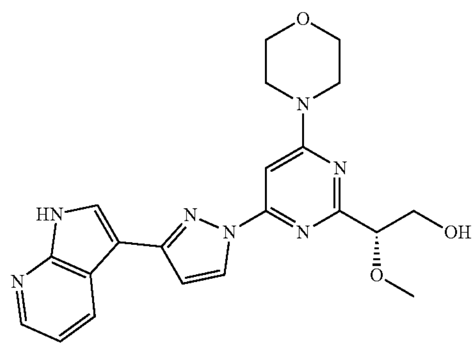 [SMILES: CO[C@@H](CO)c1nc(N2CCOCC2)cc(-n2ccc(-c3c[nH]c4ncccc34)n2)n1]
165
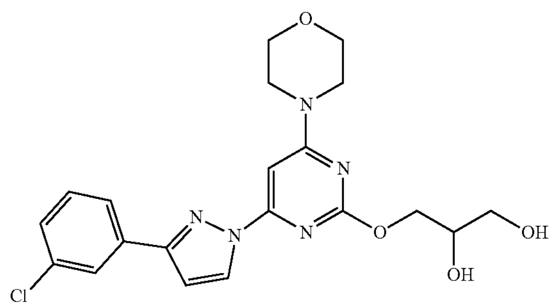
294
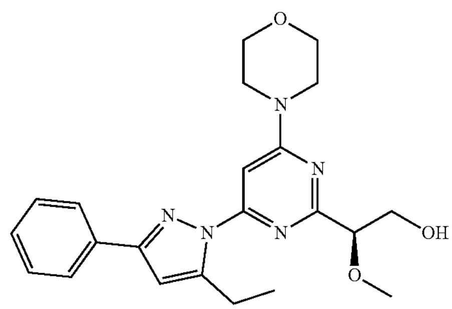 [SMILES: CCc1cc(-c2ccccc2)nn1-c1cc(N2CCOCC2)nc([C@@H](CO)OC)n1]
166
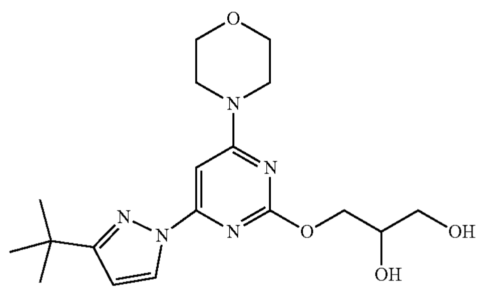
295
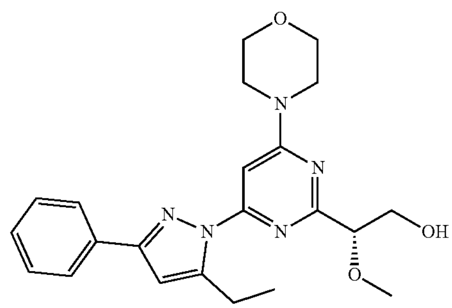 [SMILES: CCc1cc(-c2ccccc2)nn1-c1cc(N2CCOCC2)nc([C@H](CO)OC)n1]
167
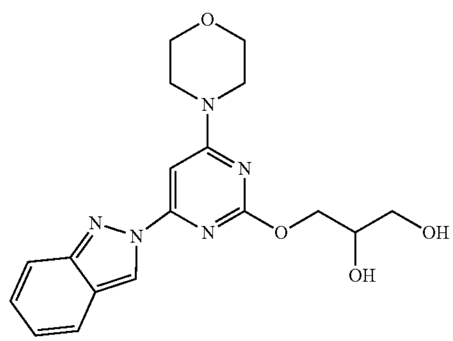
296
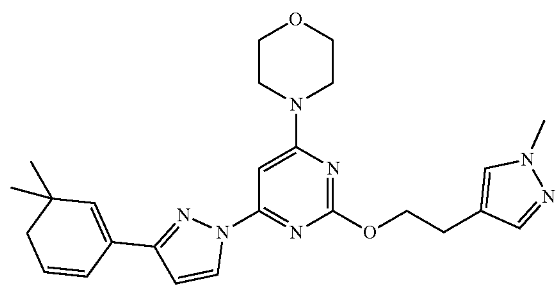

-continued
168
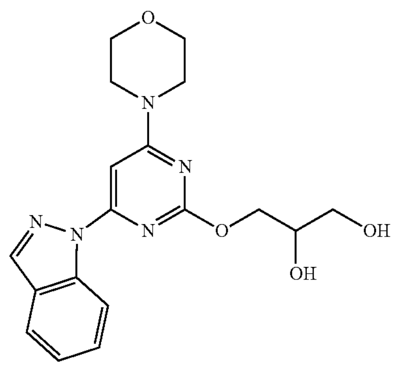
169
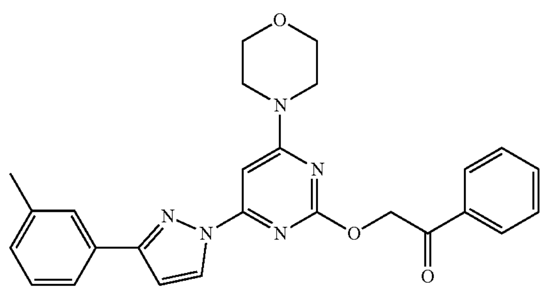
170
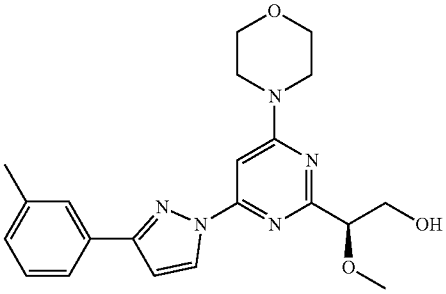
171
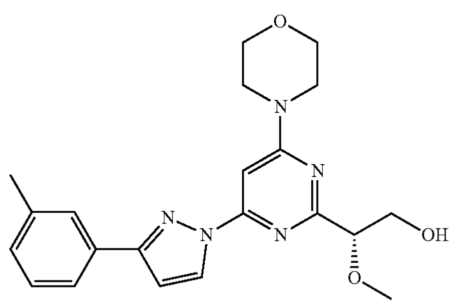
172
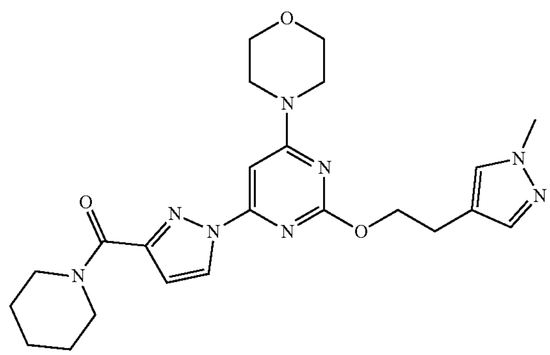
297
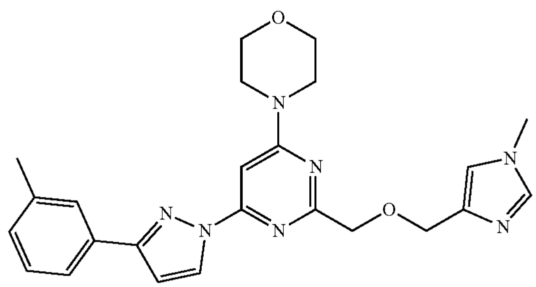
298
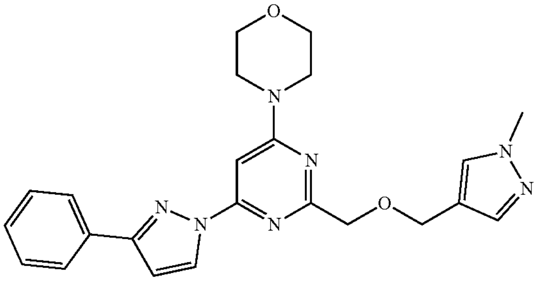
299
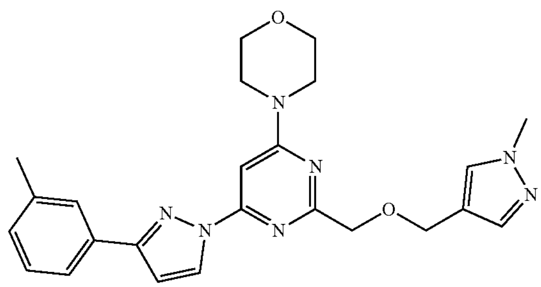 [SMILES: Cc1cccc(-c2ccn(-c3cc(N4CCOCC4)nc(COCc4cnn(C)c4)n3)n2)c1]
300
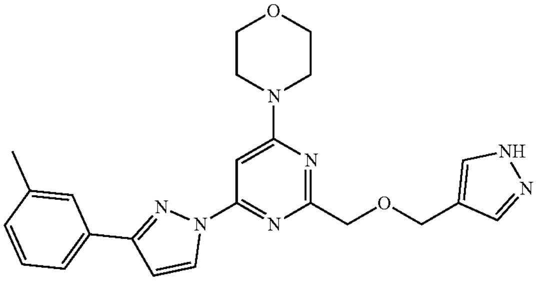 [SMILES: Cc1cccc(-c2ccn(-c3cc(N4CCOCC4)nc(COCc4cn[nH]c4)n3)n2)c1]
301
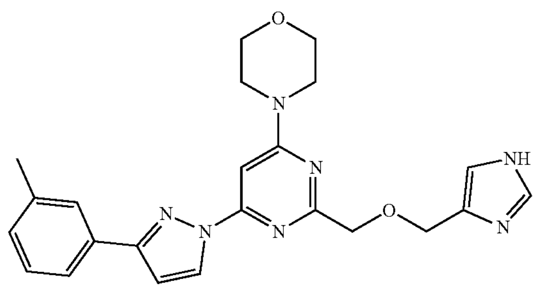 [SMILES: Cc1cccc(-c2ccn(-c3cc(N4CCOCC4)nc(COCc4c[nH]cn4)n3)n2)c1]

-continued
173
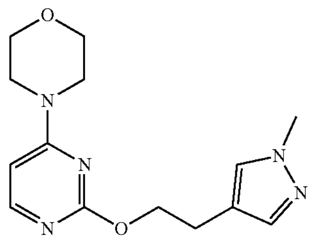
302
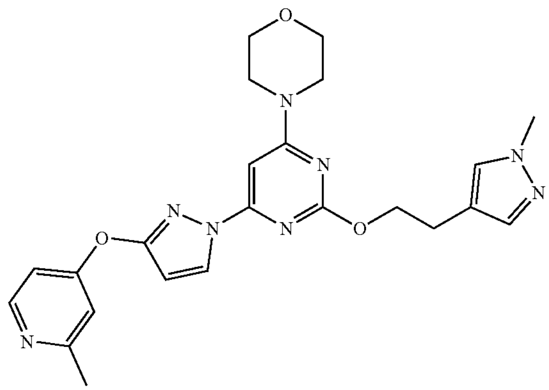
174
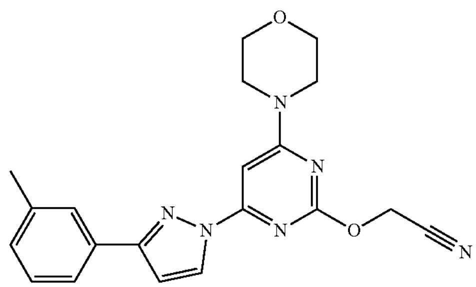
303
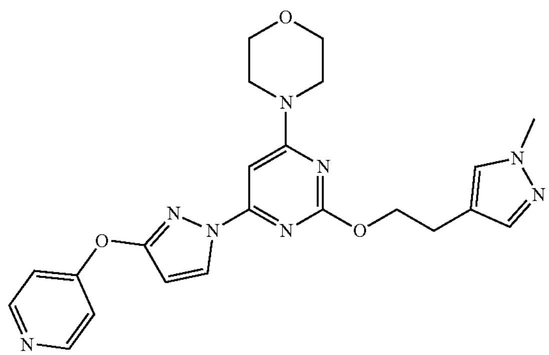
175
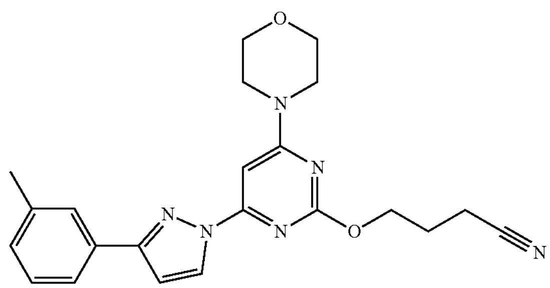
304
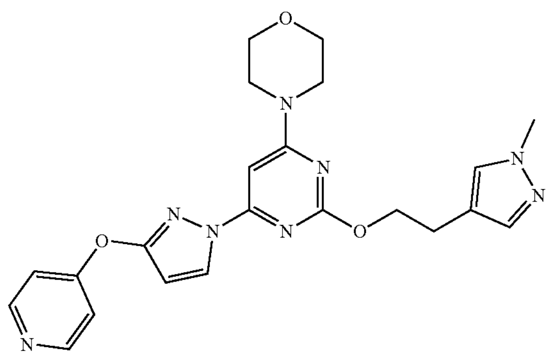
176
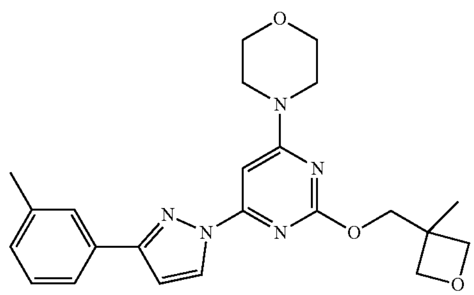
305
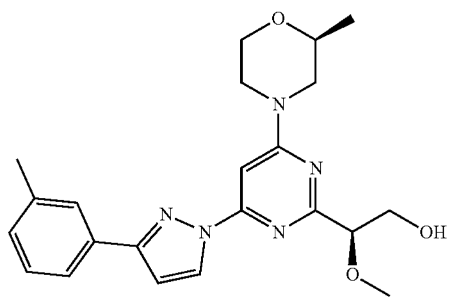

-continued
177
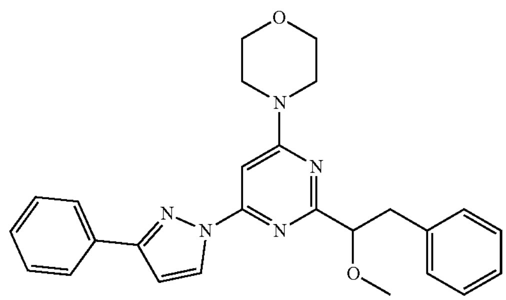
306
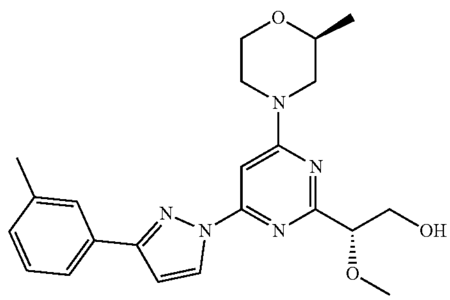
178
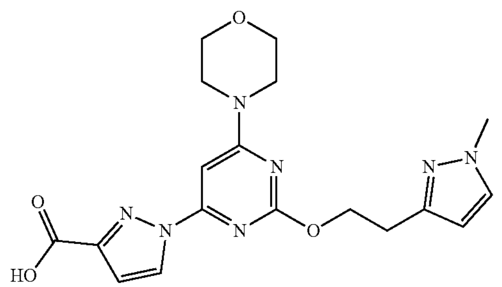
307
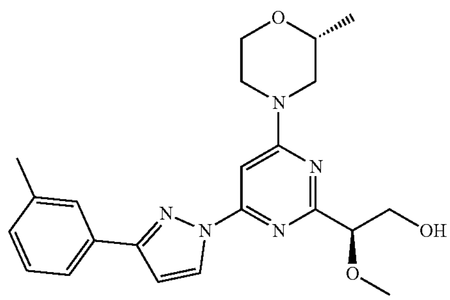
179
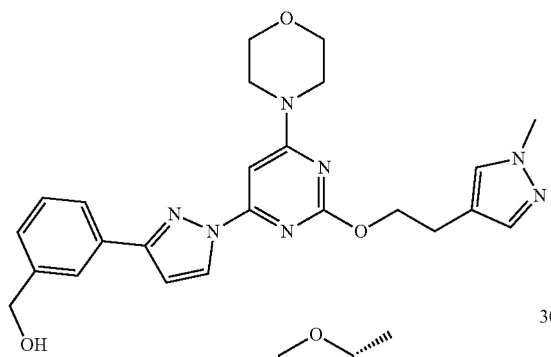
308
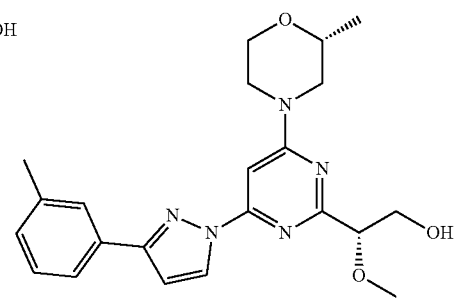
180
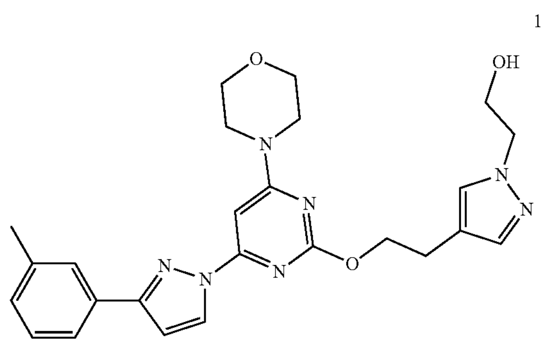
-continued
309
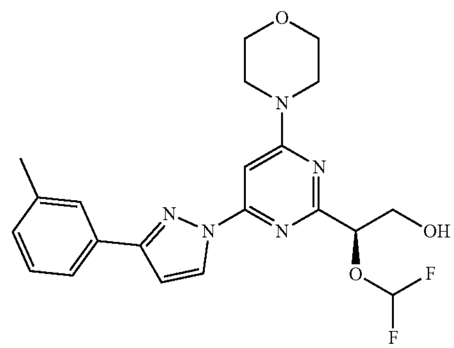
181
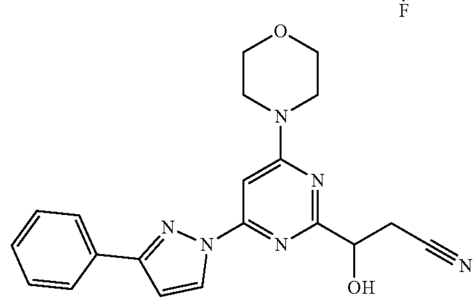
310
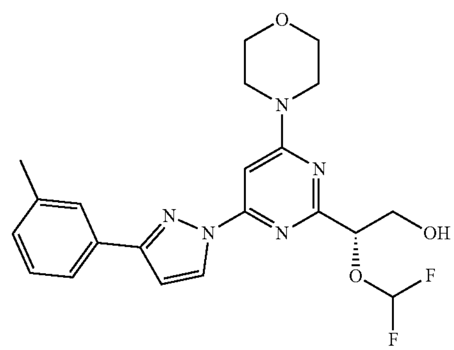

-continued
182
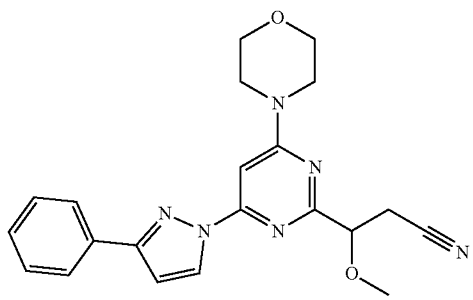
311
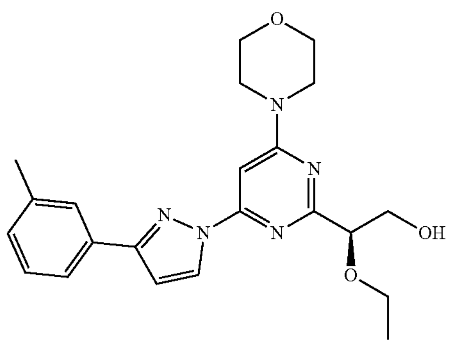
183
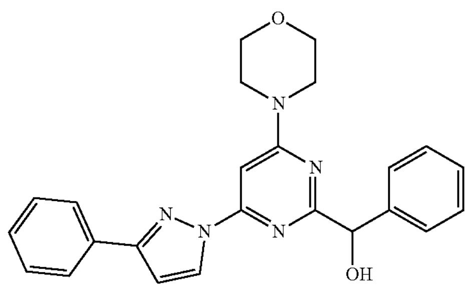
312
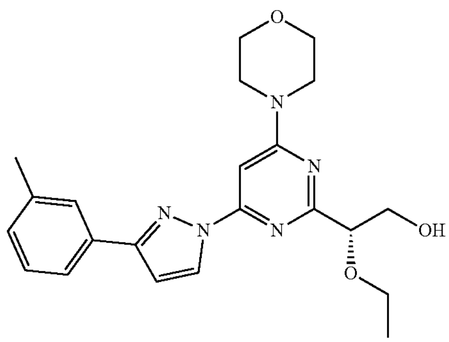
184
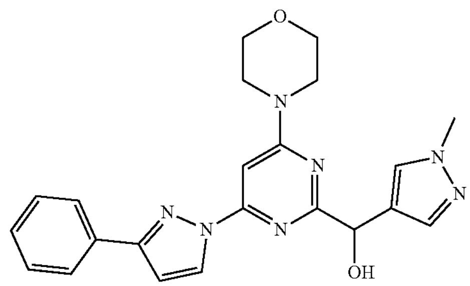
-continued
313
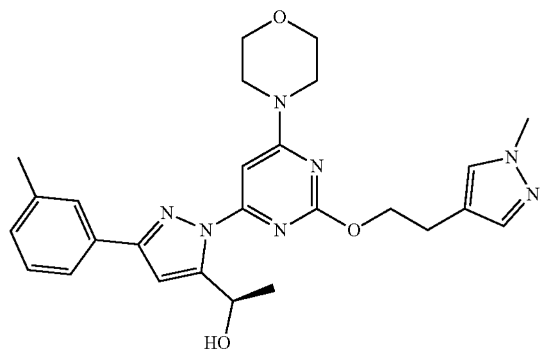
185
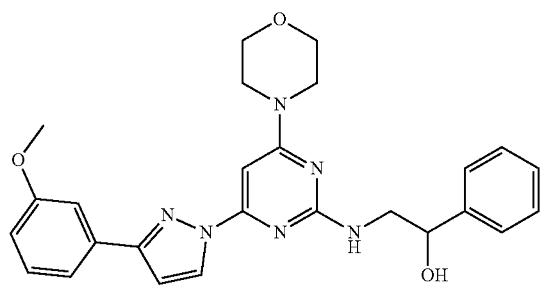
314
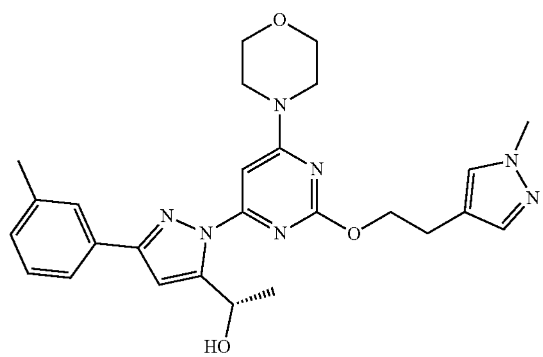
186
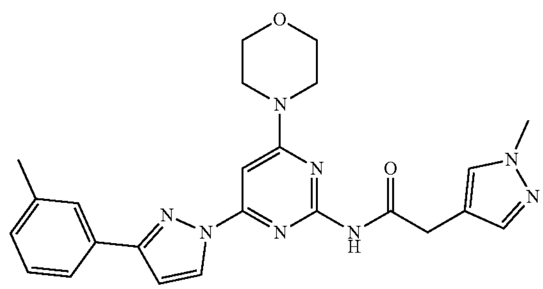

-continued
315
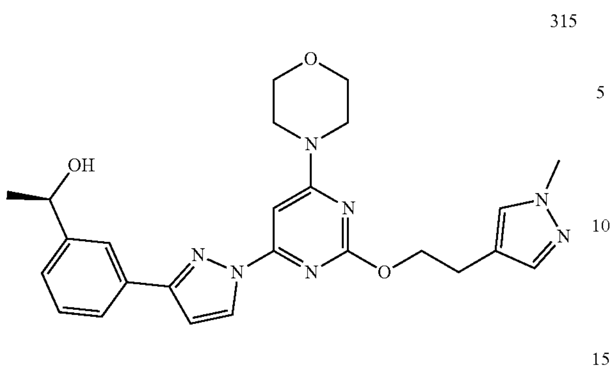
187
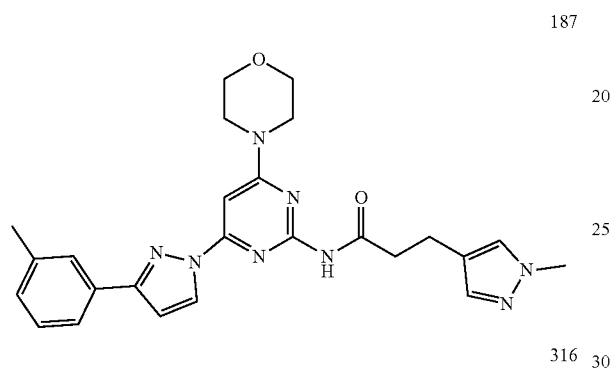
316
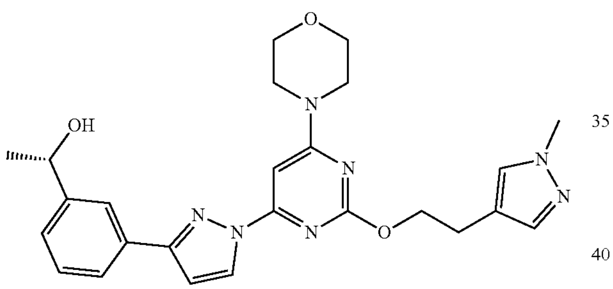
188
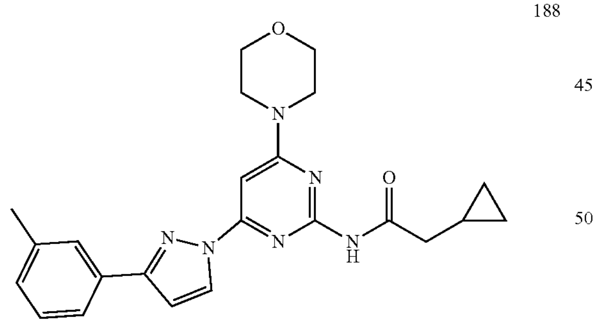
317
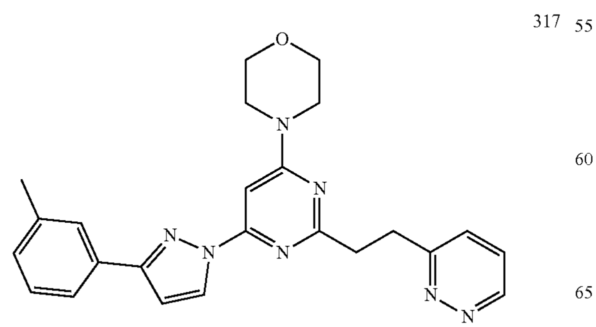
-continued
189
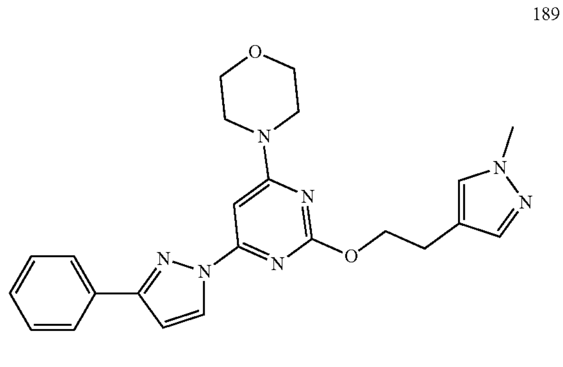
318
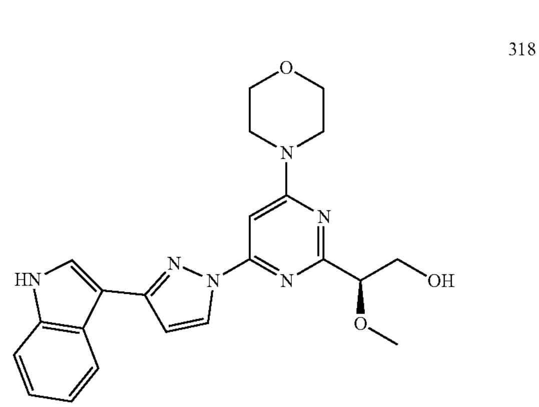
190
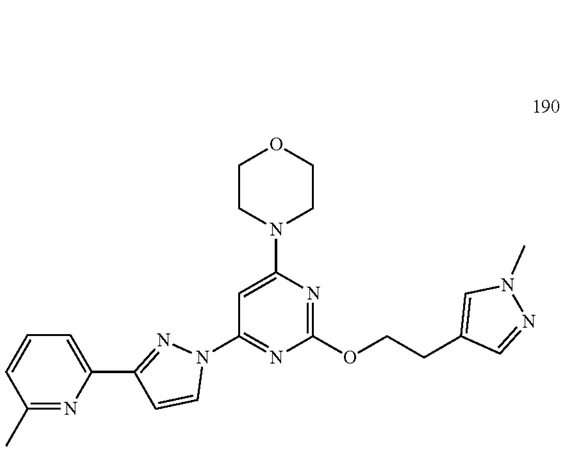
319
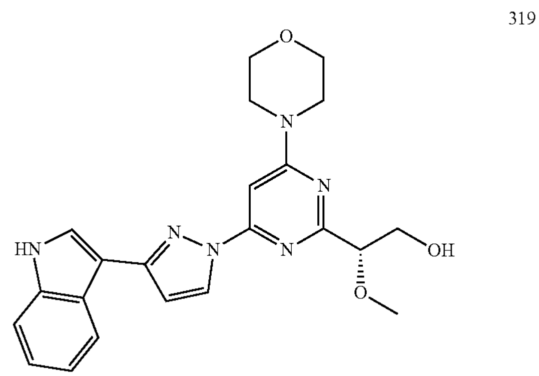

-continued
191
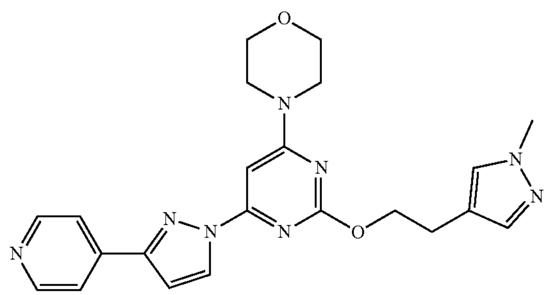
320
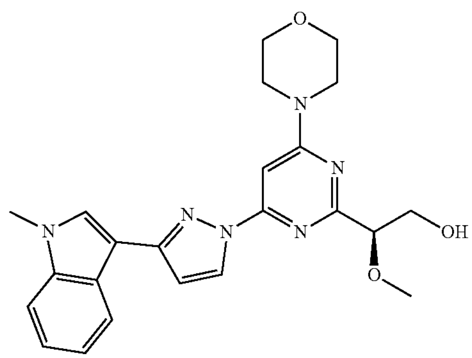
192
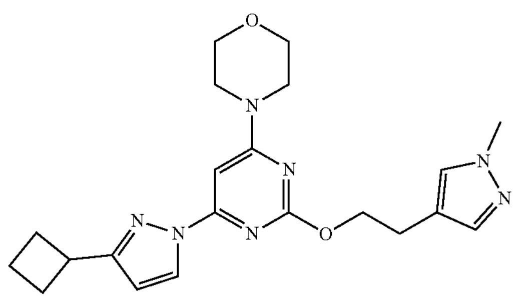
321
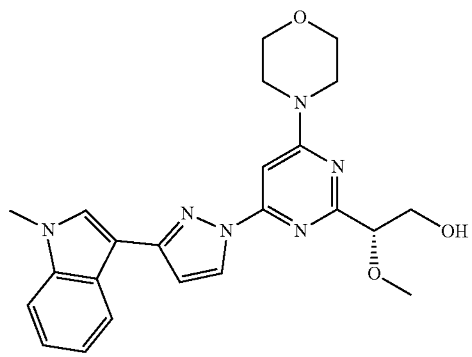
-continued
193
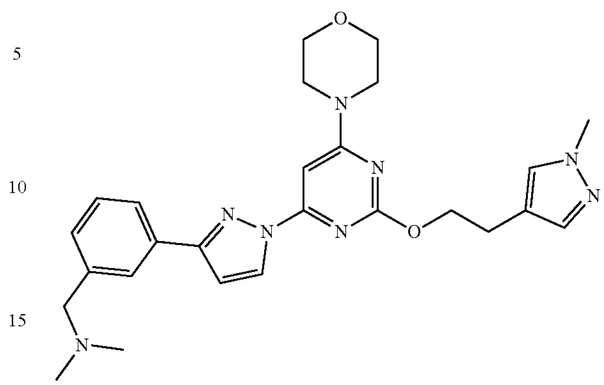
322
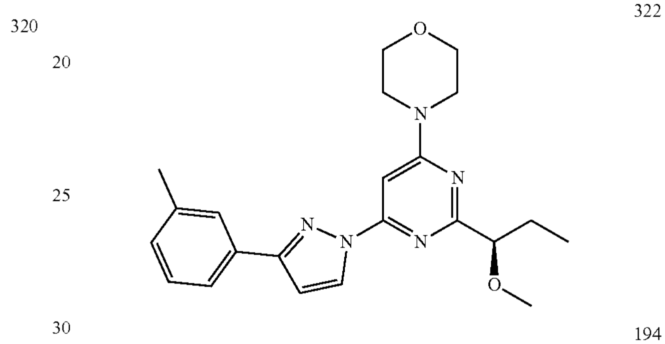
194
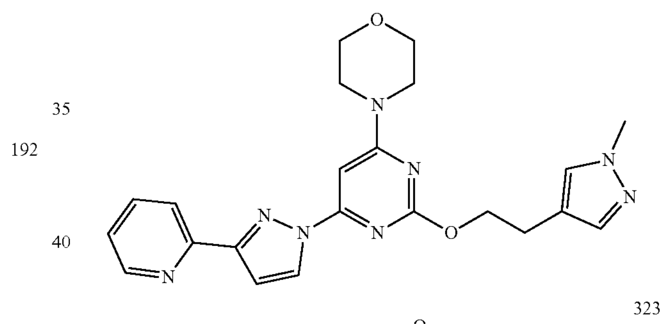
323
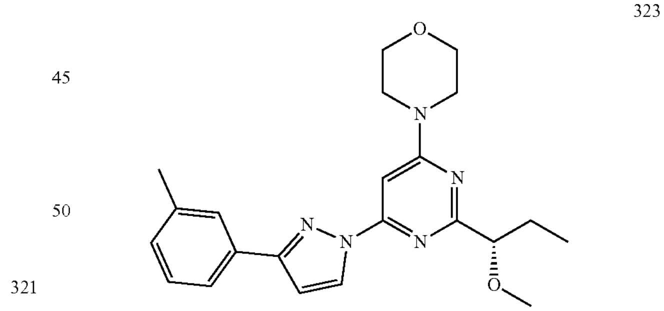
195
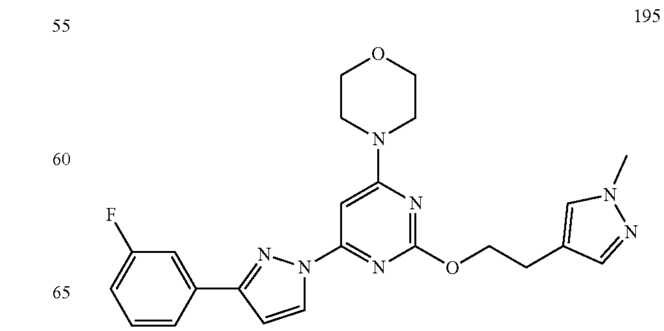

-continued
324
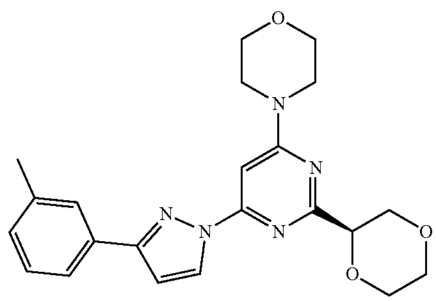
196
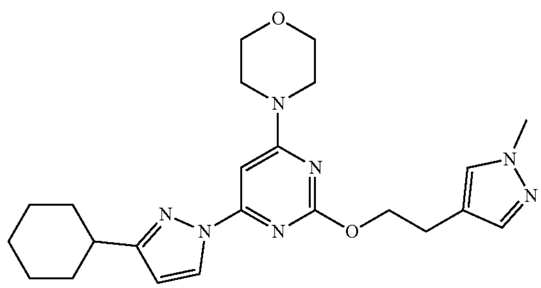
325
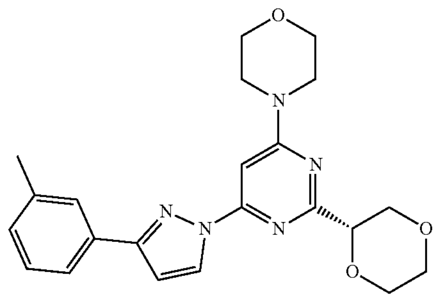
197
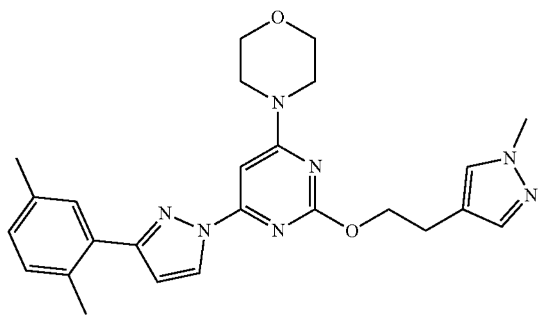
326
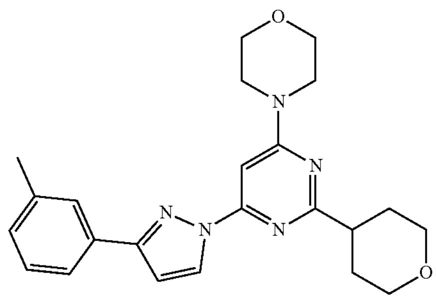
-continued
198
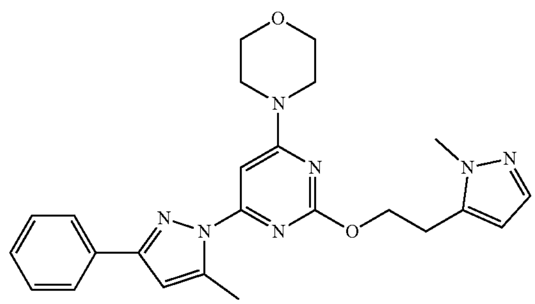
327
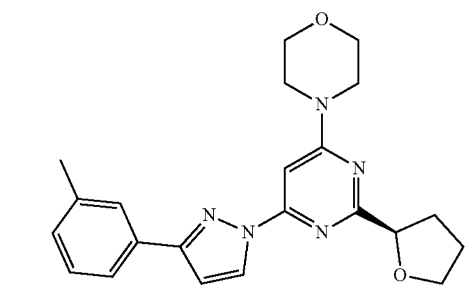
199
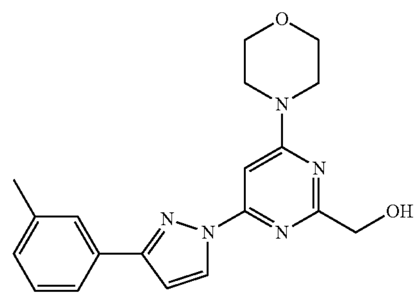
328
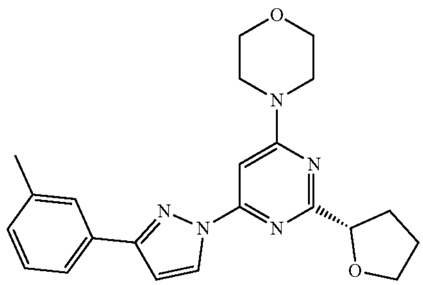
200
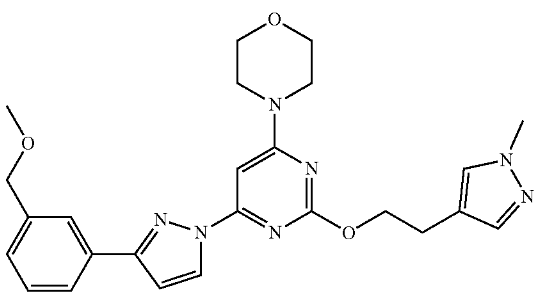

-continued
329
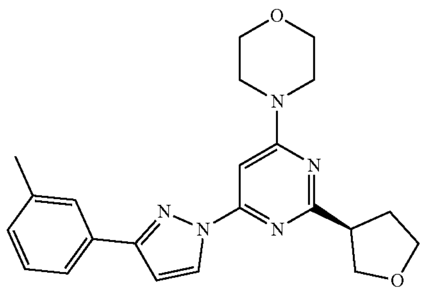
201
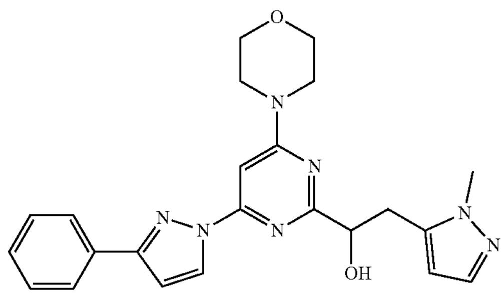
330
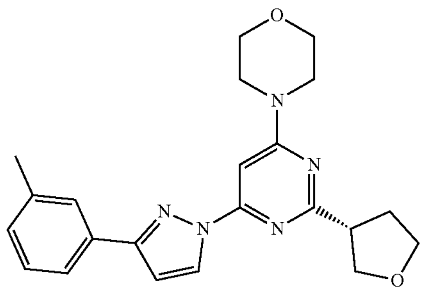
202
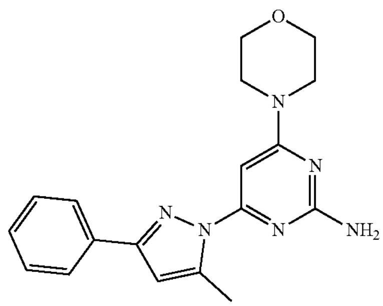
331
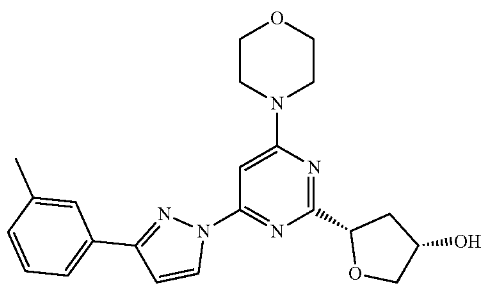
203
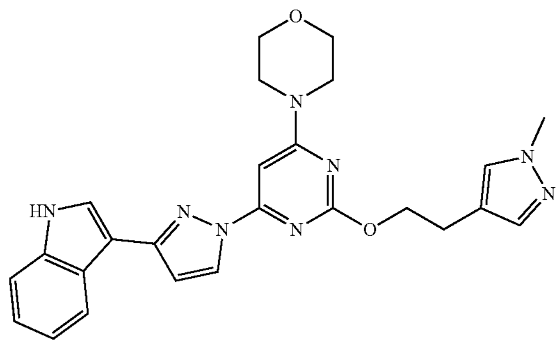
332
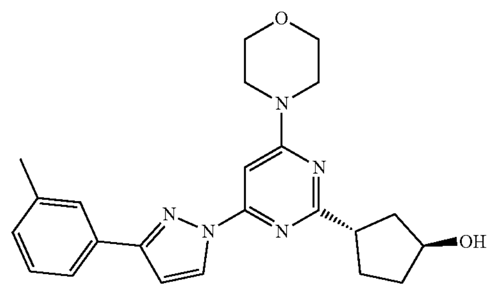
204
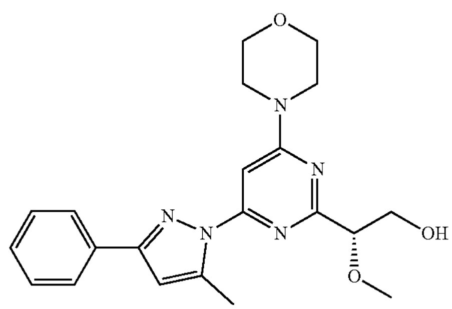
333
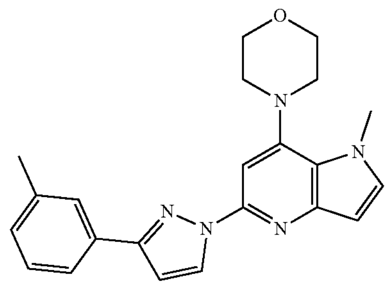
205
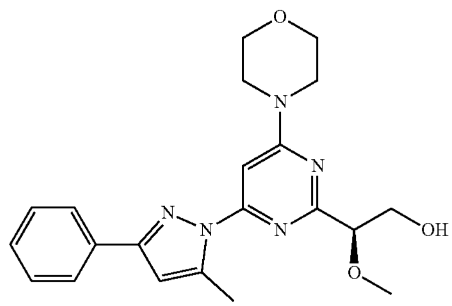

-continued
334
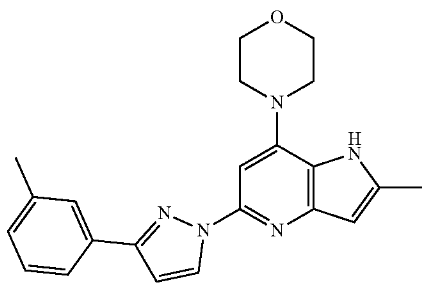
206
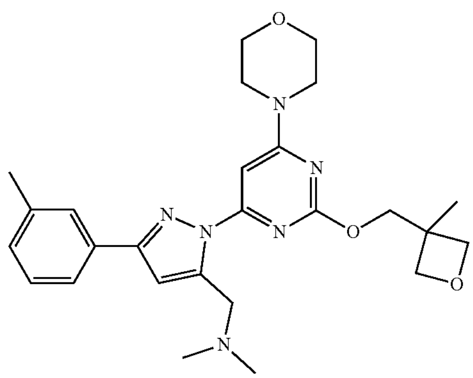
335
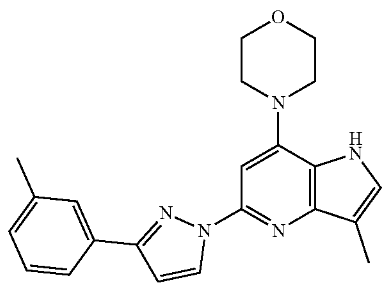
207
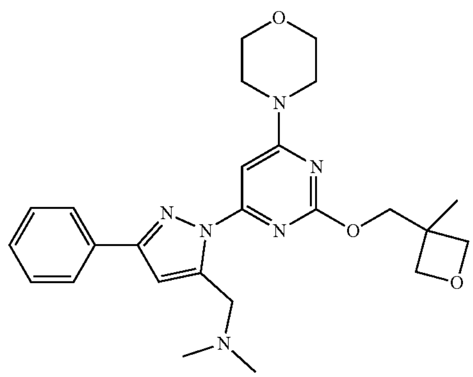
336
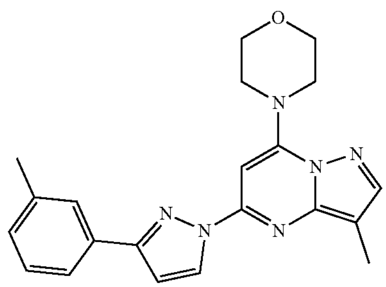
-continued
208
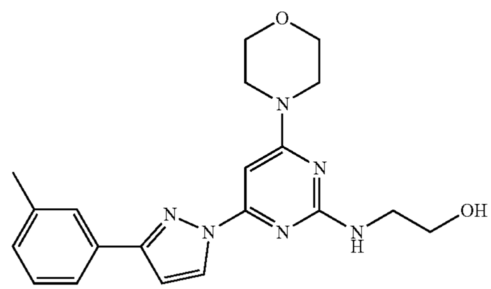
337
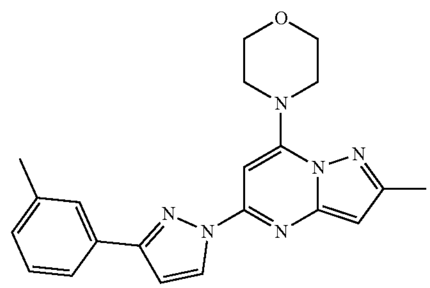
209
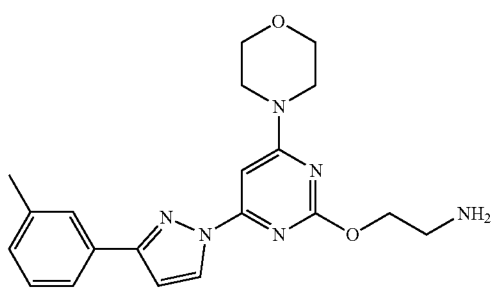
338
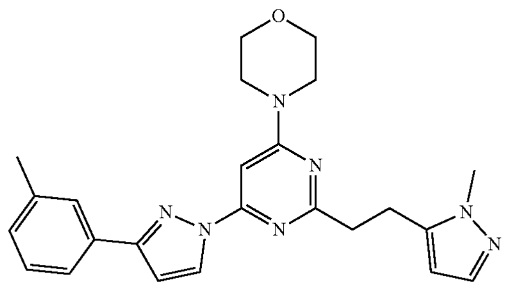
210
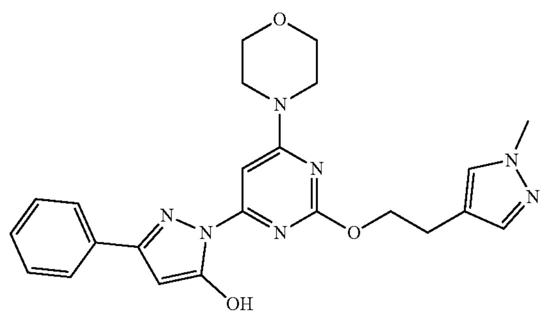

-continued
339
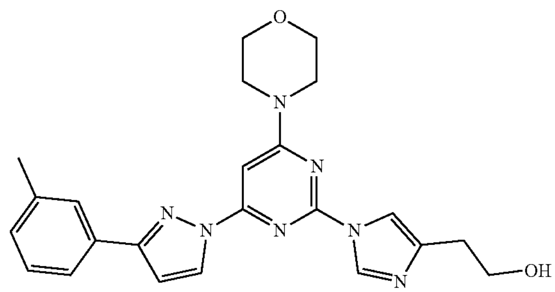
211
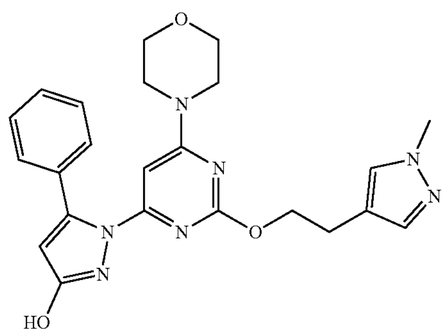
340
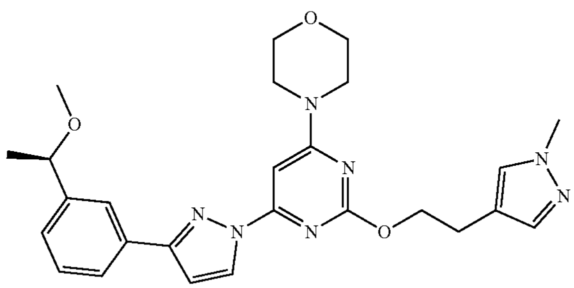
212
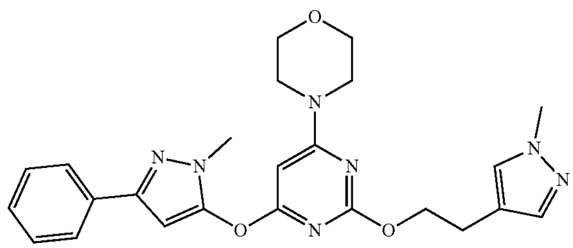
341
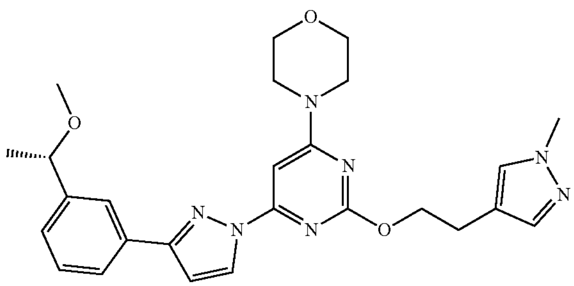
-continued
213
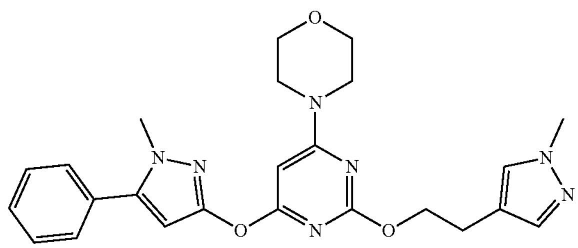
342
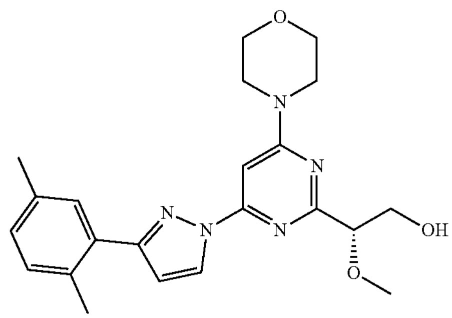
214
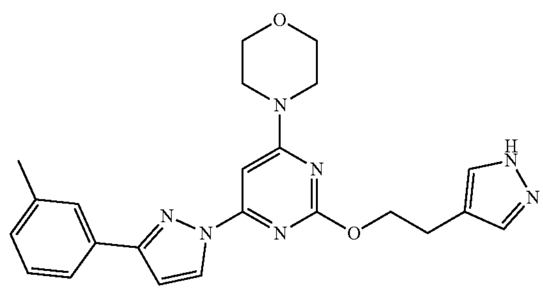
343
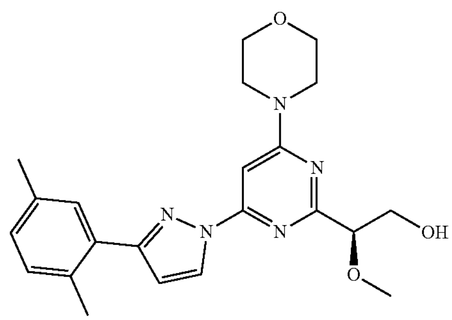
215
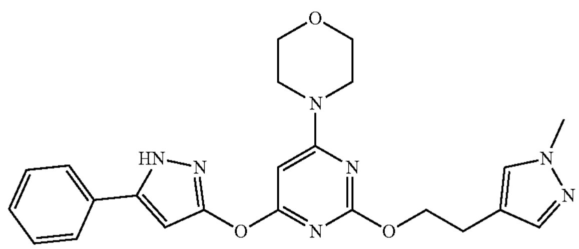

-continued
344
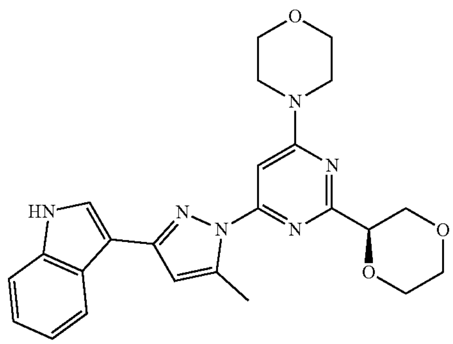
216
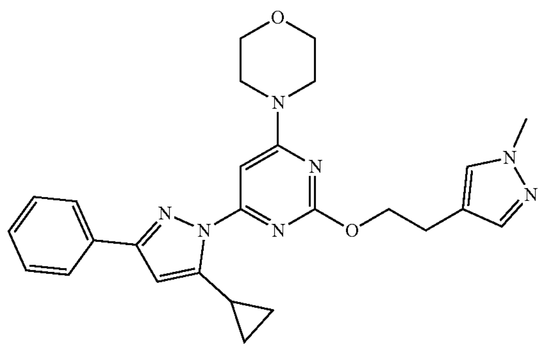
345
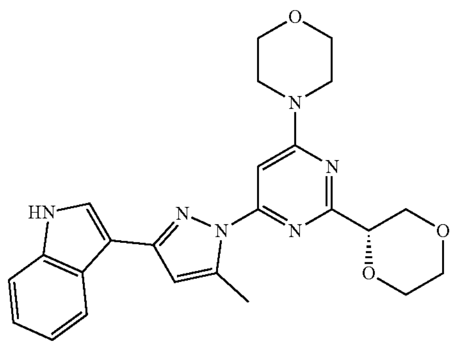
217
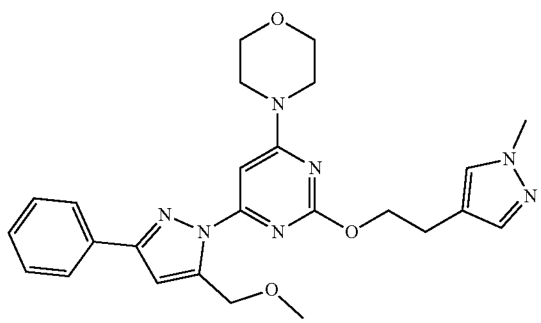
-continued
346
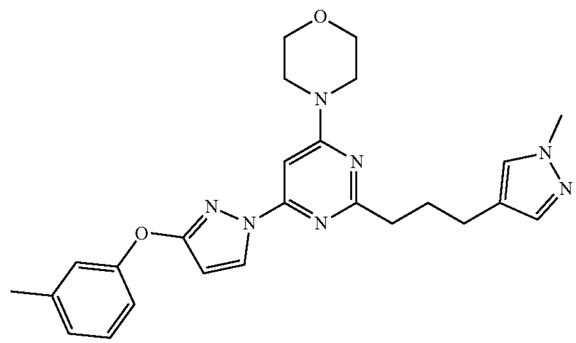
218
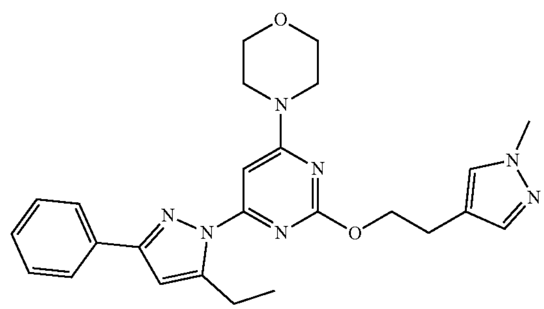
219
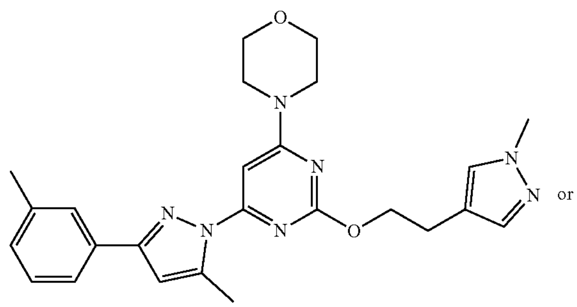
or
347
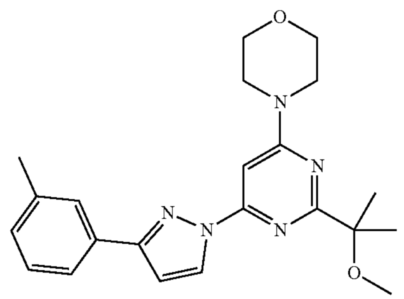
,
or a pharmaceutically acceptable salt thereof.
* * * * *